(12) United States Patent
Bharathan et al.

(10) Patent No.: US 12,291,538 B2
(45) Date of Patent: May 6, 2025

(54) SMALL MOLECULE INHIBITORS OF KRAS G12C MUTANT

(71) Applicant: Merck Sharp & Dohme LLC, Rahway, NJ (US)

(72) Inventors: Indu Bharathan, Somerville, MA (US); Symon Gathiaka, Waltham, MA (US); Yongxin Han, Needham, MA (US); Xiaoshen Ma, Boston, MA (US); Ryan D. Otte, Natick, MA (US); David L. Sloman, Newton, MA (US); Thomas H. Graham, Somerville, MA (US); Timothy Henderson, Natick, MA (US); Elisabeth Hennessy, Weston, MA (US); Anandan Palani, Needham, MA (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 88 days.

(21) Appl. No.: 18/311,646

(22) Filed: May 3, 2023

(65) Prior Publication Data

US 2024/0043448 A1   Feb. 8, 2024

Related U.S. Application Data

(62) Division of application No. 17/081,477, filed on Oct. 27, 2020, now Pat. No. 11,697,657.

(Continued)

(51) Int. Cl.
*C07D 498/22*   (2006.01)
*A61K 31/519*   (2006.01)
(Continued)

(52) U.S. Cl.
CPC .......... *C07D 498/22* (2013.01); *A61K 31/519* (2013.01); *A61P 35/00* (2018.01);
(Continued)

(58) Field of Classification Search
CPC .. C07D 498/22; C07D 471/22; C07D 519/00; A61P 35/00; A61K 31/519
See application file for complete search history.

(56) References Cited

U.S. PATENT DOCUMENTS

| 4,034,075 A | 7/1977 | Bays et al. |
|---|---|---|
| 9,840,516 B2 | 12/2017 | Li et al. |

(Continued)

FOREIGN PATENT DOCUMENTS

| CN | 104011054 A | 8/2014 |
|---|---|---|
| CN | 107556289 A | 1/2018 |

(Continued)

OTHER PUBLICATIONS

Kargbo, Robert B., Small Molecule Inhibitors of KRAS G12 C Mutant, ACS Med. Chem. Letters, 12(8), pp. 1210-1211 (2021) (Year: 2021).*
J.G. Kettle, et al., "Structure-Based Design and Pharmacokinetic Optimization of Covalent Allosteric Inhibitors of the Mutant GTPase KRAS G12C", J. Med. Chem., vol. 63, pp. 4468-4483 (2020).
Q. Zheng, et al., "Drugging the Next Undruggable KRAS Allele-Gly12Asp", J. Med. Chem, vol. 65, pp. 3119-3122 (2022).
Lopez-Tapia, F., et al., "Linker Variation and Structure-Activity Relationship Analyses of Carboxylic Acid-based Small Molecule STAT3 Inhibitors", ACS Med. Chem. Lett. 2018, 9, 250-255.
Examination Report in co-pending European Patent Application No. 20815976.4 dated Jun. 13, 2023 (5 pages).
PubChem SID 469710826, available Jul. 28, 2022.
Examination Report in co-pending Canadian Patent Application No. 3,158,793 dated Feb. 20, 2024 (15 pages).

(Continued)

*Primary Examiner* — Erich A Leeser
(74) *Attorney, Agent, or Firm* — Venable LLP

(57) ABSTRACT

The disclosure provides compounds of Formula (I)

or a pharmaceutically acceptable salt thereof, wherein $W^1$, $W^2$, Y, Z, M, L, $C^y$, $C^z$, $R^1$, $R^2$, $R^3$, $R^4$, $R^{2a}$, $R^y$, $R^z$, and the subscripts m, n, q, and r are as described herein. The compounds or their pharmaceutically acceptable salts can inhibit the G12C mutant of Kirsten rat sarcoma (KRAS) protein and are expected to have utility as therapeutic agents, for example, for treating cancer. The disclosure also provides pharmaceutical compositions which comprise compounds of Formula (I) or pharmaceutically acceptable salts thereof. The disclosure also relates to methods for use of the compounds or their pharmaceutically acceptable salts in the therapy and prophylaxis of cancer and for preparing pharmaceuticals for this purpose.

6 Claims, No Drawings

Specification includes a Sequence Listing.

Related U.S. Application Data

(60) Provisional application No. 63/030,014, filed on May 26, 2020, provisional application No. 62/926,879, filed on Oct. 28, 2019.

(51) Int. Cl.
  *A61P 35/00* (2006.01)
  *C07D 471/22* (2006.01)
  *C07D 519/00* (2006.01)

(52) U.S. Cl.
  CPC ......... *C07D 471/22* (2013.01); *C07D 519/00* (2013.01); *C07B 2200/05* (2013.01)

(56) References Cited

U.S. PATENT DOCUMENTS

| | | |
|---|---|---|
| 10,125,134 B2 | 11/2018 | Blake et al. |
| 10,144,724 B2 | 12/2018 | Li et al. |
| 10,556,906 B2 | 2/2020 | Kuramoto et al. |
| 11,090,304 B2 | 8/2021 | Allen et al. |
| 11,453,683 B1 | 9/2022 | Wang et al. |
| 11,459,327 B1 | 10/2022 | Lv et al. |
| 2006/0135532 A1 | 6/2006 | Bryant et al. |
| 2010/0331305 A1 | 12/2010 | Bergeron et al. |
| 2014/0275070 A1 | 9/2014 | Grembecka et al. |
| 2014/0288045 A1 | 9/2014 | Ren et al. |
| 2014/0371203 A1 | 12/2014 | Madge et al. |
| 2015/0176010 A1 | 6/2015 | Wersinger |
| 2015/0239900 A1 | 8/2015 | Li et al. |
| 2015/0246934 A1 | 9/2015 | Bensen et al. |
| 2016/0046647 A1 | 2/2016 | Grembecka et al. |
| 2016/0108019 A1 | 4/2016 | Li et al. |
| 2016/0137665 A1 | 5/2016 | Grembecka et al. |
| 2016/0152634 A1 | 6/2016 | Madge et al. |
| 2016/0159738 A1 | 6/2016 | Ren et al. |
| 2016/0297774 A1 | 10/2016 | Li et al. |
| 2016/0318866 A1 | 11/2016 | Becker-Pelster et al. |
| 2017/0131278 A1 | 5/2017 | Patricelli et al. |
| 2017/0197945 A1 | 7/2017 | Li et al. |
| 2017/0253611 A1 | 9/2017 | Grembecka et al. |
| 2018/0072723 A1 | 3/2018 | Blake et al. |
| 2018/0118757 A1 | 5/2018 | Li et al. |
| 2018/0127396 A1 | 5/2018 | Li et al. |
| 2018/0141927 A1 | 5/2018 | Li et al. |
| 2018/0162812 A1 | 6/2018 | Ren et al. |
| 2018/0177767 A1 | 6/2018 | Lanman et al. |
| 2018/0334454 A1 | 11/2018 | Lanman et al. |
| 2019/0062313 A1 | 2/2019 | Li et al. |
| 2019/0062330 A1 | 2/2019 | Blake et al. |
| 2019/0127336 A1 | 5/2019 | Li et al. |
| 2019/0144444 A1 | 5/2019 | Blake et al. |
| 2019/0248767 A1 | 8/2019 | Planken et al. |
| 2019/0270743 A1 | 9/2019 | Marx et al. |
| 2019/0276432 A1 | 9/2019 | Beaumont et al. |
| 2019/0284144 A1 | 9/2019 | Li et al. |
| 2019/0292182 A1 | 9/2019 | Kuramoto et al. |
| 2019/0343838 A1 | 11/2019 | Allen et al. |
| 2019/0374542 A1 | 12/2019 | Allen et al. |
| 2020/0055845 A1 | 2/2020 | Lanman et al. |
| 2020/0069657 A1 | 3/2020 | Lanman et al. |
| 2020/0115363 A1 | 4/2020 | Li et al. |
| 2020/0115375 A1 | 4/2020 | Barda et al. |
| 2020/0140437 A1 | 5/2020 | Kuramoto et al. |
| 2020/0165231 A1 | 5/2020 | Shin et al. |
| 2020/0181118 A1 | 6/2020 | Malhotra et al. |
| 2020/0237771 A1 | 7/2020 | Hallur et al. |
| 2020/0262837 A1 | 8/2020 | Marx et al. |
| 2020/0289503 A1 | 9/2020 | Huang |
| 2020/0331911 A1 | 10/2020 | Marx et al. |
| 2021/0009577 A1 | 1/2021 | Lanman et al. |
| 2021/0024501 A1 | 1/2021 | Li et al. |
| 2021/0040089 A1 | 2/2021 | Gao et al. |
| 2021/0047297 A1 | 2/2021 | Schulze et al. |
| 2021/0395234 A1 | 12/2021 | Sakamoto et al. |
| 2022/0064141 A1 | 3/2022 | Fang et al. |
| 2022/0298174 A1 | 9/2022 | Guo et al. |
| 2022/0315597 A1 | 10/2022 | Su et al. |
| 2022/0315598 A1 | 10/2022 | Xu et al. |
| 2022/0370416 A1 | 11/2022 | Chu et al. |
| 2022/0389029 A1 | 12/2022 | Guo et al. |
| 2022/0402916 A1 | 12/2022 | Hoover et al. |
| 2023/0023023 A1 | 1/2023 | Shibata et al. |
| 2023/0049402 A1 | 2/2023 | Sakamoto et al. |
| 2023/0174518 A1 | 6/2023 | Kawai |
| 2023/0181536 A1 | 6/2023 | Abe et al. |
| 2023/0348495 A1 | 11/2023 | Kawai et al. |
| 2023/0416266 A1 | 12/2023 | Han et al. |
| 2024/0124478 A1 | 4/2024 | Han et al. |
| 2024/0239788 A1 | 7/2024 | Sloman et al. |
| 2024/0246968 A1 | 7/2024 | Shibata et al. |
| 2024/0262842 A1 | 8/2024 | Shibata et al. |
| 2024/0317759 A1 | 9/2024 | Kobayakawa et al. |

FOREIGN PATENT DOCUMENTS

| | | |
|---|---|---|
| CN | 109843856 A | 6/2019 |
| CN | 112430234 A | 3/2021 |
| CN | 114615981 A | 6/2022 |
| EP | 3871673 A1 | 9/2021 |
| EP | 4053120 A1 | 9/2022 |
| JP | 2016-519072 A | 6/2016 |
| JP | 2016-532656 A | 10/2016 |
| JP | 2017-528498 A | 9/2017 |
| WO | 03/037898 A1 | 5/2003 |
| WO | 2005/019177 A1 | 3/2005 |
| WO | 2009/114575 A1 | 9/2009 |
| WO | 2010/064705 A1 | 6/2010 |
| WO | 2013/072694 A1 | 5/2013 |
| WO | 2014/043272 A1 | 3/2014 |
| WO | 2014/143659 A1 | 9/2014 |
| WO | 2014/152588 A1 | 9/2014 |
| WO | 2014/164543 A1 | 10/2014 |
| WO | 2015/054572 A1 | 4/2015 |
| WO | 2015/091415 A1 | 6/2015 |
| WO | 2015/131005 A1 | 9/2015 |
| WO | 2016/029454 A1 | 3/2016 |
| WO | 2016/044772 A1 | 3/2016 |
| WO | 2016/049524 A1 | 3/2016 |
| WO | 2016/049565 A1 | 3/2016 |
| WO | 2016/049568 A1 | 3/2016 |
| WO | 2016/164675 A1 | 10/2016 |
| WO | 2016/168540 A1 | 10/2016 |
| WO | 2017/015562 A1 | 1/2017 |
| WO | 2017/058728 A1 | 4/2017 |
| WO | 2017/058768 A1 | 4/2017 |
| WO | 2017/058792 A1 | 4/2017 |
| WO | 2017/058805 A1 | 4/2017 |
| WO | 2017/058807 A1 | 4/2017 |
| WO | 2017/058902 A1 | 4/2017 |
| WO | 2017/058915 A1 | 4/2017 |
| WO | 2017/070256 A2 | 4/2017 |
| WO | 2017/087528 A1 | 5/2017 |
| WO | 2017/100546 A1 | 6/2017 |
| WO | 2017/172979 A1 | 10/2017 |
| WO | 2017/201161 A1 | 11/2017 |
| WO | 2018/022897 A1 | 2/2018 |
| WO | 2018/064510 A1 | 4/2018 |
| WO | 2018/068017 A1 | 4/2018 |
| WO | 2018/119183 A2 | 6/2018 |
| WO | 2018/140512 A1 | 8/2018 |
| WO | 2018/140513 A1 | 8/2018 |
| WO | 2018/140514 A1 | 8/2018 |
| WO | 2018/140598 A1 | 8/2018 |
| WO | 2018/140599 A1 | 8/2018 |
| WO | 2018/140600 A1 | 8/2018 |
| WO | 2018/143315 A1 | 8/2018 |
| WO | 2018/206539 A1 | 11/2018 |
| WO | 2018/217651 A1 | 11/2018 |
| WO | 2018/218069 A1 | 11/2018 |
| WO | 2018/218070 A2 | 11/2018 |
| WO | 2018/218071 A1 | 11/2018 |
| WO | 2019/051291 A1 | 3/2019 |
| WO | 2019/058132 A1 | 3/2019 |
| WO | 2019/058393 A1 | 3/2019 |

(56) References Cited

FOREIGN PATENT DOCUMENTS

| | | |
|---|---|---|
| WO | 2019/077631 A1 | 4/2019 |
| WO | 2019/099524 A1 | 5/2019 |
| WO | 2019/099703 A1 | 5/2019 |
| WO | 2019/110751 A1 | 6/2019 |
| WO | 2019/155399 A1 | 8/2019 |
| WO | 2019/167000 A1 | 9/2019 |
| WO | 2019/185525 A1 | 10/2019 |
| WO | 2019/215203 A1 | 11/2019 |
| WO | 2020/035031 A1 | 2/2020 |
| WO | 2020/041331 A1 | 2/2020 |
| WO | 2020/050890 A2 | 3/2020 |
| WO | 2020/085493 A1 | 4/2020 |
| WO | 2020/097537 A2 | 5/2020 |
| WO | 2020/101736 A1 | 5/2020 |
| WO | 2020/113071 A1 | 6/2020 |
| WO | 2020/146613 A1 | 7/2020 |
| WO | 2020/156285 A1 | 8/2020 |
| WO | 2020/177629 A1 | 9/2020 |
| WO | 2020/178282 A1 | 9/2020 |
| WO | 2020/221239 A1 | 11/2020 |
| WO | 2020/233592 A1 | 11/2020 |
| WO | 2020/234103 A1 | 11/2020 |
| WO | 2020/236940 A1 | 11/2020 |
| WO | 2020/238791 A1 | 12/2020 |
| WO | 2020/239077 A1 | 12/2020 |
| WO | 2020/239123 A1 | 12/2020 |
| WO | 2020/244637 A1 | 12/2020 |
| WO | 2020/259432 A1 | 12/2020 |
| WO | 2020/259513 A1 | 12/2020 |
| WO | 2020/259573 A1 | 12/2020 |
| WO | 2021/000885 A1 | 1/2021 |
| WO | 2021/023154 A1 | 2/2021 |
| WO | 2021/027911 A1 | 2/2021 |
| WO | 2021/027943 A1 | 2/2021 |
| WO | 2021/031952 A1 | 2/2021 |
| WO | 2021/037018 A1 | 3/2021 |
| WO | 2021/041671 A1 | 3/2021 |
| WO | 2021/043322 A1 | 3/2021 |
| WO | 2021/052499 A1 | 3/2021 |
| WO | 2021/055728 A1 | 3/2021 |
| WO | 2021/057832 A1 | 4/2021 |
| WO | 2021/058018 A1 | 4/2021 |
| WO | 2021/063346 A1 | 4/2021 |
| WO | 2021/078312 A1 | 4/2021 |
| WO | 2021/081212 A1 | 4/2021 |
| WO | 2021/083167 A1 | 5/2021 |
| WO | 2021/084765 A1 | 5/2021 |
| WO | 2021/085653 A1 | 5/2021 |
| WO | 2021/088458 A1 | 5/2021 |
| WO | 2021/093758 A1 | 5/2021 |
| WO | 2021/098859 A1 | 5/2021 |
| WO | 2021/104431 A1 | 6/2021 |
| WO | 2021/106230 A1 | 6/2021 |
| WO | 2021/106231 A1 | 6/2021 |
| WO | 2021/107160 A1 | 6/2021 |
| WO | 2021/109737 A1 | 6/2021 |
| WO | 2021/113595 A1 | 6/2021 |
| WO | 2021/118877 A1 | 6/2021 |
| WO | 2021/121330 A1 | 6/2021 |
| WO | 2021/121367 A1 | 6/2021 |
| WO | 2021/121371 A1 | 6/2021 |
| WO | 2021/124222 A1 | 6/2021 |
| WO | 2021/127404 A1 | 6/2021 |
| WO | 2021/129824 A1 | 7/2021 |
| WO | 2021/147965 A1 | 7/2021 |
| WO | 2021/147967 A1 | 7/2021 |
| WO | 2021/215544 A1 | 10/2021 |
| WO | 2021/215545 A1 | 10/2021 |
| WO | 2021/219072 A1 | 11/2021 |
| WO | 2022/066646 A1 | 3/2022 |
| WO | 2022/105857 A1 | 5/2022 |
| WO | 2022/109485 A1 | 5/2022 |
| WO | 2022/109487 A1 | 5/2022 |
| WO | 2022/132200 A1 | 6/2022 |
| WO | 2022/133038 A1 | 6/2022 |
| WO | 2022/173870 A1 | 8/2022 |
| WO | 2022/177917 A2 | 8/2022 |
| WO | 2022/221739 A1 | 10/2022 |
| WO | 2022/232318 A1 | 11/2022 |
| WO | 2022/232320 A1 | 11/2022 |
| WO | 2022/250170 A1 | 12/2022 |
| WO | 2022/251576 A1 | 12/2022 |
| WO | 2022/256459 A1 | 12/2022 |
| WO | 2023/046135 A1 | 3/2023 |
| WO | 2023/097227 A1 | 6/2023 |
| WO | 2023/103523 A1 | 6/2023 |
| WO | 2024/009191 A1 | 1/2024 |
| WO | 2024/015262 A1 | 1/2024 |
| WO | 2024/032704 A1 | 2/2024 |
| WO | 2024/041573 A1 | 2/2024 |
| WO | 2024/044667 A2 | 2/2024 |
| WO | 2024/063578 A1 | 3/2024 |
| WO | 2024/083168 A1 | 4/2024 |
| WO | 2024/103010 A1 | 5/2024 |
| WO | 2024/120433 A1 | 6/2024 |
| WO | 2024/209339 A1 | 10/2024 |
| WO | 2024/213979 A1 | 10/2024 |
| WO | 2024/233776 A1 | 11/2024 |
| WO | 2024/238343 A1 | 11/2024 |

OTHER PUBLICATIONS

R.B. Kargbo, "Small Molecule Inhibitors of KRAS G12C Mutant", Acs Med. Chem. Lett., vol. 12, pp. 1210-1211 (2021).
D.S. Hong, et al., "KRASG12C Inhibition with Sotorasib in Advanced Solid Tumors", The New England Journal of Medicine, vol. 383 No. 13 pp. 1207-1217 (2020).
D. Gentile, et al., "Ras Binder Induces a Modified Switch-II Pocket in GTP and GDP States", Cell Chemical Biology, 24, pp. 1455-1466 (2017).
D. Kessler, et al, "Drugging an undruggable pocket on KRAS", Proceedings of the National Academy of Sciences (PNAS), vol. 116, No. 32, pp. 15823-15829 (2019).
Y. Mao, et al., "Design, synthesis and biological evaluation of novel pyrimidine, 3-cyanopyridine and m-amino-N-phenylbenzamide based monocyclic EGFR tyrosine kinase inhibitors", Bioorganic & Medicinal Chemistry, 21, pp. 3090-3104 (2013).
PubChem CID 10121096, PubChem release Jun. 18, 2019, modify date Nov. 21, 2020, retrieved on Feb. 10, 2021 (9 pages).
International Search Report and Written Opinion in corresponding international application No. PCT/US2020/057496, dated Feb. 23, 2021 (14 pages).
G. Palfy, et al., "1H, 15N backbone assignment and comparative analysis of the wild type and G12C, G12D, G12V mutants of K-Ras bound to GDP at physiological pH", Biomolecular NMR Assignment, vol. 14, No. 1, pp. 1-7 (2019).
M.R. Janes, et al., "Targeting KRAS Mutant Cancers with a Covalent G12C-Specific Inhibitor", Cell, 172, pp. 578-589 (2018).
M.P. Patricelli, et al., "Selective Inhibition of Oncogenic KRAS Output with Small Molecules Targeting the Inactive State", Cancer Discovery, 6(3), pp. 316-329 (2016).
H. Chuang, et al., "Pharmacological strategies to target oncogenic KRAS signaling in pancreatic cancer", Pharmacological Research, 117, pp. 370-376 (2017).

* cited by examiner

SMALL MOLECULE INHIBITORS OF KRAS G12C MUTANT

The present application is a divisional of U.S. patent application Ser. No. 17/081,477, filed Oct. 27, 2020, which claims the benefit of U.S. Provisional Application Nos. 62/926,879, filed Oct. 28, 2019, and 63/030,014, filed May 26, 2020, the entirety of each of which is incorporated by reference herein.

FIELD OF THE INVENTION

The present disclosure relates to certain heteroaryl compounds and pharmaceutically acceptable salts thereof that inhibit the G12C mutant of Kirsten rat sarcoma (KRAS) protein and are expected to have utility as therapeutic agents, for example, for treatment of cancer. The present application also relates to pharmaceutical compounds containing such compounds as well as methods of using the compounds for treating cancer.

BACKGROUND OF THE INVENTION

RAS proteins are membrane-associated guanine nucleotide-binding proteins which function as molecular switches. RAS proteins function as components of signalling pathways transmitting signals from cell-surface receptors to regulate cellular proliferation, survival and differentiation. RAS proteins cycle between an inactive GDP-bound state and an active GTP-bound state.

The most notable members of the RAS subfamily are HRAS, KRAS and NRAS, mainly being implicated in many types of cancer. However, there are many other members including DIRAS1; DIRAS2; DIRAS3; ERAS; GEM; MRAS; KIRAS1; KIRAS2; NRAS; RALA; RALB; RAPIA; RAPIB; RAP2A; RAP2B; RAP2C; RASD1; RASD2; RASL10A; RASL10B; RASL11A; RASL11B; RASL12; REM1; REM2; RERG; RERGL; RRAD; RRAS and RRAS2.

Mutations in any one of the three main isoforms of RAS (HRAS, NRAS, or KRAS) genes are among the most common events in human tumorigenesis. KRAS mutations are detected in 25-30% of tumors. By comparison, the rates of oncogenic mutation occurring in the NRAS and HRAS family members are much lower (8% and 3% respectively).

Exchange of a glycine for a cysteine at residue 12 of RAS (the G12C mutation) results from a mutation commonly found in RAS genes. Large-scale cancer sequencing studies indicate that the G12C mutation appeared most frequently in lung, colorectal and pancreatic cancers. Histological analysis of seven cancer types indicated non-small cell lung cancer contributed the most, 70-75%, to cancer cases having the KRAS G12C mutation. See Lindsay, C. R., et al., *Br J Cancer* 121, 197-198 (2019).

Accordingly, while progress has been made in this field, there remains a need in the art for improved compounds and methods for treatment of cancer, for example, by inhibition of a mutant KRAS, HRAS or NRAS protein (e.g., KRAS G12C). Embodiments of the present disclosure fulfill this need and provide further related advantages.

SUMMARY OF THE DISCLOSURE

The present disclosure provides compounds which modulate mutant KRAS, HRAS, and/or NRAS proteins and may be valuable pharmaceutically active compounds for the treatment of cancer. In some embodiments the disclosed compounds selectively inhibit the KRAS (G12C) protein. The compounds of Formula (I)

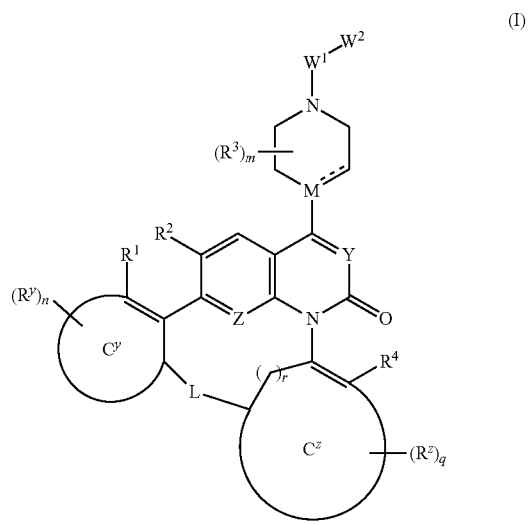

and their pharmaceutically acceptable salts, can modulate the activity of KRAS, HRAS and/or NRAS activity and thereby effect the signaling pathway which regulates cell growth, differentiation, and proliferation associated with oncological disorders. In certain embodiments, the compounds of Formula (I) can inhibit the KRAS (G12C) protein. The disclosure furthermore provides processes for preparing compounds of Formula (I), methods for using such compounds to treat oncological disorders, and pharmaceutical compositions which comprise compounds of Formula (I).

DETAILED DESCRIPTION OF THE INVENTION

Compounds of the Disclosure

In embodiment no. 1, the present disclosure provides a compound having structural Formula (I) as shown above wherein:
Y is N or C(H);
Z is N or C($R^5$);
M is C or N;
the dashed line in the illustrated ring containing M indicates an optional double bond;
L is $C_1$-$C_7$ alkylene or $C_1$-$C_7$ heteroalkylene,
  wherein said alkylene or heteroalkylene is unsubstituted or substituted by 1 to 5 substituents which are independently selected from oxo, fluoro, $C_1$-$C_3$ alkyl, $C_1$-$C_3$ fluoroalkyl, amino, and hydroxy;
  or alternatively, two geminal, vicinal or hominal substitutions of said alkylene or heteroalkylene can, together with the carbon atoms to which they are attached, form a ring CL, wherein said ring CL is $C_3$-$C_6$ cycloalkyl, and
    wherein said ring CL is unsubstituted or substituted by 1 to 3 fluoro;
$R^1$ is halo, H, $C_1$-$C_4$ alkyl, $C_1$-$C_4$ fluoroalkyl, or $C_1$-$C_4$ hydroxyalkyl;
$R^2$ is H, $CH_3$, or halo;
each $R^3$ is independently:
  (a) $C_1$-$C_4$ alkyl, $C_1$-$C_4$ cyanoalkyl, $C_1$-$C_4$ fluoroalkyl, $C_1$-$C_4$ hydroxyalkyl, $C_1$-$C_4$ alkylphenyl, oxo, or carboxy;

(b) or, alternatively, two $R^3$ substituents, together with the carbon atoms to which they are attached, can form a 3- to 6-membered bicyclo- or spirocyclic ring system with the illustrated ring containing M;

$W^1$ is —C(O)— or —S(O)$_2$—;

$W^2$ is a group of the formula:

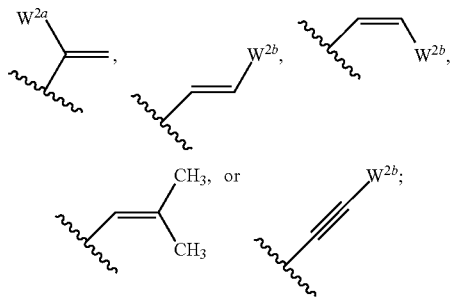

wherein $W^2a$ is H, CH$_3$, F, cyano, CH$_2$OH, CH$_2$CH$_2$OH, or CH$_2$Br;

$W^{2b}$ is CH$_3$, CH$_2$NH$_2$, CH$_2$N(H)CH$_3$, CH$_2$N(CH$_3$)$_2$, CH$_2$—NH-cyclopropyl,

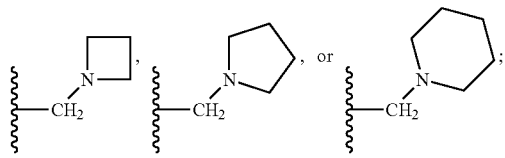

$R^4$ is H, C$_1$-C$_4$ alkyl, or C$_3$-C$_5$ cycloalkyl;

$R^5$ is H or halo;

ring $C^y$ is:
(a) phenyl,
(b) a 5- to 6-membered monocyclic heteroaryl containing one to three heteroatoms selected from N, O, and S; or
(c) a 9- to 10-membered bicyclic heteroaryl containing one to four heteroatoms selected from N, O, and S;

each $R^y$ is independently halo, hydroxy, C$_1$-C$_3$ alkyl, C$_1$-C$_3$ fluoroalkyl, C$_1$-C$_3$ alkoxy, cyano, hydroxy, or C$_1$-C$_3$ hydroxyalkyl;

ring $C^z$ is:
(a) phenyl, or
(b) a 5- to 6-membered heteroaryl containing one to three heteroatoms selected from N, O, and S;

each $R^z$ is independently halo, hydroxy, C$_1$-C$_3$ alkyl, C$_1$-C$_3$ fluoroalkyl, C$_1$-C$_3$ alkoxy, cyano, or C$_1$-C$_3$ hydroxyalkyl;

the subscript m is 0, 1, 2, or 3;

the subscript n is 0, 1, 2, 3, or 4;

the subscript q is 0, 1, 2, 3, or 4; and the subscript r is 0 or 1;

or a pharmaceutically acceptable salt thereof.

In embodiment no. 2, group

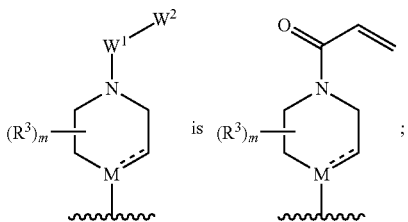

each $R^3$ is independently:
(a) C$_1$-C$_4$ alkyl, C$_1$-C$_4$ cyanoalkyl, C$_1$-C$_4$ fluoroalkyl, C$_1$-C$_4$ hydroxyalkyl, C$_1$-C$_4$ alkylphenyl, oxo, or carboxy;
(b) or, alternatively, two $R^3$ substituents, together with the carbon atoms to which they are attached, can form a 3- to 6-membered bicyclo- or spirocyclic ring system with the illustrated ring containing M; and each $R^y$ is independently halo, hydroxy, C$_1$-C$_3$ alkyl, C$_1$-C$_3$ fluoroalkyl, C$_1$-C$_3$ alkoxy, cyano, hydroxy, or C$_1$-C$_3$ hydroxyalkyl.

and the remaining variables are as set forth in embodiment no. 1.

In embodiment no. 3, the present disclosure provides a compound of Formula (I), wherein L is a group -$X^1$-$X^2$-$X^5$-$X^4$-$X^3$-, wherein:

$X^1$ and $X^3$ are independently —CH$_2$—, —O—, —S—, —C(O)—, —C(H)(CH$_3$)—, or —N(H)—;

$X^2$ is —CH$_2$—, —CF$_2$—, —C(H)(F)—, —C(H)(OH)—, —C(H)(CH$_3$)—, —O—, —S—, —N(H)—, or —C(O)—;

$X^4$ is absent, —CF$_2$—, —C(H)(F)—, —C(H)(OH)—, —C(H)(CH$_3$)—, —CH$_2$—, —O—, —S—, —N(H)—, or —C(O)—;

$X^5$ is absent, —CH$_2$—, —CF$_2$—, —C(H)(F)—, —O—, —S—, —N(H)—, —CH$_2$CH$_2$—, —CH$_2$CH$_2$CH$_2$—, —O—CH$_2$—, —CH$_2$—O—;

wherein:
when $X^1$ is —O—, —S—, or —N(H)—, then $X^2$ is —CH$_2$— or —C(O)—;
when $X^2$ is —O—, —S—, or —N(H)—, then $X^1$ is —CH$_2$— or —C(O)— and $X^5$, if present, is —CH$_2$—, —CF$_2$—, —CH$_2$CH$_2$—, or —CH$_2$CH$_2$CH$_2$—;
when $X^3$ is —O—, —S—, or —N(H)—, then $X^4$ is —CH$_2$— or —C(O)—;
when $X^4$ is —O—, —S—, or —N(H)— then $X^3$ is —CH$_2$— and $X^5$, if present, is —CH$_2$—, —CH$_2$CH$_2$—, or —CH$_2$CH$_2$CH$_2$—; and
when $X^5$ is —O—, —S—, or —N(H)—, then $X^2$ and $X^4$ are both —CH$_2$—;

and the remaining variables are as set forth in embodiment no. 1 or 2. In embodiment no. 3 and all other embodiments wherein L is the group —$X^1$—$X^2$-$X^5$-$X^4$-$X^3$—, $X^1$ is bonded to ring $C^y$ and $X^3$ is bonded to ring $C^z$.

In embodiment no. 4, the present disclosure provides a compound of Formula (I), wherein L is:
—O—CH$_2$CH$_2$CH$_2$—O—;
—CH$_2$CH$_2$CH$_2$—O—;
—O—CH$_2$CH$_2$CH$_2$—;
—O—C(H)(CH$_3$)CH$_2$CH$_2$—;
—O—CH$_2$CH$_2$CH$_2$—;
—O—CH$_2$CF$_2$CH$_2$CH$_2$—;
—CH$_2$CH$_2$CH$_2$CH$_2$—O—;
—CH$_2$CH$_2$CH$_2$CH$_2$—;

—CH₂CH₂CH₂—;
—CH₂CH₂C(H)(OH)CH₂—;
—CH₂C(H)(OH)CH₂CH₂—;
—O—CH₂CH₂—;
—CH₂CH₂—O—;
—O—CH₂CH₂—O—;
—O—CH₂C(H)(CH₃)—O—;
—O—C(H)(CH₃) CH₂—O—;
—O—CH₂CF₂CH₂—O—;
—CH₂CH₂—O—CH₂CH₂—;
—O—CH₂CH₂—O—CH₂CH₂—O—;
—CH₂—O—CH₂CH₂—;
—CH₂CH₂—O—CH₂—;
—N(H)—CH₂CH₂CH₂—;
—O—CH₂CH₂—O—CH₂—;
—C(O)—N(H)—CH₂CH₂CH₂—;
—CH₂CH₂CH₂—N(H)—C(O)—;
—N(H)—CH₂CH₂—O—CH₂—;

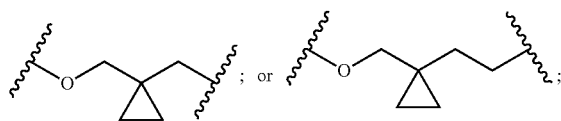 [SMILES: *CC1(CO*)CC1 ; *CCC1(CO*)CC1]

and the remaining variables are as set forth in embodiment no. 1 or 2. In these radicals, the left-most linker chain atom is bonded to ring C^y and the right-most linker chain atom is bonded to ring C^z.

In embodiment no. 5, the present disclosure provides a compound of Formula (I), wherein L is:
—O—CH₂CH₂CH₂—O—;
—CH₂CH₂CH₂—O—;
—O—CH₂CH₂CH₂—;
—O—CH₂CH₂CH₂CH₂—;
—CH₂CH₂CH₂CH₂—;
—O—CH₂CH₂—;
—O—CH₂CH₂—O—;
—O—CH₂CF₂CH₂—O—;
—CH₂CH₂—O—CH₂CH₂—;
—C(O)—N(H)—CH₂CH₂CH₂—; or
—CH₂—O—CH₂CH₂—;
and the remaining variables are as set forth in embodiment no. 1 or 2.

In embodiment no. 6, the present disclosure provides a compound of Formula (I), wherein the group -X¹-X²-X⁵-X⁴-X³- is:
—O—CH₂CH₂CH₂—;
—O—CH₂CH₂CH₂CH₂—;
—O—CH₂CH₂—O—; or
—O—CH₂CF₂CH₂CH₂—;
and the remaining variables are as set forth in embodiment no. 1 or 2.

In embodiment no. 7, the present disclosure provides a compound of Formula (I), wherein R¹ is fluoro, and the remaining variables are as set forth in any one of embodiment nos. 1-6.

In embodiment no. 8, the present disclosure provides a compound of Formula (I), wherein R² is fluoro or chloro, and the remaining variables are as set forth in in any one of embodiment nos. 1-7.

In embodiment no. 9, the present disclosure provides a compound of Formula (I), wherein R⁴ is H or isopropyl, and the remaining variables are as set forth in in any one of embodiment nos. 1-8.

In embodiment no. 10, the present disclosure provides a compound of Formula (I), wherein the subscript m is 0, 1 or 2, and the remaining variables are as set forth in in any one of embodiment nos. 1-9.

In embodiment no. 11, the present disclosure provides a compound of Formula (I), wherein the subscript m is 0 or 1, and the remaining variables are as set forth in in any one of embodiment nos. 1-9.

In embodiment no. 12, the subscript m is 0, and the remaining variables are as set forth in in any one of embodiment nos. 1-9.

In embodiment no. 13, the subscript m is 1, and the remaining variables are as set forth in in any one of embodiment nos. 1-9.

In embodiment no. 14, the subscript m is 2, and the remaining variables are as set forth in in any one of embodiment nos. 1-9.

In embodiment no. 15, the present disclosure provides a compound of Formula (I) as set forth in embodiment no. 10, 11, 13, or 14, wherein R³ is methyl or —CH₂—CN, and the remaining variables are as set forth in any one of embodiment nos. 1-9.

In embodiment no. 16, the present disclosure provides a compound of Formula (I), wherein M is N, and the remaining variables are as set forth in any one of embodiment nos. 1-15.

In embodiment, no. 17, the present disclosure provides a compound of Formula (I), wherein in the group

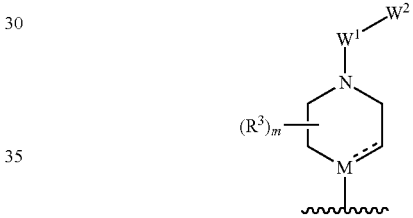

the double bond is absent, M is N and the remaining variables are as set forth in any one of embodiment nos. 1-15.

In embodiment no. 18, the present disclosure provides a compound of Formula (I) wherein the group

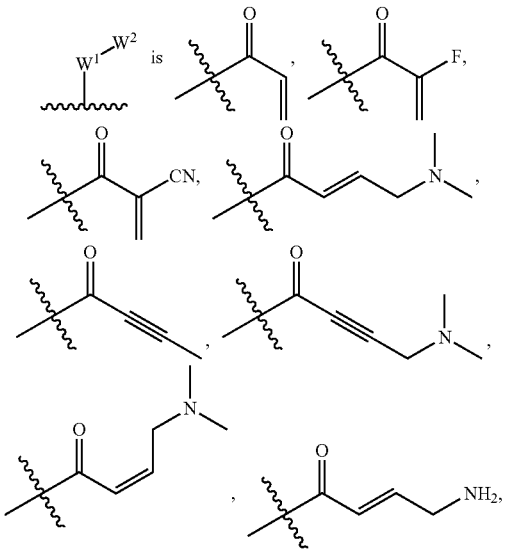

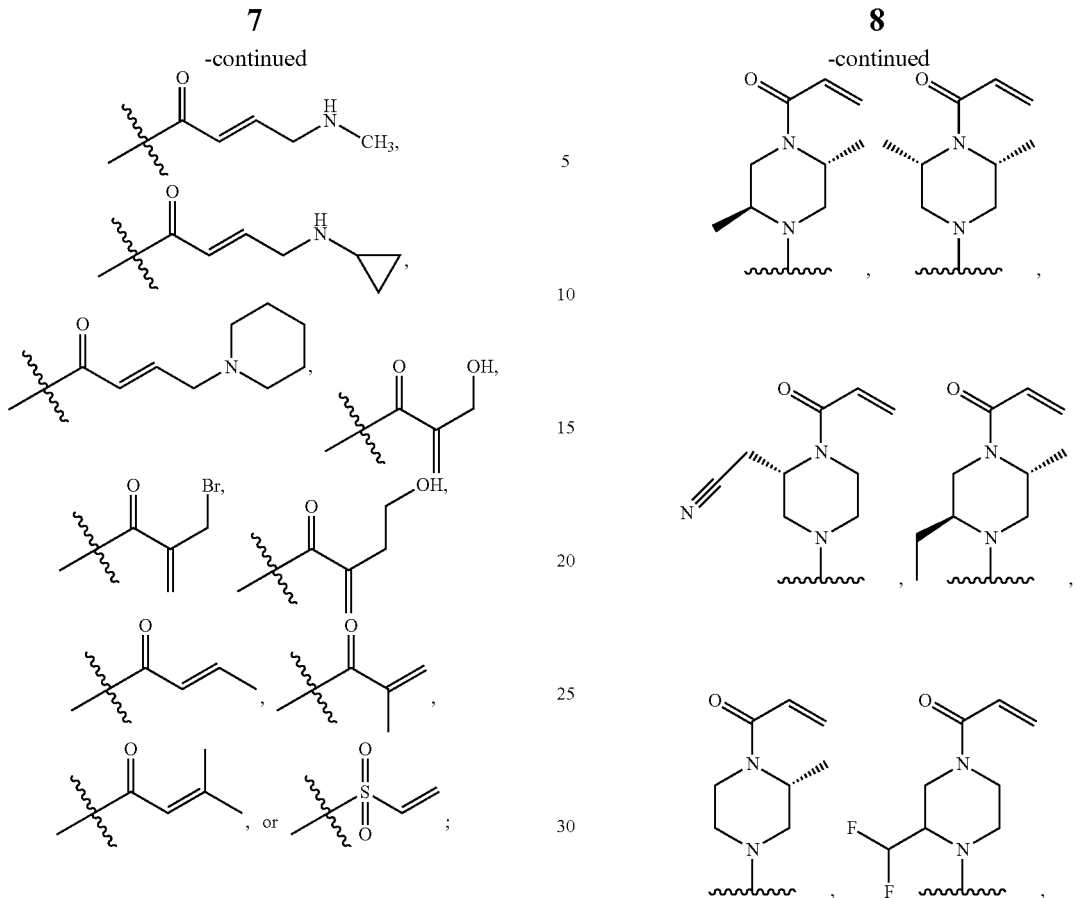

and the remaining variables are as set forth in embodiment no. 1.

In embodiment, no. 19, the present disclosure provides a compound of Formula (I), wherein in the group

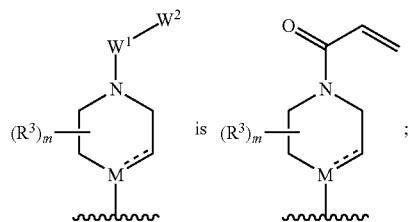

and the double bond is absent, M is N and the remaining variables are as set forth in any one of embodiment nos. 1-15.

In embodiment, no. 20, the present disclosure provides a compound of Formula (I), as set forth in embodiment no. 19, wherein the group

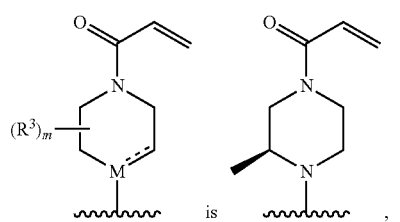

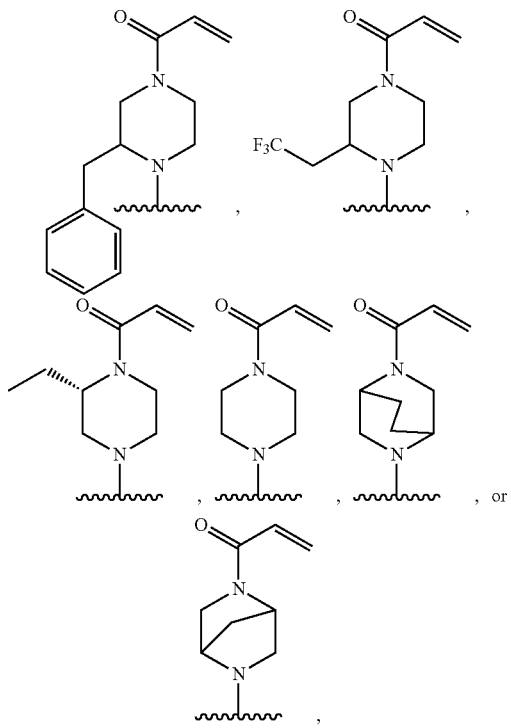

and the remaining variables are as set forth in any one of embodiment nos.

In embodiment no. 21, the present disclosure provides a compound of Formula (I) as set forth in embodiment no. 19, wherein the group

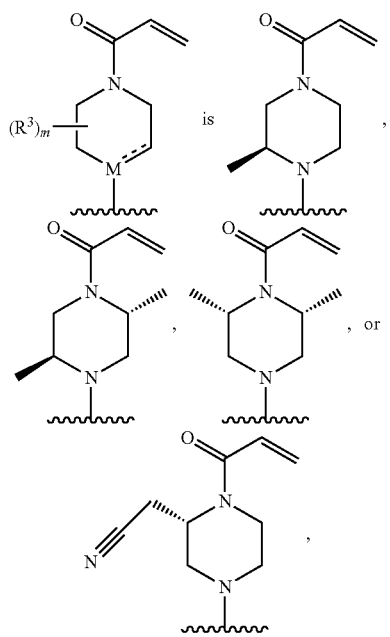

remaining variables are as set forth in any one of embodiment nos. 1-15.

In embodiment no. 22, the present disclosure provides a compound of Formula (I), wherein $C^y$ is phenyl or a 5- to 6-membered monocyclic heteroaryl containing one to three heteroatoms selected from N, O, and S; and the remaining variables are as set forth in any one of embodiment nos. 1-21.

In embodiment no. 23, $C^y$ is phenyl, and the remaining variables are as set forth in any one of embodiment nos. 1-22.

In embodiment no. 24, the present disclosure provides a compound of Formula (I), wherein the group

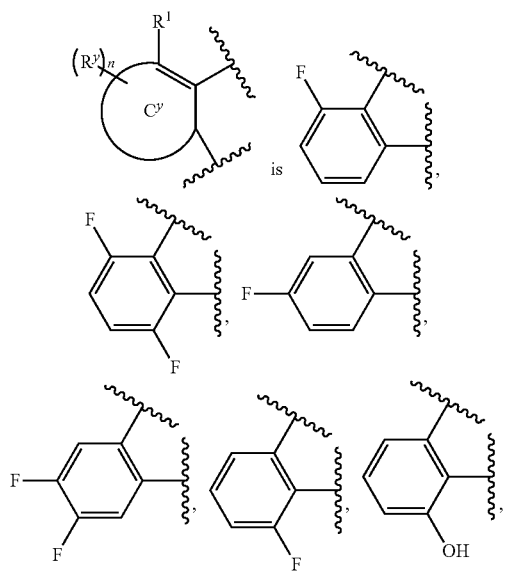

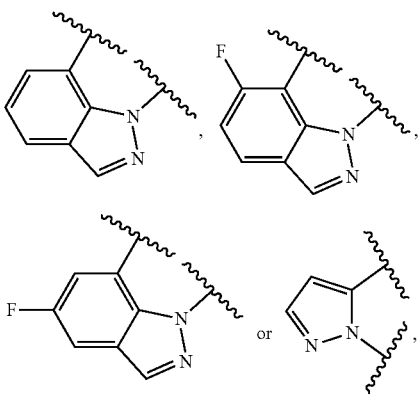

and the remaining variables are as set forth in any one of embodiment nos. 1-6 and 8-21.

In embodiment no. 25, the present disclosure provides a compound of Formula (I), wherein the group

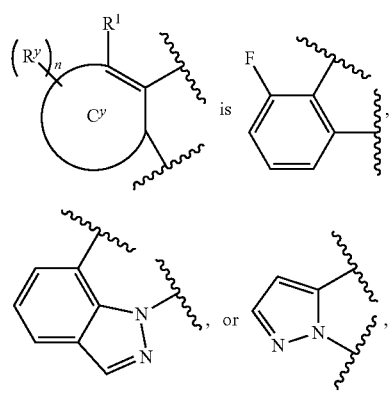

and the remaining variables are as set forth in any one of embodiment nos. 1-6 and 8-21.

In embodiment no. 26, the present disclosure provides a compound of Formula (I), wherein $C^z$ is phenyl or a 5- to 6-membered monocyclic heteroaryl containing one to three heteroatoms selected from N, O, and S; and the remaining variables are as set forth in any one of embodiment nos. 1-25.

In embodiment no. 27, $C^z$ is phenyl or pyridine, and the remaining variables are as set forth in any one of embodiment nos. 1-26.

In embodiment no. 28, the present disclosure provides a compound of Formula (I), wherein the group

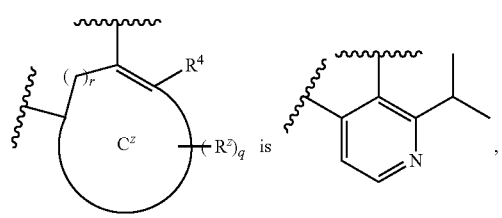

-continued

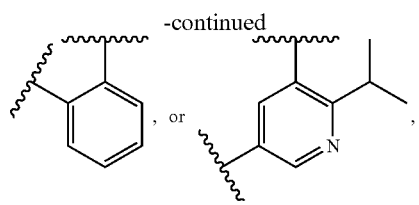, or remaining variables are as set forth in any one of embodiment nos. 1-25.

In embodiment no. 29, the group

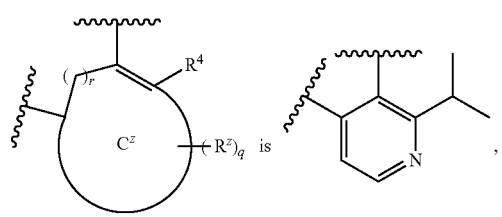 is and the remaining variables are as set forth in any one of embodiment nos. 1-25.

In embodiment no. 30, the present disclosure provides a compound of Formula (I) wherein Y is N, and the remaining variables are as set forth in any one of embodiment nos. 1-29.

In embodiment no. 31, the present disclosure provides a compound of Formula (I) wherein Z is N, and the remaining variables are as set forth in any one of embodiment nos. 1-30.

In embodiment no. 32, the present disclosure provides a compound of Formula (I) wherein the group

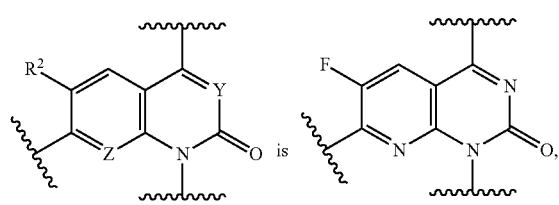 is and the remaining variables are as set forth in any one of embodiment nos. 1-29.

In embodiment no. 33, the present disclosure provides a compound of Formula (I), wherein the group

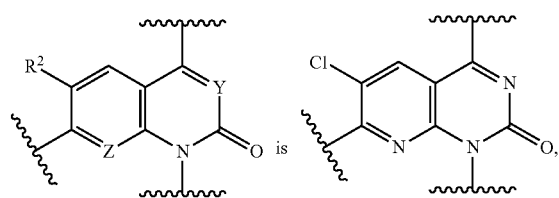 is and the remaining variables are as set forth in any one of embodiment nos. 1-29.

In embodiment no. 34, the present disclosure provides a compound of Formula (I) wherein the subscript r is 0, and the remaining variables are as set forth in any one of embodiment nos. 1-27 and 30-33.

In embodiment no. 35, the present disclosure provides a compound of Formula (I) wherein the subscript r is 1, and the remaining variables are as set forth in any one of embodiment nos. 1-27 and 30-33.

In embodiment no. 36, the compound of Formula (I) has the Formula (IA)

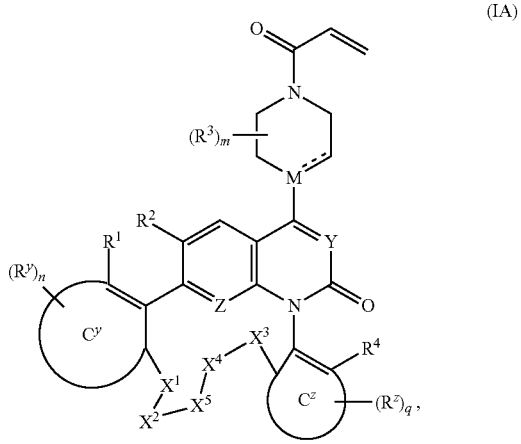

(IA)

wherein the group $-X^1-X^2-X^5-X^4-X^3-$ is as set forth in embodiment no. 3;

each $R^3$ and each $R^y$ are as set forth in embodiment no. 2; and $R^1$, $R^2$, $R^4$, $R^z$, Y, Z, ring $C^y$, ring $C^z$, and the subscripts m, n and q are as set forth in embodiment no. 1.

In embodiment no. 37 of the compound having Formula (IA), the group $-X^1-X^2-X^5-X^4-X^3-$ is as set forth in embodiment no. 5.

In embodiment no. 38, the present disclosure provides a compound of Formula (IA) wherein the group

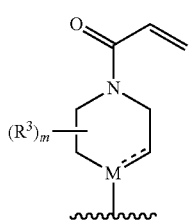

is as set forth in embodiment no. 21, the group

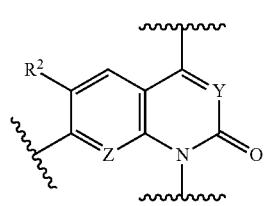

is as set forth in embodiment no. 32,
the group

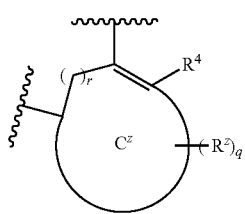

is as set forth in embodiment no. 28,
the group

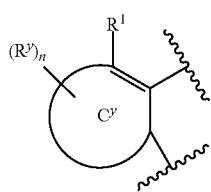

is as set forth in embodiment no. 25, and
L is as set forth in embodiment no. 5.

In embodiment no. 39, the present disclosure provides the compound of Formula (I) having Formula (IB)
wherein:

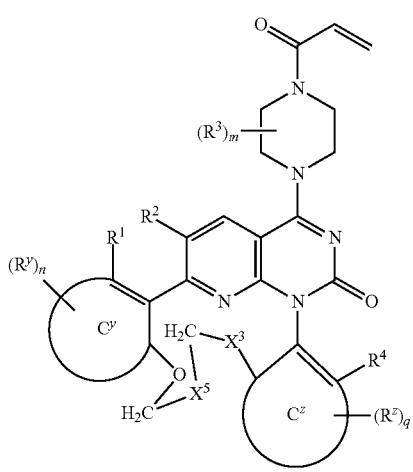

(IB)

$C^y$ is phenyl;
$C^z$ is pyridyl;
$X^3$ is —CH$_2$— or —O—;
$X^5$ is absent, —CH$_2$—, —CF$_2$—, or —C(H)(F)—;
$R^1$ is fluoro or chloro;
$R^2$ is fluoro or chloro;
$R^4$ is $C_1$-$C_4$ alkyl; and
the remaining variables are as set forth in embodiment no. 1.

In embodiment no. 40, the compound has Formula (IB) and the group
—O—CH$_2$-X$^5$—CH$_2$-X$^3$- is:
—O—CH$_2$CH$_2$CH$_2$—;
—O—CH$_2$CH$_2$CH$_2$CH$_2$—;
—O—CH$_2$CH$_2$—O—; or
—O—CH$_2$CF$_2$CH$_2$CH$_2$—; and
the remaining variables are as set forth in embodiment no. 39.

In embodiment no. 41, the compound has Formula (IB) and the group —O—CH$_2$-X$^5$—CH$_2$-X$^3$- is —O—CH$_2$CH$_2$CH$_2$—.

In embodiment no. 42, the compound has Formula (IB) and the group —O—CH$_2$-X$^5$—CH$_2$-X$^3$- is —O—CH$_2$CH$_2$CH$_2$CH$_2$—.

In embodiment no. 43, the compound has Formula (IB) and the group —O—CH$_2$-X$^5$—CH$_2$-X$^3$- is —O—CH$_2$CH$_2$—O—.

In embodiment no. 44, the compound has Formula (IB) and the group —O—CH$_2$-X$^5$—CH$_2$-X$^3$- is —O—CH$_2$CF$_2$CH$_2$CH$_2$—.

In embodiment no. 45, the compound has Formula (IB), wherein
the group

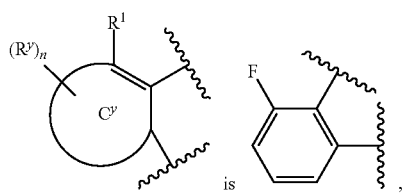

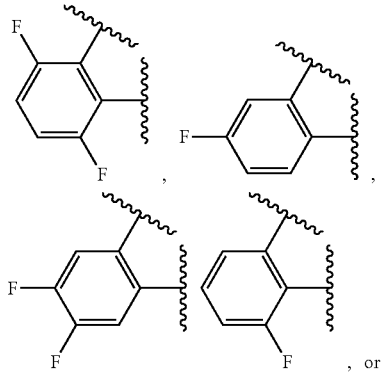

the group —O—CH$_2$-X$^5$—CH$_2$-X$^3$- is as set forth in any one of embodiment nos. 39-44; and the remaining variables are as set forth in embodiment no. 39.

In embodiment no. 46, the compound has the Formula (IB), wherein
the group

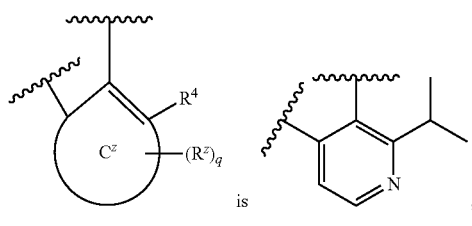

the group

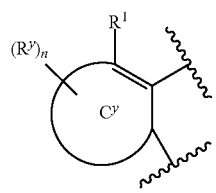

is as set forth in embodiment no. 39 or 45;
the group —O—CH$_2$-X$^5$—CH$_2$-X$^3$- is as set forth in any one of embodiment nos. 39-44; and the remaining variables are as set forth in embodiment no. 39.

In embodiment no. 47, the compound has the Formula (IB) as set forth in embodiment no. 39 or 46, wherein the group

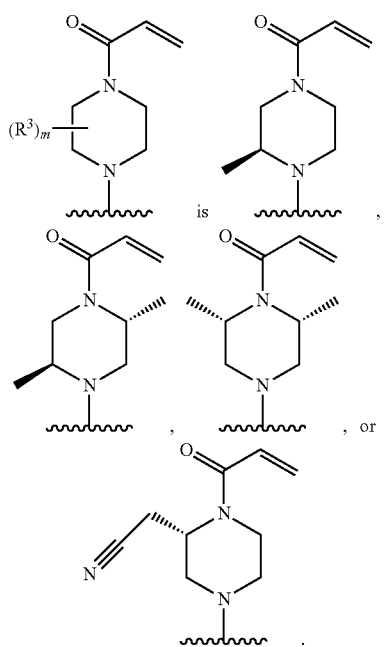

In embodiment no. 48, the present disclosure provides a compound as described in any one of Examples 1-20, 50-52, 54-68, 70, and 73-126 as set forth below, or a pharmaceutically acceptable salt thereof.

In some embodiments, the present disclosure provides compounds which have low predicted oral human doses (e.g., <500 mg, preferably <200 mg once daily oral administration) which result from high cellular potencies (e.g., IC50<100 nM at 2 h incubation time in the phospho-ERK assay), and superior preclinical pharmacokinetic and stability properties (e.g., as measured in the compounds' concentration in rat and dog plasma and in plasma clearance studies).

The present disclosure includes the pharmaceutically acceptable salts of the compounds defined herein, including the pharmaceutically acceptable salts of all structural formulas, embodiments and classes defined herein. Reference to the compounds of structural Formula (I) includes the compounds of other generic structural Formulas, such as Formulae (IA) and (IB), and embodiments that fall within the scope of Formula (I).

Definitions

Unless defined otherwise, all technical and scientific terms used herein have the same meaning as is commonly understood by one of skill in the art to which this invention belongs.

As used throughout this disclosure, "a compound of Formula (I)" is to be understood to include "a compound of Formula (I) or a pharmaceutically acceptable salt thereof". And "a compound of Formula (I)" is to be understood as to include "a compound of Formula (IA)" and "a compound of Formula (IB)" (and pharmaceutically acceptable salts of the compound of Formula (IA) and Formula (IB)).

"Alkyl", as well as other groups having the prefix "alk", such as alkoxy, and the like, means carbon chains which may be linear or branched, or combinations thereof, containing the indicated number of carbon atoms. In particular embodiments, linear alkyl groups have 1-6 carbon atoms and branched alkyl groups have 3-7 carbon atoms. Examples of alkyl groups include methyl, ethyl, propyl, isopropyl, butyl, sec- and tert-butyl, pentyl, hexyl, heptyl, octyl, nonyl and the like.

"Alkylene" refers to optionally substituted alkylene radicals. A numerical range, which refers to the chain length in total, may be given. For example, C$_3$-C$_4$ alkylene has a chain length of 3 or 4 atoms. Unless otherwise stated in the specification, alkylene groups may be substituted at carbon atoms in the radicals with one or more substituents which independently are oxo, fluoro, C$_1$-C$_3$ alkyl, C$_1$-C$_3$ fluoroalkyl, amino, hydroxy or two geminal or vicinal or hominal substitutions can combine with the carbon atoms to which they are substituted to form a C$_3$-C$_6$ cycloalkyl.

"Alkoxy" and "alkyl-O—" are used interchangeably and refer to an alkyl group linked to oxygen.

"Alkylphenyl" refers to a C$_1$-C$_4$ alkyl substituted with a phenyl group. The phenyl group may be anywhere on the carbon chain, e.g., at the end of the carbon chain.

"Bicyclo-ring system" refers to two joined rings. The rings may be fused, i.e., share two adjacent atoms, or "spirocyclic", i.e., share only a single atom.

"Cyanoalkyl" refers to an alkyl group substituted with a cyano group.

"Cycloalkyl" means a saturated cyclic hydrocarbon radical. In particular embodiments, the cycloalkyl group has 3-12 carbon atoms, forming 1-3 carbocyclic rings that are fused. Examples of cycloalkyl include cyclopropyl, cyclobutyl, cyclopentyl, cyclohexyl, cycloheptyl, adamantyl, and the like.

"Fluoroalkyl" include mono-substituted as well as multiple fluoro-substituted alkyl groups, up to perfluoro substituted alkyl. For example, fluoromethyl, 1,1-difluoroethyl, trifluoromethyl or 1,1,1,2,2-pentafluorobutyl are included.

"Geminally substituted" refers to substitutions (e.g., functional groups) that are attached to the same atom in a molecule. For instance, 1,1-dichloroethane is an ethane molecule which is geminally substituted with two chlorine atoms.

The term "heteroalkylene" refers to optionally substituted alkylene radicals, which have one or more skeletal chain atoms selected from an atom other than carbon, e.g., oxygen, nitrogen, or sulfur, thereof. A numerical range, which refers to the chain length in total, may be given. For example, C$_1$-C$_7$ heteroalkylene has a chain length of 1 to 7 atoms. For example, a —OCH$_2$CH$_2$CH$_2$O— radical is referred to as a "C$_5$ heteroalkylene", which includes two heteroatoms in the atom chain length description. Connections to the rest of the molecule are through terminal carbon, nitrogen, oxygen or sulfur atoms in the heteroalkylene chain (e.g., to ring atoms of $C^y$ and $C^z$). The heteroalkylene groups may be substituted. Unless otherwise stated in the specification, heteroalkylene groups may be substituted at carbon atoms in the radicals with one or more substituents which independently are oxo, fluoro, $C_1$-$C_3$ alkyl, $C_1$-$C_3$ fluoroalkyl, amino, hydroxy or two geminal or vicinal or hominal substitutions can combine with the carbon atoms to which they are substituted to form a $C_3$-$C_6$ cycloalkyl. In some embodiments, the heteroalkylene groups have 1-2 heteroatoms selected from nitrogen and oxygen atoms in the atom chain. In some embodiments, the heteroalkylene groups have 1 heteroatom selected from nitrogen and oxygen atoms in the atom chain.

"Heteroaryl" refers to aromatic monocyclic and bicyclic ring structures in which one or more atoms in the ring, the heteroatom(s), is an element other than carbon. Heteroatoms are typically O, S, or N atoms. Examples of heteroaromatic groups include pyridinyl, pyrimidinyl, pyrrolyl, pyridazinyl, isoxazolyl, thiazolyl, oxazolyl, indolyl, benzoxazolyl, benzothiazolyl, and imidazolyl.

"Halogen" or "halo" unless otherwise indicated, includes fluorine (fluoro), chlorine (chloro), bromine (bromo) and iodine (iodo). In one embodiment, halo is fluoro (—F) or chloro (—Cl).

"Hominally substituted" refers to substitutions or groups that are attached on a molecule in a 1,3-relationship. For instance, 1,3-dichloropropane $ClCH_2CH_2CH_2Cl$ is a propane molecule which is hominally substituted with two chlorine atoms.

"Hydroxyalkyl" includes mono-substituted as well as multiple hydroxy-substituted alkyl groups.

When any variable (e.g., $R^3$, $R^y$, etc.) occurs more than one time in any constituent or in Formula (I) or other generic formulas herein, its definition on each occurrence is independent of its definition at every other occurrence. Combinations of substituents and/or variables are permissible only if such combinations result in stable compounds. In choosing compounds of the present disclosure, one of ordinary skill in the art will recognize that the various substituents, i.e., $R^3$, $R^y$, etc., are to be chosen in conformity with well-known principles of chemical structure connectivity and stability. Unless expressly stated to the contrary, substitution by a named substituent is permitted on any atom in a ring (e.g., aryl, a heteroaryl ring, or a saturated heterocycloalkyl ring) provided such ring substitution is chemically allowed and results in a stable compound. A "stable" compound is a compound which can be prepared and isolated and whose structure and properties remain or can be caused to remain essentially unchanged for a period of time sufficient to allow use of the compound for the purposes described herein (e.g., therapeutic or prophylactic administration to a subject).

The term "substituted" shall be deemed to include multiple degrees of substitution by a named substituent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

"Vicinally substituted" refers to substitutions or groups that are attached to the adjacent atoms in a molecule. For instance, 1,2-dichloroethane is an ethane molecule which is vicinally substituted with two chlorine atoms.

Unless expressly depicted or described otherwise, variables depicted in a structural formula with a "floating" bond, such as $R^3$ or $R^y$ in Formula (I), are permitted on any available carbon atom in the ring to which the variable is attached. When a moiety is noted as being "optionally substituted" in Formula (I) or any embodiment thereof, it means that Formula (I) or the embodiment thereof encompasses compounds that contain the noted substituent (or substituents) on the moiety and also compounds that do not contain the noted substituent (or substituents) on the moiety.

The wavy line ∼∼∼, as used herein, indicates a point of attachment to the rest of the compound.

Compounds of Formula (I) may contain one or more asymmetric centers and can thus occur as racemates and racemic mixtures, single enantiomers, diastereoisomeric mixtures and individual diastereoisomers. Centers of asymmetry that are present in the compounds of Formula (I) can all independently of one another have S configuration or R configuration. The compounds of this disclosure include all possible enantiomers and diastereomers and mixtures of two or more stereoisomers, for example, mixtures of enantiomers and/or diastereomers, in all ratios. Thus, enantiomers are a subject of the disclosure in enantiomerically pure form, both as levorotatory and as dextrorotatory antipodes, in the form of racemates and in the form of mixtures of the two enantiomers in all ratios. In the case of a cis/trans isomerism, the disclosure includes both the cis form and the trans form as well as mixtures of these forms in all ratios. The present disclosure is meant to comprehend all such stereoisomeric forms of the compounds of Formula (I). Where a structural formula or chemical name specifies a particular configuration at a stereocenter, the enantiomer or stereoisomer of the compound resulting from that specified stereocenter is intended. Where a structural formula of the compounds of Formula (I) indicates a straight line at a chiral center, the structural formula includes both the S and R stereoisomers associated with the chiral center and mixtures thereof.

Compounds of Formula (I) may be separated into their individual diastereoisomers by, for example, fractional crystallization from a suitable solvent, for example, methanol or ethyl acetate or a mixture thereof, or via chiral chromatography using an optically active stationary phase. Absolute stereochemistry may be determined by X-ray crystallography of crystalline products or crystalline intermediates which are derivatized, if necessary, with a reagent containing an asymmetric center of known absolute configuration. Vibrational circular dichroism (VCD) may also be used to determine the absolute stereochemistry. Alternatively, any stereoisomer or isomers of a compound of Formula (I) may be obtained by stereospecific synthesis using optically pure starting materials or reagents of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereoisomeric mixture, followed by separation of the individual diastereoisomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

For compounds of Formula (I) described herein which contain olefinic double bonds, unless specified otherwise, they are meant to include both E and Z geometric isomers.

Some of the compounds described herein may exist as tautomers which have different points of attachment of hydrogen accompanied by one or more double bond shifts. For example, a ketone and its enol form are keto-enol tautomers. The individual tautomers as well as mixtures thereof are encompassed with compounds of Formula I of the present disclosure.

Some of the compounds described herein may exist as atropisomers when the rotational energy barrier around a single bond is sufficiently high to prevent free rotation at a given temperature, thus allowing isolation of individual conformers with distinct properties. A typical example of stable atropisomers are exemplified by intermediates Int-4d-1 and Int-4d-2 (described below), which can be resolved by supercritical fluid chromatography separation. The individual atropisomers as well as mixtures thereof are encompassed with compounds of Formula I of the present disclosure. When resolved, individual atropisomers can be designated by established conventions such as those specified by the International Union of Pure Applied Chemistry (IUPAC) 2013 Recommendations.

In the compounds of Formula (I), the atoms may exhibit their natural isotopic abundances, or one or more of the atoms may be artificially enriched in a particular isotope having the same atomic number, but an atomic mass or mass number different from the atomic mass or mass number predominantly found in nature. The present disclosure as described and claimed herein is meant to include all suitable isotopic variations of the compounds of Formula (I) and embodiments thereof. For example, different isotopic forms of hydrogen (H) include protium ($^1$H) and deuterium ($^2$H, also denoted herein as D). Protium is the predominant hydrogen isotope found in nature. Enriching for deuterium may afford certain therapeutic advantages, such as increasing in vivo half-life or reducing dosage requirements or may provide a compound useful as a standard for characterization of biological samples. Isotopically-enriched compounds of Formula (I), can be prepared without undue experimentation by conventional techniques well known to those skilled in the art or by processes analogous to those described in the Schemes and Examples herein using appropriate isotopically-enriched reagents and/or intermediates.

The term "pharmaceutically acceptable salts" refers to salts prepared from pharmaceutically acceptable non-toxic bases or acids. When the compound of the present disclosure is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Preferred are the ammonium, calcium, magnesium, potassium and sodium salts. Salts prepared from pharmaceutically acceptable organic non-toxic bases include salts of primary, secondary, and tertiary amines derived from both naturally occurring and synthetic sources. Pharmaceutically acceptable organic non-toxic bases from which salts can be formed include, for example, arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, dicyclohexylamine, lysine, methylglucamine, morpholine, piperazine, piperidine, polyamine resins, procaine, purines, theobromine, triethylamine, trimethylamine, tripropylamine, tromethamine and the like.

When the compound of the present disclosure is basic, its corresponding salt can be conveniently prepared from pharmaceutically acceptable non-toxic inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids. If the compounds of Formula (I) simultaneously contain acidic and basic groups in the molecule, the disclosure also includes, in addition to the salt forms mentioned, inner salts or betaines (zwitterions). Salts can be obtained from the compounds of Formula (I) by customary methods which are known to the person skilled in the art, for example, by combination with an organic or inorganic acid or base in a solvent or dispersant, or by anion exchange or cation exchange from other salts. The present disclosure also includes all salts of the compounds of Formula (I) which, owing to low physiological compatibility, are not directly suitable for use in pharmaceuticals but which can be used, for example, as intermediates for chemical reactions or for the preparation of pharmaceutically acceptable salts.

Furthermore, compounds of the present disclosure may exist in amorphous form and/or one or more crystalline forms, and as such all amorphous and crystalline forms and mixtures thereof of the compounds of Formula (I), including the Examples, are intended to be included within the scope of the present disclosure. In addition, some of the compounds of the instant disclosure may form solvates with water (i.e., a hydrate) or common organic solvents such as but not limited to ethyl acetate. Such solvates and hydrates, particularly the pharmaceutically acceptable solvates and hydrates, of the instant compounds are likewise encompassed within the scope of this disclosure, along with un-solvated and anhydrous forms.

Any pharmaceutically acceptable pro-drug modification of a compound of this disclosure which results in conversion in vivo to a compound within the scope of this disclosure is also within the scope of this disclosure.

The present disclosure also relates to processes for the preparation of the compounds of Formula (I) which are described in the following and by which the compounds of the disclosure are obtainable.

The terms "therapeutically effective (or efficacious) amount" and similar descriptions such as "an amount efficacious for treatment" are intended to mean that amount of a compound of Formula (I) that will elicit the biological or medical response of a tissue, a system, animal or human that is being sought by a researcher, veterinarian, medical doctor or other clinician. In a preferred embodiment, the term "therapeutically effective amount" means an amount of a compound of Formula (I) that alleviates at least one clinical symptom in a human patient. The terms "prophylactically effective (or efficacious) amount" and similar descriptions such as "an amount efficacious for prevention" are intended to mean that amount of a compound of Formula (I) that will prevent or reduce the risk of occurrence of the biological or medical event that is sought to be prevented in a tissue, a system, animal or human by a researcher, veterinarian, medical doctor or other clinician.

Dosages of the Compounds of Formula (I)

The dosage regimen utilizing a compound of the instant disclosure is selected in accordance with a variety of factors including type, species, age, weight, sex and medical condition of the patient; the severity of the condition to be treated; the potency of the compound chosen to be administered; the route of administration; and the renal and hepatic function of the patient. A consideration of these factors is well within the purview of the ordinarily skilled clinician for the purpose of determining the therapeutically effective or prophylactically effective dosage amount needed to prevent, counter, or arrest the progress of the condition. It is understood that a specific daily dosage amount can simultaneously be both a therapeutically effective amount, e.g., for treatment of an oncological condition, and a prophylactically effective amount, e.g., for prevention of an oncological condition.

While individual needs vary, determination of optimal ranges of effective amounts of the compound of the disclosure is within the skill of the art. For administration to a human in the curative or prophylactic treatment of the conditions and disorders identified herein, for example, typical dosages of the compounds of the present disclosure can be about 0.05 mg/kg/day to about 50 mg/kg/day, for example at least 0.05 mg/kg, at least 0.08 mg/kg, at least 0.1 mg/kg, at least 0.2 mg/kg, at least 0.3 mg/kg, at least 0.4 mg/kg, or at least 0.5 mg/kg, and preferably 50 mg/kg or less, 40 mg/kg or less, 30 mg/kg or less, 20 mg/kg or less, or 10 mg/kg or less, which can be about 2.5 mg/day (0.5 mg/kg×5 kg) to about 5000 mg/day (50 mg/kg×100 kg), for example. For example, dosages of the compounds can be about 0.1 mg/kg/day to about 50 mg/kg/day, about 0.05 mg/kg/day to about 10 mg/kg/day, about 0.05 mg/kg/day to about 5 mg/kg/day, about 0.05 mg/kg/day to about 3 mg/kg/day, about 0.07 mg/kg/day to about 3 mg/kg/day, about 0.09 mg/kg/day to about 3 mg/kg/day, about 0.05 mg/kg/day to about 0.1 mg/kg/day, about 0.1 mg/kg/day to about 1 mg/kg/day, about 1 mg/kg/day to about 10 mg/kg/day, about 1 mg/kg/day to about 5 mg/kg/day, about 1 mg/kg/day to about 3 mg/kg/day, about 3 mg/day to about 500 mg/day, about 5 mg/day to about 250 mg/day, about 10 mg/day to about 100 mg/day, about 3 mg/day to about 10 mg/day, or about 100 mg/day to about 250 mg/day. Such doses may be administered in a single dose or may be divided into multiple doses.

Pharmaceutical Compositions

The compounds of Formula (I) and their pharmaceutically acceptable salts can be administered to animals, preferably to mammals, and in particular to humans, as pharmaceuticals by themselves, in mixtures with one another or in the form of pharmaceutical compositions. The term "subject" or "patient" includes animals, preferably mammals and especially humans, who use the instant active agents for the prevention or treatment of a medical condition. Administering of the drug to the subject includes both self-administration and administration to the patient by another person. The subject may be in need of, or desire, treatment for an existing disease or medical condition, or may be in need of or desire prophylactic treatment to prevent or reduce the risk of occurrence of said disease or medical condition. As used herein, a subject "in need" of treatment of an existing condition or of prophylactic treatment encompasses both a determination of need by a medical professional as well as the desire of a patient for such treatment.

The present disclosure therefore also provides the compounds of Formula (I) and their pharmaceutically acceptable salts for use as pharmaceuticals, their use for modulating the activity of mutant KRAS, HRAS and/or NRAS proteins and in particular their use in the therapy and prophylaxis of the below-mentioned diseases or disorders as well as their use for preparing medicaments for these purposes. In certain embodiments, the compounds of Formula (I) and their pharmaceutically acceptable salts inhibit the KRAS G12C protein.

Furthermore, the present disclosure provides pharmaceutical compositions which comprise as active component an effective dose of at least one compound of Formula (I) and/or a pharmaceutically acceptable salt thereof and a customary pharmaceutically acceptable carrier, i.e., one or more pharmaceutically acceptable carrier substances and/or additives.

Thus, the present disclosure provides, for example, said compound and its pharmaceutically acceptable salts for use as pharmaceutical compositions which comprise as active component an effective dose of the compound of Formula (I) and/or a pharmaceutically acceptable salt thereof and a customary pharmaceutically acceptable carrier, and the uses of said compound and/or a pharmaceutically acceptable salt thereof in the therapy or prophylaxis of the below-mentioned diseases or disorders, e.g., cancer, as well as their use for preparing medicaments for these purposes.

The pharmaceutical compositions according to the disclosure can be administered orally, for example, in the form of pills, tablets, lacquered tablets, sugar-coated tablets, granules, hard and soft gelatin capsules, aqueous, alcoholic or oily solutions, syrups, emulsions or suspensions, or rectally, for example, in the form of suppositories. Administration can also be carried out parenterally, for example subcutaneously, intramuscularly or intravenously in the form of solutions for injection or infusion.

Other suitable administration forms are, for example, percutaneous or topical administration, for example, in the form of ointments, tinctures, sprays or transdermal therapeutic systems, or, for example, microcapsules, implants or rods. The preferred administration form depends, for example, on the disease to be treated and on its severity.

The amount of active compound of Formula (I) and/or its pharmaceutically acceptable salts in the pharmaceutical composition normally is from 0.01 to 200 mg, such as from 0.1 to 200 mg, preferably from 1 to 200 mg, per dose, but depending on the type of the pharmaceutical composition, it can also be higher. In some embodiments, the amount of active compound of Formula (I) and/or its pharmaceutically acceptable salts in the pharmaceutical composition is from 0.01 to 10 mg per dose. The pharmaceutical compositions usually comprise 0.5 to 90 percent by weight of the compound of Formula (I) and/or their pharmaceutically acceptable salts. The preparation of the pharmaceutical compositions can be carried out in a manner known per se. For this purpose, one or more compounds of Formula (I) and/or their pharmaceutically acceptable salts, together with one or more solid or liquid pharmaceutical carrier substances and/or additives (or auxiliary substances) and, if desired, in combination with other pharmaceutically active compounds having therapeutic or prophylactic action, are brought into a suitable administration form or dosage form which can then be used as a pharmaceutical in human or veterinary medicine.

For the production of pills, tablets, sugar-coated tablets and hard gelatin capsules, it is possible to use, for example, lactose, starch, for example, maize starch, or starch derivatives, talc, stearic acid or its salts, etc. Carriers for soft gelatin capsules and suppositories are, for example, fats, waxes, semisolid and liquid polyols, natural or hardened oils, etc. Suitable carriers for the preparation of solutions, for example, of solutions for injection, or of emulsions or syrups are, for example, water, physiologically acceptable sodium chloride solution, alcohols such as ethanol, glycerol, polyols, sucrose, invert sugar, glucose, mannitol, vegetable oils, etc. It is also possible to lyophilize the compounds of Formula (I) and their pharmaceutically acceptable salts and to use the resulting lyophilisates, for example, for preparing preparations for injection or infusion. Suitable carriers for microcapsules, implants or rods are, for example, copolymers of glycolic acid and lactic acid.

Besides the active compounds and carriers, the pharmaceutical compositions can also contain customary additives, for example, fillers, disintegrants, binders, lubricants, wetting agents, stabilizers, emulsifiers, dispersants, preservatives, sweeteners, colorants, flavorings, aromatizers, thickeners, diluents, buffer substances, solvents, solubilizers, agents for achieving a depot effect, salts for altering the osmotic pressure, coating agents or antioxidants.

Methods of Using the Compounds of Formula (I)

The present application provides a method of inhibiting RAS-mediated cell signaling comprising contacting a cell with a compound of Formula (I) or a pharmaceutically acceptable salt thereof. Inhibition of RAS-mediated signal transduction can be assessed and demonstrated by a wide variety of ways known in the art. Non-limiting examples include (a) a decrease in GTPase activity of RAS; (b) a decrease in GTP binding affinity or an increase in GDP binding affinity; (c) an increase in $K_{off}$ of GTP or a decrease in $K_{off}$ of GDP; (d) a decrease in the levels of signaling transduction molecules downstream in the RAS pathway, such as a decrease in pMEK, pERK, or pAKT levels; and/or (e) a decrease in binding of RAS complex to downstream signaling molecules including but not limited to Raf. Kits and commercially available assays can be utilized for determining one or more of the above.

The present application also provides methods of using the compounds of Formula (I) (or their pharmaceutically acceptable salts) or pharmaceutical compositions containing such compounds to treat disease conditions, including but not limited to, conditions implicated by mutant KRAS, HRAS and/or NRAS proteins (e.g., cancer), and in some embodiments the KRAS G12C mutant.

In some embodiments, a method for treatment of cancer is provided, the method comprising administering a therapeutically effective amount a compound of Formula (I) (or a pharmaceutically acceptable salt thereof) or any of the foregoing pharmaceutical compositions comprising such a compound to a subject in need of such treatment. In some embodiments, the cancer is mediated by a KRAS, HRAS or NRAS mutation, e.g., the KRAS G12C mutation. In various embodiments, the cancer is pancreatic cancer, colorectal cancer or lung cancer. In some embodiments, the cancer is gall bladder cancer, thyroid cancer, or bile duct cancer.

In some embodiments the present disclosure provides a method of treating a disorder in a subject in need thereof, wherein said method comprises determining if the subject has a KRAS, HRAS or NRAS mutation (e.g., KRAS G12C mutation) and if the subject is determined to have the KRAS, HRAS or NRAS mutation, then administering to the subject a therapeutically effective amount of a compound of Formula (I) or a pharmaceutically acceptable salt thereof.

The disclosed compounds inhibit anchorage-independent cell growth and therefore have the potential to inhibit tumor metastasis. Accordingly, another embodiment of the present disclosure provides a method for inhibiting tumor metastasis, the method comprising administering an effective amount a compound disclosed herein.

KRAS, HRAS or NRAS mutations have also been identified in hematological malignancies (e.g., cancers that affect blood, bone marrow and/or lymph nodes). Accordingly, certain embodiments are directed to administration of the compounds of Formula (I) (e.g., in the form of a pharmaceutical composition) to a subject in need of treatment of a hematological malignancy. Such malignancies include, but are not limited to leukemias and lymphomas. For example, the presently disclosed compounds can be used for treatment of diseases such as acute lymphoblastic leukemia (ALL), acute myelogenous leukemia (AML), chronic lymphocytic leukemia (CLL), small lymphocytic lymphoma (SLL), chronic myelogenous leukemia (CML), acute monocytic leukemia (AMoL) and/or other leukemias. In other embodiments, the compounds are useful for treatment of lymphomas such as Hodgkins lymphoma or non-Hodgkins lymphoma. In various embodiments, the compounds are useful for treatment of plasma cell malignancies such as multiple myeloma, mantle cell lymphoma, and Waldenstrom's macroglubunemia.

Determining whether a tumor or cancer comprises a KRAS, HRAS or NRAS mutation (e.g., the KRAS G12C mutation) can be undertaken by assessing the nucleotide sequence encoding the KRAS, HRAS or NRAS protein, by assessing the amino acid sequence of the KRAS, HRAS or NRAS protein, or by assessing the characteristics of a putative KRAS, HRAS or NRAS mutant protein. The sequences of wild-type human KRAS, HRAS or NRAS are known in the art.

Methods for detecting a mutation in a KRAS, HRAS or NRAS nucleotide sequence are also known by those of skill in the art. These methods include, but are not limited to, polymerase chain reaction-restriction fragment length polymorphism (PCR-RFLP) assays, polymerase chain reaction-single strand conformation polymorphism (PCR-SSCP) assays, real-time PCR assays, PCR sequencing, mutant allele-specific PCR amplification (MASA) assays, direct sequencing, primer extension reactions, electrophoresis, oligonucleotide ligation assays, hybridization assays, TaqMan assays, SNP genotyping assays, high resolution melting assays and microarray analyses. In some embodiments, samples are evaluated for KRAS, HRAS or NRAS mutations (e.g., the KRAS G12C mutation) by real-time PCR. In real-time PCR, fluorescent probes specific for the KRAS, HRAS or NRAS G12C mutation are used. When a mutation is present, the probe binds and fluorescence is detected. In some embodiments, the KRAS, HRAS or NRAS mutation is identified using a direct sequencing method of specific regions (e.g., exon 2 and/or exon 3) in the KRAS, HRAS or NRAS gene.

Methods for detecting a mutation in a KRAS, HRAS or NRAS protein (e.g., the KRAS G12C mutation) are known by those of skill in the art. These methods include, but are not limited to, detection of a KRAS, HRAS or NRAS mutant using a binding agent (e.g., an antibody) specific for the mutant protein, protein electrophoresis and Western blotting, and direct peptide sequencing.

A number of tissue samples can be assessed for determining whether a tumor or cancer comprises a KRAS, HRAS or NRAS mutation (e.g., the KRAS G12C mutation). In some embodiments, the sample is taken from a subject having a tumor or cancer. In some embodiments, the sample is a fresh tumor/cancer sample. In some embodiments, the sample is a frozen tumor/cancer sample. In some embodiments, the sample is a formalin-fixed paraffin-embedded sample. In some embodiments, the sample is a circulating tumor cell (CTC) sample. In some embodiments, the sample is processed to a cell lysate. In some embodiments, the sample is processed to DNA or RNA.

The present application also provides a method of treating a hyperproliferative disorder comprising administering a therapeutically effective amount of a compound of the disclosure, or a pharmaceutically acceptable salt thereof to a subject in need thereof. In some embodiments, said method relates to the treatment of a subject who suffers from a cancer such as acute myeloid leukemia, cancer in adolescents, adrenocortical carcinoma childhood, AIDS-related cancers (e.g., Lymphoma and Kaposi's Sarcoma), anal cancer, appendix cancer, astrocytomas, atypical teratoid, basal cell carcinoma, bile duct cancer, bladder cancer, bone cancer, brain stem glioma, brain tumor, breast cancer, bronchial tumors, Burkitt lymphoma, carcinoid tumor, atypical teratoid, embryonal tumors, germ cell tumor, primary lymphoma, cervical cancer, childhood cancers, chordoma, cardiac tumors, chronic lymphocytic leukemia (CLL), chronic myelogenous leukemia (CML), chronic myleoproliferative disorders, colon cancer, colorectal cancer, craniopharyngioma, cutaneous T-cell lymphoma, extrahepatic ductal carcinoma in situ (DCIS), embryonal tumors, CNS cancer, endometrial cancer, ependymoma, esophageal cancer, esthesioneuroblastoma, ewing sarcoma, extracranial germ cell tumor, extragonadal germ cell tumor, eye cancer, fibrous histiocytoma of bone, gall bladder cancer, gastric cancer, gastrointestinal carcinoid tumor, gastrointestinal stromal tumors (GIST), germ cell tumor, gestational trophoblastic tumor, hairy cell leukemia, head and neck cancer, heart cancer, liver cancer, Hodgkin lymphoma, hypopharyngeal cancer, intraocular melanoma, islet cell tumors, pancreatic neuroendocrine tumors, kidney cancer, laryngeal cancer, lip and oral cavity cancer, liver cancer, lobular carcinoma in situ (LCIS), lung cancer, lymphoma, metastatic squamous neck cancer with occult primary, midline tract carcinoma, mouth cancer; multiple endocrine neoplasia syndromes, multiple myeloma/plasma cell neoplasm, mycosis fungoides, myelodysplasia syndromes, myelodysplastic/myeloproliferative neoplasms, multiple myeloma, merkel cell carcinoma, malignant mesothelioma, malignant fibrous histiocytoma of bone and osteosarcoma, nasal cavity and paranasal sinus cancer, nasopharyngeal cancer, neuroblastoma, non-hodgkin lymphoma, non-small cell lung cancer (NSCLC), oral cancer, lip and oral cavity cancer, oropharyngeal cancer, ovarian cancer, pancreatic cancer, papillomatosis, paraganglioma, paranasal sinus and nasal cavity cancer, parathyroid cancer, penile cancer, pharyngeal cancer, pleuropulmonary blastoma, primary central nervous system (CNS) lymphoma, prostate cancer, rectal cancer, transitional cell cancer, retinoblastoma, rhabdomyosarcoma, salivary gland cancer, skin cancer, stomach (gastric) cancer, small cell lung cancer; small intestine cancer, soft tissue sarcoma, T-Cell lymphoma, testicular cancer, throat cancer, thymoma and thymic carcinoma, thyroid cancer, transitional cell cancer of the renal pelvis and ureter, trophoblastic tumor, unusual cancers of childhood, urethral cancer, uterine sarcoma, vaginal cancer, vulvar cancer, or viral-induced cancer. In some embodiments, said method relates to the treatment of a non-cancerous hyperproliferative disorder such as benign hyperplasia of the skin (e.g., psoriasis), restenosis, or prostate (e.g., benign prostatic hypertrophy (BPH)).

In some embodiments, the methods for treatment are directed to treating lung cancers, and the methods comprise administering a therapeutically effective amount of the compounds of the disclosure (or pharmaceutical composition comprising such compounds) to a subject in need thereof. In certain embodiments, the lung cancer is a non-small cell lung carcinoma (NSCLC), for example, adenocarcinoma, squamous-cell lung carcinoma or large-cell lung carcinoma.

In some embodiments, the lung cancer is a small cell lung carcinoma. Other lung cancers which the compounds of Formula (I) may provide therapeutic benefit for include, but are not limited to, glandular tumors, carcinoid tumors and undifferentiated carcinomas.

The present disclosure also provides methods of modulating a mutant KRAS, HRAS or NRAS protein activity (e.g., activity resulting from the KRAS G12C mutation) by contacting the protein with an effective amount of a compound of Formula (I). Modulation can be inhibiting or activating protein activity. In some embodiments, the present disclosure provides methods of inhibiting protein activity by contacting the mutant KRAS, HRAS or NRAS protein (e.g., KRAS G12C mutany) with an effective amount of a compound of Formula (I) in solution. In some embodiments, the present disclosure provides methods of inhibiting the mutant KRAS, HRAS or NRAS protein activity by contacting a cell, tissue, or organ that expresses the protein of interest. In some embodiments, the disclosure provides methods of inhibiting protein activity in subjects including, but not limited to, rodents and mammals (e.g., humans) by administering into the subjects an effective amount of a compound of Formula (I).

Combination Therapies

One or more additional pharmacologically active agents may be administered in combination with a compound of Formula (I) (or a pharmaceutically acceptable salt thereof). An additional active agent (or agents) is intended to mean a pharmaceutically active agent (or agents) that is active in the body, including pro-drugs that convert to pharmaceutically active form after administration, which are different from the compound of Formula (I). The additional active agents also include free-acid, free-base and pharmaceutically acceptable salts of said additional active agents. Generally, any suitable additional active agent or agents, including chemotherapeutic agents or therapeutic antibodies, may be used in any combination with the compound of Formula (I) in a single dosage formulation (e.g., a fixed dose drug combination), or in one or more separate dosage formulations which allows for concurrent or sequential administration of the active agents (co-administration of the separate active agents) to subjects. In addition, the compounds of Formula (I) (or pharmaceutically acceptable salts thereof) can be administered in combination with radiation therapy, hormone therapy, surgery or immunotherapy.

The present application also provides methods for combination therapies in which the additional active agent is known to modulate other pathways, or other components of the same pathway, or even overlapping sets of target enzymes which are used in combination with a compound of Formula (I), or a pharmaceutically acceptable salt thereof. In one embodiment, such therapy includes, but is not limited to, the combination of one or more compounds of Formula (I) with chemotherapeutic agents, immunotherapeutic agents, hormonal and anti-hormonal agents, targeted therapy agents, and anti-angiogenesis agents, to provide a synergistic or additive therapeutic effect. In another embodiment, such therapy includes radiation treatment to provide a synergistic or additive therapeutic effect.

Examples of additional active agents (i.e., additional anti-cancer agents) include chemotherapeutic agents (e.g., cytotoxic agents), immunotherapeutic agents, hormonal and anti-hormonal agents, targeted therapy agents, and anti-angiogenesis agents. Many anti-cancer agents can be classified within one or more of these groups. While certain anti-cancer agents have been categorized within a specific group(s) or subgroup(s) herein, many of these agents can also be listed within one or more other group(s) or subgroup(s), as would be presently understood in the art. It is to be understood that the classification herein of a particular agent into a particular group is not intended to be limiting. Many anti-cancer agents are presently known in the art and can be used in combination with the compounds of the present disclosure.

Further, an agent can be an agonist, antagonist, allosteric modulator, toxin or, more generally, may act to inhibit or stimulate its target (e.g., receptor or enzyme activation or inhibition). For example, suitable for use are one or more agents (e.g., antibodies, antigen binding regions, or soluble receptors) that specifically bind and inhibit the activity of growth factors, such as antagonists of hepatocyte growth factor (HGF, also known as Scatter Factor), and antibodies or antigen binding regions that specifically bind its receptor "c-met".

In an embodiment, the additional anti-cancer agent is a chemotherapeutic agent, an immunotherapeutic agent, a hormonal agent, an anti-hormonal agent, a targeted therapy agent, or an anti-angiogenesis agent (or angiogenesis inhibitor). In an embodiment, the additional anti-cancer agent is selected from the group consisting of a chemotherapeutic agent, a mitotic inhibitor, a plant alkaloid, an alkylating agent, an anti-metabolite, a platinum analog, an enzyme, a topoisomerase inhibitor, a retinoid, an aziridine, an antibiotic, a hormonal agent, an anti-hormonal agent, an anti-estrogen, an anti-androgen, an anti-adrenal, an androgen, a targeted therapy agent, an immunotherapeutic agent, a biological response modifier, a cytokine inhibitor, a tumor vaccine, a monoclonal antibody, an immune checkpoint inhibitor, an anti-PD-1 agent, an anti-PD-L1 agent, a colony-stimulating factor, an immunomodulator, an immunomodulatory imide (IMiD), an anti-CTLA4 agent, an anti-LAG1 agent, an anti-OX40 agent, a GITR agonist, a CAR-T cell, a BiTE, a signal transduction inhibitor, a growth factor inhibitor, a tyrosine kinase inhibitor, an EGFR inhibitor, a histone deacetylase (HDAC) inhibitor, a proteasome inhibitor, a cell-cycle inhibitor, an anti-angiogenesis agent, a matrix-metalloproteinase (MMP) inhibitor, a hepatocyte growth factor inhibitor, a TOR inhibitor, a KDR inhibitor, a VEGF inhibitor, a HIF-1a inhibitor a HIF-2α inhibitor, a fibroblast growth factor (FGF) inhibitor, a RAF inhibitor, a MEK inhibitor, an ERK inhibitor, a PI3K inhibitor, an AKT inhibitor, an MCL-1 inhibitor, a BCL-2 inhibitor, an SHP2 inhibitor, a HER-2 inhibitor, a BRAF-inhibitor, a gene expression modulator, an autophagy inhibitor, an apoptosis inducer, an antiproliferative agent, and a glycolysis inhibitor.

In one embodiment, the additional anti-cancer agent(s) is a chemotherapeutic agent. Non-limiting examples of chemotherapeutic agents include mitotic inhibitors and plant alkaloids, alkylating agents, anti-metabolites, platinum analogs, enzymes, topoisomerase inhibitors, retinoids, aziridines, and antibiotics.

Non-limiting examples of mitotic inhibitors and plant alkaloids include taxanes such as cabazitaxel, docetaxel, larotaxel, ortataxel, paclitaxel, and tesetaxel; demecolcine; epothilone; eribulin; etoposide (VP-16); etoposide phosphate; navelbine; noscapine; teniposide; thaliblastine; vinblastine; vincristine; vindesine; vinflunine; and vinorelbine.

Non-limiting examples of alkylating agents include nitrogen mustards such as chlorambucil, chlornaphazine, cholophosphamide, cytophosphane, estramustine, ifosfamide, mannomustine, mechlorethamine, mechlorethamine oxide hydrochloride, melphalan, novembichin, phenesterine, prednimustine, tris(2-chloroethyl)amine, trofosfamide, and uracil mustard; alkyl sulfonates such as busulfan, improsulfan, and piposulfan; nitrosoureas such as carmustine, chlorozotocin, fotemustine, lomustine, nimustine, ranimustine, streptozotocin, and TA-07; ethylenimines and methylamelamines such as altretamine, thiotepa, triethylenemelamine, triethylenethiophosphaoramide, trietylenephosphoramide, and trimethylolomelamine; ambamustine; bendamustine; dacarbazine; etoglucid; irofulven; mafosfamide; mitobronitol; mitolactol; pipobroman; procarbazine; temozolomide; treosulfan; and triaziquone.

Non-limiting examples of anti-metabolites include folic acid analogues such as aminopterin, denopterin, edatrexate, methotrexate, pteropterin, raltitrexed, and trimetrexate; purine analogs such as 6-mercaptopurine, 6-thioguanine, fludarabine, forodesine, thiamiprine, and thioguanine; pyrimidine analogs such as 5-fluorouracil (5-FU), 6-azauridine, ancitabine, azacytidine, capecitabine, carmofur, cytarabine, decitabine, dideoxyuridine, doxifiuridine, doxifluridine, enocitabine, floxuridine, galocitabine, gemcitabine, and sapacitabine; 3-aminopyridine-2-carboxaldehyde thiosemicarbazone; broxuridine; cladribine; cyclophosphamide; cytarabine; emitefur; hydroxyurea; mercaptopurine; nelarabine; pemetrexed; pentostatin; tegafur; and troxacitabine.

Non-limiting examples of platinum analogs include carboplatin, cisplatin, dicycloplatin, heptaplatin, lobaplatin, nedaplatin, oxaliplatin, satraplatin, and triplatin tetranitrate.

Non-limiting examples of enzymes include asparaginase and pegaspargase.

Non-limiting examples of topoisomerase inhibitors include acridine carboxamide, amonafide, amsacrine, belotecan, elliptinium acetate, exatecan, indolocarbazole, irinotecan, lurtotecan, mitoxantrone, razoxane, rubitecan, SN-38, sobuzoxane, and topotecan.

Non-limiting examples of retinoids include alitretinoin, bexarotene, fenretinide, isotretinoin, liarozole, RII retinamide, and tretinoin.

Non-limiting examples of aziridines include benzodopa, carboquone, meturedopa, and uredopa.

Non-limiting examples of antibiotics include intercalating antibiotics; anthracenediones; anthracycline antibiotics such as aclarubicin, amrubicin, daunomycin, daunorubicin, doxorubicin, epirubicin, idarubicin, menogaril, nogalamycin, pirarubicin, and valrubicin; 6-diazo-5-oxo-L-norleucine; aclacinomysins; actinomycin; authramycin; azaserine; bleomycins; cactinomycin; calicheamicin; carabicin; carminomycin; carzinophilin; chromomycins; dactinomycin; detorubicin; esorubicin; esperamicins; geldanamycin; marcellomycin; mitomycins; mitomycin C; mycophenolic acid; olivomycins; novantrone; peplomycin; porfiromycin; potfiromycin; puromycin; quelamycin; rebeccamycin; rodorubicin; streptonigrin; streptozocin; tanespimycin; tubercidin; ubenimex; zinostatin; zinostatin stimalamer; and zorubicin.

In one embodiment, the additional anti-cancer agent(s) is a hormonal and/or anti-hormonal agent (i.e., hormone therapy). Non-limiting examples of hormonal and anti-hormonal agents include anti-androgens such as abiraterone, apalutamide, bicalutamide, darolutamide, enzalutamide, flutamide, goserelin, leuprolide, and nilutamide; anti-estrogens such as 4-hydroxy tamoxifen, aromatase inhibiting 4(5)-imidazoles, EM-800, fosfestrol, fulvestrant, keoxifene, LY 117018, onapristone, raloxifene, tamoxifen, toremifene, and trioxifene; anti-adrenals such as aminoglutethimide, dex-aminoglutethimide, mitotane, and trilostane; androgens such as calusterone, dromostanolone propionate, epitiostanol, mepitiostane, and testolactone; abarelix; anastrozole; cetrorelix; deslorelin; exemestane; fadrozole; finasteride; formestane; histrelin (RL 0903); human chorionic gonadotropin; lanreotide; LDI 200 (Milkhaus); letrozole; leuprorelin; mifepristone; nafarelin; nafoxidine; osaterone; prednisone; thyrotropin alfa; and triptorelin.

In one embodiment, the additional anti-cancer agent(s) is an immunotherapeutic agent (i.e., immunotherapy). Non-limiting examples of immunotherapeutic agents include biological response modifiers, cytokine inhibitors, tumor vaccines, monoclonal antibodies, immune checkpoint inhibitors, colony-stimulating factors, and immunomodulators.

Non-limiting examples of biological response modifiers, including cytokine inhibitors (cytokines) such as interferons and interleukins, include interferon alfa/interferon alpha such as interferon alfa-2, interferon alfa-2a, interferon alfa-2b, interferon alfa-n1, interferon alfa-n3, interferon alfacon-1, peginterferon alfa-2a, peginterferon alfa-2b, and leukocyte alpha interferon; interferon beta such as interferon beta-1a, and interferon beta-1b; interferon gamma such as natural interferon gamma-1a, and interferon gamma-1b; aldesleukin; interleukin-1 beta; interleukin-2; oprelvekin; sonermin; tasonermin; and virulizin.

Non-limiting examples of tumor vaccines include APC 8015, AVICINE, bladder cancer vaccine, cancer vaccine (Biomira), gastrin 17 immunogen, Maruyama vaccine, melanoma lysate vaccine, melanoma oncolysate vaccine (New York Medical College), melanoma vaccine (New York University), melanoma vaccine (Sloan Kettering Institute), TICE® BCG (*Bacillus* Calmette-Guerin), and viral melanoma cell lysates vaccine (Royal Newcastle Hospital). Non-limiting examples of monoclonal antibodies include abagovomab, adecatumumab, aflibercept, alemtuzumab, blinatumomab, brentuximab vedotin, CA 125 MAb (Biomira), cancer MAb (Japan Pharmaceutical Development), daclizumab, daratumumab, denosumab, edrecolomab, gemtuzumab zogamicin, HER-2 and Fc MAb (Medarex), ibritumomab tiuxetan, idiotypic 105AD7 MAb (CRC Technology), idiotypic CEA MAb (Trilex), ipilimumab, lintuzumab, LYM-1-iodine 131 MAb (Techni clone), mitumomab, moxetumomab, ofatumumab, polymorphic epithelial mucin-yttrium 90 MAb (Antisoma), ranibizumab, rituximab, and trastuzumab.

Non-limiting examples of immune checkpoint inhibitors include anti-PD-1 agents or antibodies such as cemiplimab, nivolumab, and pembrolizumab; anti-PD-L1 agents or antibodies such as atezolizumab, avelumab, and durvalumab; anti-CTLA-4 agents or antibodies such as ipilumumab; anti-LAG1 agents; and anti-OX40 agents.

Non-limiting examples of colony-stimulating factors include darbepoetin alfa, epoetin alfa, epoetin beta, filgrastim, granulocyte macrophage colony stimulating factor, lenograstim, leridistim, mirimostim, molgramostim, nartograstim, pegfilgrastim, and sargramostim.

Non-limiting examples of additional immunotherapeutic agents include BiTEs, CAR-T cells, GITR agonists, imiquimod, immunomodulatory imides (IMiDs), mismatched double stranded RNA (Ampligen), resiquimod, SRL 172, and thymalfasin.

In one embodiment, the additional anti-cancer agent(s) is a targeted therapy agent (i.e., targeted therapy). Targeted therapy agents include, for example, monoclonal antibodies and small molecule drugs. Non-limiting examples of targeted therapy agents include signal transduction inhibitors, growth factor inhibitors, tyrosine kinase inhibitors, EGFR inhibitors, histone deacetylase (HDAC) inhibitors, proteasome inhibitors, cell-cycle inhibitors, angiogenesis inhibitors, matrix-metalloproteinase (MMP) inhibitors, hepatocyte growth factor inhibitors, TOR inhibitors, KDR inhibitors, VEGF inhibitors, fibroblast growth factors (FGF) inhibitors, MEK inhibitors, ERK inhibitors, PI3K inhibitors, AKT inhibitors, MCL-1 inhibitors, BCL-2 inhibitors, SHP2 inhibitors, HER-2 inhibitors, BRAF-inhibitors, gene expression modulators, autophagy inhibitors, apoptosis inducers, antiproliferative agents, and glycolysis inhibitors.

Non-limiting examples of signal transduction inhibitors include tyrosine kinase inhibitors, multiple-kinase inhibitors, anlotinib, avapritinib, axitinib, dasatinib, dovitinib, imatinib, lenvatinib, lonidamine, nilotinib, nintedanib, pazopanib, pegvisomant, ponatinib, vandetanib, and EGFR inhibitory agents.

Non-limiting examples of EGFR inhibitory agents include small molecule antagonists of EGFR such as afatinib, brigatinib, erlotinib, gefitinib, lapatinib, and osimertinib; and antibody-based EGFR inhibitors, including any anti-EGFR antibody or antibody fragment that can partially or completely block EGFR activation by its natural ligand. Antibody-based EGFR inhibitory agents may include, for example, those described in Modjtahedi, H., et al., 1993, Br. J. Cancer 67:247-253; Teramoto, T., et al., 1996, Cancer 77:639-645; Goldstein et al, 1995, Clin. Cancer Res. 1: 1311-1318; Huang, S. M., et al., 1999, Cancer Res. 15:59(8): 1935-40; and Yang, X., et al., 1999, Cancer Res. 59: 1236-1243; monoclonal antibody Mab E7.6.3 (Yang, 1999 supra); Mab C225 (ATCC Accession No. HB-8508), or an antibody or antibody fragment having the binding specificity thereof, specific antisense nucleotide or siRNA; afatinib, cetuximab; matuzumab; necitumumab; nimotuzumab; panitumumab; and zalutumumab.

Non-limiting examples of histone deacetylase (HDAC) inhibitors include belinostat, panobinostat, romidepsin, and vorinostat.

Non-limiting examples of proteasome inhibitors include bortezomib, carfilzomib, ixazomib, marizomib (salinosporamide a), and oprozomib.

Non-limiting examples of cell-cycle inhibitors, including CDK inhibitors, include abemaciclib, alvocidib, palbociclib, and ribociclib.

In one embodiment, the additional anti-cancer agent(s) is an anti-angiogenic agent (or angiogenesis inhibitor) including, but not limited to, matrix-metalloproteinase (MMP) inhibitors; VEGF inhibitors; EGFR inhibitors; TOR inhibitors such as everolimus and temsirolimus; PDGFR kinase inhibitory agents such as crenolanib; HIF-1a inhibitors such as PX 478; HIF-2α inhibitors such as belzutifan and the HIF-2α inhibitors described in WO 2015/035223; fibroblast growth factor (FGF) or FGFR inhibitory agents such as B-FGF and RG 13577; hepatocyte growth factor inhibitors; KDR inhibitors; anti-Ang1 and anti-Ang2 agents; anti-Tie2 kinase inhibitory agents; Tek antagonists (US 2003/0162712; U.S. Pat. No. 6,413,932); anti-TWEAK agents (U.S. Pat. No. 6,727,225); ADAM distintegrin domain to antagonize the binding of integrin to its ligands (US 2002/0042368); anti-eph receptor and/or anti-ephrin antibodies or antigen binding regions (U.S. Pat. Nos. 5,981,245; 5,728,813; 5,969,110; 6,596,852; 6,232,447; and 6,057,124); and anti-PDGF-BB antagonists as well as antibodies or antigen binding regions specifically binding to PDGF-BB ligands.

Non-limiting examples of matrix-metalloproteinase (MMP) inhibitors include MMP-2 (matrix-metalloproteinase 2) inhibitors, MMP-9 (matrix-metalloproteinase 9) inhibitors, prinomastat, RO 32-3555, and RS 13-0830. Examples of useful matrix metalloproteinase inhibitors are described, for example, in WO 96/33172, WO 96/27583, EP 1004578, WO 98/07697, WO 98/03516, WO 98/34918, WO 98/34915, WO 98/33768, WO 98/30566, EP 0606046, EP 0931788, WO 90/05719, WO 99/52910, WO 99/52889, WO 99/29667, WO 1999/007675, EP 1786785, EP 1181017, US 2009/0012085, U.S. Pat. Nos. 5,863,949, 5,861,510, and EP 0780386. Preferred MMP-2 and MMP-9 inhibitors are those that have little or no activity inhibiting MMP-1. More preferred, are those that selectively inhibit MMP-2 and/or MMP-9 relative to the other matrix-metalloproteinases (i.e., MAP-1, MMP-3, MMP-4, MMP-5, MMP-6, MMP-7, MMP-8, MMP-10, MMP-11, MMP-12, and MMP-13).

Non-limiting examples of VEGF and VEGFR inhibitory agents include bevacizumab, cediranib, CEP 7055, CP 547632, KRN 633, orantinib, pazopanib, pegaptanib, pegaptanib octasodium, semaxanib, sorafenib, sunitinib, VEGF antagonist (Borean, Denmark), and VEGF-TRAP™.

The additional anti-cancer agent(s) may also be another anti-angiogenic agent including, but not limited to, 2-methoxyestradiol, AE 941, alemtuzumab, alpha-D148 Mab (Amgen, US), alphastatin, anecortave acetate, angiocidin, angiogenesis inhibitors, (SUGEN, US), angiostatin, anti-Vn Mab (Crucell, Netherlands), atiprimod, axitinib, AZD 9935, BAY RES 2690 (Bayer, Germany, BC 1 (Genoa Institute of Cancer Research, Italy), beloranib, benefin (Lane Labs, US), cabozantinib, CDP 791 (Celltech Group, UK), chondroitinase AC, cilengitide, combretastatin A4 prodrug, CP 564959 (OSI, US), CV247, CYC 381 (Harvard University, US), E 7820, EHT 0101, endostatin, enzastaurin hydrochloride, ER-68203-00 (WAX, US), fibrinogen-E fragment, Flk-1 (ImClone Systems, US), forms of FLT 1 (VEGFR 1), FR-111142, GCS-100, GW 2286 (GlaxoSmithKline, UK), IL-8, ilomastat, IM-862, irsogladine, KM-2550 (Kyowa Hakko, Japan), lenalidomide, lenvatinib, MAb alpha5beta3 integrin, second generation (Applied Molecular Evolution, USA and MedImmune, US), MAb VEGF (Xenova, UK), marimastat, maspin (Sosei, Japan), metastatin, motuporamine C, M-PGA, ombrabulin, OXI4503, PI 88, platelet factor 4, PPI 2458, ramucirumab, rBPI 21 and BPI-derived antiangiogenic (XOMA, US), regorafenib, SC-236, SD-7784 (Pfizer, US), SDX 103 (University of California at San Diego, US), SG 292 (Telios, US), SU-0879 (Pfizer, US), TAN-1120, TBC-1635, tesevatinib, tetrathiomolybdate, thalidomide, thrombospondin 1 inhibitor, Tie-2 ligands (Regeneron, US), tissue factor pathway inhibitors (EntreMed, US), tumor necrosis factor-alpha inhibitors, tumstatin, TZ 93, urokinase plasminogen activator inhibitors, vadimezan, vandetanib, vasostatin, vatalanib, VE-cadherin-2 antagonists, xanthorrhizol, XL 784 (Exelixis, US), ziv-aflibercept, and ZD 6126.

In embodiments, the additional anti-cancer agent(s) is an additional active agent that disrupts or inhibits RAS-RAF-ERK or PI3K-AKT-TOR signaling pathways or is a PD-1 and/or PD-L1 antagonist. In embodiments, the additional anti-cancer agent(s) is a RAF inhibitor, EGFR inhibitor, MEK inhibitor, ERK inhibitor, PI3K inhibitor, AKT inhibitor, TOR inhibitor, MCL-1 inhibitor, BCL-2 inhibitor, SHP2 inhibitor, proteasome inhibitor, or immune therapy, including monoclonal antibodies, immunomodulatory imides (IMiDs), anti-PD-1, anti-PDL-1, anti-CTLA4, anti-LAG1, and anti-OX40 agents, GITR agonists, CAR-T cells, and BiTEs.

Non-limiting examples of RAF inhibitors include dabrafenib, encorafenib, regorafenib, sorafenib, and vemurafenib.

Non-limiting examples of MEK inhibitors include binimetinib, $C_1$-1040, cobimetinib, PD318088, PD325901, PD334581, PD98059, refametinib, selumetinib, and trametinib.

Non-limiting examples of ERK inhibitors include LY3214996, LTT462, MK-8353, SCH772984, ravoxertinib, ulixertinib, and an ERKi as described in WO 2017/068412.

Non-limiting examples of PI3K inhibitors include 17-hydroxywortmannin analogs (e.g., WO 06/044453); AEZS-136; alpelisib; AS-252424; buparlisib; CAL263; copanlisib; CUDC-907; dactolisib (WO 06/122806); demethoxyviridin; duvelisib; GNE-477; GSK1059615; IC87114; idelalisib; INK1117; LY294002; Palomid 529; paxalisib; perifosine; PI-103; PI-103 hydrochloride; pictilisib (e.g., WO 09/036,082; WO 09/055,730); PIK 90; PWT33597; SF1126; sonolisib; TGI 00-115; TGX-221; XL147; XL-765; wortmannin; and ZSTK474.

Non-limiting examples of AKT inhibitors include Akt-1-1 (inhibits Akt1) (Barnett et al. (2005) Biochem. J., 385 (Pt. 2), 399-408); Akt-1-1,2 (Barnett et al. (2005) Biochem. J. 385 (Pt. 2), 399-408); API-59CJ-Ome (e.g., Jin et al. (2004) Br. J. Cancer 91, 1808-12); 1-H-imidazo[4,5-c]pyridinyl compounds (e.g., WO05011700); indole-3-carbinol and derivatives thereof (e.g., U.S. Pat. No. 6,656,963; Sarkar and Li (2004) J Nutr. 134(12 Suppl), 3493S-3498S); perifosine, Dasmahapatra et al. (2004) Clin. Cancer Res. 10(15), 5242-52, 2004); phosphatidylinositol ether lipid analogues (e.g., Gills and Dennis (2004) Expert. Opin. Investig. Drugs 13, 787-97); triciribine (Yang et al. (2004) Cancer Res. 64, 4394-9); imidazooxazone compounds including trans-3-amino-1-methyl-3-[4-(3-phenyl-5H-imidazo[1,2-c]pyrido[3,4-e][1,3]oxazin-2-yl)phenyl]-cyclobutanol hydrochloride (WO 2012/137870); afuresertib; capivasertib; MK2206; and patasertib.

Non-limiting examples of TOR inhibitors include deforolimus; ATP-competitive TORC1/TORC2 inhibitors, including PI-103, PP242, PP30, and Torin 1; TOR inhibitors in FKBP12 enhancer, rapamycins and derivatives thereof, including temsirolimus, everolimus, WO 9409010; rapalogs, e.g. as disclosed in WO 98/02441 and WO 01/14387, e.g. AP23573, AP23464, or AP23841; 40-(2-hydroxyethyl)rapamycin, 40-[3-hydroxy(hydroxymethyl)methylpropanoate]-rapamycin; 40-epi-(tetrazolyl)-rapamycin (also called ABT578); 32-deoxorapamycin; 16-pentynyloxy-32(S)-dihydrorapanycin, and other derivatives disclosed in WO 05/005434; derivatives disclosed in U.S. Pat. No. 5,258,389, WO 94/090101, WO 92/05179, U.S. Pat. Nos. 5,118,677, 5,118,678, 5,100,883, 5,151,413, 5,120,842, WO 93/111130, WO 94/02136, WO 94/02485, WO 95/14023, WO 94/02136, WO 95/16691, WO 96/41807, WO 96/41807 and U.S. Pat. No. 5,256,790; and phosphorus-containing rapamycin derivatives (e.g., WO 05/016252).

Non-limiting examples of MCL-1 inhibitors include AMG-176, MIK665, and S63845.

Non-limiting examples of SHP2 inhibitors include SHP2 inhibitors described in WO 2019/167000 and WO 2020/022323.

Additional non-limiting examples of anti-cancer agents that are suitable for use include 2-ethylhydrazide, 2,2',2"-trichlorotriethylamine, ABVD, aceglatone, acemannan, aldophosphamide glycoside, alpharadin, amifostine, aminolevulinic acid, anagrelide, ANCER, ancestim, anti-CD22 immunotoxins, antitumorigenic herbs, apaziquone, arglabin, arsenic trioxide, azathioprine, BAM 002 (Novelos), bcl-2 (Genta), bestrabucil, biricodar, bisantrene, bromocriptine, brostallicin, bryostatin, buthionine sulfoximine, calyculin, cell-cycle nonspecific antineoplastic agents, celmoleukin, clodronate, clotrimazole, cytarabine ocfosfate, DA 3030 (Dong-A), defofamine, denileukin diftitox, dexrazoxane, diaziquone, dichloroacetic acid, dilazep, discodermolide, docosanol, doxercalciferol, edelfosine, eflornithine, EL532

(Elan), elfomithine, elsamitrucin, eniluracil, etanidazole, exisulind, ferruginol, folic acid replenisher such as frolinic acid, gacytosine, gallium nitrate, gimeracil/oteracil/tegafur combination (S-1), glycopine, histamine dihydrochloride, HIT diclofenac, HLA-B7 gene therapy (Vical), human fetal alpha fetoprotein, ibandronate, ibandronic acid, ICE chemotherapy regimen, imexon, iobenguane, IT-101 (CRLX101), laniquidar, LC 9018 (Yakult), leflunomide, lentinan, levamisole+fluorouracil, lovastatin, lucanthone, masoprocol, melarsoprol, metoclopramide, miltefosine, miproxifene, mitoguazone, mitozolomide, mopidamol, motexafin gadolinium, MX6 (Galderma), naloxone+pentazocine, nitracrine, nolatrexed, NSC 631570 octreotide (Ukrain), olaparib, P-30 protein, PAC-1, palifermin, pamidronate, pamidronic acid, pentosan polysulfate sodium, phenamet, picibanil, pixantrone, platinum, podophyllinic acid, porfimer sodium, PSK (Polysaccharide-K), rabbit antithymocyte polyclonal antibody, rasburiembodiment, retinoic acid, rhenium Re 186 etidronate, romurtide, samarium (153 Sm) lexidronam, sizofiran, sodium phenylacetate, sparfosic acid, spirogermanium, strontium-89 chloride, suramin, swainsonine, talaporfin, tariquidar, tazarotene, tegafur-uracil, temoporfin, tenuazonic acid, tetrachlorodecaoxide, thrombopoietin, tin ethyl etiopurpurin, tirapazamine, TLC ELL-12, tositumomab-iodine 131, trifluridine and tipiracil combination, troponin I (Harvard University, US), urethan, valspodar, verteporfin, zoledronic acid, and zosuquidar.

The present disclosure further provides a method for using the compounds of Formula (I) or pharmaceutical compositions provided herein, in combination with radiation therapy to treat cancer. Techniques for administering radiation therapy are known in the art, and these techniques can be used in the combination therapy described herein. The administration of the compound of Formula (I) in this combination therapy can be determined as described herein.

Radiation therapy can be administered through one of several methods, or a combination of methods, including, without limitation, external-beam therapy, internal radiation therapy, implant radiation, stereotactic radiosurgery, systemic radiation therapy, radiotherapy and permanent or temporary interstitial brachy therapy. The term "brachytherapy," as used herein, refers to radiation therapy delivered by a spatially confined radioactive material inserted into the body at or near a tumor or other proliferative tissue disease site. The term is intended, without limitation, to include exposure to radioactive isotopes (e.g., At-211, I-131, I-125, Y-90, Re-186, Re-188, Sm-153, Bi-212, P-32, and radioactive isotopes of Lu). Suitable radiation sources for use as a cell conditioner of the present disclosure include both solids and liquids. By way of non-limiting example, the radiation source can be a radionuclide, such as I-125, I-131, Yb-169, Ir-192 as a solid source, I-125 as a solid source, or other radionuclides that emit photons, beta particles, gamma radiation, or other therapeutic rays. The radioactive material can also be a fluid made from any solution of radionuclide(s), e.g., a solution of I-125 or I-131, or a radioactive fluid can be produced using a slurry of a suitable fluid containing small particles of solid radionuclides, such as Au-198, Y-90. Moreover, the radionuclide(s) can be embodied in a gel or radioactive microspheres.

The present disclosure also provides methods for combination therapies in which the additional active agent is known to modulate other pathways, or other components of the same pathway, or even overlapping sets of target enzymes which are used in combination with a compound of Formula (I), or a pharmaceutically acceptable salt thereof. In one embodiment, such therapy includes, but is not limited to, the combination of one or more compounds of Formula (I) with chemotherapeutic agents, immunotherapeutic agents, hormonal therapy agents, therapeutic antibodies, targeted therapy agents, and radiation treatment, to provide a synergistic or additive therapeutic effect.

The compounds of the disclosure can be used in combination with the agents disclosed herein or other suitable agents, depending on the condition being treated. Hence, in some embodiments the one or more compounds of the disclosure will be co-administered with other agents as described above. When used in combination therapy, the compounds described herein are administered with the second agent simultaneously or separately. This administration in combination can include simultaneous administration of the two agents in the same dosage form, simultaneous administration in separate dosage forms, and separate administration. That is, a compound of Formula (I) and any of the agents described above can be formulated together in the same dosage form and administered simultaneously. Alternatively, a compound of Formula (I) and any of the agents described above can be simultaneously administered, wherein both the agents are present in separate formulations. In another alternative, a compound of Formula (I) can be administered just followed by and any of the agents described above, or vice versa. In some embodiments of the separate administration protocol, a compound of Formula (I) and any of the agents described above are administered a few minutes apart, or a few hours apart, or a few days apart.

As one aspect of the present disclosure contemplates the treatment of the disease/conditions with a combination of pharmaceutically active compounds that may be administered separately, the disclosure further relates to combining separate pharmaceutical compositions in kit form. The kit comprises two separate pharmaceutical compositions: a compound of Formula (I), and a second pharmaceutical compound. The kit comprises a container for containing the separate compositions such as a divided bottle or a divided foil packet. Additional examples of containers include syringes, boxes, and bags. In some embodiments, the kit comprises directions for the use of the separate components. The kit form is particularly advantageous when the separate components are preferably administered in different dosage forms (e.g., oral and parenteral), are administered at different dosage intervals, or when titration of the individual components of the combination is desired by the prescribing health care professional.

The present disclosure also provides for the compound of Formula (I), or the pharmaceutically acceptable salt thereof, for use in therapy, or use of the compound of Formula (I), or the pharmaceutically acceptable salt thereof, in therapy. The present disclosure also provides for the compound of Formula (I), or the pharmaceutically acceptable salt thereof, for use in treating cancer, or use of a compound of Formula (I), or the pharmaceutically acceptable salt thereof, for treating cancer. The present disclosure also provides for the compound of Formula (I), or the pharmaceutically acceptable salt thereof, for the preparation of a medicament for the treatment of cancer, or use of the compound of Formula (I), or the pharmaceutically acceptable salt thereof, for the preparation of a medicament for the treatment of cancer. The present disclosure also provides for the compound of Formula (I), or the pharmaceutically acceptable salt thereof, and an additional anti-cancer agent, for use in the treatment of cancer, or use of the compound of Formula (I), or the pharmaceutically acceptable salt thereof, and the additional anti-cancer agent for treating cancer. The disclosure also provides the compound of Formula (I), or the pharmaceutically acceptable salt thereof, and an additional anti-cancer agent, for the preparation of a medicament for the treatment of cancer, or use of the compound of Formula (I), or the pharmaceutically acceptable salt thereof, and the additional anti-cancer agent, for the preparation of a medicament for the treatment of cancer. The present disclosure also provides for a pharmaceutical composition comprising the compound of Formula (I), or the pharmaceutically acceptable salt thereof, for use in the treatment of cancer, or use of the pharmaceutical composition comprising the compound of Formula (I), or the pharmaceutically acceptable salt thereof, for treating cancer. The present disclosure also provides for a pharmaceutical composition comprising the compound of Formula (I), or the pharmaceutically acceptable salt thereof, and an additional anti-cancer agent, for use in the treatment of cancer, or use of the pharmaceutical composition comprising the compound of Formula (I), or the pharmaceutically acceptable salt thereof, and the additional anti-cancer agent, for treating cancer.

Methods of Preparing the Compounds of the Disclosure

Several methods for preparing the compounds of this disclosure are described in the following Examples. Starting materials and intermediates are purchased, made from known procedures, or as otherwise illustrated.

Throughout the synthetic schemes and examples, abbreviations and acronyms may be used with the following meanings unless otherwise indicated: anhydr.=Anhydrous; aq.=aqueous; atm=atmosphere; Bodipy-GDP=mixture of ((2R,3S,4R,5R)-5-(2-amino-6-oxo-1,6-dihydro-9H-purin-9-yl)-3-(((2-(3-(5,5-difluoro-7,9-dimethyl-5H-414,514-dipyrrolo[1,2-c:2',1'-f][1,3,2]diazaborinin-3-yl)propanamido)ethyl)carbamoyl)oxy)-4-hydroxytetrahydrofuran-2-yl) methyl hydrogen diphosphate and ((2R,3R,4R,5R)-5-(2-amino-6-oxo-1,6-dihydro-9H-purin-9-yl)-4-(((2-(3-(5,5-difluoro-7,9-dimethyl-5H-414,514-dipyrrolo[1,2-c:2',1'-f][1,3,2]diazaborinin-3-yl)propanamido)ethyl)carbamoyl)oxy)-3-hydroxytetrahydrofuran-2-yl)methyl hydrogen diphosphate (Invitrogen™, catalog number G22360); br s=broad singlet; Bu=butyl; t-Bu=tert-butyl; cataCxium® C=trans-Diµ-acetato)bis[o-(di-o-tolylphosphino)benzyl]dipalladium(II), C=CDCl$_3$=deuterated chloroform; CDI=1,1'-carbonyldiimidazole, CELITE=diatomaceous earth; CF$_3$=trifluoromethyl; cGMP=cyclic guanosine monophosphate; CH$_3$NO$_2$=nitromethane; DCM=dichloromethane; DETA-NO=Diethylenetriamine/nitric oxide adduct; DIAD=Diisopropyl azodicarboxylate; DIEA/DIPEA=N,N-Diisopropylethylamine; DME=dimethoxyethane, DMEA=N,N-Dimethylethanamine, DMF=N,N-dimethylformamide; DMP=Dess-Martin periodinane; DMS=dimethylsulfide; DMSO=dimethylsulfoxide; DPPF or dppf=1,1'-bis(diphenylphosphino)ferrocene; DTJ=dithiothreitol; EDTA=ethylenediaminetetraacetic acid; equiv, eq.=equivalent(s); Et=ethyl; Et$_3$N=triethylamine; EtOAc=ethyl acetate; EtOH=ethanol; Grubbs Catalyst=(1,3-Bis(2,4,6-trimethylphenyl)-2-imidazolidinylidene)dichloro(phenylmethylenextricyclohexylphosphine)ruthenium; GTP=guanosine triphosphate; h=hour; HEPES=4-(2-hydroxyethyl)-1-piperazineethanesulfonic acid; HMDS=hexamethydisilazane; HPLC=High pressure liquid chromatography; Int.=intermediate; iPr=isopropyl; IP=inflection points; i-PrOH=Isopropanol; KHMDS=Potassium bis(trimethylsilyl)amide; LCMS, LC/MS=liquid chromatography-mass spectrometry; min, min.=minute; LDA=lithium diisopropylamide; M=Molar; Me=methyl; MCCN, ACN=acetonitrile; MeOH=methanol; mp, m.p.=melting point; mpk=milligrams per kilogram; MsCl=Methanesulfonyl chloride; MPLC=medium pressure liquid chromatography; N=Normal; NaOMe=sodium methoxide; NMR=nuclear magnetic resonance; N.D.=not determined; PDA=photodiode array; Pet. ether=petroleum ether; Pd—C=palladium on carbon; Pd2(dba)$_3$=tris(dibenzylideneacetone)dipalladium (0); Ph=phenyl; Pr=propyl; psi=pounds per square inch gauge; POCl$_3$=phosphorus(V) oxide chloride; PTLC, prep TLC=preparative thin layer chromatography; rac=racemic; RJ=retention time; RP-HPLC=reverse phase HPLC; rt=room temperature; sat.=saturated; SFC=supercritical fluid chromatography; SOS=Son of Sevenless; Sphos Pd G3=(2-Dicyclohexylphosphino-2',6'-dimethoxybiphenyl) [2-(2'-amino-1,1'-biphenyl)]palladium(II) methanesulfonate; TBAF=tetra-n-butylammonium fluoride; TBSCl=tert-butyldimethylsilyl chloride; TFA=trifluoroacetic acid; TLC=thin layer chromatography; THF=tetrahydrofuran; TMS=trimethylsilyl; TWEEN=polyoxyethylene (20) sorbitan monolaurate; VCD=vibrational circular dichroism; v, v/v=volume, volume to volume; w, w/w=weight, weight to weight, XPhos-Pd-G3=(2-dicyclohexylphosphino-2',4',6'-triisopropyl-1,1'-biphenyl)[2-(2'-amino-1,1'-biphenyl)]palladium(II) methanesulfonate; µm=micrometer.

EXAMPLES

The compounds described herein can be prepared according to the procedures of the following schemes and examples, using appropriate materials and are further exemplified by the following specific examples. The compounds illustrated in the examples are not, however, to be construed as forming the only genus that is considered as the disclosure. The examples further illustrate details for the preparation of the compounds of the present disclosure. Those skilled in the art will readily understand that known variations of the conditions and processes of the following preparative procedures can be used to prepare these compounds. These examples are provided for the purpose of further illustration only and are not intended to be limitations on the disclosure. Any intermediates described below may be referred to herein by their number preceded by "Int-."

Concentration refers to the removal of the volatile components at reduced pressure (e.g., by rotary evaporation) unless otherwise noted. All temperatures are in degrees Celsius unless otherwise noted. Mass spectra (MS) were measured by electrospray ion-mass spectroscopy (ESI) in positive ion detection mode and m/z refers to the [M+H]$^+$ ion unless otherwise noted. $^1$H NMR spectra were recorded at 400-500 MHz at ambient temperature unless otherwise noted. Protons reported as 0.5H are due to rotameric signals. RP-HPLC refers to reverse-phase HPLC on C18-functionalized preparative or semi-preparative columns with gradient elution using acetonitrile and water modified with trifluoroacetic acid or ammonium hydroxide as eluents and fractions were lyophilized or concentrated by rotary evaporation unless otherwise noted. Purification by column chromatography on silica gel was accomplished using a flash chromatography system (e.g., ISCO® or Biotage®) and commercial pre-packed silica gel columns with elution using the stated solvent systems. Compounds described herein were synthesized as the racemates unless otherwise noted in the experimental procedures and compound tables. Certain products/intermediates in the examples include indication of "Peak 1" and/or "Peak 2", which refer to the order of elution of the indicated product/intermediate from the chromatography column (e.g., an SFC column) used to isolate the compound under the specified conditions. Thus, for example, Peak 1 refers to the first eluting compound, e.g., first eluting stereoisomer (e.g., a first eluting atropisomer), under the specified conditions. The starting materials 2,5-dichloro-3-nitropyridine and (E)-tert-butyldimethyl((4-(4,4,5,5-tetramethyl-1,3,2-dioxaborolan-2-yl)but-3-en-1-yl)oxy)silane were purchased from Sigma Aldrich.

SFC Columns used in the chiral resolution of stereoisomers are summarized in the following Table:

| SFC Column | SFC Column Abbreviation |
|---|---|
| AD-H, 21 mm × 250 mm | Column A |
| AD-H, 30 mm × 250 mm | Column B |
| AD-H, 50 mm × 250 mm | Column C |
| AD, 30 mm × 250 mm | Column D |
| AS, 30 mm × 250 mm | Column E |
| OD-H, 30 mm × 250 mm | Column F |
| OD-H, 21 mm x250 mm | Column G |
| OD, 30 mm × 250 mm | Column H |
| IA, 21 mm × 250 mm | Column I |
| IC, 30 mm × 250 mm | Column J |
| IF, 21 mm × 250 mm | Column K |
| IG, 30 mm × 250 mm | Column L |
| IG, 50 mm × 250 mm | Column M |
| Phenomenex-Cellulose-2, 50 mm × 250 mm | Column N |
| Phenomenex Lux Cellulose-4 , 30 mm × 250 mm | Column O |
| Phenomenex-Cellulose-2, 30 mm × 250 mm | Column P |
| Lux-2, 21 mm × 250 mm | Column Q |
| Lux-2, 30 mm × 250 mm | Column R |
| OJ-H, 21 mm × 250 mm | Column S |
| (R,R)-Whelk-O1, 21 mm × 250 mm | Column T |
| ChromegaChiral SFC CCO, 21 mm × 250 mm | Column U |
| AD, 50 mm × 250 mm | Column V |

Example 1a: 18,21-Difluoro-2-[(2S)-2-methyl-4-(prop-2-enoyl)piperazin-1-yl]-6-(propan-2-yl-12,13-dihydro-4H,11H-1,19-ethenopyrido[4,3-f]pyrimido[1,6-h][1.5.8.10]benzodioxadiazacyclotridecin-4-one

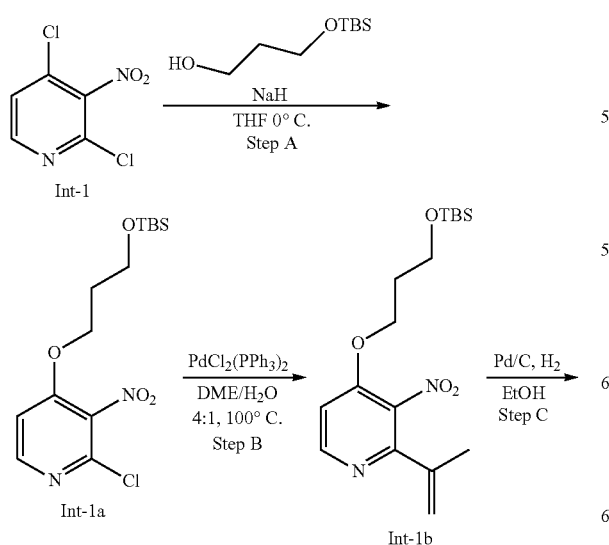

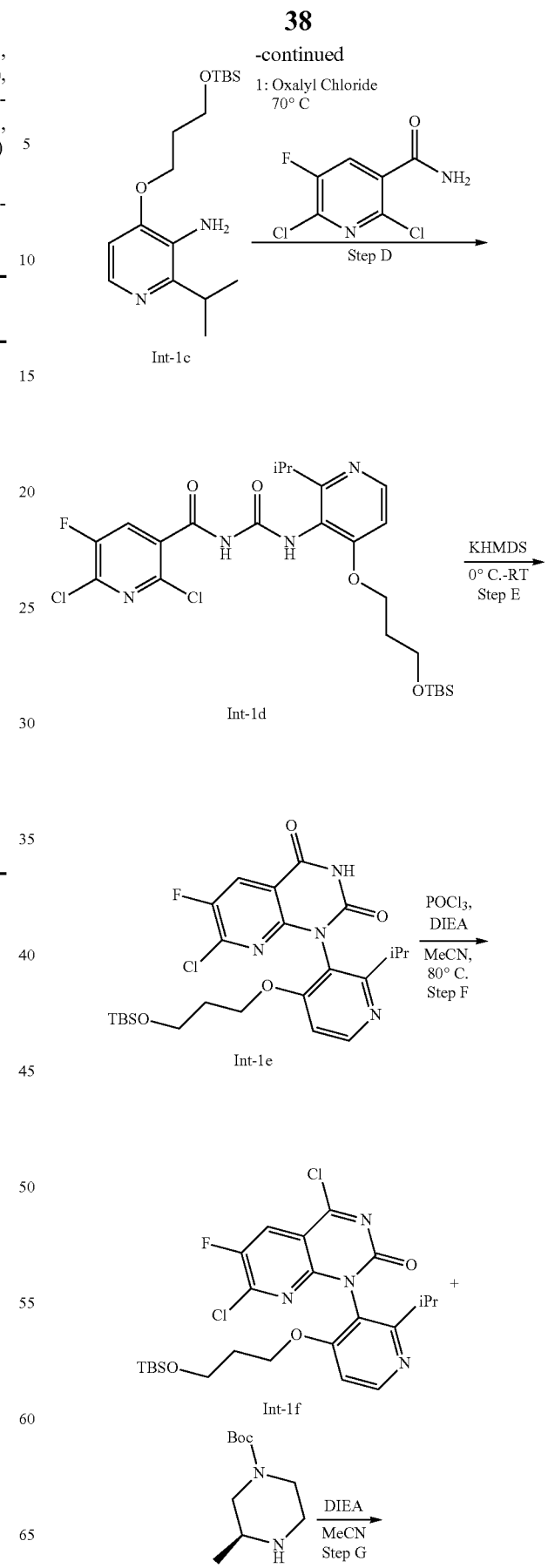

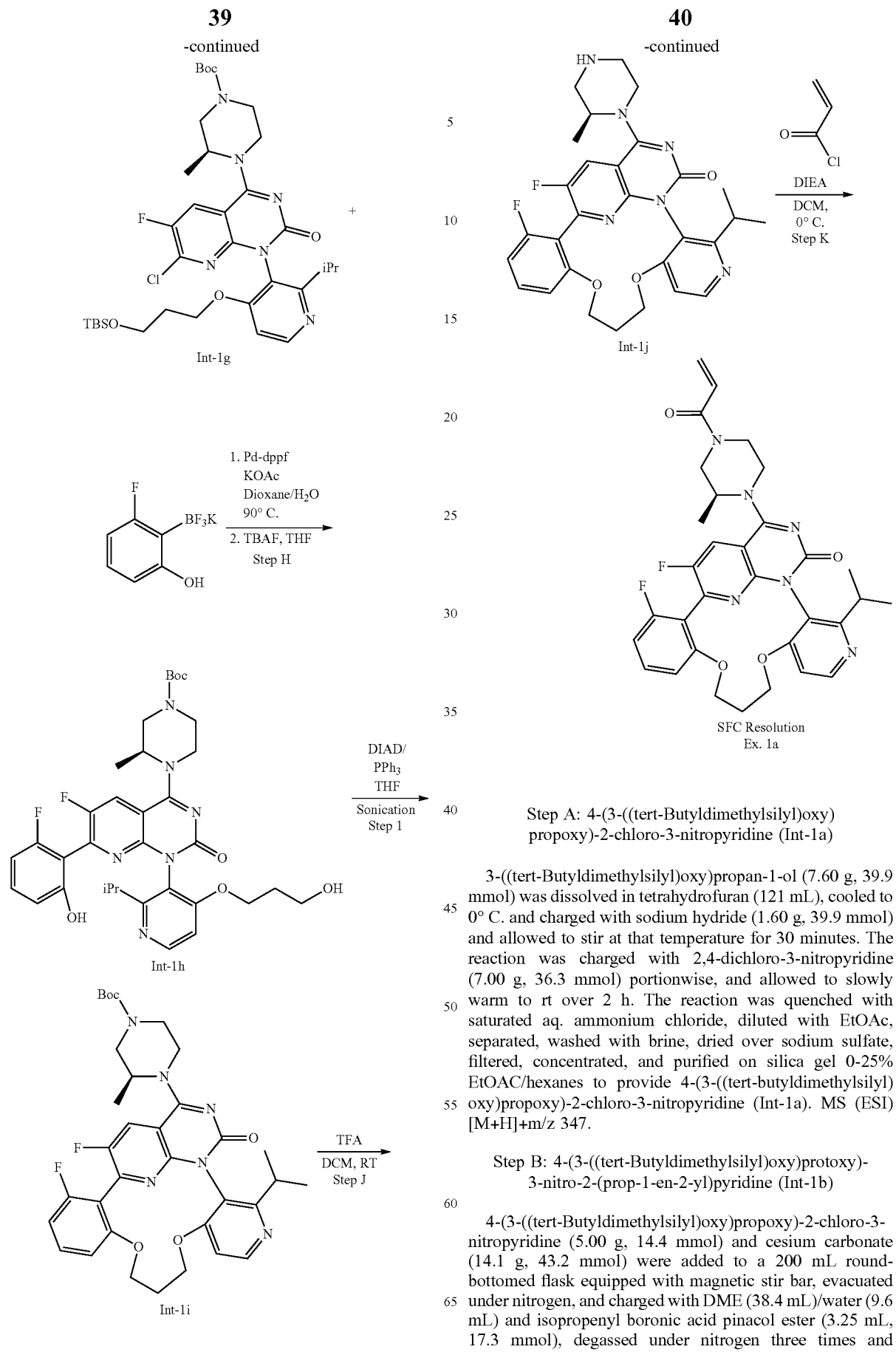

Step A: 4-(3-((tert-Butyldimethylsilyl)oxy) propoxy)-2-chloro-3-nitropyridine (Int-1a)

3-((tert-Butyldimethylsilyl)oxy)propan-1-ol (7.60 g, 39.9 mmol) was dissolved in tetrahydrofuran (121 mL), cooled to 0° C. and charged with sodium hydride (1.60 g, 39.9 mmol) and allowed to stir at that temperature for 30 minutes. The reaction was charged with 2,4-dichloro-3-nitropyridine (7.00 g, 36.3 mmol) portionwise, and allowed to slowly warm to rt over 2 h. The reaction was quenched with saturated aq. ammonium chloride, diluted with EtOAc, separated, washed with brine, dried over sodium sulfate, filtered, concentrated, and purified on silica gel 0-25% EtOAC/hexanes to provide 4-(3-((tert-butyldimethylsilyl)oxy)propoxy)-2-chloro-3-nitropyridine (Int-1a). MS (ESI) [M+H]+m/z 347.

Step B: 4-(3-((tert-Butyldimethylsilyl)oxy)protoxy)-3-nitro-2-(prop-1-en-2-yl)pyridine (Int-1b)

4-(3-((tert-Butyldimethylsilyl)oxy)propoxy)-2-chloro-3-nitropyridine (5.00 g, 14.4 mmol) and cesium carbonate (14.1 g, 43.2 mmol) were added to a 200 mL round-bottomed flask equipped with magnetic stir bar, evacuated under nitrogen, and charged with DME (38.4 mL)/water (9.6 mL) and isopropenyl boronic acid pinacol ester (3.25 mL, 17.3 mmol), degassed under nitrogen three times and charged with bis(triphenylphosphine) palladium(II) dichloride (1.01 g, 1.44 mmol). The reaction was degassed under nitrogen, affixed with a reflux condenser and heated to 100° C. overnight. The reaction was cooled to room temperature, quenched with 50 mL saturated aq. ammonium chloride extracted 2×100 mL EtOAc, washed with brine, dried over sodium sulfate, filtered, concentrated and purified on silica gel 10-50% EtOAc/hexanes to provide 4-(3-((tert-butyldimethylsilyl)oxy)propoxy)-3-nitro-2-(prop-1-en-2-yl)pyridine (Int-1b). MS (ESI) m/z 353.

Step C: 4-(3-((tert-Butyldimethylsilyl)oxy)propoxy-2-isopropylpyridin-3-amine (Int-1c)

4-(3-((tert-Butyldimethylsilyl)oxy)propoxy)-3-nitro-2-(prop-1-en-2-yl)pyridine (4.20 g, 11.9 mmol) was dissolved in ethanol (100 mL), degassed under nitrogen, charged with Pd—C (10% w/w, wetted) (840 mg) degassed under nitrogen, evacuated under hydrogen balloon and allowed to stir for 24 h at room temperature under hydrogen atmosphere. The reaction was filtered through CELITE and concentrated in vacuo to provide 4-(3-((tert-butyldimethylsilyl)oxy)propoxy)-2-isopropylpyridin-3-amine (Int-1c), which was used without further purification. MS (ESI) [M+H]$^+$: m/z 325.

Step D: N-((4-(3-((tert-Butyldimethylsilyl)oxy)propoxy-2-isopropylpyridin-3-yl)carbamoyl)-2,6-dichloro-5-fluoronicotinamide (Int-1d)

To a stirred solution of 2,6-dichloro-5-fluoronicotinamide (1.15 g, 5.48 mmol) in THF (25 mL) was added a 2 M solution of oxalyl chloride in DCM (2.60 mL, 5.20 mmol) and the reaction was heated to 75° C. with a reflux condenser attached for 1 h. The reaction was cooled to 0° C. and a solution of 4-(3-((tert-butyldimethylsilyl)oxy)propoxy)-2-isopropylpyridin-3-amine (1.87 g, 5.75 mmol) in THF (5 mL) was added dropwise. The reaction was allowed to stir for 1 h. The reaction was quenched with 10 mL saturated sodium ammonium chloride, extracted 2×50 mL EtOAc, washed with brine, dried over sodium sulfate, filtered, concentrated in vacuo, and purified on silica gel 0-100% hexanes/3:1 EtOAc/EtOH to provide N-((4-(3-((tert-butyldimethylsilyl)oxy)propoxy)-2-isopropylpyridin-3-yl)carbamoyl)-2,6-dichloro-5-fluoronicotinamide (Int-id). MS (ESI) [M+H]$^+$: m/z 559/561.

Step 1-(4-(3-((tert-Butyldimethylsilyl)oxy)propoxy-2-isopropylpyridin-3-yl-7-chloro-6-fluoropyrido[2,3-d]pyrimidine-2,4(1H,3H)-dione (Int-1e)

N-((4-(3-((tert-Butyldimethylsilyl)oxy)propoxy)-2-isopropylpyridin-3-yl)carbamoyl)-2,6-dichloro-5-fluoronicotinamide (1.72 g, 3.07 mmol) was dissolved in THF (20 mL), cooled to 0° C., charged with a 1 M solution of KHMDS in THF (6.46 mL, 6.46 mmol) and allowed to warm to rt over 1 h. The reaction was quenched with 10 mL saturated ammonium chloride, extracted 2×50 mL EtOAc, washed with brine, dried over sodium sulfate, filtered and concentrated in vacuo to provide 1-(4-(3-((tert-butyldimethylsilyl)oxy)propoxy)-2-isopropylpyridin-3-yl)-7-chloro-6-fluoropyrido[2,3-d]pyrimidine-2,4(1H,3H)-dione (Int-1e), which was used without further purification. MS (ESI) [M+H]$^+$: m/z 523.

Step F: 1-(4-(3-((tert-Butyldimethylsilyl)oxy)propoxy-2-isopropylpyridin-3-yl-4,7-dichloro-6-fluoropyrido[2,3-d]pyrimidin-2(1H-one (Int-1f)

1-(4-(3-((tert-Butyldimethylsilyl)oxy)propoxy)-2-isopropylpyridin-3-yl)-7-chloro-6-fluoropyrido[2,3-d]pyrimidine-2,4(1H,3H)-dione (1.57 g, 3.00 mmol) was dissolved in CH$_3$CN (20 mL), charged with DIEA (1.05 mL, 6.00 mmol) and POCl$_3$ (0.336 mL, 3.60 mmol) and heated to 80° C. for 1 h. The reaction was evaporated on the rotovap and dried under high vacuum for 10 minutes to provide 1-(4-(3-((tert-butyldimethylsilyl)oxy)propoxy)-2-isopropylpyridin-3-yl)-4,7-dichloro-6-fluoropyrido[2,3-d]pyrimidin-2(1H)-one (Int-1f), and used without further purification MS (ESI) [M+H]$^+$: m/z 540.8/542.9.

Step G: tert-butyl (S)-4-(1-(4-(3-((tert-Butyldimethylsilyloxy)propoxy)-2-isopropylpyridin-3-yl-7-chloro-6-fluoro-2-oxo-1,2-dihydropyrido[2,3-d]pyrimidin-4-yl-3-methylpiperazine-1-carboxylate (Int-1g)

1-(4-(3-((tert-Butyldimethylsilyl)oxy)propoxy)-2-isopropylpyridin-3-yl)-4,7-dichloro-6-fluoropyrido[2,3-d]pyrimidin-2(1H)-one (1.63 g, 3.00 mmol) was dissolved in acetonitrile (20 mL), cooled to 0° C., charged with DIEA (2.01 mL, 12.0 mmol) then tert-butyl (S)-3-methylpiperazine-1-carboxylate (0.721 g, 3.60 mmol) and allowed to stir for 30 minutes. The reaction was quenched with 1:1 saturated sodium bicarbonate/water, allowed to stir for 5 minutes, and the organics were separated. The aqueous layer was extracted with 2×25 mL EtOAc, combined, washed with brine, dried over sodium sulfate, filtered, concentrated and purified on silica gel 0-100% 3:1 EtOAc/EtOH/hexanes to provide tert-butyl (S)-4-(1-(4-(3-((tert-butyldimethylsilyl)oxy)propoxy)-2-isopropylpyridin-3-yl)-7-chloro-6-fluoro-2-oxo-1,2-dihydropyrido[2,3-d]pyrimidin-4-yl)-3-methylpiperazine-1-carboxylate (Int-1g) MS (ESI) [M+H]$^+$ m/z: 705.

Step H: tert-Butyl (3S)-4-(6-fluoro-7-(2-fluoro-6-hydroxyphenyl)-1-(4-(3-hydroxypropoxy)-2-isopropylpyridin-3-yl)-2-oxo-1,2-dihydropyrido[2,3-d]pyrimidin-4-yl)-3-methylpiperazine-1-carboxylate (Int-1h)

tert-Butyl (S)-4-(1-(4-(3-((tert-butyldimethylsilyl)oxy)propoxy)-2-isopropylpyridin-3-yl)-7-chloro-6-fluoro-2-oxo-1,2-dihydropyrido[2,3-d]pyrimidin-4-yl)-3-methylpiperazine-1-carboxylate (0.500 g, 0.709 mmol), potassium 3-fluoro-2-(trifluoro-λ$^4$-boraneyl)phenolate (0.200 g, 0.922 mmol), potassium acetate (0.278 g, 2.84 mmol), 1,1'-bis(diphenylphosphino)ferrocene-palladium(II) dichloride were added to a 20 mL scintillation vial equipped with magnetic stir bar, degassed under nitrogen, charged with dioxane (3.0 mL)/water (0.50 mL), degassed 3 times under nitrogen and heated to 90° C. for 1 h. The reaction was cooled to room temperature, quenched with 10 mL 1:1 water/saturated sodium bicarbonate, extracted 2×25 mL EtOAc, washed with brine and concentrated in vacuo. The crude residue was taken up in 10 mL THF, charged with a 1 M solution of TBAF in THF (1.77 mL, 1.77 mmol) and allowed to stir for 1.5 h at room temperature. The reaction was quenched with saturated NH$_4$C$_1$, extracted once EtOAc, washed with brine, dried over sodium sulfate, filtered, concentrated in vacuo, and purified on silica gel 0-100% 3:1 EtOAc/EtOH/hexanes to provide tert-butyl (3S)-4-(6-fluoro-7-(2-fluoro-6-hydroxyphenyl)-1-(4-(3-hydroxypropoxy)-2-isopropylpyridin-3-yl)-2-oxo-1,2-dihydropyrido[2,3-d]pyrimidin-4-yl)-3-methylpiperazine-1-carboxylate (Int-1h). MS (ESI) [M+H]$^+$ m/z:667.

Step I: (Int-1i)

tert-Butyl (3S)-4-(6-fluoro-7-(2-fluoro-6-hydroxyphenyl)-1-(4-(3-hydroxypropoxy)-2-isopropylpyridin-3-yl)-2- oxo-1,2-dihydropyrido[2,3-d]pyrimidin-4-yl)-3-methylpiperazine-1-carboxylate (61 mg, 0.091 mmol) and triphenylphosphine (60.0 mg, 0.229 mmol) were charged with THF (4.7 mL), degassed under nitrogen, charged with diisopropyl azodicarboxylate (36.0 µl, 0.183 mmol) and sonicated for 10 minutes. The solvents were removed in vacuo and the residue was purified on silica gel 0-100% hexanes/3:1 EtOAc/EtOH to provide Int-1i. MS (ESI) [M+H]$^+$ m/z:647.

Step J: Int-1j

Int-1i (137 mg, 0.211 mmol) was dissolved in DCM (4 mL) charged with TFA (0.814 mL, 10.6 mmol) and allowed to stir at rt for 1 h. The reaction was evaporated in vacuo to provide crude Int-1j+3TFA, and used without further purification. MS (ESI) [M+H]$^+$ m/z: 549.

Step K: Ex. 1a: 18,21-difluoro-2-[(2S)-2-methyl-4-(prop-2-enoyl)piperazin-1-yl]-6-(propan-2-yl)-12,13-dihydro-4H,11H-1,19-ethenopyrido[4,3-f]pyrimido[1,6-h][1.5.8.10]benzodioxadiazacyclotridecin-4-one Int-1j+3TFA (200 mg, 0.225 mmol) was dissolved in DCM (2.25 mL), cooled to 0° C., charged with DIEA (157 µL, 0.898 mmol), acryloyl chloride (20 µL, 0.25 mmol) and allowed to stir for 1 h. The reaction was quenched by addition of 2 mL saturated sodium bicarbonate, extracted 2×10 mL EtOAc, washed with brine, dried over sodium sulfate, filtered and concentrated in vacuo, purified on silica gel, 0-100% 3:1 EtOAc/EtOH. The racemic material was resolved by SFC Column A, Condition: MeOH w/0.1% NH$_4$OH to provide 18,21-difluoro-2-[(2S)-2-methyl-4-(prop-2-enoyl)piperazin-1-yl]-6-(propan-2-yl)-12,13-dihydro-4H,11H-1,19-ethenopyrido[4,3-f]pyrimido[1,6-h][1,5,8,10]benzodioxadiazacyclotridecin-4-one (Ex. 1a, peak 1) as a single atropisomer.

MS (ESI) [M+H]$^+$ m/z: 603 $^1$H NMR (500 MHz, DMSO-d$_6$) δ 8.38 (d, J=5.7 Hz, 1H), 8.17 (m, 1H), 7.52-7.45 (m, 1H), 7.06 (d, J=5.9 Hz, 1H), 6.98-6.90 (m, 2H), 6.90-6.79 (m, 1H), 6.26-6.16 (m, 1H), 5.77 (d, J=10.4 Hz, 1H), 4.73 (m, 1H), 4.45 (m, 2H), 4.32 (m, 1H), 4.19-4.06 (m, 2H), 3.99 (m, 2H), 3.67-3.47 (m, 2H), 3.19 (m, 1H), 2.87 (m, 1H), 1.96 (m, 1H), 1.90-1.76 (m, 1H), 1.41 (m, 3H), 1.13 (d, J=6.7 Hz, 3H), 0.90 (d, J=6.7 Hz, 3H).

Example 2a was Prepared as Described in Example 1 Using Int-1g with (2-Hydroxypyridin-3-yl)Boronic Acid

| Ex. No. | Structure | Compound Name | [M + H]$^+$ Found | SFC Conditions |
|---|---|---|---|---|
| 2a | 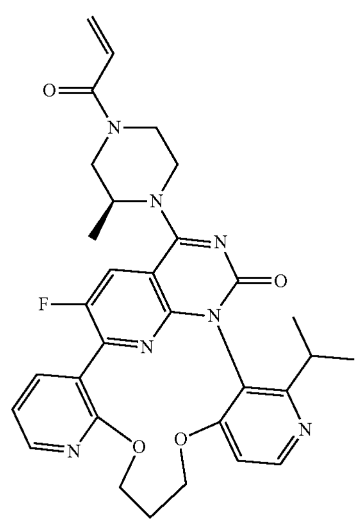 [SMILES: C=CC(=O)N1CCN(c2nc(=O)n3c4nc(c(F)cc24)-c2cccnc2OCCCOc2ccnc(C(C)C)c2-3)[C@@H](C)C1] | 21-fluoro-2-[(2S)-2-methyl-4-(prop-2-enoyl)piperazin-1-yl]-6-(propan-2-yl)-12,13-dihydro-4H,11H-1,19-(ethanediylidene)dipyrido[4,3-b:3',2'-h]-pyrimido[1,6-d]-[1,10,4,6]dioxadiazacyclotridecin-4-one (Peak 1) | 586 | Column S MeOH w/ 0.1% NH$_4$OH 20% CO$_2$ Peak 1 |

Example 3a/3b: 22-fluoro-2-[(2S)-2-methyl-4-(prop-2-enoyl)piperazin-1-yl]-6-(propan-2-yl)-12,13-dihydro-4H,11H-1,20-ethenopyrido[4',3':2,3]pyrimido[1',6':4,5][1,4,6,10]oxatriazacyclotridecino[8,9,10-hi]indazol-4-one

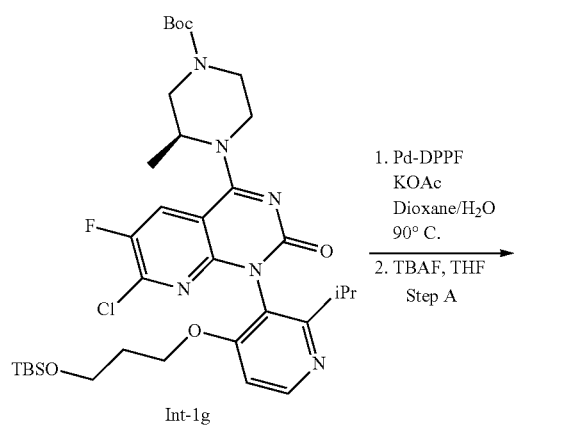

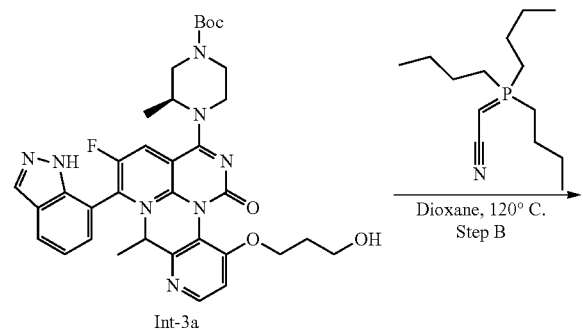

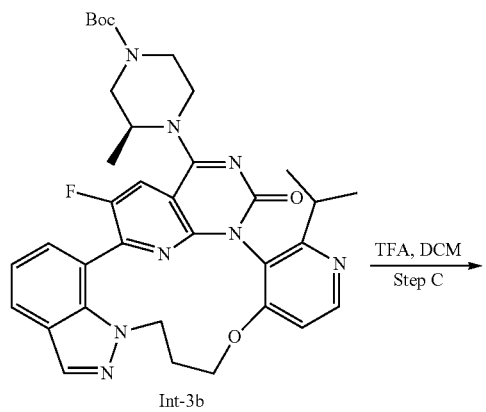

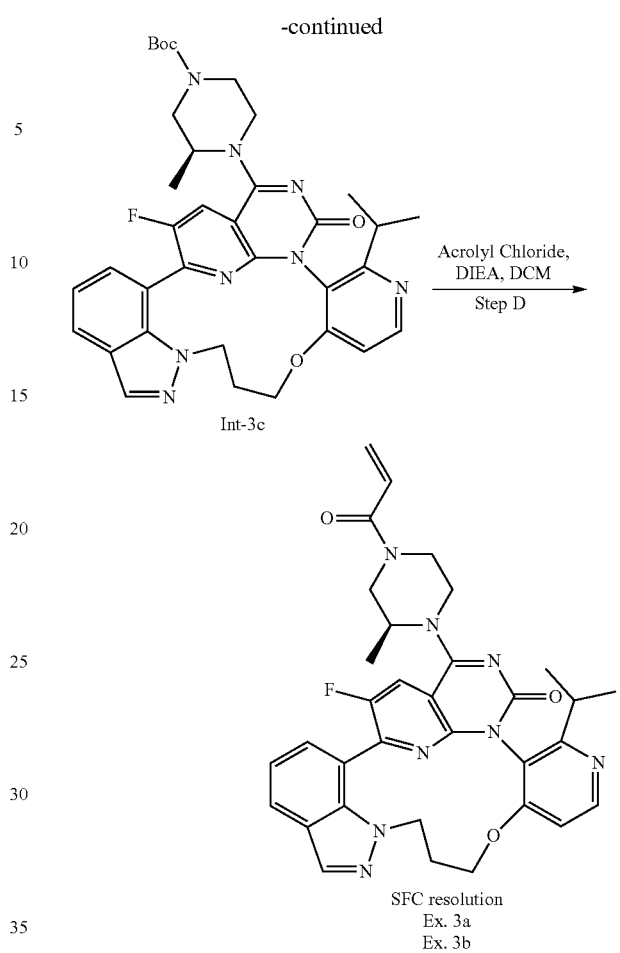

Step A: tert-butyl (S)-4-(6-fluoro-1-(4-(3-hydroxypropoxy)-2-isopropylpyridin-3-yl)-7-(1H-indazol-7-yl)-2-oxo-1,2-dihydropyrido[2,3-d]pyrimidin-4-yl)-3-methylpiperazine-1-carboxylate (Int-3a tert-Butyl (S)-4-(1-(4-(3-((tert-butyldimethylsilyl)oxy)propoxy)-2-isopropylpyridin-3-yl)-7-chloro-6-fluoro-2-oxo-1,2-dihydropyrido[2,3-d]pyrimidin-4-yl)-3-methylpiperazine-1-carboxylate (Int-1g) (71.4 mg, 0.101 mmol), 7-(4,4,5,5-tetramethyl-1,3,2-dioxaborolan-2-yl)-1H-indazole (0.037 g, 0.152 mmol), potassium acetate (0.040 g, 0.405 mmol), 1,1'-bis(diphenylphosphino)ferrocene-palladium (II) dichloride dichloromethane complex (8.3 mg, 10.1 μmol) were added to a 20 mL scintillation vial equipped with magnetic stir bar, degassed under nitrogen, charged with dioxane (0.87 mL)/water (0.15 mL), degassed three times under nitrogen and heated to 90° C. for 30 min. The reaction was cooled to room temperature, quenched with 2 mL 1:1 water/saturated ammonium chloride, extracted 1×25 mL EtOAc, washed with brine and concentrated in vacuo. The crude residue was taken up in 5 mL THF, charged with 1.0 M solution of TBAF in THF (0.506 mL, 0.506 mmol) and allowed to stir for 1.5 h at room temperature. The reaction was quenched with saturated NH₄Cl, extracted 1×15 mL EtOAc, washed with brine, dried over sodium sulfate, filtered, concentrated in vacuo, and purified on silica gel 0-100% 3:1 EtOAc/EtOH/DCM to provide tert-butyl (S)-4-(6-fluoro-1-(4-(3-hydroxypropoxy)-2-isopropylpyridin-3- yl)-7-(1H-indazol-7-yl)-2-oxo-1,2-dihydropyrido[2,3-d]pyrimidin-4-yl)-3-methylpiperazine-1-carboxylate. Int-3a MS (ESI) [M+H]⁺ m/z 673.

Step B: Int-3b tert-Butyl (S)-4-(6-fluoro-1-(4-(3-hydroxypropoxy)-2-isopropylpyridin-3-yl)-7-(1H-indazol-7-yl)-2-oxo-1,2-dihydropyrido[2,3-d]pyrimidin-4-yl)-3-methylpiperazine-1-carboxylate (58 mg, 0.086 mmol) was dissolved in dioxane (4.3 mL), charged with cyanomethylenetributylphosphorane (45.2 µl, 0.172 mmol), degassed under nitrogen and heated to 120° C. overnight. The reaction was concentrated in vacuo, purified on silica gel, 0-100% 3:1 (EtOAc/EtOH)/DCM to provide Int 3b with impurities. The resin was triturated with hexanes, sonicated, filtered, washed 1×hexanes to provide Int-3b MS (ESI) [M+H]⁺ m/z 655.

Step C: Int-3c

Int-3b (68 mg, 0.104 mmol) was dissolved in DCM (2.0 mL), charged with TFA (800 µl, 10.4 mmol) and allowed to stir for 1 h at rt. The reaction was concentrated in vacuo to provide Int-3c+3TFA as a crude residue used without further purification. MS (ESI) [M+H]⁺ m/z 555.

Step D: Ex. 3a/3b 22-fluoro-2-[(2S)-2-methyl-4-(prop-2-enoyl)piperazin-1-yl]-6-(propan-2-yl)-12,13-dihydro-4H,11H-1,20-ethenopyrido[4',3':2,3]pyrimido[1',6':4,5][1,4,6,10]oxatriazacyclotridecino[8,9,10-hi]indazol-4-one Int-3c (90 mg, 0.146 mmol) was dissolved in 4 mL DCM, charged with DIEA (153 µl, 0.876 mmol), cooled to 0° C., charged with acryloyl chloride (14.0 µl, 0.175 mmol) and allowed to stir at that temperature for 1 h. The reaction was quenched with 2 mL of 1:1 saturated sodium bicarbonate/water, filtered through a 4 mL phase separator, extracted once with 5 mL DCM, concentrated in vacuo and purified on silica gel, 0-100% 3:1 EtOAc/EtOH/DCM to provide racemic product. The product was resolved via SFC chromatography, using Column T, Condition: MeOH w/0.25% DMEA, 50% CO₂ to provide 22-fluoro-2-[(2S)-2-methyl-4-(prop-2-enoyl)piperazin-1-yl]-6-(propan-2-yl)-12,13-dihydro-4H,11H-1,20-ethenopyrido[4',3':2,3]pyrimido[1',6':4,5][1,4,6,10]oxatriazacyclotridecino[8,9,10-hi]indazol-4-one (Ex. 3a, peak 1) as a single atropisomer.

MS (ESI) [M+H]⁺ m/z 609. ¹H NMR (600 MHz, DMSO-d₆) δ 8.52 (d, J=8.4 Hz, 1H), 8.31 (d, J=5.7 Hz, 1H), 8.28 (s, 1H), 7.92 (d, J=8.0 Hz, 1H), 7.31 (d, J=6.7 Hz, 1H), 7.21 (t, J=7.5 Hz, 1H), 6.96 (d, J=5.7 Hz, 1H), 6.88 (dd, J=16.9, 10.4 Hz, 1H), 6.22 (dd, J=16.8, 8.6 Hz, 1H), 5.78 (dd, J=10.4, 2.4 Hz, 1H), 5.11 (m, 1H), 4.45 (d, J=13.6 Hz, 0.5H), 4.34 (d, J=13.4 Hz, 0.5H), 4.18 (m, 2.5H), 4.08 (d, J=13.9 Hz, 0.5H), 4.00-3.77 (m, 3H), 3.72 (d, J=13.5 Hz, 0.5H), 3.53 (dt, J=14.0, 7.6 Hz, 1H), 3.37 (m, ov. 1H) 3.00 (t, J=11.8 Hz, 0.5H), 2.91 (m, 1H), 2.41-2.24 (m, 1H), 2.16 (s, 1H), 1.37-1.23 (m, 3H), 1.15 (d, J=6.8 Hz, 3H), 0.88 (d, J=6.8 Hz, 3H).

Ex. 3b, Peak 2—22-fluoro-2-[(2S)-2-methyl-4-(prop-2-enoyl)piperazin-1-yl]-6-(propan-2-yl)-12,13-dihydro-4H,11H-1,20-ethenopyrido[4',3':2,3]pyrimido[1',6':4,5][1,4,6,10]oxatriazacyclotridecino[8,9,10-hi]indazol-4-one (Ex. 3b). MS (ESI) [M+H]⁺ m/z 609. ¹H NMR (600 MHz, DMSO-d₆) δ 8.35 (d, J=8.6 Hz, 1H), 8.31 (d, J=5.6 Hz, 1H), 8.29 (s, 1H), 7.92 (d, J=8.0 Hz, 1H), 7.31 (d, J=7.0 Hz, 1H), 7.22 (t, J=7.5 Hz, 1H), 6.95 (d, J=5.7 Hz, 1H), 6.88 (td, J=17.5, 11.1 Hz, 1H), 6.22 (t, J=14.1 Hz, 1H), 5.78 (d, J=10.7 Hz, 1H), 4.80 (m, 0.5H), 4.77 (m, 0.5H), 4.48 (d, J=13.7 Hz, 1H), 4.42 (d, J=13.3 Hz, 0.5H), 4.27 (d, J=13.4 Hz, 0.5H), 4.17 (m, 1.5zH), 4.03 (d, J=13.8 Hz, 0.5H), 3.93-3.75 (m, 2H), 3.74-3.54 (m, 2H), 3.50 (dt, J=13.8, 7.4 Hz, 1H), 3.29 (m, ov. 0.5H), 3.23 (d, J=13.3 Hz, 0.5H), 2.91 (p, J=6.7 Hz, 1H), 2.36-2.25 (m, 1H), 2.14 (m, 1H), 1.47-1.39 (m, 3H), 1.15 (d, J=6.7 Hz, 3H), 0.89 (d, J=6.7 Hz, 3H).

Example 4: 18,21-difluoro-2-[(2S)-2-methyl-4-(prop-2-enoyl)piperazin-1-yl]-6-(propan-2-yl)-10,11,12,13-tetrahydro-4H-1,19-ethenopyrido[4,3-f]pyrimido[1,6-h][1,8,10]benzoxadiazacyclotridecin-4-one

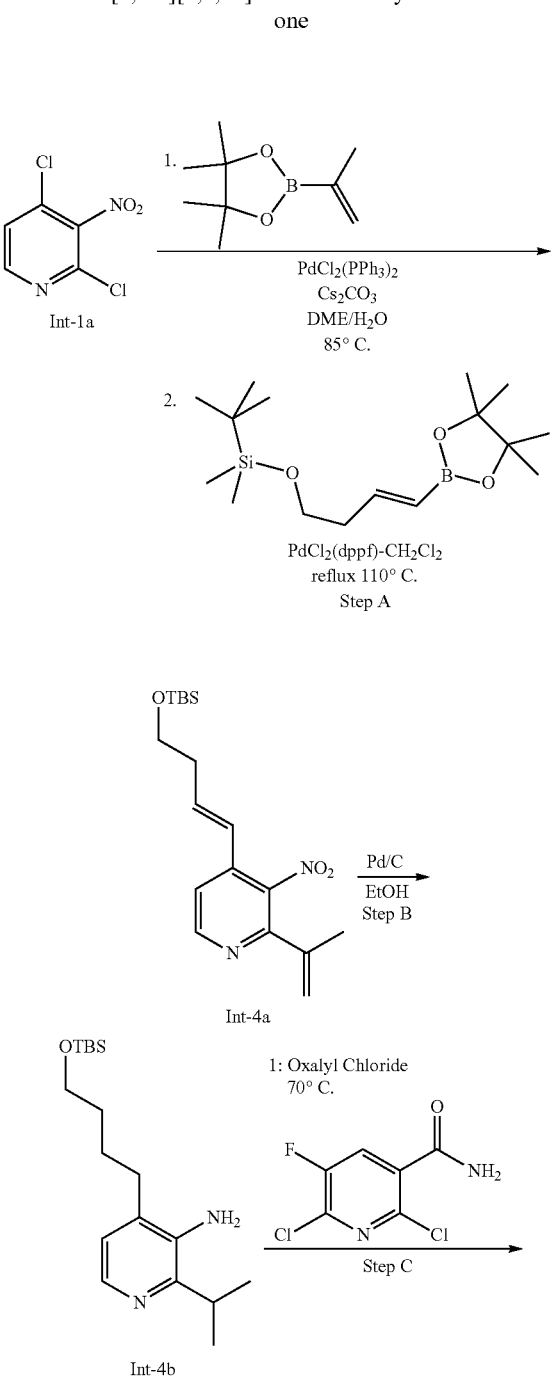

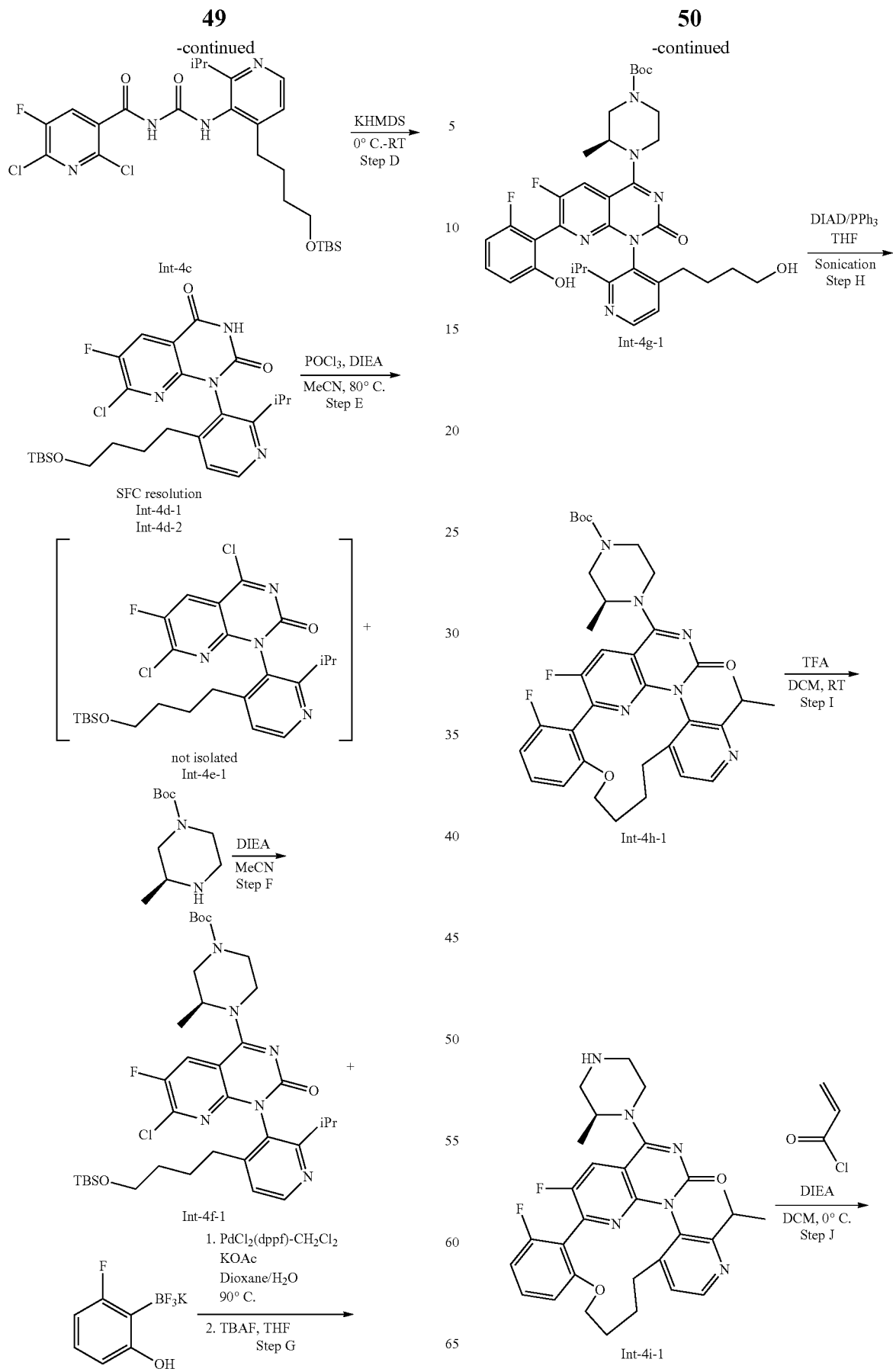

-continued

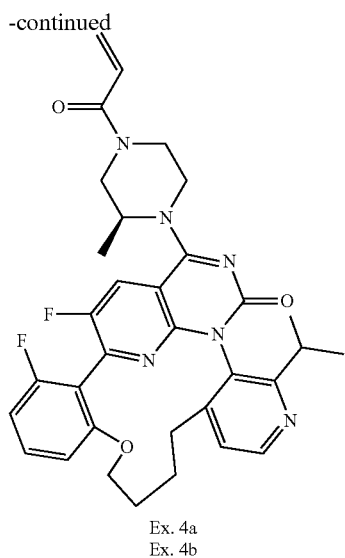

Ex. 4a
Ex. 4b

Step, A: (E)-4-(4-((tert-butyldimethylsilyl)oxy)but-1-en-1-yl)-3-nitro-2-(prop-1-en-2-yl)pyridine. (Int-4a)

2,4-Dichloro-3-nitropyridine (Int-1a) (10.7 g, 55.5 mmol), cesium carbonate (63.3 g, 194 mmol), bis(triphenylphosphite) palladium(II) dichloride (3.90 g, 5.55 mmol) were added to a 250 mL round-bottomed flask equipped with magnetic stir bar, degassed under nitrogen, charged with DME (90 mL)/water (22.5 mL), degassed two times under nitrogen, charged with isopropenylboronic acid pinacol ester (11.0 mL, 58.3 mmol). The flask was fitted with a reflux condenser and allowed to stir for 5 h at 85° C. The reaction was cooled to room temperature in an ice bath and over a funnel of argon, charged with (E)-tert-butyldimethyl((4-(4,4,5,5-tetramethyl-1,3,2-dioxaborolan-2-yl)but-3-en-1-yl)oxy)silane (22.7 mL, 63.8 mmol) and 1,1'-bis(diphenylphosphino)ferrocene-palladium(II) dichloride dichloromethane complex (4.53 g, 5.55 mmol). The reaction was degassed 3 times under nitrogen and heated to reflux at 110° C. for 16 h. The reaction was diluted with 300 mL EtOAc and 200 mL saturated ammonium chloride. The aqueous and organic layers were filtered through a pad of CELITE and the organic layer was separated. The aqeuous layer was extracted with 250 mL EtOAc. The combined organics were washed with brine, dried over sodium sulfate, filtered and concentrated in vacuo. The residue obtained was purified on silica gel 0-40% EtOAc/hexanes, followed by slow gradient 0-15% EtOAc/hexanes to provide (E)-4-(4-((tert-butyldimethylsilyl)oxy)but-1-en-1-yl)-3-nitro-2-(prop-1-en-2-yl)pyridine (Int-4a). MS (ESI) [M+H]⁺ m/z:349.

Step B: 4-(4-((tert-butyldimethylsilyl)oxy)butyl)-2-isopropylpyridin-3-amine (Int-4b)

4-(4-((tert-Butyldimethylsilyl)oxy)butyl)-3-nitro-2-(prop-1-en-2-yl)pyridine (1.67 g, 4.76 mmol) was dissolved in EtOH (24.0 mL), degassed under nitrogen, charged with Pd—C (0.101 g, 0.953 mmol), degassed under nitrogen, and allowed to stir under hydrogen atmosphere overnight. The reaction was filtered through a pad of CELITE and concentrated in vacuo. The residue was dissolved in 5 mL DCM and filtered through 0.2 uM filter to remove trace residual palladium on carbon to provide 4-(4-((tert-butyldimethylsilyl)oxy)butyl)-2-isopropylpyridin-3-amine. (Int-4b) MS (ESI) [M+H]⁺ m/z:323. ¹H NMR (500 MHz, CDCl₃) δ 8.00 (d, J=4.8 Hz, 1H), 6.86 (d, J=4.8 Hz, 1H), 3.70 (m, 4H), 3.07 (hept, J=6.7 Hz, 1H), 2.55-2.50 (m, 2H), 1.73 (m, 2H), 1.68-1.62 (m, 2H), 1.33 (m, 6H), 0.92 (s, 9H), 0.08 (s, 6H).

Step C: N-((4-(4-((tert-butyldimethylsily)oxy)butyl)-2-isopropylpyridin-3-yl)carbamoyl)-2,6-dichloro-5-fluoronicotinamide (Int-4c)

To a stirred solution of 2,6-dichloro-5-fluoronicotinamide (4.42 g, 21.2 mmol) in THF (20 mL) at 75° C. was added a 2 M solution of oxalyl chloride in DCM (12.5 mL, 25.0 mmol) and the reaction was heated to 75° C. with reflux condenser attached for 1 h. The reaction was evaporated in vacuo and dried under high vacuum for 30 minutes. The residue was charged with 20 mL THF, cooled to 0° C. and a solution of 4-(4-((tert-butyldimethylsilyl)oxy)butyl)-2-isopropylpyridin-3-amine (6.20 g, 19.2 mmol) in THF (10 mL) was added dropwise. The reaction was allowed to stir for 1 h at 0° C. then was quenched at 0° C. with saturated ammonium chloride, and diluted with 100 mL EtOAc. The reaction was washed with brine, dried over sodium sulfate, filtered and concentrated in vacuo. Purification on silica gel, 0-50% 3:1 EtOAc-EtOH/DCM gave N-((4-(4-((tert-butyldimethylsilyl)oxy)butyl)-2-isopropylpyridin-3-yl)carbamoyl)-2,6-dichloro-5-fluoronicotinamide (Int-4c). MS (ESI) [M+H]⁺ m/z 557/559.

Step D: 1-(4-(4-((tert-butyldimethylsilyl)oxy)butyl-2-isopropylpyridin-3-yl-7-chloro-6-fluoropyrido[2,3-d]pyrimidine-2,4(1H.3H)-dione (Peak 1 SFC) (Int-4d-1)

N-((4-(4-((tert-Butyldimethylsilyl)oxy)butyl)-2-isopropylpyridin-3-yl)carbamoyl)-2,6-dichloro-5-fluoronicotinamide (5.10 g, 9.15 mmol) was dissolved in THF (15.2 mL), cooled to 0° C., charged with KHMDS (19.2 mL, 19.2 mmol) and allowed to warm to rt for 1h. The reaction was cooled to 0° C., quenched with 100 mL saturated ammonium chloride, extracted 2×150 mL EtOAc, washed with brine, dried over sodium sulfate, filtered and concentrated in vacuo. The residue was purified on silica gel, 0-100% 3:1 EtOAc/EtOH/DCM to provide 1-(4-(4-((tert-butyldimethylsilyl)oxy)butyl)-2-isopropylpyridin-3-yl)-7-chloro-6-fluoropyrido[2,3-d]pyrimidine-2,4(1H,3H)-dione (mixture of atropisomers). The product was resolved by SFC, Column Q, Condition: 100% MeOH, 15% modifier in CO₂, to provide:
Peak 1-Int-4d-1—1-(4-(4-((tert-butyldimethylsilyl)oxy)butyl)-2-isopropylpyridin-3-yl)-7-chloro-6-fluoropyrido[2,3-d]pyrimidine-2,4(1H,3H)-dione. MS (ESI) [M+H]⁺ m/z 521; and
Peak 2-Int-4d-2—1-(4-(4-((tert-butyldimethylsilyl)oxy)butyl)-2-isopropylpyridin-3-yl)-7-chloro-6-fluoropyrido[2,3-d]pyrimidine-2,4(1H,3H)-dione. MS (ESI) [M+H]⁺ m/z 521.

Steps E and F: tert-Butyl (S)-4-(1-(4-(4-((tert-butyldimethylsilyl)oxy)butyl-2-isopropylpyridin-3-yl)-7-chloro-6-fluoro-2-oxo-1,2-dihydropyrido[2,3-d]pyrimidin-4-yl-3-methylpiperazine-1-carboxylate (Int-4f-1)

1-(4-(4-((tert-Butyldimethylsilyl)oxy)butyl)-2-isopropylpyridin-3-yl)-7-chloro-6-fluoropyrido[2,3-d]pyrimidine-2, 4(1H,3H)-dione (Peak 1 SFC) (Int-4d-1) (1.80 g, 3.45 mmol) was charged with acetonitrile (17.3 mL), DIEA (1.81 mL, 10.36 mmol), POCl₃ (0.386 mL, 4.15 mmol) degassed under nitrogen and heated to 80° C. for 30 minutes. The reaction mixture containing 1-(4-(4-((tert-butyldimethylsilyl)oxy)butyl)-2-isopropylpyridin-3-yl)-4,7-dichloro-6-fluoropyrido[2,3-d]pyrimidin-2(1H)-one (Int-4e-1) was cooled to 0° C., charged with DIEA (1.81 mL, 10.4 mmol) and tert-butyl (S)-3-methylpiperazine-1-carboxylate (0.830 g, 4.15 mmol) and allowed to stir at that temperature for 20 minutes. The reaction was quenched with 10 mL water, extracted 2×25 mL EtOAc, washed with brine, dried over sodium sulfate, filtered, concentrated and purified on silica gel, 0-100% 3:1 EtOAc/EtOH/hexanes to provide tert-butyl (S)-4-(1-(4-(4-((tert-butyldimethylsilyl)oxy)butyl)-2-isopropylpyridin-3-yl)-7-chloro-6-fluoro-2-oxo-1,2-dihydropyrido[2,3-d]pyrimidin-4-yl)-3-methylpiperazine-1-carboxylate (Int-4f-1). MS (ESI) [M+H]⁺ m/z 703.

Step G: tert-Butyl (3S)-4-(6-fluoro-7-(2-fluoro-6-hydroxyphenyl)-1-(4-(4-hydroxybutyl)-2-isopropylpyridin-3-yl)-2-oxo-1,2-dihydropyrido[2,3-d]pyrimidin-4-yl)-3-methylpiperazine-1-carboxylate (Int-4g-1)

tert-Butyl (S)-4-(1-(4-(4-((tert-butyldimethylsilyl)oxy)butyl)-2-isopropylpyridin-3-yl)-7-chloro-6-fluoro-2-oxo-1,2-dihydropyrido[2,3-d]pyrimidin-4-yl)-3-methylpiperazine-1-carboxylate (1.50 g, 2.13 mmol), 3-fluoro-2-(trifluoro-λ⁴-boranyl)phenolate (602 mg, 2.77 mmol), potassium acetate (837 mg, 8.53 mmol), 1,1'-bis(diphenylphosphino)ferrocene-palladium(II) dichloride dichloromethane complex (174 mg, 0.213 mmol) were added to a 20 mL scintillation vial equipped with magnetic stir bar, degassed under nitrogen, charged with dioxane (9 mL)/water (1.5 mL), degassed 3 times under nitrogen and heated to 90° C. for 1 h. The reaction was cooled to room temperature, quenched with 10 mL 1:1 water/saturated sodium bicarbonate, extracted 2×25 mL EtOAc, washed with brine and concentrated in vacuo. The crude residue was taken up in 10 mL THF, charged with a 1 M solution of TBAF in THF (6.40 mL, 6.40 mmol) and allowed to stir for 1.5 h at room temperature. The reaction was quenched with 50 mL saturated NH₄Cl/100 mL EtOAc and allowed to stir for 5 minutes with vigorous stirring. The organic layer was separated, washed 1×25 mL saturated ammonium chloride, 25 mL brine, dried over sodium sulfate, filtered, concentrated in vacuo, and purified on silica gel 0-100% 3:1 EtOAC/EtOH/hexanes to provide tert-butyl (3S)-4-(6-fluoro-7-(2-fluoro-6-hydroxyphenyl)-1-(4-(4-hydroxybutyl)-2-isopropylpyridin-3-yl)-2-oxo-1,2-dihydropyrido[2,3-d]pyrimidin-4-yl)-3-methylpiperazine-1-carboxylate (Int-4g-1). MS (ESI) [M+H]⁺ m/z 665.

Step H: (Int-4h-1)

tert-Butyl (3S)-4-(6-fluoro-7-(2-fluoro-6-hydroxyphenyl)-1-(4-(4-hydroxybutyl)-2-isopropylpyridin-3-yl)-2-oxo-1,2-dihydropyrido[2,3-d]pyrimidin-4-yl)-3-methylpiperazine-1-carboxylate (1.10 g, 1.66 mmol) and triphenylphosphine (1.09 g, 4.14 mmol) were charged with THF (66 mL), degassed under nitrogen, sonicated and charged with diisopropyl azodicarboxylate (652 µL, 3.31 mmol) dropwise. The reaction was sonicated for 30 minutes, the solvents were removed under vacuum, and the residue was purified on silica gel 0-100% 3:1 EtOAc/EtOH/hexanes to provide Int-4h-1. MS (ESI) [M+H]⁺ m/z 647.

Step I: Int-4i-1

Int-4i-1 (370 mg, 0.572 mmol) was dissolved in DCM (3.8 mL), charged with TFA (1.1 mL, 14.3 mmol) and allowed to stir for 20 minutes at rt. The solvents were removed in vacuo, and the residue was azeotroped 1×toluene/1×pentane to provide Int-4i-1 as a tris-TFA salt. MS (ESI) [M+H]⁺ m/z 547.

Step J: 18,21-difluoro-2-[(2S)-2-methyl-4-(prop-2-enoyl)piperazin-1-yl]-6-(propan-2-yl)-10,11,12,13-tetrahydro-4H-1,19-ethenopyrido[4,3-f]pyrimido[1,6-h][1,8,10]benzoxadiazacyclotridecin-4-one (Example 4a)

Int-4i-1+3TFA (385 mg, 0.433 mmol) was dissolved in DCM (5.8 mL), cooled to 0° C., charged with DIEA (378 µl, 2.17 mmol) followed by acryloyl chloride (38.7 µl, 0.48 mmol). The reaction was allowed to stir for 15 minutes and quenched with 2 mL saturated sodium bicarbonate, poured through phase separator, washed 1×6 mL DCM, evaporated in vacuo and purified on silica gel 0-100% hexanes (3:1 EtOAc/ethanol) to provide 18,21-difluoro-2-[(2S)-2-methyl-4-(prop-2-enoyl)piperazin-1-yl]-6-(propan-2-yl)-10,11,12,13-tetrahydro-4H-1,19-ethenopyrido[4,3-]pyrimido[1,6-h][1,8,10]benzoxadiazacyclotridecin-4-one (Example 4a). MS (ESI) [M+H]⁺ m/z 601. ¹H NMR (500 MHz, DMSO-d₆) δ 8.39 (d, J=4.9 Hz, 1H), 8.36-8.27 (m, 1H), 7.46 (q, J=8.3 Hz, 1H), 7.16 (d, J=4.9 Hz, 1H), 7.10 (d, J=8.4 Hz, 1H), 6.97 (t, J=8.7 Hz, 1H), 6.94-6.78 (m, 1H), 6.25-6.17 (m, 1H), 5.81-5.74 (m, 1H), 4.90 (br s, 1H), 4.46-4.36 (m, 2H), 4.31-4.11 (m, 1H), 4.06-3.98 (m, 2H), 3.91-3.83 (m, 1H), 3.72-3.6 (m, 1H), 3.61-3.52 (m, 1H), 3.29-3.11 (m, 1H), 2.73-2.56 (m, 2H), 2.45-2.35 (m, 1H), 1.36-1.29 (overlapped m, 4H), 1.30-1.11 (m, 1H), 1.05 (d, J=6.7 Hz, 3H), 0.83 (d, J=6.6 Hz, 3H).

18,21-Difluoro-2-[(2S)-2-methyl-4-(prop-2-enoyl)piperazin-1-yl]-6-(propan-2-yl)-10,11,12,13-tetrahydro-4H-1,19-ethenopyrido[4,3-f]pyrimido[1,6-h][1,8,10]benzoxadiazacyclotridecin-4-one (Example 4b)

Example 4b was prepared using the steps described above for Example 4a from the second eluting isomer from SFC, Int-4d-2.

Example 4b: MS (ESI) [M+H]⁺ m/z 601. ¹H NMR (500 MHz, DMSO-d₆) δ 8.45-8.32 (m, 2H), 7.46 (q, J=8.3 Hz, 1H), 7.16 (d, J=4.9 Hz, 1H), 7.10 (d, J=8.5 Hz, 1H), 6.96 (t, J=8.7 Hz, 1H), 6.94-6.79 (m, 1H), 6.25-6.17 (m, 1H), 5.8-5.74 (m, 1H), 5.02 (brs, 1H), 4.45-4.37 (m, 1H), 4.35-4.25 (m, 1H), 4.18-4.12 (m, 1H), 4.08-4.0 (m, 2H), 3.9-3.83 (m, 1H), 3.82-3.73 (m, 1H), 3.7-3.64 (m, 1H), 3.16-3.06 (m, 1H), 2.68-2.58 (m, 2H), 2.46-2.35 (m, 1H), 1.39-1.2 (overlapped m, 5H), 1.05 (d, J=6.7 Hz, 3H), 0.81 (d, J=6.5 Hz, 3H).

Examples 5 and 6 were prepared in a similar manner to Example 4a, with Int-4f-1 substituting (1H-pyrazol-5-yl) boronic or 7-(4,4,5,5-tetramethyl-1,3,2-dioxaborolan-2-yl)-1H-Indazole Acid for Step G.

| Ex. No. | Structure | Compound Name | [M + H]+ Found |
|---|---|---|---|
| 5 | 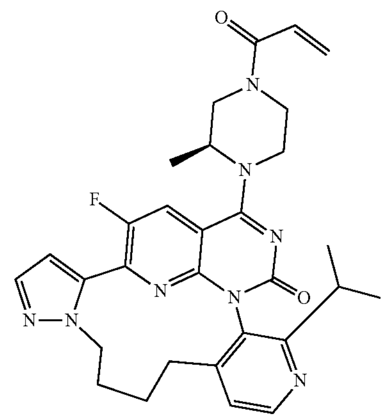 [SMILES: C=CC(=O)N1CCN(c2nc(=O)n3c4nc(c(F)cc24)-c2ccnn2CCCCc2ccnc(C(C)C)c2-3)[C@@H](C)C1] | 20-fluoro-2-[(2S)-2-methyl-4-(prop-2-enoyl)piperazin-1-yl]-6-(propan-2-yl)-10,11,12,13-tetrahydro-4H-1,18-(ethanediylidene)-pyrazolo[5,1-e]pyrido[4,3-k]pyrimido[1,6-a][1,3,6]triazacyclododecin-4-one | 557.3 |
| 6 | 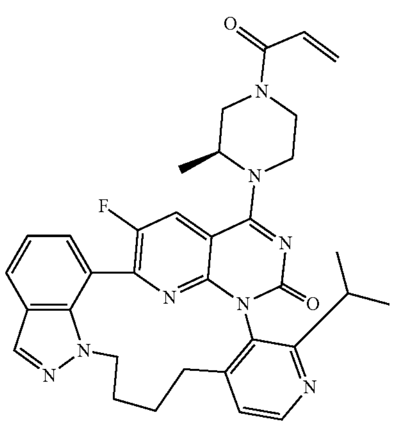 [SMILES: C=CC(=O)N1CCN(c2nc(=O)n3c4nc(c(F)cc24)-c2cccc4cnn(c24)CCCCc2ccnc(C(C)C)c2-3)[C@@H](C)C1] | 22-fluoro-2-[(2S)-2-methyl-4-(prop-2-enoyl)piperazin-1-yl]-6-(propan-2-yl)-10,11,12,13-tetrahydro-4H-1,20-(ethanediylidene)-pyrido[4',3':12,13]pyrimido[1',6':1,2][1,3,7]triazacyclotridecino[5,6,7-hi]indazol-4-one | 607.3 |

Example 7: 2-[(3R,5S)-3,5-dimethyl-4-(prop-2-enoyl)piperazin-1-yl]-18,21-difluoro-6-(propan-2-yl)-10,11,12,13-tetrahydro-4H-1,19-ethenopyrido[4,3-f]pyrimido[1,6-h][1,8,10]benzoxadiazacyclotridecin-4-one

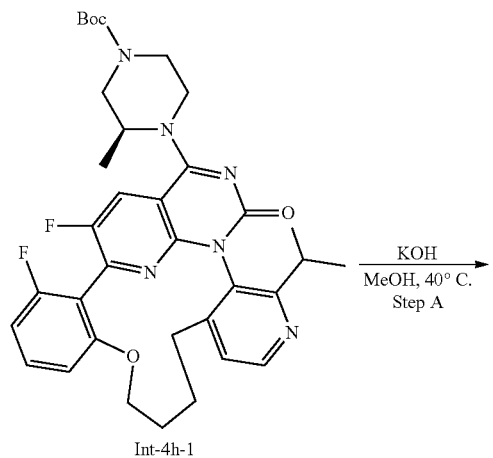

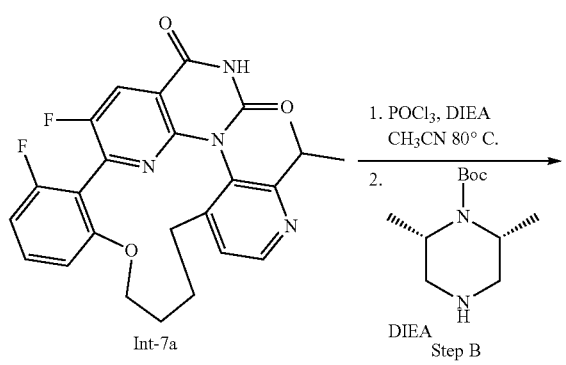

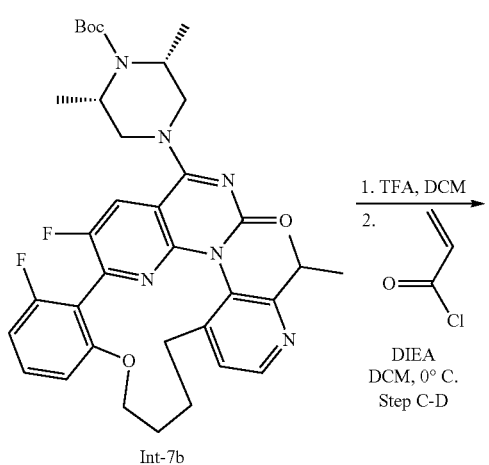

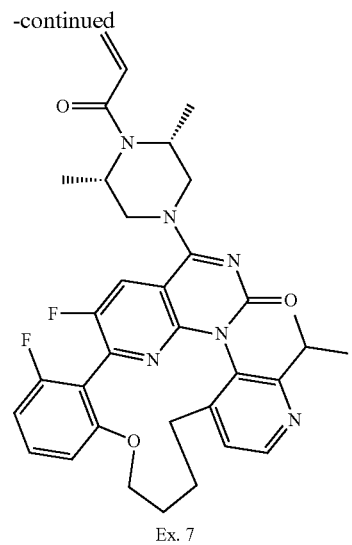

Step A: Int-7a

Int-4h-1 (330 mg, 0.510 mmol) was dissolved in MeOH (2.55 mL), charged with KOH (1 M in methanol) (1.53 mL, 1.53 mmol) and heated to 40° C. for 2 hrs, then allowed to cool to room temperature overnight. The reaction was diluted with 20 mL EtOAc, poured into 50 mL saturated ammonium chloride, stirred, and the organic layer was separated, washed with brine, dried over sodium sulfate, filtered and concentrated in vacuo. The residue obtained was purified on silica gel, 0-100%/3:1 EtOAc/EtOH/hexanes to provide Int-7a. MS (ESI) [M+H]+m/z 465.

Step B: Int-7b

Int-7a (16.5 mg, 0.036 mmol) was dissolved in acetonitrile (710 μL), charged with DIEA (18.6 μL, 0.107 mmol), POCl$_3$ (3.97 μL, 0.043 mmol) and heated to 80° C. for 30 minutes. The reaction was cooled to ° C., charged with additional portion of DIEA (18.61 μL, 0.107 mmol) and tert-butyl (2R,6S)-2,6-dimethylpiperazine-1-carboxylate (9.5 mg, 0.044 mmol) and allowed to warm to room temperature over 2 hrs. The reaction was concentrated in vacuo, purified on silica gel, 0-100%/3:1 EtOAc/EtOH/hexanes to provide Int-7b. MS (ESI) [M+H]+m/z 661.

Step C-D: Example 7

Int-7b (10 mg, 0.015 mmol) was dissolved in CH$_2$Cl$_2$, charged with TFA (58.3 μl, 0.757 mmol), allowed to stir at room temperature for 20 minutes, concentrated in vacuo, dissolved in CH$_2$Cl$_2$, charged with DIEA (13.2 μl, 0.076 mmol), cooled to 0° C., and charged with acryloyl chloride (1.2 μl, 0.015 mmol) and allowed to stir for 30 minutes. The reaction was quenched with 1 mL saturated sodium bicarbonate, poured through a phase separator, washed 1×3 mL CH$_2$Cl$_2$, concentrated and purified on silica gel, 0-100% 3:1 EtOAc/EtOH/hexanes to provide 2-[(3R,5S)-3,5-dimethyl-4-(prop-2-enoyl)piperazin-1-yl]-18,21-difluoro-6-(propan-2-yl)-10,11,12,13-tetrahydro-4H-1,19-ethenopyrido[4,3-f]pyrimido[1,6-h][1,8,10]benzoxadiazacyclotridecin-4-one (Ex. 7). MS (ESI) [M+H]$^+$ m/z 615.

Example 8 was prepared in a similar manner to Example 7, with Int-7a substituting tert-butyl (2R,5S)-2,5-dimethylpiperazine-1-carboxylate acid for the piperazine component in Step B.

| Ex. No. | Structure | Compound Name | [M + H]+ Found |
|---|---|---|---|
| 8 | 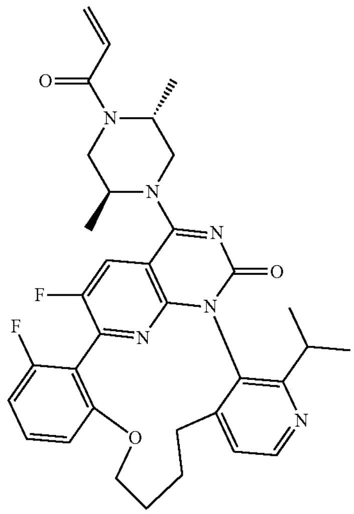 [SMILES: C=CC(=O)N1C[C@H](C)N(c2nc(=O)n3c4nc(c(F)cc24)-c2c(F)cccc2OCCCCc2ccnc(C(C)C)c2-3)C[C@H]1C] | 2-[(2S,5R)-2,5-dimethyl-4-(prop-2-enoyl)piperazin-1-yl]-18,21-difluoro-6-(propan-2-yl)-10,11,12,13-tetrahydro-4H-1,19-ethenopyrido[4,3-f]-pyrimido[1,6-h][1,8,10]ben-zoxadiazacyclotridecin-4-one | 615.3 |
Example 9: 19-Chloro-16-fluoro-2-[(2S)-2-methyl-4-(prop-2-enoyl)piperazin-1-yl]-10,11-dihydro-4H-1,17-ethenodibenzo[b,h]pyrimido[6,1-f][1,5,7]oxadi-azacycloundecin-4-one
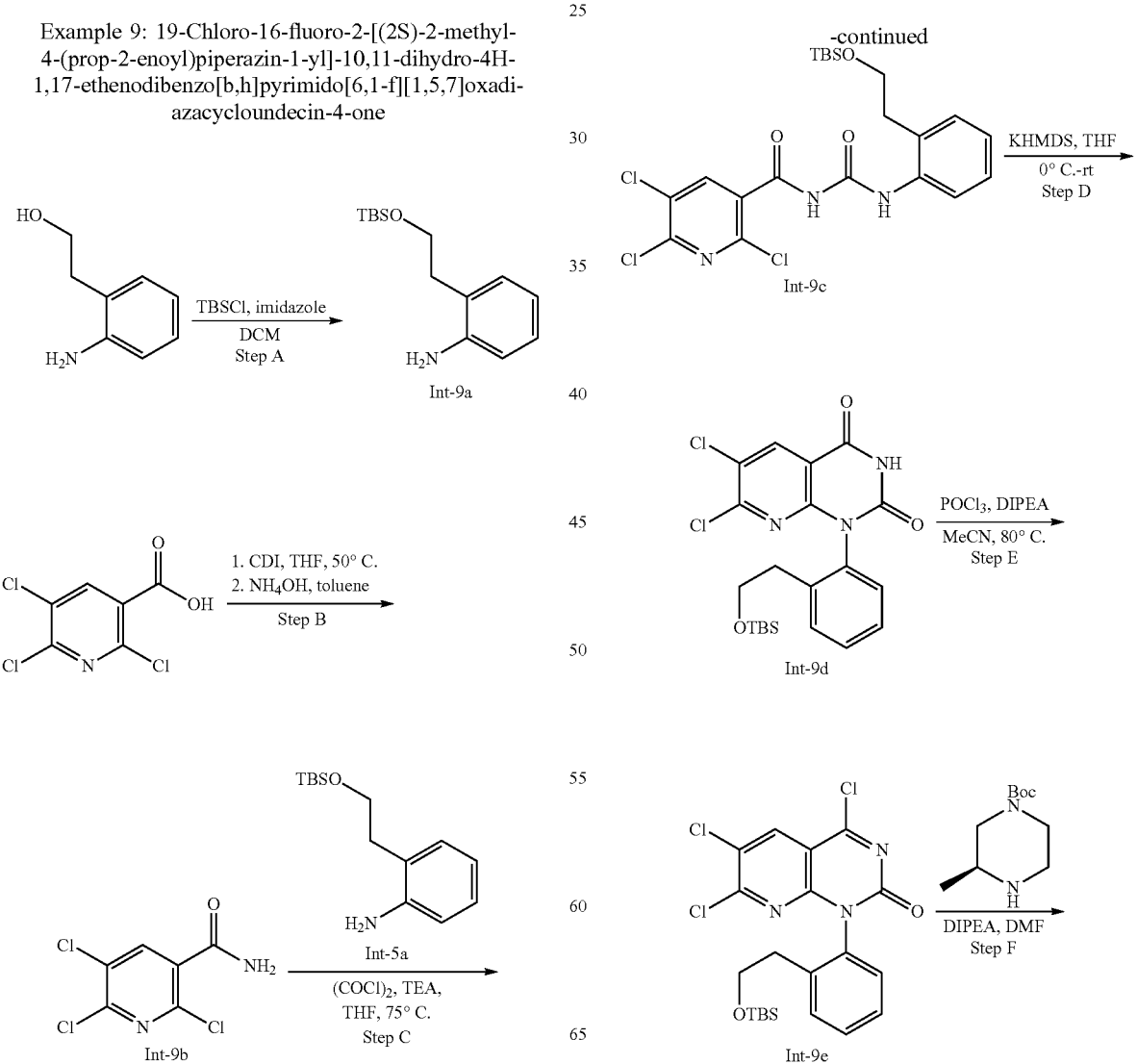

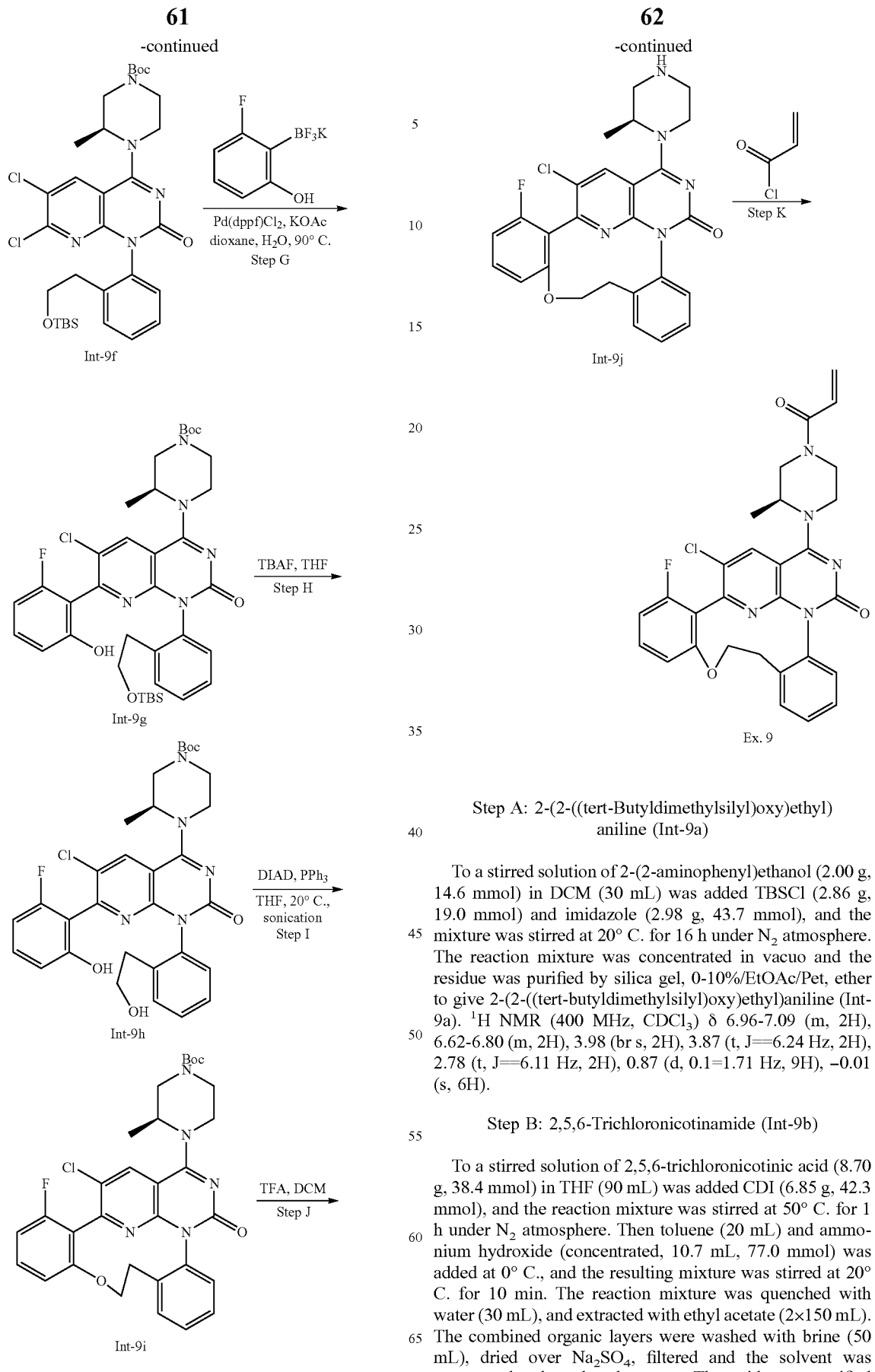

Step A: 2-(2-((tert-Butyldimethylsilyl)oxy)ethyl)aniline (Int-9a)

To a stirred solution of 2-(2-aminophenyl)ethanol (2.00 g, 14.6 mmol) in DCM (30 mL) was added TBSCl (2.86 g, 19.0 mmol) and imidazole (2.98 g, 43.7 mmol), and the mixture was stirred at 20° C. for 16 h under $N_2$ atmosphere. The reaction mixture was concentrated in vacuo and the residue was purified by silica gel, 0-10%/EtOAc/Pet, ether to give 2-(2-((tert-butyldimethylsilyl)oxy)ethyl)aniline (Int-9a). $^1$H NMR (400 MHz, CDCl$_3$) δ 6.96-7.09 (m, 2H), 6.62-6.80 (m, 2H), 3.98 (br s, 2H), 3.87 (t, J=6.24 Hz, 2H), 2.78 (t, J=6.11 Hz, 2H), 0.87 (d, 0.1=1.71 Hz, 9H), -0.01 (s, 6H).

Step B: 2,5,6-Trichloronicotinamide (Int-9b)

To a stirred solution of 2,5,6-trichloronicotinic acid (8.70 g, 38.4 mmol) in THF (90 mL) was added CDI (6.85 g, 42.3 mmol), and the reaction mixture was stirred at 50° C. for 1 h under $N_2$ atmosphere. Then toluene (20 mL) and ammonium hydroxide (concentrated, 10.7 mL, 77.0 mmol) was added at 0° C., and the resulting mixture was stirred at 20° C. for 10 min. The reaction mixture was quenched with water (30 mL), and extracted with ethyl acetate (2×150 mL). The combined organic layers were washed with brine (50 mL), dried over Na$_2$SO$_4$, filtered and the solvent was evaporated under reduced pressure. The residue was purified Step C: N-((2-(2-((tert-Butyldimethylsilyl)oxy)ethyl)
phenyl)carbamoyl)-2,5,6-trichloronicotinamide (Int-9c)

To a stirred solution of 2,5,6-trichloronicotinamide (Int-9b) (2.50 g, 11.1 mmol) in THF (50 mL) was added oxalyl chloride (0.932 mL, 10.6 mmol) at 20° C., and the mixture was stirred at 65° C. for 30 min under $N_2$ atmosphere. Then it was cooled to 20° C. and 2-(2-((tert-butyldimethylsilyl) oxy)ethyl)aniline (Int-9a) (2.93 g, 11.6 mmol) was added. The resulting mixture was stirred at 20° C. for 16 h. The reaction mixture was quenched with brine (40 mL), and extracted with ethyl acetate (2×60 mL). The combined organic layers were washed with brine (30 mL), dried over $Na_2SO_4$, filtered and the solvent was evaporated under reduced pressure. The residue was purified on silica gel, 0-30% EtOAc/Pet. ether to give N-((2-(2-((tert-butyldimethylsilyl)oxy)ethyl)phenyl)carbamoyl)-2,5,6-trichloronicotinamide (Int-9c). MS (ESI): $[M+H]^+$ m/z 502.3/504.3

Step D: 1-(2-(2-((tert-Butyldimethylsilyl)oxy)ethyl)
phenyl)-6,7-dichloropyrido[2,3-d]pyrimidine-2,4
(1H,3H)-dione (Int-9d)

To a stirred solution of N-((2-(2-((tert-butyldimethylsilyl) oxy)ethyl)phenyl)carbamoyl)-2,5,6-trichloronicotinamide (3.00 g, 5.97 mmol) in THF (50 mL) was added a 1 M solution of potassium bis(trimethylsilyl)amide in THF (11.9 mL, 11.9 mmol) at 0° C., and the mixture was stirred at 20° C. for 30 min under $N_2$ atmosphere. The reaction mixture was quenched with aqueous ammonium chloride (saturated, 35 mL), and extracted with ethyl acetate (2×80 mL). The combined organic layers were washed with brine (20 mL), dried over $Na_2SO_4$, filtered and the solvent was evaporated under reduced pressure to provide 1-(2-(2-((tert-butyldimethylsilyl)oxy)ethyl)phenyl)-6,7-dichloropyrido[2,3-d]pyrimidine-2,4(1H,3H)-dione (Int-9d). The crude product was used in the next step without further purification. MS (ESI): $[M+H]^+$ m/z 466.2/468.1

Step E: 1-(2-(2-((tert-Butyldimethylsilyl)oxy)ethyl)
phenyl)-4,6,7-trichloropyrido[2,3-d]pyrimidin-2
(1H)-one (Int-9e)

To a stirred solution of 1-(2-(2-((tert-butyldimethylsilyl) oxy)ethyl)phenyl)-6,7-dichloropyrido[2,3-d]pyrimidine-2,4 (1H,3H)-dione (2.30 g, 4.93 mmol) in acetonitrile (50 mL) was added DIEA (2.15 mL, 12.3 mmol) and $POCl_3$ (0.689 mL, 7.40 mmol) at 25° C., and the mixture was stirred at 80° C. for 1 h under $N_2$ atmosphere. The reaction mixture was concentrated to afford 1-(2-(2-((tert-butyldimethylsilyl)oxy) ethyl)phenyl)-4,6,7-trichloropyrido[2,3-d]pyrimidin-2(1H)-one (Int-9e), which was used in next step without further purification. MS (ESI): m/z (M+H)+ 484.0/486.0.

Step F: tert-Butyl (S)-4-(1-(2-(2-((tert-butyldimethylsilyl)oxy)ethyl)phenyl)-6,7-dichloro-2-oxo-1,2-
dihydropyrido[2,3-d]pyrimidin-4-yl)-3-methylpiperazine-1-carboxylate (Int-9f)

To a stirred solution of 1-(2-(2-((tert-butyldimethylsilyl) oxy)ethyl)phenyl)-4,6,7-trichloropyrido[2,3-d]pyrimidin-2 (1H)-one (2.39 g, 4.93 mmol) in DMF (40 mL) was added DIEA (2.15 mL, 12.3 mmol) and (S)-tert-butyl 3-methylpiperazine-1-carboxylate (1.23 g, 6.16 mmol) at 20° C., and the mixture was stirred at 20° C. for 16 h under $N_2$ atmosphere. The reaction mixture was concentrated, and the residue was purified on silica gel, 0-40% EtOAc/Pet. ether to give (S)-tert-butyl 4-(1-(2-(2-((tert-butyldimethylsilyl)oxy)ethyl) phenyl)-6,7-dichloro-2-oxo-1,2-dihydropyrido[2,3-d]pyrimidin-4-yl)-3-methylpiperazine-1-carboxylate (Int-9f). MS (ESI): $[M+H]^+$ m/z 648.2/650.2.

Step G: tert-Butyl (3S)-4-(1-(2-(2-((tert-butyldimethylsilyl)oxy)ethyl)phenyl)-6-chloro-7-(2-fluoro-6-
hydroxyphenyl)-2-oxo-1,2-dihydropyrido[2,3-d]
pyrimidin-4-yl)-3-methylpiperazine-1-carboxylate
(Int-9g)

To a stirred solution of (S)-tert-butyl 4-(1-(2-(2-((tert-butyldimethylsilyl)oxy)ethyl)phenyl)-6,7-dichloro-2-oxo-1, 2-dihydropyrido[2,3-d]pyrimidin-4-yl)-3-methylpiperazine-1-carboxylate (1.00 g, 1.54 mmol), potassium acetate (0.756 g, 7.71 mmol) and 1,1'-bis(diphenylphosphino)ferrocene-palladium(II)dichloride dichloromethane complex (0.063 g, 0.077 mmol) in 1,4-dioxane (10 mL) and water (2 mL) was added 3-fluoro-2-(trifluoro-$\lambda^4$-boraneyl)phenol, potassium salt (0.538 g, 2.47 mmol) in 1,4-dioxane (3 mL) at 90° C. under $N_2$ atmosphere, and the mixture was stirred at 20° C. for 2 h under $N_2$ atmosphere. The reaction mixture was quenched with brine (20 mL), and extracted with ethyl acetate (2×30 mL). The combined organic layers were washed with brine (20 mL), dried over $Na_2SO_4$, filtered and the solvent was evaporated under reduced pressure. The residue was purified on silica gel, 0-50% EtOAc/Pet. ether to give (3S)-tert-butyl 4-(1-(2-(2-((tert-butyldimethylsilyl) oxy)ethyl)phenyl)-6-chloro-7-(2-fluoro-6-hydroxyphenyl)-2-oxo-1,2-dihydropyrido[2,3-d]pyrimidin-4-yl)-3-methylpiperazine-1-carboxylate (Int-9g). MS (ESI): $[M+H]^+$ m/z 724.4.

Step H: tert-Butyl (3S)-4-(6-chloro-7-(2-fluoro-6-
hydroxyphenyl)-1-(2-(2-hydroxyethyl)phenyl)-2-
oxo-1,2-dihydropyrido[2,3-d]pyrimidin-4-yl)-3-
methylpiperazine-1-carboxylate (Int-9h)

To a stirred solution of (3S)-tert-butyl 4-(1-(2-(2-((tert-butyldimethylsilyl)oxy)ethyl)phenyl)-6-chloro-7-(2-fluoro-6-hydroxyphenyl)-2-oxo-1,2-dihydropyrido[2,3-d]pyrimidin-4-yl)-3-methylpiperazine-1-carboxylate (1.00 g, 1.38 mmol) in THF (10 mL) was added a 1 M solution of TBAF in THF (4.14 mL, 4.14 mmol), and the mixture was stirred at 20° C. for 16 h under $N_2$ atmosphere. The reaction mixture was concentrated in vacuo, and the residue was purified on silica gel, 0-8% MeOH/DCM to give (3S)-tert-butyl 4-(6-chloro-7-(2-fluoro-6-hydroxyphenyl)-1-(2-(2-hydroxyethyl)phenyl)-2-oxo-1,2-dihydropyrido[2,3-d]pyrimidin-4-yl)-3-methylpiperazine-1-carboxylate (Int-9h) MS (ESI): $[M+H]^+$ m/z 610.4

Step I: Int-9i

To a stirred solution of (3S)-tert-butyl 4-(6-chloro-7-(2-fluoro-6-hydroxyphenyl)-1-(2-(2-hydroxyethyl)phenyl)-2-oxo-1,2-dihydropyrido[2,3-d]pyrimidin-4-yl)-3-methylpiperazine-1-carboxylate (300 mg, 0.492 mmol) in THF (30 mL) was added triphenylphosphine (871 mg, 1.23 mmol) (37% load on resin), and then DIAD (0.096 mL, 0.492 mmol) was added at 70° C. The mixture was stirred at 70° C. for 1 h under $N_2$ atmosphere. The mixture was filtered and the filter cake was washed with dichloromethane (30 mL). The filtrate was concentrated in vacuo and the residue was purified by preparative HPLC water (10 mM NH₄HCO₃)/MCCN to provide Int-9i. MS (ESI): [M+H]⁺ m/z 592.2

Step J: Int-9i

To a stirred solution of Int-9i (20 mg, 0.034 mmol) in DCM (2 mL) was added TFA (0.5 mL), and the mixture was stirred at 20° C. for 30 min under N₂ atmosphere. The reaction mixture was concentrated in vacuo, and the residue was purified by preparative HPLC water (10 mM NH₄HCO₃)/MCCN to provide Int-9j. MS (ESI): [M+H]⁺ m/z 492.2

Step K: 19-Chloro-16-fluoro-2-[(2S)-2-methyl-4-(prop-2-enoyl)piperazin-1-yl]-10,11-dihydro-4H-1,17-ethenodibenzo[b,h]pyrimido[6,1-f][1,5,7]oxadi-azacycloundecin-4-one (Ex. 9)

To a stirred solution of Int-9j+TFA (20.5 mg, 0.034 mmol) in DCM (1.0 mL) was added DIEA (0.024 mL, 0.135 mmol) and acryloyl chloride (3.67 mg, 0.041 mmol), and the mixture was stirred at 20° C. for 30 min under N₂ atmosphere. It was concentrated and The residue was purified by preparative HPLC, water (10 mM NH₄HCO₃)/MCCN to provide 19-chloro-16-fluoro-2-[(2S)-2-methyl-4-(prop-2-enoyl)piperazin-1-yl]-10,11-dihydro-4H-1,17-ethenodibenzo[b,h]pyrimido[6,1-f][1,5,7]oxadiazacycloundecin-4-one (Ex. 9) as a mixture of atropisomers. MS (ESI): [M+H]⁺ m/z 546.2 (400 MHz, methanol-d₄) δ 8.43-8.30 (m, 1H), 7.47-7.38 (m, 1H), 7.37-7.27 (m, 3H), 7.20 (br d, J=8.07 Hz, 1H), 6.97 (d, J=8.31 Hz, 1H), 6.91-6.75 (m, 2H), 6.31 (br d, J=16.14 Hz, 1H), 5.84 (dd, J=1.83, 10.64 Hz, 1H), 5.32 (br s, 1H), 4.96 (br d, J=9.54 Hz, 1H), 4.81 (br s, 1H), 4.74-4.59 (m, 1H), 4.57-4.35 (m, 1H), 4.27-3.96 (m, 2H), 3.78-3.40 (m, 2H), 2.95 (br dd, J=7.70, 13.57 Hz, 1H), 2.36 (br dd, J=6.36, 15.41 Hz, 1H), 1.57-1.36 (m, 3H).

Examples 10-15

Preparation of 4-(3-((tert-Butyldimethylsilyl)oxy)propyl)-2-isopropylpyridin-3-amine (Int-10c)

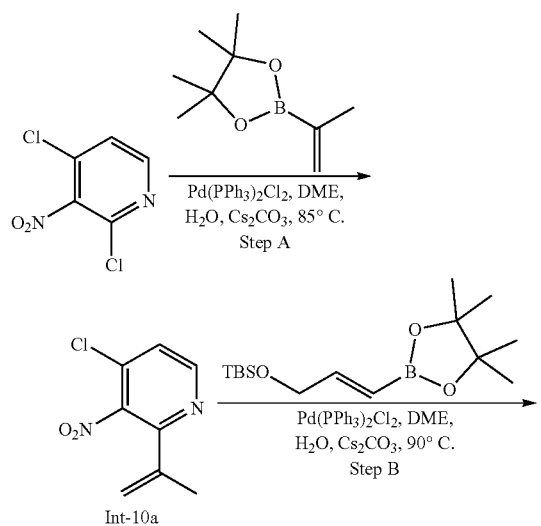

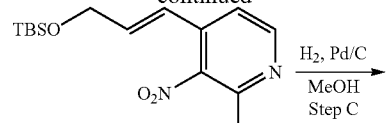

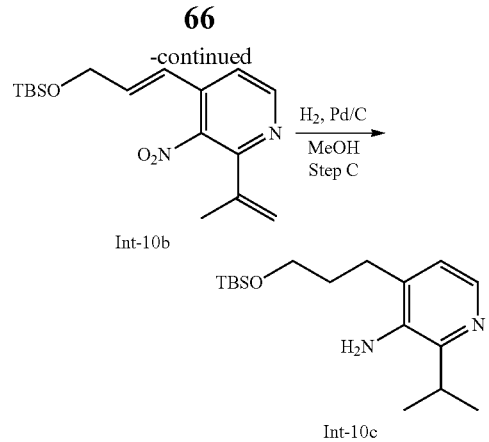

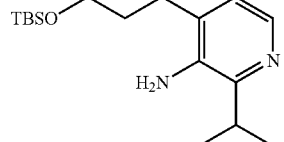

Step A: 4-Chloro-3-nitro-2-(prop-1-en-2-yl)pyridine (Int-10a)

A stirred solution of 2,4-dichloro-3-nitropyridine (11.0 g, 57.0 mmol) in DME (150 mL) and water (30 mL) was added Cs₂CO₃ (55.7 g, 171 mmol), 4,4,5,5-tetramethyl-2-(prop-1-en-2-yl)-1,3,2-dioxaborolane (9.58 g, 57.0 mmol) and bis(triphenylphosphine)palladium(II) dichloride (4.00 g, 5.70 mmol), and the resulting mixture was stirred at 85° C. for 16 h. The reaction mixture was cooled to room temperature and extracted with EtOAc (200 mL×3). The combined organic phase was dried over anhydrous Na₂SO₄, filtered and concentrated in vacuo. The residue was purified on silica gel, Pet. ether/EtOAc=10/1 to give 4-chloro-3-nitro-2-(prop-1-en-2-yl)pyridine (Int-10a). MS (ESI): [M+H]⁺ m/z 198.8.

Step B: (E)-4-(3-((tert-Butyldimethylsilyl)oxy)prop-1-en-1-yl)-3-nitro-2-(prop-1-en-2-yl)pyridine (Int-10b)

A stirred solution of 4-chloro-3-nitro-2-(prop-1-en-2-yl)pyridine (10.0 g, 50.4 mmol) in DME (100 mL) and water (20 mL) was added Cs₂CO₃ (49.2 g, 151 mmol), (E)-tert-butyldimethyl((3-(4,4,5,5-tetramethyl-1,3,2-dioxaborolan-2-yl)allyl)oxy)silane (16.52 g, 55.4 mmol) and bis(triphenylphosphine)palladium(II) dichloride (3.53 g, 5.04 mmol), and the resulting mixture was stirred at 90° C. for 16 h. The reaction was cooled to room temperature and extracted with EtOAc (200 mL×3). The combined organic phase was dried over anhydrous Na₂SO₄, filtered and concentrated in vacuo. The residue was purified on silica gel, eluting with Pet. ether/EtOAc=5/1, to give (E)-4-(3-((tert-butyldimethylsilyl)oxy)prop-1-en-1-yl)-3-nitro-2-(prop-1-en-2-yl)pyridine MS (ESI): [M+H]⁺ m/z 335.1.

Step C: 4-(3-((tert-Butyldimethylsilyl)oxy)propyl)-2-isopropylpyridin-3-amine (Int-10c)

To a mixture of (E)-4-(3-((tert-butyldimethylsilyl)oxy)prop-1-en-1-yl)-3-nitro-2-(prop-1-en-2-yl)pyridine (9.2 g, 27.5 mmol) in MeOH (300 mL) was added dry Pd—C (2.93 g, 27.5 mmol, 10% w/w) under argon atmosphere, and the mixture was degassed and purged with H₂ for three times and stirred at 25° C. for 15 h under H₂ atmosphere (40 psi). The reaction mixture was filtered and concentrated in vacuo to give crude product. The crude product was purified on silica gel, 0-30% EtOAc/Pet. ether to give 4-(3-((tert-butyldimethylsilyl)oxy)propyl)-2-isopropylpyridin-3-amine (Int-10c). MS (ESI): [M+H]⁺ m/z 309.3. ¹H NMR (400

MHz, CDCl₃) δ: 7.87 (d, J=4.9 Hz, 1H), 6.74 (d, J=4.9 Hz, 1H), 3.79 (br s, 2H), 3.57 (t, J=5.7 Hz, 2H), 2.97 (spt, J=6.7 Hz, 1H), 2.52 (t, J=7.5 Hz, 2H), 1.79-1.68 (m, 2H), 1.23 (d, J=6.6 Hz, 6H), 0.85-0.83 (m, 9H), 0.00 (s, 6H).

Preparation of 4-(2-((tert-Butyldimethylsilyl)oxy)ethoxy)-2-isopropylpyridin-3-amine (Int-10f)

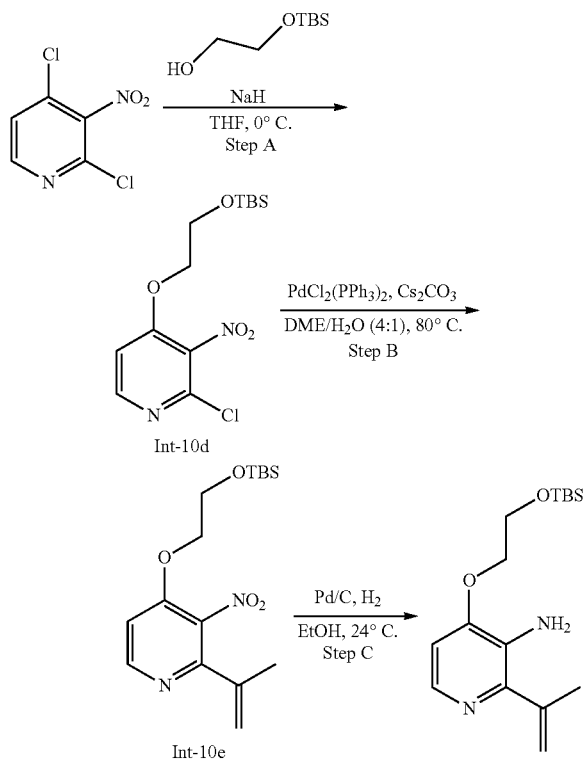

Step A: 4-(2-((tert-butyldimethylsilyl)oxy)ethoxy-2-chloro-3-nitropyridine (Int-10d)

2-((tert-Butyldimethylsilyl)oxy)ethan-1-ol (9.05 g, 51.3 mmol) was dissolved in tetrahydrofuran (155 mL), cooled to 0° C. and charged with sodium hydride (2.05 g, 51.3 mmol) and allowed to stir at that temperature for 30 minutes. The reaction was charged with 2,4-dichloro-3-nitropyridine (9.00 g, 46.6 mmol) portion wise, and allowed to slowly warm to rt over 2 h. The reaction was quenched with ammonium chloride, diluted with EtOAc, separated, washed with brine, dried over sodium sulfate, filtered, concentrated, and purified on silica gel eluting with 0-25% EtOAc/hexanes to provide 4-(2-((tert-butyldimethylsilyl)oxy)ethoxy)-2-chloro-3-nitropyridine (Int-10d). MS (ESI) [M+H]⁺ m/z 333.

Step B: 4-(2-((tert-Butyldimethylsilyl)oxy)ethoxy)-3-nitro-2-(prop-1-en-2-yl)pyridine (Int-10e)

4-(2-((tert-Butyldimethylsilyl)oxy)ethoxy)-2-chloro-3-nitropyridine (12.0 g, 36.1 mmol), cesium carbonate (35.2 g, 108 mmol), bis(triphenylphosphine)palladium(II) dichloride (2.53 g, 3.61 mmol) were added to a 250 mL round-bottomed flask equipped with magnetic stir bar, degassed under nitrogen, charged with DME (72 mL) and water (18 mL), degassed two times under nitrogen, charged with isopropenylboronic acid pinacol ester (7.45 mL, 39.7 mmol) and allowed to stir for 3 h at 85° C. The reaction was cooled to rt, diluted with 100 mL EtOAc, washed with 50 mL saturated ammonium chloride, brine, dried over sodium sulfate, filtered and concentrated in vacuo. Purification on silica gel 0-20% EtOAc/hexanes gave 4-(2-((tert-butyldimethylsilyl)oxy)ethoxy)-3-nitro-2-(prop-1-en-2-yl)pyridine (Int-10e). MS (ESI) [M+H]⁺ m/z 339.

Step C: 4-(2-((tert-butyldimethylsilyl)oxy)ethoxy)-2-isopropylpyridin-3-amine (Int-10f)

4-(2-((tert-Butyldimethylsilyl)oxy)ethoxy)-3-nitro-2-(prop-1-en-2-yl)pyridine (10.0 g, 29.5 mmol) was dissolved in EtOH (148 mL), degassed under nitrogen, charged with Pd—C (0.629 g, 5.91 mmol, 10% w/w), degassed under nitrogen, and allowed to stir under a hydrogen atmosphere for 24 h. The product mixture was thoroughly purged with nitrogen. The purged product mixture was filtered through a pad of CELITE. The filtrate was concentrated to dryness to afford 4-(2-((tert-butyldimethylsilyl)oxy)ethoxy)-2-isopropylpyridin-3-amine (Int-10f). ¹H NMR (500 MHz, DMSO-d₆) δ 7.73 (d, J=5.3 Hz, 1H), 6.73 (d, J=5.3 Hz, 1H), 4.45 (s, 2H), 4.09 (d, J=4.5 Hz, 2H), 3.95 (dd, J=5.4, 4.1 Hz, 2H), 3.16 (p, J=6.7 Hz, 1H), 1.14 (d, J=6.7 Hz, 6H), 0.88 (s, 9H), 0.07 (s, 6H).

Preparation of 4-(3-((tert-Butyldimethylsilyl)oxy)-2,2-difluoropropoxy)-2-isopropylpyridin-3-amine (Int-10i)

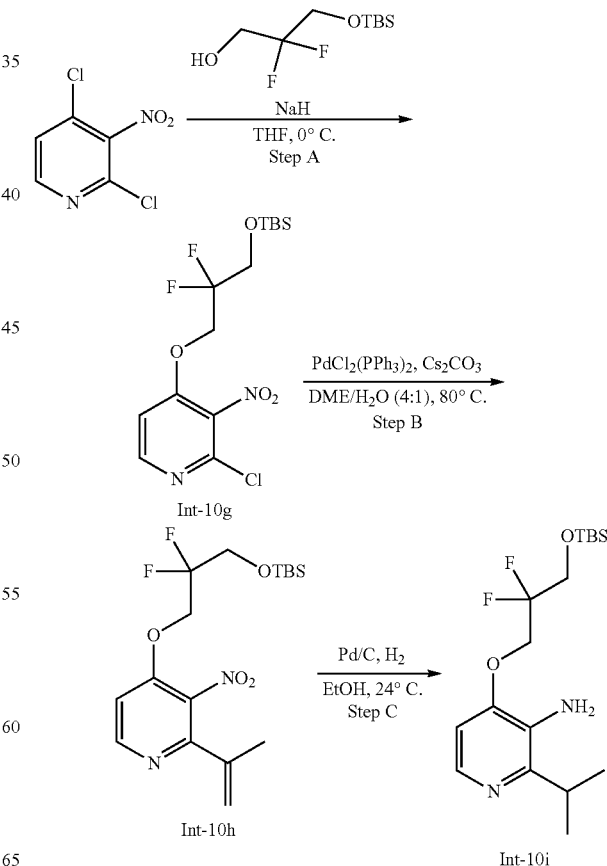

Step A: 4-(3-((tert-butyldimethylsilyl)oxy)-2,2-difluoropropoxy-2-chloro-3-nitropyridine (Int-10g)

3-((tert-Butyldimethylsilyl)oxy)-2,2-difluoropropan-1-ol (6.45 g, 28.5 mmol) was dissolved in tetrahydrofuran (86 mL), cooled to 0° C. and charged with sodium hydride (1.14 g, 28.5 mmol) and allowed to stir at that temperature for 30 minutes. The reaction was charged with 2,4-dichloro-3-nitropyridine (5.00 g, 25.9 mmol) portion wise, and allowed to slowly warm to rt over 2 h. The reaction was quenched with ammonium chloride, diluted with EtOAc, separated, washed with brine, dried over sodium sulfate, filtered, concentrated, and purified on silica gel, eluting with 0-25% EtOAc/hexanes, to provide 4-(3-((tert-butyldimethylsilyl)oxy)-2,2-difluoropropoxy)-2-chloro-3-nitropyridine (Int-10g). MS (ESI) [M+H]$^+$ m/z 383.

Step B: 4-(3-((tert-Butyldimethylsilyl)oxy)-2,2-difluoropropoxy)-3-nitro-2-(prop-1-en-2-yl)pyridine (Int-10h)

4-(3-((tert-Butyldimethylsilyl)oxy)-2,2-difluoropropoxy)-2-chloro-3-nitropyridine (7.00 g, 18.3 mmol), cesium carbonate (17.9 g, 54.8 mmol), bis(triphenylphosphine)palladium(II) dichloride (1.28 g, 1.83 mmol) were added to a 250 mL round-bottomed flask equipped with magnetic stirbar, degassed under nitrogen, charged with DME (36 mL) and water (9.1 mL), degassed two times under nitrogen, charged with isopropenylboronic acid pinacol ester (3.78 mL, 20.1 mmol) and allowed to stir for 3 h at 85° C. The reaction was cooled to rt, diluted with 100 mL EtOAc, washed with 50 mL saturated ammonium chloride, brine, dried over sodium sulfate, filtered and concentrated in vacuo. Purification on silica gel 0-20% EtOAc/hexanes gave 4-(3-((tert-butyldimethylsilyl)oxy)-2,2-difluoropropoxy)-3-nitro-2-(prop-1-en-2-yl) (Int-10h). MS (ESI) [M+H]$^+$ m/z 389.

Step C: 4-(3-((tert-Butyldimethylsilyl)oxy)-2,2-difluoropropoxy)-2-isopropylpyridin-3-amine (Int-10i)

4-(3-((tert-Butyldimethylsilyl)oxy)-2,2-difluoropropoxy)-3-nitro-2-(prop-1-en-2-yl)pyridine (6.60 g, 17.0 mmol) was dissolved in EtOH (85 mL), degassed under nitrogen, charged with Pd—C (0.362 g, 3.40 mmol, 10% w/w), degassed under nitrogen, and allowed to stir under hydrogen atmosphere for 24 h. The product mixture was thoroughly purged with nitrogen. The purged product mixture was filtered through a pad of CELITE. The filtrate was concentrated to afford 4-(3-((tert-butyldimethylsilyl)oxy)-2,2-difluoropropoxy)-2-isopropylpyridin-3-amine (Int-10i). MS (ESI) [M+H]$^+$ m/z 361.

Examples 10-15 were prepared in a similar method to Example 1, using Int-10c, Int-10f, and Int-10i in step D, and substituting a substituted, protected piperazine for step G. Example 11 utilized benzyl (S)-2-(cyanomethyl)piperazine-1-carboxylate as the substituted, protected piperazine in step G and, substituted palladium hydroxide/H$_2$ in MeOH for step J. Examples designated as "No. ##a" correspond to the first eluting peak on SFC. Examples designated as "No. ##b" correspond to the second eluting peak on SFC. Example 15 utilized (S)-2-(piperazin-2-yl)acetonitrile bis(hydrochloride) for step G.

| Ex. No. | Structure | Compound Name | [M + H]$^+$ Found | SFC Conditions |
|---|---|---|---|---|
| 10a | 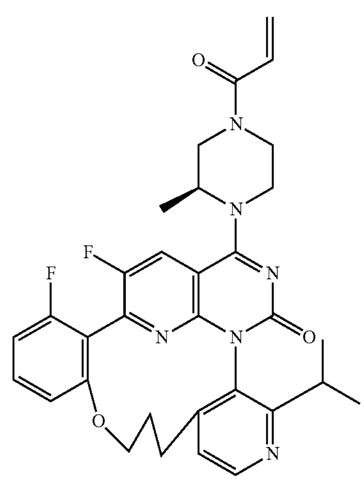 | 17,20-difluoro-2-[(2S)-2-methyl-4-(prop-2-enoyl)piperazin-1-yl]-6-(propan-2-yl)-11,12-dihydroethenopyrido[4,3-e]pyrimido[1,6-g][1,7,9]benzoxadiazacyclododecin-4-one | 587 | Column F EtOH w/ 0.1% NH$_4$OH, Peak 1 |

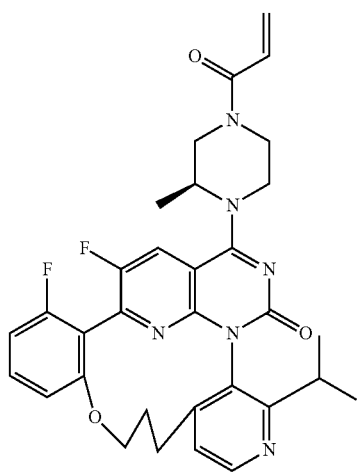 [SMILES: C=CC(=O)N1CCN(c2nc(=O)n3c4nc(c(F)cc24)-c2c(F)cccc2OCCCc2ccnc(C(C)C)c2-3)[C@@H](C)C1]

-continued

| Ex. No. | Structure | Compound Name | [M + H]+ Found | SFC Conditions |
|---|---|---|---|---|
| 10b | 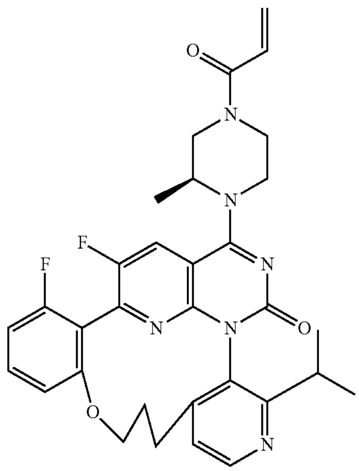 | 17,20-difluoro-2-[(2S)-2-methyl-4-(prop-2-enoyl)piperazin-1-yl]-6-(propan-2-yl)-11,12-dihydro-4H,10H-1,18-ethenopyrido[4,3-e]pyrimido[1,6-g][1,7,9]benzoxadiazacyclo-dodecin-4-one | 587 | Column F EtOH w/ 0.1% NH$_4$OH, Peak 2 |
| 11a | 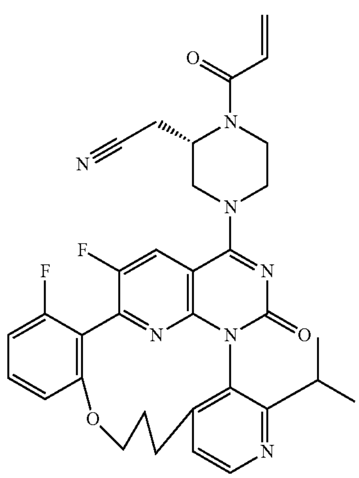 [SMILES: C=CC(=O)N1CCN(c2nc(=O)n3c4nc(c(F)cc24)-c2c(F)cccc2OCCCc2ccnc(C(C)C)c2-3)C[C@@H]1CC#N] | [(2S)-4-[17,20-difluoro-4-oxo-6-(propan-2-yl)-11,12-dihydro-4H,10H-1,18-ethenopyrido[4,3-e]pyrimido[1,6-g][1,7,9]benzoxadiazacyclo-dodecin-2-yl]-1-(prop-2-enoyl)piperazin-2-yl]acetonitrile | 612 | Column B EtOH w/0.1 NH$_4$OH, Peak 1 |
| 12a | 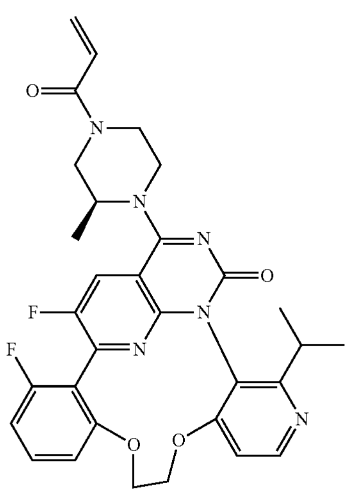 [SMILES: C=CC(=O)N1CCN(c2nc(=O)n3c4nc(c(F)cc24)-c2c(F)cccc2OCCOc2ccnc(C(C)C)c2-3)[C@@H](C)C1] | 17,20-difluoro-2-[(2S)-2-methyl-4-(prop-2-enoyl)piperazin-1-yl]-6-(propan-2-yl)-11,12-dihydro-4H-1,18-(ethanediylidene)pyrido[4,3-e]pyrimido[1,6-g][1,4,7,9]benzodioxadiaza-cyclododecin-4-one | 589 | Column G MeOH w/ 0.25% DMEA 60% CO$_2$ Peak 1 |

-continued

| Ex. No. | Structure | Compound Name | [M + H]+ Found | SFC Conditions |
|---|---|---|---|---|
| 13a | 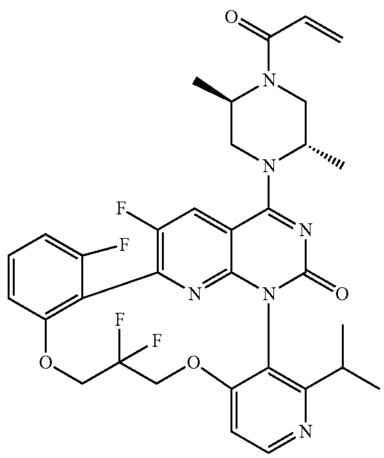 [SMILES: C=CC(=O)N1C[C@H](C)N(c2nc(=O)n3c4nc(c(F)cc24)-c2c(F)cccc2OCC(F)(F)COc2ccnc(C(C)C)c2-3)C[C@H]1C] | 2-[(2S,5R)-2,5-dimethyl-4-(prop-2-enoyl)piperazin-1-yl]-12,12,18,21-tetrafluoro-6-(propan-2-yl)-12,13-dihydro-4H,11H-1,19-(ethanediylidene)pyrido[4,3-f]pyrimido[1,6-h][1,5,8,10]benzodioxadiazacyclotridecin-4-one | 653.5 | Column G MeOH w/ 0.25% DMEA 75% $CO_2$ Peak 1 |
| 13b | 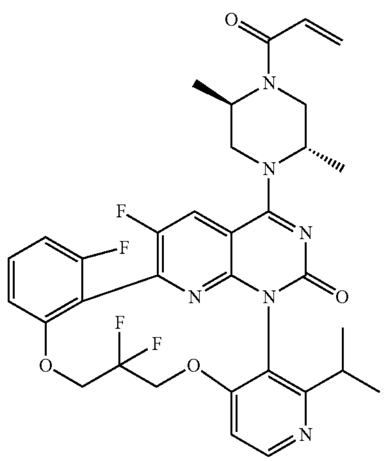 [SMILES: C=CC(=O)N1C[C@H](C)N(c2nc(=O)n3c4nc(c(F)cc24)-c2c(F)cccc2OCC(F)(F)COc2ccnc(C(C)C)c2-3)C[C@H]1C] | 2-[(2S,5R)-2,5-dimethyl-4-(prop-2-enoyl)piperazin-1-yl]-12,12,18,21-tetrafluoro-6-(propan-2-yl)-12,13-dihydro-4H,11H-1,19-(ethanediylidene)pyrido[4,3-f]pyrimido[1,6-h][1,5,8,10]benzodioxadiazacyclotridecin-4-one | 653.5 | Column G MeOH w/ 0.25% DMEA 75% $CO_2$ Peak 2 |
| 14a | 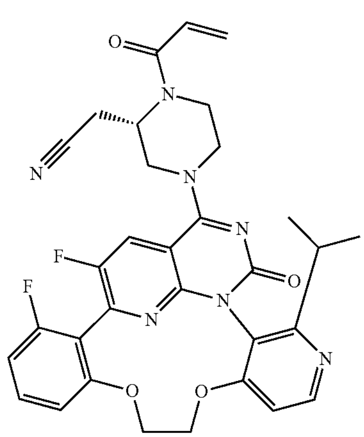 [SMILES: C=CC(=O)N1CCN(c2nc(=O)n3c4nc(c(F)cc24)-c2c(F)cccc2OCCOc2ccnc(C(C)C)c2-3)C[C@@H]1CC#N] | [(2S)-4-[17,20-difluoro-4-oxo-6-(propan-2-yl)-11,12-dihydro-4H-1,18-(ethanediylidene)pyrido[4,3-e]pyrimido[1,6-g][1,4,7,9]benzodioxadiazacyclododecin-2-yl]-1-(prop-2-enoyl)piperazin-2-yl]acetonitrile | 614.2 | Column G MeOH w/ 0.25% DMEA 60% $CO_2$ Peak 1 |

-continued

| Ex. No. | Structure | Compound Name | [M + H]+ Found | SFC Conditions |
|---|---|---|---|---|
| 15a | 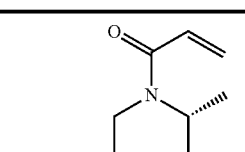 | 2-[(2S,5R)-2,5-dimethyl-4-(prop-2-enoyl)piperazin-1-yl]-17,20-difluoro-6-(propan-2-yl)-11,12-dihydro-4H-1,18-(ethanediylidene)pyrido[4,3-e]pyrimido[1,6-g][1,4,7,9]benzodioxadiazacyclo-dodecin-4-one | 603.3 | Column G MeOH w/ 0.25% DMEA 60% CO₂ Peak 1 |

Example 16a/b: 19,22-Difluoro-2-[(2S)-2-methyl-4-(prop-2-enoyl)piperazin-1-yl]-7-(propan-2-yl)-11,12,13,14-tetrahydro-4H-1,20-(ethanediylidene)-6,10-(metheno)pyrimido[1,6-k][1,8,11,13]benzoxatriazacyclohexadecin-4-one

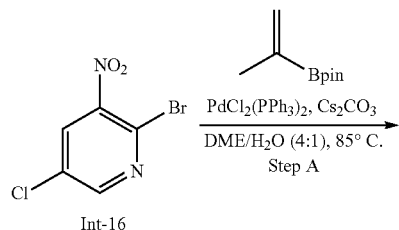

Int-16

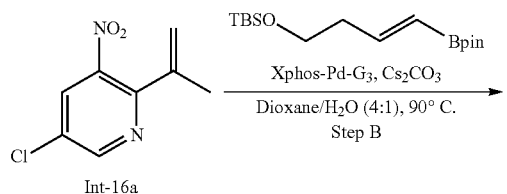

Int-16a

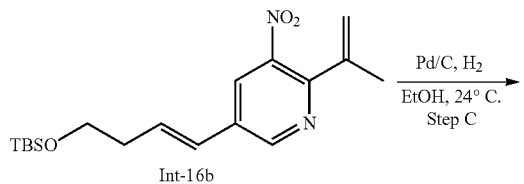

Int-16b

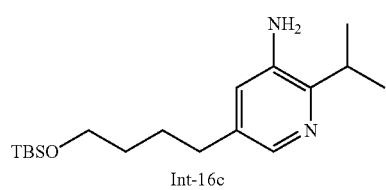

Int-16c

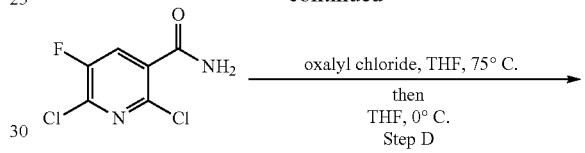

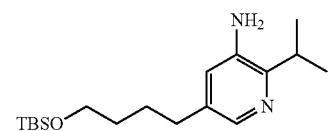

Int-16c

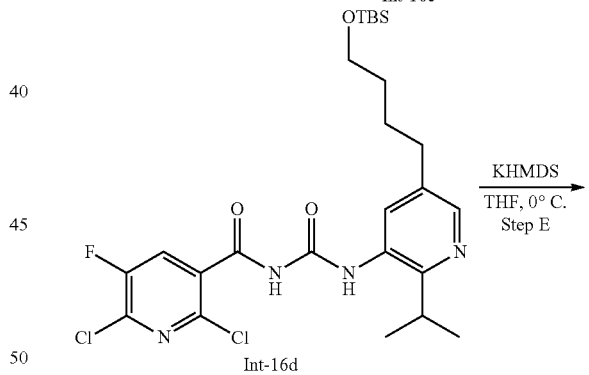

Int-16d

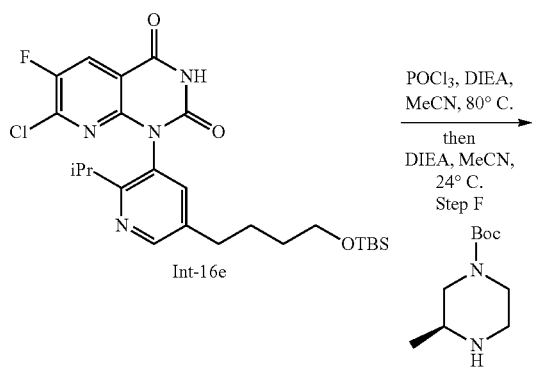

Int-16e

-continued

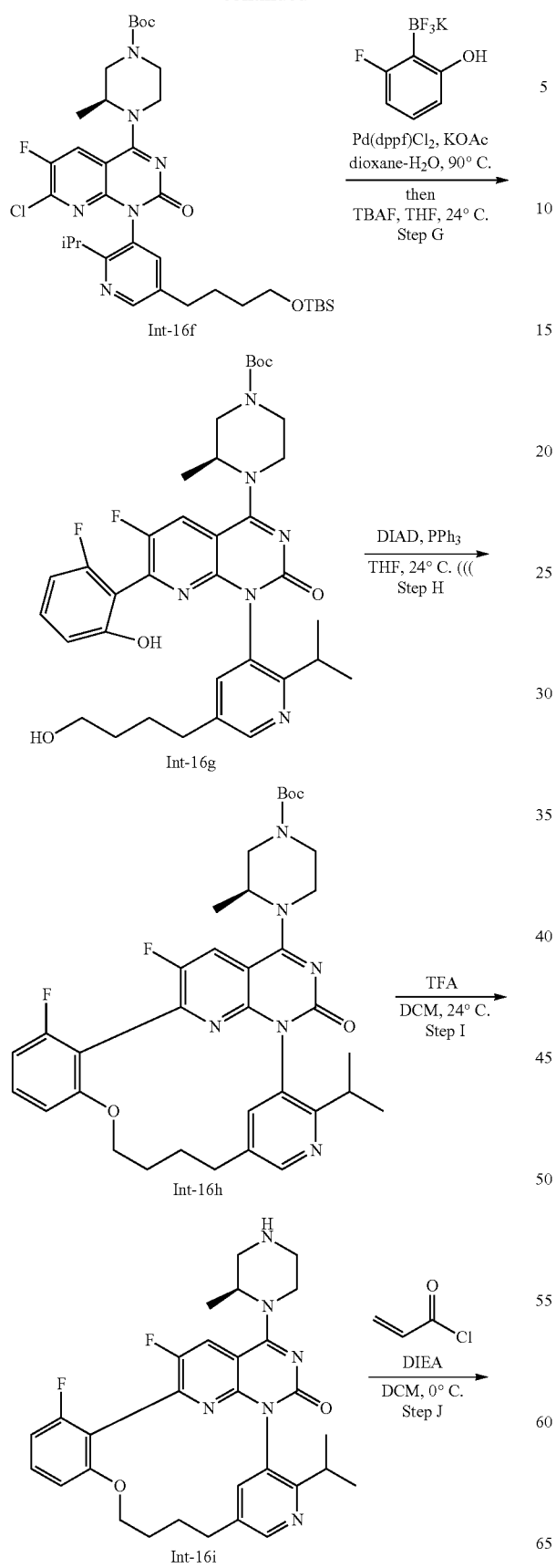

-continued

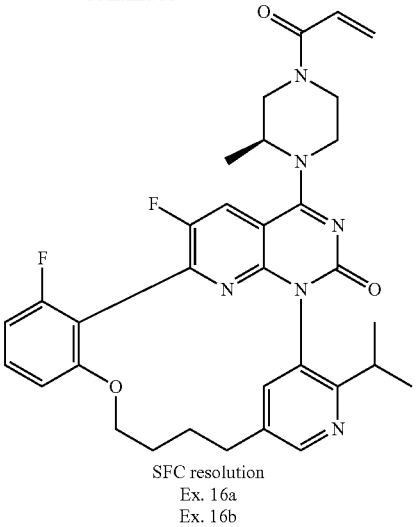

SFC resolution
Ex. 16a
Ex. 16b

Step A: 5-Chloro-3-nitro-2-(prop-1-en-2-yl)pyridine (Int-16a)

2-Bromo-5-chloro-3-nitropyridine (Int-16) (5.00 g, 21.1 mmol), bis(triphenylphosphine)palladium(II) dichloride (1.48 g, 2.11 mmol), and cesium carbonate (13.7 g, 42.1 mmol) were added in a 250 mL round-bottomed flask. The reaction vessel was evacuated and backfilled with a balloon of nitrogen three times. DME (56 mL) and water (14 mL) were added into the reaction vessel and the resulting mixture was evacuated and backfilled with a balloon of nitrogen three times. 4,4,5,5-Tetramethyl-2-(prop-1-en-2-yl)-1,3,2-dioxaborolane (4.16 mL, 22.1 mmol) was added into the reaction vessel and the resulting mixture was heated to 85° C. for 4 h. The product mixture was diluted with ethyl acetate (100 mL). The diluted product mixture was washed three times with saturated sodium bicarbonate aqueous solution (3×10 mL). The organic layer was dried over sodium sulfate. The dried solution was filtered and the filtrate was concentrated to dryness. The residue obtained was purified by flash column chromatography with silica gel, eluting with hexanes initially, grading to 20% ethyl acetate-hexanes, linear gradient to afford 5-chloro-3-nitro-2-(prop-1-en-2-yl)pyridine (Int-16a). $^1$H NMR (500 MHz, CDCl$_3$) δ 8.74 (d, J=2.2 Hz, 1H), 8.09 (d, J=2.2 Hz, 1H), 5.38 (dd, J=1.7, 0.7 Hz, 1H), 5.17 (t, J=1.0 Hz, 1H), 2.22 (t, J=1.2 Hz, 3H).

Step B: (E)-5-(4-((tert-Butyldimethylsilyl)oxy)but-1-en-1-yl)-3-nitro-2-(prop-1-en-2-yl)pyridine (Int-16b)

5-Chloro-3-nitro-2-(prop-1-en-2-yl)pyridine (3.80 g, 19.1 mmol), cesium carbonate (12.t g, 38.3 mmol), and XPhos-Pd-G3 (0.810 g, 0.957 mmol) were added into a 250 mL round-bottomed flask. The reaction vessel was evacuated and backfilled with a balloon of nitrogen. Dioxane (51 mL) and water (13 mL) were added into the reaction vessel and the resulting mixture was degassed by bubbling nitrogen for 30 seconds. (E)-tert-Butyldimethyl((4-(4,4,5,5-tetramethyl-1,3,2-dioxaborolan-2-yl)but-3-en-1-yl)oxy)silane (7.17 g, 23.0 mmol) was added into the reaction vessel and the resulting mixture was heated at 90° C. for 2 h. The product mixture was cooled down to room temperature. The cooled product mixture was transferred to a separatory funnel. The organic layer was isolated and the isolated organic layer was dried over sodium sulfate. The dried solution was filtered and the filtrate was concentrated to dryness. The residue obtained was purified by flash column chromatography with silica gel, eluting with hexanes initially, grading to 20% ethyl acetate-hexanes, linear gradient, to afford (E)-5-(4-((tert-butyldimethylsilyl)oxy)but-1-en-1-yl)-3-nitro-2-(prop-1-en-2-yl)pyridine (Int-16b). $^1$H NMR (500 MHz, CDCl$_3$) δ 8.67 (d, J=2.0 Hz, 1H), 8.00 (d, J=2.0 Hz, 1H), 6.46 (t, J=1.8 Hz, 2H), 5.34 (d, J=1.2 Hz, 1H), 5.19-5.04 (m, 1H), 3.76 (t, J=6.4 Hz, 2H), 2.49 (q, J=6.2 Hz, 2H), 2.20 (s, 3H), 0.90 (s, 9H), 0.07 (s, 6H).

Step C: 5-(4-((tert-Butyldimethylsilyl)oxy)butyl)-2-isopropylpyridin-3-amine (Int-16c)

(E)-5-(4-((tert-Butyldimethylsilyl)oxy)but-1-en-1-yl)-3-nitro-2-(prop-1-en-2-yl)pyridine (6.42 g, 18.4 mmol) was dissolved in EtOH (92 mL), degassed under nitrogen, charged with Pd—C (0.392 g, 3.68 mmol, 10% w/w), degassed under nitrogen, and allowed to stir under hydrogen atmosphere for 24 h. The product mixture was thoroughly purged with nitrogen. The purged product mixture was filtered through a pad of CELITE. The filtrate was concentrated to provide 5-(4-((tert-butyldimethylsilyl)oxy)butyl)-2-isopropylpyridin-3-amine (Int-16c). MS (ESI): [M+H]$^+$ m/z 323.

Step D: N-((5-(4-((tert-Butyldimethylsily)oxy)butyl)-2-isopropylpyridin-3-yl)carbamoyl)-2,6-dichloro-5-fluoronicotinamide (Int-16d)

2,6-di-chloro-5-fluoronicotinamide (2.00 g, 9.57 mmol) was added in a 40 mL vial. The reaction vessel was evacuated and backfilled with a balloon of nitrogen three times. THF (9.57 mL) was added into the reaction vessel to dissolve the starting material. A 2 M solution of oxalyl dichloride (5.74 mL, 11.5 mmol) was added dropwise into the reaction vessel and the resulting mixture was heated at 75° C. for 1 h. The intermediate solution was allowed to cool to room temperature. The cooled intermediate solution was concentrated to half of its volume. THF (5 mL) was added into the reaction vessel and the resulting mixture was cooled to 0° C. In a separate 4 mL vial, 5-(4-((tert-butyldimethylsilyl)oxy)butyl)-2-isopropylpyridin-3-amine (Int-16c, 3.09 g, 9.57 mmol) was dissolved in THF (5 mL). The amine solution was added dropwise into the reaction vessel and the resulting mixture was stirred for 1h at 0° C. The product mixture was warmed up to room temperature. The warmed product mixture was quenched with 2 mL of 1:1 mixture of saturated sodium chloride aqueous solution and ammonium chloride aqueous solution. The quenched product mixture was extracted three times with ethyl acetate (3×20 mL). The combined organic layers were dried over sodium sulfate and concentrated to dryness. The residue obtained was purified by flash column chromatography on silica gel, eluting with 5% (ethyl acetate:ethanol=3:1 v/v)-dichloromethane, initially, grading to 100% (ethyl acetate:ethanol=3:1 v/v), linear gradient, to afford N-((5-(4-((tert-butyldimethylsilyl)oxy)butyl)-2-isopropylpyridin-3-yl)carbamoyl)-2,6-dichloro-5-fluoronicotinamide (Int-16d). MS (ESI) [M+H]$^+$ m/z: 557/559.

Step E: 1-(5-(4-((tert-Butyldimethylsilyl)oxy)butyl)-2-isopropylpyridin-3-yl)-7-chloro-6-fluoropyrido[2,3-d]pyrimidine-2,4(1H,3H)-dione (Int-16e)

N-((5-(4-((tert-Butyldimethylsilyl)oxy)butyl)-2-isopropylpyridin-3-yl)carbamoyl)-2,6-dichloro-5-fluoronicotinamide (2.90 g, 5.20 mmol) was added in a 30 mL vial. The reaction vessel was evacuated and backfilled with a balloon of nitrogen three times. THF (10.4 mL) was added into the reaction vessel and the resulting mixture was cooled to 0° C. A 1 M solution of potassium bis(trimethylsilyl)amide (10.4 mL, 10.4 mmol) was added into the reaction vessel and the resulting mixture was stirred for 1 h at 0° C. The product mixture was quenched with saturated ammonium chloride aqueous solution (3 mL). The quenched product mixture was extracted three times with ethyl acetate (3×20 mL). The organic layers were combined and the combined organic layers were dried over sodium sulfate. The dried solution was filtered and the filtrate was concentrated to dryness. The residue obtained was purified by silica gel flash column chromatography 0-100 EtOAc/hexanes, to provide 1-(5-(4-((tert-butyldimethylsilyl)oxy)butyl)-2-isopropylpyridin-3-yl)-7-chloro-6-fluoropyrido[2,3-d]pyrimidine-2,4(1H,3H)-dione (Int-16e). MS (ESI) [M+H]$^+$ m/z: 521.

Step F: tert-Butyl (S)-4-(1-(5-(4-((tert-butyldimethylsilyl)oxy)butyl)-2-isopropylpyridin-3-yl)-7-chloro-6-fluoro-2-oxo-1,2-dihydropyrido[2,3-d]pyrimidin-4-yl)-3-methylpiperazine-1-carboxylate (Int-16f)

1-(5-(4-((tert-Butyldimethylsilyl)oxy)butyl)-2-isopropylpyridin-3-yl)-7-chloro-6-fluoropyrido[2,3-d]pyrimidine-2,4(1H,3H)-dione (500 mg, 0.959 mmol) was added in a 20 mL vial. The reaction vessel was evacuated and backfilled with a balloon of nitrogen three times. Acetonitrile (1.9 mL), N,N-diisopropylethylamine (256 µL, 1.44 mmol), and phosphoryl trichloride (116 µL, 1.25 mmol) were added into the reaction vessel and the resulting mixture was heated to 80° C. for 1 h. The product mixture was concentrated to dryness. The residue was dissolved in acetonitrile (1.9 mL). N,N-Diisopropylethylamine (512 µl, 2.88 mmol) and tert-butyl (S)-3-methylpiperazine-1-carboxylate (288 mg, 1.44 mmol) were added sequentially into the reaction vessel. The resulting mixture was stirred for 1 h at 24° C. The product mixture was diluted with ethyl acetate (100 mL). The diluted product mixture was washed three times with saturated sodium bicarbonate aqueous solution (3×10 mL). The organic layer was dried over sodium sulfate. The dried solution was filtered and the filtrate was concentrated to dryness. The residue obtained was purified by flash column chromatography with silica gel, eluting with hexanes initially, grading to 66% (ethyl acetate-ethanol=3:1 v/v)-hexanes, linear gradient, to provide tert-butyl (S)-4-(1-(5-(4-((tert-butyldimethylsilyl)oxy)butyl)-2-isopropylpyridin-3-yl)-7-chloro-6-fluoro-2-oxo-1,2-dihydropyrido[2,3-d]pyrimidin-4-yl)-3-methylpiperazine-1-carboxylate (Int-16f). MS (ESI) [M+H]$^+$ m/z: 703.

Step G: tert-Butyl (3S)-4-(6-fluoro-7-(2-fluoro-6-hydroxyphenyl)-1-(5-(4-hydroxybutyl)-2-isopropylpyridin-3-yl)-2-oxo-1,2-dihydropyrido[2,3-d]pyrimidin-4-yl)-3-methylpiperazine-1-carboxylate (Int-16g)

tert-Butyl (S)-4-(1-(5-(4-((tert-butyldimethylsilyl)oxy)butyl)-2-isopropylpyridin-3-yl)-7-chloro-6-fluoro-2-oxo-1,2-dihydropyrido[2,3-d]pyrimidin-4-yl)-3-methylpiperazine-1-carboxylate (535 mg, 0.761 mmol), potassium 3-fluoro-2-(trifluoro-V-boraneyl)phenolate (215 mg, 0.989 mmol), potassium acetate (299 mg, 3.04 mmol), 1,1'-bis(diphenylphosphino)ferrocene-palladium(II)dichloride dichloromethane complex (62.1 mg, 0.076 mmol) were added to a 20 mL scintillation vial equipped with magnetic stir bar, degassed under nitrogen, charged with dioxane (3.3 mL) and water (543 μl), degassed 3×under nitrogen and heated to 90° C. for 1 h. The reaction was cooled to rt, quenched with 10 mL 1:1 water/saturated sodium bicarbonate, extracted 2×25 mL EtOAc, washed with brine and concentrated in vacuo. The crude residue was taken up in 10 mL THF, charged with a 1 M solution of TBAF in THF (1.90 mL, 1.90 mmol) and allowed to stir for 1.5 h at rt. The reaction was quenched with saturated ammonium chloride, extracted 1×EtOAc, washed with brine, dried over sodium sulfate, filtered, concentrated in vacuo, and purified on silica gel 0-100% EtOAc:EtOH, 3:1/hexanes to provide tert-butyl (3S)-4-(6-fluoro-7-(2-fluoro-6-hydroxyphenyl)-1-(5-(4-hydroxybutyl)-2-isopropylpyridin-3-yl)-2-oxo-1,2-dihydropyrido[2,3-d]pyrimidin-4-yl)-3-methylpiperazine-1-carboxylate (Int-16g). MS (ESI) [M+H]+ m/z: 665.

Step H: (Int-16h)

tert-Butyl (3S)-4-(6-fluoro-7-(2-fluoro-6-hydroxyphenyl)-1-(5-(4-hydroxybutyl)-2-isopropylpyridin-3-yl)-2-oxo-1,2-dihydropyrido[2,3-d]pyrimidin-4-yl)-3-methylpiperazine-1-carboxylate (100 mg, 0.150 mmol) and triphenylphosphine (99 mg, 0.376 mmol) were dissolved in THF (7.5 mL) in a 100 mL round-bottomed flask under nitrogen. Upon sonication, diisopropyl diazene-1,2-dicarboxylate (59.2 μl, 0.301 mmol) was added dropwise. The reaction mixture was sonicated for 15 min. The product mixture was concentrated to dryness. The residue obtained was purified by flash column chromatography with silica gel, eluting with hexanes initially, grading to 100% (ethyl acetate-ethanol=3:1 v/v), linear gradient, to provide (Int-16h). MS (ESI) [M+H]+ m/z: 647.

Step I: Int-16i

Int-16h (130 mg, 0.201 mmol) was added in a 20 mL vial. The reaction vessel was evacuated and backfilled with a balloon of nitrogen three times. DCM (2.0 mL) was added into the reaction vessel. Trifluoroacetic acid (769 μL, 10.1 mmol) was added dropwise into the reaction vessel and the resulting mixture was stirred for 1h at 24° C. The product mixture was concentrated to provide Int-16i. MS (ESI) [M+H]+ m/z: 547.

Step J: 19,22-difluoro-2-[(2S)-2-methyl-4-(prop-2-enoyl)piperazin-1-yl]-7-(propan-2-yl)-11,12,13,14-tetrahydro-4H-1,20-(ethanediylidene)-6,10-(metheno)pyrimido[1,6-k][1,8,11,13]benzoxatriazacyclohexadecin-4-one (Ex. 16a)

Int-16i+3-TFA (160 mg, 0.180 mmol) was added in a 20 mL vial. The reaction vessel was evacuated and backfilled with a balloon of nitrogen three times. DCM (1.8 mL) was added into the reaction vessel and the resulting solution was cooled down to 0° C. N,N-Diisopropylethylamine (160 μL, 0.900 mmol) and acryloyl chloride (21.4 μL, 0.270 mmol) were added into the reaction vessel and the resulting mixture was stirred for 1 h at 0° C. The product mixture was diluted with ethyl acetate (50 mL). The diluted product mixture was washed three times with saturated sodium bicarbonate aqueous solution (3×10 mL). The organic layer was dried over sodium sulfate. The dried solution was filtered and the filtrate was concentrated to dryness. The residue obtained was purified by flash column chromatography with silica gel, eluting with hexanes initially, grading to 100% (ethyl acetate:ethanol=3:1). The racemic material was resolved by SFC Column U, Condition: 35% modifier: MeOH w/0.25% N,N-dimethylethylamine to provide the separated atropisomers:

Peak 1—Ex. 16a—MS (ESI) [M+H]+ m/z: 601. $^1$H NMR (500 MHz, DMSO-d$_6$) δ 8.38 (d, J=2.0 Hz, 1H), 8.22 (dd, J=18.8, 9.2 Hz, 1H), 7.57-7.34 (m, 2H), 7.10 (d, J=8.5 Hz, 1H), 7.01-6.78 (m, 2H), 6.21 (dd, J=16.8, 9.3 Hz, 1H), 5.90-5.71 (m, 1H), 4.80 (s, 1H), 4.55-3.91 (m, 3H), 3.82 (td, J=9.7, 4.7 Hz, 1H), 3.67-3.47 (m, 3H), 3.19 (d, J=21.4 Hz, 1H), 2.96 (p, J=6.8 Hz, 1H), 2.86-2.70 (m, 1H), 2.57 (d, J=4.2 Hz, 1H), 1.85 (td, J=10.8, 10.2, 5.7 Hz, 1H), 1.72 (t, J=18.1 Hz, 1H), 1.54-1.42 (m, 1H), 1.40 (d, J=6.5 Hz, 3H), 1.28 (d, J=6.3 Hz, 1H), 1.17 (d, J=6.7 Hz, 3H), 0.87 (d, J=6.8 Hz, 3H); and Peak 2-Ex. 16b-19,22-difluoro-2-[(2S)-2-methyl-4-(prop-2-enoyl)piperazin-1-yl]-7-(propan-2-yl)-11,12,13,14-tetrahydro-4H-1,20-(ethanediylidene)-6,10-(metheno)pyrimido[1,6-k][1,8,11,13]benzoxatriazacyclohexadecin-4-one. MS (ESI) [M+H]+ m/z: 601.

Example 17: 18,21-Difluoro-2-[(2S)-2-methyl-4-(prop-2-enoyl)piperazin-1-yl]-6-(propan-2-yl)-10,11,13,14-tetrahydro-4H-1,19-ethenopyrido[3,4-e]pyrimido[6,1-c][9,2,4]benzoxadiazacyclotridecin-4-one

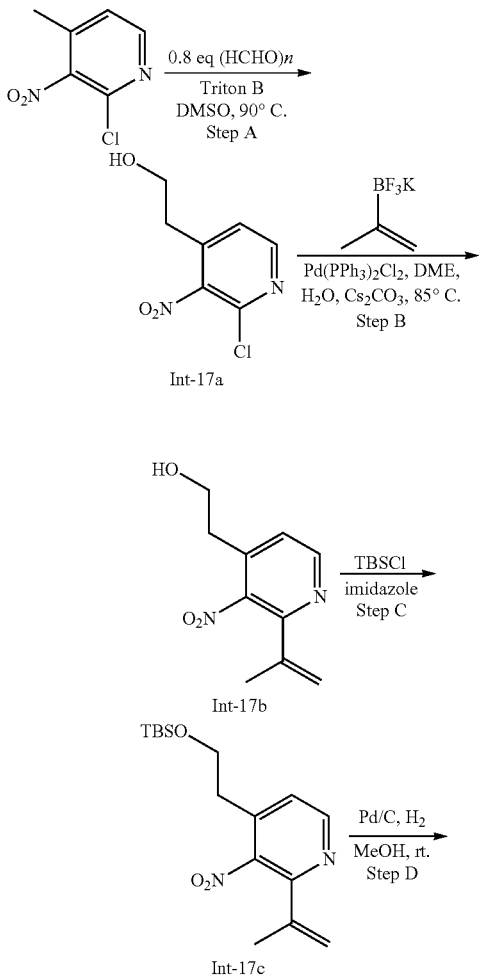

-continued
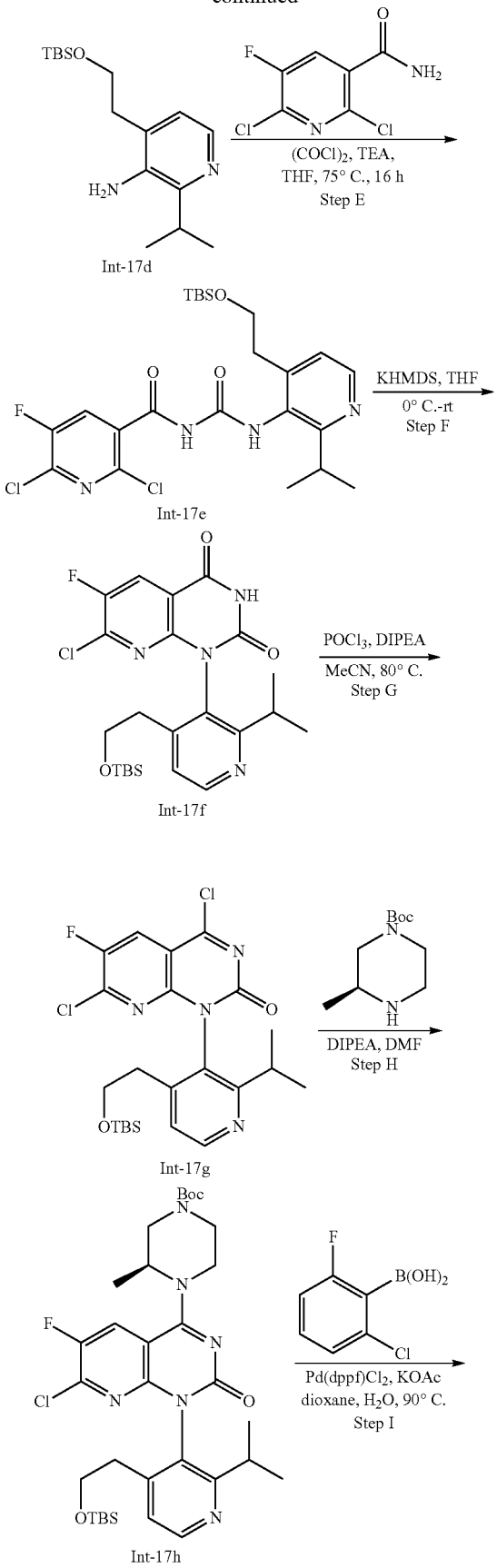
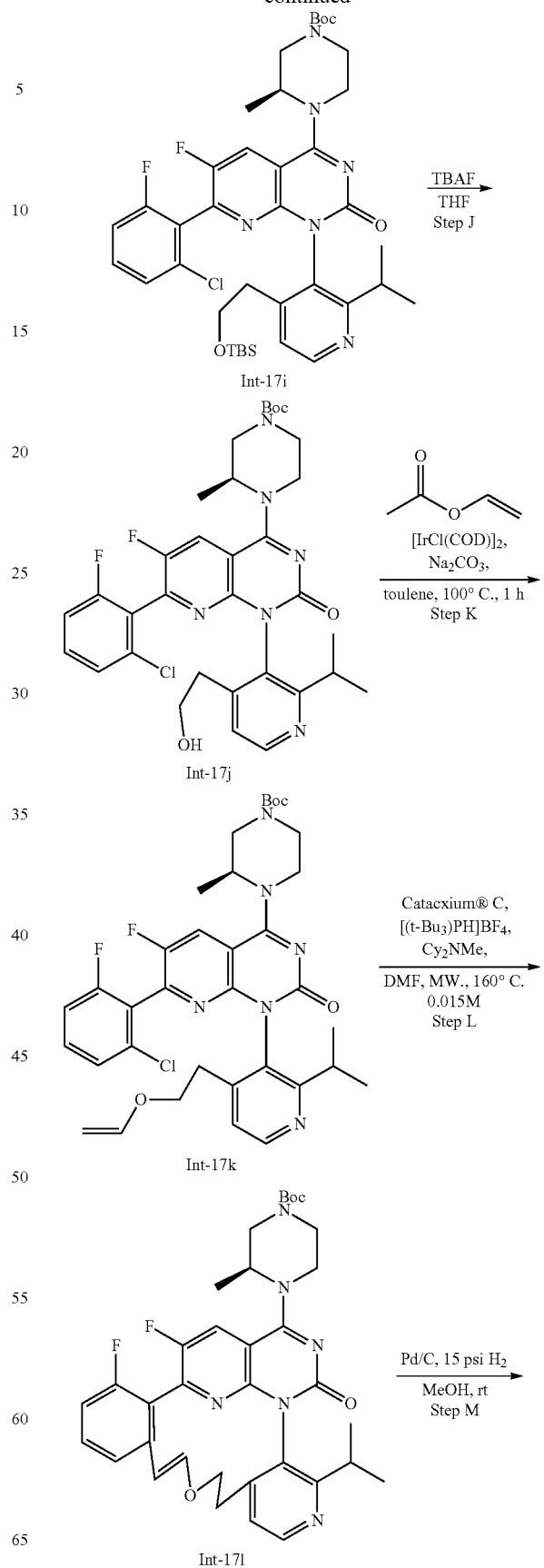

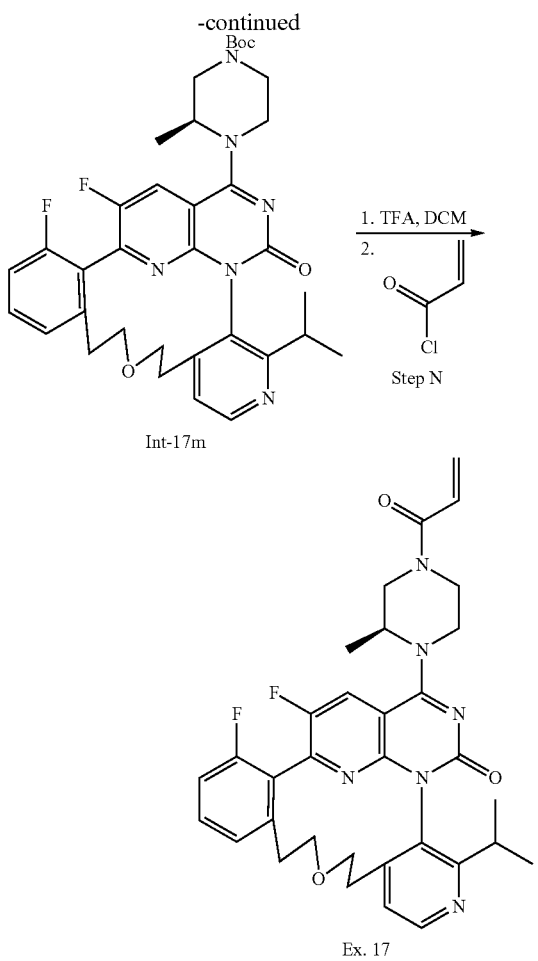

Int-17m

Ex. 17

Step A: 2-(2-chloro-3-nitropyridin-4-yl)ethanol (Int-17a)

To a stirred solution of 2-chloro-4-methyl-3-nitropyridine (50.0 g, 290 mmol) in DMSO (150 mL) were added paraformaldehyde (6.96 g, 232 mmol) and benzyltrimethylammonium hydroxide (5.3 mL, ~0.02 eq, 40% in methanol) at 20° C., and the mixture was stirred at 90° C. for 4 h under $N_2$ atmosphere. The reaction mixture was quenched with water (100 mL), and extracted with ethyl acetate (2×400 mL). The combined organic layers were washed with brine (4×60 mL), dried over $Na_2SO_4$, filtered and the solvent was evaporated under reduced pressure. The residue was purified by flash silica gel chromatography eluent of 0~60% EtOAc/Pet. Ether to provide 2-(2-chloro-3-nitropyridin-4-yl)ethanol (Int-17a). MS (ESI): [M+H]⁺ m/z: 202.

Step B: 2-(3-nitro-2-(prop-1-en-2-yl)pyridin-4-yl)ethanol (Int-17b)

To a stirred solution of 2-(2-chloro-3-nitropyridin-4-yl)ethanol (10 g, 49.4 mmol) in DME (100 mL) and water (20 mL) was added $Cs_2CO_3$ (48.2 g, 148 mmol), 4,4,5,5-tetramethyl-2-(prop-1-en-2-yl)-1,3,2-dioxaborolane (9.95 g, 59.2 mmol) and bis(triphenylphosphine)palladium(II) dichloride (1.73 g, 2.47 mmol), and the resulting mixture was stirred at 85° C. for 16 h. The reaction was extracted with EtOAc (200 mL×3). The combined organic phase was dried over anhydrous $Na_2SO_4$, filtered and concentrated in vacuo. The residue was purified by flash silica gel chromatography Pet. ether/EtOAc=10/1, to provide 2-(3-nitro-2-(prop-1-en-2-yl)pyridin-4-yl)ethanol (Int-17b). MS (ESI): [M+H]⁺ m/z:208.

Step C: 4-(2-(((tert-Butyldimethylsilyl)oxy)ethyl)-3-nitro-2-(prop-1-en-2-yl)pyridine (Int-17c)

To a stirred solution of 2-(3-nitro-2-(prop-1-en-2-yl)pyridin-4-yl)ethanol (9.1 g, 43.7 mmol) in DCM (120 mL) was added TBSCl (8.56 g, 56.8 mmol) and imidazole (8.93 g, 131 mmol), and the mixture was stirred at 20° C. for 16 h under $N_2$ atmosphere. The reaction mixture was quenched with water (60 mL), and extracted with dichloromethane (100 mL×2). The combined organic layers were washed with brine (80 mL), dried over $Na_2SO_4$, filtered and the solvent was evaporated under reduced pressure, which was purified by flash silica gel chromatography eluent of 0-8% EtOAc/Pet. ether gradient to provide 4-(2-((tert-butyldimethylsilyl)oxy)ethyl)-3-nitro-2-(prop-1-en-2-yl)pyridine (Int-17c). MS (ESI): [M+H]⁺ m/z:323.

Step D: 4-(2-(((tert-Butyldimethylsilyl)oxy)ethyl)-2-isopropylpyridin-3-amine (Int-17d)

To a stirred solution 4-(2-(((tert-butyldimethylsilyl)oxy)ethyl)-3-nitro-2-(prop-1-en-2-yl)pyridine (13 g, 40.3 mmol) in MeOH (100 mL) was added PdC (2.15 g, 2.02 mmol, 10% w/w) under $N_2$ atmosphere, and the mixture was degassed and purged with hydrogen for three times. The resulting mixture was stirred at 20° C. for 16 h under hydrogen balloon (pressure: 15 psi). The mixture was filtered and the filtered cake was washed with methanol (100 mL). The filtrate was concentrated in vacuo to give 4-(2-((tert-butyldimethylsilyl)oxy)ethyl)-2-isopropylpyridin-3-amine (Int-17d) which was used in next step without further purification. MS (ESI): [M+H]⁺ m/z:295.

Step E: N-((4-(2-(((tert-Butyldimethylsilyl)oxy)ethyl)-2-isopropylpyridin-3-yl)carbamoyl)-2,6-dichloro-5-fluoronicotinamide (Int-17e)

To a stirred solution of 2,6-dichloro-5-fluoronicotinamide (3.00 g, 14.4 mmol) in THF (40 mL) was added oxalyl dichloride (1.19 mL, 13.6 mmol) at 20° C., and the mixture was stirred at 65° C. for 30 min under $N_2$ atmosphere. The mixture was cooled to 20° C., and added to a mixture of 4-(2-(((tert-butyldimethylsilyl)oxy)ethyl)-2-isopropylpyridin-3-amine (Int-17d, 4.65 g, 15.8 mmol) in DCM (40 mL) at 0° C. The resulting mixture was stirred at 0° C. for 10 min. The reaction mixture was quenched with aqueous sodium hydrogen carbonate (saturated, 30 mL), and extracted with dichloromethane (2×60 mL). The combined organic layers were washed with brine (50 mL), dried over $Na_2SO_4$, filtered and the solvent was evaporated under reduced pressure. The residue was purified by flash silica gel chromatography eluent of 0~40% EtOAc/Pet. ether to give N-((4-(2-(((tert-butyldimethylsilyl)oxy)ethyl)-2-isopropylpyridin-3-yl)carbamoyl)-2,6-dichloro-5-fluoronicotinamide (Int-17e). MS (ESI): [M+H]⁺ m/z:529.

Step F: 1-(4-(2-(((tert-Butyldimethylsilyl)oxy)ethyl-2-isopropylpyridin-3-yl)-7-chloro-6-fluoropyrido[2,3-d]pyrimidine-2,4(1H.3H-dione (Int-17f)

To a stirred solution of N-((4-(2-(((tert-butyldimethylsilyl)oxy)ethyl)-2-isopropylpyridin-3-yl)carbamoyl)-2,6-dichloro-5-fluoronicotinamide (4.00 g, 7.55 mmol) in THF (60 mL) was added potassium bis(trimethylsilyl)amide (15.1 mL, 15.1 mmol) at 0° C., and the mixture was stirred at 20° C. for 30 min under $N_2$ atmosphere. The reaction mixture was quenched with aqueous ammonium chloride (saturated, 20 mL), and extracted with ethyl acetate (2×50 mL). The combined organic layers were washed with brine (30 mL), dried over $Na_2SO_4$, filtered and the solvent was evaporated under reduced pressure to give the crude product 1-(4-(2-((tert-butyldimethylsilyl)oxy)ethyl)-2-isopropylpyridin-3-yl)-7-chloro-6-fluoropyrido[2,3-d]pyrimidine-2,4(1H,3H)-dione (Int-17f), which was used in next step without further purification. MS (ESI): $[M+H]^+$ m/z:493.

Step G: 1-(4-(2-((tert-Butyldimethylsilyl)oxy)ethyl)-2-isopropylpyridin-3-yl-4,7-dichloro-6-fluoropyrido[2,3-d]pyrimidin-2(1H-one (Int-17g)

To a stirred solution of 1-(4-(2-((tert-butyldimethylsilyl)oxy)ethyl)-2-isopropylpyridin-3-yl)-7-chloro-6-fluoropyrido[2,3-d]pyrimidine-2,4(1H,3H)-dione (3.72 g, 7.54 mmol) in acetonitrile (50 mL) was added DIEA (3.29 mL, 18.9 mmol) and $POCl_3$ (1.06 mL, 11.3 mmol) at 25° C., and the mixture was stirred at 80° C. for 1 h under $N_2$ atmosphere. The reaction mixture was concentrated in vacuo to afford the crude product 1-(4-(2-((tert-butyldimethylsilyl)oxy)ethyl)-2-isopropylpyridin-3-yl)-4,7-dichloro-6-fluoropyrido[2,3-d]pyrimidin-2(1H)-one (Int-17g), which was used in next step without further purification. MS (ESI): $[M-Cl+MeOH]^+$ m/z: 507.

Step H: tert-Butyl (S)-4-(1-(4-(2-((tert-butyldimethylsilyl)oxy)ethyl)-2-isopropylpyridin-3-yl)-7-chloro-6-fluoro-2-oxo-1,2-dihydropyrido[2,3-d]pyrimidin-4-yl)-3-methylpiperazine-1-carboxylate (Int-17h)

To a stirred solution of 1-(4-(2-((tert-butyldimethylsilyl)oxy)ethyl)-2-isopropylpyridin-3-yl)-4,7-dichloro-6-fluoropyrido[2,3-d]pyrimidin-2(1H)-one (3.86 g, 7.55 mmol) in DMF (40 mL) was added DIPEA (3.30 mL, 18.9 mmol) and (S)-tert-butyl 3-methylpiperazine-1-carboxylate (1.89 g, 9.43 mmol) at 25° C., and the mixture was stirred at 20° C. for 30 min under $N_2$ atmosphere. The reaction was concentrated in vacuo, and the residue was purified by flash silica gel chromatography, eluent of 0~40% EtOAc/Pet. ether to give (S)-tert-butyl 4-(1-(4-(2-((tert-butyldimethylsilyl)oxy)ethyl)-2-isopropylpyridin-3-yl)-7-chloro-6-fluoro-2-oxo-1,2-dihydropyrido[2,3-d]pyrimidin-4-yl)-3-methylpiperazine-1-carboxylate (Int-17h). MS (ESI): $[M+H]^+$ m/z:675.

Step I: (3S)-tert-Butyl 4-(1-(4-(2-((tert-butyldimethylsilyloxy)ethyl)-2-isopropylpyridin-3-yl)-7-(2-chloro-6-fluorophenyl)-6-fluoro-2-oxo-1,2-dihydropyrido[2,3-d]pyrimidin-4-yl-3-methylpiperazine-1-carboxylate (Int-17i)

To a stirred solution of tert-butyl (S)-4-(1-(4-(2-((tert-butyldimethylsilyl)oxy)ethyl)-2-isopropylpyridin-3-yl)-7-chloro-6-fluoro-2-oxo-1,2-dihydropyrido[2,3-d]pyrimidin-4-yl)-3-methylpiperazine-1-carboxylate (300 mg, 0.444 mmol), potassium acetate (218 mg, 2.22 mmol) and 1,1'-bis(diphenylphosphino)ferrocene-palladium(II) dichloride dichloromethane complex (18 mg, 0.022 mmol) in 1,4-dioxane (10 mL), water (2 mL) was added (2-chloro-6-fluorophenyl)boronic acid (116 mg, 0.666 mmol), and the resulting mixture was stirred at 90° C. for 2 h under $N_2$ atmosphere. The reaction mixture was quenched with brine (10 mL), and extracted with ethyl acetate (2×10 mL). The combined organic layers were washed with brine (10 mL), dried over $Na_2SO_4$, filtered and the solvent was evaporated under reduced pressure.

The residue was purified by flash silica gel chromatography eluent of 0-50% EtOAc/Pet. ether gradient to give (3S)-tert-butyl 4-(1-(4-(2-((tert-butyldimethylsilyl)oxy)ethyl)-2-isopropylpyridin-3-yl)-7-(2-chloro-6-fluorophenyl)-6-fluoro-2-oxo-1,2-dihydropyrido[2,3-d]pyrimidin-4-yl)-3-methylpiperazine-1-carboxylate (Int-17i). MS (ESI): $[M+H]^+$ m/z: 769.

Step J: (3S)-tert-Butyl 4-(7-(2-chloro-6-fluorophenyl)-6-fluoro-1-(4-(2-hydroxyethyl)-2-isopropylpyridin-3-yl)-2-oxo-1,2-dihydropyrido[2,3-d]pyrimidin-4-yl)-3-methylpiperazine-1-carboxylate (Int-17j)

To a stirred solution of (3S)-tert-butyl 4-(1-(4-(2-((tert-butyldimethylsilyl)oxy)ethyl)-2-isopropylpyridin-3-yl)-7-(2-chloro-6-fluorophenyl)-6-fluoro-2-oxo-1,2-dihydropyrido[2,3-d]pyrimidin-4-yl)-3-methylpiperazine-1-carboxylate (240 mg, 0.312 mmol) in THF (5 mL) was added a 1 M solution of TBAF in THF (0.936 mL, 0.936 mmol), and the mixture was stirred at 20° C. for 1 h under $N_2$ atmosphere. The reaction mixture was concentrated in vacuo, and the residue was purified by flash silica gel chromatography eluent of 0-8% MeOH/DCM to give (3S)-tert-butyl 4-(7-(2-chloro-6-fluorophenyl)-6-fluoro-1-(4-(2-hydroxyethyl)-2-isopropylpyridin-3-yl)-2-oxo-1,2-dihydropyrido[2,3-d]pyrimidin-4-yl)-3-methylpiperazine-1-carboxylate (Int-17j). MS (ESI): $[M+H]^+$ m/z: 655.

Step K: (3S)-tert-Butyl 4-(7-(2-chloro-6-fluorophenyl)-6-fluoro-1-(2-isopropyl-4-(2-(vinyloxy)ethyl)pyridin-3-yl)-2-oxo-1,2-dihydropyrido[2,3-d]pyrimidin-4-yl)-3-methylpiperazine-1-carboxylate (Int-17k)

To a stirred solution of (3S)-tert-butyl 4-(7-(2-chloro-6-fluorophenyl)-6-fluoro-1-(4-(2-hydroxyethyl)-2-isopropylpyridin-3-yl)-2-oxo-1,2-dihydropyrido[2,3-d]pyrimidin-4-yl)-3-methylpiperazine-1-carboxylate (500 mg, 0.763 mmol) in toluene (10 mL) was added chloro(1,5-cyclooctadiene)iridium(I) dimer (103 mg, 0.153 mmol), $Na_2CO_3$ (162 mg, 1.53 mmol) and vinyl acetate (131 mg, 1.53 mmol), and the mixture was stirred at 100° C. for 3 h under $N_2$ atmosphere. The reaction mixture was concentrated in vacuo, and the residue was purified by flash silica gel chromatography eluent of 0~40% EtOAc/Pet. ether to provide (3S)-tert-butyl 4-(7-(2-chloro-6-fluorophenyl)-6-fluoro-1-(2-isopropyl-4-(2-(vinyloxy)ethyl)pyridin-3-yl)-2-oxo-1,2-dihydropyrido[2,3-d]pyrimidin-4-yl)-3-methylpiperazine-1-carboxylate (Int-17k). MS (ESI): $[M+H]^+$ m/z:681.

Step L: Int-17l

To a stirred solution of (3S)-tert-butyl 4-(7-(2-chloro-6-fluorophenyl)-6-fluoro-1-(2-isopropyl-4-(2-(vinyloxy)ethyl)pyridin-3-yl)-2-oxo-1,2-dihydropyrido[2,3-d]pyrimidin-4-yl)-3-methylpiperazine-1-carboxylate (150 mg, 0.220 mmol) in DMF (15 mL) was added N,N-dicyclohexylmethylamine (688 mg, 3.52 mmol), tri-tert-butylphosphonium tetrafluoroborate (128 mg, 0.440 mmol) and cataCxium® C (206 mg, 0.220 mmol), and the mixture was stirred at 160° C. for 1 h under $N_2$ atmosphere in the microwave. The reaction mixture was concentrated in vacuum, and the residue was purified by Al₂O₃ chromatography (eluent of 0~10% MeOH/DCM) to give Int-17l. MS (ESI): [M+H]⁺ m/z:645.

Step M: Int-17m

To a stirred mixture of Int-17l (90 mg, 0.070 mmol) in MeOH (10 mL) was added Pd—C (22 mg, 0.021 mmol, 10% w/w), and the mixture was degassed and purged with hydrogen three times. The resulting mixture was stirred at 20° C. for 16 h under hydrogen (pressure: 15 psi). The mixture was filtered and the filter cake was washed with methanol (20 mL). The filtrate was concentrated in vacuo and the residue was purified by preparative HPLC chromatography, water (0.1% TFA)-MeCN to give Int-17m. MS (ESI): [M+H]⁺ m/z:647.

Step N: 18,21-difluoro-2-[(2S)-2-methyl-4-(prop-2-enoyl)-6-(propan-2-yl)-10,11,13,14-tetrahydro-4H-1,19-ethenopyrido[3,4-e]pyrimido[6,1-c][9,2,4]benzoxadiazacyclotridecin-4-one (Ex. 17a and 17b)

To a stirred solution of Int-17m (30 mg, 0.046 mmol) in DCM (2 mL) was added TFA (0.5 mL), and the mixture was stirred at 20° C. for 10 min. The reaction mixture was concentrated in vacuum, and the residue was dissolved in DCM (2 mL), and then DIEA (0.041 mL, 0.23 mmol) and acryloyl chloride (6.3 mg, 0.070 mmol) was added. The resulting mixture was stirred at 20° C. for 5 min. The reaction mixture was concentrated in vacuum, and the residue was purified by preparative TLC plate eluting with 10% MeOH/DCM. The racemic material was resolved by SFC Column B, Condition: water (0.1% NH₄OH)—MeOH 35% to provide the separated atropisomers:

Peak 1—Ex. 17a—18,21-difluoro-2-[(2S)-2-methyl-4-(prop-2-enoyl)piperazin-1-yl]-6-(propan-2-yl)-10,11,13,14-tetrahydro-4H-1,19-ethenopyrido[3,4-e]pyrimido[6,1-c][9,2,4]benzoxadiazacyclotridecin-4-one. MS (ESI): [M+H]⁺ m/z:601; ¹H NMR (500 MHz, methanol-d₄) δ 8.42 (d, J=5.0 Hz, 1H), 8.33-8.21 (m, 1H), 7.37 (dt, J=5.9, 8.0 Hz, 1H), 7.30 (d, J=5.2 Hz, 1H), 7.08 (d, J=7.6 Hz, 1H), 7.01 (t, J=8.9 Hz, 1H), 6.93-6.76 (m, 1H), 6.32 (br d, J=16.0 Hz, 1H), 5.84 (dd, J=1.8, 10.6 Hz, 1H), 5.02 (br s, 1H), 4.67-4.50 (m, 2H), 4.43-4.26 (m, 1H), 4.02-3.71 (m, 2H), 3.61-3.53 (m, 1H), 3.47 (br s, 1H), 3.42-3.32 (m, 3H), 2.86 (br d, J=7.9 Hz, 1H), 2.73-2.63 (m, 2H), 2.49-2.33 (m, 2H), 1.55 (br t, J=6.7 Hz, 3H), 1.20 (d, J=6.9 Hz, 3H), 0.99 (br d, J=6.1 Hz, 3H); and Peak 2—Ex. 17b—18,21-difluoro-2-[(2S)-2-methyl-4-(prop-2-enoyl)piperazin-1-yl]-6-(propan-2-yl)-10,11,13,14-tetrahydro-4H-1,19-ethenopyrido[3,4-e]pyrimido[6,1-c][9,2,4]benzoxadiazacyclotridecin-4-one. MS (ESI) m/z (M+H)⁺: 601; ¹H NMR (400 MHz, methanol-d₄) δ 8.42 (d, J=5.5 Hz, 1H), 8.33 (br t, J=8.2 Hz, 1H), 7.45-7.35 (m, 1H), 7.31 (d, J=5.1 Hz, 1H), 7.08 (d, J=7.4 Hz, 1H), 7.02 (t, J=8.6 Hz, 1H), 6.93-6.76 (m, 1H), 6.33 (br d, J=17.2 Hz, 1H), 5.84 (dd, J=2.0, 10.6 Hz, 1H), 5.23 (br s, 1H), 4.60 (br s, 2H), 4.46 (br d, J=13.7 Hz, 1H), 4.26-4.09 (m, 1H), 3.97 (br s, 1H), 3.78-3.40 (m, 3H), 3.37-3.15 (m, 2H), 2.84 (br d, J=6.7 Hz, 1H), 2.68 (br dd, J=5.5, 13.3 Hz, 2H), 2.47 (br s, 1H), 2.35 (td, J=6.8, 12.9 Hz, 1H), 1.46 (d, J=7.0 Hz, 3H), 1.19 (d, J=7.0 Hz, 3H), 0.99 (br d, J=6.3 Hz, 3H).

Example 18a: 17,20-difluoro-2-[(2S)-2-methyl-4-(prop-2-enoyl)piperazin-1-yl]-6-(propan-2-yi-10,11-dihydro-1,18-ethenopyrido[3,4-e]pyrimido[6,1-c][9,2,4]benzoxadiazacyclododecin-4(13H)-one

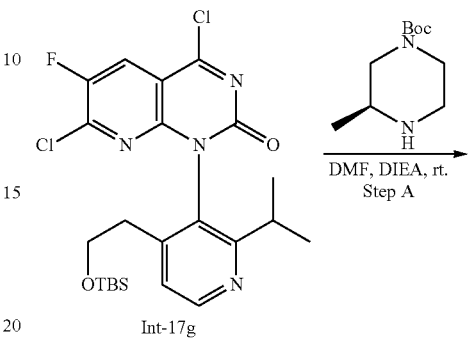

Int-17g

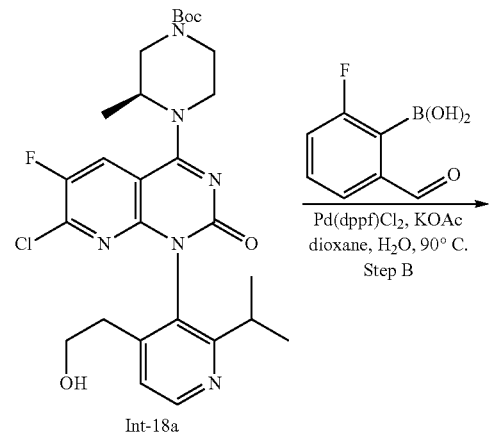

Int-18a

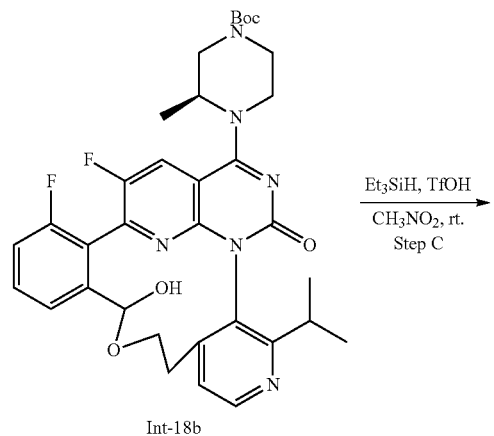

Int-18b

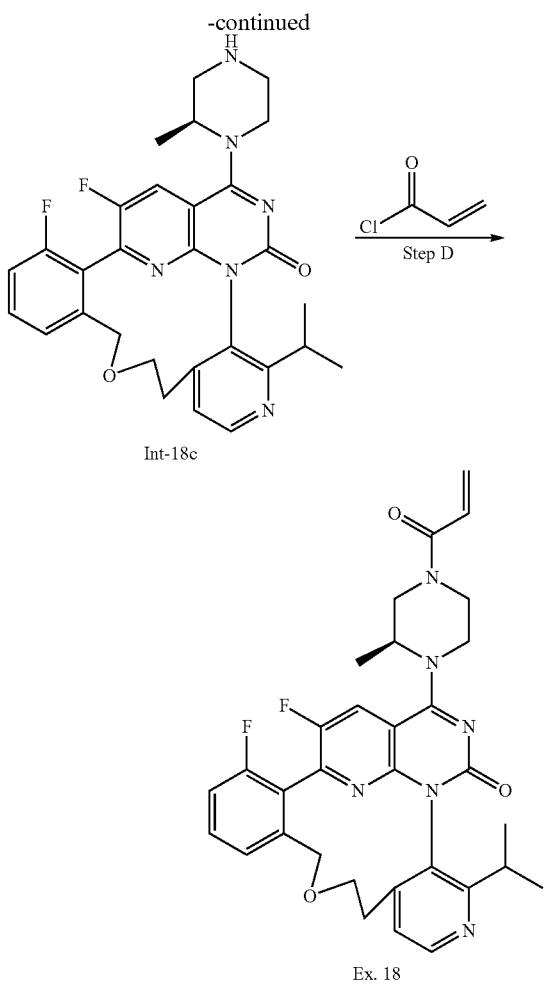

Step D

Int-18c

Ex. 18

Step A: (S)-tert-Butyl 4-(7-chloro-6-fluoro-1-(4-(2-hydroxyethyl)-2-isopropylpyridin-3-yl)-2-oxo-1,2-dihydropyrido[2,3-d]pyrimidin-4-yl)-3-methylpiperazine-1-carboxylate (Int-18a)

To a stirred solution of 1-(4-(2-((tert-butyldimethylsilyl)oxy)ethyl)-2-isopropylpyridin-3-yl)-4,7-dichloro-6-fluoro-pyrido[2,3-d]pyrimidin-2(1H)-one (Int-17g, 3.20 g, 6.26 mmol) in DMF (50 mL) was added DIEA (2.73 mL, 15.6 mmol) and (S)-tert-butyl 3-methylpiperazine-1-carboxylate (1.57 g, 7.82 mmol) at 25° C., and the mixture was stirred at 20° C. for 30 min under N₂ atmosphere. The reaction was concentrated in vacuum, and the residue was purified by flash silica gel chromatography with an eluent of 0~100% EtOAc/Pet. ether gradient to give (S)-tert-butyl 4-(7-chloro-6-fluoro-1-(4-(2-hydroxyethyl)-2-isopropylpyridin-3-yl)-2-oxo-1,2-dihydropyrido[2,3-d]pyrimidin-4-yl)-3-methylpiperazine-1-carboxylate (Int-18a). MS (ESI): [M+H]⁺ m/z: 561.

Step B: Int-18b

To a stirred solution of (S)-tert-butyl 4-(7-chloro-6-fluoro-1-(4-(2-hydroxyethyl)-2-isopropylpyridin-3-yl)-2-oxo-1,2-dihydropyrido[2,3-d]pyrimidin-4-yl)-3-methylpiperazine-1-carboxylate (300 mg, 0.535 mmol), potassium acetate (262 mg, 2.67 mmol) and 1,1'-bis(diphenylphosphino)ferrocene-palladium(II)dichloride dichloromethane complex (43.7 mg, 0.053 mmol) in 1,4-dioxane (4 mL) and water (1 mL) was added (2-fluoro-6-formylphenyl)boronic acid (180 mg, 1.07 mmol), and the mixture was stirred at 90° C. for 30 min under N₂ atmosphere. The reaction mixture was separated and the organic layer was dried over Na₂SO₄, filtered and the solvent was evaporated under reduced pressure. The residue was purified by flash silica gel chromatography with an eluent of 0-5% MeOH/DCM gradient, followed by reverse-phase MPLC 0%~100% MeCN (0.5TFA)/H₂O to give Int-18b MS (ESI): [M+H]⁺ m/z: 649.

Step C: Int-18c

To a stirred solution of Int-18b (60 mg, 0.092 mmol) in CH₃NO₂ (6 mL) were added triethylsilane (0.120 mL, 0.751 mmol) and TfOH (0.0500 mL, 0.563 mmol), and the mixture was stirred at 20° C. for 30 min under a N₂ atmosphere. The reaction mixture was concentrated in vacuo, and the residue was purified by preparative HPLC eluting with water (0.04% NH₃H₂O+10 mM NH₄HCO₃)-MeCN 10-100% B to provide Int-18c. MS (ESI): [M+H]⁺ m/z:533.

Step D: 17,20-Difluoro-2-[(2S)-2-methyl-4-(prop-2-enoyl)piperazin-1-yl]-6-(propan-2-yl)-10,11-dihydro-1,18-ethenopyrido[3,4-e]pyrimido[6,1-c][9,2,4]benzoxadiazacyclododecin-4(13H)-one (Ex. 18a)

To a stirred solution of Int-18c (99.0 mg, 0.186 mmol) in DCM (2.0 mL) were added DIEA (0.0970 mL, 0.558 mmol) and acryloyl chloride (20.2 mg, 0.223 mmol), and the mixture was stirred at 20° C. for 10 min under N₂ atmosphere. The reaction mixture was concentrated in vacuo, and the residue was purified by preparative HPLC, eluting with water (0.04% NH₃H₂O+10 mM NH₄HCO₃)-MeCN. The racemic material was resolved by preparative SFC Column L, Condition: 0.1% NH₄OH EtOH, 55%, to provide the separated atropisomers:

Peak 1-Ex 18a—17,20-difluoro-2-[(2S)-2-methyl-4-(prop-2-enoyl)piperazin-1-yl]-6-(propan-2-yl)-10,11-dihydro-1,18-ethenopyrido[3,4-e]pyrimido[6,1-c][9,2,4]benzoxadiazacyclododecin-4(13H)-one. MS (ESI) m/z (M+H)⁺: 587; ¹H NMR (400 MHz, methanol-d₄) δ 8.50 (d, J=5.1 Hz, 1H), 8.19 (br t, J=10.8 Hz, 1H), 7.56 (d, J=5.1 Hz, 1H), 7.46 (dt, 0.1=5.5, 8.0 Hz, 1H), 7.24-7.15 (m, 2H), 6.96-6.76 (m, 1H), 6.32 (br d, 0.1=17.2 Hz, 1H), 5.84 (br d, 0.1=11.0 Hz, 1H), 4.97-4.91 (m, 1H), 4.70 (br t, 0.1=15.1 Hz, 1H), 4.59-4.37 (m, 2H), 4.22-4.05 (m, 2H), 4.00 (d, J=9.4 Hz, 1H), 3.86-3.63 (m, 3H), 3.44-3.32 (m, 1H), 3.07 (quin, J=6.7 Hz, 1H), 2.59-2.47 (m, 1H), 2.44-2.29 (m, 1H), 1.58 (br t, 0.1=7.2 Hz, 3H), 1.27 (d, 0.1=6.7 Hz, 3H), 1.01 (d, 0.1=7.0 Hz, 3H).

Example 19: 18,21-Difluoro-2-[(2S)-2-methyl-4-(prop-2-enoyl)piperazin-1-yl]-6-(propan-2-yl)-10,11,12,13-tetrahydro-1,19-ethenopyrido[3,4-e]pyrimido[6,1-c][2,4,10]benzotriazacyclotridecine-4,14-dione

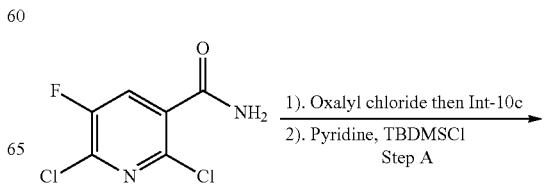

1). Oxalyl chloride then Int-10c
2). Pyridine, TBDMSCl

Step A

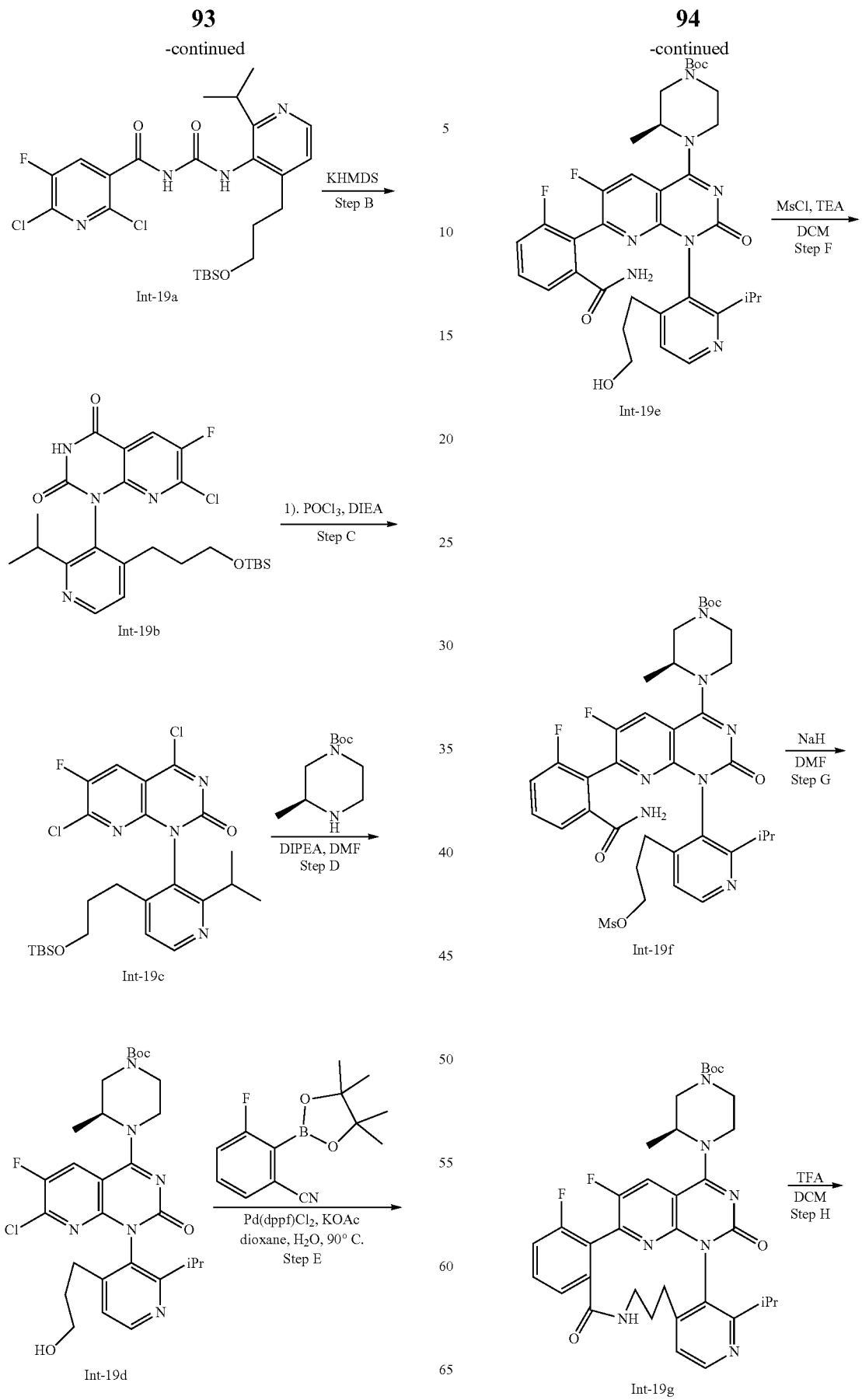

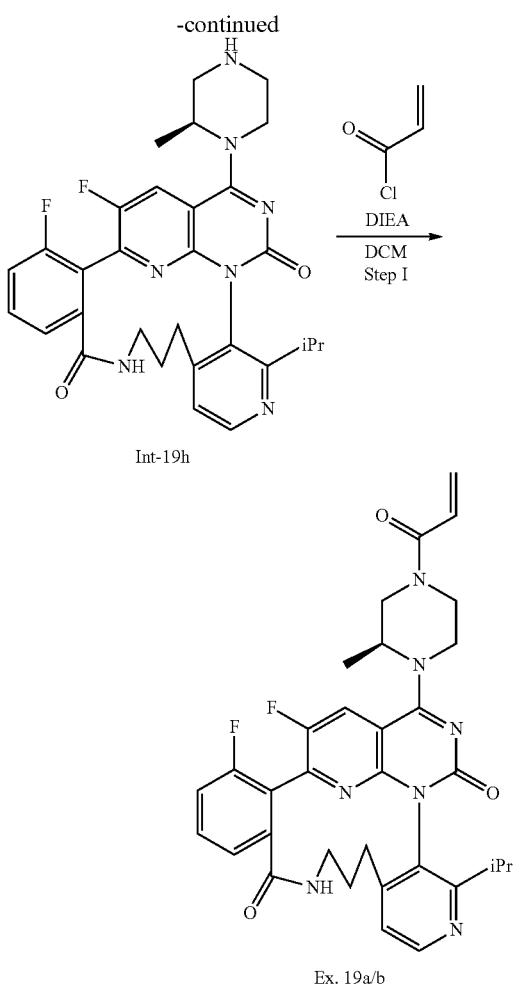

Int-19h

Ex. 19a/b

Step A: N-((4-(3-((tert-butyldimethylsily)oxy)propyl)-2-isopropylpyridin-3-yl)carbamoyl):2,6 dichloro-5-fluoronicotinamide (Int-19a)

Under a nitrogen atmosphere, a flask was charged with 2,6-dichloro-5-fluoronicotinamide (2.0 g, 9.6 mmol), THF (40 mL) and oxalyl chloride (2.0 M in DCM, 4.8 mL, 9.6 mmol). The mixture was heated to 65° C. for 30 minutes. After 30 minutes, the mixture was cooled to room temperature and then a mixture of 4-(3-((tert-butyldimethylsilyl)oxy)propyl)-2-isopropylpyridin-3-amine (Int-10c, 3.25 g, 10.5 mmol) in THF (20 mL) was added. The resulting mixture was stirred at room temperature for 1 hour. After 1 hour, the mixture was concentrated under reduced pressure. To the resulting mixture was added pyridine (50 mL) and the mixture was then cooled to 0° C. Tert-butyldimethylchlorosilane (1.6 g, 10 mmol) was added. The mixture was allowed to warm to room temperature and was allowed to stir at room temperature for one hour. After one hour, the mixture was concentrated under reduced pressure and then purified by silica column chromatography (0-60%/ethyl acetate gradient in hexanes) to afford an impure mixture. The mixture was re-purified (0-70% methyl tert-butyl ether gradient in hexanes) to afford N-((4-(3-((tert-butyldimethylsilyl)oxy)propyl)-2-isopropylpyridin-3-yl)carbamoyl)-2, 6-dichloro-5-fluoronicotinamide (Int-19a). MS (ESI) m/z 543 [M+H]+

Step B: 1-(4-(3-((tert-butyldimethylsily)oxy)propyl)-2-isopropylpyridin-3-yl)-7-chloro-6-fluoro-pyrido[2,3-d]pyrimidine-2,4(1H.3H)-dione (Int-19b)

To a mixture of N-((4-(3-((tert-butyldimethylsilyl)oxy)propyl)-2-isopropylpyridin-3-yl)carbamoyl)-2,6-dichloro-5-fluoronicotinamide (Int-19a, 6.3 g, 12 mmol) in THF (60 mL) at 0° C. under a nitrogen atmosphere was added potassium bis(trimethylsilyl)amide (1.0 M in THF, 23 mL, 23 mmol). The mixture was then allowed to warm to room temperature and was then stirred for 30 minutes as room temperature. After 30 minutes, the mixture was quenched with saturated aqueous ammonium chloride (15 mL) and then extracted with ethyl acetate (2×200 mL). The combined organic layers were washed with brine (100 mL), dried over sodium sulfate, filtered and concentrated under reduced pressure to afford crude 1-(4-(3-((tert-butyldimethylsilyl)oxy)propyl)-2-isopropylpyridin-3-yl)-7-chloro-6-fluoro-pyrido[2,3-d]pyrimidine-2,4(1H,3H)-dione (Int-19b) that was used without further purification or characterization. MS (ESI) m/z 507 [M+H]+

Step C: 1-(4-(3-((tert-butyldimethylsilyl)oxy)propyl)-2-isopropylpyridin-3-yl)-4,7-dichloro-6-fluoro-pyrido[2,3-d]pyrimidin-2(1H)-one (Int-19c)

To a flask containing crude 1-(4-(3-((tert-butyldimethylsilyl)oxy)propyl)-2-isopropylpyridin-3-yl)-7-chloro-6-fluoro-pyrido[2,3-d]pyrimidine-2,4(1H,3H)-dione (Int-19b) in acetonitrile (100 mL) under a nitrogen atmosphere was added DIEA (11 mL, 62 mmol) and phosphorous oxychloride (1.7 mL, 18 mmol) at room temperature. The mixture was then heated to 80° C. for 2 hours. After 2 hours, the mixture was allowed to cool to room temperature and was then concentrated under reduced pressure to afford 1-(4-(3-((tert-butyldimethylsilyl)oxy)propyl)-2-isopropylpyridin-3-yl)-4,7-dichloro-6-fluoropyrido[2,3-d]pyrimidin-2(1H)-one (Int-19c) that was used without further purification or characterization. MS (ESI) m/z 526 [M+H]+

Step D: (S)-tert-Butyl 4-(7-chloro-6-fluoro-1-(4-(3-hydroxypropyl)-2-isopropylpyridin-3-yl)-2-oxo-1,2-dihydropyrido[2,3-d]pyrimidin-4-yl)-3-methylpiperazine-1-carboxylate (Int-19d)

To a stirred solution of 1-(4-(3-((tert-butyldimethylsilyl)oxy)propyl)-2-isopropylpyridin-3-yl)-4,7-dichloro-6-fluoropyrido[2,3-d]pyrimidin-2(1H)-one (Int-19c, 6.22 g, 11.8 mmol) in acetonitrile (60 mL) was added DIPEA (4.13 mL, 23.7 mmol) and (S)-tert-butyl 3-methylpiperazine-1-carboxylate (3.56 g, 17.8 mmol) at 30° C. and the mixture was stirred at 30° C. for 1 h under N2 atmosphere. The residue was purified by flash silica gel chromatography eluent of 0~100% EtOAc/Pet. to provide (S)-tert-butyl 4-(7-chloro-6-fluoro-1-(4-(3-hydroxypropyl)-2-isopropylpyridin-3-yl)-2-oxo-1,2-dihydropyrido[2,3-d]pyrimidin-4-yl)-3-methylpiperazine-1-carboxylate (Int-19d). MS (ESI): [M+H]+ m/z:575.

Step E: (3S1-tert-Butyl 4-(7-(2-carbamoyl-6-fluorophenyl-6-fluoro-1-(4-(3-hydroxypropyl)-2-isopropylpyridin-3-yl-2-oxo-1,2-dihydropyrido[2,3-d]pyrimidin-4-yl-3-methylpiperazine-1-carboxylate (Int-19E)

To a stirred solution of 3-fluoro-2-(4,4,5,5-tetramethyl-1,3,2-dioxaborolan-2-yl)benzonitrile (387 mg, 1.56 mmol), (S)-tert-butyl 4-(7-chloro-6-fluoro-1-(4-(3-hydroxypropyl)-

2-isopropylpyridin-3-yl)-2-oxo-1,2-dihydropyrido[2,3-d]pyrimidin-4-yl)-3-methylpiperazine-1-carboxylate (Int-19d, 600 mg, 1.04 mmol) and potassium acetate (512 mg, 5.22 mmol) in 1,4-dioxane (7 mL) and water (2 mL) was added 1,1'-bis(diphenylphosphino)ferrocene-palladium(II)dichloride dichloromethane complex (85.0 mg, 0.104 mmol) at 20° C. under $N_2$ atmosphere, and the mixture was stirred at 90° C. for 15 h under $N_2$ atmosphere. The reaction mixture was quenched with brine (10 mL) and extracted with ethyl acetate (2×30 mL). The combined organic layers were washed with brine (10 mL), dried over $Na_2SO_4$, filtered and the solvent was evaporated under reduced pressure. The residue was purified by flash silica gel chromatography eluent of 0~10% DCM/MeOH gradient to provide (3S)-tert-butyl 4-(7-(2-carbamoyl-6-fluorophenyl)-6-fluoro-1-(4-(3-hydroxypropyl)-2-isopropylpyridin-3-yl)-2-oxo-1,2-dihydropyrido[2,3-d]pyrimidin-4-yl)-3-methylpiperazine-1-carboxylate (Int-19e). MS (ESI): [M+H]$^+$ m/z:678.

Step F: (3S)-tert-Butyl 4-(7-(2-carbamoyl-6-fluorophenyl-6-fluoro-1-(2-isopropyl-4-(3-((methylsulfonyl)oxy)propyl)pyridin-3-yl)-2-oxo-1,2-dihydropyrido[2,3-d]pyrimidin-4-yl-3-methylpiperazine-1-carboxylate (Int-19f)

To a stirred solution of (3S)-tert-butyl 4-(7-(2-carbamoyl-6-fluorophenyl)-6-fluoro-1-(4-(3-hydroxypropyl)-2-isopropylpyridin-3-yl)-2-oxo-1,2-dihydropyrido[2,3-d]pyrimidin-4-yl)-3-methylpiperazine-1-carboxylate (Int-19e, 600 mg, 0.885 mmol) in DCM (10 mL) was added $Et_3N$ (0.370 mL, 2.66 mmol) and MsCl (0.207 mL, 2.66 mmol) at 0° C., and the mixture was stirred at 30° C. for 15 h under $N_2$ atmosphere. The reaction mixture quenched with water (10 mL) and extracted with DCM (2×20 mL). The combined organic layers were washed with brine (10 mL), dried over $Na_2SO_4$, filtered and the solvent was evaporated under reduced pressure to give the crude product, which was purified by flash silica gel chromatography, 0-100% Pet. ether/EtOAc, to give (3S)-tert-butyl 4-(7-(2-carbamoyl-6-fluorophenyl)-6-fluoro-1-(2-isopropyl-4-(3-((methylsulfonyl)oxy)propyl)pyridin-3-yl)-2-oxo-1,2-dihydropyrido[2,3-d]pyrimidin-4-yl)-3-methylpiperazine-1-carboxylate (Int-19f). MS (ESI): [M+H]$^+$ m/z:756.

Step G: Int-19g

To a stirred solution of tert-butyl (3S)-4-(7-(2-carbamoyl-6-fluorophenyl)-6-fluoro-1-(2-isopropyl-4-(3-((methylsulfonyl)oxy)propyl)pyridin-3-yl)-2-oxo-1,2-dihydropyrido[2,3-d]pyrimidin-4-yl)-3-methylpiperazine-1-carboxylate (Int-19f, 371 mg, 0.491 mmol) in DMF (5 mL) was added NaH (39.3 mg, 0.982 mmol) (60% in mineral oil) at 0° C., and the mixture was stirred at 30° C. for 15 h under $N_2$ atmosphere. The reaction mixture was quenched with aqueous ammonium chloride (saturated, 15 mL) and extracted with ethyl acetate (2×50 mL). The combined organic layers were washed with brine (40 mL), dried over $Na_2SO_4$, filtered and the solvent was evaporated under reduced pressure. The residue was purified by prep-TLC (pure EtOAc) to give Int-19g. MS (ESI): [M+H]$^+$ m/z:660.

Step H: Int-19h

To a stirred solution of Int-19g (220 mg, 0.333 mmol) in $CH_2Cl_2$ (3 mL) was added TFA (1.5 mL) at 30° C., and the mixture was stirred at 30° C. for 1 h. The reaction mixture was concentrated in vacuo to afford Int-19h. MS (ESI): [M+H]$^+$ m/z:560.

Step I: 18,21-Difluoro-2-[(2S)-2-methyl-4-(prop-2-enoyl)piperazin-1-yl]-6-(propan-2-yl)-10,11,12,13-tetrahydro-1,19-ethenopyrido[3,4-e]pyrimido[6,1-c][2,4,10]benzotriazacyclotridecine-4,14-dione (Ex. 19a and 19b)

To a stirred solution of crude Int-19h+TFA (91.0 mg, 0.163 mmol) in DCM (2 mL) were added DIEA (0.0280 mL, 0.163 mmol) and acryloyl chloride (14.7 mg, 0.163 mmol) at 0° C., and the mixture was stirred at 0° C. for 10 min. The residue was purified by prep-TLC (DCM:MeOH=10:1). The racemic material was separated by preparative SFC Column H, Condition: 0.1% $NH_4OH$ EtOH 35% to provide:

Peak 1—Ex. 19a—18,21-difluoro-2-[(2S)-2-methyl-4-(prop-2-enoyl)piperazin-1-yl]-6-(propan-2-yl)-10,11,12,13-tetrahydro-1,19-ethenopyrido[3,4-e]pyrimido[6,1-c][2,4,10]benzotriazacyclotridecine-4,14-dione. MS (ESI): [M+H]$^+$ m/z:614; (500 HMz, methanol-$d_4$) δ: 8.48 (d, J=5.0 Hz, 1H), 8.33 (br dd, J=9.1, 14.1 Hz, 1H), 7.54 (dt, J=5.3, 8.0 Hz, 1H), 7.42 (d, J=5.2 Hz, 1H), 7.32 (t, J=8.7 Hz, 1H), 7.26 (d, J=7.5 Hz, 1H), 6.98-6.78 (m, 1H), 6.34 (br dd, J=4.7, 16.8 Hz, 1H), 5.86 (dd, J=1.8, 10.5 Hz, 1H), 5.19-5.07 (m, 1H), 4.55-4.46 (m, 2H), 4.24-4.12 (m, 1H), 3.90 (br d, J=9.9 Hz, 1H), 3.83-3.60 (m, 2H), 3.40-3.30 (br s, 1H), 3.19-3.06 (m, 1H), 2.78-2.65 (m, 1H), 2.64-2.47 (m, 2H), 2.21-2.08 (m, 1H), 1.99-1.82 (m, 1H), 1.52 (br t, J=5.5 Hz, 3H), 1.16 (d, J=6.9 Hz, 3H), 0.82 (br d, J=6.6 Hz, 3H); and Peak 2—Ex. 19b-18,21-difluoro-2-[(2S)-2-methyl-4-(prop-2-enoyl)piperazin-1-yl]-6-(propan-2-yl)-10,11,12,13-tetrahydro-1,19-ethenopyrido[3,4-e]pyrimido[6,1-c][2,4,10]benzotriazacyclotridecine-4,14-dione. MS (ESI): [M+H]$^+$ m/z: 614; $^1$H NMR (500 HMz, methanol-$d_4$) δ: 8.36 (d, J=5.2 Hz, 1H), 8.21 (br t, J=9.1 Hz, 1H), 7.41 (dt, J=5.3, 8.0 Hz, 1H), 7.30 (d, J=5.2 Hz, 1H), 7.19 (t, J=8.7 Hz, 1H), 7.13 (d, J=7.5 Hz, 1H), 6.82-6.68 (m, 1H), 6.22 (br dd, J=4.0, 16.8 Hz, 1H), 5.74 (br d, J=10.7 Hz, 1H), 5.09-4.97 (m, 1H), 4.48-4.29 (m, 2H), 4.13-4.00 (m, 1H), 3.79 (br s, 1H), 3.70-3.46 (m, 2H), 3.34-3.13 (m, 1H), 2.99 (td, J=4.5, 14.0 Hz, 1H), 2.65-2.51 (m, 1H), 2.50-2.38 (m, 2H), 2.08-1.96 (m, 1H), 1.88-1.75 (m, 1H), 1.38 (d, J=6.7 Hz, 3H), 1.03 (d, J=6.7 Hz, 3H), 0.68 (br d, J=6.6 Hz, 3H).

Examples 20a and 20b: 17,20-Difluoro-2-[(2S)-2-methyl-4-(prop-2-enoyl)piperazin-1-yl]-6-(propan-2-yl)-12,13-dihydro-1,18-ethenopyrido[3,4-e]pyrimido[6,1-c][7,2,4]benzoxadiazacyclododecin-4(11H)-one

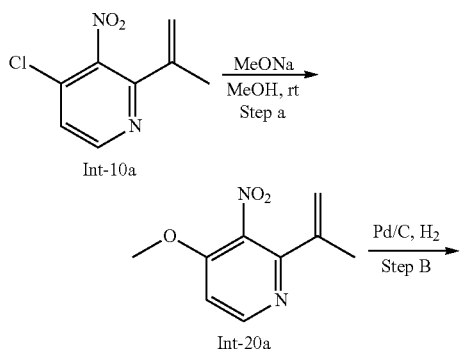

-continued
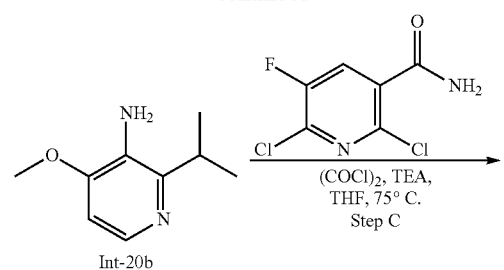
Int-20b
(COCl)₂, TEA,
THF, 75° C.
Step C
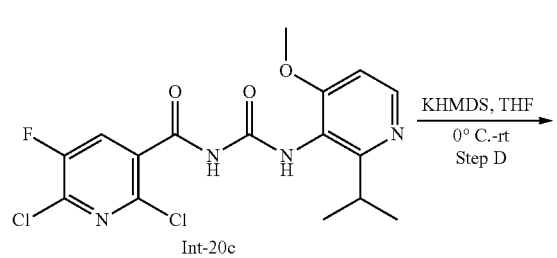
Int-20c
KHMDS, THF
0° C.-rt
Step D
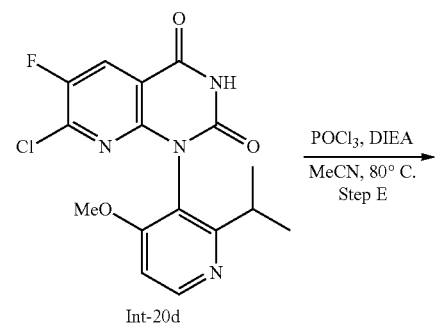
Int-20d
POCl₃, DIEA
MeCN, 80° C.
Step E
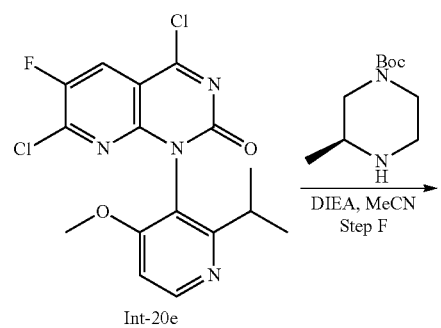
Int-20e
DIEA, MeCN
Step F
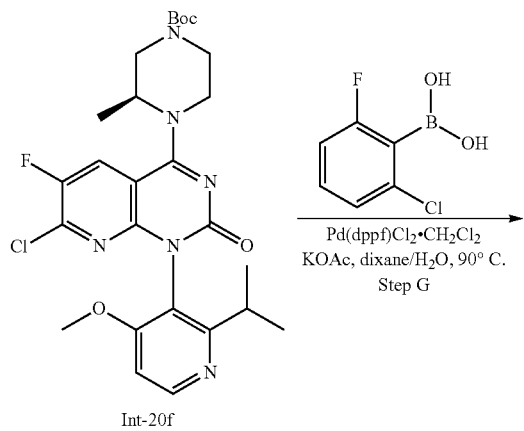
Int-20f
Pd(dppf)Cl₂·CH₂Cl₂
KOAc, dixane/H₂O, 90° C.
Step G
-continued
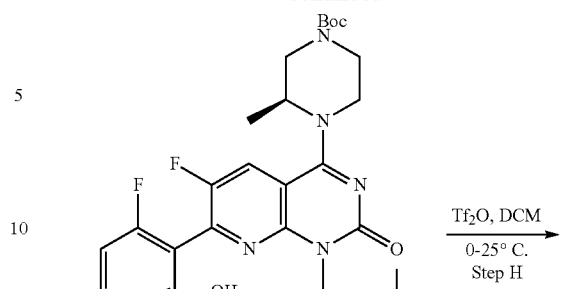
Int-20g
Tf₂O, DCM
0-25° C.
Step H
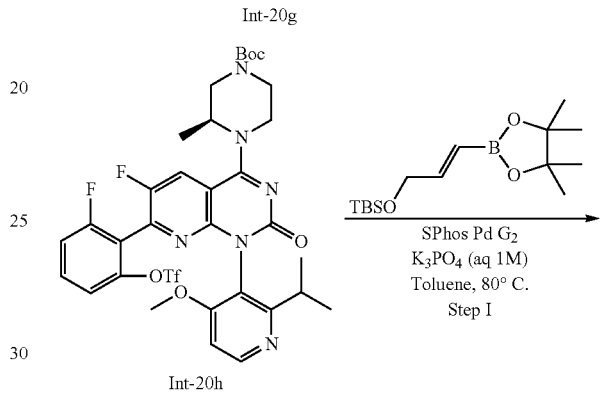
Int-20h
SPhos Pd G₂
K₃PO₄ (aq 1M)
Toluene, 80° C.
Step I
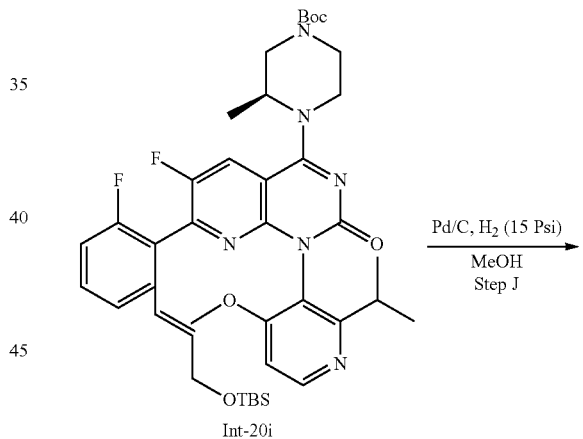
Int-20i
Pd/C, H₂ (15 Psi)
MeOH
Step J
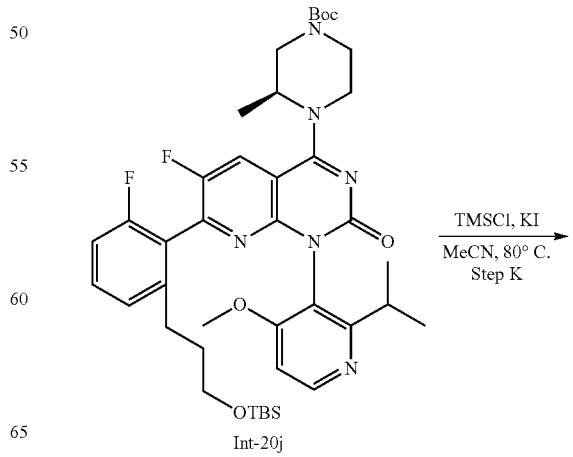
Int-20j
TMSCl, KI
MeCN, 80° C.
Step K

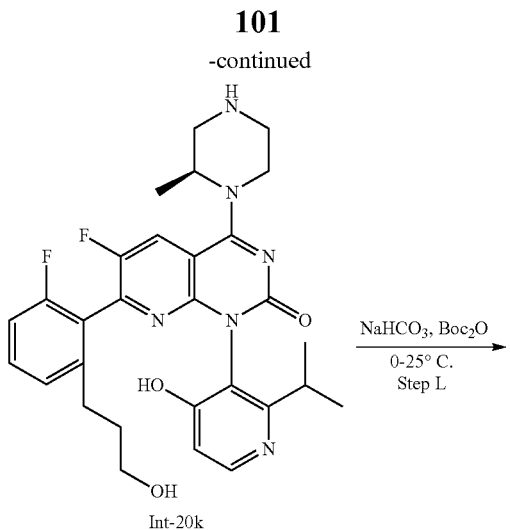

Int-20k

NaHCO₃, Boc₂O
0-25° C.
Step L

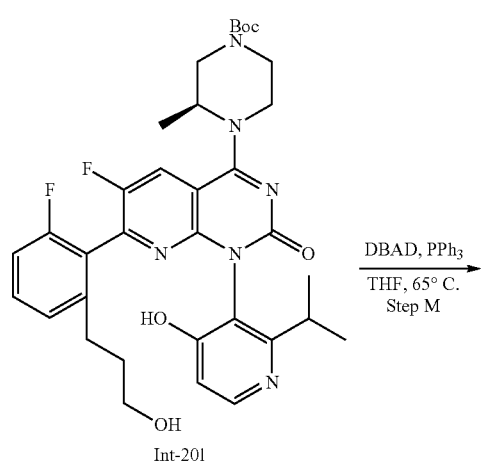

Int-20l

DBAD, PPh₃
THF, 65° C.
Step M

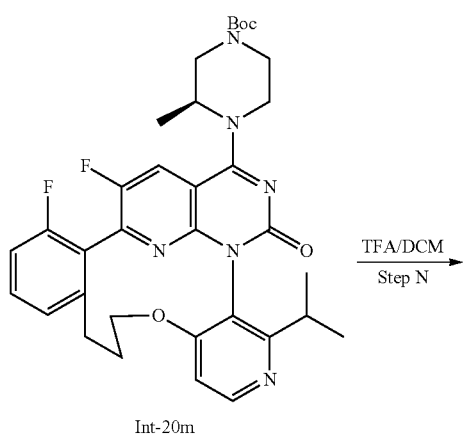

Int-20m

TFA/DCM
Step N

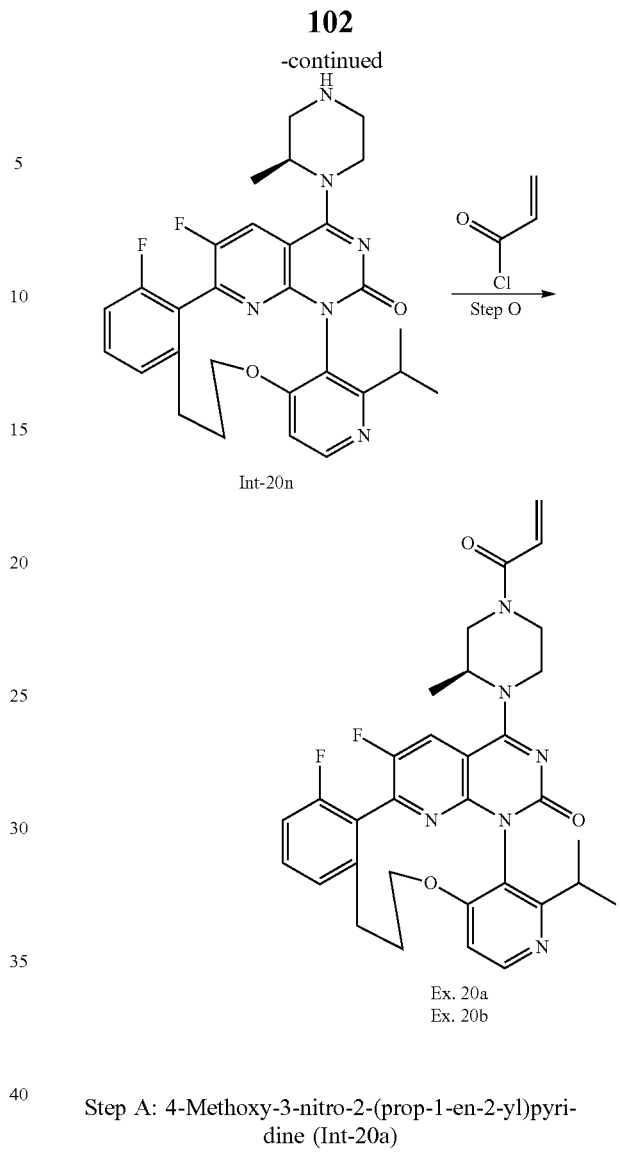

Int-20n

Step O

Ex. 20a
Ex. 20b

Step A: 4-Methoxy-3-nitro-2-(prop-1-en-2-yl)pyridine (Int-20a)

To a stirred solution of 4-chloro-3-nitro-2-(prop-1-en-2-yl)pyridine (Int-10a, 8.00 g, 40.3 mmol) in MeOH (80 mL) was added sodium methoxide (5.44 g, 101 mmol). The resulting mixture was stirred at 75° C. for 16 h. The reaction mixture was concentrated in vacuo and the residue was partitioned between water (40 mL) and EtOAc (100 mL×3). The combined organic phase was dried over anhydrous Na₂SO₄, filtered and concentrated in vacuo. The residue was purified by flash silica gel chromatography, Pet. ether/EtOAc=3/1, to give 4-methoxy-3-nitro-2-(prop-1-en-2-yl)pyridine (Int-20a). MS (ESI): [M+H]⁺ m/z:195.

Step B: 2-Isopropyl-4-methoxypyridin-3-amine (Int-20b)

To a solution of 4-methoxy-3-nitro-2-(prop-1-en-2-yl)pyridine (Int-20a, 13.0 g, 66.9 mmol) in MeOH (300 mL) was added Pd—C (1.59 g, 0.67 mmol, 5% w/w) under argon atmosphere at 25° C. The mixture was stirred at 25° C. under H₂ atmosphere (15 psi) for 15 h. After 15 h, another batch Pd—C (4.76 g, 2.01 mmol, 5% w/w) was added, and the mixture was stirred at 25° C. under H₂ atmosphere (30 psi) for 15 h. The mixture was filtered and the filtrate was evaporated under reduced pressure to give the crude product, which was purified by flash silica gel chromatography with an eluent of 0~30% ethyl acetate/petroleum ether gradient to give 2-isopropyl-4-methoxypyridin-3-amine (Int-20b). MS (ESI): [M+H]$^+$ m/z:167.

Step C: 2,6-Dichloro-5-fluoro-N-((2-isopropyl-4-methoxypyridin-3-yl)carbamoyl)nicotinamide (Int-20c)

To a solution of 2,6-dichloro-5-fluoronicotinamide (8.70 g, 41.6 mmol) in THF (82 mL) was added oxalyl chloride (3.52 mL, 41.6 mmol) at 25° C. under N$_2$ atmosphere, and the mixture was stirred at 65° C. for 30 min. Then the reaction was cooled to room temperature, 2-isopropyl-4-methoxypyridin-3-amine (Int-20b, 6.92 g, 41.6 mmol) in THF (65 mL) was added, and the mixture was stirred at 25° C. for 1 h. The mixture was evaporated under reduced pressure to give the crude product, which was purified by flash silica gel chromatography eluent of 0~10% MeOH/DCM gradient to give 2,6-dichloro-5-fluoro-N-((2-isopropyl-4-methoxypyridin-3-yl)carbamoyl)nicotinamide (Int-20c). MS (ESI): [M+H]$^+$ m/z:401.

Step D: 7-chloro-6-fluoro-1-(2-isopropyl-4-methoxypyridin-3-yl)pyrido[2,3-d]pyrimidine-2,4(1H,3H)-dione (Int-20d)

To a solution of 2,6-dichloro-5-fluoro-N-((2-isopropyl-4-methoxypyridin-3-yl)carbamoyl)nicotinamide (Int-20c, 11.5 g, 28.7 mmol) in THF (220 mL) was added KHMDS (71.7 mL, 71.7 mmol) (1.0 M in THF) at 0° C. under N$_2$ atmosphere. The mixture was stirred at 25° C. for 30 min. The mixture was evaporated under reduced pressure to give the crude product, which was purified by flash silica gel chromatography with an eluent of 0~10% MeOH/DCM gradient to give 7-chloro-6-fluoro-1-(2-isopropyl-4-methoxypyridin-3-yl)pyrido[2,3-d]pyrimidine-2,4(1H,3H)-dione (Int-20d). MS (ESI): [M+H]$^+$ m/z:365.

Step E: 4,7-Dichloro-6-fluoro-1-(2-isopropyl-4-methoxypyridin-3-yl)pyrido[2,3-d]pyrimidin-2(1H)-one (Int-20e)

To a stirred solution of 7-chloro-6-fluoro-1-(2-isopropyl-4-methoxypyridin-3-yl)pyrido[2,3-d]pyrimidine-2,4(1H,3H)-dione (Int-20d, 3.64 g, 9.98 mmol) in MCCN (40 mL) was added DIEA (4.36 mL, 25.0 mmol) and POCl$_3$ (2.33 mL, 25.0 mmol) at 25° C. The mixture was stirred at 80° C. for 30 min. The reaction mixture was concentrated in vacuo to give 4,7-dichloro-6-fluoro-1-(2-isopropyl-4-methoxypyridin-3-yl)pyrido[2,3-d]pyrimidin-2(1H)-one, which was used in the next step without further purification (Int-20e). MS (ESI): [M+H]$^+$ m/z:383.

Step F: tert-Butyl (S)-4-(7-chloro-6-fluoro-1-(2-isopropyl-4-methoxypyridin-3-yl)-2-oxo-1,2-dihydropyrido[2,3-d]pyrimidin-4-yl)-3-methylpiperazine-1-carboxylate (Int-20f)

To a stirred solution of 4,7-dichloro-6-fluoro-1-(2-isopropyl-4-methoxypyridin-3-yl)pyrido[2,3-d]pyrimidin-2(1H)-one (Int-20e, 3.80 g, 9.92 mmol) in MeCN (40 mL) was added DIEA (5.20 mL, 29.7 mmol) and (S)-tert-butyl 3-methylpiperazine-1-carboxylate (3.97 g, 19.8 mmol) at 25° C., and the mixture was stirred at 80° C. for 30 min. The reaction mixture was concentrated in vacuo, and the residue was purified by column chromatography on silica gel with an eluent of Pet. ether/EtOAc=1/1, to give (S)-tert-butyl 4-(7-chloro-6-fluoro-1-(2-isopropyl-4-methoxypyridin-3-yl)-2-oxo-1,2-dihydropyrido[2,3-d]pyrimidin-4-yl)-3-methylpiperazine-1-carboxylate (Int-20f). MS (ESI): [M+H]$^+$ m/z:548.

Step G: tert-Butyl (3S)-4-(6-fluoro-7-(2-fluoro-6-hydroxyphenyl)-1-(2-isopropyl-4-methoxypyridin-3-yl)-2-oxo-1,2-dihydropyrido[2,3-d]pyrimidin-4-yl)-3-methylpiperazine-1-carboxylate (Int-20g)

To a stirred solution of (S)-tert-butyl 4-(7-chloro-6-fluoro-1-(2-isopropyl-4-methoxypyridin-3-yl)-2-oxo-1,2-dihydropyrido[2,3-d]pyrimidin-4-yl)-3-methylpiperazine-1-carboxylate (Int-20f, 1.14 g, 2.08 mmol), potassium acetate (1.02 g, 10.4 mmol) and 1,1'-bis(diphenylphosphino)ferrocene-palladium(II)dichloride dichloromethane complex (0.170 g, 0.208 mmol) in 1,4-dioxane (15 mL) and water (3 mL) was added potassium trifluoro(2-fluoro-6-hydroxyphenyl)borate (0.909 g, 4.17 mmol) dissolved in 1,4-dioxane (0.5 mL) at 90° C. under N$_2$ atmosphere. The mixture was stirred at 90° C. for 0.5 h under N$_2$ atmosphere. The reaction mixture was quenched with brine (10 mL), and extracted with ethyl acetate (2×100 mL). The combined organic layers were washed with brine (10 mL), dried over Na$_2$SO$_4$, filtered and the solvent was evaporated under reduced pressure. The residue was purified by flash silica gel chromatography eluent of 0~50% DCM/MeOH gradient to give (3S)-tert-butyl 4-(6-fluoro-7-(2-fluoro-6-hydroxyphenyl)-1-(2-isopropyl-4-methoxypyridin-3-yl)-2-oxo-1,2-dihydropyrido[2,3-d]pyrimidin-4-yl)-3-methylpiperazine-1-carboxylate (Int-20g). MS (ESI): [M+H]$^+$ m/z:624.

Step H: tert-Butyl (3S)-4-(6-fluoro-7-(2-fluoro-6-(((trifluoromethyl)sulfonyl)oxy)phenyl)-1-(2-isopropyl-4-methoxypyridin-3-yl-2-oxo-1,2-dihydropyrido[2,3-d]pyrimidin-4-yl-3-methylpiperazine-1-carboxylate (Int-20h)

To a stirred solution of (3S)-tert-butyl 4-(6-fluoro-7-(2-fluoro-6-hydroxyphenyl)-1-(2-isopropyl-4-methoxypyridin-3-yl)-2-oxo-1,2-dihydropyrido[2,3-d]pyrimidin-4-yl)-3-methylpiperazine-1-carboxylate (Int-20g, 500 mg, 0.803 mmol) in DCM (8 mL) was added pyridine (191 mg, 2.41 mmol), followed by Tf$_2$O (0.407 mL, 2.41 mmol) at 0° C. under a N$_2$ atmosphere. The mixture was stirred at 20° C. for 2 h under the N$_2$ atmosphere. The reaction mixture was quenched with brine (10 mL), and extracted with ethyl acetate (2×50 mL). The combined organic layers were washed with brine (10 mL), dried over Na$_2$SO$_4$, filtered and the solvent was evaporated under reduced pressure. The residue was purified by flash silica gel chromatography using an eluent of 0~10% DCM/MeOH gradient to give (3S)-tert-butyl 4-(6-fluoro-7-(2-fluoro-6-(((trifluoromethyl)sulfonyl)oxy)phenyl)-1-(2-isopropyl-4-methoxypyridin-3-yl)-2-oxo-1,2-dihydropyrido[2,3-d]pyrimidin-4-yl)-3-methylpiperazine-1-carboxylate (Int-20h). MS (ESI): [M+H]$^+$ m/z:755.

Step I: tert-Butyl (3S)-4-(7-(2-((E)-3-((tert-butyldimethylsilyl)oxy)prop-1-en-1-yl-6-fluorophenyl-6-fluoro-1-(2-isopropyl-4-methoxypyridin-3-yl-2-oxo-1,2-dihydropyrido[2,3-d]pyrimidin-4-yl-3-methylpiperazine-1-carboxylate (Int-20i)

To a stirred solution of (3S)-tert-butyl 4-(6-fluoro-7-(2-fluoro-6-((((trifluoromethyl)sulfonyl)oxy)phenyl)-1-(2-isopropyl-4-methoxypyridin-3-yl)-2-oxo-1,2-dihydropyrido[2,3-d]pyrimidin-4-yl)-3-methylpiperazine-1-carboxylate (Int-20h, 350 mg, 0.464 mmol) in toluene (6 mL) was added (E)-tert-butyldimethyl((3-(4,4,5,5-tetramethyl-1,3,2-dioxaborolan-2-yl)allyl)oxy)silane (208 mg, 0.696 mmol), potassium phosphate (1.39 mL, 1.39 mmol) (1M in water) and chloro(2-dicyclohexylphosphino-2',6'-dimethoxy-1,1'-biphenyl)[2-(2'-amino-1,1'-biphenyl)]palladium(II) (33.4 mg, 0.046 mmol) at 25° C. under $N_2$ atmosphere, and the mixture was stirred at 60° C. for 12 h under $N_2$ atmosphere. The reaction was quenched with water (10 mL) and extracted with EtOAc (50 mL×3). The combined organic phase was dried over anhydrous $Na_2SO_4$, filtered and concentrated in vacuo. The residue was purified by flash silica gel chromatography, eluting with Pet. ether/EtOAc=1/2, to give (3S)-tert-butyl 4-(7-(2-((E)-3-((tert-butyldimethylsilyl)oxy)prop-1-en-1-yl)-6-fluorophenyl)-6-fluoro-1-(2-isopropyl-4-methoxypyridin-3-yl)-2-oxo-1,2-dihydropyrido[2,3-d]pyrimidin-4-yl)-3-methylpiperazine-1-carboxylate Int-20i. MS (ESI): $[M+H]^+$ m/z:777.

Step J: tert-Butyl (3S)-4-(7-(2-(3-((tert-butyldimethylsilyl)oxy)propyl)-6-fluorophenyl)-6-fluoro-1-(2-isopropyl-4-methoxypyridin-3-yl)-2-oxo-1,2-dihydropyrido[2,3-d]pyrimidin-4-yl)-3-methylpiperazine-1-carboxylate (Int-20 j)

To a stirred solution of (3S)-tert-butyl 4-(7-(2-((E)-3-((tert-butyldimethylsilyl)oxy)prop-1-en-1-yl)-6-fluorophenyl)-6-fluoro-1-(2-isopropyl-4-methoxypyridin-3-yl)-2-oxo-1,2-dihydropyrido[2,3-d]pyrimidin-4-yl)-3-methylpiperazine-1-carboxylate (Int-20i, 200 mg, 0.257 mmol) in MeOH (5 mL) was added Pd—C (27.4 mg, 0.257 mmol, 10% w/w) at 25° C. under $N_2$ atmosphere. The mixture was degassed and purged with hydrogen three times and stirred at 25° C. for 12 h under Hz balloon (15 psi). The mixture was filtered and the filtrate was concentrated in vacuo to give (3S)-tert-butyl 4-(7-(2-(3-((tert-butyldimethylsilyl)oxy)propyl)-6-fluorophenyl)-6-fluoro-1-(2-isopropyl-4-methoxypyridin-3-yl)-2-oxo-1,2-dihydropyrido[2,3-d]pyrimidin-4-yl)-3-methylpiperazine-1-carboxylate (Int-20j). MS (ESI): $[M+H]^+$ m/z:779.

Step K: 6-fluoro-7-(2-fluoro-6-(3-hydroxypropyl)phenyl)-1-(4-hydroxy-2-isopropylpyridin-3-yl)-4-((S)-2-methylpiperazin-1-yl)pyrido[2,3-d]pyrimidin-2(1H)-one (Int-20k)

To a stirred solution of (3S)-tert-butyl 4-(7-(2-(3-((tert-butyldimethylsilyl)oxy)propyl)-6-fluorophenyl)-6-fluoro-1-(2-isopropyl-4-methoxypyridin-3-yl)-2-oxo-1,2-dihydropyrido[2,3-d]pyrimidin-4-yl)-3-methylpiperazine-1-carboxylate (Int-20j, 110 mg, 0.141 mmol) in MeCN (1.5 mL) were added KI (23.4 mg, 0.141 mmol) and chlorotrimethylsilane (15.3 mg, 0.141 mmol), and the resulting mixture was stirred at 80° C. for 16 h. The reaction mixture was used directly in the next step without further purification. (Int-20k). MS (ESI): $[M+H]^+$ m/z:551.

Step L: tert-Butyl (3S)-4-(6-fluoro-7-(2-fluoro-6-(3-hydroxypropyl)phenyl)-1-(4-hydroxy-2-isopropylpyridin-3-yl)-2-oxo-1,2-dihydropyrido[2,3-d]pyrimidin-4-yl)-3-methylpiperazine-1-carboxylate (Int-20l)

To a stirred solution of 6-fluoro-7-(2-fluoro-6-(3-hydroxypropyl)phenyl)-1-(4-hydroxy-2-isopropylpyridin-3-yl)-4-((S)-2-methylpiperazin-1-yl)pyrido[2,3-d]pyrimidin-2(1H)-one (Int-20k, 110 mg, 0.100 mmol) in MeCN (1 mL) were added sodium bicarbonate (8.4 mg, 0.10 mmol) in water (0.2 mL) and $Boc_2O$ (0.035 mL, 0.15 mmol) at 0° C. under $N_2$ atmosphere. The mixture was stirred at 25° C. for 1 h under $N_2$ atmosphere. The mixture was extracted with EtOAc (10 mL×3), and the combined organic phase was dried over anhydrous $Na_2SO_4$, filtered and the filtrate was concentrated in vacuo. The residue was purified by preparative TLC plate ($SiO_2$, DCM/MeOH=10/1) to give tert-butyl (3S)-4-(6-fluoro-7-(2-fluoro-6-(3-hydroxypropyl)phenyl)-1-(4-hydroxy-2-isopropylpyridin-3-yl)-2-oxo-1,2-dihydropyrido[2,3-d]pyrimidin-4-yl)-3-methylpiperazine-1-carboxylate (Int-20l). MS (ESI): $[M+H]^+$ m/z:651.

Step M: Int-20m

To a stirred solution of (3S)-tert-butyl 4-(6-fluoro-7-(2-fluoro-6-(3-hydroxypropyl)phenyl)-1-(4-hydroxy-2-isopropylpyridin-3-yl)-2-oxo-1,2-dihydropyrido[2,3-d]pyrimidin-4-yl)-3-methylpiperazine-1-carboxylate (Int-20l, 35.0 mg, 0.0550 mmol) in THF (3.0 mL) was added triphenylphosphine (36.0 mg, 0.137 mmol). The mixture was stirred at 65° C. under $N_2$ atmosphere, and then (E)-di-tert-butyl diazene-1,2-dicarboxylate (25.3 mg, 0.110 mmol) was added. The reaction was stirred at 65° C. for 3 h. The mixture was cooled to rt and was directly purified by preparative TLC plate ($SiO_2$, DCM/MeOH=10/1) to provide Int-20m. MS (ESI): $[M+H]^+$ m/z:633.

Step N: Int-20n

A solution of Int-20m (22 mg, 0.035 mmol) in DCM (0.5 mL) and TFA (0.1 mL) was stirred at 25° C. for 10 min. The mixture was concentrated in vacuo to give Int-20n, which was used in the next step with further purification. MS (ESI): $[M+H]^+$ m/z:533.

Step O: 17,20-difluoro-2-[(2S)-2-methyl-4-(prop-2-enoyl)piperazin-1-yl]-6-(propan-2-yl)-12,13-dihydro-1,18-ethenopyrido[3,4-e]pyrimido[6,1-c][7.2.4]benzoxadiazacyclododecin-4(11H)-one (Ex. 20a and 20b)

To a stirred solution of Int-20n (18.5 mg, 0.0350 mmol) in DCM (0.5 mL) were added DIEA (0.0180 mL, 0.104 mmol) and acryloyl chloride (6.3 mg, 0.070 mmol). The resulting mixture was stirred at 0° C. for 10 min. The mixture was purified by preparative TLC plate directly ($SiO_2$, DCM/MeOH=10/1). The racemic material was separated by preparative SFC Column N; Condition: 0.1% $NH_4OH$ MeOH, 55%, to afford resolved atropisomers:

Peak 1—Ex. 20a-17,20-difluoro-2-[(2S)-2-methyl-4-(prop-2-enoyl)piperazin-1-yl]-6-(propan-2-yl)-12,13-dihydro-1,18-ethenopyrido[3,4-e]pyrimido[6,1-c][7,2,4]benzoxadiazacyclododecin-4(11H)-one. MS (ESI): $[M+H]^+$ m/z:587; $^1H$ NMR (400 MHz, methanol-$d_4$) δ: 8.40 (d, J=5.9 Hz, 1H), 8.17 (br d, J=8.2 Hz, 1H), 7.49-7.32 (m, 1H), 7.18-7.09 (m, 2H), 7.05 (t, J=9.0 Hz, 1H), 6.95-6.74 (m, 1H), 6.31 (br d, J=16.4 Hz, 1H), 5.84 (br d, J=10.2 Hz, 1H), 4.77-4.62 (m, 2H), 4.59 (br s, 1H), 4.51-4.15 (m, 1H), 4.03-3.94 (m, 1H), 3.70 (br d, J=13.7 Hz, 2H), 3.43-3.31 (m, 1H), 3.07-2.93 (m, 1H), 2.85 (br, 1H), 2.18-2.06 (m, 1H), 1.94 (br, 1H), 1.81-1.65 (m, 2H), 1.57 (br t, J=7.4 Hz, 3H), 1.28 (d, J=6.7 Hz, 3H), 0.99 (d, J=6.7 Hz, 3H); and Peak 2—Ex. 20b-17,20-difluoro-2-[(2S)-2-methyl-4-(prop-2-enoyl)piperazin-1-yl]-6-(propan-2-yl)-12,13-dihydro-1,18-ethenopyrido[3,4-e]pyrimido[6,1-c][7,2,4]benzoxadiazacyclododecin-4(11H)-one. MS (ESI): [M+H]⁺ m/z:587; ¹H NMR (400 MHz, methanol-$d_4$) δ: 8.40 (d, J=5.9 Hz, 1H), 8.32 (br d, J=8.6 Hz, 1H), 7.46-7.37 (m, 1H), 7.13 (dd, J=12.5, 7.0 Hz, 2H), 7.04 (t, J=9.0 Hz, 1H), 6.84 (br dd, J=16.4, 9.8 Hz, 1H), 6.32 (br d, J=16.8 Hz, 1H), 5.84 (dd, J=10.6, 2.0 Hz, 1H), 5.33 (br s, 1H), 4.72 (br d, J=11.7 Hz, 1H), 4.59 (br, 1H), 4.46-4.22 (m, 2H), 4.12-3.78 (m, 3H), 3.46 (br s, 1H), 3.00 (br d, J=6.7 Hz, 1H), 2.83 (br s, 1H), 2.11 (br t, J=10.6 Hz, 1H), 1.93 (br s, 1H), 1.79-1.64 (m, 1H), 1.37 (br s, 3H), 1.28 (d, J=7.0 Hz, 3H), 0.99 (d, J=6.7 Hz, 3H).

Preparation of 2-chloro-5-fluoro-6-(2-fluoro-6-hydroxyphenyl)nicotinonitrile (Int-21)

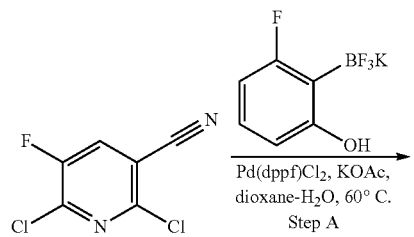

2,6-dichloro-5-fluoronicotinonitrile (2.86 g, 15 mmol), potassium trifluoro(2-fluoro-6-hydroxyphenyl)borate (3.60 g, 16.5 mmol), [1,1'-bis(diphenylphosphino)ferrocene]dichloropalladium(II) (0.549 g, 0.750 mmol) and potassium acetate (2.94 g, 30.0 mmol) were combined in a 500 mL round bottom flask. The flask was purged with nitrogen 3 times. Dioxane (150 mL) and water (15 mL) (10:1) were added. The reaction mixture was stirred at 60° C. for 16 h. The mixture was diluted with water and extracted with ethyl acetate 3-4 times and dried with anhydrous Na₂SO₄, then the solvent was evaporated under vacuum and purified by silica gel column chromatography using 10%-30% EtOAc/Hexane to give 2-chloro-5-fluoro-6-(2-fluoro-6-hydroxyphenyl)nicotinonitrile (Int-21). ¹H NMR (400 MHz, CDCl₃) δ: 8.91 (s, 1H), 7.90 (d, J=8.0 Hz, 1H), 7.39 (q, J=1.6 Hz, 1H), 6.89 (d, J=8.4 Hz, 1H), 6.79-6.75 (m, 1H).

Preparation of 2-(3-amino-2-isopropylpyridin-4-yl)ethanol (Int-22)

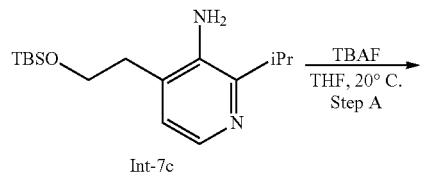

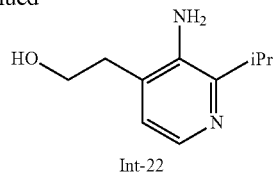

To a stirred solution of 4-(2-((tert-butyldimethylsilyl)oxy)ethyl)-2-isopropylpyridin-3-amine (Int-7c, 1 g, 3.4 mmol) in THF (10 mL) was added TBAF (8.49 mL, 8.49 mmol) (1 M in THF) at 20° C., and the mixture was stirred at 20° C. for 4 h under nitrogen atmosphere. The reaction was concentrated and the residue was purified by flash silica gel chromatography using an eluent of 0~100% EtOAc/Pet. ether to give 2-(3-amino-2-isopropylpyridin-4-yl)ethanol (Int-22). ¹H NMR (400 MHz, CDCl₃) δ: 7.99 (d, J=4.7 Hz, 1H), 6.84 (d, J=4.7 Hz, 1H), 3.97 (t, J=6.1 Hz, 4H), 3.16-2.95 (m, 1H), 2.80 (t, J=6.1 Hz, 2H), 1.31 (d, J=6.7 Hz, 6H).

Preparation of potassium (3,6-difluoro-2-hydroxyphenyl)trifluoroborate (Int-23c)

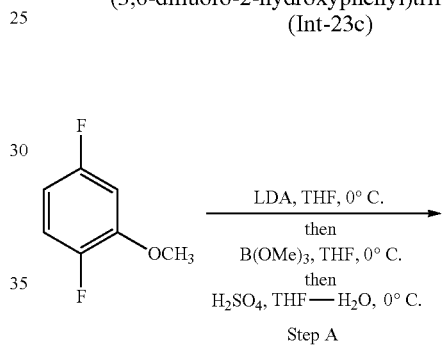

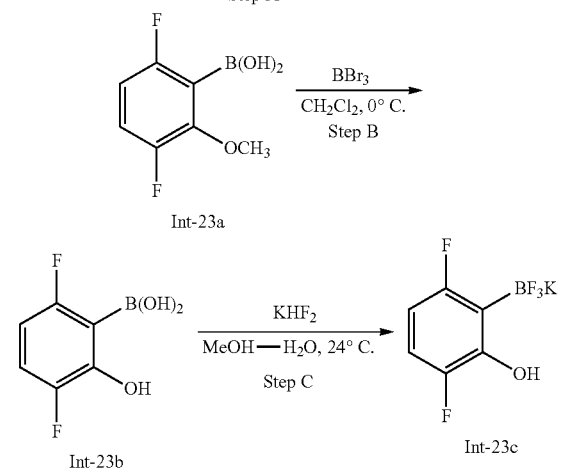

Step A: (3,6-difluoro-2-methoxyphenyl)boronic acid (Int-23a)

1,4-Difluoro-2-methoxybenzene (2.40 mL, 20.8 mmol) was dissolved in THF (20.8 mL) under nitrogen. The resulting solution was cooled down to 0° C. A 1 M solution of lithium diisopropylamide (25.0 mL, 25.0 mmol) in THF-hexanes was added dropwise into the reaction mixture at 0° C. The resulting mixture was stirred for 15 min at 0° C. and then trimethyl borate (2.79 mL, 25.0 mmol) was added dropwise into the reaction vessel. The resulting mixture was stirred for 30 min at 0° C. An ice-cold 2 M aqueous solution of sulfuric acid (52.0 mL, 104 mmol) was added dropwise into the reaction mixture and the resulting mixture was stirred for 2 h at 0° C. The product mixture was extracted three times with chloroform (3×100 mL). The organic layers were combined and the combined organic layers were dried over sodium sulfate. The dried solution was filtered and the filtrate was concentrated to dryness. The residue obtained containing (3,6-difluoro-2-methoxyphenyl)boronic acid (Int-23a) was used directly in the next step without purification.

Step B: (3,6-difluoro-2-hydroxyphenylboronic acid (Int-23b)

(3,6-Difluoro-2-methoxyphenyl)boronic acid (2.8 g, 14.9 mmol) was dissolved in DCM (49.7 mL) under nitrogen. The resulting solution was cooled down to 0° C. Neat tribromoborane (4.31 mL, 44.7 mmol) was added dropwise into the reaction vessel carefully. The reaction mixture was stirred for 15 min at 0° C. when TLC showed full conversion of the starting material. The product mixture was carefully quenched by dropwise addition of ice-cold water (5 mL). The product mixture was extracted three times with chloroform (3×100 mL). The organic layers were dried over sodium sulfate. The dried solution was filtered and the filtrate was concentrated to dryness. The residue obtained containing (3,6-difluoro-2-hydroxyphenyl)boronic acid (Int-23b) was used directly into the next step without purification.

Step C: potassium (3,6-difluoro-2-hydroxyphenyl)trifluoroborate (Int-23c)

(3,6-Difluoro-2-hydroxyphenyl)boronic acid (2.59 g, 14.9 mmol) was added into a 250 mL round bottom flask. The reaction vessel was evacuated and backfilled with nitrogen three times. Methanol (18.6 mL) was added into the reaction vessel to dissolve the starting material. In a separate 40 mL vial was added potassium bifluoride (4.65 g, 59.6 mmol) and water (18.6 mL). The resulting fluoride solution was added streamwise into the reaction vessel. The resulting mixture was stirred for 16 h at 24° C. The product mixture was diluted with acetone (50 mL). The diluted product mixture was filtered and the filtrate was concentrated to dryness. The residue obtained was diluted with acetone (100 mL). The diluted mixture was filtered and the filtrate was concentrated to dryness. The residue obtained was diluted with acetone (3 mL) and then the solution was triturated with hexanes (200 mL). The product was collected by filtration to afford potassium (3,6-difluoro-2-hydroxyphenyl)trifluoroborate (Int-23c). $^1$H NMR (500 MHz, DMSO-$d_6$) δ 8.14 (q, J=14.7 Hz, 1H), 6.86 (ddd, J=10.8, 8.8, 5.2 Hz, 1H), 6.32 (td, J=8.3, 3.2 Hz, 1H).

Preparation of potassium (3,6-difluoro-2-hydroxyphenyl)trifluoroborate (Int-24)

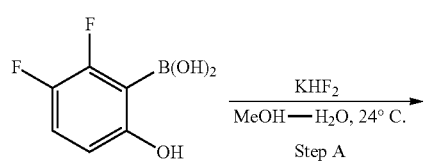

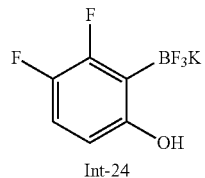

(2,3-Difluoro-6-hydroxyphenyl)boronic acid (0.500 g, 2.88 mmol) was added into a 250 mL round bottomed flask. The reaction vessel was evacuated and backfilled with a balloon of nitrogen three times. Methanol (3.59 mL) was added into the reaction vessel to dissolve the starting material. In a separate 40 mL vial was added potassium bifluoride (0.898 g, 11.5 mmol) and water (3.59 mL). The resulting fluoride solution was added streamwise into the reaction vessel. The resulting mixture was stirred for 16h at 24° C. The product mixture was diluted with acetone (20 mL). The diluted product mixture was filtered and the filtrate was concentrated to dryness. The residue obtained was diluted with acetone (40 mL). The diluted mixture was filtered and the filtrate was concentrated to dryness. The residue obtained was diluted with acetone (3 mL) and then the solution was triturated with hexanes (200 mL). The product was collected by filtration to afford potassium (3,6-difluoro-2-hydroxyphenyl)trifluoroborate (Int-24). $^1$H NMR (500 MHz, DMSO-$d_6$) δ 7.84 (q, J=13.3 Hz, 1H), 6.91 (q, J=8.3 Hz, 1H), 6.32 (dd, J=10.0, 5.0 Hz, 1H).

Preparation of potassium trifluoro(2-hydroxy-3-(trifluoromethyl)phenyl)borate (Int-25)

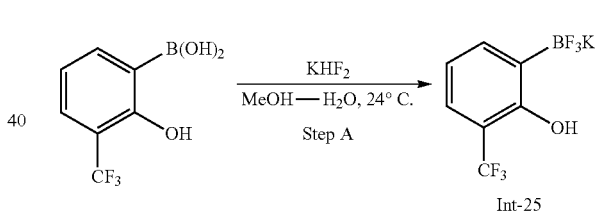

To 2-hydroxy-3-(trifluoromethyl)phenylboronic acid (500 mg, 2.43 mmol) in methanol (3.04 mL)/water (3.04 mL) was added potassium bifluoride (759 mg, 9.71 mmol). The reaction mixture was stirred overnight at room temperature. The reaction mixture was diluted with acetone (20 mL) and filtered. The filtrate was concentrated in vacuo and redissolved exclusively in acetone. Hexane was added (~4 mL) and the mixture was again filtered. The organics were concentrated again to give potassium trifluoro(2-hydroxy-3-(trifluoromethyl)phenyl)borate (Int-25). MS (ESI) m/z 229 [M−K]$^−$.

Preparation of potassium trifluoro(2-hydroxy-5-(trifluoromethyl)phenyl)borate (In-26)

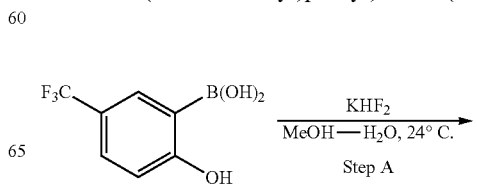

-continued

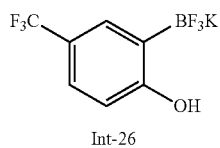

Int-26

(2-Hydroxy-5-(trifluoromethyl)phenyl)boronic acid (0.500 g, 2.43 mmol) was added into a 250 mL round bottomed flask. The reaction vessel was evacuated and backfilled with nitrogen three times. Methanol (3.04 mL) was added into the reaction vessel to dissolve the starting material. In a separate 40 mL vial was added potassium bifluoride (0.759 g, 9.71 mmol) and water (3.04 mL). The resulting fluoride solution was added streamwise into the reaction vessel. The resulting mixture was stirred for 16h at 24° C. The product mixture was diluted with acetone (25 mL). The diluted product mixture was filtered and the filtrate was concentrated to dryness. The residue obtained was diluted with acetone (50 mL). The diluted mixture was filtered and the filtrate was concentrated to dryness. The residue obtained was diluted with acetone (3 mL) and then the solution was triturated with hexanes (50 mL). The product was collected by filtration to afford potassium trifluoro(2-hydroxy-5-(trifluoromethyl)phenyl)borate (Int-26). $^1$H NMR (500 MHz, DMSO-$d_6$) δ 7.91 (q, J=9.7 Hz, 1H), 7.41 (d, J=2.5 Hz, 1H), 7.28 (dd, J=8.4, 2.5 Hz, 1H), 6.69 (d, J=8.4 Hz, 1H).

Preparation of potassium trifluoro(3-fluoro-2-hydroxyphenyl)borate (Int-271

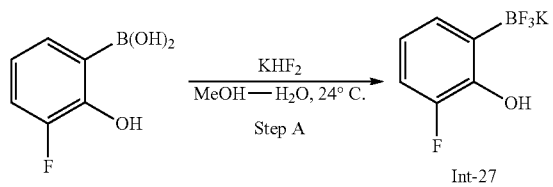

Int-27

(3-Fluoro-2-hydroxyphenyl)boronic acid (1.15 g, 7.38 mmol) was added into a 50 mL round-bottomed flask. The reaction vessel was evacuated and backfilled with a balloon of nitrogen three times. Methanol (14.8 mL) was added into the reaction vessel to dissolve the starting material. In a separate 40 mL vial was added potassium bifluoride (2.30 g, 29.5 mmol) and water (14.8 mL). The resulting fluoride solution was added streamwise into the reaction vessel. The resulting mixture was stirred for 16h at 24° C. The product mixture was diluted with acetone (50 mL). The diluted product mixture was filtered and the filtrate was concentrated to dryness. The residue obtained was diluted with acetone (100 mL). The diluted mixture was filtered and the filtrate was concentrated to dryness. The residue obtained was diluted with acetone (3 mL) and then the solution was triturated with hexanes (200 mL). The product was collected by filtration to afford potassium trifluoro(3-fluoro-2-hydroxyphenyl)borate (Int-27). $^1$H NMR (500 MHz, DMSO-$d_6$) δ 7.43 (d, J=9.6 Hz, 1H), 6.92 (dd, J=7.2, 1.6 Hz, 1H), 6.83 (ddd, J=11.8, 7.9, 1.7 Hz, 1H), 6.60 (td, J=7.6, 4.3 Hz, 1H).

Preparation of potassium (4,5-difluoro-2-hydroxyphenyl)trifluoroborate (Int-28)

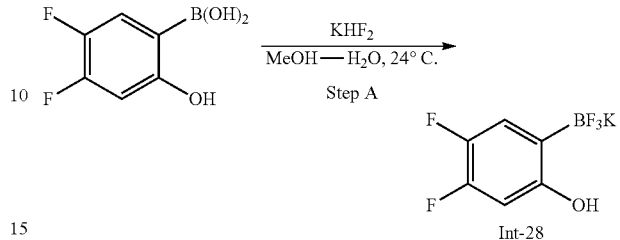

Int-28

(4,5-Difluoro-2-hydroxyphenyl)boronic acid (0.500 g, 2.88 mmol) was added into a 250 mL round-bottomed flask. The reaction vessel was evacuated and backfilled with a balloon of nitrogen three times. Methanol (3.59 mL) was added into the reaction vessel to dissolve the starting material. In a separate 40 mL vial was added potassium bifluoride (0.898 g, 11.5 mmol) and water (3.59 mL). The resulting fluoride solution was added streamwise into the reaction vessel. The resulting mixture was stirred for 16 h at 24° C. The product mixture was diluted with acetone (25 mL). The diluted product mixture was filtered and the filtrate was concentrated to dryness. The residue obtained was diluted with acetone (40 mL). The diluted mixture was filtered and the filtrate was concentrated to dryness. The residue obtained was diluted with acetone (3 mL) and then the solution was triturated with hexanes (~20 mL). The product was collected by filtration to afford potassium (4,5-difluoro-2-hydroxyphenyl)trifluoroborate (Int-28). $^1$H NMR (500 MHz, DMSO-$d_6$) δ 7.52 (qd, J=9.7, 1.4 Hz, 1H), 6.92 (t, J=10.9 Hz, 1H), 6.51 (dd, J=12.8, 6.5 Hz, 1H).

Preparation of potassium (2-chloro-6-hydroxyphenyl)trifluoroborate (Int-29)

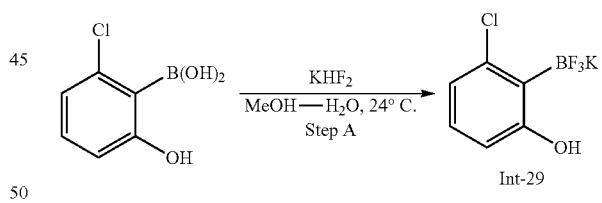

Int-29

(2-Chloro-6-hydroxyphenyl)boronic acid (0.500 g, 2.90 mmol) was added into a 250 mL round bottomed flask. The reaction vessel was evacuated and backfilled with a balloon of nitrogen three times. Methanol (3.63 mL) was added into the reaction vessel to dissolve the starting material. In a separate 40 mL vial was added potassium bifluoride (0.906 g, 11.6 mmol) and water (3.63 mL). The resulting fluoride solution was added streamwise into the reaction vessel. The resulting mixture was stirred for 16 h at 24° C. The product mixture was diluted with acetone (50 mL). The diluted product mixture was filtered and the filtrate was concentrated to dryness. The residue obtained was diluted with acetone (100 mL). The diluted mixture was filtered and the filtrate was concentrated to dryness. The residue obtained was diluted with acetone (3 mL) and then the solution was triturated with hexanes (200 mL). The product was collected by filtration to afford potassium (2-chloro-6-hydroxyphenyl)trifluoroborate (Int-29). $^1$H NMR (500 MHz, DMSO-d$_6$) δ 8.45 (q, J=16.7 Hz, 1H), 6.92 (t, J=7.9 Hz, 1H), 6.65 (d, J=7.8 Hz, 1H), 6.48 (d, J=8.0 Hz, 1H).

Preparation of potassium trifluoro(2-hydroxy-6-(trifluoromethyl)phenyl)borate(Int-30)

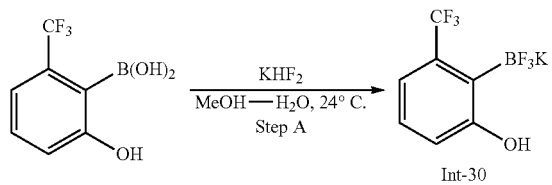

(2-Hydroxy-6-(trifluoromethyl)phenyl)boronic acid (0.500 g, 2.43 mmol) was added into a 250 mL round bottomed flask. The reaction vessel was evacuated and backfilled with a balloon of nitrogen three times. Methanol (3.04 mL) was added into the reaction vessel to dissolve the starting material. In a separate 40 mL vial was added potassium bifluoride (0.759 g, 9.71 mmol) and water (3.04 mL). The resulting fluoride solution was added streamwise into the reaction vessel. The resulting mixture was stirred for 16 h at 24° C. The product mixture was diluted with acetone (25 mL). The diluted product mixture was filtered and the filtrate was concentrated to dryness. The residue obtained was diluted with acetone (40 mL). The diluted mixture was filtered and the filtrate was concentrated to dryness. The residue obtained was diluted with acetone (3 mL) and then the solution was triturated with hexanes (~20 mL). The product was collected by filtration to afford potassium trifluoro(2-hydroxy-6-(trifluoromethyl)phenyl)borate (Int-30). $^1$H NMR (500 MHz, DMSO-d$_6$) δ 8.60 (q, J=16.7 Hz, 1H), 7.12 (t, J=7.9 Hz, 1H), 7.01 (d, J=7.7 Hz, 1H), 6.79 (d, J=8.0 Hz, 1H).

Preparation of 2-chloro-6-(3,6-difluoro-2-hydroxyphenyl)-5-fluoronicotinonitrile (Int-31)

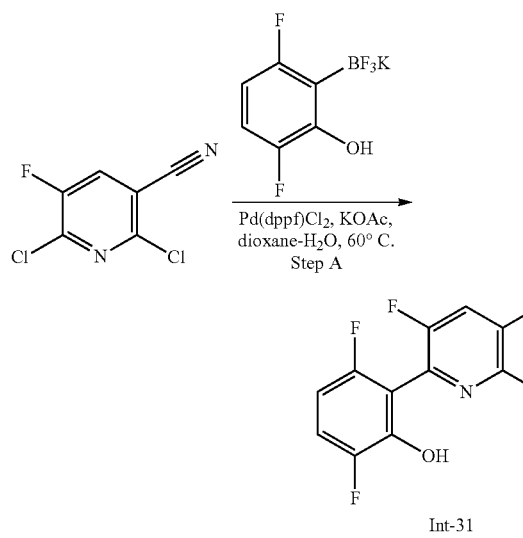

2,6-Dichloro-5-fluoronicotinonitrile (0.382 g, 2.00 mmol), potassium (3,6-difluoro-2-hydroxyphenyl)trifluoroborate (0.472 g, 2.00 mmol), [1,1'-bis(diphenylphosphino)ferrocene]dichloropalladium(II) (0.146 g, 0.200 mmol) and potassium acetate (0.393 g, 4.00 mmol) were combined in a 50 mL round bottom flask. The flask was purged with nitrogen 3 times. Dioxane (15.3 mL) and water (0.955 mL) (15:1) were added. The reaction mixture was stirred at 60° C. overnight. The reaction mixture was filtered and the crude product was purified by column chromatography using ethyl acetate-hexane 10%-20% to afford 2-chloro-6-(3,6-difluoro-2-hydroxyphenyl)-5-fluoronicotinonitrile (Int-31). $^1$H NMR (600 MHz, CDCl$_3$) δ 7.94 (d, J=7.8 Hz, 1H), 7.83 (d, J=2.0 Hz, 1H), 7.26 (td, J=9.5, 5.0 Hz, 1H), 6.75 (td, J=9.2, 3.7 Hz, 1H).

Preparation of 3-(3-amino-2-isopropylpyridin-4-yl)propan-1-ol (Int-32)

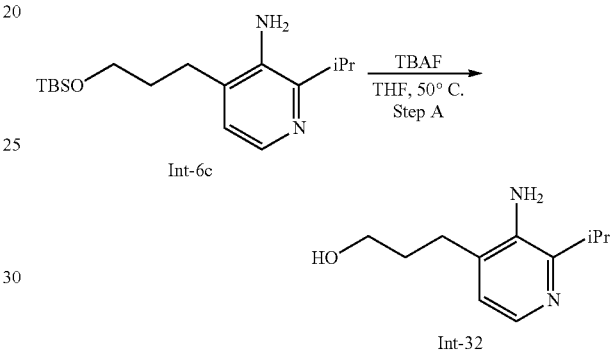

To a flask containing 4-(3-((tert-butyldimethylsilyl)oxy)propyl)-2-isopropylpyridin-3-amine (Int-10c, 2.00 g, 6.48 mmol) was added THF (13 mL) and then TBAF (19.5 mL, 19.5 mmol, 1M in THF). The mixture was heated to 50° C. for one hour. Upon cooling to room temperature, the mixture was concentrated under reduced pressure and then the crude product was purified by column chromatography using 0-30% ethyl acetate in hexanes to afford 3-(3-amino-2-isopropylpyridin-4-yl)propan-1-ol (Int-32). MS (ESI) m/z 195 [M+H]$^+$.

Preparation of (R)-3-(3-amino-2-isopropylpyridin-4-yl)propan-1-ol (Int-33b)

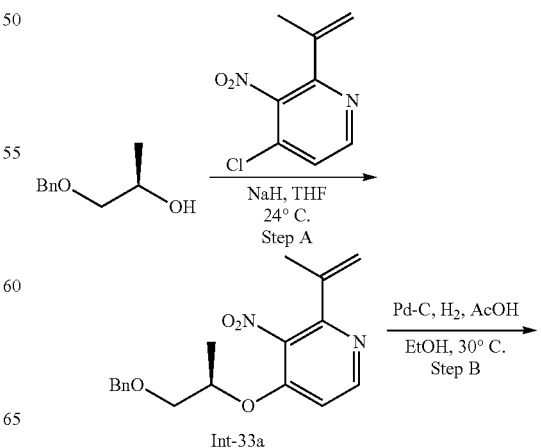

-continued

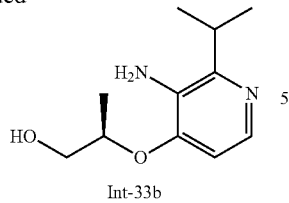

Int-33b

Step A: (R)-4-((1-(benzyloxy)propan-2-yl)oxy)-3-nitro-2-(prop-1-en-2-yl)pyridine (Int-33a)

(R)-1-(Benzyloxy)propan-2-ol (0.178 mL, 1.10 mmol) was dissolved in THF (2.98 mL) and cooled to 0° C. Next, sodium hydride (0.044 g, 1.1 mmol, 60 wt % in mineral oil) was added slowly and the reaction was stirred at 0° C. for 30 min. After that, 4-chloro-3-nitro-2-(prop-1-en-2-yl)pyridine (Int-10a, 0.199 g, 1.00 mmol) was added dropwise and the reaction mixture was stirred at this temperature for 2 h until the starting material was consumed. Then it was quenched with saturated ammonium chloride and diluted with ethyl acetate. The layers were separated and the aqueous layer was extracted with EtOAc. The combined organic layers were washed with water, brine, dried over sodium sulfate, and concentrated. The crude was purified by column chromatography to afford (R)-4-((1-(benzyloxy)propan-2-yl)oxy)-3-nitro-2-(prop-1-en-2-yl)pyridine (Int-33a). $^1$H NMR (600 MHz, CDCl$_3$) δ 8.47 (d, J=5.8 Hz, 1H), 7.40-7.29 (m, 5H), 6.98 (d, J=5.8 Hz, 1H), 5.36 (dq, J=2.1, 1.3 Hz, 1H), 5.30-5.22 (m, 1H), 4.78 (pd, J=6.5, 3.9 Hz, 1H), 4.62-4.50 (m, 2H), 3.66 (dd, J=10.6, 6.8 Hz, 1H), 3.62 (dd, J=10.6, 3.9 Hz, 1H), 2.19 (t, J=1.2 Hz, 3H), 1.38 (d, J=6.3 Hz, 3H).

Step B: (R)-2-((3-amino-2-isopropylpyridin-4-yl)oxy)propan-1-ol (Int-33b)

The mixture of (R)-4-((1-(benzyloxy)propan-2-yl)oxy)-3-nitro-2-(prop-1-en-2-yl)pyridine (4 g, 12 mmol), AcOH (4 mL) and Pd/C (2 g) in EtOH (40 mL) was stirred overnight at 30° C. under H$_2$. The reaction mixture was filtered and concentrated to afford (R)-2-((3-amino-2-isopropylpyridin-4-yl)oxy)propan-1-ol (Int-33b). $^1$H NMR (400 MHz, methanol-d$_4$) δ 7.78 (d, J=5.6 Hz, 1H), 6.80 (d, J=5.6 Hz, 1H), 4.64-4.56 (m, 1H), 3.78-3.68 (m, 2H), 3.19 (s, 1H), 1.33 (d, J=6.4 Hz, 3H), 1.25 (dd, J=1.2, 6.6 Hz, 6H).

Preparation of (S)-3-(3-amino-2-isopropylpyridin-4-yl)propan-1-ol (Int-34c)

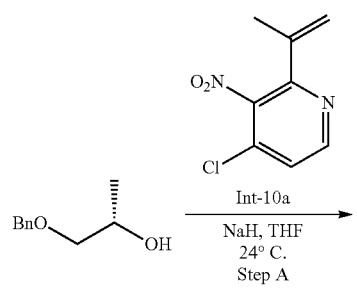

-continued

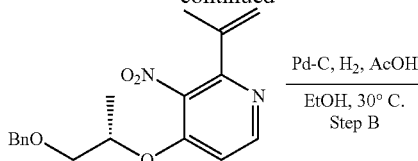

Int-34a

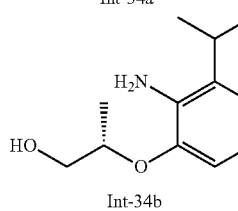

Int-34b

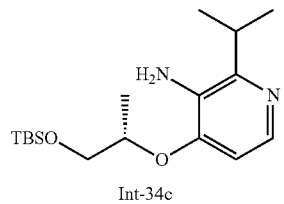

Int-34c

Step A: (S)-4-((1-(benzyloxy)propan-2-yl)oxy)-3-nitro-2-(prop-1-en-2-yl)pyridine (Int-34a)

To a mixture of (S)-1-(benzyloxy)propan-2-ol (4.20 g, 25.3 mmol) in THF (40 mL) was added NaH (2.50 g, 63.3 mmol, 60 wt %) at 0° C. The mixture was stirred for 1 h at room temperature and then 4-chloro-3-nitro-2-(prop-1-en-2-yl)pyridine (Int-10a, 5.00 g, 25.3 mmol) in THF (10 mL) was added. The reaction mixture was stirred at room temperature overnight. The above solution was poured into NH$_4$Cl solution. The solution was extracted with EtOAc (80 mL×3). The combined organic layers were washed with brine, dried over Na$_2$SO$_4$ and concentrated. The crude was purified by column chromatography on silica gel (Pet. ether/EtOAc=50:1) to give (S)-4-((1-(benzyloxy)propan-2-yl)oxy)-3-nitro-2-(prop-1-en-2-yl)pyridine (Int-34a). $^1$H NMR (400 MHz, CDCl$_3$) δ 8.47 (d, J=5.6 Hz, 1H), 7.40-7.28 (m, 5H), 6.97 (d, J=6.0 Hz, 1H), 5.36-5.24 (m, 2H), 4.81-4.75 (m, 1H), 4.61-4.52 (m, 2H), 3.69-3.57 (m, 2H), 2.19 (s, 3H), 1.38 (d, J=6.4 Hz, 3H).

Step B: (S)-2-((3-amino-2-isopropylpyridin-4-yl)oxy)propan-1-ol (Int-34b)

The mixture of (S)-4-((1-(benzyloxy)propan-2-yl)oxy)-3-nitro-2-(prop-1-en-2-yl)pyridine (4.0 g, 12 mmol), AcOH (4 mL) and Pd/C (2.0 g, 10 wt %) in EtOH (40 mL) was stirred overnight at 30° C. under H$_2$. The reaction mixture was filtered and concentrated to give (S)-2-((3-amino-2-isopropylpyridin-4-yl)oxy)propan-1-ol (Int-34b) without further purification.

Step C: (S)-3-(3-amino-2-isopropylpyridin-4-yl)propan-1-ol (Int-34c)

To a mixture of (S)-2-((3-amino-2-isopropylpyridin-4-yl)oxy)propan-1-ol (10.0 g, 47.6 mmol) and imidazole (6.50 g, 95.2 mmol) in DCM (100 mL) was added tert-butylchlorodimethylsilane (10.7 g, 71.4 mol) at room temperature. The reaction mixture was stirred at room temperature overnight. The reaction mixture was washed with water (20 mL) and concentrated. The crude was purified by column chromatography on silica gel (DCM/MeOH=100:1) to give (S)-3-(3-amino-2-isopropylpyridin-4-yl)propan-1-ol (Int-34c). MS (ESI) m/z 325 [M+H]$^+$.

Preparation of 4-(2-((tert-butyldimethylsilyl)oxy)ethoxy-1,1,2,2-d$_4$)-2-isopropylpyridin-3-amine (Int-35c)

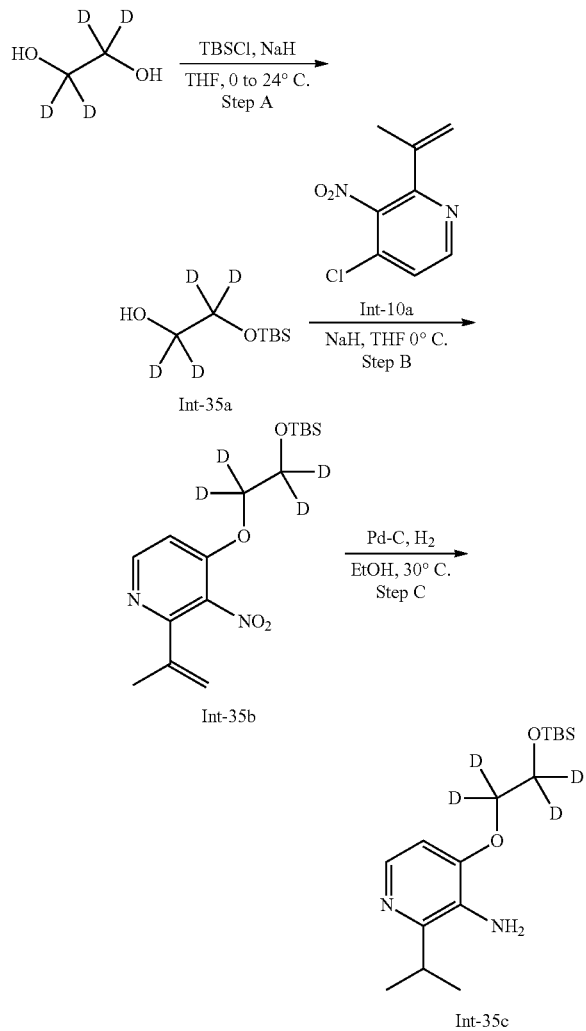

Step A: 2-((tert-butyldimethylsilyl)oxy)ethan-1,1,2,-d$_4$-1-ol (Int-35a)

Ethane-d$_4$-1,2-diol (5.0 g, 76 mmol) was added in a 500 mL round bottomed flask. The reaction vessel was evacuated and backfilled with nitrogen three times. THF (100 mL) was added into the reaction vessel. Sodium hydride (3.0 g, 76 mmol 60% suspension in mineral oil) was added into the reaction vessel in six equal portions over 15 min at 24° C. The resulting mixture was stirred for 1 h at 24° C. In a 200 mL pointed flask, tert-butylchlorodimethylsilane (11.4 g, 76.0 mmol) was dissolved in 30 mL of THF under nitrogen. The resulting mixture was added dropwise into the reaction vessel via cannula. THF (2×10 mL) was added into the vessel containing the silyl chloride and the rinses were added dropwise into the reaction vessel. The resulting mixture was stirred for 1h at 24° C. The product mixture was quenched with saturated ammonium chloride aqueous solution (20 mL). The quenched product mixture was extracted three times with ether (3×50 mL). The combined organic layers were dried over sodium sulfate. The dried solution was filtered and the filtrate was concentrated to dryness. The residue was purified by flash column chromatography, eluting with 0 to 30% ethyl acetate-hexanes to afford 2-((tert-butyldimethylsilyl)oxy)ethan-1,1,2,2-d$_4$-1-ol (Int-35a). $^1$H NMR (500 MHz, CDCl$_3$) δ 0.93 (s, 9H), 0.11 (s, 6H).

Step B: 4-(2-((tert-butyldimethylsilyl)oxy)ethoxy-1,1,2,2-d$_4$)-3-nitro-2-(prop-1-en-2-yl)pyridine (Int-35b)

2-((tert-Butyldimethylsilyl)oxy)ethan-1,1,2,2-d$_4$-1-ol (4.82 g, 26.7 mmol) was added into a 500 mL round bottomed flask. The reaction vessel was evacuated and backfilled with nitrogen three times. THF (50 mL) was added into the reaction vessel. The resulting mixture was cooled down to 0° C. Sodium hydride (1.12 g, 28.0 mmol 60% suspension in mineral oil) was added in five equal portions in 15 min. The resulting mixture was stirred for 30 min at 0° C. In a pointed 100 mL flask, 4-chloro-3-nitro-2-(prop-1-en-2-yl)pyridine (Int-10a, 5.05 g, 25.4 mmol) was dissolved in THF (25 mL) under nitrogen. The resulting solution was transferred to the reaction mixture dropwise via cannula at 0° C. The resulting mixture was stirred for 2 h at 0° C. The product mixture was quenched with saturated ammonium chloride aqueous solution (10 mL). The quenched product mixture was extracted three times with ethyl acetate (3×50 mL). The combined organic layers were dried over sodium sulfate. The dried solution was filtered and the filtrate was concentrated to dryness. The residue obtained was purified by flash column chromatography eluting with 0 to 40% ethyl acetate-hexanes to afford 4-(2-((tert-butyldimethylsilyl)oxy)ethoxy-1,1,2,2-d$_4$)-3-nitro-2-(prop-1-en-2-yl)pyridine (Int-35b). $^1$H NMR (500 MHz, Acetonitrile-d$_3$) δ 8.49 (d, J=5.8 Hz, 1H), 7.13 (d, J=5.8 Hz, 1H), 5.45-5.26 (m, 1H), 5.21-4.97 (m, 1H), 2.11 (s, 3H), 0.85 (s, 9H), 0.04 (s, 6H).

Step C: 4-(2-((tert-butyldimethylsilyl)oxy)ethoxy-1,1,2,2-d$_4$)-2-isopropylpyridin-3-amine (Int-35c)

4-(2-((tert-Butyldimethylsilyl)oxy)ethoxy-1,1,2,2-d$_4$)-3-nitro-2-(prop-1-en-2-yl)pyridine (4.82 g, 14.1 mmol) was dissolved in EtOH (70 mL), degassed under nitrogen, charged with Pd—C (10 wt %, 0.300 g, 2.81 mmol), degassed under nitrogen, and allowed to stir under hydrogen atmosphere for 24h. The product mixture was thoroughly purged with nitrogen. The purged reaction mixture was filtered through a pad of CELITE. The filtrate was concentrated to dryness. The residue obtained was diluted with ethyl acetate (20 mL) and the diluted product mixture was filtered through a syringe filter to further remove the residue catalyst/activated carbon. The filtrate was concentrated to dryness to afford 4-(2-((tert-butyldimethylsilyl)oxy)ethoxy-1,1,2,2-d$_4$)-2-isopropylpyridin-3-amine (Int-35c). $^1$H NMR (500 MHz, Acetonitrile-d$_3$) δ 7.84 (d, J=5.5 Hz, 1H), 6.73 (d, J=5.5 Hz, 1H), 4.03 (s, 2H), 3.11 (p, J=6.7 Hz, 1H), 1.23 (d, J=6.7 Hz, 6H), 0.92 (s, 9H), 0.11 (s, 6H).

Preparation of 4-(3-((tert-butyldimethylsilyl)oxy) propyl)-6-isopropylpyrimidin-5-amine (Int-36a)

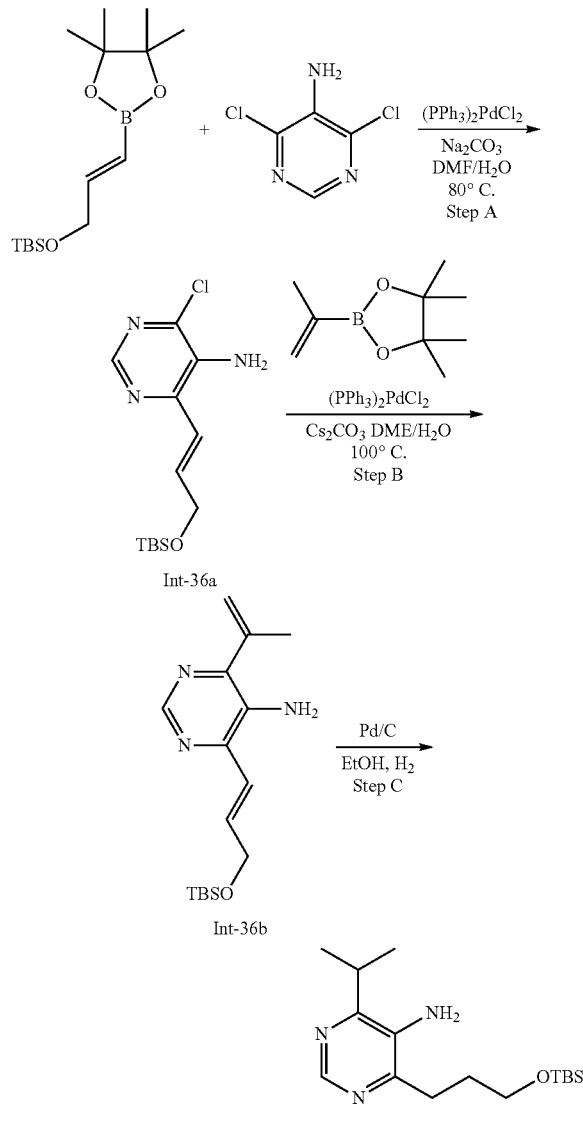

Step A: 4-[(1E)-3-[(tert-butyldimethylsilyl)oxy] prop-1-en-1-yl]-6-chloropyrimidin-5-amine (Int-36a)

Into a 5000-mL 3-necked round-bottom flask purged and maintained with an inert atmosphere of nitrogen, was placed DME (2000 mL), H₂O (400 mL), Na₂CO₃ (248 g, 2343 mmol, 3.00 equiv), tert-butyldimethyl[[(2E)-3-(4,4,5,5-tetramethyl-1,3,2-dioxaborolan-2-yl)prop-2-en-1-yl]oxy]silane (233 g, 781 mmol, 1.00 equiv), 4,6-dichloropyrimidin-5-amine (128 g, 781 mmol, 1.00 equiv), Pd(PPh₃)₂Cl₂ (47 g, 67 mmol, 0.10 equiv). The resulting solution was stirred for 3 h at 80° C. in an oil bath. The resulting solution was cooled to room temperature, extracted with 2×500 mL of ethyl acetate and the organic layers were combined and concentrated under vacuum. The residue was purified by column chromatography using ethyl acetate/petroleum ether (1:1) to afford 4-[(1E)-3-[(tert-butyldimethylsilyl)oxy]prop-1-en-1-yl]-6-chloropyrimidin-5-amine (Int-36a). MS (ESI) m/z 300 [M+H]⁺.

Step B: 4-[(1E)-3-[(tert-butyldimethylsily)oxy]prop-1-en-1-yl]-6-(prop-1-en-2-yl)pyrimidin-5-amine (Int-36b)

Into a 5000-mL 3-necked round-bottom flask purged and maintained with an inert atmosphere of nitrogen, was placed DME (2000 mL), H₂O (400 mL), Cs₂CO₃ (531 g, 1630 mmol, 3 equiv), 4-[(1E)-3-[(tert-butyldimethylsilyl)oxy] prop-1-en-1-yl]-6-chloropyrimidin-5-amine (163 g, 543 mmol, 1.00 equiv), 4,4,5,5-tetramethyl-2-(prop-2-en-1-yl)-1,3,2-dioxaborolane (91 g, 544 mmol, 1.00 equiv), Pd(PPh₃)₂Cl₂ (38 g, 54 mmol, 0.1 equiv). The resulting solution was stirred for 12 h at 100° C. in an oil bath. The resulting solution was cooled to room temperature, and extracted with 2×500 mL of ethyl acetate. The organic layers were combined and concentrated under vacuum. The residue was purified by column chromatography with ethyl acetate/petroleum ether (1:1) to afford 4-[(1E)-3-[(tert-butyldimethylsilyl)oxy]prop-1-en-1-yl]-6-(prop-1-en-2-yl)pyrimidin-5-amine (Int-36b). MS (ESI) m/z 306 [M+H]⁺.

Step C: 4-[3-[(tert-butyldimethylsilyl)oxy]propyl]-6-isopropylpyrimidin-5-amine (Int-36c)

Into a 3000-mL 3-necked round-bottom flask purged and maintained with an inert atmosphere of nitrogen, were placed ethanol (1500 mL), 4-[(1E)-3-[(tert-butyldimethylsilyl)oxy]prop-1-en-1-yl]-6-(prop-1-en-2-yl)pyrimidin-5-amine (107 g, 350 mmol, 1.00 equiv), and Pd/C (3.73 g, 35.0 mmol, 0.1 equiv). Hz (gas) was introduced into the mixture. The resulting solution was stirred for 12 h at 25° C. The solids were filtered out. The resulting mixture was concentrated. The residue was purified by column chromatography (EtOAc:Pet. ether=1:1) to afford 4-[3-[(tert-butyldimethylsilyl)oxy]propyl]-6-isopropylpyrimidin-5-amine (Int-36c). ¹H-NMR (300 MHz, DMSO-d₆): δ 8.28 (s, 1H), 5.00 (s, 2H), 3.66 (t, J=6.5 Hz, 2H), 3.29-3.12 (m, 1H), 2.63 (t, J=7.4 Hz, 2H), 1.93-1.77 (m, 2H), 1.14 (d, J=6.6 Hz, 6H), 0.86 (s, 9H), 0.02 (s, 6H).

Preparation of 4-(4-((tert-butyldimethylsily)oxy) butan-2-yl)-2-isopropylpyridin-3-amine (Int-37d-1 and Int-37d-2)

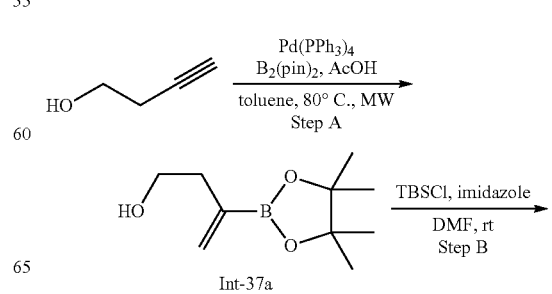

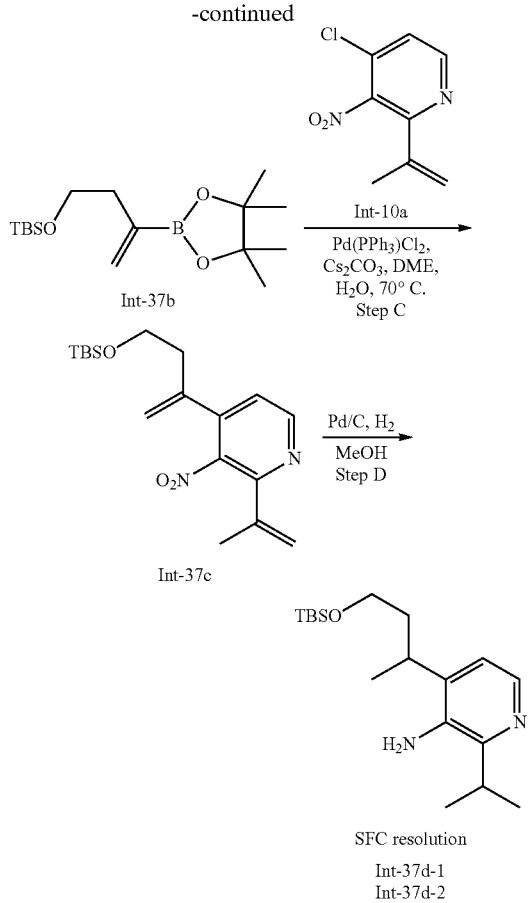

Step A: 3-(4,4,5,5-tetramethyl-1,3,2-dioxaborolan-2-yl)but-3-en-1-ol (Int-37a)

A microwave vial containing a magnetic stir bar was charged with Pd(Ph₃P)₄ (4.01 g, 3.47 mmol) and 4,4,4',4',5,5,5',5'-octamethyl-2,2'-bi(1,3,2-dioxaborolane) (26.4 g, 104 mmol). The vial was evacuated and backfilled with nitrogen three times. Toluene (24 mL) was added, followed by but-3-yn-1-ol (6.08 g, 87 mmol) and acetic acid (4.4 mL). The reaction mixture was prestirred for 5 min before heating to 80° C. for 30 min in the microwave. After allowing to cool to room temperature, the mixture was concentrated in vacuo, and the residue purified by column chromatography on silica gel (Pet. ether:EtOAc=50:1 to 20:1) to give 3-(4,4,5,5-tetramethyl-1,3,2-dioxaborolan-2-yl)but-3-en-1-ol (Int-37a). The reaction was set up in four batches (1.52 g each). $^1$H NMR (500 MHz, CDCl₃) δ 5.89 (d, J=3.0 Hz, 1H), 5.70 (s, 1H), 3.67 (t, J=6.0 Hz, 2H), 2.42 (t, J=6.0 Hz, 2H), 1.26 (s, 12H).

Step B: tert-butyldimethyl((3-(4,4,5,5-tetramethyl-1,3,2-dioxaborolan-2-yl)but-3-en-1-yl)oxy)silane (Int-37b)

To a stirred solution of 3-(4,4,5,5-tetramethyl-1,3,2-dioxaborolan-2-yl)but-3-en-1-ol (15 g, 76 mmol) in DCM (260 mL) was added tert-butylchlorodimethylsilane (17.1 g, 114 mmol) and imidazole (10.3 g, 151 mmol), and the mixture was stirred at 20° C. for 16 h under a N₂ atmosphere. The reaction mixture was quenched with water (200 mL), and extracted with dichloromethane (250 mL×3). The combined organic layers were washed with brine (180 mL), dried over Na₂SO₄, filtered and the solvent was evaporated under reduced pressure, which was purified by column chromatography on silica gel (petroleum ether: ethyl acetate=60:1 to 30:1) to give tert-butyldimethyl((3-(4,4,5,5-tetramethyl-1,3,2-dioxaborolan-2-yl)but-3-en-1-yl)oxy)silane (Int-37b). $^1$H NMR (400 MHz, CDCl₃) δ 5.78 (d, J=3.2 Hz, 1H), 5.62 (s, 1H), 3.61 (t, J=7.2 Hz, 2H), 2.33 (t, J=7.2 Hz, 2H), 1.21 (s, 12H), 0.84 (s, 9H), 0.00 (s, 6H).

Step C: 4-(4-((tert-butyldimethylsilyl)oxy)but-1-en-2-yl)-3-nitro-2-(prop-1-en-2-yl)pyridine (Int-37c)

A stirred solution of 4-chloro-3-nitro-2-(prop-1-en-2-yl)pyridine (Int-10a, 4.00 g, 20.1 mmol) in DME (175 mL) and water (25 mL) was added cesium carbonate (13.1 g, 40.3 mmol), tert-butyldimethyl((3-(4,4,5,5-tetramethyl-1,3,2-dioxaborolan-2-yl)but-3-en-1-yl)oxy)silane (9.44 g, 30.2 mmol) and bis(triphenylphosphine)palladium(II) dichloride (0.707 g, 1.01 mmol), and the resulting mixture was stirred at 70° C. for 16 h under a N₂ balloon. The mixture was cooled, diluted with water (200 mL), extracted with EtOAc (2×300 mL), dried over Na₂SO₄, filtered and the solvent was evaporated under reduced pressure to give the crude product. The crude product was purified by chromatographed on silica gel (EtOAc/Pet. ether, 1:10 to 1:5) to give 4-(4-((tert-butyldimethylsilyl)oxy)but-1-en-2-yl)-3-nitro-2-(prop-1-en-2-yl)pyridine (Int-37c). MS (ESI) m/z 349 [M+H]⁺. $^1$H NMR (400 MHz, CDCl₃) δ 8.58 (d, J=5.2 Hz, 1H), 7.18 (d, 0.1=5.2 Hz, 1H), 5.31 (d, J=4.4 Hz, 2H), 5.15 (d, J=11.2 Hz, 2H), 3.69 (t, J=6.4 Hz, 2H), 2.57 (t, J=6.4 Hz, 2H), 2.18 (s, 3H), 0.86 (s, 9H), 0.00 (s, 6H).

Step D: 4-(4-((tert-butyldimethylsilyl)oxy)butan-2-yl)-2-isopropylpyridin-3-amine (Int-37d-1 and Int-37d-2)

To a stirred solution 4-(4-((tert-butyldimethylsilyl)oxy)but-1-en-2-yl)-3-nitro-2-(prop-1-en-2-yl)pyridine (4.00 g, 11.5 mmol) in MeOH (50 mL) was added Pd—C (1.22 g, 1.15 mmol) (10 wt %) under nitrogen atmosphere, and the mixture was degassed and purged with hydrogen for three times. The resulting mixture was stirred at 20° C. for 4 h under (Pressure: 15 psi) hydrogen balloon. The mixture was filtered and the filtered cake was washed with methanol (100 mL). The filtrate was concentrated in vacuum to give 4-(4-((tert-butyldimethylsilyl)oxy)butan-2-yl)-2-isopropylpyridin-3-amine. The racemic material was separated by preparative SFC Column M, Condition: 0.1% NH₃H₂O IPA to give 4-(4-((tert-butyldimethylsilyl)oxy)butan-2-yl)-2-isopropylpyridin-3-amine (Int-37d-1) as peak 1. MS (ESI) m/z 323 [M+H]⁺. And 4-(4-((tert-butyldimethylsilyl)oxy)butan-2-yl)-2-isopropylpyridin-3-amine (Int-37d-2) as peak 2. MS (ESI) m/z 323 [M+H]⁺.

Preparation of 4-((1-(((tert-butyldimethylsilyl)oxy)methylcyclopropyl)methyl)-2-isopropylpyridin-3-amine (Int-38g)

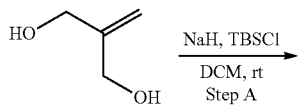

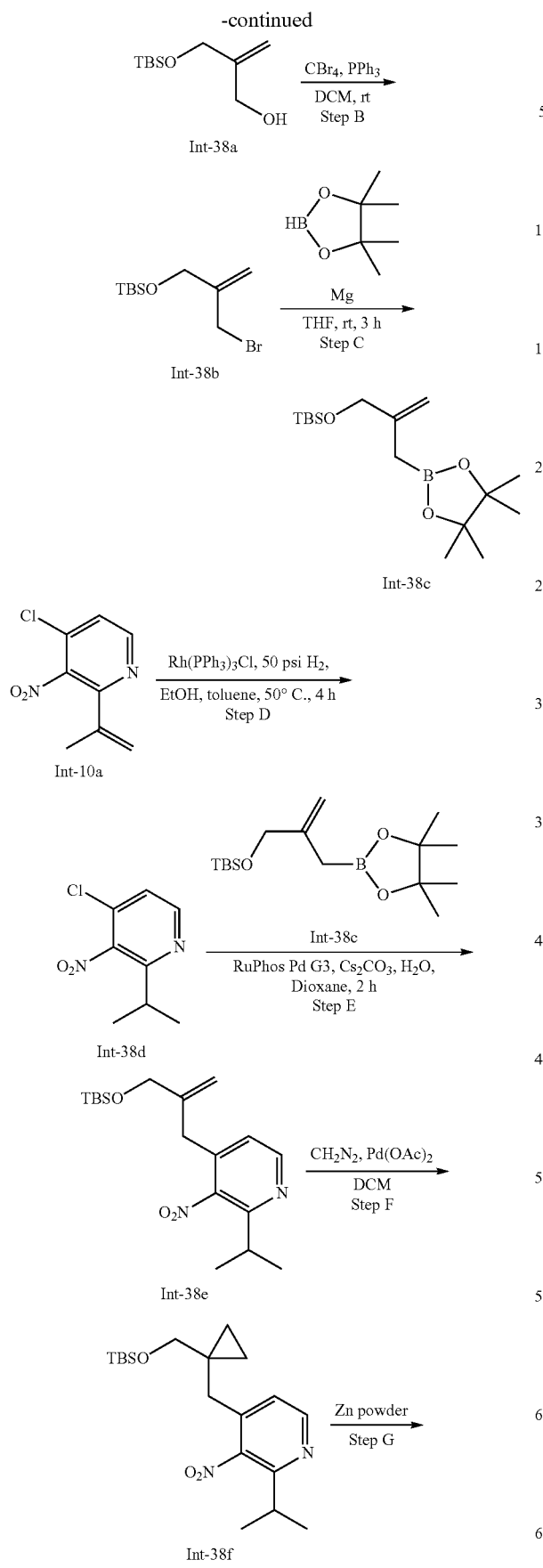

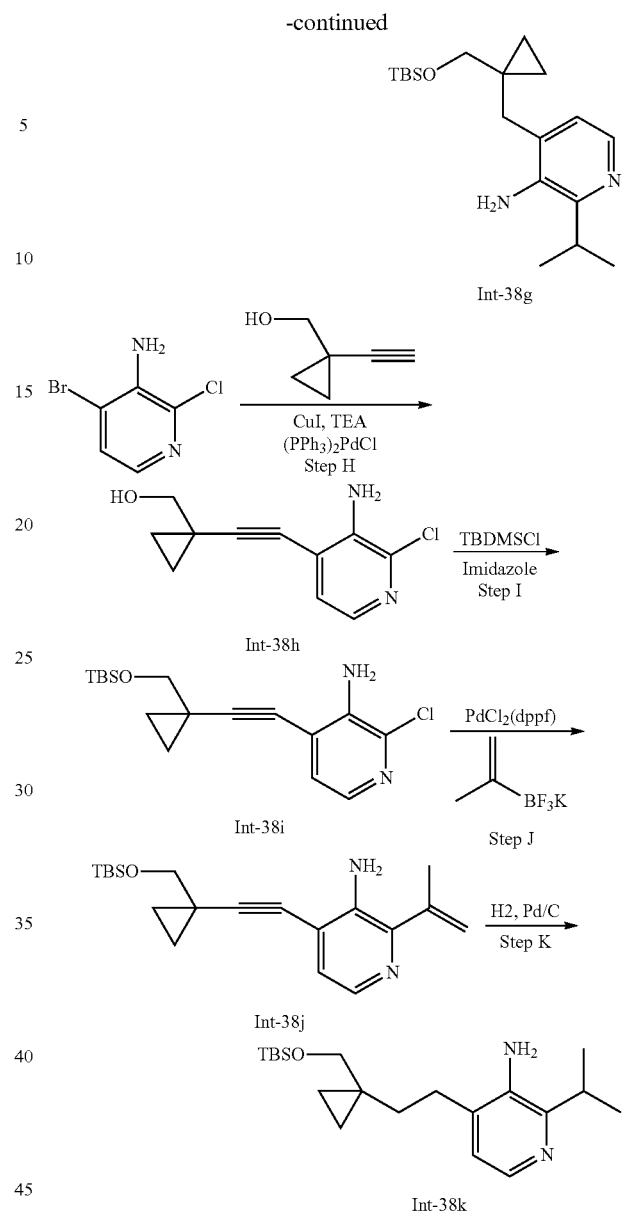

Step A: 2-(((tert-butyldimethylsilyl)oxy)methyl) prop-2-en-1-ol (Int-38a)

NaH (60%) (8.85 g, 221 mmol) was added to a solution of 2-methylenepropane-1,3-diol (15.0 g, 170 mmol) in THF (800 mL) at 0° C. After stirring at 0° C. for 0.5 h, tert-butylchlorodimethylsilane (26.9 g, 179 mmol) was added to the mixture at 0° C. to give a white mixture. The resulting mixture was stirred at 20° C. for another 2 h. The reaction was then slowly poured into 200 mL of ice-water. The resulting solution was extracted with ethyl acetate (2×300 mL), and the organic layers combined. The organic layers were washed with brine (500 mL), dried over $Na_2SO_4$, filtered and concentrated to give the crude product as an oil. The oil was purified by flash silica gel chromatography (0-3% EtOAc/Pet. ether) to give 2-(((tert-butyldimethylsilyl)oxy)methyl)prop-2-en-1-ol (Int-38a). $^1$H NMR (500 MHz, $CDCl_3$) δ 5.09 (dd, J=0.8, 9.0 Hz, 2H), 4.25 (s, 2H), 4.17 (d, J=5.8 Hz, 2H), 0.91 (s, 9H), 0.09 (s, 6H).

Step B: ((2-(bromomethyl)allyl)oxy)(tert-butyldimethylsilane (Int-38b)

To a stirred solution of 2-(((tert-butyldimethylsilyl)oxy)methyl)prop-2-en-1-ol (33.0 g, 163 mmol) in $CH_2Cl_2$ (500 mL) at 0° C. was added triphenylphosphine (51.3 g, 196 mmol) followed by perbromomethane (64.9 g, 196 mmol). The solution was stirred at 15° C. for 17 h. The solution was filtered and the filtrate was concentrated under vacuum. The residue was chromatographed on silica gel (EtOAc/Pet. ether, grading from 0:100 to 5:95) to give ((2-(bromomethyl)allyl)oxy)tert-butyl)dimethylsilane (Int-38b). $^1H$ NMR (500 MHz, $CDCl_3$) δ 5.27-5.21 (m, 2H), 4.27 (s, 2H), 4.01 (s, 2H), 0.92 (s, 9H), 0.10 (s, 6H).

Step C: tert-butyldimethyl((2-((4,4,5,5-tetramethyl-1,3,2-dioxaborolan-2-yl)methyl)allyl)oxy)silane (Int-38c)

A two necked round-bottom flask equipped with a magnetic stir bar and condenser was charged with magnesium (3.30 g, 136 mmol) and fitted with a rubber septum. The flask was purged with argon and charged with dry THF (500 mL) followed by 4,4,5,5-tetramethyl-1,3,2-dioxaborolane (14.5 g, 113 mmol). To the reaction mixture was added ((2-(bromomethyl)allyl)oxy)tert-butyl)dimethylsilane (30.0 g, 113 mmol) dropwise with constant stirring at 25° C. After 90 min of stirring at 25° C., the reaction was then diluted with hexanes (200 mL) and quenched with saturated $NH_4Cl$ (50 mL), and extracted with EtOAc (50 mL×3). The combined organic phases were washed with brine (100 mL), dried over anhydrous $Na_2SO_4$, filtered and concentrated under reduced pressure to give tert-butyldimethyl((2-((4,4,5,5-tetramethyl-1,3,2-dioxaborolan-2-yl)methyl)allyl)oxy)silane (Int-38c). $^1H$ NMR (500 MHz, $CDCl_3$) δ 5.00 (d, J=1.8 Hz, 1H), 4.81 (d, J=1.7 Hz, 1H), 4.07 (s, 2H), 1.67 (s, 2H), 1.24 (s, 12H), 0.91 (s, 9H), 0.06 (s, 6H).

Step D: 4-chloro-2-isopropyl-3-nitropyridine (Int-38d)

To a stirred solution 4-chloro-3-nitro-2-(prop-1-en-2-yl)pyridine (Int-10a, 6.00 g, 30.2 mmol) in ethanol (100 mL) and toluene (20 mL) was added tris(triphenylphosphine)rhodium(I) chloride (2.80 g, 3.02 mmol) under nitrogen atmosphere, and the mixture was degassed and purged with hydrogen for three times. The resulting mixture was stirred at 50° C. for 6 h under (Pressure: 50 psi) hydrogen. The reaction mixture was concentrated in vacuum, and the residue was purified by flash silica gel chromatography (eluent of 0-8% EtOAc/Pet. ether gradient) to give 4-chloro-2-isopropyl-3-nitropyridine (Int-38d). $^1H$ NMR (400 MHz, $CDCl_3$) δ 8.59 (d, J=5.1 Hz, 1H), 7.33 (d, J=5.1 Hz, 1H), 3.12-3.01 (m, 1H), 1.31 (d, J=6.7 Hz, 6H).

Step E: 4-(2-(((tert-butyldimethylsilyl)oxy)methyl)allyl)-2-isopropyl-3-nitropyridine (Int-38e)

To a stirred solution of 4-chloro-2-isopropyl-3-nitropyridine (4.90 g, 24.4 mmol) in dioxane (100 mL) was added tert-butyldimethyl((2-((4,4,5,5-tetramethyl-1,3,2-dioxaborolan-2-yl)methyl)allyl)oxy)silane (22.9 g, 73.3 mmol), $Cs_2CO_3$ (16.3 mL, 48.8 mmol) (aq. 3 M) and RuPhos Pd G3 (1.90 g, 2.44 mmol) at 25° C. under $N_2$ atmosphere, and the mixture was stirred at 80° C. for 3 h under $N_2$ atmosphere. The reaction mixture was quenched with water (30 mL), and extracted with ethyl acetate (100 mL). The combined organic layers were washed with brine (2×20 mL), dried over $Na_2SO_4$, filtered and the solvent was evaporated under reduced pressure. The residue was purified by flash silica gel chromatography (eluent of 0-2% EtOAc/Pet. ether) to give 4-(2-(((tert-butyldimethylsilyl)oxy)methyl)allyl)-2-isopropyl-3-nitropyridine (Int-38e). $^1H$ NMR (500 MHz, $CDCl_3$) δ 8.59 (d, J=4.9 Hz, 1H), 7.19-7.12 (m, 1H), 5.23 (s, 1H), 4.83 (d, 0.1=1.2 Hz, 1H), 4.08-3.99 (m, 2H), 3.40-3.31 (m, 2H), 3.11-2.99 (m, 1H), 1.31 (d, J=6.7 Hz, 6H), 0.88 (s, 9H), 0.05-0.02 (m, 6H).

Step F: 4-((1-(((tert-butyldimethylsilyl)oxy)methyl-cyclopropyl)methyl)-2-isopropyl-3-nitropyridine (Int-38f)

To a stirred solution of 4-(2-(((tert-butyldimethylsilyl)oxy)methyl)allyl)-2-isopropyl-3-nitropyridine (6.00 g, 17.1 mmol) and $Pd(OAc)_2$ (0.192 g, 0.856 mmol) in DCM (200 mL) was added dropwise diazomethane (1.03 L, 514 mmol) (~0.5 M $Et_2O$ solution) at −20° C. to −10° C. in 3 h. The mixture was filtered and the filtered cake was washed with dichloromethane (50 mL).

The filtrate was concentrated in vacuo. The residue was purified by flash silica gel chromatography (eluent of 0-10% EtOAc/Pet. ether) to give 4-((1-(((tert-butyldimethylsilyl)oxy)methyl)cyclopropyl)methyl)-2-isopropyl-3-nitropyridine (Int-38f). $^1H$ NMR (400 MHz, $CDCl_3$) δ 8.57 (d, J=5.1 Hz, 1H), 7.36 (d, J=5.1 Hz, 1H), 3.39-3.29 (m, 2H), 3.02 (td, J=6.7, 13.4 Hz, 1H), 2.77-2.67 (m, 2H), 1.30 (d, J=6.6 Hz, 6H), 0.86 (s, 9H), 0.55-0.49 (m, 2H), 0.48-0.43 (m, 2H), 0.00--0.05 (m, 6H).

Step G: 4-((1-(((tert-butyldimethylsilyl)oxy)methyl)cyclopropyl)methyl)-2-isopropylpyridin-3-amine (Int-38g)

To a stirred solution of 4-((1-(((tert-butyldimethylsilyl)oxy)methyl)cyclopropyl)methyl)-2-isopropyl-3-nitropyridine (2.60 g, 7.13 mmol) in THF (30 mL) were added zinc powder (3.73 g, 57.1 mmol) and ammonium chloride (6.10 mL, saturated aqueous solution) in water (5 mL) at 0° C., and the mixture was stirred at 20° C. for 2 h. The mixture was filtered and the filtered cake was washed with EtOAc (100 mL). The organic layer was washed with brine (30 mL), dried over sodium sulfate, filtered and concentrated in vacuo. The residue was purified by flash silica gel chromatography (eluent of 0~20% EtOAc/Pet. ether) to give 4-((1-(((tert-butyldimethylsilyl)oxy)methyl)cyclopropyl)methyl)-2-isopropylpyridin-3-amine (Int-38g). $^1H$ NMR (400 MHz, $CDCl_3$) δ 7.92 (d, J=4.9 Hz, 1H), 6.75 (d, 0.1=4.9 Hz, 1H), 4.23-4.08 (s, 2H), 3.37 (s, 2H), 3.06 (spt, J=6.7 Hz, 1H), 2.71 (s, 2H), 0.97 (s, 9H), 0.91-0.82 (m, 6H), 0.38 (br d, J=3.4 Hz, 4H), 0.03 (s, 6H).

Step H: (1-((3-amino-2-chloropyridin-4-yl)ethynyl)cyclopropyl)methanol (Int-38h)

To a flask containing 4-bromo-2-chloropyridin-3-amine (0.45 g, 2.2 mmol) in TEA (5.4 mL, 39 mmol) was added (1-ethynylcyclopropyl)methanol (0.25 g, 2.6 mmol), copper (I) iodide (21 mg, 0.11 mmol) and bis(triphenylphosphine)palladium(II) dichloride (29 mg, 0.043 mmol). The flask was purged with nitrogen and then heated to 75° C. for three hours. After 3 hours, the mixture was allowed to cool to room temperature and then more (1-ethynylcyclopropyl)methanol (98 mg, 1.02 mmol) was added. The mixture was then heated to 75° C. for 1 hour. After 1 hour, the mixture was allowed to cool to room temperature and then concentrated under reduced pressure. Ethyl acetate and brine were added. The organic layer was separated, dried over anhydrous magnesium sulfate, filtered and concentrated under reduced pressure. The resulting residue was purified by silica gel column chromatography (hexanes and a 3:1 mixture of ethyl acetate:ethanol) to afford (1-((3-amino-2-chloropyridin-4-yl)ethynyl)cyclopropyl)methanol (Int-38h). MS (ESI) m/z 223 [M+H]$^+$ Step I: 4-((1-(((tert-butyldimethylsilyl)ox)methylcyclopropyl)ethynyl)-2-chloropyridin-3-amine (Int-38i)

A flask containg (1-((3-amino-2-chloropyridin-4-yl)ethynyl)cyclopropyl)methanol (Int-38h, 0.38g, 1.7 mmol) in DCM (5.0 mL) and DMF (0.50 mL) was cooled to 0° C. Tert-butylchlorodimethylsilane (0.34 g, 2.2 mmol) and imidazole (0.35 g, 5.2 mmol) were added, the mixture was allowed to warm to room temperature and was then stirred for 3 hours. After 3 hours, the mixture was concentrated under reduced pressure. Ethyl acetate and brine were added. The organic layer was separated, dried over magnesium sulfate, filtered and then concentrated under reduced pressure. The resulting residue was purified by silica gel column chromatography (ethyl acetate gradient in hexanes) to afford 4-((1-(((tert-butyldimethylsilyl)oxy)methyl)cyclopropyl)ethynyl)-2-chloropyridin-3-amine (Int-38i). MS (ESI) m/z 337 [M+H]$^+$ Step J: 4-((1-(((tert-butyldimethylsily)oxy)methylcyclopropyl)ethynyl)-2-(prop-1-en-2-yl)pyridin-3-amine (Int-38j)

To a vial containing 4-((1-(((tert-butyldimethylsilyl)oxy)methyl)cyclopropyl)ethynyl)-2-chloropyridin-3-amine (Int-38i, 0.32 g, 0.96 mmol), potassium isopropenyltrifluoroborate (0.17 g, 1.1 mmol), PdCl$_2$(dppf)-CH$_2$Cl$_2$ adduct (78 mg, 0.096 mmol) and potassium carbonate (0.26 g, 1.9 mmol) was added dioxane (1.0 mL) and water (0.15 mL). The vial was purged with nitrogen and then heated to 90° C. for 3 hours. After 3 hours, the mixture was allowed to cool to room temperature. The mixture was then filtered and the filtrate was concentrated under reduced pressure. The resulting residue was purified by silica gel column chromatography (hexanes and a 3:1 mixture of ethyl acetate:ethanol) to afford 4-((1-(((tert-butyldimethylsilyl)oxy)methyl)cyclopropyl)ethynyl)-2-(prop-1-en-2-yl)pyridin-3-amine (Int-38j). MS (ESI) m/z 343 [M+H]$^+$ Step K: 4(2-(1-(((tert-butyldimethylsilyl)oxy)methylcyclopropyl)ethyl)-2-isopropylpyridin-3-amine (Int-38k)

A flask containing 4-((1-(((tert-butyldimethylsilyl)oxy)methyl)cyclopropyl)ethynyl)-2-(prop-1-en-2-yl)pyridin-3-amine (Int-38j, 0.32 g, 0.94 mmol) in methanol (10 mL) was purged with nitrogen. Palladium on carbon (10% catalyst loading, 32 mg, 0.030 mmol) was added. The flask was then evacuated and purged with hydrogen. The mixture was then stirred at room temperature for one hour. After one hour, the mixture was filtered through celite. The filtrate was concentrated under reduced pressure and was the resulting residue was purified by silica gel column chromatography (hexanes and a 3:1 mixture of ethyl acetate:ethanol) to afford 4-(2-(1-(((tert-butyldimethylsilyl)oxy)methyl)cyclopropyl)ethyl)-2-isopropylpyridin-3-amine (Int-38k). MS (ESI) m/z 349 [M+H]$^+$ Preparation of tert-butyl (2R,5S)-4-(1-(4-(2-((tert-butyldimethylsilyloxy)ethoxy)-2-isopropylpyridin-3-yl)-7-chloro-6-fluoro-2-oxo-1,2-dihydropyrido[2,3-d]pyrimidin-4-yl)-2,5-dimethylpiperazine-1-carboxylate (Int-39c)

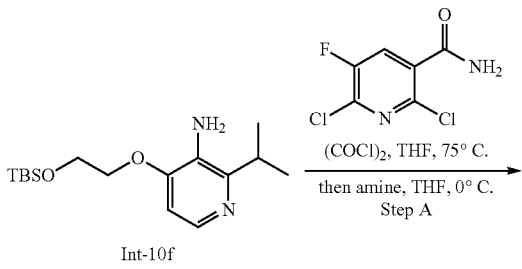

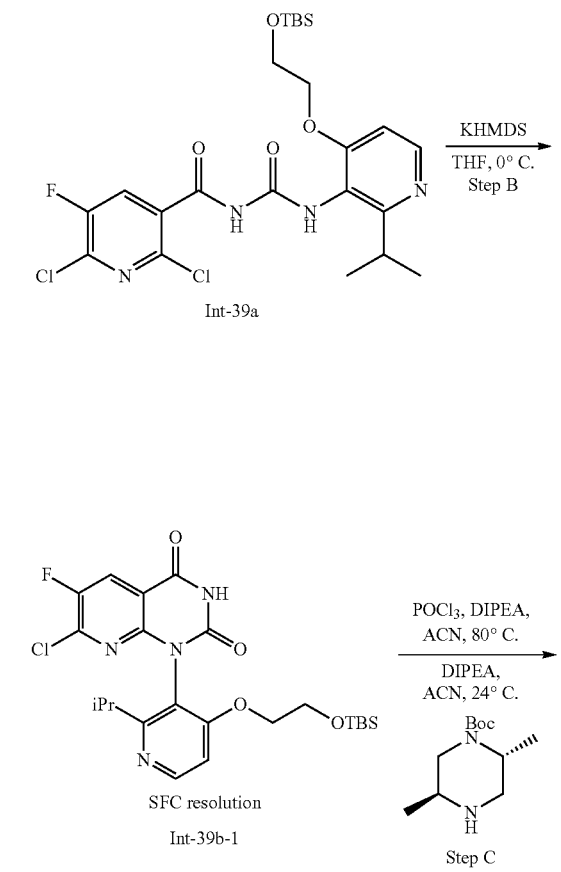

-continued

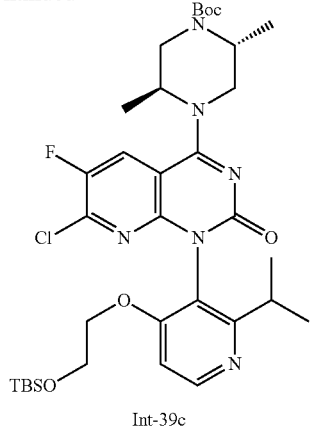

Int-39c

Step A: N-((4-(2-((tert-butyldimethylsilyl)oxy)ethoxy)-2-isopropylpyridin-3-yl)carbamyl)-2,6-dichloro-5-fluoronicotinamide (Int-39a)

2,6-Dichloro-5-fluoronicotinamide (500 mg, 2.39 mmol) was added in a 8 mL vial. The reaction vessel was evacuated and backfilled with a balloon of nitrogen three times. THF (2.4 mL) was added into the reaction vessel to dissolve the starting material. A 2 M solution of oxalyl dichloride (1.44 mL, 2.87 mmol) was added dropwise into the reaction vessel and the resulting mixture was heated at 75° C. for 1 h. The intermediate solution was allowed to cool down to room temperature. The cooled intermediate solution was concentrated to half of its volume. THF (200 µL) was added into the reaction vessel and the resulting mixture was cooled down to 0° C. In a separate 4 mL vial, 4-(2-((tert-butyldimethylsilyl)oxy)ethoxy)-2-isopropylpyridin-3-amine (Int-10f, 743 mg, 2.39 mmol) was dissolved in THF (200 µL). The amine solution was added dropwise into the reaction vessel and the resulting mixture was stirred for 1h at 0° C. The product mixture was warmed up to room temperature. The reaction mixture was quenched with 2 mL of 1:1 mixture of saturated sodium chloride aqueous solution and ammonium chloride aqueous solution. The mixture was extracted three times with ethyl acetate (3×20 mL). The organic layers were combined and the combined organic layers were dried over sodium sulfate. The dried solution was filtered and the filtrate was concentrated to dryness. The residue obtained was purified by flash column chromatography eluting with 5% (ethyl acetate:ethanol, 3:1, v/v)-dichloromethane to 50% (ethyl acetate:ethanol, 3:1, v/v)-dichloromethane to afford N-((4-(2-((tert-butyldimethylsilyl)oxy)ethoxy)-2-isopropylpyridin-3-yl)carbamoyl)-2,6-dichloro-5-fluoronicotinamide (Int-39a). MS (ESI) m/z 545 [M+H]+

Step B: 1-(4-(2-((tert-butyldimethylsilyloxy)ethoxy)-2-isopropylpyridin-3-yl)-7-chloro-6-fluoropyrido[2,3-d]pyrimidine-2,4(1H,3H)-dione (Int-39b-1)

N-((4-(2-((tert-Butyldimethylsilyl)oxy)ethoxy)-2-isopropylpyridin-3-yl)carbamoyl)-2,6-dichloro-5-fluoronicotinamide (830 mg, 1.52 mmol) was added into a 20 mL vial. The reaction vessel was evacuated and backfilled with nitrogen three times. THF (3.0 mL) was added into the reaction vessel. The resulting mixture was cooled down to 0° C. Potassium bis(trimethylsilyl)amide (3.04 mL, 3.04 mmol, 1 M in THF) was added dropwise into the reaction vessel. The resulting mixture was stirred for 1 h at 0° C. The product mixture was quenched with saturated ammonium bicarbonate aqueous solution (2 mL). The resulting mixture was extracted three times with ethyl acetate (3×20 mL). The combined organic layers were dried over sodium sulfate. The dried solution was filtered and the filtrate was concentrated to dryness. The residue obtained was purified by flash column chromatography eluting with hexanes to to 66% (ethyl acetate-ethanol=3:1 v/v)-hexanes. The racemic material was resolved by SFC Column C, Condition: MeOH w/0.05% diethylamine to provide Peak 1 1-(4-(2-((tert-butyldimethylsilyl)oxy)ethoxy)-2-isopropylpyridin-3-yl)-7-chloro-6-fluoropyrido[2,3-d]pyrimidine-2,4(1H,3H)-dione (Int-39b-1). MS (ESI) m/z: 509 [M+H]+.

Step C: tert-butyl (2R,5S)-4-(1-(4-(2-((tert-butyldimethylsilyl)oxy)ethoxy)-2-isopropylpyridin-3-yl)-7-chloro-6-fluoro-2-oxo-1,2-dihydropyrido[2,3-d]pyrimidin-4-yl)-2,5-dimethylpiperazine-1-carboxylate (Int-39c-1)

1-(4-(2-((tert-Butyldimethylsilyl)oxy)ethoxy)-2-isopropylpyridin-3-yl)-7-chloro-6-fluoropyrido[2,3-d]pyrimidine-2,4(1H,3H)-dione (Int-39b-1, 630 mg, 1.24 mmol) was added into a 20 mL vial. The reaction vessel was evacuated and backfilled with nitrogen three times. Acetonitrile (2.5 mL), N-ethyl-N-isopropylpropan-2-amine (330 µL, 1.86 mmol) and phosphoryl trichloride (150 µL, 1.601 mmol) were added into the reaction vessel and the resulting mixture was heated at 80° C. for 1 h. The mixture was concentrated to dryness. The residue obtained was dissolved in acetonitrile (1.3 mL) in a 20 mL vial. N-Ethyl-N-isopropylpropan-2-amine (341 µL, 1.91 mmol) and tert-butyl (2R,5S)-2,5-dimethylpiperazine-1-carboxylate (205 mg, 0.956 mmol) were added into the reaction vessel. The resulting mixture was stirred for 1 h at 24° C. The product mixture was diluted with ethyl acetate (100 mL). The mixture was washed three times with saturated sodium bicarbonate aqueous solution (3×10 mL). The organic layer was dried over sodium sulfate. The dried solution was filtered and the filtrate was concentrated to dryness. The residue obtained was purified by flash column chromatography eluting with hexanes to 66% (ethyl acetate-ethanol=3:1 v/v)-hexanes to afford tert-butyl (2R,5S)-4-(1-(4-(2-((tert-butyldimethylsilyl)oxy)ethoxy)-2-isopropylpyridin-3-yl)-7-chloro-6-fluoro-2-oxo-1,2-dihydropyrido[2,3-d]pyrimidin-4-yl)-2,5-dimethylpiperazine-1-carboxylate (Int-39c-1). MS (ESI) m/z 706 [M+H]+.

Intermediates Int-40-1 to Int-48 were prepared in a similar manner to Intermediate Int-39c-1, using the appropriate starting materials.

| Intermediate No. | Structure | Compound Name | [M + H]+ Found | SFC Conditions and Peak Fraction Isolated |
|---|---|---|---|---|
| Int-40-1 | 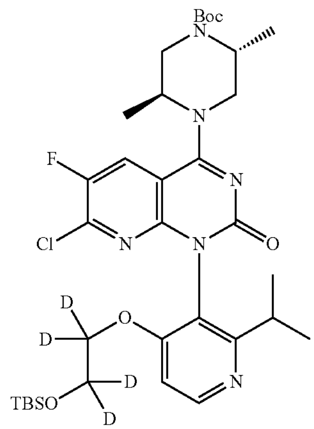 [SMILES: [2H]C([2H])(Oc1ccnc(C(C)C)c1-n1c(=O)nc(N2C[C@@H](C)N(C(=O)OC(C)(C)C)C[C@@H]2C)c2cc(F)c(Cl)nc21)C([2H])([2H])O[Si](C)(C)C(C)(C)C] | tert-Butyl (2R,5S)-4-(1-(4-(2-((tert-butyldimethylsilyl)oxy)ethoxy-1,1,2,2-$d_4$)-2-isopropylpyridin-3-yl)-7-chloro-6-fluoro-2-oxo-1,2-dihydropyrido[2,3-d]pyrimidin-4-yl)-2,5-dimethylpiperazine-1-carboxylate | 709 | Column I MeOH w/ 0.1% NH$_4$OH 80% CO$_2$ Peak 1 |
| Int-41-1 | 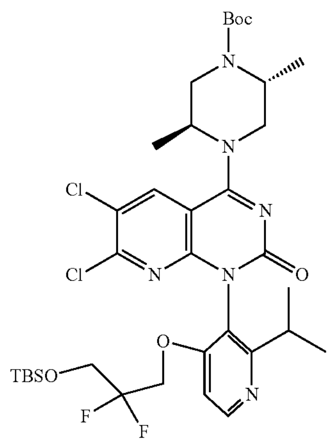 | tert-Butyl (2R,5S)-4-(1-(4-(3-((tert-butyldimethylsilyl)oxy)-2,2-difluoropropoxy)-2-isopropylpyridin-3-yl)-6,7-dichloro-2-oxo-1,2-dihydropyrido[2,3-d]pyrimidin-4-yl)-2,5-dimethylpiperazine-1-carboxylate | 771 | Column I MeOH w/ 0.1% NH$_4$OH 90% CO$_2$ Peak 1 |
| Int-42-1 | 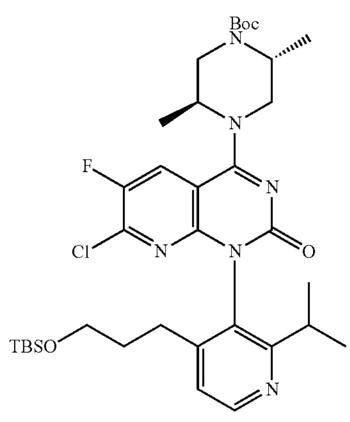 [SMILES: CC(C)c1nccc(CCCO[Si](C)(C)C(C)(C)C)c1-n1c(=O)nc(N2C[C@@H](C)N(C(=O)OC(C)(C)C)C[C@@H]2C)c2cc(F)c(Cl)nc21] | tert-Butyl (2R,5S)-4-(1-(4-(3-((tert-butyldimethylsilyl)oxy)propyl)-2-isopropylpyridin-3-yl)-7-chloro-6-fluoro-2-oxo-1,2-dihydropyrido[2,3-d]pyrimidin-4-yl)-2,5-dimethylpiperazine-1-carboxylate | 703 | Column N MeOH w/ 0.1% NH$_4$OH 70% CO$_2$ Peak 1 |

-continued

| Intermediate No. | Structure | Compound Name | [M + H]+ Found | SFC Conditions and Peak Fraction Isolated |
|---|---|---|---|---|
| Int-43-1 | 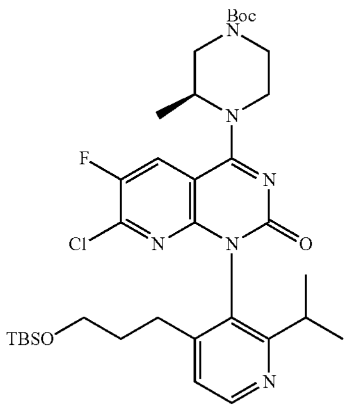 [SMILES: CC(C)c1nccc(CCCO[Si](C)(C)C(C)(C)C)c1-n1c(=O)nc(N2CCN(C(=O)OC(C)(C)C)C[C@@H]2C)c2cc(F)c(Cl)nc21] | tert-Butyl (S)-4-(1-(4-(3-((tert-butyldimethylsilyl)oxy)propyl)-2-isopropylpyridin-3-yl)-7-chloro-6-fluoro-2-oxo-1,2-dihydropyrido[2,3-d]pyrimidin-4-yl)-3-methylpiperazine-1-carboxylate | 689 | Column N MeOH w/ 0.1% NH4OH 70% CO2 Peak 1 |
| Int-44 | 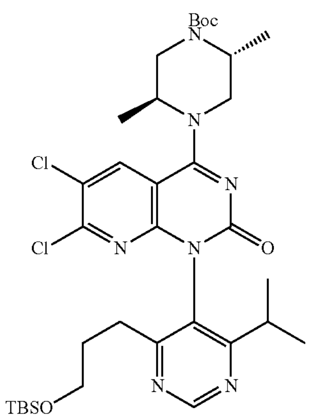 [SMILES: CC(C)c1ncnc(CCCO[Si](C)(C)C(C)(C)C)c1-n1c(=O)nc(N2C[C@@H](C)N(C(=O)OC(C)(C)C)C[C@@H]2C)c2cc(Cl)c(Cl)nc21] | tert-Butyl (2R,5S)-4-(1-(4-(3-((tert-butyldimethylsilyl)oxy)propyl)-6-isopropylpyrimidin-5-yl)-6,7-dichloro-2-oxo-1,2-dihydropyrido[2,3-d]pyrimidin-4-yl)-2,5-dimethylpiperazine-1-carboxylate | 722 | This intermediate was not resolved. |
| Int-45 | 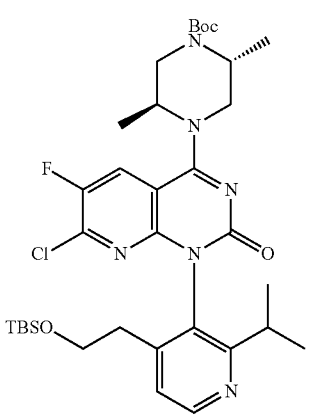 [SMILES: CC(C)c1nccc(CCO[Si](C)(C)C(C)(C)C)c1-n1c(=O)nc(N2C[C@@H](C)N(C(=O)OC(C)(C)C)C[C@@H]2C)c2cc(F)c(Cl)nc21] | tert-butyl (2R,5S)-4-(1-(4-(2-((tert-butyldimethylsilyl)oxy)ethyl)-2-isopropylpyridin-3-yl)-7-chloro-6-fluoro-2-oxo-1,2-dihydropyrido[2,3-d]pyrimidin-4-yl)-2,5-dimethylpiperazine-1-carboxylate | 689 | This intermediate was not resolved. |

-continued

| Intermediate No. | Structure | Compound Name | [M + H]+ Found | SFC Conditions and Peak Fraction Isolated |
|---|---|---|---|---|
| Int-46 | 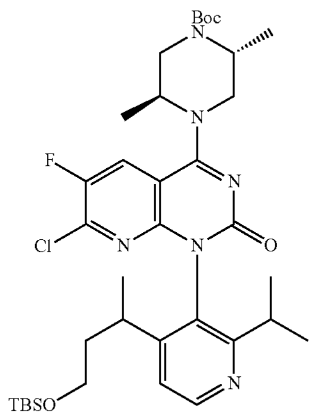 [SMILES: CC(C)c1nccc(C(C)CCO[Si](C)(C)C(C)(C)C)c1-n1c(=O)nc(N2C[C@@H](C)N(C(=O)OC(C)(C)C)C[C@@H]2C)c2cc(F)c(Cl)nc21] | tert-butyl (2R,5S)-4-(1-butyldimethylsilyl)oxy)butan-2-yl)-2-isopropylpyridin-3-yl)-7-chloro-6-fluoro-2-oxo-1,2-dihydropyrido[2,3-d]pyrimidin-4-yl)-2,5-dimethylpiperazine-1-carboxylate | 718 | Atropisomers were not resolved.* |
| Int-47 | 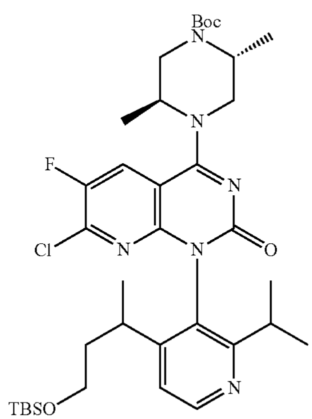 [SMILES: CC(C)c1nccc(C(C)CCO[Si](C)(C)C(C)(C)C)c1-n1c(=O)nc(N2C[C@@H](C)N(C(=O)OC(C)(C)C)C[C@@H]2C)c2cc(F)c(Cl)nc21] | tert-butyl (2R,5S)-4-(1-(4-(4-((tert-butyldimethylsilyl)oxy)butan-2-yl)-2-isopropylpyridin-3-yl)-7-chloro-6-fluoro-2-oxo-1,2-dihydropyrido[2,3-d]pyrimidin-4-yl)-2,5-dimethylpiperazine-1-carboxylate | 718 | Atropisomers were not resolved.* |
| Int-48 | 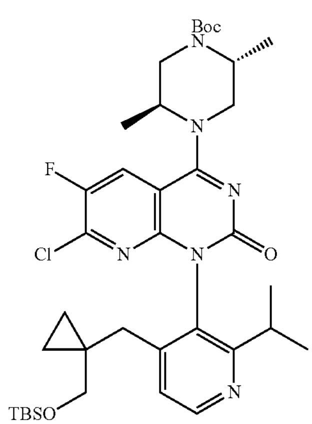 [SMILES: CC(C)c1nccc(CC2(CO[Si](C)(C)C(C)(C)C)CC2)c1-n1c(=O)nc(N2C[C@@H](C)N(C(=O)OC(C)(C)C)C[C@@H]2C)c2cc(F)c(Cl)nc21] | tert-butyl (2R,5S)-4-(1-(4-((1-(((tert-butyldimethylsilyl)oxy)methyl)cyclopropyl)methyl)-2-isopropyl-pyridin-3-yl)-7-chloro-6-fluoro-2-oxo-1,2-dihydropyrido[2,3-d]pyrimidin-4-yl)-2,5-dimethylpiperazine-1-carboxylate | 730 | This intermediate was not resolved. |

*Int-46 and Int-47 resulted from the resolution of the starting substituted aminopyridine and carrying forth of the resolved enantiomers through Steps A-C.

Preparation of 17,20-difluoro-6-(propan-2-yl)-11,12-dihydro-2H,11OH-1,18-ethenopyrido[4,3-e]pyrimido[1,6-g][1,7,9]benzoxadiazacyclododecine-2,4(3H)-dione (Int-49d)

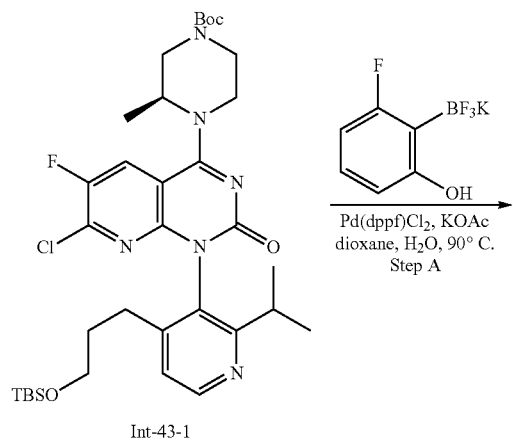

Int-43-1

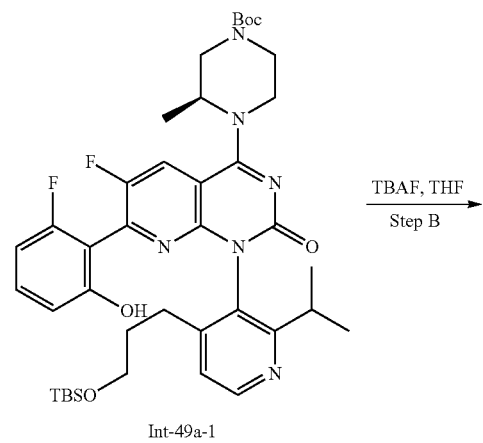

Int-49a-1

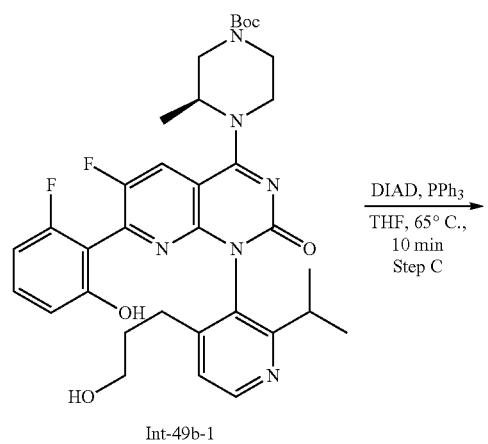

Int-49b-1

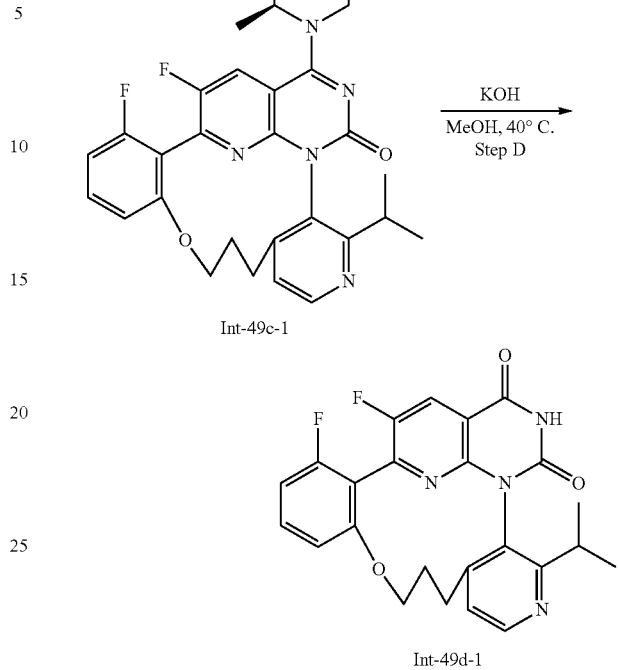

Int-49c-1

Int-49d-1

Step A: (3S)-tert-butyl 4-(1-(4-(3-((tert-butyldimethylsilyl)oxy)propyl)-2-isopropylpyridin-3-yl)-6-fluoro-7-(2-fluoro-6-hydroxyphenyl)-2-oxo-1,2-dihydropyrido[2,3-d]pyrimidin-4-yl)-3-methylpiperazine-1-carboxylate (Int-49a-1)

To a stirred solution of (S)-tert-butyl 4-(1-(4-(3-((tert-butyldimethylsilyl)oxy)propyl)-2-isopropylpyridin-3-yl)-7-chloro-6-fluoro-2-oxo-1,2-dihydropyrido[2,3-d]pyrimidin-4-yl)-3-methylpiperazine-1-carboxylate (Int-43-1, 10.5 g, 15.2 mmol), potassium acetate (7.47 g, 76.0 mmol) and 1,1'-bis(diphenyl phosphino ferrocene-palladium(II)dichloride dichloromethane complex (0.62 g, 0.76 mmol) in 1,4-dioxane (100 mL) and water (20 mL) were added 3-fluoro-2-(trifluoro-14-boraneyl)phenol, potassium salt (4.98 g, 22.8 mmol) in 1,4-dioxane (0.2 mL)/water (0.1 mL) at 90° C. under a $N_2$ atmosphere, and the mixture was stirred at 90° C. for 2 h under a $N_2$ atmosphere. The reaction mixture was extracted with ethyl acetate (2×100 mL). The combined organic layers were washed with brine (100 mL), dried over $Na_2SO_4$, filtered and the solvent was evaporated under reduced pressure. The residue was purified by flash silica gel chromatography eluent of 0~50% EtOAc/Pet. ether to give (3S)-tert-butyl 4-(1-(4-(3-((tert-butyldimethylsilyl)oxy)propyl)-2-isopropylpyridin-3-yl)-6-fluoro-7-(2-fluoro-6-hydroxyphenyl)-2-oxo-1,2-dihydropyrido[2,3-d]pyrimidin-4-yl)-3-methylpiperazine-1-carboxylate (Int-49a-1). MS (ESI) m/z 765 [M+H]+.

Step B: (3S)-tert-butyl 4-(6-fluoro-7-(2-fluoro-6-hydroxyphenyl)-1-(4-(3-hydroxypropyl)-2-isopropylpyridin-3-yl)-2-oxo-1,2-dihydropyrido[2,3-d]pyrimidin-4-yl)-3-methylpiperazine-1-carboxylate (Int-49b-1)

To a stirred solution of (3S)-tert-butyl 4-(1-(4-(3-((tert-butyldimethylsilyl)oxy)propyl)-2-isopropylpyridin-3-yl)-6- fluoro-7-(2-fluoro-6-hydroxyphenyl)-2-oxo-1,2-dihydropyrido[2,3-d]pyrimidin-4-yl)-3methylpiperazine-1-carboxylate (Int-49a-1, 8.90 g, 11.6 mmol) in THF (100 mL) was added TBAF (34.9 mL, 34.9 mmol) (1 M in THF), and the mixture was stirred at 20° C. for 16 h under a N₂ atmosphere. The residue was purified by flash silica gel chromatography using an eluent of 0~8% MeOH/DCM to give (3S)-tert-butyl 4-(6-fluoro-7-(2-fluoro-6-hydroxyphenyl)-1-(4-(3-hydroxypropyl)-2-isopropylpyridin-3-yl)-2-oxo-1,2-dihydropyrido[2,3-d]pyrimidin-4-yl)-3-methylpiperazine-1-carboxylate (Int-49b-1). MS (ESI) m/z 651 [M+H]⁺.

Step C: Int-49c-1

To a stirred solution of (3S)-tert-butyl 4-(6-fluoro-7-(2-fluoro-6-hydroxyphenyl)-1-(4-(3-hydroxypropyl)-2-isopropylpyridin-3-yl)-2-oxo-1,2-dihydropyrido[2,3-d]pyrimidin-4-yl)-3-methylpiperazine-1-carboxylate (Int-49b-1, 7.10 g, 10.9 mmol) in THF (350 mL) was added triphenylphosphine (7.15 g, 27.3 mmol), and the mixture was stirred at 65° C. under N₂ atmosphere, and then DIAD (4.24 mL, 21.8 mmol) was added. The reaction was stirred at 65° C. for 10 min. The reaction mixture was concentrated in vacuo. The residue was purified by flash silica gel chromatography eluent of 0~10% CH₂Cl₂/MeOH to give Int-49c-1. MS (ESI) m/z 633 [M+H]⁺.

Step D: 17,20-difluoro-6-(propan-2-yl)-11,12-dihydro-2H,10H-1,18-ethenopyrido[4,3-e]pyrimido[1,6-g][1,7,9]benzoxadiazacyclododecine-2,4(3H)-dione (Int-49d-1)

Int-49c-1 (3.50 g, 5.53 mmol) was dissolved in MeOH (50 mL). Then KOH (0.93 g, 16.6 mmol) was added to the mixture and heated to 40° C. The reaction mixture was stirred at 40° C. for 15 h. The mixture was cooled to room temperature, quenched with 100 mL of saturated ammonium chloride, diluted with 150 mL of EtOAc, the combined organics were washed with brine, dried over sodium sulfate, filtered and concentrated in vacuo. The residue was purified by flash silica gel chromatography eluent of 0~60% EtOAc/Pet. ether to give 17,20-difluoro-6-(propan-2-yl)-11,12-dihydro-2H,10H-1,18-ethenopyrido[4,3-e]pyrimido[1,6-g][1,7,9]benzoxadiazacyclododecine-2,4(3H)-dione (Int-49d-1). MS (ESI) m/z 451 [M+H]⁺.

Example 50: (5aS_a,17aR_a)-20-chloro-2-[(2S,5R)-2,5-dimethyl-4-(prop-2-enoyl)piperazin-1-yl]-14,17-difluoro-6-(propan-2-yl)-11,12-dihydro-4H-1,18-(ethanediylidene)pyrido[4,3-e]pyrimido[1,6-g][1,4,7,9]benzodioxadiazacyclododecin-4-one

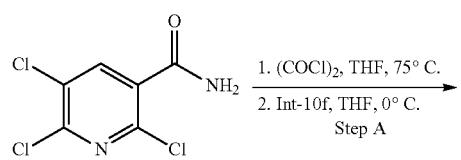

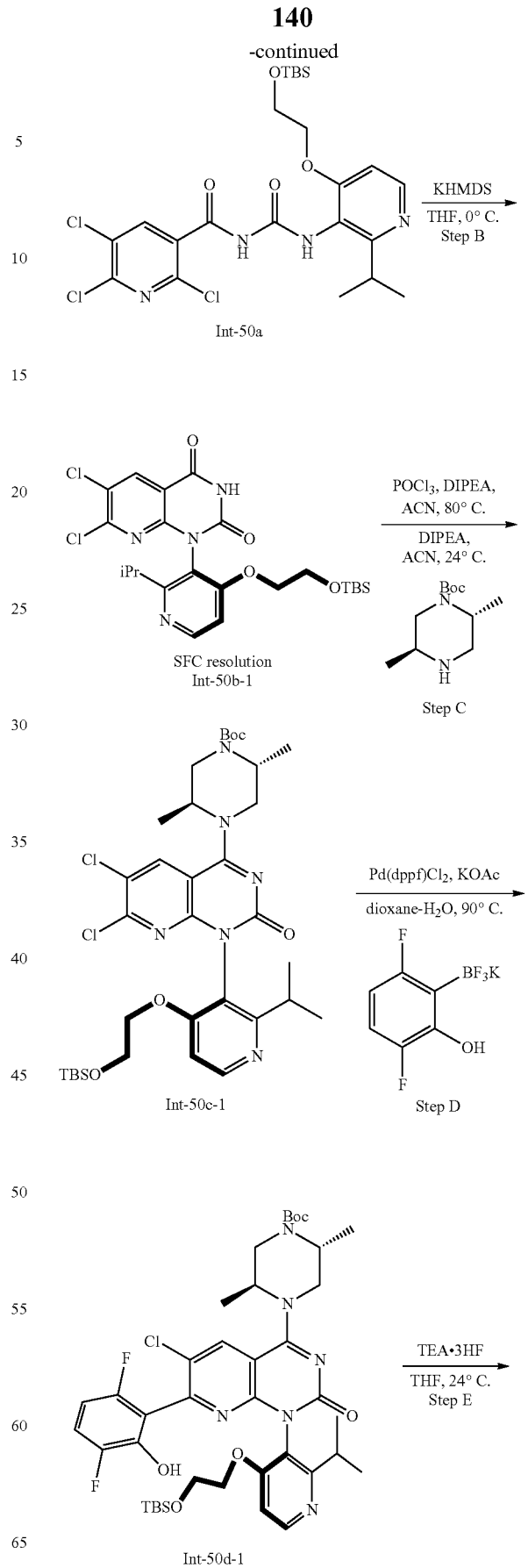

-continued

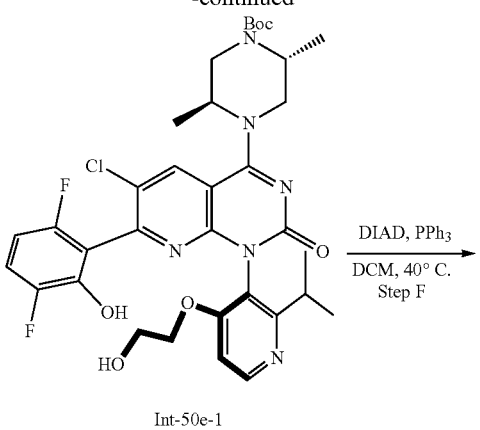

Int-50e-1

DIAD, PPh₃
DCM, 40° C.
Step F

-continued

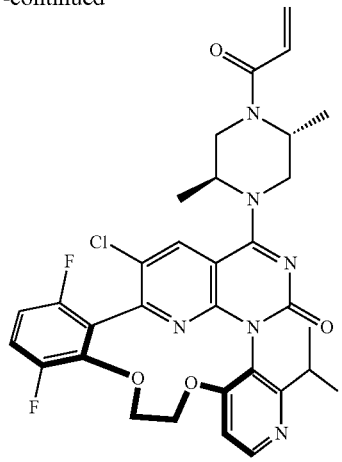

Ex. 50

Step A: N-((4-(2-((tert-butyldimethylsilyl)oxy)
ethoxy)-2-isopropylpyridin-3-yl)carbamoyl)-2,5,6-
trichloronicotinamide (Int-50a)

2,5,6-Trichloronicotinamide (1.09 g, 4.83 mmol) was added in a 100 mL round-bottomed flask. The reaction vessel was evacuated and backfilled with a balloon of nitrogen three times. THF (4.83 mL) was added into the reaction vessel to dissolve the starting material. A 2 M solution of oxalyl dichloride (2.90 mL, 5.80 mmol) was added dropwise into the reaction vessel, and the resulting mixture was heated at 75° C. for 1 h. The intermediate solution was allowed to cool down to room temperature. The cooled intermediate solution was concentrated to dryness. The residue obtained was dried under vacuum for 1 h. The reaction vessel was backfilled with a balloon of nitrogen, and THF (10 mL) was added into the reaction vessel. The resulting mixture was cooled down to 0° C. In a separate 25 mL flask, 4-(2-((tert-butyldimethylsilyl)oxy)ethoxy)-2-isopropylpyridin-3-amine (Int-10f, 1.50 g, 4.83 mmol) was dissolved in THF (9.3 mL). The amine solution was added dropwise into the reaction vessel, and the resulting mixture was stirred for 1 h at 0° C. The product mixture was carefully quenched by addition of pH 7 buffer (10 mL). The quenched product mixture was extracted three times with ethyl acetate (3×20 mL). The organic layers were combined, and the combined organic layers were dried over sodium sulfate. The dried solution was filtered, and the filtrate was concentrated to dryness. The residue obtained was purified by flash column chromatography with a silica gel column, eluting with 5% (ethyl acetate:ethanol, 3:1, v/v)-dichloromethane, initially, grading to 50% (ethyl acetate:ethanol, 3:1, v/v)-dichloromethane, linear gradient, to afford N-((4-(2-((tert-butyldimethylsilyl)oxy)ethoxy)-2-isopropylpyridin-3-yl)carbamoyl)-2,5,6-trichloronicotinamide (Int-50a). MS (ESI) m/z 563 [M+H]⁺.

Step B: 5aS$_a$-1-(4-(2-((tert-butyldimethylsilyl)oxy)
ethoxy)-2-isopropylpyridin-3-yl)-6,7-dichloropyrido
[2,3-d]pyrimidine-2,4(1H,3H)-dione (Int-50b-1)

N-((4-(2-((tert-Butyldimethylsilyl)oxy)ethoxy)-2-isopropylpyridin-3-yl)carbamoyl)-2,5,6-trichloronicotinamide (Int-50a, 2.00 g, 3.56 mmol) was added into a 100 mL flask. The reaction vessel was evacuated and backfilled with a

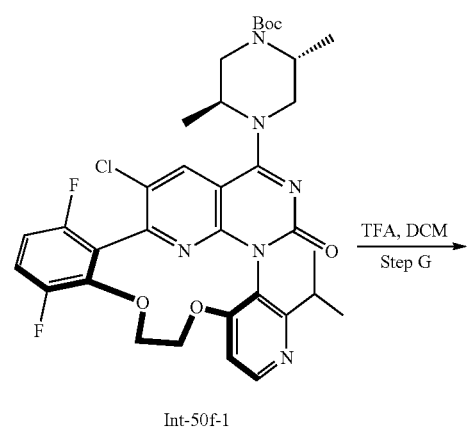

Int-50f-1

TFA, DCM
Step G

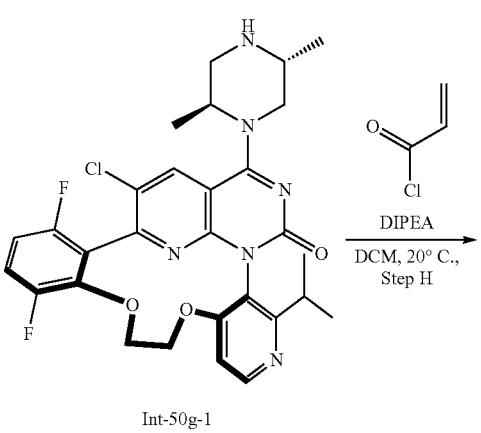

Int-50g-1

DIPEA
DCM, 20° C.,
Step H balloon of nitrogen three times. THF (7.1 mL) was added into the reaction vessel. The resulting mixture was cooled down to 0° C. A 1 M THF solution of potassium bis (trimethylsilyl)amide (7.12 mL, 7.12 mmol) was added dropwise into the reaction vessel. The resulting mixture was stirred for 30 min at 0° C. The product mixture was quenched with saturated ammonium bicarbonate aqueous solution (25 mL). The resulting mixture was extracted three times with ethyl acetate (3×100 mL). The organic layer was dried over sodium sulfate. The dried solution was filtered, and the filtrate was concentrated to dryness. The residue obtained was purified by flash column chromatography with a silica gel column, eluting with hexanes initially, grading to 66% (ethyl acetate-ethanol=3:1 v/v)-hexanes, linear gradient, to afford 1-(4-(2-(((tert-butyldimethylsilyl)oxy)ethoxy)-2-isopropylpyridin-3-yl)-6,7-dichloropyrido[2,3-d]pyrimidine-2,4(1H,3H)-dione. The racemic material was resolved by SFC Column K, condition: MeOH w/0.1% NH$_4$OH to provide Peak 1 5aS$_a$-1-(4-(2-((tert-butyldimethylsilyl)oxy) ethoxy)-2-isopropylpyridin-3-yl)-6,7-dichloropyrido[2,3-d] pyrimidine-2,4(1H,3H)-dione (Int-50b-1) as a single atropisomer. $^1$H-NMR (400 MHz, CDCl$_3$) δ: 8.62 (d, J=5.6 Hz, 1H), 8.50 (s, 1H), 6.87 (d, J=6.0 Hz, 1H), 4.06-4.09 (m, 2H), 3.75-3.79 (m, 2H), 2.74-2.81 (m, 1H), 1.23 (d, J=5.2 Hz, 3H), 1.18 (d, J=6.8 Hz, 3H), 0.76 (s, 9H), 0.07 (s, 3H), 0.11 (s, 3H).

Step C: tert-butyl (2R,5S)-4-(1-(4-(2-(((tert-butyldimethylsilyl)oxy)ethoxy)-2-isopropylpyridin-3-yl)-6,7-dichloro-2-oxo-1,2-dihydropyrido[2,3-d]pyrimidin-4-yl)-2,5-dimethylpiperazine-1-carboxylate (Int-50c-1)

5aS$_a$-1-(4-(2-((tert-Butyldimethylsilyl)oxy)ethoxy)-2-isopropylpyridin-3-yl)-6,7-dichloropyrido[2,3-d]pyrimidine-2,4(1H,3H)-dione (Int-50b-1, 800 mg, 1.52 mmol) was added in a 20 mL vial. The reaction vessel was evacuated and backfilled with a balloon of nitrogen three times. Acetonitrile (3.0 mL), N-ethyl-N-isopropylpropan-2-amine (407 μL, 2.28 mmol), and phosphoryl trichloride (184 μL, 1.97 mmol) were added into the reaction vessel, and the resulting mixture was heated to 80° C. for 1 h. The product mixture was cooled down to room temperature. The cooled product mixture was concentrated to dryness. The residue was dissolved in acetonitrile (3.04 mL) in a 20 mL vial. N-ethyl-N-isopropylpropan-2-amine (812 μL, 4.56 mmol) and tert-butyl (2R,5S)-2,5-dimethylpiperazine-1-carboxylate (489 mg, 2.28 mmol) were added into the reaction vessel. The resulting mixture was stirred for 1h at 24° C. The product mixture was diluted with ethyl acetate (100 mL). The diluted product mixture was washed three times with saturated sodium bicarbonate aqueous solution (3×10 mL). The organic layer was dried over sodium sulfate. The dried solution was filtered, and the filtrate was concentrated to dryness. The residue obtained was purified by flash column chromatography with a silica gel column, eluting with hexanes initially, grading to 66% (ethyl acetate-ethanol=3:1 v/v)-hexanes, linear gradient, to afford tert-butyl (2R,5S)-4-(1-(4-(2-(((tert-butyldimethylsilyl)oxy)ethoxy)-2-isopropylpyridin-3-yl)-6,7-dichloro-2-oxo-1,2-dihydropyrido[2,3-d] pyrimidin-4-yl)-2,5-dimethylpiperazine-1-carboxylate (Int-50c-1). $^1$H-NMR (400 MHz, DMSO-d$_6$) δ: 8.48 (s, 1H), 8.43 (s, 1H), 7.07 (d, J=5.6 Hz, 1H), 4.65 (s, 1H), 4.34 (s, 1H), 4.00-4.04 (m, 3H), 3.95 (s, 1H), 3.64-3.67 (m, 3H), 2.63-2.69 (m, 1H), 1.44 (s, 9H), 1.29 (d, J=6.4 Hz, 3H), 1.13 (d, J=4.4 Hz, 3H), 1.07 (d, J=6.8 Hz, 3H), 1.02 (d, J=6.4 Hz, 3H), 0.68 (s, 9H), 0.17 (s, 6H).

Step D: (2R,5S)-tert-butyl 4-(1-(4-(2-(((tert-butyldimethylsilyl)oxy)ethoxy)-2-isopropylpyridin-3-yl)-6-chloro-7-(3,6-difluoro-2-hydroxyphenyl)-2-oxo-1,2-dihydropyrido[2,3-d]pyrimidin-4-yl)-2,5-dimethylpiperazine-1-carboxylate (Int-50d-1)

To a stirred solution of tert-butyl (2R,5S)-4-(1-(4-(2-((tert-butyldimethylsilyl)oxy)ethoxy)-2-isopropylpyridin-3-yl)-6,7-dichloro-2-oxo-1,2-dihydropyrido[2,3-d]pyrimidin-4-yl)-2,5-dimethylpiperazine-1-carboxylate (Int-50c-1, 12.0 g, 16.6 mmol) in dioxane (200 mL) and water (20 mL) was added potassium acetate (6.53 g, 66.5 mmol) and [1,1'-bis (diphenylphosphino)ferrocene]dichloropalladium(II), complex with dichloromethane (1.35 g, 1.66 mmol) at 25° C., and the mixture was stirred at 90° C. for 5 min under a N$_2$ atmosphere. Then potassium (3,6-difluoro-2-hydroxyphenyl)trifluoroborate (Int-23c, 6.50 g, 27.5 mmol) in 1,4-dioxane (20 mL) and water (20 mL) was added to the above mixture, and the mixture was stirred at 90° C. for 30 min. The reaction mixture was quenched with brine (50 mL) and extracted with ethyl acetate (200 mL×3). The combined organic layers were washed with brine (50 mL), dried over Na$_2$SO$_4$, and filtered, and the solvent was evaporated under reduced pressure. The residue was purified by flash silica gel chromatography eluent of 0~100% EtOAc/Pet. ether to give (2R,5S)-tert-butyl 4-(1-(4-(2-(((tert-butyldimethylsilyl)oxy) ethoxy)-2-isopropylpyridin-3-yl)-6-chloro-7-(3,6-difluoro-2-hydroxyphenyl)-2-oxo-1,2-dihydropyrido[2,3-d]pyrimidin-4-yl)-2,5-dimethylpiperazine-1-carboxylate (Int-50d-1). $^1$H NMR (400 MHz, Methanol-d$_4$) δ 8.44-8.32 (m, 2H), 7.10 (dt, J=5.3, 9.7 Hz, 1H), 6.99 (d, J=5.9 Hz, 1H), 6.55 (dt, J=3.4, 8.8 Hz, 1H), 4.92-4.86 (m, 1H), 4.59-4.38 (m, 2H), 4.09-4.04 (m, 1H), 4.00-3.93 (m, 1H), 3.91-3.79 (m, 2H), 3.77-3.69 (m, 1H), 3.68-3.61 (m, 1H), 3.59-3.39 (m, 1H), 2.93 (td, J=6.5, 13.3 Hz, 1H), 1.57-1.49 (m, 12H), 1.36 (d, J=6.8 Hz, 3H), 1.23-1.20 (m, 3H), 1.07 (d, J=6.6 Hz, 3H), 0.78 (s, 9H), −0.11 (d, J=5.6 Hz, 6H).

Step E: (2R,5S)-tert-butyl 4-(6-chloro-7-(3,6-difluoro-2-hydroxyphenyl-1-(4-(2-hydroxyethoxy-2-isopropylpyridin-3-yl)-2-oxo-1,2-dihydropyrido[2,3-d]pyrimidin-4-yl-2,5-dimethylpiperazine-1-carboxylate (Int-50e-1)

To a stirred solution of (2R,5S)-tert-butyl 4-(1-(4-(2-((tert-butyldimethylsilyl)oxy)ethoxy)-2-isopropylpyridin-3-yl)-6-chloro-7-(3,6-difluoro-2-hydroxyphenyl)-2-oxo-1,2-dihydropyrido[2,3-d]pyrimidin-4-yl)-2,5-dimethylpiperazine-1-carboxylate (Int-50d-1, 17.0 g, 20.9 mmol) in DCM (200 mL) was added triethylamine trihydrofluoride (10.2 mL, 62.5 mmol) at 20° C., and the mixture was stirred at 20° C. for 2 h. The reaction mixture was diluted with 300 mL of DCM, quenched with aqueous sodium hydrogen carbonate (saturated, 200 mL), and extracted with dichloromethane (200 mL). The combined organic layers were washed with brine (200 mL), dried over Na$_2$SO$_4$, and filtered, and the solvent was evaporated under reduced pressure to give (2R,5S)-tert-butyl 4-(6-chloro-7-(3,6-difluoro-2-hydroxyphenyl)-1-(4-(2-hydroxyethoxy)-2-isopropylpyridin-3-yl)-2-oxo-1,2-dihydropyrido[2,3-d]pyrimidin-4-yl)-2,5-dimethylpiperazine-1-carboxylate (Int-50e-1). $^1$H NMR (400 MHz, Methanol-d$_4$) δ 8.45-8.33 (m, 2H), 7.06 (dt, J=5.4, 9.7 Hz, 1H), 7.00 (d, J=5.9 Hz, 1H), 6.58-6.39 (m, 1H), 4.97-4.88 (m, 1H), 4.55-4.31 (m, 2H), 4.17-4.08 (m, 1H), 3.98 (td, J=4.9, 10.1 Hz, 1H), 3.94-3.79 (m, 2H), 3.66-3.46 (m, 3H), 2.98-2.84 (m, 1H), 1.51 (s, 12H), 1.31 (br d, J=6.4 Hz, 3H), 1.23-1.18 (m, 3H), 1.07 (d, J=6.8 Hz, 3H).

Step F: Int-50f-1

To a stirred solution of (2R,5S)-tert-butyl 4-(6-chloro-7-(3,6-difluoro-2-hydroxyphenyl)-1-(4-(2-hydroxyethoxy)-2-isopropylpyridin-3-yl)-2-oxo-1,2-dihydropyrido[2,3-d]pyrimidin-4-yl)-2,5-dimethylpiperazine-1-carboxylate (Int-50e-1, 14.0 g, 20.0 mmol) and triphenylphosphine (10.5 g, 39.9 mmol) in DCM (750 mL) was added dropwise DIAD (8.07 g, 39.9 mmol) at 40° C. The resulting mixture was stirred at 40° C. for 30 min under nitrogen atmosphere. The reaction mixture was concentrated in vacuo, and the residue was purified by flash silica gel chromatography eluent of 0-0.5% MeOH/DCM to give Int-50f-1. $^1$H NMR (400 MHz, Methanol-$d_4$) δ 8.41 (d, 0.1=5.9 Hz, 1H), 8.33 (s, 1H), 7.30 (ddd, 0.1=5.1, 9.4, 11.0 Hz, 1H), 7.05 (d, J=5.9 Hz, 1H), 6.95 (dt, J=3.5, 8.8 Hz, 1H), 4.83-4.60 (m, 4H), 4.59-4.45 (m, 1H), 4.39-4.28 (m, 1H), 4.17-4.08 (m, 1H), 3.87 (d, 0.1=13.7 Hz, 1H), 3.70-3.61 (m, 1H), 3.51-3.33 (m, 1H), 3.10 (td, J=6.9, 13.5 Hz, 1H), 1.60 (br d, 0.1=5.9 Hz, 3H), 1.52 (br d, J=5.5 Hz, 9H), 1.40 (br d, 0.1=6.3 Hz, 3H), 1.29 (d, 0.1=7.0 Hz, 3H), 1.05 (d, J=7.0 Hz, 3H).

Step G: Int-502-1

To a solution of Int-50f-1 (11.0 g, 16.1 mmol) in CH$_2$Cl$_2$ (100 mL) was added TFA (50 mL), and the mixture was stirred at 20° C. for 30 min. The reaction mixture was concentrated in vacuo to afford Int-50g-1. MS (ESI) m/z 583 [M+H]$^+$.

Step H: (5aS$_a$,17aR$_a$)-20-chloro-2-[(2S,5R)-2,5-dimethyl-4-(prop-2-enoyl)piperazin-1-yl]-14,17-difluoro-6-(propan-2-yl)-11,12-dihydro-4H-1,18-(ethanediylidene)pyrido[4,3-e]pyrimido[1,6-g][1,4,7,9]benzodioxadiazacyclododecin-4-one (Ex. 50)

To a stirred solution of (Int-50g-1, 16.4 g, 20.5 mmol) and DIEA (35.9 mL, 205 mmol) in CH$_2$Cl$_2$ (200 mL) was added dropwise acryloyl chloride (2.42 g, 26.7 mmol), and the mixture was stirred at 20° C. for 30 min. The reaction mixture was washed with water (50 mL), and the aqueous layer was extracted with DCM (100 mL). The combined organic layer was dried over sodium sulfate, filtered and concentrated in vacuo. The residue was purified by flash silica gel chromatography using an eluent of 0~10% MeOH/DCM, followed by preparative HPLC (Column: YMC Triart C18 250 mm*50 mm, 7 μm; water (0.04% NH$_3$H$_2$O+10 mM NH$_4$HCO$_3$)-MeOH Begin B 25, End B 60; Gradient Time (min): 20; 100% B Hold Time (min): 3; FlowRate (mL/min) 110. The product was further purified by preparative SFC Column E, Condition: 0.1% NH$_3$·H$_2$O MeOH, Begin B 25%, End B 25%; FlowRate (mL/min): 200; Injections: 210") to give (5aS$_a$,17aR$_a$)-20-chloro-2-[(2S,5R)-2,5-dimethyl-4-(prop-2-enoyl)piperazin-1-yl]-14,17-difluoro-6-(propan-2-yl)-11,12-dihydro-4H-1,18-(ethanediylidene)pyrido[4,3-e]pyrimido[1,6-g][1,4,7,9]benzodioxadiazacyclododecin-4-one (Ex. 50) as a single atropisomer. MS (ESI) m/z 637 [M+H]$^+$. $^1$H NMR (500 MHz, Methanol-$d_4$) δ 8.41 (d, J=5.8 Hz, 1H), 8.33 (d, J=17.9 Hz, 1H), 7.30 (ddd, J=5.1, 9.4, 10.8 Hz, 1H), 7.05 (d, J=6.0 Hz, 1H), 6.95 (dt, J=3.4, 8.8 Hz, 1H), 6.92-6.74 (m, 1H), 6.34-6.25 (m, 1H), 5.86-5.79 (m, 1H), 5.06-4.88 (m, 1H), 4.83 (br d, J=10.8 Hz, 1H), 4.78-4.27 (m, 5H), 4.18-4.09 (m, 1H), 3.95-3.72 (m, 1H), 3.66 (br d, J=14.0 Hz, 1H), 3.10 (qd, J=6.8, 10.5 Hz, 1H), 1.59 (br dd, J=7.0, 9.2 Hz, 3H), 1.47 (dd, J=6.7, 19.2 Hz, 3H), 1.29 (d, J=6.7 Hz, 3H), 1.05 (dd, 0.1=3.4, 6.8 Hz, 3H).

Example 51-1: (5aS$_a$, 17aR$_a$)-20-Chloro-2-[(2S, 5R)-2,5-dimethyl-4-(prop-2-enoyl)piperazin-1-yl]-14,17-difluoro-6-(propan-2-yl)-11,12-di[($^2$H)hydro] (11,12-$^2$H$_2$-4H-1,18-(ethanediylidene)pyrido[4,3-e]pyrimido[1,6 g][1,4,7,9]benzodioxadiazacyclododecin-4-one

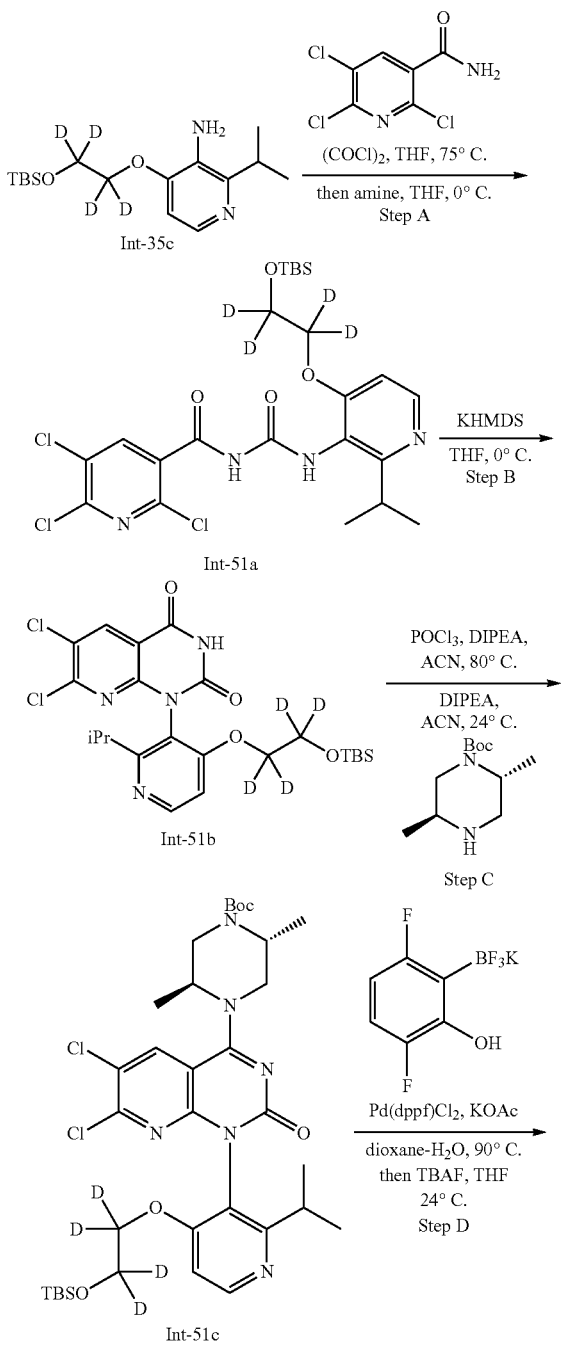

-continued

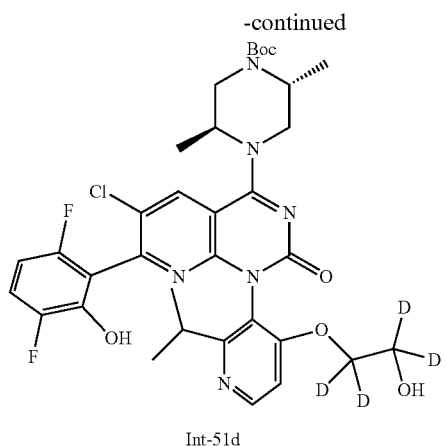

Int-51d

Bu3P=CN
toluene,
60° C.
Step E

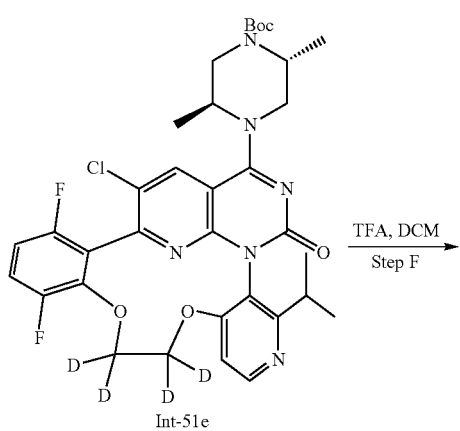

Int-51e

TFA, DCM
Step F

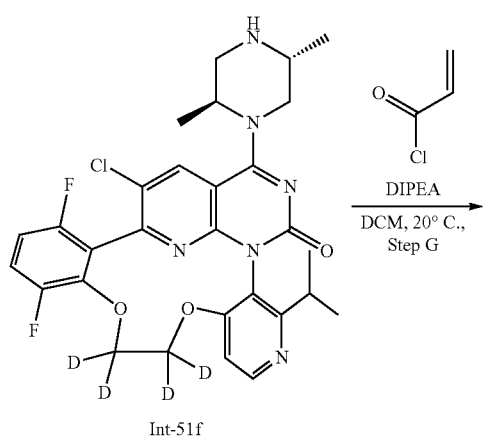

Int-51f

DIPEA
DCM, 20° C.,
Step G

-continued

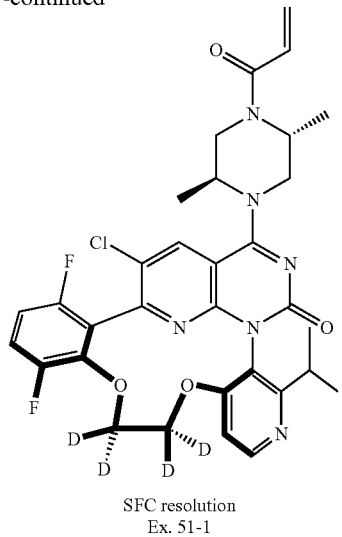

SFC resolution
Ex. 51-1

Step A: N-((4-(2-(((tert-butyldimethylsilyl)oxy)ethoxy-11,22-$d_4$)-2-isopropylpyridin-3-yl)carbamoyl)-2,5,6-trichloronicotinamide (Int-51a)

2,5,6-Trichloronicotinamide (1.72 g, 7.63 mmol) was added into a 100 mL round-bottomed flask equipped with a reflux condensor. The reaction vessel was evacuated and backfilled with a balloon of nitrogen three times. THF (7.6 mL) was added into the reaction vessel to dissolve the starting material. A 2 M solution of oxalyl dichloride (4.58 mL, 9.16 mmol) was added dropwise into the reaction vessel and the resulting mixture was heated at 75° C. for 1 h. The intermediate solution was allowed to cool down to room temperature. The cooled intermediate solution was concentrated to half of its volume. THF (3.8 mL) was added into the reaction vessel and the resulting mixture was cooled down to 0'C. In a separate 20 mL vial, 4-(2-((tert-butyldimethylsilyl)oxy)ethoxy-1,1,2,2-$d_4$)-2-isopropylpyridin-3-amine (Int-35c, 2.40 g, 7.63 mmol) was dissolved in THF (3.8 mL). The amine solution was added dropwise into the reaction vessel and the resulting mixture was stirred for 1 h at 0° C. The product mixture was warmed up to room temperature. The warmed product mixture was quenched with 20 mL of pH 7 solution. The quenched product mixture was extracted three times with ethyl acetate (3×20 mL). The organic layers were combined and the combined organic layers were dried over sodium sulfate. The dried solution was filtered and the filtrate was concentrated to dryness. The residue obtained was purified by flash column chromatography with a silica gel column, eluting with 5% (ethyl acetate:ethanol, 3:1, v/v)-dichloromethane, initially, grading to 50% (ethyl acetate:ethanol, 3:1, v/v)-dichloromethane, linear gradient, to afford N-((4-(2-((tert-butyldimethylsilyl)oxy)ethoxy-1,1,2,2-$d_4$)-2-isopropylpyridin-3-yl)carbamoyl)-2,5,6-trichloronicotinamide (Int-51a). MS (ESI) m/z 567 [M+H]$^+$.

Step B: 1-(4-(2-((tert-butyldimethylsilyl)oxy)ethoxy-1,1,2,2-$d_4$)-2-isopropylpyridin-3-yl)-6,7-dichloropyrido[2,3-d]pyrimidine-2,4(1H,3H)-dione (Int-51b)

N-((4-(2-((tert-Butyldimethylsilyl)oxy)ethoxy-1,1,2,2-$d_4$)-2-isopropylpyridin-3-yl)carbamoyl)-2,5,6-trichloronicotinamide (3.35 g, 5.92 mmol) was added into a 100 mL flask. The reaction vessel was evacuated and backfilled with a balloon of nitrogen three times. THF (11.8 mL) was added into the reaction vessel. The resulting mixture was cooled down to 0° C. A 1 M THF solution of potassium bis (trimethylsilyl)amide (11.8 mL, 11.8 mmol) was added dropwise into the reaction vessel. The resulting mixture was stirred for 30 min at 0° C. The product mixture was quenched with saturated ammonium bicarbonate aqueous solution (25 mL). The resulting mixture was extracted three times with ethyl acetate (3×100 mL). The organic layer was dried over sodium sulfate. The dried solution was filtered and the filtrate was concentrated to dryness. The residue obtained was purified by flash column chromatography with a silica gel column, eluting with hexanes initially, grading to 66% (ethyl acetate-ethanol=3:1 v/v)-hexanes, linear gradient, to afford 1-(4-(2-((tert-butyldimethylsilyl)oxy)ethoxy-1,1,2,2-d$_4$)-2-isopropylpyridin-3-yl)-6,7-dichloropyrido[2,3-d]pyrimidine-2,4(1H,3H)-dione (Int-51b). MS (ESI) m/z 529 [M+H]$^+$.

Step C: tert-butyl (2R,5S)-4-(1-(4-(2-((tert-butyldimethylsilyl)oxy)ethoxy-1,1,2,2-d$_4$)-2-isopropylpyridin-3-yl)-6,7-dichloro-2-oxo-1,2-dihydropyrido[2,3-d]pyrimidin-4-yl)-2,5-dimethylpiperazine-1-carboxylate (Int-51c)

1-(4-(2-((tert-Butyldimethylsilyl)oxy)ethoxy-1,1,2,2-d$_4$)-2-isopropylpyridin-3-yl)-6,7-dichloropyrido[2,3-d]pyrimidine-2,4(1H,3H)-dione (2.95 g, 5.57 mmol) was added into a 20 mL vial. The reaction vessel was evacuated and backfilled with a balloon of nitrogen three times. Acetonitrile (11.1 mL), N-ethyl-N-isopropylpropan-2-amine (1.49 mL, 8.36 mmol), and phosphoryl trichloride (0.67 mL, 7.2 mmol) were added into the reaction vessel and the resulting mixture was heated to 80° C. for 1 h. The resulting mixture was cooled down to 0° C. N-Ethyl-N-isopropylpropan-2-amine (2.98 mL, 16.7 mmol) and tert-butyl (2R,5S)-2,5-dimethylpiperazine-1-carboxylate (1.79 g, 8.36 mmol) were added into the reaction mixture and the resulting mixture was stirred for 30 min at 0° C. The product mixture was diluted with ethyl acetate (200 mL). The diluted product mixture was washed three times with saturated sodium bicarbonate aqueous solution (3×50 mL). The organic layer was dried over sodium sulfate. The dried solution was filtered and the filtrate was concentrated to dryness. The residue obtained was purified by flash column chromatography with 80-g silica gel column, eluting with DCM initially, grading to 50% ethyl acetate:ethanol=3:1-DCM, linear gradient, to afford tert-butyl (2R,5S)-4-(1-(4-(2-((tert-butyldimethylsilyl)oxy)ethoxy-1,1,2,2-d$_4$)-2-isopropylpyridin-3-yl)-6,7-dichloro-2-oxo-1,2-dihydropyrido[2,3-d]pyrimidin-4-yl)-2,5-dimethylpiperazine-1-carboxylate (Int-51c). MS (ESI) m/z 725 [M+H]$^+$.

Step D: tert-butyl (2R,5S)-4-(6-chloro-7-(3,6-difluoro-2-hydroxyphenyl)-1-(4-(2-hydroxyethoxy-1,1,2,2-d$_4$-(2-isopropylpyridin-3-yl)-2-oxo-1,2-dihydropyrido[2,3-d]pyrimidin-4-yl)-2,5-dimethylpiperazine-1-carboxylate (Int-51d)

tert-Butyl (2R,5S)-4-(1-(4-(2-((tert-butyldimethylsilyl)oxy)ethoxy-1,1,2,2-d$_4$)-2-isopropylpyridin-3-yl)-6,7-dichloro-2-oxo-1,2-dihydropyrido[2,3-d]pyrimidin-4-yl)-2,5-dimethylpiperazine-1-carboxylate (1.00 g, 1.38 mmol), potassium (3,6-difluoro-2-hydroxyphenyl)trifluoroborate (Int-23c, 0.421 g, 1.79 mmol), potassium acetate (0.540 g, 5.51 mmol), 1,1'-bis(diphenylphosphino)ferrocene-palladium(II)dichloride dichloromethane complex (0.113 g, 0.138 mmol) were added to a 20 mL scintillation vial equipped with magnetic stir bar, degassed under nitrogen, charged with dioxane (5.9 mL)/water (0.98 mL), degassed three times under nitrogen and heated to 90° C. for 1h. The reaction was cooled to 24° C., quenched with 10 mL 1:1 water/saturated sodium bicarbonate, extracted 2×25 mL EtOAc, washed with brine and concentrated in vacuo. The crude residue was taken up in 10 mL THF, charged with 1 M TBAF solution in THF (3.44 mL, 3.44 mmol) and allowed to stir for 1.5 h at 24° C. The reaction was quenched with saturated NH$_4$Cl, extracted once with EtOAc, washed with brine, dried over sodium sulfate, filtered, concentrated in vacuo, and purified on silica gel 0-100% 3:1 EtOAc/EtOH/hexanes to provide tert-butyl (2R,5S)-4-(6-chloro-7-(3,6-difluoro-2-hydroxyphenyl)-1-(4-(2-hydroxyethoxy-1,1,2,2-d$_4$)-2-isopropylpyridin-3-yl)-2-oxo-1,2-dihydropyrido[2,3-d]pyrimidin-4-yl)-2,5-dimethylpiperazine-1-carboxylate (Int-51d). MS (ESI) m/z 705 [M+H]$^+$.

Step E: Int-51e tert-Butyl (2R,5S)-4-(6-chloro-7-(3,6-difluoro-2-hydroxyphenyl)-1-(4-(2-hydroxyethoxy-1,1,2,2-d$_4$)-2-isopropylpyridin-3-yl)-2-oxo-1,2-dihydropyrido[2,3-d]pyrimidin-4-yl)-2,5-dimethylpiperazine-1-carboxylate (802 mg, 1.14 mmol) was added in a 100 mL flask equipped with a reflux condenser. The reaction vessel was evacuated and backfilled with a balloon of nitrogen three times. Toluene (45.5 mL) and cyanomethylenetributylphosphorane (1.0 M in toluene, 2.3 mL, 2.3 mmol) were added into the reaction vessel. The resulting mixture was heated to 60° C. for 24 h. The product mixture was concentrated to dryness. The residue obtained was purified by flash column chromatography with a silica gel column, eluting with hexanes, initially, grading to 100% ethyl acetate:ethanol 3:1, linear gradient to afford Int-51e. MS (ESI) m/z 687 [M+H]$^+$.

Step F: Int-51f

Int-51e (2.21 g, 0.322 mmol) was dissolved in DCM (3.2 mL) under nitrogen. Trifluoroacetic acid (1.23 mL, 16.1 mmol) was added into the reaction vessel. The resulting mixture was stirred for 1 h and the product mixture was concentrated to dryness. The residue obtained containing Int-51f was used directly in the next step without purification.

Step G: (5aS$_a$,17aR$_a$)-20-chloro-2-[(2S,5R)-2,5-dimethyl-4-(prop-2-enoyl)piperazin-1-yl]-14,17-difluoro-6-(propan-2-yl)-11,12-di[($^2$H)hydro](11,12-$^2$H$_2$)-4H-1,18-(ethanediylidene)pyrido[4,3-e]pyrimido[1,6-g][1,4,7,9]benzodioxadiazacyclododecin-4-one (Ex. 51-1)

Int-51f (299 mg, 322 μmol) was added into a 20 mL vial. The resulting mixture was dissolved with DCM (1.6 mL). The solution obtained was cooled down to 0° C. N-Ethyl-N-isopropylpropan-2-amine (287 μL, 1.61 mmol) and acryloyl chloride (39 μL, 0.48 mmol) were added into the reaction vessel. The reaction mixture was stirred for 1 h at 0° C. The product mixture was quenched with saturated ammonium bicarbonate aqueous solution (2 mL). The resulting mixture was extracted three times with ethyl acetate (3×20 mL). The organic layer was dried over sodium sulfate. The dried solution was filtered and the filtrate was concentrated to dryness. The racemic material was resolved by SFC Column G, Condition: MeOH w/0.25% DMEA to provide Peak 1 (5aS$_a$,17aR$_a$)-20-Chloro-2-[(2S,5R)-2,5-dimethyl-4-(prop-2-enoyl)piperazin-1-yl]-14,17-difluoro-6-(propan-2-yl)-11,12-di[($^2$H)hydro](11,12-$^2$H$_2$)-4H-1,18-(ethanediylidene)pyrido[4,3-e]pyrimido[1,6-g][1,4,7,9]benzodioxadiazacyclododecin-4-one (Ex. 51-1) as a single atropisomer. MS (ESI) m/z 641 [M+H]$^+$. $^1$H NMR (500 MHz, DMSO-d) S 8.41 (d, J=5.7 Hz, 1H), 8.23 (d, J=19.9 Hz, 1H), 7.50 (ddd, J=11.1, 9.3, 5.2 Hz, 1H), 7.34-7.09 (m, 2H), 6.84 (ddd, J=50.1, 16.7, 10.5 Hz, 1H), 6.19 (ddd, J=16.8, 8.1, 2.4 Hz, 1H), 5.76 (ddd, J=10.4, 4.9, 2.3 Hz, 1H), 4.88 (s, 0.5H), 4.74 (s, 0.5H), 4.69-4.49 (m, 2H), 4.21 (d, J=13.8 Hz, 0.5H), 3.85 (d, J=14.1 Hz, 0.5H), 3.77-3.58 (m, 0.5H), 3.52 (t, J=15.8 Hz, 1H), 3.25 (dd, J=13.9, 3.9 Hz, 0.5), 3.05 (q, J=6.4 Hz, 1H), 1.46 (t, J=7.8 Hz, 3H), 1.40-1.32 (m, 3H), 1.17 (dd, J=6.8, 2.0 Hz, 3H), 0.98 (dd, J=6.7, 4.1 Hz, 3H).

Example 52: (5aR$_a$,18aR$_a$)-2-[(2S,5R)-2,5-dimethyl-4-(prop-2-enoyl)piperazin-1-yl]-12,12,18,21-tetrafluoro-6-(propan-2-yl)-10,11,12,13-tetrahydro-4H-1,19-(ethanediylidene)pyrido[4,3-f]pyrimido[1,6-h][1,8,10]benzoxadiazacyclotridecin-4-one

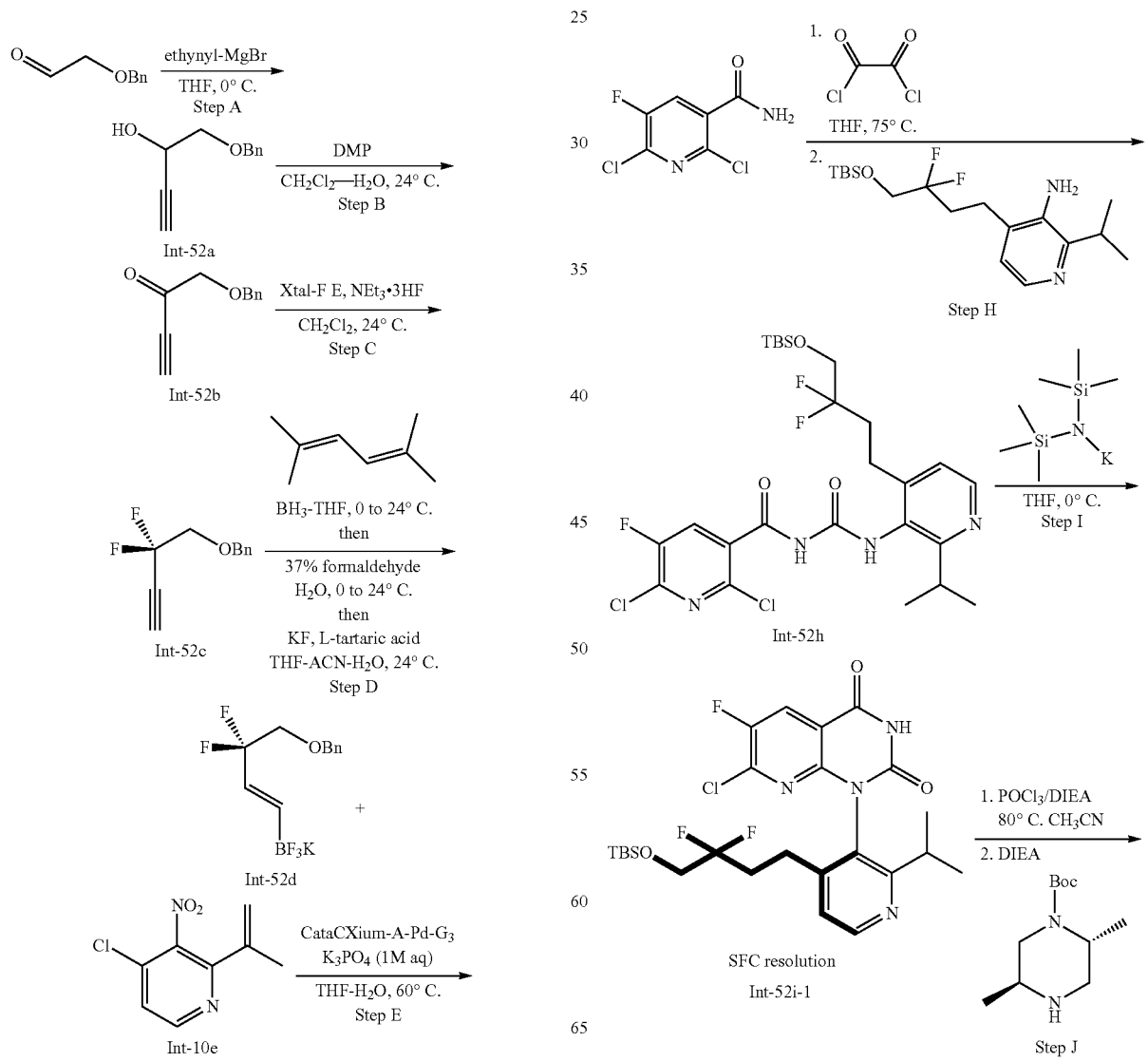

-continued
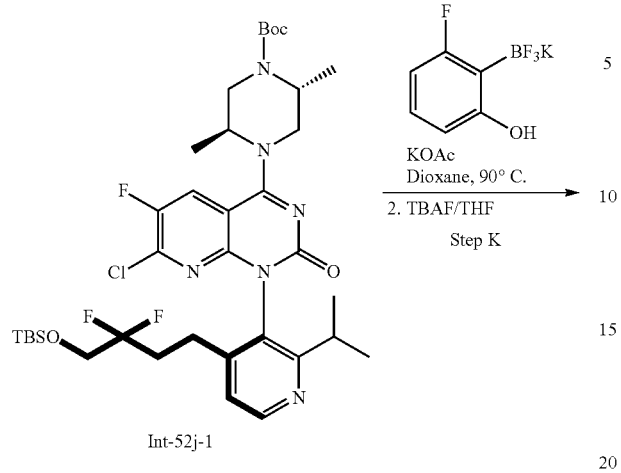
Int-52j-1
1. Pd(dppf)Cl$_2$·CH$_2$Cl$_2$
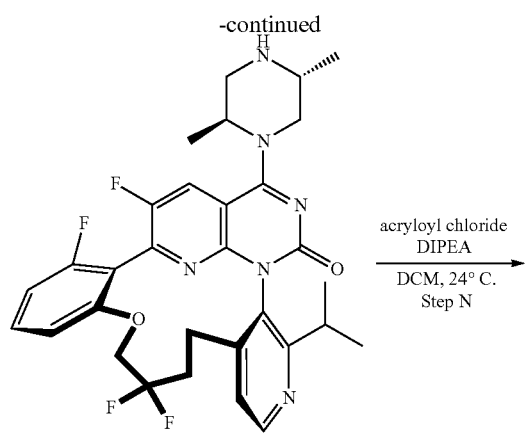
KOAc
Dioxane, 90° C.
2. TBAF/THF
Step K
Int-52m-1
acryloyl chloride
DIPEA
DCM, 24° C.
Step N
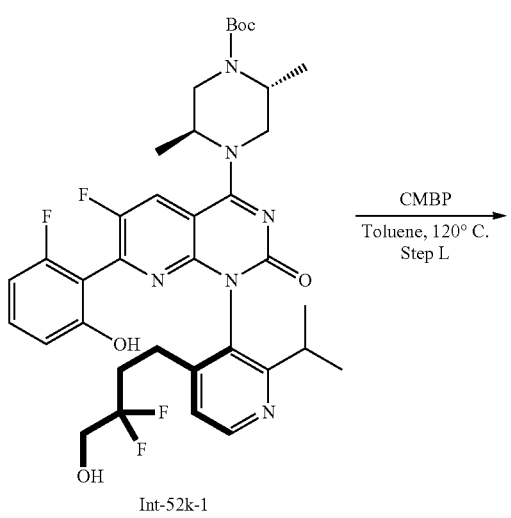
Int-52k-1
CMBP
Toluene, 120° C.
Step L
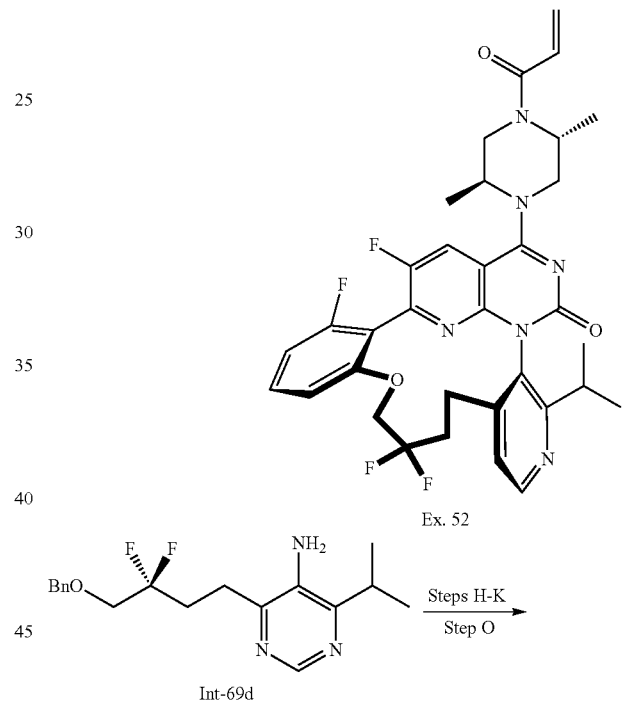
Ex. 52
Int-69d
Steps H-K
Step O
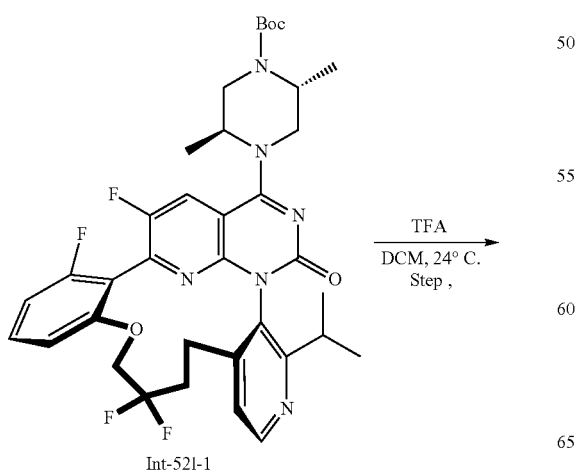
Int-52l-1
TFA
DCM, 24° C.
Step ,
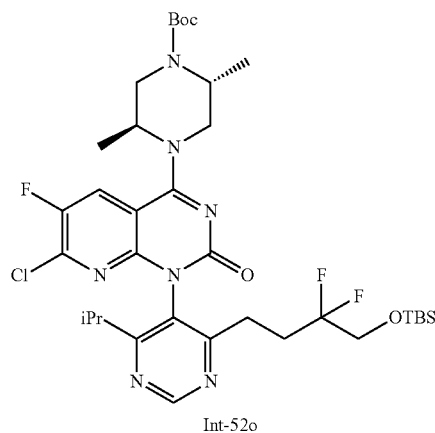
Int-52o

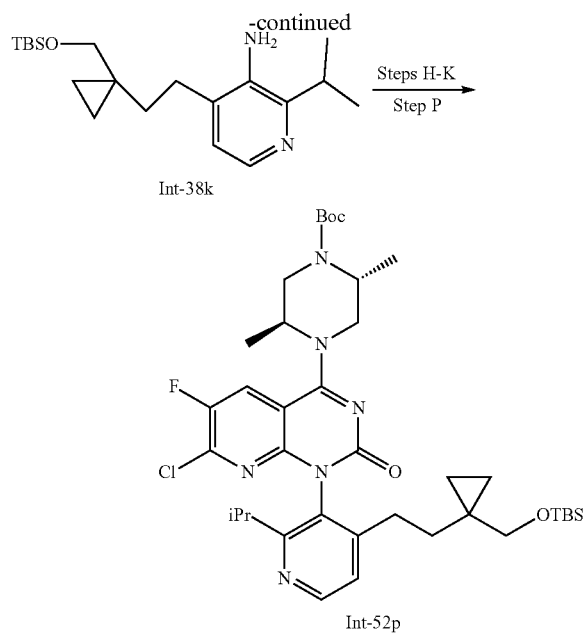

Step A: 1-(benzyloxy)but-3-yn-2-ol (Int-52a)

2-(Benzyloxy)acetaldehyde (6.20 g, 41.3 mmol) was added into a 250 mL round-bottomed flask. The reaction vessel was evacuated and backfilled with a balloon of nitrogen three times. THF (103 mL) was added into the reaction vessel. The resulting mixture was cooled down to 0° C. Ethynylmagnesium bromide (0.50 M in THF, 100 mL, 49.5 mmol) was added dropwise and stirred for 2 h at 0° C. The product mixture was quenched with saturated ammonium chloride aqueous solution (30 mL). The quenched product mixture was extracted three times with ethyl acetate (3×100 mL). The organic layer was dried over sodium sulfate, filtered, and the filtrate was concentrated to dryness. The residue obtained was purified by flash column chromatography with a silica gel column, eluting with hexanes initially, grading to 30% ethyl acetate-hexanes, linear gradient, to afford 1-(benzyloxy)but-3-yn-2-ol. (Int-52a). $^1$H NMR (500 MHz, CDCl$_3$): δ 7.41-7.28 (m, 5H), 4.69-4.58 (m, 2H), 3.67 (dd, J=9.8, 3.6 Hz, 1H), 3.59 (dd, J=9.8, 7.1 Hz, 1H), 2.46 (d, J=2.2 Hz, 1H).

Step B: 1-(benzyloxy)but-3-yn-2-one (Int-52b)

1-(Benzyloxy)but-3-yn-2-ol (Int-52a, 7.10 g, 40.3 mmol) was dissolved in DCM (water saturated) (101 mL) in a 250 mL round bottomed flask. Dess-Martin periodinane (20.5 g, 48.4 mmol) was added in 5 equal portions into the reaction vessel. The resulting mixture was stirred for 30 min. The product mixture was diluted with ether (100 mL). The diluted product mixture was quenched with saturated sodium bicarbonate aqueous solution (50 mL) and saturated sodium thiosulfate aqueous solution (50 mL). The quenched mixture was extracted three times with ether (3×100 mL). The organic layers were, dried over sodium sulfate. The dried solution was, filtered, and the filtrate was concentrated to dryness. The residue obtained was purified twice by flash column chromatography with a silica gel column, eluting with hexanes initially, grading to 25% ethyl acetate-hexanes, linear gradient to afford 1-(benzyloxy)but-3-yn-2-one (Int-52b). $^1$H NMR (500 MHz, CDCl$_3$): δ 7.54-7.30 (m, 5H), 4.67 (s, 2H), 4.27 (s, 2H), 3.34 (s, 1H).

Step C: 2,2-difluorobut-3-yn-1-yl)oxy)methyl)benzene (Int-52c)

Diethylamino(difluoro)sulfanium tetrafluoroborate (13.0 g, 56.8 mmol) was added into a 100 mL plastic tube. Triethylamine trihydrofluoride (12.3 mL, 76.0 mmol) was added into the reaction vessel. The resulting mixture was stirred for 5 min. In a separate vial, 1-(benzyloxy)but-3-yn-2-one (Int-52b, 6.60 g, 37.9 mmol) was dissolved in DCM (30 mL). The starting material solution was added dropwise into the reaction mixture via a plastic pipette. The starting material vessel was rinsed twice with DCM (2×4 mL). The rinses were added into the reaction vessel. The resulting mixture was stirred for 16 h at 24° C. The product mixture was cooled down to 0° C. Saturated sodium bicarbonate aqueous solution (10 mL) was added into the reaction vessel. The resulting biphasic mixture was further quenched by dropwise transfer into a chilled (0° C.) supersaturated sodium bicarbonate solution (100 mL+20 g solid). The resulting mixture was stirred for 30 min. The resulting mixture was extracted three times with ether (3×200 mL). The organic layer was dried over sodium sulfate. The dried solution was filtered and the filtrate was concentrated to dryness. The residue obtained was purified by flash column chromatography twice with a silica gel column, eluting with hexanes initially, grading to 20% ethyl acetate-hexanes, linear gradient to afford (((2,2-difluorobut-3-yn-1-yl)oxy) methyl)benzene (Int-52c). $^1$H NMR (500 MHz, CDCl$_3$): δ 7.52-7.30 (m, 5H), 4.74 (s, 2H), 3.81 (t, J=12.1 Hz, 2H), 2.85 (t, J=5.1 Hz, 1H).

Step D: Potassium (E)-(4-(benzyloxy)-3,3-difluorobut-1-en-1-yl)trifluoroborate (Int-52d)

2,5-Dimethylhexa-2,4-diene (26.0 mL, 182 mmol) was added into a 500 mL round-bottomed flask under nitrogen. THF (14.3 mL) was added into the reaction vessel and the resulting solution was cooled down to 0° C. A 1 M solution of borane-THF adduct (83.0 mL, 83.0 mmol) in THF was added dropwise into the reaction vessel over 15 min to maintain reaction temperature below 5° C. The resulting mixture was stirred for 3 h at 0° C. In a separate vessel, (((2,2-difluorobut-3-yn-1-yl)oxy)methyl)benzene (Int-52c, 6.50 g, 33.1 mmol) was dissolved in THF (25 mL) under nitrogen. The starting material solution was added dropwise into the reaction vessel over 25 min to maintain reaction temperature below 5° C. The vessel containing the starting material was rinsed with THF (2×5 mL) and the rinses were added dropwise into the reaction vessel. The cooling bath was removed, and the reaction was allowed to warm up to rt over 30 min. The resulting mixture was stirred for 3 h at rt. The resulting mixture was cooled back down to 0° C. and water (11.9 mL) was added dropwise into the reaction vessel maintaining the reaction temperature below 5° C. The resulting mixture was allowed to warm up to rt over 30 min and the resulting mixture was stirred for 2 h at 24° C. A 37% w/w aqueous solution of formaldehyde (29.6 mL, 398 mmol) was added dropwise into the reaction mixture. A slight exothermic event was observed. The resulting mixture was cooled with a water bath and stirred at 24° C. for 12 h. The resulting mixture was quenched with saturated sodium chloride aqueous solution (30 mL) The resulting mixture was transferred to a separatory funnel. The aqueous layer was extracted three times with ethyl acetate (3×50 mL). The organic layers were combined, and the combined organic layers were dried over sodium sulfate. The dried solution was filtered, and the filtrate was concentrated to dryness. The residue obtained was diluted with acetonitrile (143 mL). In a separate vessel, potassium fluoride (7.70 g, 133 mmol) was dissolved in water (11.0 mL). The potassium fluoride solution was added streamwise into the reaction vessel and the resulting mixture was stirred for 15 min, when no cloudiness was observed. In a separate vessel, L-(+)-tartaric acid (9.94 g, 66.3 mmol) was dissolved in tetrahydrofuran (51.0 mL). The resulting solution was transferred to an addition funnel. The tartaric acid solution was added dropwise into the reaction mixture over 20 min at 24° C. The resulting mixture was stirred for 30 min at 24° C. The resulting mixture was filtered, and the filter cake was washed thoroughly with acetonitrile (3×50 mL). The residue obtained was azeotroped three times with ether (3×200 mL). The residue obtained was diluted with ether (100 mL). The mixture was stirred vigorously and cooled down to 0° C. Ether (200 mL) and hexanes (200 mL) were added into the mixture and the resulting mixture was stirred for 1 h at 0° C. The precipitation was collected and the solid obtained was washed with 20% ether-hexanes (10×50 mL). The product was potassium (E)-(4-(benzyloxy)-3,3-difluorobut-1-en-1-yl)trifluoroborate. (Int-52d). $^1$H NMR (500 MHz, DMSO-$d_6$): δ 7.40-7.26 (m, 5H), 5.97 (dq, J=18.2, 3.1 Hz, 1H), 5.75-5.46 (m, 1H), 4.57 (s, 2H), 3.66 (t, J=13.7 Hz, 2H).

Step E: E)-4-(4-(benzyloxy)-3,3-difluorobut-1-en-1-yl)-3-nitro-2-(prop-1-en-2-yl)pyridine (Int-52e 4-Chloro-3-nitro-2-(prop-1-en-2-yl)pyridine (Int-10a, 2.10 g, 10.6 mmol), potassium (E)-(4-(benzyloxy)-3,3-difluorobut-1-en-1-yl)trifluoroborate (Int-52d, 3.54 g, 11.6 mmol), and Catacxium®A-Pd-G3 (0.385 g, 0.529 mmol) were added into a 3-neck 250 mL round-bottomed flask fitted with two septa and one reflux condenser. The reaction vessel was evacuated and backfilled with a balloon of nitrogen three times. THF (35 mL) and a 1 M aqueous solution of potassium phosphate tribasic (21.2 mL, 21.2 mmol) was added into the reaction vessel. The resulting mixture was degassed twice and heated at 60° C. for 16 h. TLC analysis showed full conversion. The product mixture was cooled, diluted with ether (100 mL), and washed with saturated sodium chloride aqueous solution (50 mL). The organic layer was dried over sodium sulfate. The dried solution was filtered and the filtrate was concentrated to dryness. The residue obtained was purified by flash column chromatography with a silica gel column, eluting with hexanes initially, grading to 20% ethyl acetate-hexanes, linear gradient to afford the desired product (E)-4-(4-(benzyloxy)-3,3-difluorobut-1-en-1-yl)-3-nitro-2-(prop-1-en-2-yl)pyridine (Int-52e). $^1$H NMR (500 MHz, Acetonitrile-$d_3$): δ 8.72 (d, J=5.2 Hz, 1H), 7.62 (d, J=5.2 Hz, 1H), 7.44-7.26 (m, 5H), 6.89 (dt, J=16.0, 2.6 Hz, 1H), 6.71 (dt, J=16.1, 10.9 Hz, 1H), 5.50-5.30 (m, 1H), 5.17 (d, J=1.0 Hz, 1H), 4.65 (s, 2H), 3.88 (t, J=12.8 Hz, 2H), 2.19 (t, J=1.2 Hz, 3H).

Step F: 4-(4-(benzyloxy)-3,3-difluorobutyl)-2-isopropylpyridin-3-amine (Int-52f)

(E)-4-(4-(Benzyloxy)-3,3-difluorobut-1-en-1-yl)-3-nitro-2-(prop-1-en-2-yl)pyridine (Int-52e, 3.13 g, 8.69 mmol) was added into a 500 mL Parr shaker vessel. Methanol (87 mL) was added into the reaction vessel. The reaction vessel was evacuated and backfilled with a balloon of nitrogen three times. Palladium on carbon (0.924 g, 0.869 mmol, 10 wt % Pd) was added into the reaction vessel. The resulting mixture was charged with 50 psi of hydrogen and reacted for 16 h. The product mixture was filtered and the filtrate was concentrated to dryness to provide 4-(4-(benzyloxy)-3,3-difluorobutyl)-2-isopropylpyridin-3-amine (Int-52f). MS (ESI): m/z 335 [M+H]$^+$.

Step G: 4-(4-((tert-butyldimethylsilyl)oxy)-3,3-difluorobutyl-2-isopropylpyridin-3-amine (Int-52)

4-(4-(Benzyloxy)-3,3-difluorobutyl)-2-isopropylpyridin-3-amine (Int-52f, 3.00 g, 8.97 mmol) was added into a 500 mL Parr shaker vessel. Methanol (45 mL) was added into the reaction vessel. The reaction vessel was evacuated and backfilled with a balloon of nitrogen three times. A 1.25 M solution of hydrochloric acid (28.7 mL, 35.9 mmol) in methanol was added into the reaction vessel followed by palladium on carbon (0.955 g, 0.897 mmol), the reaction vessel was charged with 50 psi of hydrogen in a Parr shaker and reacted for 16 h. The resulting mixture was purged with nitrogen and the mixture was filtered and the filtrate was concentrated to dryness. The residue obtained was dissolved in DMF (20 mL). Triethylamine (25.0 mL, 179 mmol) and tert-butylchlorodimethylsilane (13.5 g, 90.0 mmol) were added into the reaction vessel and the resulting mixture was heated to 45° C. for 6 h. The product mixture was diluted with ethyl acetate (400 mL) The diluted product mixture was washed once with saturated sodium bicarbonate aqueous solution (100 mL) and five times with saturated sodium chloride aqueous solution (5×30 mL). The organic layer was dried over sodium sulfate. The dried solution was filtered, and the filtrate was concentrated to dryness. The residue obtained was purified with 220-g silica gel column, eluting with hexanes initially, grading to 100% ethyl acetate:ethano=3:1, linear gradient, to afford 4-(4-((tert-butyldimethylsilyl)oxy)-3,3-difluorobutyl)-2-isopropylpyridin-3-amine (Int-52g). $^1$H NMR (500 MHz, Acetonitrile-$d_3$): δ 7.84 (d, J=4.8 Hz, 1H), 6.87 (d, J=4.8 Hz, 1H), 4.08 (q, J=5.4, 3.8 Hz, 2H), 3.88 (t, J=12.9 Hz, 2H), 3.13 (hept, J=6.6 Hz, 1H), 2.81-2.52 (m, 2H), 2.31-2.19 (m, 2H), 1.23 (d, J=6.7 Hz, 6H), 0.93 (s, 9H), 0.13 (s, 6H).

Step H: N-((4-(4-((tert-butyldimethylsilyl)oxy)-2,2-difluorobutyl-2-isopropylpyridin-3-yl)carbamoyl)-2,6-dichloro-5-fluoronicotinamide (Int-52h)

To a stirred solution of 2,6-dichloro-5-fluoronicotinamide (1.34 g, 6.41 mmol) in THF (6.4 mL) at 75° C. was added oxalyl chloride (3.85 mL, 7.70 mmol, 2 M in dichloromethane) and the reaction was heated to 75° C. with reflux condenser for 1 h. The reaction mixture was evaporated to dryness and dried in vacuo for 30 minutes. The residue was then charged with THF (6.4 mL), cooled to 0° C. and a solution of 4-(4-((tert-butyldimethylsilyl)oxy)-2,2-difluorobutyl)-2-isopropylpyridin-3-amine (Int-52g, 2.3 g, 6.41 mmol) in THF (6.4 mL) was added dropwise. The reaction was allowed to stir for 1 h at 0° C. and quenched at 0° C. with 130 mL 1:1 pH 7 buffer/brine. This mixture was then diluted with 100 mL EtOAc, extracted a second time with 100 mL EtOAc, dried over sodium sulfate, filtered and concentrated in vacuo. Purification on silica gel, 0-50% 3:1 EtOAc/EtOH/hexanes gave N-((4-(4-((tert-butyldimethylsilyl)oxy)-2,2-difluorobutyl)-2-isopropylpyridin-3-yl)carbamoyl)-2,6-dichloro-5-fluoronicotinamide (Int-52h). MS (ESI): m/z 593 [M+H]$^+$.

Step I: 1-(4-(4-((tert-butyldimethylsilyl)oxy-3,3-difluorobutyl)-2-isopropylpyridin-3-yl-7-chloro-6-fluoropyrido[2,3-d]pyrimidine-2,4(1H,3H)-dione (Int-52i-1)

N-((4-(4-(((tert-Butyldimethylsilyl)oxy)-3,3-difluorobutyl)-2-isopropylpyridin-3-yl)carbamoyl)-2,6-dichloro-5-fluoronicotinamide (Int-52h, 3.35 g, 5.64 mmol) was dissolved in THF (9.4 mL), cooled to 0° C., charged with KHMDS (11.8 mL, 11.8 mmol, 1M in THF) and allowed to stir for 5 minutes. The reaction was complete by LC/MS. It was then cooled to 0° C., quenched with 100 mL saturated ammonium chloride and extracted with 2×150 mL EtOAc. The extracts were washed with brine, dried over sodium sulfate, filtered and concentrated in vacuo. The residue was purified on a silica gel column, 10-100% hexanes/3:1 EtOAc/EtOH. The racemic material was resolved by SFC Column R, Condition: 15% $CO_2$/MeOH to provide: to provide Peak 1 as 1-(4-(4-(((tert-butyldimethylsilyl)oxy)-3,3-difluorobutyl)-2-isopropylpyridin-3-yl)-7-chloro-6-fluoropyrido[2,3-d]pyrimidine-2,4(1H,3H)-dione (Int-52i-1) as a single atropisomer MS (ESI): m/z 557 [M+H]$^+$.

Step J: (2R,5S)-4-(1-(4-(4-((tert-butyldimethylsilyl)oxy)-3,3-difluorobutyl)-2-isopropylpyridin-3-yl)-7-chloro-6-fluoro-2-oxo-1,2-dihydropyrido[2,3-d]pyrimidin-4-yl-2,5-dimethylpiperazine-1-carboxylate (Int-52i-1)

1-(4-(4-(((tert-Butyldimethylsilyl)oxy)-3,3-difluorobutyl)-2-isopropylpyridin-3-yl)-7-chloro-6-fluoropyrido[2,3-d]pyrimidine-2,4(1H,3H)-dione (Int-52i-1, 658 mg, 1.18 mmol) was charged with acetonitrile (4725 µL), DIEA (619 µL, 3.54 mmol), POCl$_3$ (132 µL, 1.42 mmol), degassed under nitrogen and heated to 80° C. for 30 minutes. The reaction was cooled to 0° C., a second portion of DIEA (619 µl, 3.54 mmol) was added, followed by solid tert-butyl (2R,5S)-2,5-dimethylpiperazine-1-carboxylate (304 mg, 1.42 mmol) and the reaction was allowed to stir for 20 minutes at the same temperature. The reaction was evaporated in vacuo and purified on silica gel, 0-60% 3:1 EtOAc/EtOH/hexanes to provide tert-butyl (2R,5S)-4-(1-(4-(4-(((tert-butyldimethylsilyl)oxy)-3,3-difluorobutyl)-2-isopropylpyridin-3-yl)-7-chloro-6-fluoro-2-oxo-1,2-dihydropyrido[2,3-d]pyrimidin-4-yl)-2,5-dimethylpiperazine-1-carboxylate (Int-52j-1). MS (ESI): m/z 753 [M+H]$^+$.

Step K: tert-butyl (2R,5S)-4-(1-(4-(3,3-difluoro-4-hydroxybutyl-2-isopropylpyridin-3-yl-6-fluoro-7-(2-fluoro-6-hydroxyphenyl)-2-oxo-1,2-dihydropyrido[2,3-d]pyrimidin-4-yl)-2,5-dimethylpiperazine-1-carboxylate (Int-52k-1)

tert-Butyl (2R,5S)-4-(1-(4-(4-((tert-butyldimethylsilyl)oxy)-3,3-difluorobutyl)-2-isopropylpyridin-3-yl)-7-chloro-6-fluoro-2-oxo-1,2-dihydropyrido[2,3-d]pyrimidin-4-yl)-2,5-dimethylpiperazine-1-carboxylate (200 mg, 0.265 mmol), potassium trifluoro(2-fluoro-6-hydroxyphenyl)borate (75 mg, 0.35 mmol), [1,1'-bis(diphenylphosphino)ferrocene]dichloropalladium(II), complex with dichloromethane (22 mg, 0.027 mmol), potassium acetate (104 mg, 1.06 mmol), were added to a 20 mL scintillation vial, degassed under nitrogen, charged with dioxane (1.1 mL)/water (190 µL), degassed three times under nitrogen and heated to 90° C. for 30 minutes. The reaction was cooled to 24° C., quenched with 3 mL saturated aq. ammonium chloride and with diluted with 10 mL EtOAc. The organics were separated, washed once brine, dried over sodium sulfate, filtered and concentrated in vacuo. The residue was dissolved in 4 mL THF, charged with 1 M THF solution of TBAF (1.06 mL, 1.06 mmol) and allowed to stir at 24° C. for 3 h. The reaction was quenched with 5 mL saturated ammonium chloride, diluted 5 mL EtOAc, the layers were separated, washed with brine, dried over sodium sulfate, filtered and concentrated in vacuo. The orange residue was purified on silica gel 0-80% 3:1 EtOAc/EtOH/hexanes to provide tert-butyl (2R,5S)-4-(1-(4-(3,3-difluoro-4-hydroxybutyl)-2-isopropylpyridin-3-yl)-6-fluoro-7-(2-fluoro-6-hydroxyphenyl)-2-oxo-1,2-dihydropyrido[2,3-d]pyrimidin-4-yl)-2,5-dimethylpiperazine-1-carboxylate (Int-52k-1). MS (ESI): m/z 715 [M+H]$^+$.

Step L: Int-52l-1 tert-Butyl (2R,5S)-4-(1-(4-(3,3-difluoro-4-hydroxybutyl)-2-isopropylpyridin-3-yl)-6-fluoro-7-(2-fluoro-6-hydroxyphenyl)-2-oxo-1,2-dihydropyrido[2,3-d]pyrimidin-4-yl)-2,5-dimethylpiperazine-1-carboxylate (100 mg, 0.140 mmol) was added in a 20 mL vial. The reaction vessel was evacuated and back filled with a balloon of nitrogen three times. Toluene (7.0 mL) and CMBP (67.5 mg, 0.280 mmol) were added into the reaction vessel. The reaction mixture was heated at 120° C. for 16 h. The product mixtures was cooled down to room temperature. The cooled product mixture was concentrated to dryness. The residue obtained was purified by flash column chromatography with a silica gel column, eluting with hexanes initially, grading to 100% ethyl acetate:ethanol=3:1, linear gradient, to afford Int-52l-1. MS (ESI): m/z 697 [M+H]$^+$.

Step M: Int-52m-1

Int-52l-1 (67.9 mg, 0.097 mmol) was added into a 20 mL vial. The reaction vessel was evacuated and backfilled with a balloon of nitrogen. DCM (975 µL) was added into the reaction vessel followed by dropwise addition of trifluoroacetic acid (373 µL, 4.87 mmol). The reaction mixture was stirred for 1 h at 24° C. The product mixture was concentrated to dryness. The residue obtained was azeotroped once with toluene (5 mL). The residue obtained containing Int-52m-1 was used directly in the next step without purification.

Step N: (5aR$_a$,18aR$_a$)-2-[(2S,5R)-2,5-dimethyl-4-(prop-2-enoyl)piperazin-1-yl]-12,12,18,21-tetrafluoro-6-(propan-2-yl)-10,11,12,13-tetrahydro-4H-1,19-(ethanediylidene)pyrido[4,3-f]pyrimido[1,6-h][1,8,10]benzoxadiazacyclotridecin-4-one (Ex. 52)

Int-52m-1 was added into a 20 mL vial. The resulting mixture was dissolved with DCM (485 µL). The solution obtained was cooled down to 0° C. N-Ethyl-N-isopropylpropan-2-amine (86 µL, 0.49 mmol) and acryloyl chloride (12 µL, 0.15 mmol) were added into the reaction vessel. The reaction mixture was stirred for 1 h at 0° C. The product mixture was quenched with saturated ammonium bicarbonate aqueous solution (2 mL). The resulting mixture was extracted three times with ethyl acetate (3×20 mL). The organic layer was dried over sodium sulfate. The dried solution was filtered and the filtrate was concentrated to dryness. The residue obtained was purified by flash column chromatography with a silica gel column, eluting with hexanes initially, grading to 100% ethyl acetate-ethanol=3:1 v/v, linear gradient, to afford (5aR$_a$,18aR$_a$)-2-[(2S,5R)-2,5-dimethyl-4-(prop-2-enoyl)piperazin-1-yl]-12,12,18,21-tetrafluoro-6-(propan-2-yl)-10,11,12,13-tetrahydro-4H-1,19-(ethanediylidene)pyrido[4,3-f]pyrimido[1,6-h][1,8,10]benzoxadiazacyclotridecin-4-one (Ex. 52). MS (ESI): m/z 651 [M+H]$^+$. $^1$H NMR (500 MHz, Acetonitrile-d$_3$): δ 8.48 (d, J=5.0 Hz, 1H), 8.11 (dd, J=8.9, 6.7 Hz, 1H), 7.50 (td, J=8.5, 6.8 Hz, 1H), 7.22 (d, J=5.0 Hz, 1H), 7.04 (d, J=8.4 Hz, 1H), 6.98 (t, J=8.8 Hz, 1H), 6.76 (ddd, J=47.1, 16.8, 10.5 Hz, 1H), 6.37-6.19 (m, 1H), 5.84-5.65 (m, 1H), 4.52-4.85 (m, 1.5H), 4.58-4.25 (m, 2H), 4.15 (q, J=10.1 Hz, 1H), 3.96-3.65 (m, 3H), 3.40 (dd, J=13.9, 4.0 Hz, 0.5H), 2.83 (h, J=6.9 Hz, 1H), 2.75 (dd, J=8.0, 5.9 Hz, 2H), 2.25-2.18 (m, 2H), 1.49 (dd, J=6.8, 2.7 Hz, 3H), 1.32 (d, J=7.1 Hz, 3H), 1.12 (d, J=6.7 Hz, 3H), 0.92-0.87 (m, 3H).

Step O: tert-butyl (2R,5S)-4-(1-(4-(4-(((tert-butyldimethylsilyl)oxy)-3,3-difluorobutyl-6-isopropylpyrimidin-5-yl)-7-chloro-6-fluoro-2-oxo-1,2-dihydropyrido[2,3-d]pyrimidin-4-yl-2,5-dimethylpiperazine-1-carboxylate (Int-52o)

Int-52o was prepared in a similar fashion to Int-52k-1 using Int-69d following steps h-k. MS (ESI): m/z 754 [M+H]$^+$.

Step P: tert-butyl (2R,5S)-(1-(4-(2-(1-(((tert-butyldimethylsilyl)oxy)methyl)cyclopropyl)ethyl)-2-isopropylpyridin-3-yl)-7-chloro-6-fluoro-2-oxo-1,2-dihydropyrido[2,3-d]pyrimidin-4-yl)-2,5-dimethylpiperazine-1-carboxylate (Int-52p)

Int-52p was prepared in a similar fashion to Int-52k-1 using Int-38k following steps h-k. MS (ESI): m/z 743 [M+H]$^+$.

Preparation of potassium (2,4-difluoro-6-hydroxyphenyl)trifluoroborate (Int-53d)

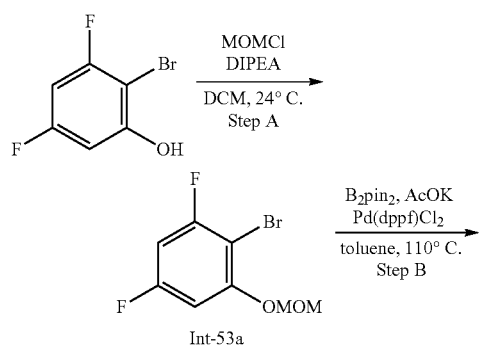

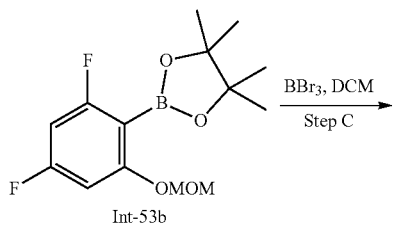

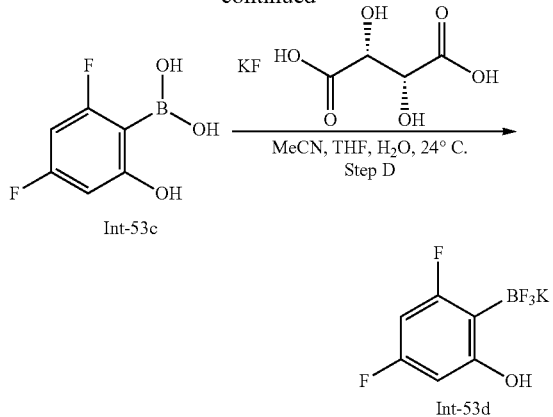

Step A: 2-bromo-1,5-difluoro-3-(methoxymethoxy)benzene (Int-53a)

To a solution of 2-bromo-3,5-difluorophenol (4.00 g, 19.1 mmol) and DIPEA (4.01 mL, 23.0 mmol) in DCM (40 mL) was added chloro(methoxy)methane (1.75 mL, 23.0 mmol) dropwise at 0° C. The mixture was stirred for 2 h at room temperature under N$_2$ atmosphere. The solvent of the reaction was evaporated under reduced pressure to yield a crude product. The crude product was purified by flash silica gel chromatography Pet. Ether/EtOAc=1/1 to give 2-bromo-1,5-difluoro-3-(methoxymethoxy)benzene (Int-53a). $^1$H NMR (400 MHz, CDCl$_3$): δ 6.75 (dt, J=10.39, 2.26 Hz, 1H), 6.58 (td, J=8.56, 2.69 Hz, 1H), 5.23 (s, 2H), 3.50 (s, 3H).

Step B: 2-(2,4-difluoro-6-(methoxymethoxy)phenyl)-4,4,5,5-tetramethyl-1,3,2-dioxaborolane (Int-53b)

To a stirred solution of 2-bromo-1,5-difluoro-3-(methoxymethoxy)benzene (2.50 g, 9.88 mmol), 4,4,4',4',5,5,5'-heptamethyl-2,2'-bi(1,3,2-dioxaborolane) (7.11 g, 29.6 mmol) and potassium acetate (3.88 g, 39.5 mmol) in toluene (25 mL) was added [1,1'-bis(diphenylphosphino)ferrocene]dichloropalladium(II), complex with dichloromethane (0.807 g, 0.988 mmol) under N$_2$ atmosphere. The mixture was stirred at 100° C. for 16 h under a N$_2$ atmosphere. The mixture was filtered and the filtrate was concentrated in vacuo to afford the crude product. The crude product was purified by flash silica gel chromatography Pet. ether/EtOAc=1/1, to give 2-(2,4-difluoro-6-(methoxymethoxy)phenyl)-4,4,5,5-tetramethyl-1,3,2-dioxaborolane (Int-53b). $^1$H NMR (400 MHz, CDCl$_3$): δ 6.59-6.51 (m, 1H), 6.44-6.34 (m, 1H), 5.11 (s, 2H), 3.44 (s, 3H), 1.34 (s, 12H).

Step C: (2,4-difluoro-6-hydroxyphenylboronic acid (Int-53c)

To a stirred solution of 2-(2,4-difluoro-6-(methoxymethoxy)phenyl)-4,4,5,5-tetramethyl-1,3,2-dioxaborolane (300 mg, 1.00 mmol) in dry DCM (3 mL) was added BBr$_3$ (0.473 mL, 5.00 mmol) dropwise at 0° C. under N$_2$ atmosphere. After stirring for 20 min, the reaction mixture was poured into ice water, basified to pH~10 by 3 N NaOH and the organic layer was separated. The separated aqueous layer was adjusted to pH~3 with 1 N HCl and extracted with EtOAc (20 mL×3). The combined organic layers were washed with brine, dried over Na$_2$SO$_4$ and concentrated in vacuo to yield (2,4-difluoro-6-hydroxyphenyl)boronic acid (Int-53c). $^1$H NMR (400 MHz, Methanol-d$_4$): δ 6.44-6.23 (m, 2H).

Step D: potassium (2,4-difluoro-6-hydroxyphenyl)trifluoroborate (Int-53d)

To a stirred solution of (2,4-difluoro-6-hydroxyphenyl)boronic acid (170 mg, 0.978 mmol) in MeCN (3 mL) was added potassium fluoride (227 mg, 3.91 mmol) dissolved in water (0.5 mL), and the mixture was stirred at 20° C. for 10 min. A solution of L-(+)-tartaric acid (367 mg, 2.44 mmol) in THF (2 mL) was added to the above solution dropwise and the resulting mixture was stirred at 20° C. for 15 h. The mixture was filtered and the filtrate was concentrated in vacuo to afford the crude product. Acetonitrile (3.0 mL) was added and the mixture was then filtered. The resulting solids were collected to afford potassium (2,4-difluoro-6-hydroxyphenyl)trifluoroborate (Int-53d). $^1$H NMR (400 MHz, Methanol-d$_4$): δ 6.44-5.94 (m, 2H).

Example 54: (5aR$_a$,18aR$_a$)-2-[(2S,5R)-2,5-dimethyl-4-(prop-2-enoyl)piperazin-1-yl]-12,12,17,18,21-pentafluoro-6-(propan-2-yl)-10,11,12,13-tetrahydro-4H-1,19-(ethanediylidene)pyrido[4,3-f]pyrimido[1,6-h][1,8,10]benzoxadiazacyclotridecin-4-one

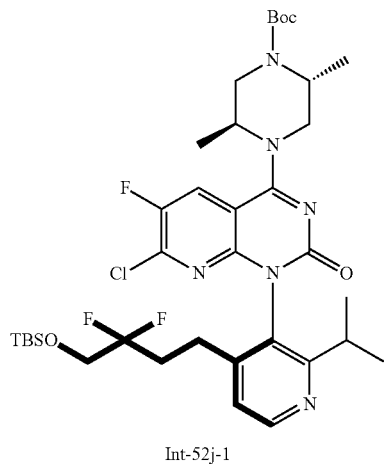

Int-52j-1

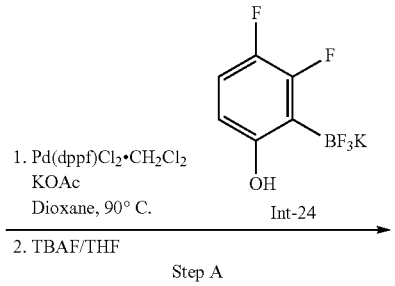

Int-24

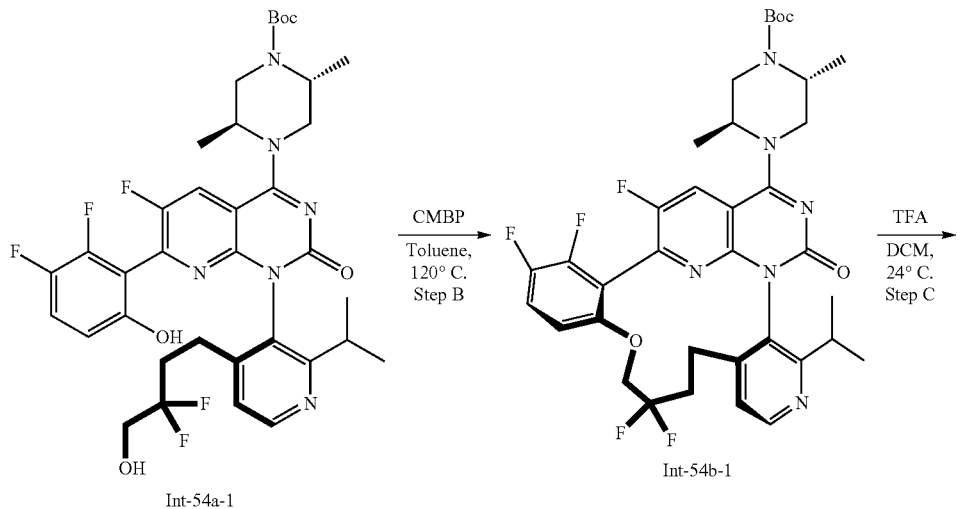

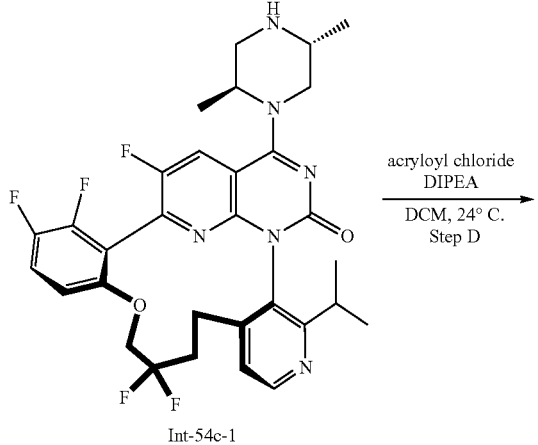

Int-54c-1 acryloyl chloride
DIPEA
DCM, 24° C.
Step D

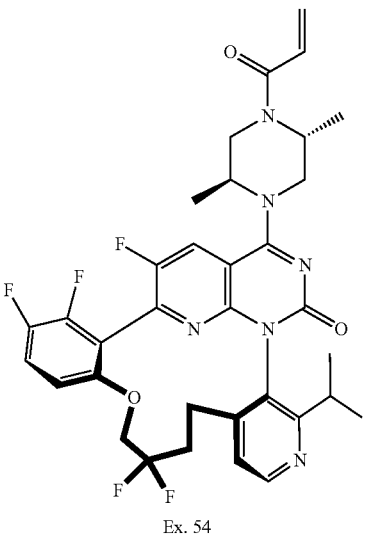

Ex. 54

Step A: tert-butyl (2R,5S)-4-(1-(4-(3,3-difluoro-4-hydroxybutyl)-2-isopropylpyridin-3-yl)-7-(2,3-difluoro-6-hydroxyphenyl-6-fluoro-2-oxo-1,2-dihydropyrido[2,3-d]pyrimidin-4-yl)-2,5-dimethylpiperazine-1-carboxylate (Int-54a-1)

tert-Butyl (2R,5S)-4-(1-(4-(4-((tert-butyldimethylsilyl)oxy)-3,3-difluorobutyl)-2-isopropylpyridin-3-yl)-7-chloro-6-fluoro-2-oxo-1,2-dihydropyrido[2,3-d]pyrimidin-4-yl)-2,5-dimethylpiperazine-1-carboxylate (Int-52j-1, 150 mg, 0.199 mmol), potassium 3,4-difluoro-2-(trifluoro-14-boranenyl)phenolate (Int-24, 61 mg, 0.26 mmol), potassium acetate (78 mg, 0.80 mmol), and 1,1'-bis(diphenylphosphino)ferrocene-palladium(II)dichloride dichloromethane complex (16 mg, 0.020 mmol) were added to a 20 mL scintillation vial equipped with magnetic stir bar, degassed under nitrogen, charged with dioxane (853 μL)/water (142 μL), degassed three times under nitrogen and heated to 90° C. for 1 h. The reaction was cooled to 24° C., quenched with 10 mL 1:1 water/saturated sodium bicarbonate, extracted twice with 25 mL EtOAc, washed with brine and concentrated in vacuo. The crude residue was taken up in 10 mL THF, charged with a 1 M THF solution of TBAF (498 μL, 0.498 mmol) and allowed to stir for 1.5 h at 24° C. The reaction was quenched with saturated NH$_4$Cl, extracted once with EtOAc, washed with brine, dried over sodium sulfate, filtered, and concentrated in vacuo. The residue was purified on silica gel 0-100% 3:1 EtOAc/EtOH/hexanes to provide tert-butyl (2R,5S)-4-(1-(4-(3,3-difluoro-4-hydroxybutyl)-2-isopropylpyridin-3-yl)-7-(2,3-difluoro-6-hydroxyphenyl)-6-fluoro-2-oxo-1,2-dihydropyrido[2,3-d]pyrimidin-4-yl)-2,5-dimethylpiperazine-1-carboxylate (Int-54a-1). MS (ESI): m/z 733 [M+H]$^+$.

Step B: Int-54b-1 tert-Butyl (2R,5S)-4-(1-(4-(3,3-difluoro-4-hydroxybutyl)-2-isopropylpyridin-3-yl)-7-(2,3-difluoro-6-hydroxyphenyl)-6-fluoro-2-oxo-1,2-dihydropyrido[2,3-d]pyrimidin-4-yl)-2,5-dimethylpiperazine-1-carboxylate (Int-54a-1, 125 mg, 0.171 mmol) was added into a 20 mL vial. The reaction vessel was evacuated and back filled with a balloon of nitrogen three times. Toluene (8.5 mL) and CMBP (82 mg, 0.34 mmol) were added into the reaction vessel. The reaction mixture was heated at 120° C. for 16 h. The product mixture was cooled down to room temperature and concentrated to dryness. The residue obtained was purified by flash column chromatography with a silica gel column, eluting with DCM initially, grading to 100% ethyl acetate:ethanol 3:1, linear gradient, to afford Int-54b-1. MS (ESI): m/z 715 [M+H]$^+$.

Step C: Int-54c-1

Int-54b-1 (76.7 mg, 0.107 mmol) was added into a 20 mL vial. The reaction vessel was evacuated and backfilled with a balloon of nitrogen. DCM (1.1 mL) was added into the reaction vessel followed by dropwise addition of trifluoroacetic acid (411 μL, 5.37 mmol). The reaction mixture was stirred for 1 h at 24° C. The product mixture was concentrated to dryness. The residue obtained was azeotroped once with toluene (5 mL). The residue obtained containing Int-54c-1 was used directly in the next step without purification.

Step D: (5aR$_a$,18aR$_a$)-2-[(2S,5R)-2,5-dimethyl-4-(prop-2-enoyl)piperazin-1-yl]-12,12,17,18,21-pentafluoro-6-(propan-2-yl)-10,11,12,13-tetrahydro-4H-1,19-(ethanediylidene)pyrido[4,3-f]pyrimido[1,6-h][1,8,10]benzoxadiazacyclotridecin-4-one (Ex. 54)

Int-54c-1 was added into a 20 mL vial. The resulting mixture was dissolved with DCM (550 μL). The solution obtained was cooled down to 0° C. N-Ethyl-N-isopropylpropan-2-amine (98 μL, 0.55 mmol) and acryloyl chloride (13 μL, 0.17 mmol) were added into the reaction vessel. The reaction mixture was stirred for 1 h at 0° C. The product mixture was quenched with saturated ammonium bicarbonate aqueous solution (2 mL). The resulting mixture was extracted three times with ethyl acetate (3×20 mL). The organic layer was dried over sodium sulfate. The dried solution was filtered and the filtrate was concentrated to dryness. The residue obtained was purified by flash column chromatography with silica gel column, eluting with hexanes initially, grading to 100% ethyl acetate-ethanol=3:1 v/v, linear gradient, to afford (5aR$_a$,18aR$_a$)-2-[(2S,5R)-2,5-dimethyl-4-(prop-2-enoyl)piperazin-1-yl]-12,12,17,18,21-pentafluoro-6-(propan-2-yl)-10,11,12,13-tetrahydro-4H-1,19-(ethanediylidene)pyrido[4,3-f]pyrimido[1,6-h][1,8,10]benzoxadiazacyclotridecin-4-one (Ex. 54). MS (ESI): m/z 669 [M+H]$^+$. $^1$H NMR (500 MHz, Acetonitrile-d$_3$) δ 8.48 (d, J=5.0 Hz, 1H), 8.14 (dd, J=9.0, 6.3 Hz, 1H), 7.40 (dt, J=10.3, 9.3 Hz, 1H), 7.22 (d, J=4.9 Hz, 1H), 7.02 (ddd, J=9.3, 3.7, 1.9 Hz, 1H), 6.76 (ddd, J=46.0, 16.7, 10.6 Hz, 1H), 6.25

(ddd, J=16.8, 5.9, 2.3 Hz, 1H), 5.75 (ddd, J=10.2, 7.4, 2.2 Hz, 1H), 4.90 (br s, 1.5H), 4.50-4.21 (m, 2H), 4.18-4.05 (m, 1H), 3.80 (q, J=9.9, 8.6 Hz, 3H), 3.41 (dd, J=13.9, 4.1 Hz, 0.5H), 3.05-2.60 (m, 3H), 2.23-2.18 (m, 1H), 2.15-2.07 (m, 1H), 1.48 (dd, J=6.8, 3.5 Hz, 3H), 1.34 (dd, J=33.8, 6.8 Hz, 3H), 1.11 (d, J=6.7 Hz, 3H), 0.92 (dd, J=6.7, 3.0 Hz, 3H).

Examples 55 Through 68 were Prepared Using Procedures Similar to Those Described in Example 54 from the Indicated Intermediates

| Ex. No. | Intermediate Used | Structure | Compound Name | [M + H]+ Found |
|---|---|---|---|---|
| 55 | Int-52j-1 | 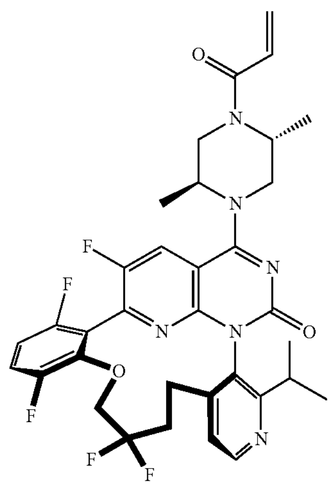 | (5aR$_a$,18aR$_a$)-2-[(2S,5R)-2,5-dimethyl-4-(prop-2-enoyl)piperazin-1-yl]-12,12,15,18,21-pentafluoro-6-(propan-2-yl)-10,11,12,13-tetrahydro-4H-1,19-(ethanediylidene)pyrido[4,3-f]pyrimido[1,6-h][1,8,10]benzoxadiazacyclotri-decin-4-one | 669 |
| 56 | Int-52j-1 | 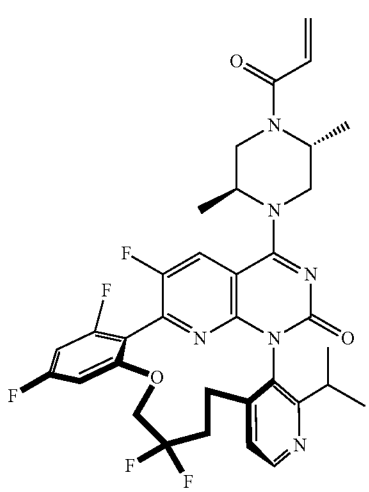 | (5aR$_a$,18aR$_a$)-2-[(2S,5R)-2,5-dimethyl-4-(prop-2-enoyl)piperazin-1-yl]-12,12,16,18,21-pentafluoro-6-(propan-2-yl)-10,11,12,13-tetrahydro-4H-1,19-(ethanediylidene)pyrido[4,3-f]pyrimido[1,6-h][1,8,10]benzoxadiazacyclotri-decin-4-one | 669 |

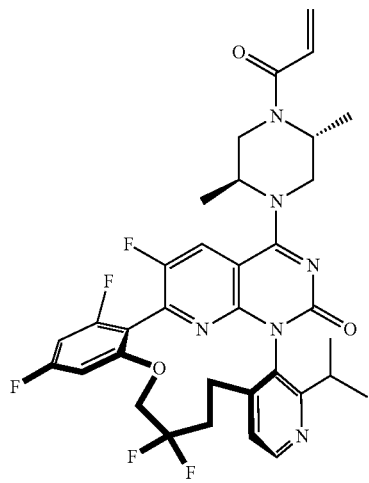

| Ex. No. | Intermediate Used | Structure | Compound Name | [M + H]+ Found |
|---|---|---|---|---|
| 57 | Int-51c | 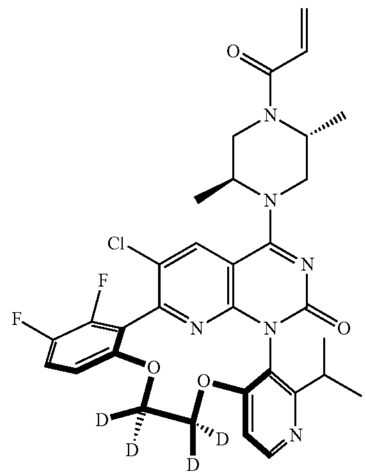 | (5aS_a,17aR_a)-20-chloro-2-[(2S,5R)-2,5-dimethyl-4-(prop-2-enoyl)piperazin-1-yl]-16,17-difluoro-6-(propan-2-yl)-11,12-di[(²H)hydro](11,12-²H₂)-4H-1,18-(ethanediylidene)pyrido[4,3-e]pyrimido[1,6-g][1,4,7,9]benzodioxadiaza-cyclododecin-4-one | 641 |
| 58 | Int-52o | 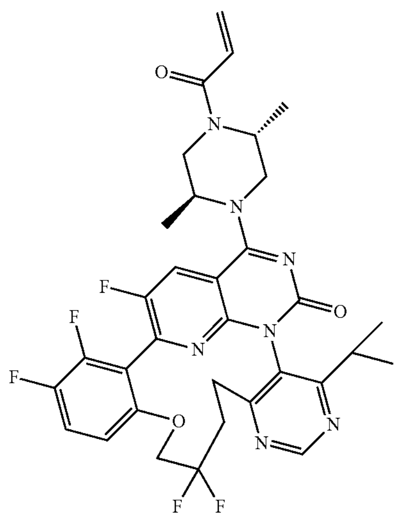 [SMILES: C=CC(=O)N1C[C@H](C)N(c2nc(=O)n3c4nc(c(F)cc24)-c2c(ccc(F)c2F)OCC(F)(F)CCc2ncnc(C(C)C)c2-3)C[C@H]1C] | 2-[(2S,5R)-2,5-dimethyl-4-(prop-2-enoyl)piperazin-1-yl]-12,12,17,18,21-pentafluoro-6-(propan-2-yl)-10,11,12,13-tetrahydro-4H-1,19-(ethanediylidene)dipyrimido[4,5-f:1',6'-h][1,8,10]benzoxadiazacyclo-tridecin-4-one | 670 |
| 59 | Int-41-1 | 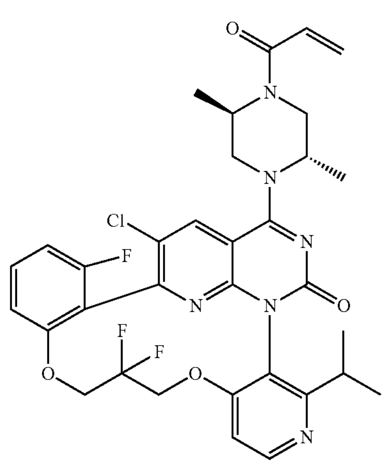 [SMILES: C=CC(=O)N1C[C@H](C)N(c2nc(=O)n3c4nc(c(Cl)cc24)-c2c(F)cccc2OCC(F)(F)COc2ccnc(C(C)C)c2-3)C[C@H]1C] | 21-chloro-2-[(2S,5R)-2,5-dimethyl-4-(prop-2-enoyl)piperazin-1-yl]-12,12,18-trifluoro-6-(propan-2-yl)-12,13-dihydro-4H,11H-1,19-(ethanediylidene)pyrido[4,3-f]pyrimido[1,6-h][1,5,8,10]benzodioxadiazacyclo-tridecin-4-one | 669 |

-continued

| Ex. No. | Intermediate Used | Structure | Compound Name | [M + H]+ Found |
|---|---|---|---|---|
| 60 | Int-52p | 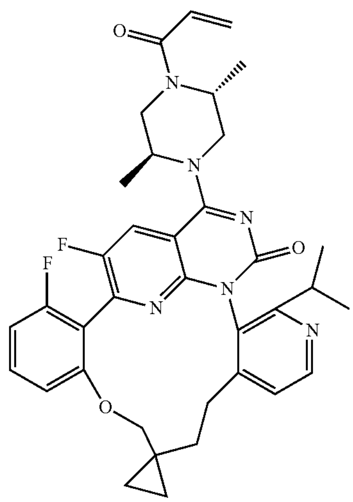 [SMILES: C=CC(=O)N1C[C@H](C)N(c2nc(=O)n3c4nc(c(F)cc24)-c2c(F)cccc2OCC2(CCc4ccnc(C(C)C)c4-3)CC2)C[C@H]1C] | 2'-[(2S,5R)-2,5-dimethyl-4-(prop-2-enoyl)piperazin-1-yl]-18',21'-difluoro-6'-(propan-2-yl)-10',11'-dihydro-4'H,13'H-spiro[cyclopropane-1,12'-[14]oxa[3,5,7,20]tetraaza[1,19](ethanediylidene)pyrido[4,3-f]pyrimido[1,6-h][1,8,10]benzoxadiazacyclotridecin]-4'-one | 641 |
| 61 | Int-52p | 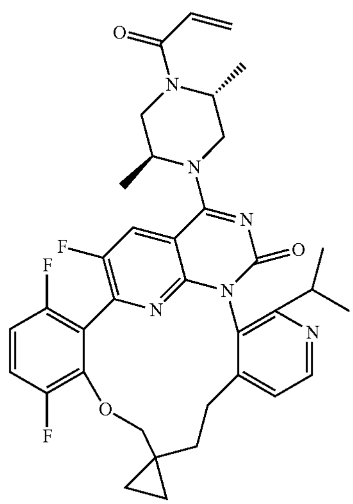 [SMILES: C=CC(=O)N1C[C@H](C)N(c2nc(=O)n3c4nc(c(F)cc24)-c2c(F)ccc(F)c2OCC2(CCc4ccnc(C(C)C)c4-3)CC2)C[C@H]1C] | 2'-[(2S,5R)-2,5-dimethyl-4-(prop-2-enoyl)piperazin-1-yl]-15',18',21'-trifluoro-6'-(propan-2-yl)-10',11'-dihydro-4'H,13'H-spiro[cyclopropane-1,12'-[14]oxa[3,5,7,20]tetraaza[1,19](ethanediylidene)pyrido[4,3-f]pyrimido[1,6-h][1,8,10]benzoxadiazacyclotridecin]-4'-one | 659 |
| 62 | Int-52p | 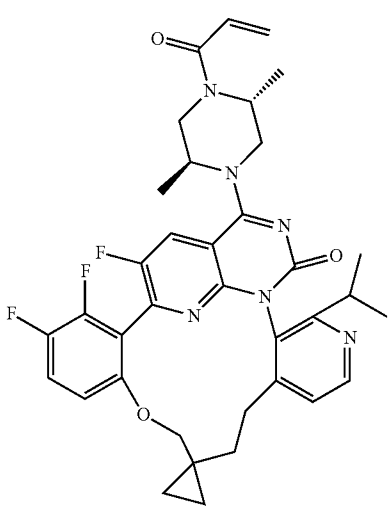 [SMILES: C=CC(=O)N1C[C@H](C)N(c2nc(=O)n3c4nc(c(F)cc24)-c2c(ccc(F)c2F)OCC2(CCc4ccnc(C(C)C)c4-3)CC2)C[C@H]1C] | 2'-[(2S,5R)-2,5-dimethyl-4-(prop-2-enoyl)piperazin-1-yl]-17',18',21'-trifluoro-6'-(propan-2-yl)-10',11'-dihydro-4'H,13'H-spiro[cyclopropane-1,12'-[14]oxa[3,5,7,20]tetraaza[1,19](ethanediylidene)pyrido[4,3-f]pyrimido[1,6-h][1,8,10]benzoxadiazacyclotridecin]-4'-one | 659 |

-continued

| Ex. No. | Inter-mediate Used | Structure | Compound Name | [M + H]+ Found |
|---|---|---|---|---|
| 63 | Int-44 | 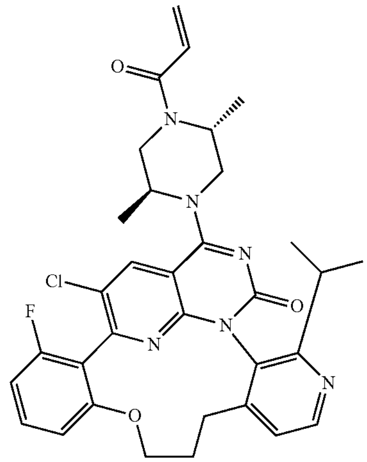 [SMILES: C=CC(=O)N1C[C@H](C)N(c2nc(=O)n3c4nc(c(Cl)cc24)-c2c(F)cccc2OCCCc2ccnc(C(C)C)c2-3)C[C@H]1C] | 20-chloro-2-[(2S,5R)-2,5-dimethyl-4-(prop-2-enoyl)piperazin-1-yl]-17-fluoro-6-(propan-2-yl)-11,12-dihydro-4H,10H-1,18-(ethanediylidene)pyrido[4,3-e]pyrimido[1,6-g][1,7,9]benzoxadiazacyclodo-decin-4-one | 617 |
| 64 | Int-40-1 | 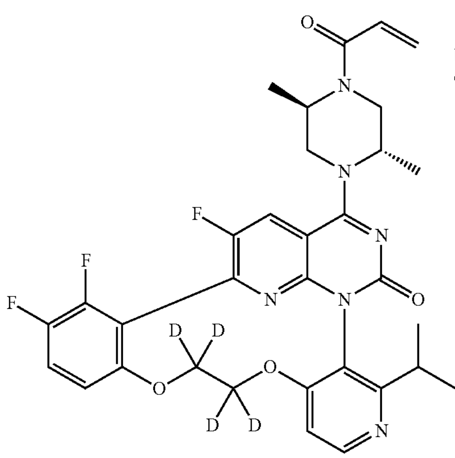 [SMILES: [2H]C1([2H])Oc2ccc(F)c(F)c2-c2nc3c(cc2F)c(N2C[C@@H](C)N(C(=O)C=C)C[C@@H]2C)nc(=O)n3-c2c(ccnc2C(C)C)OC1([2H])[2H]] | 2-[(2S,5R)-2,5-Dimethyl-4-(prop-2-enoyl)piperazin-1-yl]-16,17,20-trifluoro-6-(propan-2-yl)-11,12-di[($^2$H)hydro](11,12-$^2$H$_2$)-4H-1,18-(ethanediylidene)pyrido[4,3-e]pyrimido[1,6-g][1,4,7,9]benzodioxadiazacyclo-dodecin-4-one | 625 |
| 65 | Int-52j-1 | 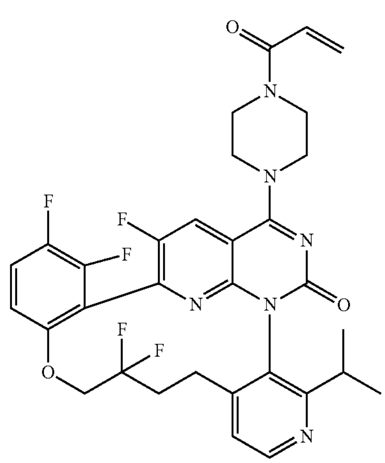 [SMILES: C=CC(=O)N1CCN(c2nc(=O)n3c4nc(c(F)cc24)-c2c(ccc(F)c2F)OCC(F)(F)CCc2ccnc(C(C)C)c2-3)CC1] | 12,12,17,18,21-pentafluoro-6-(propan-2-yl)-2-[4-(prop-2-enoyl)piperazin-1-yl]-10,11,12,13-tetrahydro-4H-1,19-(ethanediylidene)pyrido[4,3-f]pyrimido[1,6-h][1,8,10]benzoxadiazacyclotri-decin-4-one | 641 |

-continued

| Ex. No. | Intermediate Used | Structure | Compound Name | [M + H]+ Found |
|---|---|---|---|---|
| 66 | Int-52j-1 | 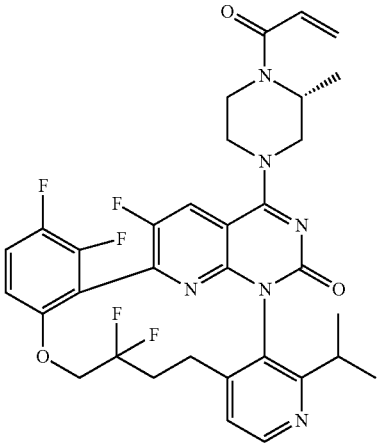 [SMILES: C=CC(=O)N1CCN(c2nc(=O)n3c4nc(c(F)cc24)-c2c(ccc(F)c2F)OCC(F)(F)CCc2ccnc(C(C)C)c2-3)C[C@H]1C] | 12,12,17,18,21-pentafluoro-2-[(3R)-3-methyl-4-(prop-2-enoyl)piperazin-1-yl]-6-(propan-2-yl)-10,11,12,13-tetrahydro-4H-1,19-(ethanediylidene)pyrido[4,3-f]pyrimido[1,6-h][1,8,10]benzoxadiazacyclotridecin-4-one | 655 |
| 67 | Int-40-1 | 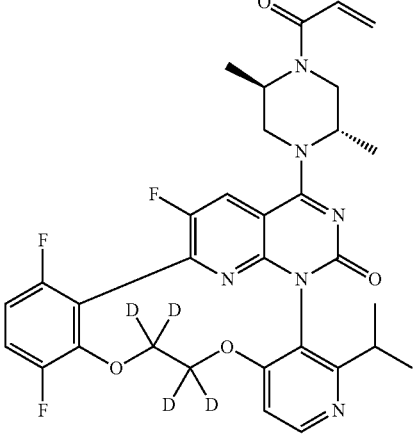 | 2-[(2S,5R)-2,5-Dimethyl-4-(prop-2-enoyl)piperazin-1-yl]-14,17,20-trifluoro-6-(propan-2-yl)-11,12-di[($^2$H)hydro](11,12-$^2$H$_2$)-4H-1,18-(ethanediylidene)pyrido[4,3-e]pyrimido[1,6-g][1,4,7,9]benzodioxadiazacyclododecin-4-one | 625 |
| 68 | Int-16f | 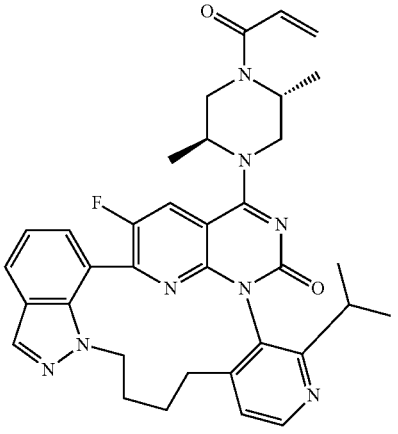 [SMILES: C=CC(=O)N1C[C@H](C)N(c2nc(=O)n3c4nc(c(F)cc24)-c2cccc4cnn(c24)CCCCc2ccnc(C(C)C)c2-3)C[C@H]1C] | 2-[(2S,5R)-2,5-dimethyl-4-(prop-2-enoyl)piperazin-1-yl]-22-fluoro-6-(propan-2-yl)-10,11,12,13-tetrahydro-4H-1,20-(ethanediylidene)pyrido[4',3':12,13]pyrimido[1',6':1,2][1,3,7]triazacyclotridecino[5,6,7-hi]indazol-4-one | 621 |

Preparation of 4-(4-((tert-butyldimethylsilyl)oxy)-3,3-difluorobutyl)-6-isopropylpyrimidin-5-amine (Int-69d)

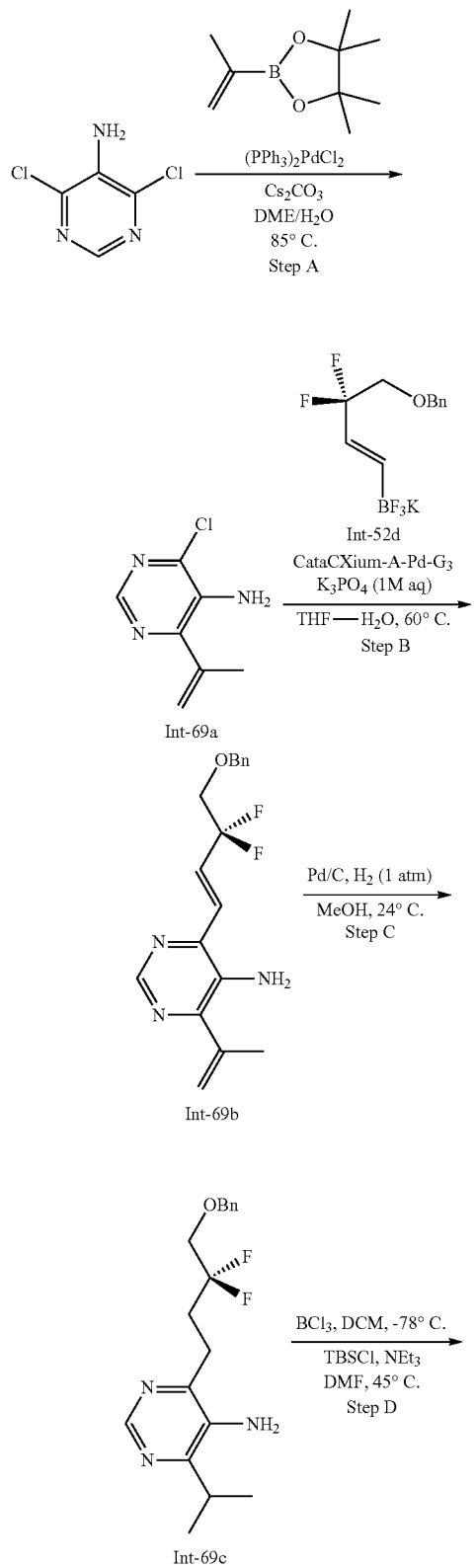

Step A: 4-chloro-6-(prop-1-en-2-yl)pyrimidin-5-amine (Int-69a)

Isopropenylboronic acid pinacol ester (6.88 mL, 36.6 mmol) was taken up in DME (81 mL) and added to a microwave vial containing 4,6-dichloropyrimidin-5-amine (5.00 g, 30.5 mmol). Cesium carbonate (29.8 g, 91.0 mmol) followed by water (20.3 mL) were added and argon was bubbled through the mixture. Bis(triphenylphosphine)palladium(II) dichloride (2.14 g, 3.05 mmol) was added and argon was bubbled through the mixture for 4 minutes. The mixture was then heated to 85° C. for 3 h. Upon cooling to 24° C., the mixture was diluted with ethyl acetate and saturated sodium bicarbonate aqueous solution. The organic layer was separated, dried over magnesium sulfate, filtered and concentrated under reduced pressure. Column chromatography was used for purification (0-20% ethyl acetate gradient in hexanes) to afford 4-chloro-6-(prop-1-en-2-yl)pyrimidin-5-amine (Int-69a). $^1$H NMR (500 MHz, DMSO-$d_6$): δ 8.22 (s, 1H), 5.61-5.57 (m, 1H), 5.50 (s, 2H), 5.46 (t, J=1.1 Hz, 1H), 2.07 (t, J=1.3 Hz, 3H).

Step B: (E)-4-(4-(benzyloxy)-3,3-difluorobut-1-en-1-yl)-6-(prop-1-en-2-yl)pyrimidin-5-amine (Int-69b)

4-Chloro-6-(prop-1-en-2-yl)pyrimidin-5-amine (1.00 g, 5.90 mmol) and potassium (E)-(4-(benzyloxy)-3,3-difluorobut-1-en-1-yl)trifluoroborate (Int-52d, 1.97, 6.49 mmol) were placed in a vial and THF (13.8 mL) was added. Argon was bubbled through the mixture. Catacxium A-Pd-G3 (215 mg, 0.295 mmol), potassium phosphate tribasic (2.50 g, 11.8 mmol) and then water (5.9 mL) were added and argon was bubbled through the mixture for five minutes. The reaction was then heated to 60° C. for 16 h. Upon cooling to 24° C., the mixture was diluted with ethyl acetate and water. The organic layer was separated, dried over magnesium sulfate, filtered and concentrated under reduced pressure. The resulting mixture was purified by column chromatography (0-20% ethyl acetate gradient in hexanes) to afford (E)-4-(4-(benzyloxy)-3,3-difluorobut-1-en-1-yl)-6-(prop-1-en-2-yl)pyrimidin-5-amine (Int-69b). $^1$H NMR (500 MHz, DMSO-$d_6$): δ 8.39 (s, 1H), 7.47 (dt, J=15.3, 2.7 Hz, 1H), 7.43-7.22 (m, 5H), 6.95 (dt, J=15.3, 12.3 Hz, 1H), 5.62-5.49 (m, 3H), 5.38 (t, J=1.2 Hz, 1H), 4.64 (s, 2H), 3.93 (t, J=13.3 Hz, 2H), 2.07 (d, J=1.2 Hz, 3H).

Step C: 4-(4-(benzyloxy)-3,3-difluorobutyl)-6-isopropylpyrimidin-5-amine (Int-69c)

A flask containing (E)-4-(4-(benzyloxy)-3,3-difluorobut-1-en-1-yl)-6-(prop-1-en-2-yl)pyrimidin-5-amine (903 mg, 2.73 mmol) and methanol (14 mL) was degassed with nitrogen via subsurface bubbling. Pd/C (10 wt %, 29.0 mg, 0.273 mmol) was added and the flask was evacuated and then purged 5 times with hydrogen. The mixture was stirred for 16 h at 24° C. The mixture was then filtered through CELITE and the filtrate was concentrated under reduced pressure. The resulting mixture containing 4-(4-(benzyloxy)-3,3-difluorobutyl)-6-isopropylpyrimidin-5-amine (Int-69c) was used in the subsequent reaction without further purification.

Step D: 4-(4-((tert-butyldimethylsilyl)oxy)-3,3-difluorobutyl)-6-isopropylpyrimidin-5-amine (Int-69d)

4-(4-(Benzyloxy)-3,3-difluorobutyl)-6-isopropylpyrimidin-5-amine (710 mg, 2.12 mmol) was dissolved in DCM (11 mL) under nitrogen. The resulting mixture was cooled down to −78° C. Trichloroborane (1.0 M in DCM, 6.4 mL, 6.4 mmol) was added dropwise. The resulting mixture was stirred for 2 h at −78° C. and quenched with a 1:1 MeOH/DCM mixture (2 mL) at −78° C. The resulting mixture was warmed to room temperature and concentrated to dryness. The residue obtained was dissolved in DMF (1 mL). Triethylamine (2.93 mL, 21.2 mmol) and tert-butyldimethylchlorosilane (638 mg, 4.23 mmol) were added into the reaction vessel. The resulting mixture was heated to 45° C. for 2 h. Upon cooling to room temperature, the product mixture was diluted with ethyl acetate (20 mL). The diluted product mixture was washed three times with saturated sodium bicarbonate aqueous solution (3×20 mL). The organic layer was dried over magnesium sulfate, filtered and concentrated under reduced pressure. The residue obtained was purified by flash column chromatography with silica gel column, eluting with DCM initially, grading to 80% ethyl acetate:ethanol 3:1-DCM, linear gradient to afford 4-(4-((tert-butyldimethylsilyl)oxy)-3,3-difluorobutyl)-6-isopropylpyrimidin-5-amine (Int-69d). MS (ESI): m/z 360 [M+H]$^+$.

Example 70: 9-chloro-2-[(2S,5R)-2,5-dimethyl-4-(prop-2-enoyl)piperazin-1-yl]-17,20-difluoro-6-(propan-2-yl)-11,12-dihydro-4H-1,18-(ethanediylidene)pyrido[4,3-e]pyrimido[1,6-g][1,4,7,9]benzodioxadiazacyclododecin-4-one

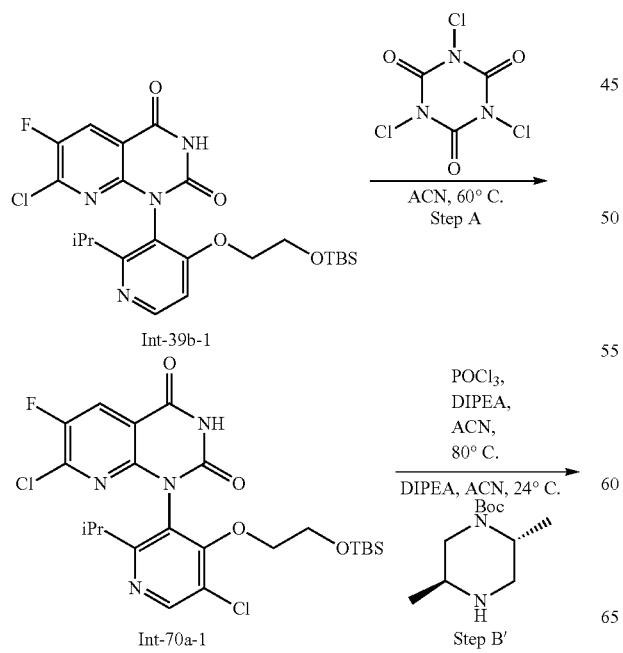

-continued

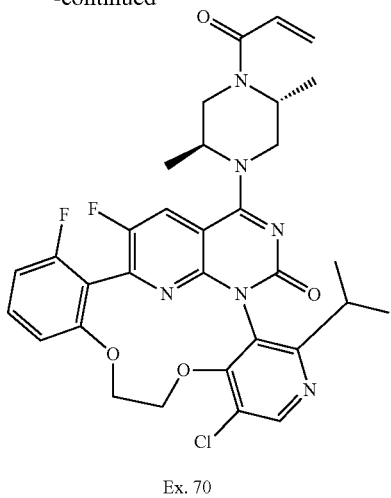

Ex. 70

Step A: 1-(4-(2-(((tert-butyldimethylsilyl)oxy)
ethoxy)-5-chloro-2-isopropylpyridin-3-yl)-7-chloro-
6-fluoropyrido[2,3-d]pyrimidine-2,4(1H,3H)-dione
(Int-70a-1)

1-(4-(2-((tert-Butyldimethylsilyl)oxy)ethoxy)-2-isopropylpyridin-3-yl)-7-chloro-6-fluoropyrido[2,3-d]pyrimidine-2,4(1H,3H)-dione (Int-39b-1, 100 mg, 0.196 mmol) in acetonitrile (2.0 mL) was treated at 24° C. with trichloroisocyanuric acid (91 mg, 0.39 mmol). The vial was capped and heated at 60° C. for 24 h. The mixture was cooled to 0° C. and treated with saturated aqueous sodium carbonate solution (1 mL) followed by saturated aqueous sodium thiosulfate solution (0.5 mL) and then water (0.5 mL, to facilitate stirring). The mixture obtained was extracted with ethyl acetate (3×2 mL). The combined organic layers were dried with anhydrous sodium sulfate, filtered and the filtrate was concentrated. The residue was dissolved in minimal dichloromethane and applied to a silica gel column. Purification by column chromatography on silica gel (0 to 100% EtOAc/hexanes; product elutes at 30%) afforded 1-(4-(2-((tert-butyldimethylsilyl)oxy)ethoxy)-5-chloro-2-isopropylpyridin-3-yl)-7-chloro-6-fluoropyrido[2,3-d]pyrimidine-2,4(1H,3H)-dione (Int-70a-1). MS (ESI) m/z 543 [M+H]$^+$.

Step B: tert-butyl (2R,5S)-4-(1-(4-(2-(((tert-butyldimethylsilyl)oxy)ethoxy)-5-chloro-2-isopropylpyridin-3-yl)-7-chloro-6-fluoro-2-oxo-1,2-dihydropyrido[2,3-d]pyrimidin-4-yl-2,5-dimethylpiperazine-1-carboxylate (Int-70b-1)

1-(4-(2-((tert-Butyldimethylsilyl)oxy)ethoxy)-5-chloro-2-isopropylpyridin-3-yl)-7-chloro-6-fluoropyrido[2,3-d]pyrimidine-2,4(1H,3H)-dione (Int-70a-1, 169 mg, 0.311 mmol) in acetonitrile (2.0 mL) was treated at 24° C. with DIEA (0.109 mL, 0.622 mmol) and POCl$_3$ (0.043 mL, 0.47 mmol). The mixture was heated at 80° C. for 2 h. The resulting mixture was cooled to 24° C. and concentrated. The residue was dissolved in acetonitrile (2.0 mL) and treated with DIEA (0.109 mL, 0.622 mmol) and (2R,5S)-tert-butyl 2,5-dimethylpiperazine-1-carboxylate (133 mg, 0.622 mmol). The resulting mixture was stirred at 24° C. for 16 h. The resulting mixture was diluted with ethyl acetate (10 mL) and water (10 mL). The mixture was extracted with ethyl acetate. The combined organic layers were dried with anhydrous sodium sulfate, filtered and the filtrate was concentrated. The residue was dissolved in minimal dichloromethane and loaded onto a silica gel column. Purification by column chromatography on silica gel (0 to 100% EtOAc/hexanes; product eluted at 60-65%) afforded tert-butyl (2R,5S)-4-(1-(4-(2-((tert-butyldimethylsilyl)oxy)ethoxy)-5-chloro-2-isopropylpyridin-3-yl)-7-chloro-6-fluoro-2-oxo-1,2-dihydropyrido[2,3-d]pyrimidin-4-yl)-2,5-dimethylpiperazine-1-carboxylate (Int-70b-1). MS (ESI) m/z 739 [M+H]$^+$.

Step C: tert-butyl (2R,5S)-4-(1-(5-chloro-4-(2-hydroxyethoxy-2-isopropylpyridin-3-yl-6-fluoro-7-(2-fluoro-6-hydroxyphenyl)-2-oxo-1,2-dihydropyrido[2,3-d]pyrimidin-4-yl-2,5-dimethylpiperazine-1-carboxylate (Int-70c-1)

tert-Butyl (2R,5S)-4-(1-(4-(2-((tert-butyldimethylsilyl)oxy)ethoxy)-5-chloro-2-isopropylpyridin-3-yl)-7-chloro-6-fluoro-2-oxo-1,2-dihydropyrido[2,3-d]pyrimidin-4-yl)-2,5-dimethylpiperazine-1-carboxylate (Int-70b-1, 110 mg, 0.149 mmol), potassium trifluoro(2-fluoro-6-hydroxyphenyl)borate (48.4 mg, 0.223 mmol), potassium acetate (58.4 mg, 0.595 mmol), 1,1′-bis(diphenylphosphino)ferrocene-palladium(II)dichloride dichloromethane complex (24 mg, 0.030 mmol) were added to a 20 mL scintillation vial equipped with magnetic stir bar, degassed under nitrogen, charged with dioxane (1 mL)/water (167 µL), degassed three times under nitrogen and heated at 100° C. for 30 minutes. The mixture was cooled to 24° C. The mixture was diluted with ethyl acetate and filtered through a pad o 1:1 v/v FLORISIL/anhydrous sodium sulfate. The pad displacement was rinsed with ethyl acetate and the combined filtrate was concentrated. This residue was dissolved in THF (6 mL) to afford a pale yellow solution and treated with TBAF (1 M in THF, 297 µL, 0.297 mmol) followed by acetic acid (10 µL, 0.18 mmol). This mixture was stirred at 24° C. for 16 h. The product mixture was quenched with saturated aqueous sodium bicarbonate (10 mL), extracted with ethyl acetate, and the combined organic layers were washed with water, dried with anhydrous sodium sulfate, filtered and the filtrate was concentrated. The residue obtained was purification by column chromatography on silica gel (0 to 100% EtOAc/hexanes; product eluted at 60%) afforded tert-butyl (2R,5S)-4-(1-(5-chloro-4-(2-hydroxyethoxy)-2-isopropylpyridin-3-yl)-6-fluoro-7-(2-fluoro-6-hydroxyphenyl)-2-oxo-1,2-dihydropyrido[2,3-d]pyrimidin-4-yl)-2,5-dimethylpiperazine-1-carboxylate (Int-70c-1). MS (ESI) m/z 701 [M+H]$^+$. $^1$H NMR (500 MHz, Acetone-d$_6$): δ 8.56 (s, 1H), 8.29 (d, J=9.3 Hz, 1H), 7.33 (td, J=8.3, 6.5 Hz, 1H), 6.78 (d, J=8.4 Hz, 1H), 6.72 (t, J=9.0 Hz, 1H), 4.99 (s, 1H), 4.49 (d, J=38.4 Hz, 1H), 4.34-4.17 (m, 2H), 4.11-3.93 (m, 3H), 3.93-3.79 (m, 1H), 3.72-3.49 (m, 4H), 2.07 (p, J=2.2 Hz, 1H), 1.51 (s, 12H), 1.30 (s, 3H), 1.18 (d, J=6.7 Hz, 3H), 1.03 (d, J=6.8 Hz, 3H).

Step D: Int-70d-1

A solution of triphenylphosphine (187 mg, 0.713 mmol) in tetrahydrofuran (3.0 mL) was cooled to 0° C. under nitrogen and treated dropwise with DIAD (0.139 mL, 0.713 mmol). The resulting slurry was stirred at 0° C. for 15 minutes and then treated dropwise with a solution of tert-butyl (2R,5S)-4-(1-(5-chloro-4-(2-hydroxyethoxy)-2-isopropylpyridin-3-yl)-6-fluoro-7-(2-fluoro-6-hydroxyphenyl)-2-oxo-1,2-dihydropyrido[2,3-d]pyrimidin-4-yl)-2,5-dimethylpiperazine-1-carboxylate (Int-70c-1, 100 mg, 0.143 mmol) in tetrahydrofuran (2.00 mL). The mixture was warmed to rt and stirred to 1 h resulting in a slurry. Water (0.2 mL) was added and the slurry dissolved to afford a clear solution. The mixture was diluted with additional water (5 mL) and extracted with ethyl acetate (5 mL). The combined organic layers was washed with water, dried with anhydrous sodium sulfate, filtered and the filtrate was concentrated. Purification by column chromatography on silica gel (0 to 100% [1:3 EtOH/EtOAc]/hexanes) afforded Int-70d-1. MS (ESI) m/z 683 [M+H]+.

Step E: 9-chloro-2-[(2S,5R)-2,5-dimethyl-4-(prop-2-enoyl)piperazin-1-yl]-17,20-difluoro-6-(propan-2-yl)-11,12-dihydro-4H-1,18-(ethanediylidene)pyrido[4,3-e]pyrimido[1,6-g][1,4,7,9]benzodioxadiazacyclododecin-4-one (Ex. 70)

Int-70d-1 (25 mg, 0.037 mmol) in dichloromethane (1.0 mL) was treated at 24° C. with TFA (0.250 mL). The mixture was stirred at 24° C. for 16 h. The reaction mixture was concentrated. The residue was dissolved in acetonitrile (2 mL) and concentrated. The residue was dried under vacuum overnight and then dissolved in dichloromethane (2 mL) cooled to 0° C. and treated with N-methylmorpholine (100 µL, 0.910 mmol) and acrylic anhydride (50 µL, 0.43 mmol). The resulting mixture stirred at 24° C. for 1 h. The residue was loaded directly onto a 40 g silica gel column. Purification by column chromatography on silica gel (0 to 100% EtOAc/hexanes) then flushed with 3:1 ethyl acetate/ethanol. The fractions were concentrated, the residue obtained was further purified by reverse-phase HPLC on a C18-functionalized column with gradient elution using acetonitrile and water modified with ammonium hydroxide to afford 9-chloro-2-[(2S,5R)-2,5-dimethyl-4-(prop-2-enoyl)piperazin-1-yl]-17,20-difluoro-6-(propan-2-yl)-11,12-dihydro-4H-1,18-(ethanediylidene)pyrido[4,3-e]pyrimido[1,6-g][1,4,7,9]benzodioxadiazacyclododecin-4-one (Ex. 70). MS (ESI) m/z 637 [M+H]+. 1H NMR (500 MHz, Acetone-d6): δ 8.40 (s, 1H), 8.16 (dd, J=18.3, 9.1 Hz, 1H), 7.52 (td, J=8.4, 6.7 Hz, 1H), 7.16 (d, J=8.3 Hz, 1H), 6.99 (t, J=8.8 Hz, 1H), 6.94-6.75 (m, 1H), 6.37-6.16 (m, 1H), 5.74 (t, J=9.0 Hz, 1H), 5.62 (dd, J=13.7, 2.6 Hz, 1H), 5.06-4.87 (m, 1.5H), 4.81 (d, J=13.9 Hz, 0.5H), 4.73-4.57 (m, 2H), 4.42 (d, J=13.8 Hz, 0.5H), 4.35 (ddd, J=14.1, 9.7, 1.3 Hz, 1H), 4.08-4.02 (m, 1H), 3.97 (d, J=14.1 Hz, 0.5H), 3.84 (dd, J=13.9, 3.7 Hz, 0.5H), 3.79-3.64 (m, 1H), 3.41-3.31 (m, 0.5H), 3.02-2.91 (m, 1H), 1.60 (t, J=7.3 Hz, 3H), 1.54-1.48 (m, 3H), 1.18 (d, J=6.7 Hz, 3H), 0.94 (dd, J=6.8, 4.3 Hz, 3H).

Preparation of tert-butyl (2R,5S)-4-(7-(3,6-difluoro-2-hydroxyphenyl)-6-fluoro-1-(4-(2-hydroxyethoxy)-2-isopropylpyridin-3-yl)-2-oxo-1,2-dihydroquinazolin-4-yl)-2,5-dimethylpiperazine-1-carboxylate (Int-71d-2)

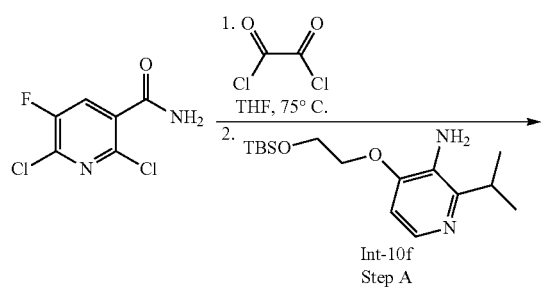

Int-10f
Step A

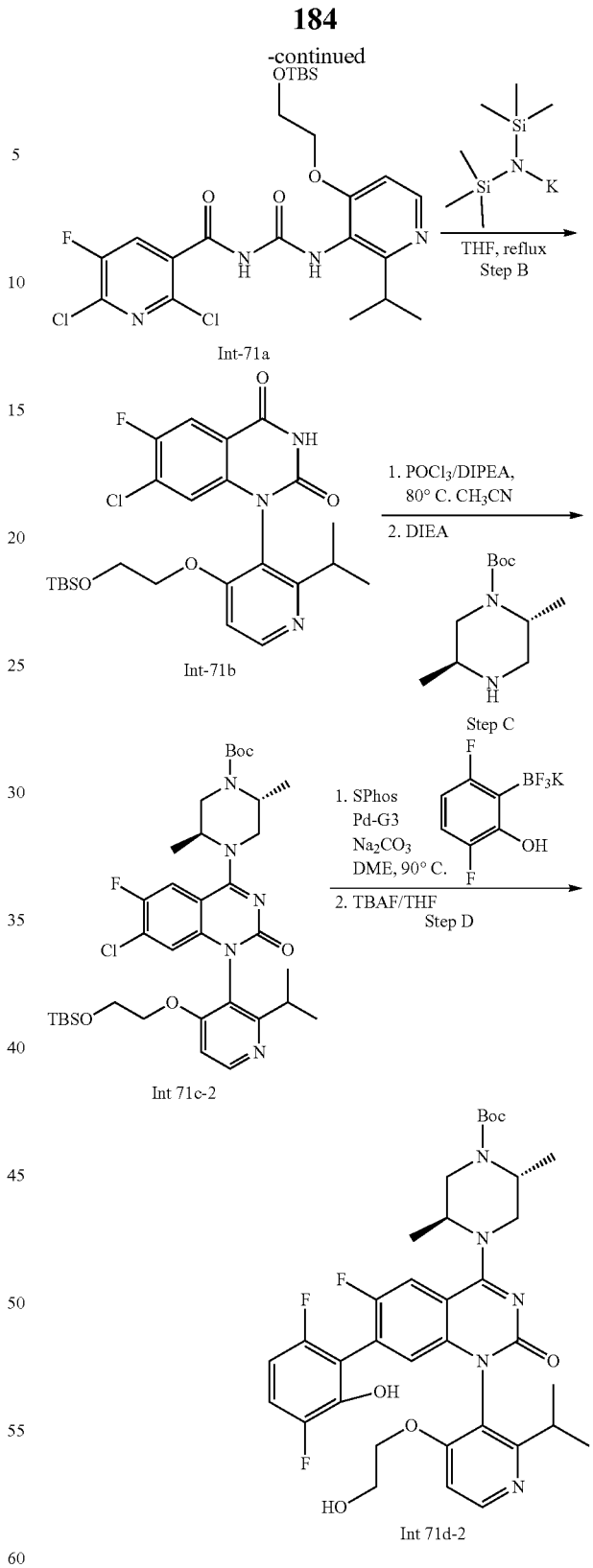

Step A: N-((4-(2-((tert-butyldimethylsilyl)oxy)ethoxy-2-isopropylpyridin-3-yl)carbamoyl)-2,4-dichloro-5-fluorobenzamide (Int-71a)

To a stirred solution of 2,4-dichloro-5-fluorobenzamide (2.04 g, 9.81 mmol) in THF (9.8 mL) at 24° C. was added oxalyl chloride (5.86 mL, 11.7 mmol, 2 M solution in dichloromethane) and the reaction was heated to 75° C. with reflux condenser for 1 h. The reaction was evaporated to dryness and dried under high vacuum for 30 minutes. The residue was then charged with 20 mL THF, cooled to 0° C. and a solution of 4-(2-((tert-butyldimethylsilyl)oxy)ethoxy)-2-isopropylpyridin-3-amine (Int-10f, 3.26 g, 9.76 mmol) in THF (9.8 mL) was added dropwise. The reaction was allowed to stir for 1 h at 0° C. then was quenched at 0° C. with 130 mL 1:1 pH 7 buffer/brine. and diluted with 100 mL EtOAc. The reaction was extracted a second time with 100 mL EtOAc, dried over anhydrous sodium sulfate, filtered and concentrated in vacuo. Purification on silica gel, 0-10% DCM/MeOH gave N-((4-(2-((tert-butyldimethylsilyl)oxy)ethoxy)-2-isopropylpyridin-3-yl)carbamoyl)-2,4-dichloro-5-fluorobenzamide (Int-71a). MS (ESI) m/z 544 [M+H]$^+$ Step B: 1-(4-(2-((tert-butyldimethylsilyl)oxy)ethoxy)-2-isopropylpyridin-3-yl)-7-chloro-6-fluoroquinazoline-2,4(1H,3H)-dione (Int-71b)

N-((4-(2-((tert-Butyldimethylsilyl)oxy)ethoxy)-2-isopropylpyridin-3-yl)carbamoyl)-2,4-dichloro-5-fluorobenzamide (Int-71a, 3.00 g, 5.51 mmol) was dissolved in THF (22.0 mL), cooled to −20° C., charged with 1 M THF solution of KHMDS (11.6 mL, 11.6 mmol), then heated to reflux for 1 h. The reaction was cooled to 24° C., quenched with saturated ammonium chloride, extracted twice with 100 mL EtOAc, washed with brine, dried over anhydrous sodium sulfate, filtered and concentrated in vacuo. The residue was purified on silica gel 0-10% MeOH/DCM to provide 1-(4-(2-((tert-butyldimethylsilyl)oxy)ethoxy)-2-isopropylpyridin-3-yl)-7-chloro-6-fluoroquinazoline-2,4(1H,3H)-dione (Int-71b) MS (ESI) m/z 508 [M+H]$^+$.

Step C: tert-butyl (2R,5S)-4-(1-(4-(2-((tert-butyldimethylsilyl)oxy)ethoxy)-2-isopropylpyridin-3-yl)-7-chloro-6-fluoro-2-oxo-1,2-dihydroquinazolin-4-yl)-2,5-dimethylpiperazine-1-carboxylate (Int-71c-2)

1-(4-(2-((tert-Butyldimethylsilyl)oxy)ethoxy)-2-isopropylpyridin-3-yl)-7-chloro-6-fluoroquinazoline-2,4(1H,3H)-dione (Int-71b) was dissolved in acetonitrile (13.0 mL), charged with DIEA (1.36 mL, 7.79 mmol) followed by POCl$_3$ (0.291 mL, 3.12 mmol) and heated to 80° C. for 1 h. The reaction was cooled to 0° C., charged with an additional portion of DIEA (1.36 mL, 7.79 mmol) and charged with tert-butyl (2R,5S)-2,5-dimethylpiperazine-1-carboxylate (0.67 g, 3.1 mmol) and allowed to stir for 20 minutes. The reaction was evaporated in vacuo, loaded onto a silica gel column and eluted with 0-5% MeOH/DCM to provide tert-butyl (2R,5S)-4-(1-(4-(2-((tert-butyldimethylsilyl)oxy)ethoxy)-2-isopropylpyridin-3-yl)-7-chloro-6-fluoro-2-oxo-1,2-dihydroquinazolin-4-yl)-2,5-dimethylpiperazine-1-carboxylate. The racemic material was submitted for SFC purification using Column T, Condition: MeOH w/0.1% NH$_4$OH, 20% CO$_2$ to provide Peak 2 as tert-butyl (2R,5S)-4-(1-(4-(2-((tert-butyldimethylsilyl)oxy)ethoxy)-2-isopropylpyridin-3-yl)-7-chloro-6-fluoro-2-oxo-1,2-dihydroquinazolin-4-yl)-2,5-dimethylpiperazine-1-carboxylate (Int-71c-2) MS (ESI) m/z 704 [M+H]$^+$ Step D: tert-butyl (2R,5S)-4-(7-(3,6-difluoro-2-hydroxyphenyl-6-fluoro-1-(4-(2-hydroxyethoxy)-2-isopropylpyridin-3-yl)-2-oxo-1,2-dihydroquinazolin-4-yl)-2,5-dimethylpiperazine-1-carboxylate (Int-71d-2)

tert-Butyl (2R,5S)-4-(1-(4-(2-((tert-butyldimethylsilyl)oxy)ethoxy)-2-isopropylpyridin-3-yl)-7-chloro-6-fluoro-2-oxo-1,2-dihydroquinazolin-4-yl)-2,5-dimethylpiperazine-1-carboxylate (Int-71c-2, 299 mg, 0.425 mmol), (2-dicyclohexylphosphino-2',6'-dimethoxybiphenyl) [2-(2'-amino-1,1'-biphenyl)]palladium(II) methanesulfonate (33 mg, 0.042 mmol), potassium (3,6-difluoro-2-hydroxyphenyl)trifluoroborate (Int-23c, 200 mg, 0.849 mmol) were added to a 20 mL scintillation vial, degassed under nitrogen and charged with DME (4.2 mL), 2 M aqueous solution of sodium carbonate (637 µL, 1.27 mmol) and heated to 90° C. for 2 h. The reaction was cooled to 24° C., quenched with 3 mL saturated ammonium chloride, extracted once with 20 mL EtOAc, washed with brine, dried over anhydrous sodium sulfate, filtered and concentrated in vacuo. The residue was charged with 5 mL THF and TBAF (1 M solution in THF, 1.27 mL, 1.27 mmol) and allowed to stir overnight at 24° C. The reaction was quenched with 3 mL saturated ammonium chloride, extracted twice with 20 mL EtOAc, washed with brine, dried over sodium sulfate filtered and concentrated in vacuo. The residue was purified on silica gel (0-100% EtOAc/EtOH 3:1/hexanes) to provide tert-butyl (2R,5S)-4-(7-(3,6-difluoro-2-hydroxyphenyl)-6-fluoro-1-(4-(2-hydroxyethoxy)-2-isopropylpyridin-3-yl)-2-oxo-1,2-dihydroquinazolin-4-yl)-2,5-dimethylpiperazine-1-carboxylate (Int-71d-2). MS (ESI) m/z 684 [M+H]$^+$ Preparation of tert-butyl (2R,5S)-4-(1-(5-(4-((tert-butyldimethylsilyloxy)butyl-2-isopropyl-4-methylpyridin-3-yl-7-chloro-6-fluoro-2-oxo-1,2-dihydropyrido[2,3-d]pyrimidin-4-yl-2,5-dimethylpiperazine-1-carboxylate (Int-72h)

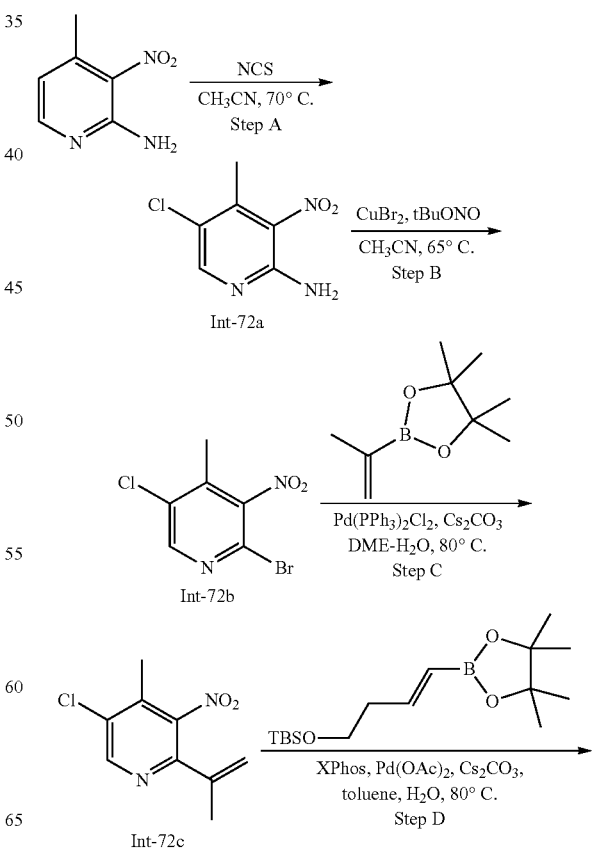

-continued

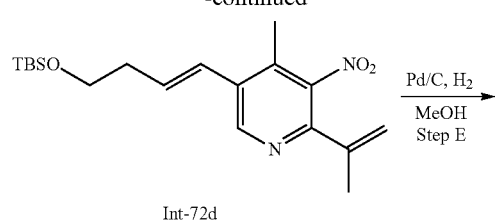

Int-72d

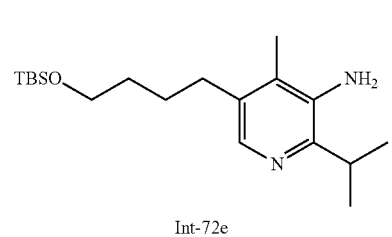

Int-72e

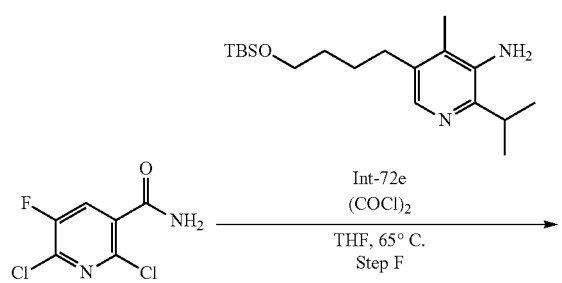

Int-72f

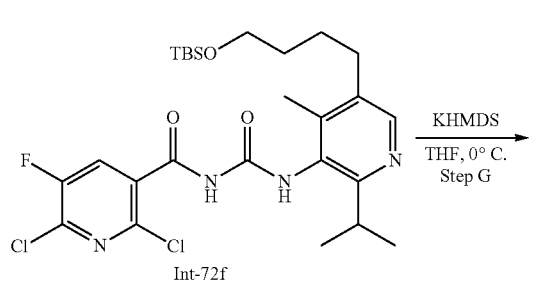

Int-72g

-continued

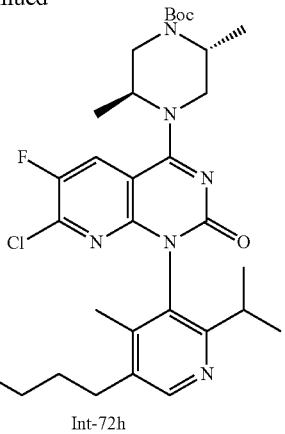

Int-72h

Step A: 5-chloro-4-methyl-3-nitropyridin-2-amine (Int-72a)

To a stirred solution of 4-methyl-3-nitropyridin-2-amine (95.0 g, 620 mmol) in MCCN (900 mL) was added 1-chloropyrrolidine-2,5-dione (108 g, 806 mmol), and the mixture was stirred at 70° C. for 12 h under $N_2$ atmosphere. The mixture was filtered, and the filtrate was concentrated in vacuo, and the residue was purified by column chromatography on silica gel (Pet. ether/EtOAc=3/1) to give 5-chloro-4-methyl-3-nitropyridin-2-amine (Int-72a). MS (ESI) m/z 188 $[M+H]^+$.

Step B: 2-bromo-5-chloro-4-methyl-3-nitropyridine (Int-72b)

To a solution of anhydrous copper(II) bromide (29.4 g, 205 mmol) and 5-chloro-4-methyl-3-nitropyridin-2-amine (32.0 g, 171 mmol) in anhydrous acetonitrile (350 mL) was added tert-butyl nitrite (26.4 g, 256 mmol) portionwise over a period of 10 min at 65° C. The reaction mixture was maintained at 65° C. for 2 h, and then allowed to cool to room temperature. The reaction mixture was then poured into 50 mL of 2 M aqueous HCl solution, followed by extraction with ethyl acetate (300 mL×2). The organic extracts were washed with brine, dried over $MgSO_4$, filtered and concentrated in vacuo. The crude product was purified by flash column chromatography using 95:5 v/v hexane:ethyl acetate as solvent to afford 2-bromo-5-chloro-4-methyl-3-nitropyridine (Int-72b). $^1$H NMR (400 MHz, $CDCl_3$): δ 8.58-8.39 (m, 1H), 2.40 (s, 3H).

Step C: 5-chloro-4-methyl-3-nitro-2-(prop-1-en-2-yl)pyridine (Int-72c)

To a stirred solution of 2-bromo-5-chloro-4-methyl-3-nitropyridine (9.00 g, 35.8 mmol) in DME (90 mL) and water (15 mL) were added $Cs_2CO_3$ (23.3 g, 71.6 mmol), 4,4,5,5-tetramethyl-2-(prop-1-en-2-yl)-1,3,2-dioxaborolane (6.31 g, 37.6 mmol) and bis(triphenylphosphine) palladium (II) dichloride (2.51 g, 3.58 mmol), and the resulting mixture was stirred at 80° C. for 16 h. The reaction was extracted with EtOAc (200 mL×3). The combined organic phase was dried over anhydrous $Na_2SO_4$, filtered and concentrated in vacuo. The residue was purified by flash silica gel chromatography (Pet. ether/EtOAc=10/1) to give 5-chloro-4-methyl-3-nitro-2-(prop-1-en-2-yl)pyridine (Int-72c). $^1$H NMR (400 MHz, CDCl₃): δ 8.59 (s, 1H), 5.33 (d, J=0.8 Hz, 1H), 5.20 (s, 1H), 2.36 (s, 3H), 2.15 (s, 3H).

Step D: (E)-5-(4-((tert-butyldimethylsilyl)oxy)but-1-en-1-yl)-4-methyl-3-nitro-2-(prop-1-en-2-yl)pyridine (Int-72d)

To a stirred solution of 5-chloro-4-methyl-3-nitro-2-(prop-1-en-2-yl)pyridine (6.40 g, 30.1 mmol) in toluene (70 mL) and water (10 mL) were added $Cs_2CO_3$ (24.2 g, 75 mmol), (E)-tert-butyldimethyl((4-(4,4,5,5-tetramethyl-1,3,2-dioxaborolan-2-yl)but-3-en-1-yl)oxy)silane (14.1 g, 45.1 mmol), 2-dicyclohexylphosphino-2',4',6'-triisopropylbiphenyl (1.44 g, 3.01 mmol) and Pd(OAc)₂ (0.338 g, 1.505 mmol), and the resulting mixture was stirred at 80° C. for 16 h under $N_2$ atmosphere. The reaction was concentrated in vacuo, and the residue was quenched with H₂O (15 mL), and extracted with EtOAc (100 mL×2). The combined organic phase was dried over anhydrous $Na_2SO_4$, filtered and concentrated in vacuo. The residue was purified by flash silica gel chromatography (Pet. ether/EtOAc=10/1) to give (E)-5-(4-((tert-butyldimethylsilyl)oxy)but-1-en-1-yl)-4-methyl-3-nitro-2-(prop-1-en-2-yl)pyridine (Int-72d). ¹H NMR (400 MHz, CDCl₃): δ 8.60 (s, 1H), 6.51 (d, J=16.0 Hz, 1H), 6.25 (td, J=6.9, 15.8 Hz, 1H), 5.30 (d, J=3.1 Hz, 1H), 5.19 (s, 1H), 3.76 (t, J=6.3 Hz, 2H), 2.48 (q, J=6.3 Hz, 2H), 2.25 (s, 3H), 2.16 (s, 3H), 0.89 (s, 9H), 0.06 (s, 6H).

Step E: 5-(4-((tert-butyldimethylsilyl)oxy)butyl)-2-isopropyl-4-methylpyridin-3-amine (Int-72e)

To a stirred solution of (E)-5-(4-((tert-butyldimethylsilyl)oxy)but-1-en-1-yl)-4-methyl-3-nitro-2-(prop-1-en-2-yl)pyridine (7.00 g, 19.3 mmol) in MeOH (100 mL) was added 10% Pd—C (2.06 g, 19.3 mmol, 10% wt %) under $N_2$ atmosphere, and the resulting mixture was stirred at 25° C. for 16 h under Hz atmosphere (15 psi). The reaction mixture was filtered and the filtrate was concentrated in vacuo. The residue was purified by column chromatography on silica gel (Pet. ether/EtOAc=3/1) to give 5-(4-((tert-butyldimethylsilyl)oxy)butyl)-2-isopropyl-4-methylpyridin-3-amine (Int-72e). ¹H NMR (400 MHz, CDCl₃): δ 7.85 (s, 1H), 3.65-3.54 (m, 4H), 3.07-2.88 (m, 1H), 2.57 (br t, J=7.4 Hz, 2H), 2.09 (s, 3H), 1.61-1.54 (m, 4H), 1.29 (d, J=7.0 Hz, 6H), 0.87 (s, 9H), 0.03 (s, 6H).

Step F: N-((5-(4-((tert-butyldimethylsilyl)oxy)butyl)-2-isopropyl-4-methylpyridin-3-yl)carbamoyl)-2,6-dichloro-5-fluoronicotinamide (Int-72f)

To a stirred solution of 2,6-dichloro-5-fluoronicotinamide (3.00 g, 14.4 mmol) in THF (40 mL) was added oxalyl dichloride (1.26 mL, 14.4 mmol) at 20° C., and the mixture was stirred at 65° C. for 30 min under $N_2$ atmosphere. Then the mixture was cooled to 20° C., and concentrated in vacuo. The residue was dissolved in THF (50 mL) and 5-(4-((tert-butyldimethylsilyl)oxy)butyl)-2-isopropyl-4-methylpyridin-3-amine (Int-72e. 4.83 g, 14.4 mmol) in THF (40 mL) was added. The resulting mixture was stirred at 20° C. for 1 h. The reaction mixture was quenched with NH₄Cl (20 mL), and extracted with ethyl acetate (2×100 mL). The combined organic layers were washed with brine (50 mL), dried over $Na_2SO_4$, filtered and the solvent was evaporated under reduced pressure. The residue was purified by flash silica gel chromatography (0~30% Pet. ether/EtOAc) to give N-((5-(4-((tert-butyldimethylsilyl)oxy)butyl)-2-isopropyl-4-methylpyridin-3-yl)carbamoyl)-2,6-dichloro-5-fluoronicotinamide (Int-72f). ¹H NMR (400 MHz, CDCl₃): δ 9.70 (s, 1H), 9.44 (br s, 1H), 8.33 (s, 1H), 8.01 (d, J=7.0 Hz, 1H), 3.66 (t, J=5.7 Hz, 2H), 3.22 (quin, J=6.8 Hz, 1H), 2.64 (br t, J=7.2 Hz, 2H), 2.23 (s, 3H), 1.66-1.59 (m, 4H), 1.25 (d, J=6.7 Hz, 6H), 0.89 (s, 9H), 0.05 (s, 6H).

Step G: 1-(5-(4-((tert-butyldimethylsilyl)oxy)butyl-2-isopropyl-4-methylpyridin-3-yl-7-chloro-6-fluoro-pyrido[2,3-d]pyrimidine-2,4(1H,3H)-dione (Int-72g)

To a stirred solution of N-((5-(4-((tert-butyldimethylsilyl)oxy)butyl)-2-isopropyl-4-methylpyridin-3-yl)carbamoyl)-2,6-dichloro-5-fluoronicotinamide (Int-72f, 5.00 g, 8.75 mmol) in THF (500 mL) was added potassium bis(trimethylsilyl)amide (17.5 mL, 17.5 mmol) (1 M THF solution) at 0° C., and the mixture was stirred at 20° C. for 10 min under a $N_2$ atmosphere. The reaction mixture was quenched with saturated NH₄Cl solution (10 mL), and extracted with ethyl acetate (2×100 mL). The combined organic layers were washed with brine (10 mL), dried over $Na_2SO_4$, filtered and the solvent was evaporated under reduced pressure. The residue was purified by silica gel chromatography (DCM/MeOH=10/1) to give 1-(5-(4-((tert-butyldimethylsilyl)oxy)butyl)-2-isopropyl-4-methylpyridin-3-yl)-7-chloro-6-fluoropyrido[2,3-d]pyrimidine-2,4(1H,3H)-dione (Int-72g). ¹H NMR (400 MHz, CDCl₃): δ 8.50 (s, 2H), 3.66 (t, J=5.9 Hz, 2H), 2.74-2.63 (m, 3H), 2.00 (s, 3H), 1.71-1.62 (m, 4H), 1.21 (d, J=6.7 Hz, 3H), 1.11 (d, J=6.7 Hz, 3H), 0.89 (s, 9H), 0.05 (s, 6H).

Step H: tert-butyl (2R,5S)-4-(1-(5-(4-((tert-butyldimethylsilyl)oxy)butyl-2-isopropyl-4-methylpyridin-3-yl-7-chloro-6-fluoro-2-oxo-1,2-dihydropyrido[2,3-d]pyrimidin-4-yl-2,5-dimethylpiperazine-1-carboxylate (Int-72h)

To a stirred solution of 1-(5-(4-((tert-butyldimethylsilyl)oxy)butyl)-2-isopropyl-4-methylpyridin-3-yl)-7-chloro-6-fluoropyrido[2,3-d]pyrimidine-2,4(1H,3H)-dione (Int-72g, 1.15 g, 2.15 mmol) in MeCN (20 mL) were added DIEA (1.88 mL, 10.8 mmol) and POCl₃ (1.40 mL, 15.0 mmol), and the resulting mixture was stirred at 80° C. for 2 h. The reaction mixture was concentrated in vacuo. The residue obtained was dissolved in MeCN (20 mL). DIEA (1.13 mL, 6.45 mmol) and (2R,5S)-tert-butyl 2,5-dimethylpiperazine-1-carboxylate (0.507 g, 2.37 mmol) were added into the reaction mixture at 25° C., and the mixture was stirred at 25° C. for 1 h. The reaction mixture was concentrated in vacuo, and the residue was purified by flash silica gel chromatography (Pet. ether/EtOAc=1/1) to give tert-butyl (2R,5S)-4-(1-(5-(4-((tert-butyldimethylsilyl)oxy)butyl)-2-isopropyl-4-methylpyridin-3-yl)-7-chloro-6-fluoro-2-oxo-1,2-dihydropyrido[2,3-d]pyrimidin-4-yl)-2,5-dimethylpiperazine-1-carboxylate (Int-72h). ¹H NMR (400 MHz, CDCl₃): δ 8.44 (d, J=2.7 Hz, 1H), 7.77 (br d, J=7.4 Hz, 1H), 5.10-4.74 (m, 1H), 4.61-4.27 (m, 1H), 4.05-3.70 (m, 3H), 3.65 (br t, J=5.5 Hz, 2H), 3.60-3.38 (m, 1H), 2.70-2.62 (m, 2H), 2.61-2.43 (m, 1H), 1.93 (d, J=6.3 Hz, 3H), 1.73-1.62 (m, 4H), 1.49 (s, 9H), 1.40 (br s, 3H), 1.24-1.16 (m, 6H), 1.12-1.02 (m, 3H), 0.88 (s, 9H), 0.04 (s, 6H).

Example 73: 2-[(2S,5R)-2,5-dimethyl-4-(prop-2-enoyl)piperazin-1-yl]-20-fluoro-6-(propan-2-yl)-17-(trifluoromethyl-11,12-dihydro-4H-1,18-(ethanediylidene)pyrido[4,3-e]pyrimido[1,6-g][1,4,7,9]benzodioxadiazacyclododecin-4-one
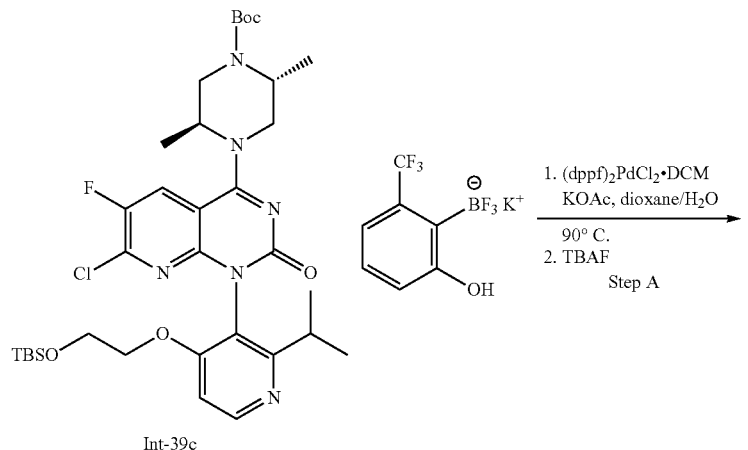
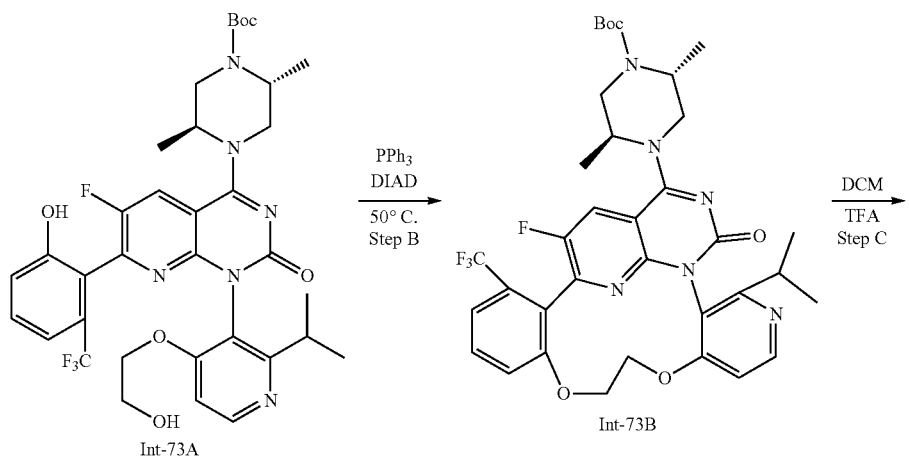
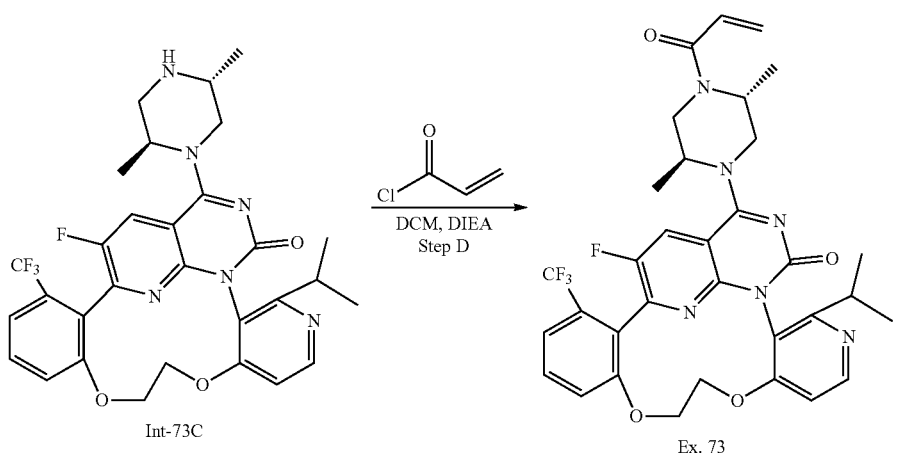

Step A: tert-butyl (2R,5S)-4-(6-fluoro-7-(2-hydroxy-6-(trifluoromethyl)phenyl-1-(4(2-hydroxyethoxy)-2-isopropylpyridin-3-yl)-2-oxo-1,2-dihydropyrido[2,3-d]pyrimidin-4-yl-2,5-dimethylpiperazine-1-carboxylate (Int-73A)

To a flask containing tert-butyl (2R,5S)-4-(1-(4-(2-((tert-butyldimethylsilyl)oxy)ethoxy)-2-isopropylpyridin-3-yl)-7-chloro-6-fluoro-2-oxo-1,2-dihydropyrido[2,3-d]pyrimidin-4-yl)-2,5-dimethylpiperazine-1-carboxylate (0.10 g, 0.14 mmol) was added dioxane (1.5 mL). Potassium trifluoro(2-hydroxy-6-(trifluoromethyl)phenyl)borate (Int-30, 57 mg, 0.21 mmol) and potassium acetate (56 mg, 0.57 mmol) were added followed by water (0.25 mL). Argon was bubbled through the mixture for 3 minutes. 1,1'-Bis(diphenylphosphino)ferrocene-palladium(II)dichloride dichloromethane complex (12 mg, 0.014 mmol) was added and argon was bubbled through the mixture. The mixture was heated to 90° C. for 18 hours and was then allowed to cool to room temperature. The mixture was diluted with ethyl acetate and saturated aqueous sodium bicarbonate. The organic layer was separated, dried over magnesium sulfate, filtered and concentrated under reduced pressure. To the resulting mixture was added THF (1.5 mL) followed by TBAF (1.0 M in THF, 0.35 mL, 0.35 mmol). The mixture was heated to 50° C. for 1 hour. After 1 hour, the mixture was allowed to cool to room temperature. The mixture was diluted with ethyl acetate and water. The organic layer was separated, dried over magnesium sulfate, filtered and concentrated under reduced pressure. The resulting residue was purified by column chromatography (0-100% (3:1 ethyl acetate:ethanol) gradient in hexanes) to afford tert-butyl (2R,5S)-4-(6-fluoro-7-(2-hydroxy-6-(trifluoromethyl)phenyl)-1-(4-(2-hydroxyethoxy)-2-isopropylpyridin-3-yl)-2-oxo-1,2-dihydropyrido[2,3-d]pyrimidin-4-yl)-2,5-dimethylpiperazine-1-carboxylate (Int-73a). MS (ESI) m/z 717 [M+H], Step B: Int-73b To a flask containing tert-butyl (2R,5S)-4-(6-fluoro-7-(2-hydroxy-6-(trifluoromethyl)phenyl)-1-(4-(2-hydroxyethoxy)-2-isopropylpyridin-3-yl)-2-oxo-1,2-dihydropyrido[2,3-d]pyrimidin-4-yl)-2,5-dimethylpiperazine-1-carboxylate (Int-73a, 69 mg, 0.096 mmol) and THF (3.9 mL) was added triphenylphosphine (63 mg, 0.24 mmol) and then diisopropyl azodicarboxylate (37 μL, 0.19 mmol). The mixture was then heated to 50° C. for 3 hours. After 3 hours, the mixture was allowed to cool to room temperature. The mixture was then concentrated under reduced pressure. The resulting oil was purified by column chromatography (0-100% gradient 3:1 ethyl acetate:ethanol gradient in hexanes) to afford Int-73b. MS (ESI) m/z 699 [M+H]+.

Step C: Int-73c

To a flask containing Int-73b (33 mg, 0.047 mmol) was added dichloromethane (1.5 mL) and then TFA (0.50 mL). The mixture was heated to 45° C. for one hour. After one hour, the mixture was concentrated under reduced pressure and taken on to the next step without further purification or characterization. MS (ESI) m/z 599 [M+H]+.

Step D: 2-[(2S,5R)-2,5-dimethyl-4-(prop-2-enoyl)piperazin-1-yl]-20-fluoro-6-(propan-2-yl)-17-(trifluoromethyl)-11,12-dihydro-4H-1,18-(ethanediylidene)pyrido[4,3-e]pyrimido[1,6-g][1,4,7,9]benzodioxadiazacyclododecin-4-one (Ex. 73)

To a flask containing Int-73c (28 mg, 0.047 mmol) was added dichloromethane (1.5 mL) followed by Hunig's base (31 μL, 0.18 mmol) and then acryloyl chloride (7.6 μL, 0.094 mmol). The mixture was stirred at room temperature for one hour. After one hour, the mixture was diluted with ethyl acetate and water. The organic layer was separated, dried over magnesium sulfate, filtered and concentrated under reduced pressure. The resulting mixture was purified by column chromatography (0-100% (3:1 ethyl acetate:ethanol) gradient in hexanes to afford 2-[(2S,5R)-2,5-dimethyl-4-(prop-2-enoyl)piperazin-1-yl]-20-fluoro-6-(propan-2-yl)-17-(trifluoromethyl)-11,12-dihydro-4H-1,18-(ethanediylidene)pyrido[4,3-e]pyrimido[1,6-g][1,4,7,9]benzodioxadiazacyclododecin-4-one (Ex. 73). MS (ESI) m/z 653 [M+H]+. $^1$H NMR (500 MHz, DMSO-$d_6$) δ 8.37 (d, J=5.6 Hz, 1H), 8.04 (dd, J=20.4, 9.0 Hz, 1H), 7.72 (t, J=8.1 Hz, 1H), 7.64 (d, J=8.3 Hz, 1H), 7.52 (d, J=7.9 Hz, 1H), 7.08 (d, J=5.7 Hz, 1H), 6.84 (ddd, J=46.9, 16.6, 10.3 Hz, 1H), 6.19 (dd, J=16.7, 6.8 Hz, 1H), 5.76 (d, J=10.3 Hz, 1H), 4.87 (s, 0.5H), 4.81-4.48 (m, 5H), 4.25 (t, J=13.2 Hz, 1.5H), 3.94-3.84 (m, 1.5H), 3.70 (d, J=14.0 Hz, 0.5H), 3.53 (d, J=12.5 Hz, 1H), 3.07 (q, J=6.9 Hz, 1H), 1.52-1.35 (m, 6H), 1.19 (d, J=6.6 Hz, 3H), 0.92 (t, J=5.7 Hz, 3H).

Examples 74 through 92 were prepared in a similar manner to Example 73. In Examples 74, 76-78, 80-82, 90, and 91, DBAD was used instead of DIAD in Step B. For Example 85, 2-fluoroacrylic acid and T3P were used instead of acryloyl chloride for Step D.

| Ex. No. | Structure | Compound Name | [M + H]+ Found |
|---|---|---|---|
| 74 | 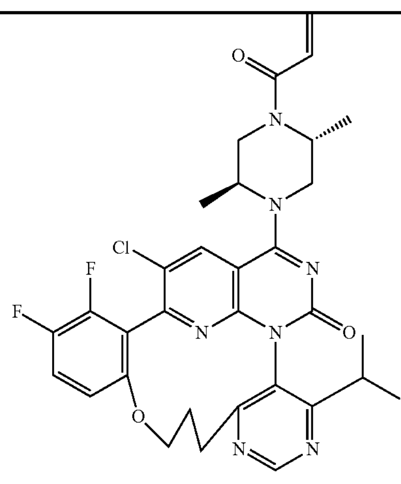 | 20-chloro-2-[(2S,5R)-2,5-dimethyl-4-(prop-2-enoyl)piperazin-1-yl]-16,17-difluoro-6-(propan-2-yl)-11,12-dihydro-4H,10H-1,18-ethenodipyrimido[4,5-e:1',6'-g][1,7,9]benzoxadiazacyclododecin-4-one | 636 |

-continued

| Ex. No. | Structure | Compound Name | [M + H]+ Found |
|---|---|---|---|
| 75 | 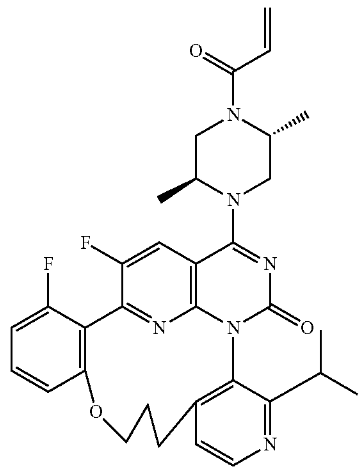 [SMILES: C=CC(=O)N1C[C@H](C)N(c2nc(=O)n3c4nc(c(F)cc24)-c2c(F)cccc2OCCCc2ccnc(C(C)C)c2-3)C[C@H]1C] | 2-[(2S,5R)-2,5-dimethyl-4-(prop-2-enoyl)piperazin-1-yl]-17,20-difluoro-6-(propan-2-yl)-11,12-dihydro-4H,10H-1,18-ethenopyrido[4,3-e]pyrimido[1,6-g][1,7,9]benzoxadiazacyclododecin-4-one | 601 |
| 76 | 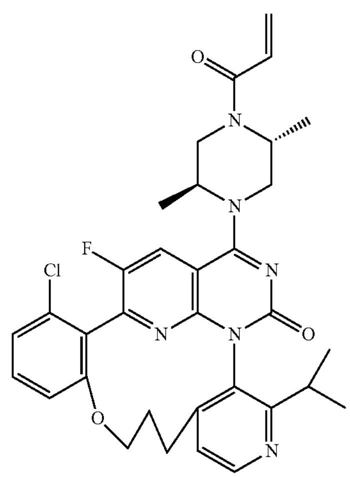 [SMILES: C=CC(=O)N1C[C@H](C)N(c2nc(=O)n3c4nc(c(F)cc24)-c2c(Cl)cccc2OCCCc2ccnc(C(C)C)c2-3)C[C@H]1C] | 17-chloro-2-[(2S,5R)-2,5-dimethyl-4-(prop-2-enoyl)piperazin-1-yl]-20-fluoro-6-(propan-2-yl)-11,12-dihydro-4H,10H-1,18-ethenopyrido[4,3-e]pyrimido[1,6-g][1,7,9]benzoxadiazacyclododecin-4-one | 617 |
| 77 | 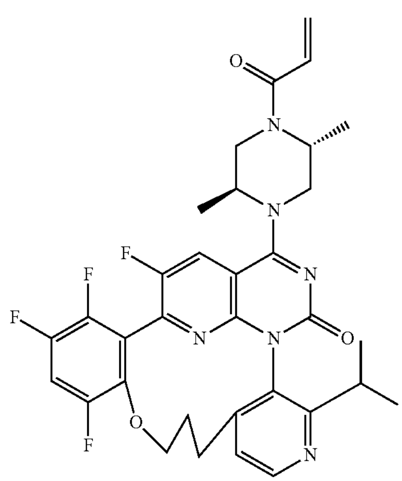 [SMILES: C=CC(=O)N1C[C@H](C)N(c2nc(=O)n3c4nc(c(F)cc24)-c2c(F)c(F)cc(F)c2OCCCc2ccnc(C(C)C)c2-3)C[C@H]1C] | 2-[(2S,5R)-2,5-dimethyl-4-(prop-2-enoyl)piperazin-1-yl]-14,16,17,20-tetrafluoro-6-(propan-2-yl)-11,12-dihydro-4H,10H-1,18-ethenopyrido[4,3-e]pyrimido[1,6-g][1,7,9]benzoxadiazacyclododecin-4-one | 637 |

-continued

| Ex. No. | Structure | Compound Name | [M + H]+ Found |
|---|---|---|---|
| 78 | 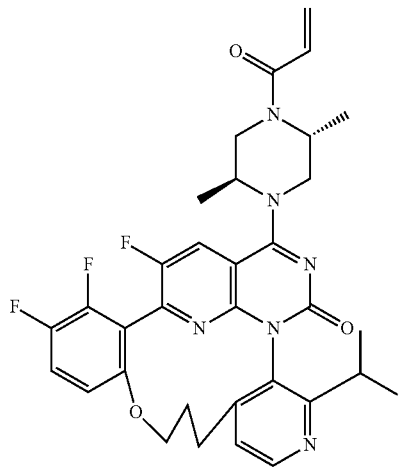 [SMILES: C=CC(=O)N1C[C@H](C)N(c2nc(=O)n3c4nc(c(F)cc24)-c2c(ccc(F)c2F)OCCCc2ccnc(C(C)C)c2-3)C[C@H]1C] | 2-[(2S,5R)-2,5-dimethyl-4-(prop-2-enoyl)piperazin-1-yl]-16,17,20-trifluoro-6-(propan-2-yl)-11,12-dihydro-4H,10H-1,18-ethenopyrido[4,3-e]pyrimido[1,6-g][1,7,9]benzoxadiazacyclododecin-4-one | 619 |
| 79 | 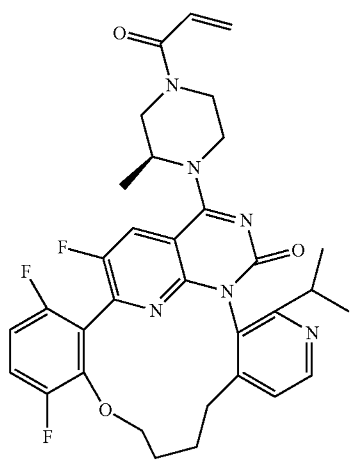 [SMILES: C=CC(=O)N1CCN(c2nc(=O)n3c4nc(c(F)cc24)-c2c(F)ccc(F)c2OCCCCc2ccnc(C(C)C)c2-3)[C@@H](C)C1] | 15,18,21-trifluoro-2-[(2S)-2-methyl-4-(prop-2-enoyl)piperazin-1-yl]-6-(propan-2-yl)-10,11,12,13-tetrahydro-4H-1,19-(ethanediylidene)pyrido[4,3-f]pyrimido[1,6-h][1,8,10]benzoxadiazacyclotridecin-4-one | 619 |
| 80 | 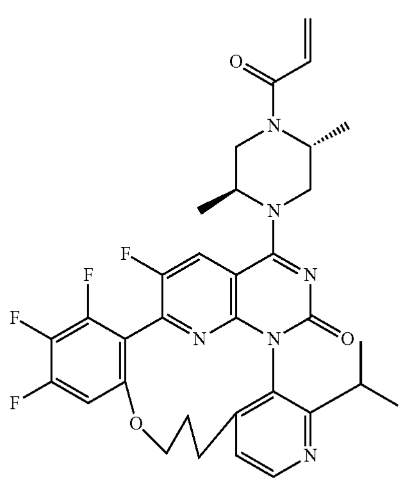 [SMILES: C=CC(=O)N1C[C@H](C)N(c2nc(=O)n3c4nc(c(F)cc24)-c2c(cc(F)c(F)c2F)OCCCc2ccnc(C(C)C)c2-3)C[C@H]1C] | 2-[(2S,5R)-2,5-dimethyl-4-(prop-2-enoyl)piperazin-1-yl]-15,16,17,20-tetrafluoro-6-(propan-2-yl)-11,12-dihydro-4H,10H-1,18-ethenopyrido[4,3-d]pyrimido[1,6-g][1,7,9]benzoxadiazacyclododecin-4-one | 637 |

| Ex. No. | Structure | Compound Name | [M + H]+ Found |
|---|---|---|---|
| 81 | 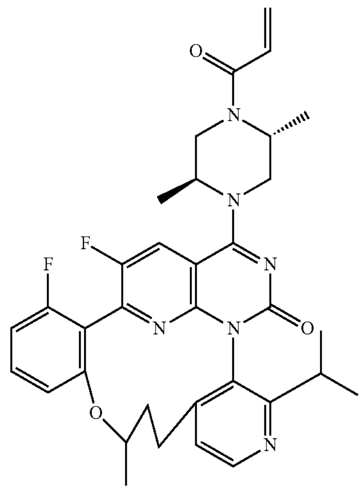 [SMILES: C=CC(=O)N1C[C@H](C)N(c2nc(=O)n3c4nc(c(F)cc24)-c2c(F)cccc2OC(C)CCc2ccnc(C(C)C)c2-3)C[C@H]1C] | 2-[(2S,5R)-2,5-dimethyl-4-(prop-2-enoyl)piperazin-1-yl]-17,20-difluoro-12-methyl-6-(propan-2-yl)-11,12-dihydro-4H,10H-1,18-ethenopyrido[4,3-e]pyrimido[1,6-g][1,7,9]benzoxadiazacyclododecin-4-one (Single Enantiomer, Absolute Configuration of Methyl Unknown) | 615 |
| 82 | 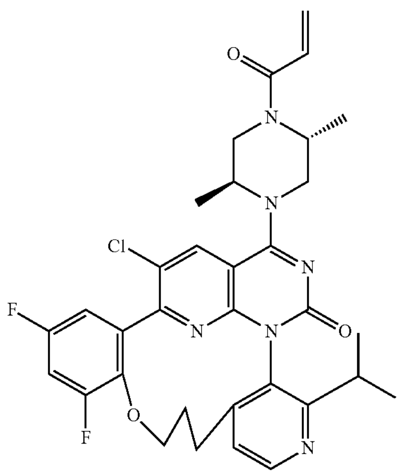 [SMILES: C=CC(=O)N1C[C@H](C)N(c2nc(=O)n3c4nc(c(Cl)cc24)-c2cc(F)cc(F)c2OCCCc2ccnc(C(C)C)c2-3)C[C@H]1C] | 20-chloro-2-[(2S,5R)-2,5-dimethyl-4-(prop-2-enoyl)piperazin-1-yl]-14,16-difluoro-6-(propan-2-yl)-11,12-dihydro-4H,10H-1,18-ethenopyrido[4,3-e]pyrimido[1,6-g][1,7,9]benzoxadiazacyclododecin-4-one | 635 |
| 83 | 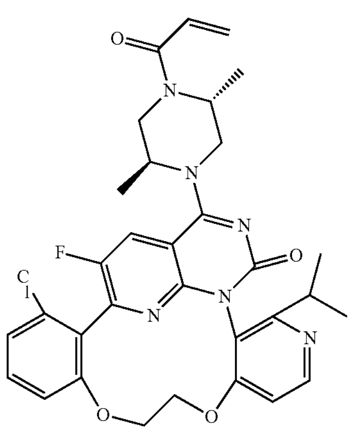 [SMILES: C=CC(=O)N1C[C@H](C)N(c2nc(=O)n3c4nc(c(F)cc24)-c2c(Cl)cccc2OCCOc2ccnc(C(C)C)c2-3)C[C@H]1C] | 17-chloro-2-[(2S,5R)-2,5-dimethyl-4-(prop-2-enoyl)piperazin-1-yl]-20-fluoro-6-(propan-2-yl)-11,12-dihydro-4H-1,18-(ethanediylidene)pyrido[4,3-e]pyrimido[1,6-g][1,4,7,9]benzodioxadiazacyclododecin-4-one | 619 |

-continued

| Ex. No. | Structure | Compound Name | [M + H]+ Found |
|---|---|---|---|
| 84 | 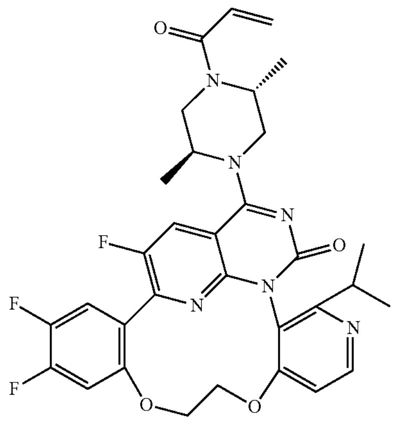 [SMILES: C=CC(=O)N1C[C@H](C)N(c2nc(=O)n3c4nc(c(F)cc24)-c2cc(F)c(F)cc2OCCOc2ccnc(C(C)C)c2-3)C[C@H]1C] | 2-[(2S,5R)-2,5-dimethyl-4-(prop-2-enoyl)piperazin-1-yl]-15,16,20-trifluoro-6-(propan-2-yl)-11,12-dihydro-4H-1,18-(ethanediylidene)pyrido[4,3-e]pyrimido[1,6-g][1,4,7,9]benzodioxadiazacyclododecin-4-one | 621 |
| 85 | 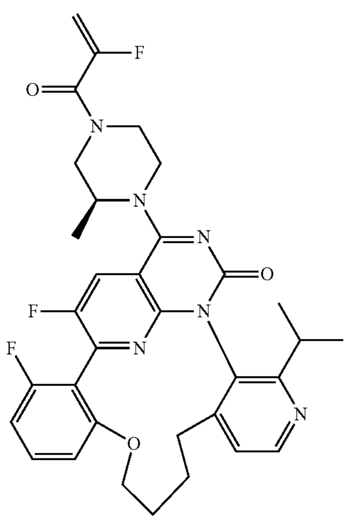 [SMILES: C=C(F)C(=O)N1CCN(c2nc(=O)n3c4nc(c(F)cc24)-c2c(F)cccc2OCCCCc2ccnc(C(C)C)c2-3)[C@@H](C)C1] | 18,21-difluoro-2-[(2S)-4-(2-fluoroprop-2-enoyl)-2-methylpiperazin-1-yl]-6-(propan-2-yl)-10,11,12,13-tetrahydro-4H-1,19-ethenopyrido[4,3-f]pyrimido[1,6-h][1,8,10]benzoxadiazacyclotridecin-4-one | 619 |
| 86 | 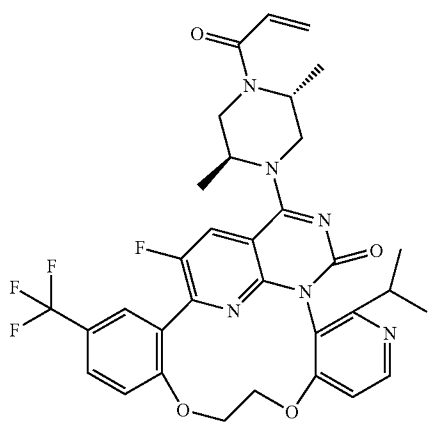 [SMILES: C=CC(=O)N1C[C@H](C)N(c2nc(=O)n3c4nc(c(F)cc24)-c2cc(C(F)(F)F)ccc2OCCOc2ccnc(C(C)C)c2-3)C[C@H]1C] | 2-[(2S,5R)-2,5-dimethyl-4-(prop-2-enoyl)piperazin-1-yl]-20-fluoro-6-(propan-2-yl)-16-(trifluoromethyl)-11,12-dihydro-4H-1,18-(ethanediylidene)pyrido[4,3-e]pyrimido[1,6-g][1,4,7,9]benzodioxadiazacyclododecin-4-one | 653 |

-continued

| Ex. No. | Structure | Compound Name | [M + H]+ Found |
|---|---|---|---|
| 87 | 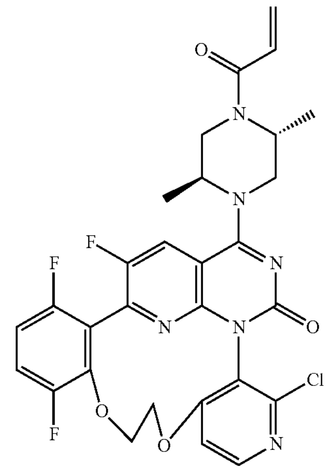 [SMILES: C=CC(=O)N1C[C@H](C)N(c2nc(=O)n3c4nc(c(F)cc24)-c2c(F)ccc(F)c2OCCOc2ccnc(Cl)c2-3)C[C@H]1C] | 6-chloro-2-[(2S,5R)-2,5-dimethyl-4-(prop-2-enoyl)piperazin-1-yl]-14,17,20-trifluoro-11,12-dihydro-4H-1,18-ethenopyrido[4,3-e]pyrimido[1,6-g][1,4,7,9]benzodioxadiazacyclododecin-4-one | 613 |
| 88 | 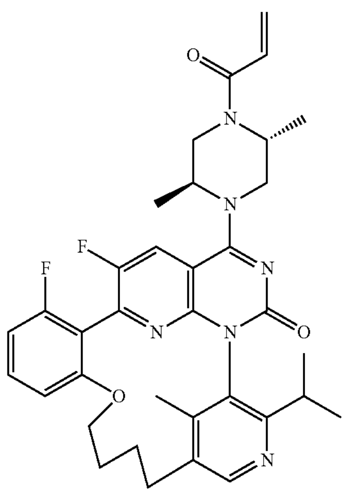 [SMILES: C=CC(=O)N1C[C@H](C)N(c2nc(=O)n3c4nc(c(F)cc24)-c2c(F)cccc2OCCCCc2cnc(C(C)C)c-3c2C)C[C@H]1C] | 2-[(2S,5R)-2,5-dimethyl-4-(prop-2-enoyl)piperazin-1-yl]-19,22-difluoro-24-methyl-7-(propan-2-yl)-11,12,13,14-tetrahydro-4H-1,20-etheno-6,10-(metheno)pyrimido[1,6-k][1,8,11,13]benzoxatriazacyclohexadecin-4-one | 629 |
| 89 | 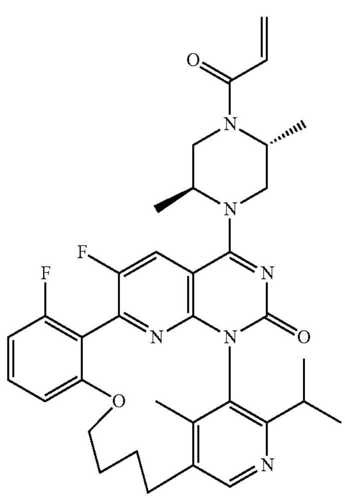 [SMILES: C=CC(=O)N1C[C@H](C)N(c2nc(=O)n3c4nc(c(F)cc24)-c2c(F)cccc2OCCCCc2cnc(C(C)C)c-3c2C)C[C@H]1C] | 2-[(2S,5R)-2,5-dimethyl-4-(prop-2-enoyl)piperazin-1-yl]-19,22-difluoro-24-methyl-7-(propan-2-yl)-11,12,13,14-tetrahydro-4H-1,20-etheno-6,10-(metheno)pyrimido[1,6-k][1,8,11,13]benzoxatriazacyclohexadecin-4-one (Atropisomer of Example 88) | 629 |

-continued

| Ex. No. | Structure | Compound Name | [M + H]+ Found |
|---|---|---|---|
| 90 | 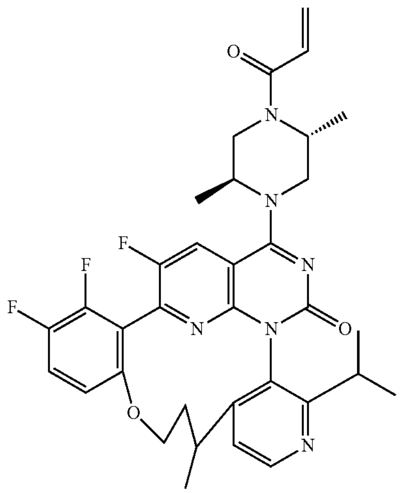 [SMILES: C=CC(=O)N1C[C@H](C)N(c2nc(=O)n3c4nc(c(F)cc24)-c2c(ccc(F)c2F)OCCC(C)c2ccnc(C(C)C)c2-3)C[C@H]1C] | 2-[(2S,5R)-2,5-dimethyl-4-(prop-2-enoyl)piperazin-1-yl]-16,17,20-trifluoro-10-methyl-6-(propan-2-yl)-11,12-dihydro-4H,10H-1,18-ethenopyrido[4,3-e]pyrimido[1,6-g][1,7,9]benzoxadiazacyclododecin-4-one (Diastereomer of Example 91) | 633 |
| 91 | 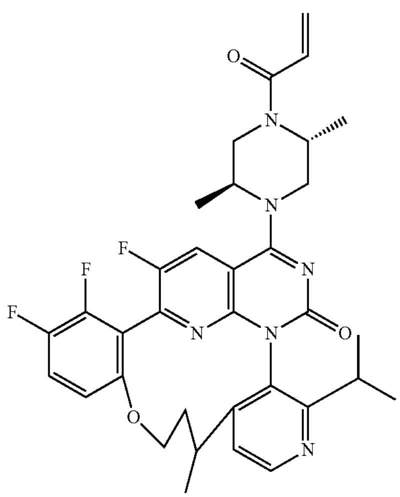 [SMILES: C=CC(=O)N1C[C@H](C)N(c2nc(=O)n3c4nc(c(F)cc24)-c2c(ccc(F)c2F)OCCC(C)c2ccnc(C(C)C)c2-3)C[C@H]1C] | 2-[(2S,5R)-2,5-dimethyl-4-(prop-2-enoyl)piperazin-1-yl]-16,17,20-trifluoro-10-methyl-6-(propan-2-yl)-11,12-dihydro-4H,10H-1,18-ethenopyrido[4,3-e]pyrimido[1,6-g][1,7,9]benzoxadiazacyclododecin-4-one (Diastereomer of Example 90) | 633 |
| 92 | 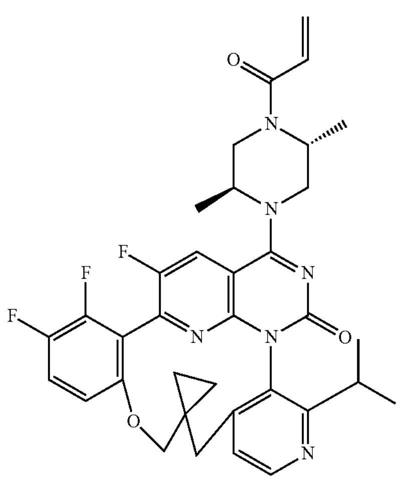 [SMILES: C=CC(=O)N1C[C@H](C)N(c2nc(=O)n3c4nc(c(F)cc24)-c2c(ccc(F)c2F)OCC2(CC2)Cc2ccnc(C(C)C)c2-3)C[C@H]1C] | 2'-[(2S,5R)-2,5-dimethyl-4-(prop-2-enoyl)piperazin-1-yl]-16',17',20'-trifluoro-6'-(propan-2-yl)-4'H,10'H,12'H-spiro[cyclopropane-1,11'-[13]oxa[3,5,7,19]tetraaza[1,18]ethenopyrido[4,3-e]pyrimido[1,6-g][1,7,9]benzoxadiazacyclododecin]-4'-one | 645 |

| Ex. No. | Structure | Compound Name | [M + H]+ Found |
|---|---|---|---|
| 93 | 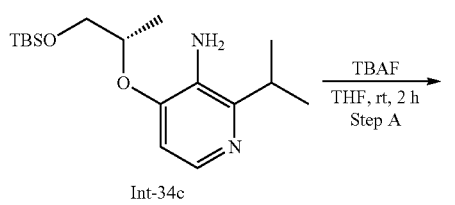 | 2-[(2S,5R)-2,5-dimethyl-4-(prop-2-enoyl)piperazin-1-yl]-14,17,20-trifluoro-6-(propan-2-yl)-11,12-dihydro-4H-1,18-(ethanediylidene)pyrido[4,3-e]pyrimido[1,6-g][1,4,7]benzodioxazacyclododecin-4-one | 620 |
Example 94: (11S)-2-[(2S,5R)-2,5-dimethyl-4-(prop-2-enoyl)piperazin-1-yl]-14,17,20-trifluoro-11-methyl-6-(propan-2-yl)-11,12-dihydro-4H-1,18-ethenopyrido[4,3-e]pyrimido[1,6-g][1,4,7,9]benzodioxadiazacyclododein-4-one
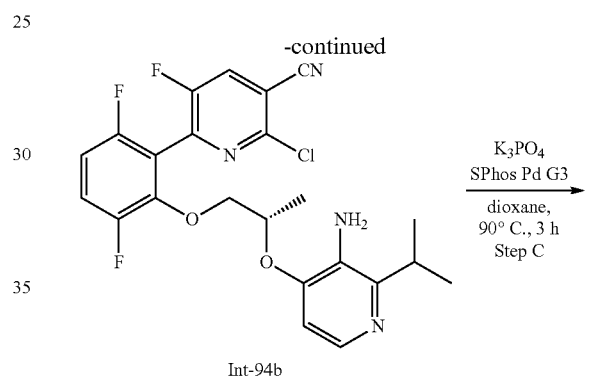
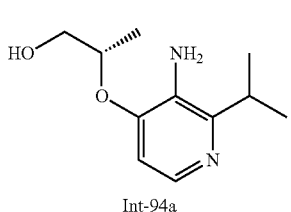
Int-94a
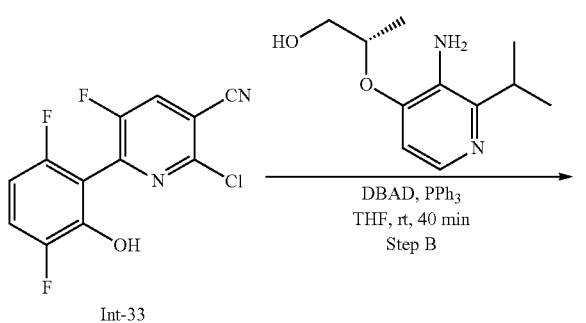
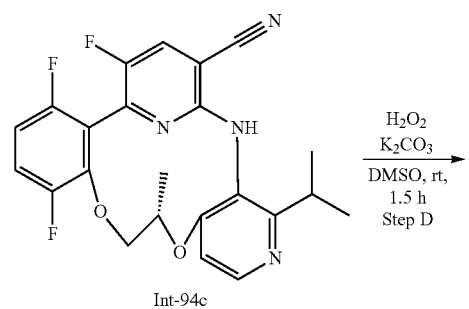
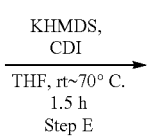
Int-94d

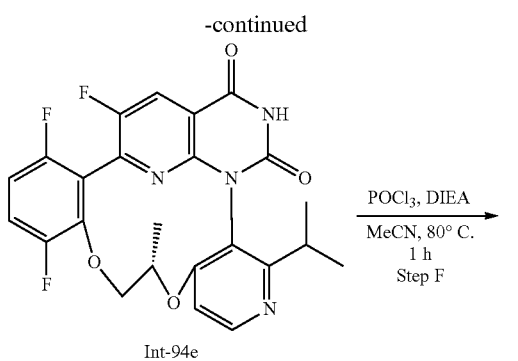

Int-94e

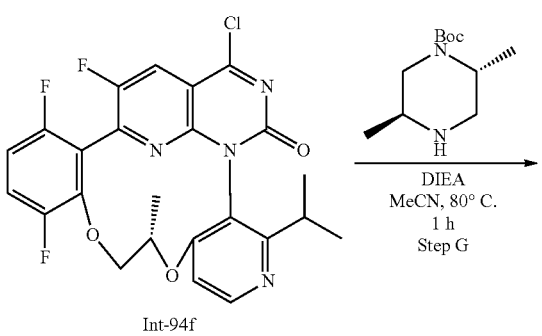

Int-94f

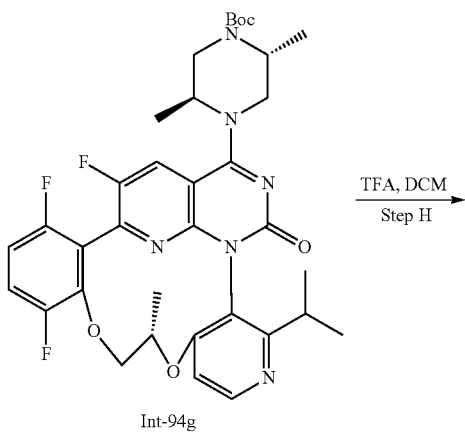

Int-94g

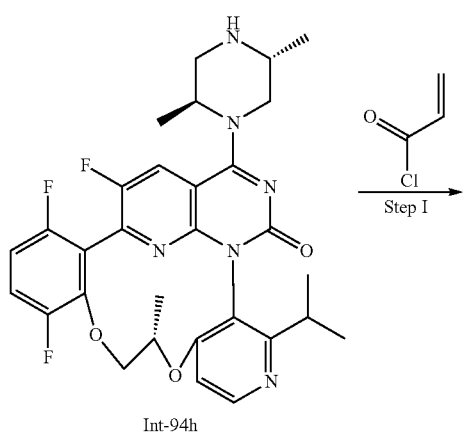

Int-94h

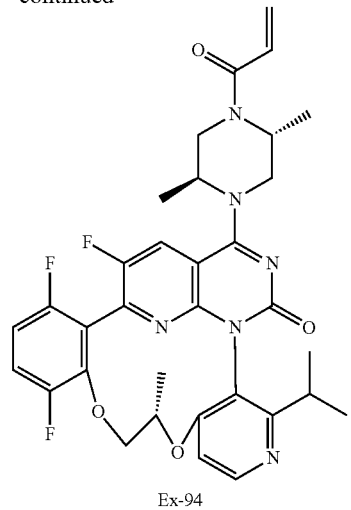

Ex-94

Step, A: (S)-2-((3-amino-2-isopropylpyridin-4-yl)oxy)propan-1-ol (Int-94a)

To a mixture of (S)-4-((1-((tert-butyldimethylsilyl)oxy)propan-2-yl)oxy)-2-isopropylpyridin-3-amine (1.0 g, 3.1 mmol) in THF (6.0 mL) was added TBAF (1.0 M in THF, 6.2 mL, 6.2 mmol) at room temperature. After 2 hours, the mixture was concentrated under reduced pressure. The resulting residue was purified by silica gel column chromatography (0-90%/ethyl acetate gradient in petroleum ether) to afford (S)-2-((3-amino-2-isopropylpyridin-4-yl)oxy)propan-1-ol (Int-94a) as a solid. MS (ESI): m/z [M+H]$^+$ 211. $^1$H NMR (400 MHz, methanol-d$_4$) δ 7.78 (d, J=5.6 Hz, 1H), 6.80 (d, J=5.6 Hz, 1H), 4.64-4.56 (m, 1H), 3.78-3.68 (m, 2H), 3.19 (s, 1H), 1.33 (d, J=6.4 Hz, 3H), 1.25 (dd, J=-1.2, 6.6 Hz, 6H).

Step B: 6-(2-((S)-2-((3-amino-2-isopropylpyridin-yl)oxy)propoxy)-3,6-difluorophenyl)-2-chloro-5-fluoronicotinonitrile (Int-94b)

To a mixture of 2-chloro-6-(3,6-difluoro-2-hydroxyphenyl)-5-fluoronicotinonitrile (0.70 g, 2.5 mmol) in THF (15 mL) was added (S)-2-((3-amino-2-isopropylpyridin-4-yl)oxy)propan-1-ol (Int-94a, 0.52 g, 2.5 mmol) and triphenylphosphine (1.3 g, 4.9 mmol) at room temperature under a nitrogen atmosphere. A mixture of di-tert-butyl azodicarboxylate (1.1 g, 4.9 mmol) in THF (5.0 mL) was added and the mixture was allowed to stir at room temperature for 40 minutes. After 40 minutes, the mixture was concentrated under reduced pressure. The resulting mixture was purifed by preparative HPLC (40% MCCN in water) to afford 6-(2-((S)-2-((3-amino-2-isopropylpyridin-4-yl)oxy)propoxy)-3,6-difluorophenyl)-2-chloro-5-fluoronicotinonitrile (Int-94b). MS (ESI): m/z [M+H]$^+$ 477. $^1$H NMR (500 MHz, methanol-d$_4$) δ 8.09 (br s, 1H), 7.73 (d, J=5.5 Hz, 1H), 7.45-7.39 (m, 1H), 7.07-7.01 (m, 1H), 6.60 (br s, 1H), 4.76-4.63 (m, 1H), 4.44 (br d, J=10.7 Hz, 1H), 4.26 (dd, J=7.3, 10.7 Hz, 1H), 3.23-3.16 (m, 1H), 1.34 (d, J=6.7 Hz, 3H), 1.23 (d, J=2.4 Hz, 3H), 1.22-1.20 (m, 3H).

Step C: Int-94c

To a mixture of 6-(2-((S)-2-((3-amino-2-isopropylpyridin-4-yl)oxy)propoxy)-3,6-difluorophenyl)-2-chloro-5- fluoronicotinonitrile (Int-94b, 0.29 g, 0.61 mmol) in 1,4-dioxane (20 mL) was added potassium phosphate, tribasic (0.20 g, 0.92 mmol) and SPhos Pd G3 (48 mg, 0.061 mmol) at room temperature in a glove box. The mixture was heated to 90° C. for 3 hours under a nitrogen atmosphere. After 3 hours, the mixture was allowed to cool to room temperature, filtered and the filtrate was concentrated under reduced pressure. The resulting residue was purifed by silica gel column chromatography (0-30% ethyl acetate gradient in petroleum ether) to afford Int-94c. MS (ESI): m/z [M+H]$^+$ 441. $^1$H NMR (400 MHz, CDCl$_3$) δ 8.36 (d, J=5.5 Hz, 1H), 7.64 (d, J=7.8 Hz, 1H), 7.11 (br d, J=6.7 Hz, 1H), 6.83 (dd, J=3.5, 8.2 Hz, 1H), 6.65 (d, J=5.9 Hz, 1H), 6.43 (s, 1H), 4.88-4.81 (m, 1H), 4.53-4.48 (m, 1H), 4.12 (s, 1H), 3.37 (s, 1H), 1.42 (d, J=6.3 Hz, 3H), 1.33 (d, J=6.7 Hz, 3H), 1.21 (d, J=6.7 Hz, 3H).

Step D: Int-94d

To a mixture of Int-94c (0.33 g, 0.75 mmol) in DMSO (5.0 mL) was added potassium carbonate (0.52 g, 3.8 mmol) and hydrogen peroxide (30% in water, 0.38 mL, 3.8 mmol) at room temperature. After 1.5 hours, the mixture was diluted with water (10 mL) and extracted with EtOAc (2×15 mL). The combined organic layers were washed with saturated aqueous sodium sulfite (10 mL), dried over sodium sulfate, filtered and the mixture was concentrated under reduced pressure. The resulting residue was purified by silica gel column chromatography (0-45% ethyl acetate gradient in petroleum ether) to afford Int-94d. MS (ESI): m/z 459 [M+H]$^+$. $^1$H NMR (500 MHz, methanol-d$_4$) δ 8.16 (d, J=5.8 Hz, 1H), 8.04 (d, J=9.2 Hz, 1H), 7.26-7.19 (m, 1H), 6.93 (d, J=6.1 Hz, 1H), 6.90 (d, J=3.4 Hz, 1H), 5.02-4.96 (m, 1H), 4.54-4.50 (m, 1H), 4.10-4.07 (m, 1H), 3.47-3.40 (m, 1H), 1.36 (d, J=6.4 Hz, 3H), 1.29 (d, J=6.7 Hz, 3H), 1.19 (d, J=7.0 Hz, 3H).

Step E: Int-94e

To a mixture of Int-94d (0.25 g, 0.55 mmol) in THF (5.0 mL) was added potassium bis(trimethylsilyl)amide (0.44 g, 2.2 mmol) at room temperature. After 30 minutes, 1,1'-carbonyldiimidazole (0.10 g, 0.65 mmol) was added. The resulting mixture was heated to 70° C. for 1 hour under a nitrogen atmosphere. After 1 hour, the mixture was allowed to cool to room temperature and was then directly purified by silica gel column chromatography (0-50% ethyl acetate in petroleum ether) to afford Int-94e. MS (ESI): m/z 485 [M+H]$^+$. $^1$H NMR (500 MHz, methanol-d$_4$) δ 8.42 (d, J=5.8 Hz, 1H), 8.36 (d, J=7.9 Hz, 1H), 7.30 (br dd, J=1.4, 5.0 Hz, 1H), 7.07 (d, J=5.8 Hz, 1H), 6.97 (dt, J=3.5, 8.8 Hz, 1H), 5.07-5.01 (m, 1H), 4.49 (br s, 1H), 4.16 (d, 0.1=11.3 Hz, 1H), 3.10-3.04 (m, 1H), 1.31 (dd, J=4.1, 6.6 Hz, 6H), 0.96 (d, J=6.7 Hz, 3H).

Step F: Int-94f

To a mixture of Int-94e (0.10 g, 0.21 mmol) in acetonitrile (3.0 mL) was added N,N-diisopropylethylamine (72 μL, 0.41 mmol) and phosphorous oxychloride (29 μL, 0.31 mmol) at room temperature. The mixture was then heated to 80° C. for 1 hour. After 1 hour, the mixture was allowed to cool to room temperature and was then concentrated under reduced pressure. The resulting crude Int-94f was taken on to the next step without further purification. MS (ESI): m/z 503 [M+H]$^+$.

Step G: Int-94g

To a mixture of Int-94f (0.10 g, 0.20 mmol) in acetonitrile (3.0 mL) was added N,N-diisopropylethylamine (0.15 mL, 0.86 mmol) and (2R,5S)-tert-butyl 2,5-dimethylpiperazine-1-carboxylate (64 mg, 0.30 mmol) at room temperature. The mixture was then heated to 80° C. for hour. After 1 hour, the mixture was allowed to cool to room temperature and then concentrated under reduced pressure. The resulting residue was purified by preparative TLC (on silica gel, with ethyl acetate as eluent) to afford Int-94g. MS (ESI): m/z 681 [M+H]$^+$. $^1$H NMR (500 MHz, methanol-d$_4$) δ 8.40 (d, J=6.1 Hz, 1H), 8.14 (d, J=8.9 Hz, 1H), 7.34-7.28 (m, 1H), 7.06 (d, J=5.8 Hz, 1H), 6.98 (br d, J=3.1 Hz, 1H), 5.04-4.98 (m, 1H), 4.84-4.73 (m, 1H), 4.72-4.61 (m, 1H), 4.60-4.44 (m, 2H), 4.20-4.15 (m, 1H), 3.89-3.84 (m, 1H), 3.72-3.64 (m, 1H), 3.50-3.36 (m, 1H), 3.06 (s, 1H), 1.59 (br d, J=6.4 Hz, 3H), 1.52 (br d, J=7.0 Hz, 9H), 1.38 (d, J=6.7 Hz, 3H), 1.29 (d, J=6.7 Hz, 3H), 1.24-1.22 (m, 3H), 1.02 (d, J=7.0 Hz, 3H).

Step H: Int-94h

To a mixture of Int-94g (50 mg, 0.073 mmol) in dichloromethane (2.0 mL) was added trifluoroacetic acid (1.0 mL, 13 mmol) at room temperature. After 1 hour, the mixture was concentrated under reduced pressure to afford crude Int-94h which was taken on to the next step without further purification or characterization. MS (ESI): m/z 581[M+H]$^+$.

Step I: (11S)-2-[(2S,5R)-2,5-dimethyl-4-(prop-2-enoyl)piperazin-1-yl]-14,17,20-trifluoro-11-methyl-6-(propan-2-yl)-11,12-dihydro-4H-1,18-etheno-pyrido[4,3-e]pyrimido[1,6-g][1,4,7,9]benzodioxadiazacyclododecin-4-one (Ex-94)

To a mixture of Int-94h (42 mg, 0.072 mmol) in dichloromethane (1.0 mL) was added N,N-diisopropylethylamine (50 μL, 0.29 mmol) and acryloyl chloride (20 μL, 0.25 mmol). After 1 hour, the mixture was concentrated under reduced pressure. The resulting residue was purified by reverse preparative HPLC (Column: Agela DuraShell C18 150*25 mm*5 um; Condition: water (0.04% NH$_3$·H$_2$O+10 mM NH$_4$HCO$_3$)-ACN; to afford (11S)-2-[(2S, 5R)-2,5-dimethyl-4-(prop-2-enoyl)piperazin-1-yl]-14,17, 20-trifluoro-11-methyl-6-(propan-2-yl)-11,12-dihydro-4H-1,18-ethenopyrido[4,3-e]pyrimido[1,6-g][1,4,7,9]benzodioxadiazacyclododecin-4-one (Ex-94). MS (ESI): m/z 635 [M+H]$^+$. $^1$H NMR (500 MHz, methanol-d$_4$) δ 8.41 (d, J=5.8 Hz, 1H), 8.15 (dd, J=8.7, 17.2 Hz, 1H), 7.34-7.28 (m, 1H), 7.07 (d, J=6.1 Hz, 1H), 6.97 (br d, J=3.4 Hz, 1H), 6.93-6.74 (m, 1H), 6.29 (ddd, J=1.7, 5.8, 16.6 Hz, 1H), 5.83 (t, J=11.1 Hz, 1H), 5.04-4.90 (m, 2H), 4.84-4.67 (m, 1H), 4.64-4.36 (m, 2H), 4.18 (d, J=11.0 Hz, 1H), 3.95-3.74 (m, 1H), 3.69 (br d, J=14.0 Hz, 1H), 3.37-3.32 (m, 1H), 3.10-3.03 (m, 1H), 1.58 (dd, J=7.0, 8.9 Hz, 3H), 1.51-1.42 (m, 3H), 1.29 (d, J=6.7 Hz, 3H), 1.24 (d, J=6.7 Hz, 3H), 1.02 (dd, J=4.9, 6.7 Hz, 3H).

Examples 95 and 96 were Prepared in a Similar Manner to Example 94 Using Appropriately-Substituted Pyridine Precursors

| Ex. No. | Structure | Compound Name | [M + H]+ Found |
|---|---|---|---|
| 95 | 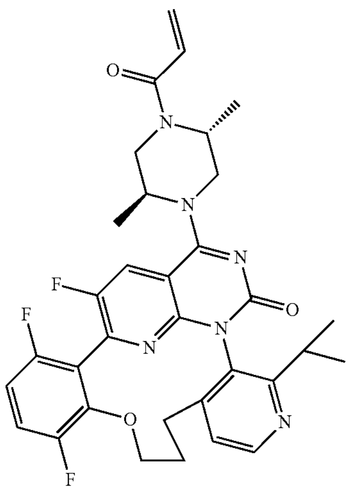 [SMILES: C=CC(=O)N1C[C@H](C)N(c2nc(=O)n3c4nc(c(F)cc24)-c2c(F)ccc(F)c2OCCCc2ccnc(C(C)C)c2-3)C[C@H]1C] | 2-[(2S,5R)-2,5-dimethyl-4-(prop-2-enoyl)piperazin-1-yl]-14,17,20-trifluoro-6-(propan-2-yl)-11,12-dihydro-4H,10H-1,18-(ethanediylidene)pyrido[4,3-e]pyrimido[1,6-g][1,7,9]benzoxadiazacyclododecin-4-one | 619 |
| 96 | 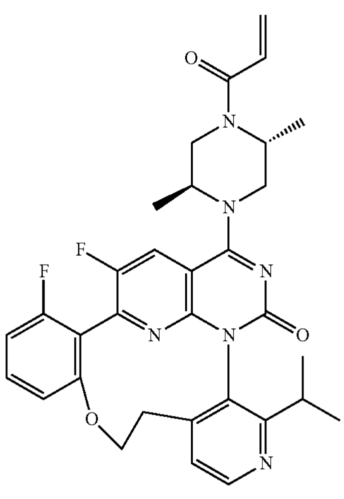 [SMILES: C=CC(=O)N1C[C@H](C)N(c2nc(=O)n3c4nc(c(F)cc24)-c2c(F)cccc2OCCc2ccnc(C(C)C)c2-3)C[C@H]1C] | 2-[(2S,5R)-2,5-dimethyl-4-(prop-2-enoyl)piperazin-1-yl]-16,19-difluoro-6-(propan-2-yl)-10,11-dihydro-4H-1,17-ethenopyrido[4,3-d]pyrimido[1,6-f][1,6,8]benzoxadiazacycloundecin-4-one | 587 |

215

Example 97: 12,12,17,18,21-pentafluoro-2-[(2S)-2-methyl-4-(prop-2-enoyl)piperazin-1-yl]-6-(propan-2-yl)-10,11,12,13-tetrahydro-4H-1,19-(ethanediylidene)pyrido[4,3-f]pyrimido[1,6-h][1,8,10]benzoxadiazacyclotridecin-4-one

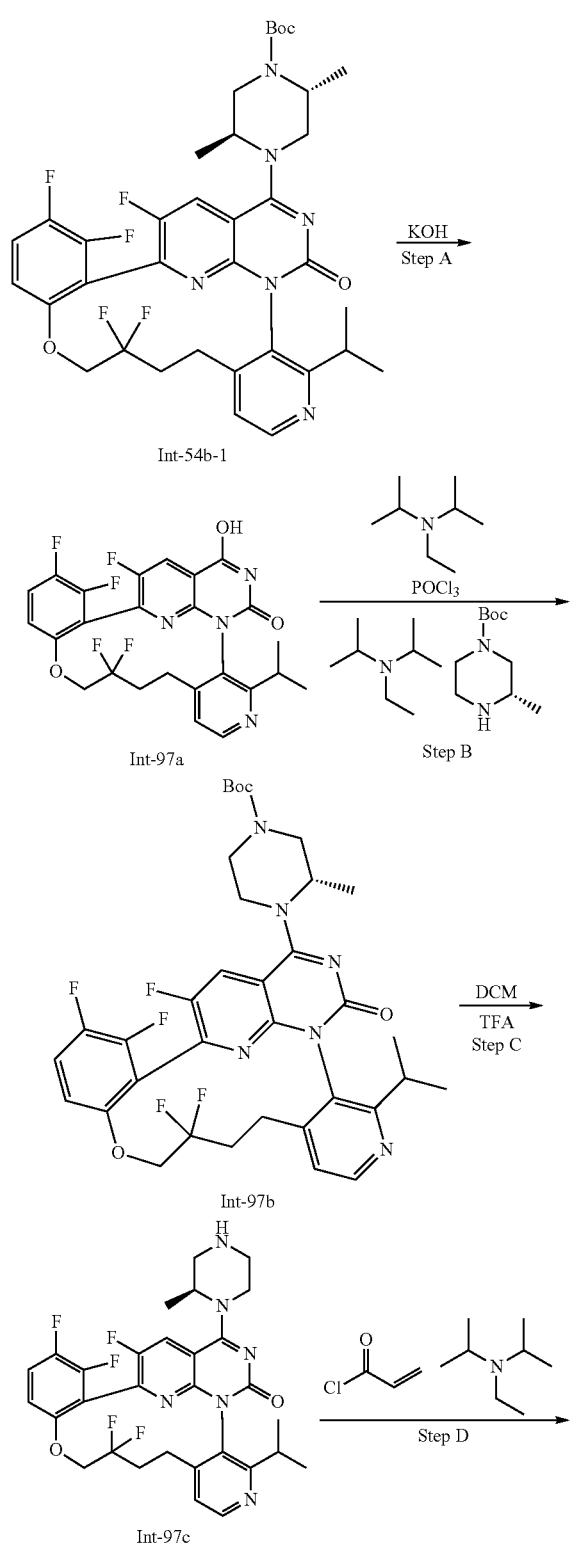

216

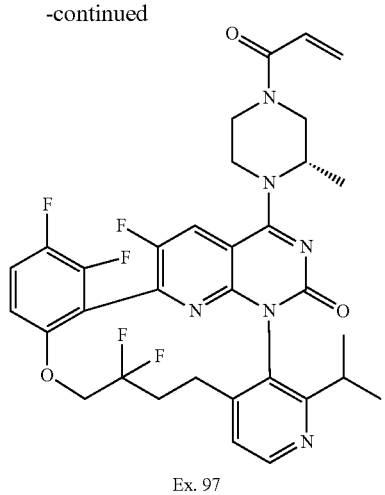

Ex. 97

Step A: Int-97a

To a flask containing Int-54b-1 (150 mg, 0.210 mmol) was added methanol (1.0 mL) and then potassium hydroxide (1.0 M in methanol, 0.63 mL, 0.63 mmol). The reaction vessel was sealed and the sealed reaction vessel was evacuated and backfilled with a balloon of nitrogen three times. The reaction mixture was heated to 40° C. for 16 hours. After 16 hours, the mixture was allowed to cool to room temperature and then quenched with saturated aqueous ammonium chloride (10 mL). The quenched product mixture was extracted three times with chloroform:isopropanol (3:1 mixture, 3×50 mL). The combined organic layers were dried over sodium sulfate, filtered and the filtrate was concentrated under reduced pressure to afford Int-97a. MS (ESI) m/z 519 [M+H]$^+$.

Step B: Int-97b

A flask containing Int-97a (40 mg, 0.077 mmol) was evacuated and backfilled with a balloon of nitrogen three times. Acetonitrile (0.40 mL), N-ethyl-N-isopropylpropan-2-amine (21 µL, 0.12 mmol), and phosphoryl trichloride (9.0 µL, 0.10 mmol) were added to the reaction vessel and the resulting mixture was heated to 80° C. for 1 h. After 1 hour, the mixture was allowed to cool to room temperature and then was concentrated to dryness under reduced pressure. The resulting mixture was dissolved in acetonitrile (0.40 mL). N-Ethyl-N-isopropylpropan-2-amine (69 µL, 0.39 mmol) was added to the reaction mixture followed by the addition of tert-butyl (S)-3-methylpiperazine-1-carboxylate (23 mg, 0.12 mmol). The resulting mixture was stirred for 1 h at room temperature. The product mixture was then diluted with ethyl acetate (50 mL). The diluted product mixture was washed three times with saturated aqueous sodium bicarbonate (3×10 mL). The organic layer was dried over sodium sulfate, filtered and the filtrate was concentrated under reduced pressure. The residue obtained was purified by flash column chromatography (0-100% (3:1 ethyl acetate:ethanol) in dichloromethane) to afford Int-97b. MS (ESI) m/z 701 [M+H]$^+$.

Step C: Int-97c

A vial containing Int-97b (39 mg, 0.056 mmol) was evacuated and backfilled with a balloon of nitrogen. Dichloromethane (0.60 mL) was added to the reaction vessel followed by the dropwise addition of trifluoroacetic acid (0.20 mL, 2.8 mmol). The reaction mixture was stirred for 1.5 h at 24° C. After 1.5 hours, the mixture was concentrated under reduced pressure. The residue obtained was azeotroped once with toluene (1 mL). The residue obtained (Int-97c) was used directly in the next step without purification or characterization.

Step D: 12,12,17,18,21-pentafluoro-2-[(2S)-2-methyl-4-(prop-2-enoyl)piperazin-1-yl]-6-(propan-2-yl)-10,11,12,13-tetrahydro-4H-1,19-(ethanediylidene)pyrido[4,3-f]pyrimido[1,6-h][1,8,10]benzoxadiazacyclotridecin-4-one (Ex. 97)

A flask containing Int-97c (53 mg, 0.056 mmol) and dichloromethane (0.30 mL) was cooled to 0° C. N-Ethyl-N-isopropylpropan-2-amine (50 µL, 0.28 mmol) and acryloyl chloride (7.0 µL, 0.084 mmol) were added into the reaction vessel. The reaction mixture was stirred for 1 hour at 0° C. After 1 hour, the product mixture was quenched with saturated aqueous ammonium bicarbonate (50 mL). The resulting mixture was extracted three times with ethyl acetate (3×100 mL). The combined organic layers were dried over sodium sulfate, filtered and then concentrated under reduced pressure. The resulting residue was purified by column chromatography (0-100% (3:1 ethyl acetate: ethanol) in hexanes) to afford 12,12,17,18,21-pentafluoro-2-[(2S)-2-methyl-4-(prop-2-enoyl)piperazin-1-yl]-6-(propan-2-yl)-10,11,12,13-tetrahydro-4H-1,19-(ethanediylidene)pyrido[4,3-f]pyrimido[1,6-h][1,8,10]benzoxadiazacyclotridecin-4-one (Ex. 97). MS (ESI) m/z 655 [M+H]$^+$. $^1$H NMR (500 MHz, DMSO-d$_6$) δ 8.46 (d, J=4.9 Hz, 1H), 8.40 (dd, J=20.8, 9.2 Hz, 1H), 7.62 (q, J=9.5 Hz, 1H), 7.24 (t, J=5.8 Hz, 2H), 6.92-6.82 (m, 1H), 6.30-6.13 (m, 1H), 5.78 (d, J=10.9 Hz, 1H), 4.96-4.83 (m, 1H), 4.49-4.41 (m, 1H), 4.41-4.35 (m, 1H), 4.31-4.19 (m, 2H), 4.19-4.12 (m, 1H), 4.08-3.97 (m, 1H), 3.91-3.77 (m, 1H), 3.74-3.61 (m, 2H), 3.29-3.22 (m, 1H), 2.75-2.61 (m, 2H), 1.46-1.32 (m, 3H), 1.06 (d, J=6.7 Hz, 3H), 0.84 (d, J=6.5 Hz, 3H).

Examples 98 Through 106 were Prepared in a Similar Manner to Example 97 Using Int-49d-1 and an Appropriately Substituted Piperazine

| Ex. No. | Structure | Compound Name | [M + H]$^+$ Found |
|---|---|---|---|
| 98 | 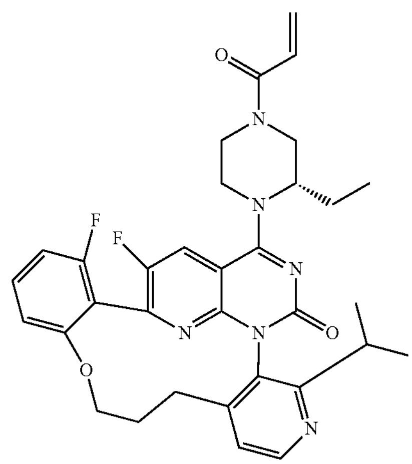 [SMILES: C=CC(=O)N1CCN(c2nc(=O)n3c4nc(c(F)cc24)-c2c(F)cccc2OCCCc2ccnc(C(C)C)c2-3)[C@@H](CC)C1] | 2-[(2S)-2-ethyl-4-(prop-2-enoyl)piperazin-1-yl]-17,20-difluoro-6-(propan-2-yl)-11,12-dihydro-4H,10H-1,18-(ethanediylidene)pyrido[4,3-e]pyrimido[1,6-g][1,7,9]benzoxadiazacyclododecin-4-one | 601 |
| 99 | 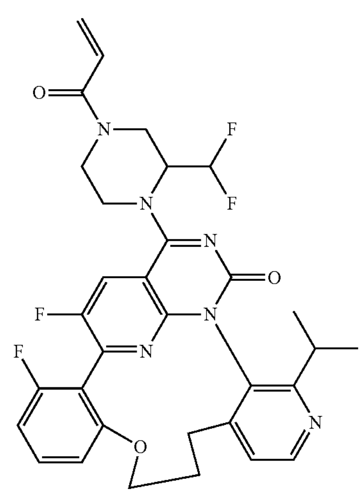 [SMILES: C=CC(=O)N1CCN(c2nc(=O)n3c4nc(c(F)cc24)-c2c(F)cccc2OCCCc2ccnc(C(C)C)c2-3)C(C(F)F)C1] | 2-[2-(difluoromethyl)-4-(prop-2-enoyl)piperazin-1-yl]-17,20-difluoro-6-(propan-2-yl)-11,12-dihydro-4H,10H-1,18-ethenopyrido[4,3-e]pyrimido[1,6-g][1,7,9]benzoxadiazacyclododecin-4-one | 623 |

| Ex. No. | Structure | Compound Name | [M + H]+ Found |
|---|---|---|---|
| 100 | 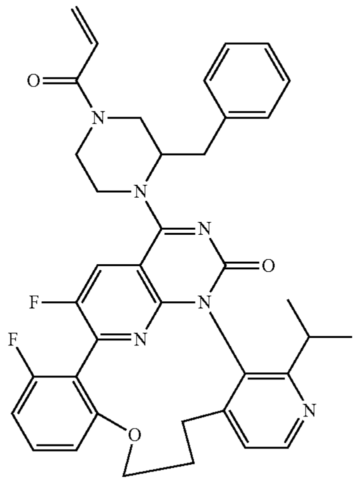 [SMILES: C=CC(=O)N1CCN(c2nc(=O)n3c4nc(c(F)cc24)-c2c(F)cccc2OCCCc2ccnc(C(C)C)c2-3)C(Cc2ccccc2)C1] | 2-[2-benzyl-4-(prop-2-enoyl)piperazin-1-yl]-17,20-difluoro-6-(propan-2-yl)-11,12-dihydro-4H,10H-1,18-ethenopyrido[4,3-e]pyrimido[1,6-g][1,7,9]benzoxadiazacyclododecin-4-one | 663 |
| 101 | 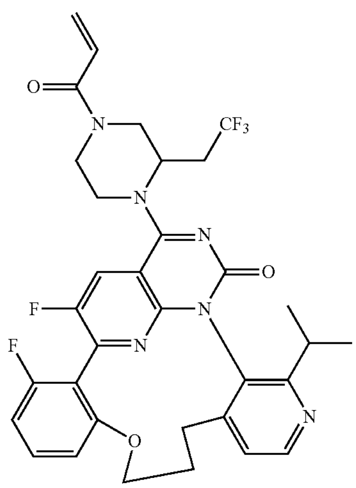 [SMILES: C=CC(=O)N1CCN(c2nc(=O)n3c4nc(c(F)cc24)-c2c(F)cccc2OCCCc2ccnc(C(C)C)c2-3)C(CC(F)(F)F)C1] | 17,20-difluoro-6-(propan-2-yl)-2-[4-(prop-2-enoyl)-2-(2,2,2-trifluoroethyl)piperazin-1-yl]-11,12-dihydro-4H,10H-1,18-(ethanediylidene)pyrido[4,3-e]pyrimido[1,6-g][1,7,9]benzoxadiazacyclododecin-4-one | 665 |
| 102 | 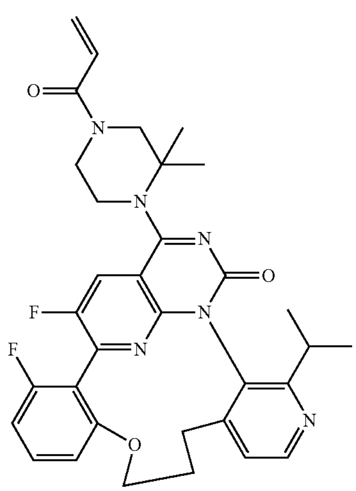 [SMILES: C=CC(=O)N1CCN(c2nc(=O)n3c4nc(c(F)cc24)-c2c(F)cccc2OCCCc2ccnc(C(C)C)c2-3)C(C)(C)C1] | 2-[2,2-dimethyl-4-(prop-2-enoyl)piperazin-1-yl]-17,20-difluoro-6-(propan-2-yl)-11,12-dihydro-4H,10H-1,18-ethenopyrido[4,3-e]pyrimido[1,6-g][1,7,9]benzoxadiazacyclododecin-4-one | 601 |

| Ex. No. | Structure | Compound Name | [M + H]+ Found |
|---|---|---|---|
| 103 | 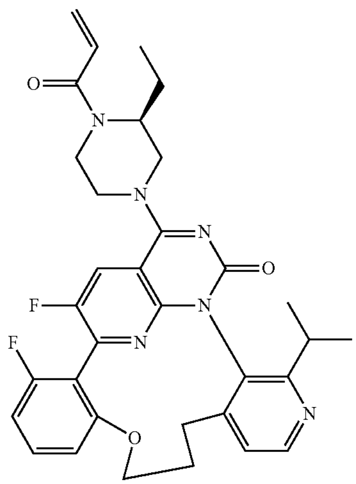 [SMILES: C=CC(=O)N1CCN(c2nc(=O)n3c4nc(c(F)cc24)-c2c(F)cccc2OCCCc2ccnc(C(C)C)c2-3)C[C@@H]1CC] | 2-[(3S)-3-ethyl-4-(prop-2-enoyl)piperazin-1-yl]-17,20-difluoro-6-(propan-2-yl)-11,12-dihydro-4H,10H-1,18-ethenopyrido[4,3-e]pyrimido[1,6-g][1,7,9]benzoxadiazacyclododecin-4-one | 601 |
| 104 | 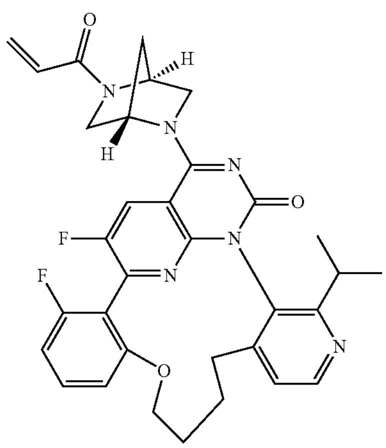 [SMILES: C=CC(=O)N1C[C@@H]2C[C@H]1CN2c1nc(=O)n2c3nc(c(F)cc13)-c1c(F)cccc1OCCCCc1ccnc(C(C)C)c1-2] | 18,21-difluoro-6-(propan-2-yl)-2-[(1S,4S)-5-(prop-2-enoyl)-2,5-diazabicyclo[2.2.1]heptan-2-yl]-10,11,12,13-tetrahydro-4H,1,19-ethenopyrido[4,3-f]pyrimido[1,6-h][1,8,10]benzoxadiazacyclotridecin-4-one | 599 |
| 105 | 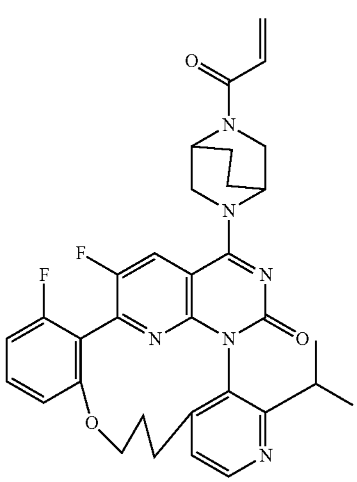 [SMILES: C=CC(=O)N1CC2CCC1CN2c1nc(=O)n2c3nc(c(F)cc13)-c1c(F)cccc1OCCCc1ccnc(C(C)C)c1-2] | 17,20-difluoro-6-(propan-2-yl)-2-[5-(prop-2-enoyl)-2,5-diazabicyclo[2.2.2]octan-2-yl]-11,12-dihydro-4H,10H-1,18-ethenopyrido[4,3-e]pyrimido[1,6-g][1,7,9]benzoxadiazacyclododecin-4-one | 599 |

| Ex. No. | Structure | Compound Name | [M + H]+ Found |
|---|---|---|---|
| 106 | 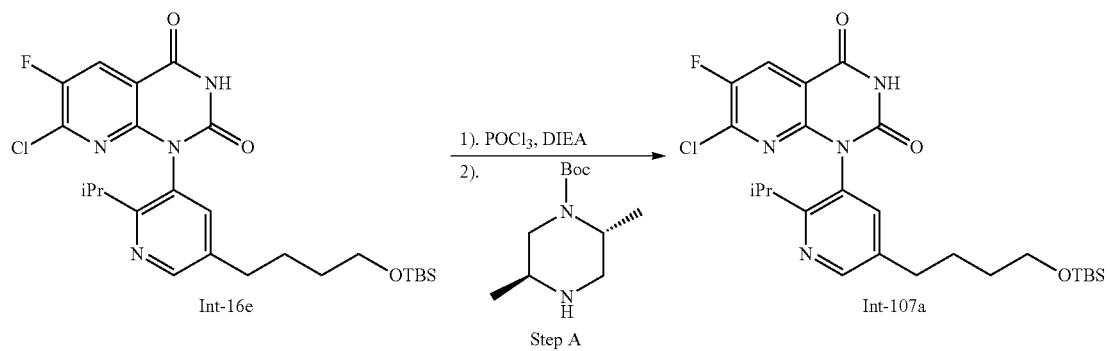 | 17,20-difluoro-4-oxo-6-(propan-2-yl)-2-[5-(prop-2-enoyl)-2,5-diazabicyclo[2.2.2]octan-2-yl]-11,12-dihydro-4H,10H-1,18-ethenopyrido[4,3-e]pyrimido[1,6-g][1,7,9]benzoxadiazacyclododecin-4-one | 599 |
Example 107: 2-[(2S,5R)-2,5-dimethyl-4-(prop-2-enoyl)piperazin-1-yl]-19,22-difluoro-6-(propan-2-yl)-10,11,12,13-tetrahydro-4H-1,20-(ethanediylidene)pyrido[4',3':12,13]pyrimido[1',6':1,2][1,3,7]triazacyclotridecino[5,6,7-hi]indazol-4-one
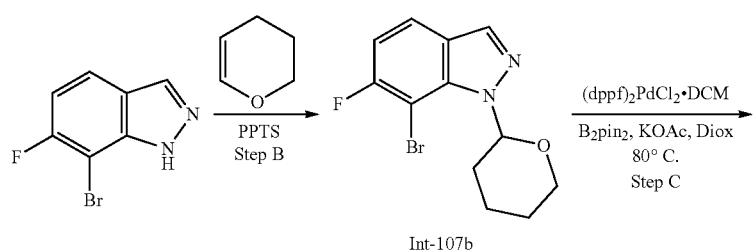

-continued
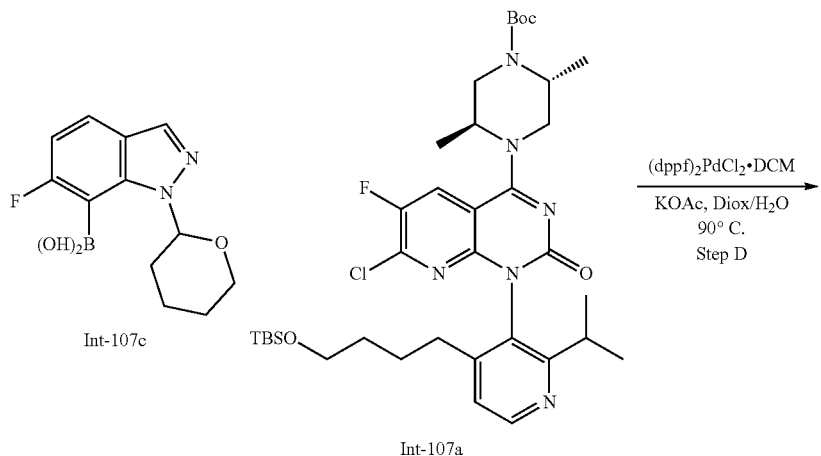
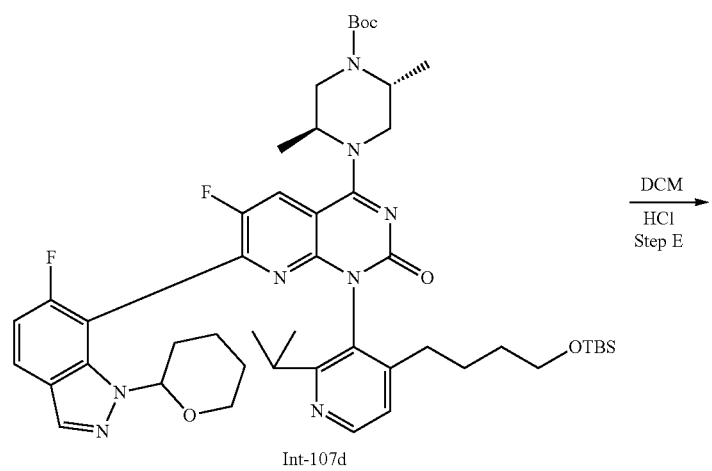
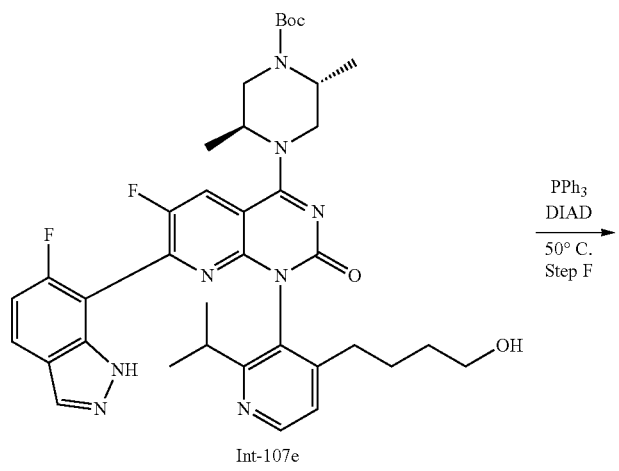

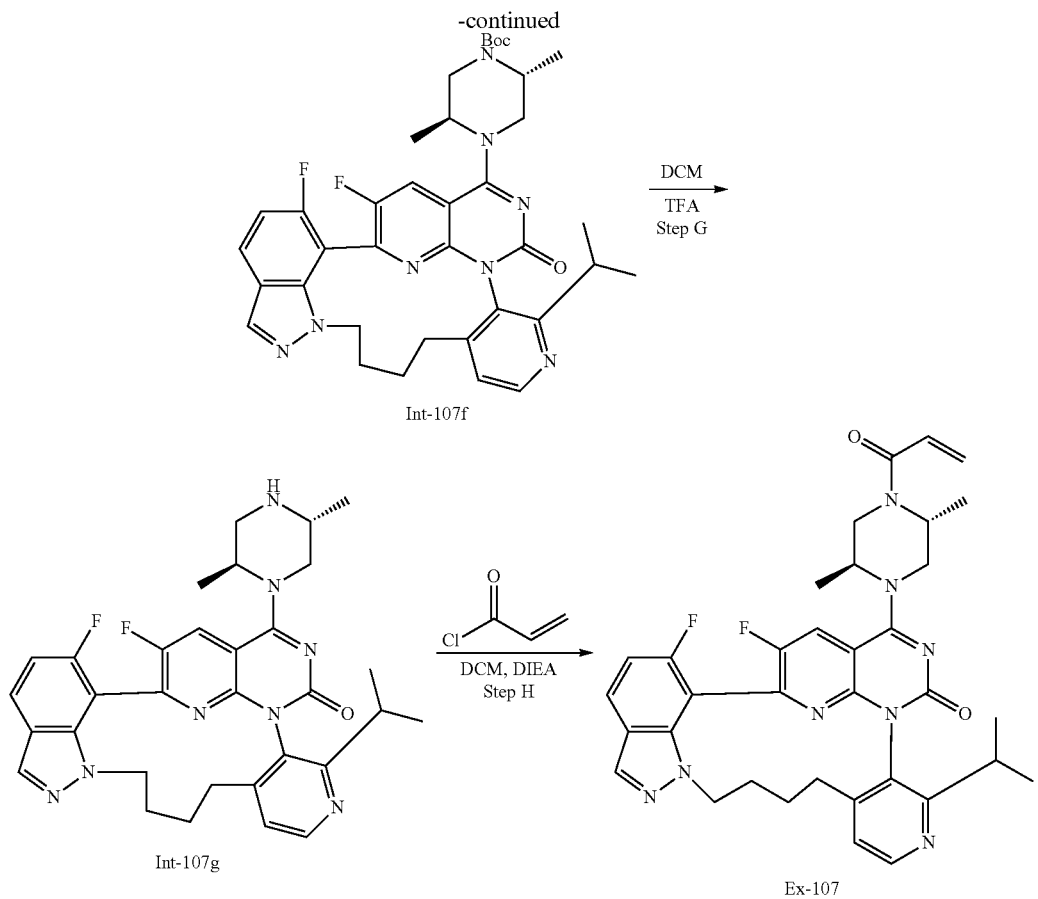

Step A: tert-butyl (2R,5S)-4-(1-(4-(4-(((tert-butyldimethylsilyl)oxy)butyl)-2-isopropylpyridin-3-yl)-7-chloro-6-fluoro-2-oxo-1,2-dihydropyrido[2,3-d]pyrimidin-4-yl)-2,5-dimethylpiperazine-1-carboxylate (Int-107a)

To a flask containing 1-(4-(4-(((tert-butyldimethylsilyl)oxy)butyl)-2-isopropylpyridin-3-yl)-7-chloro-6-fluoro-pyrido[2,3-d]pyrimidine-2,4(1H,3H)-dione (Int-16e, 0.16 mg, 0.30 mmol) in acetonitrile (2.00 ml) was added DIEA (0.10 mL, 0.60 mmol) and phosphorous oxychloride (0.034 mL, 0.36 mmol). The mixture was heated to 80° C. for one hour. After one hour, the mixture was allowed to cool to room temperature and then concentrated under reduced pressure. The resulting mixture was dried under vacuum for 15 minutes. To this mixture was added acetonitrile (2.0 mL) and the mixture was cooled to 0° C. DIEA (0.21 mL, 1.2 mmol) and then a mixture of tert-butyl (2R,5S)-2,5-dimethylpiperazine-1-carboxylate (77 mg, 0.362 mmol) in acetonitrile (0.50 mL) was added slowly. After 30 minutes, the mixture was quenched with cold water and then ethyl acetate was added. The organic layer was separated, dried over magnesium sulfate, filtered and then concentrated under reduced pressure. The resulting mixture was purified by silica gel column chromatography (hexanes and a 3:1 mixture of ethyl acetate:ethanol) to afford tert-butyl (2R,5S)-4-(1-(4-(4-(((tert-butyldimethylsilyl)oxy)butyl)-2-isopropylpyridin-3-yl)-7-chloro-6-fluoro-2-oxo-1,2-dihydropyrido[2,3-d]pyrimidin-4-yl)-2,5-dimethylpiperazine-1-carboxylate (Int-107a). MS (ESI) m/z 717 [M+H]+

Step B: 7-bromo-6-fluoro-1-(tetrahydro-2H-pyran-2-yl)-1H-indazole (Int-107b)

To a flask containing 7-bromo-6-fluoro-1H-indazole (1.0 g, 4.7 mmol) in dichloromethane (10 mL) was added pyridinium-toluenesulfonate (117 mg, 0.465 mmol) followed by 3,4-dihydro-2H-pyran (0.85 mL, 9.3 mmol). Acetonitrile (2 mL) was added and the mixture was allowed to stir for 48 hours. After 48 hours, the mixture was concentrated under reduced pressure. The resulting mixture was purified by silica gel column chromatography (0-100% (3:1 ethyl acetate:ethanol) in hexanes) to afford 7-bromo-6-fluoro-1-(tetrahydro-2H-pyran-2-yl)-1H-indazole (Int-107b). MS (ESI) m/z 299 [M+H]+.

Step C: (6-fluoro-1-(tetrahydro-2H-pyran-2-y)-1H-indazol-7-yl)boronic acid (Int-107c)

To a flask containing 7-bromo-6-fluoro-1-(tetrahydro-2H-pyran-2-yl)-1H-indazole (Int-107b, 0.50 g, 1.7 mmol) was added bis(pinacolato)diboron (0.64 g, 2.5 mmol), potassium acetate (0.49 g, 5.0 mmol) and [1,1'-bis(diphenylphosphino)ferrocene]dichloropalladium(II), complex with dichloromethane (72 mg, 0.089 mmol) and dioxane (8.3 mL). The vial purged with nitrogen via subsurface sparge and heated to 80° C. for 16 hours. After 16 h, the mixture was allowed to cool to room temperature and was then concentrated under reduced pressure. The resulting mixture was purified by silica gel column chromatography (0-100% (3:1 ethyl acetate:ethanol) in hexanes) to afford (6-fluoro-1-(tetrahydro-2H-pyran-2-yl)-1H-indazol-7-yl)boronic acid (Int-107c). MS (ESI) m/z 265 [M+H]$^+$.

Step D: tert-butyl (2R,5S)-4-(1-(4-(4-((tert-butyldimethylsilyloxy)butyl)-2-isopropylpyridin-3-yl)-6-fluoro-7-(6-fluoro-1-(tetrahydro-2H-pyran-2-yl)-1H-indazol-7-yl)-2-oxo-1,2-dihydropyrido[2,3-d]pyrimidin-4-yl)-2,5-dimethylpiperazine-1-carboxylate (Int-107d)

To a flask containing tert-butyl (2R,5S)-4-(1-(4-(4-((tert-butyldimethylsilyl)oxy)butyl)-2-isopropylpyridin-3-yl)-7-chloro-6-fluoro-2-oxo-1,2-dihydropyrido[2,3-d]pyrimidin-4-yl)-2,5-dimethylpiperazine-1-carboxylate (Int-107a, 70 mg, 0.098 mmol) was added (6-fluoro-1-(tetrahydro-2H-pyran-2-yl)-1H-indazol-7-yl)boronic acid (Int-107c, 31 mg, 0.12 mmol) 1,1'-bis(diphenylphosphino)ferrocene-palladiumdichloride dichloromethane complex (8.0 mg, 9.8 µmol), potassium acetate (38 mg, 0.39 mmol) and dioxane (0.80 mL) and water (0.20 mL). The vial was purged with nitrogen via subsurface sparge and then heated to 90° C. for 18 hours. After 18 hours, the mixture was diluted with ethyl acetate and water. The organic layer was separated, washed with brine, dried over magnesium sulfate, filtered and concentrated under reduced pressure. The resulting mixture was taken on to the next step without further purification or characterization.

Step E: tert-butyl (2R,5S)-4-(6-fluoro-7-(6-fluoro-1H-indazol-7-yl)-1-(4-(4-hydroxybutyl)-2-isopropylpyridin-3-yl)-2-oxo-1,2-dihydropyrido[2,3-d]pyrimidin-4-yl)-2,5-dimethylpiperazine-1-carboxylate (Int-107e)

To a flask containing tert-butyl (2R,5S)-4-(1-(4-(4-((tert-butyldimethylsilyl)oxy)butyl)-2-isopropylpyridin-3-yl)-6-fluoro-7-(6-fluoro-1-(tetrahydro-2H-pyran-2-yl)-1H-indazol-7-yl)-2-oxo-1,2-dihydropyrido[2,3-d]pyrimidin-4-yl)-2,5-dimethylpiperazine-1-carboxylate (Int-107d, 88 mg, 0.098 mmol) was added dichloromethane (0.5 mL) followed by HCl (4 M in water, 30 µL, 0.12 mmol). The mixture was allowed to stir at room temperature for 45 minutes. After 45 minutes, the mixture was concentrated under reduced pressure. To the mixture was added dichloromethane and the resulting mixture was concentrated under reduced pressure. This process was repeated two more times. The resulting oil was taken on to the next step without further purification or characterization.

Step F: Int-107f

To a flask containing tert-butyl (2R,5S)-4-(6-fluoro-7-(6-fluoro-1H-indazol-7-yl)-1-(4-(4-hydroxybutyl)-2-isopropylpyridin-3-yl)-2-oxo-1,2-dihydropyrido[2,3-d]pyrimidin-4-yl)-2,5-dimethylpiperazine-1-carboxylate (Int-107e, 29 mg, 0.041 mmol) was added tetrahydrofuran (1.7 mL), diisopropyl azodicarboxylate (16 µL, 0.083 mmol) and triphenylphosphine (27 mg, 0.10 mmol). The mixture was heated to 50° C. for 3 hours. After 3 hours, the mixture was allowed to cool to room temperature and the solvent was concentrated under reduced pressure. The resulting mixture was purified by silica gel column chromatography (0-100% (3:1 ethyl acetate:ethanol) in hexanes) to afford Int-107f. MS (ESI) m/z 685 [M+H]$^+$.

Step G: Int-107g

To a flask containing Int-107f (15 mg, 0.022 mmol) was added dichloromethane (1.0 mL) followed by trifluoroacetic acid (0.043 mL, 0.66 mmol). The mixture was allowed to stir at room temperature for one hour. After one hour, the mixture was concentrated under reduced pressure to afford Int-107g which was used without further purification or characterization.

Step H: 2-[(2S,5R)-2,5-dimethyl-4-(prop-2-enoyl) piperazin-1-yl]-19,22-difluoro-6-(propan-2-yl)-10, 11,12,13-tetrahydro-4H-1,20-(ethanediylidene) pyrido[4',3':12,13]pyrimido[1',6':1,2][1,3,7] triazacyclotridecino[5,6,7-hi]indazol-4-one (Ex. 107)

A flask containing crude Int-107g (15 mg, 0.026 mmol) and dichloromethane (1.7 ml) was cooled to 0° C. N,N-Diisopropylethylamine (18 µL, 0.10 mmol) and then acryloyl chloride (2.3 µL, 0.028 mmol) was added and the mixture was stirred for 30 minutes. After 30 minutes, the mixture was allowed to warm to room temperature. The mixture was diluted with ethyl acetate and brine. The organic layer was separated, dried over magnesium sulfate, filtered and concentrated under reduced pressure. The resulting residue was purified by silica gel column chromatography 0-10% MeOH/DCM to afford 2-[(2S,5R)-2,5-dimethyl-4-(prop-2-enoyl)piperazin-1-yl]-19,22-difluoro-6-(propan-2-yl)-10,11,12,13-tetrahydro-4H-1,20-(ethanediylidene) pyrido[4',3':12,13]pyrimido[1',6':1,2][1,3,7] triazacyclotridecino[5,6,7-hi]indazol-4-one (Ex. 107). MS (ESI) m/z 639 [M+H]$^+$. $^1$H NMR (500 MHz, DMSO-d$_6$) δ 8.43-8.36 (m, 2H), 8.17 (s, 1H), 7.98-7.93 (m, 1H), 7.21-7.13 (m, 2H), 6.92 (s, 1H), 6.31-5.99 (m, 2H), 5.85 (d, J=10.5 Hz, 1H), 4.99-4.82 (m, 1H), 4.47-4.32 (m, 1H), 4.21 (d, J=19.8 Hz, 1H), 4.06-3.98 (m, 1H), 3.91-3.84 (m, 1H), 3.84-3.76 (m, 1H), 2.81-2.72 (m, 1H), 2.50-2.46 (m, 2H), 1.85-1.74 (m, 1H), 1.74-1.61 (m, 1H), 1.39 (d, J=6.6 Hz, 3H), 1.31-1.23 (m, 4H), 1.21-1.17 (m, 2H), 1.07 (d, J=6.7 Hz, 3H), 0.86 (d, J=6.4 Hz, 3H).

Example 108 was Prepared in a Similar Manner to Example 107 Using an Appropriately Substituted Fluoroindazole

| Ex. No. | Structure | Compound Name | [M + H]+ Found |
|---|---|---|---|
| 108 | 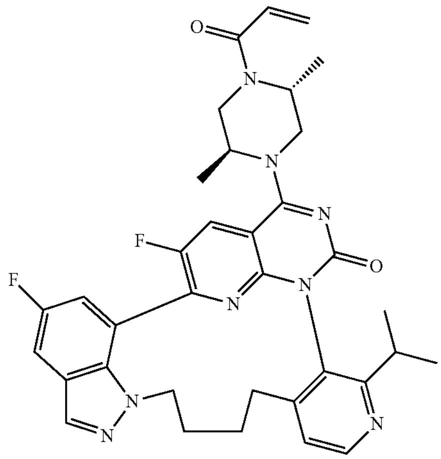 [SMILES: C=CC(=O)N1C[C@H](C)N(c2nc(=O)n3c4nc(c(F)cc24)-c2cc(F)cc4cnn(c24)CCCCc2ccnc(C(C)C)c2-3)C[C@H]1C] | 2-[(2S,5R)-2,5-dimethyl-4-(prop-2-enoyl)piperazin-1-yl]-18,22-difluoro-6-(propan-2-yl)-10,11,12,13-tetrahydro-4H-1,20-(ethanediylidene)pyrido[4',3':12,13]pyrimido[1',6':1,2][1,3,7]triazacyclotridecino[5,6,7-hi]indazol-4-one | 639 |

Example 109: 20-chloro-2-[(2S,5R)-2,5-dimethyl-4-(prop-2-enoyl)piperazin-1-yl]-17-fluoro-6-(propan-2-yl)-10,11-dihydro-1,18-ethenopyrido[3,4-e]pyrimido[6,1-c][9,2,4]benzoxadiazacyclododecin-4(13H)-one

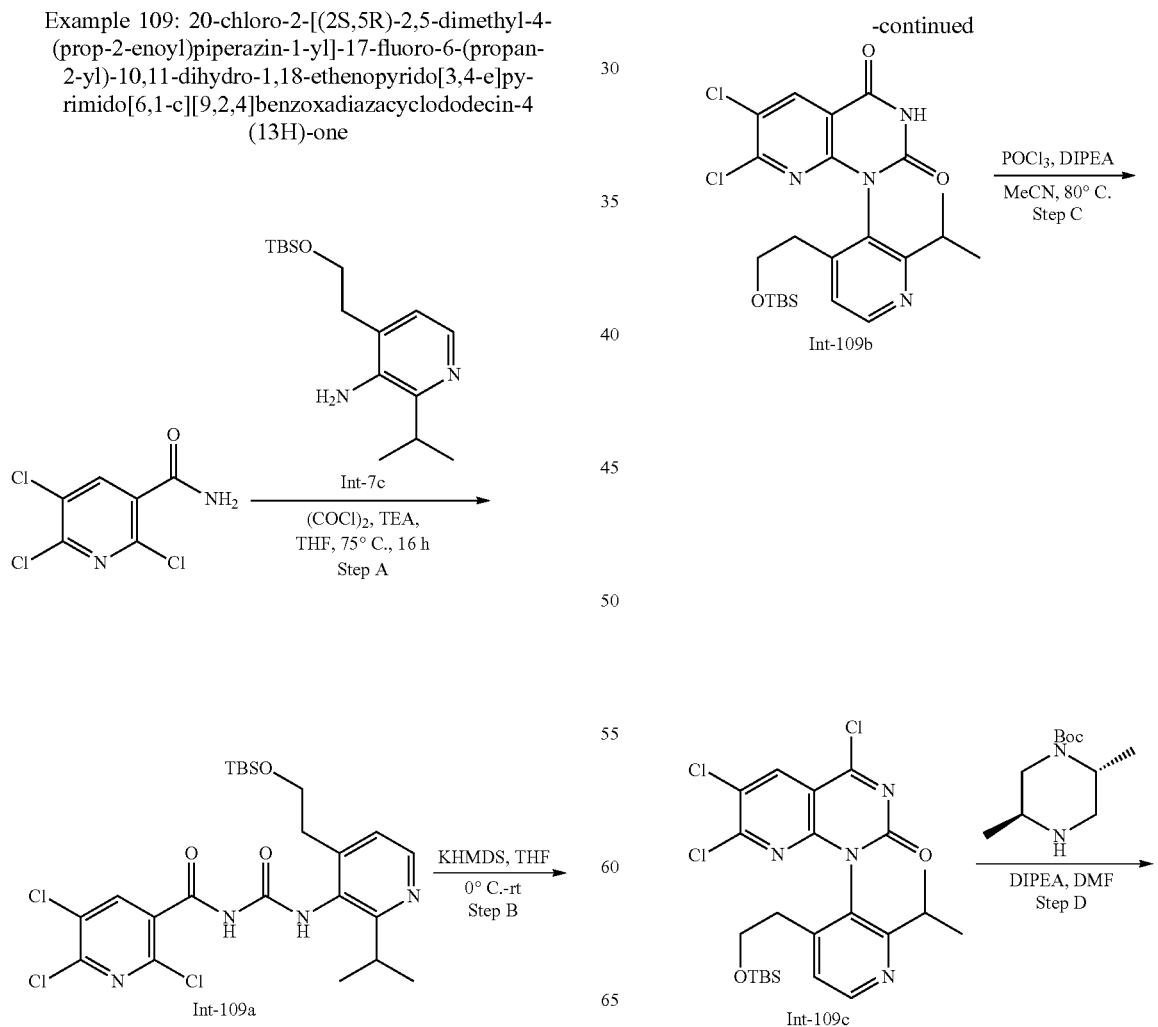

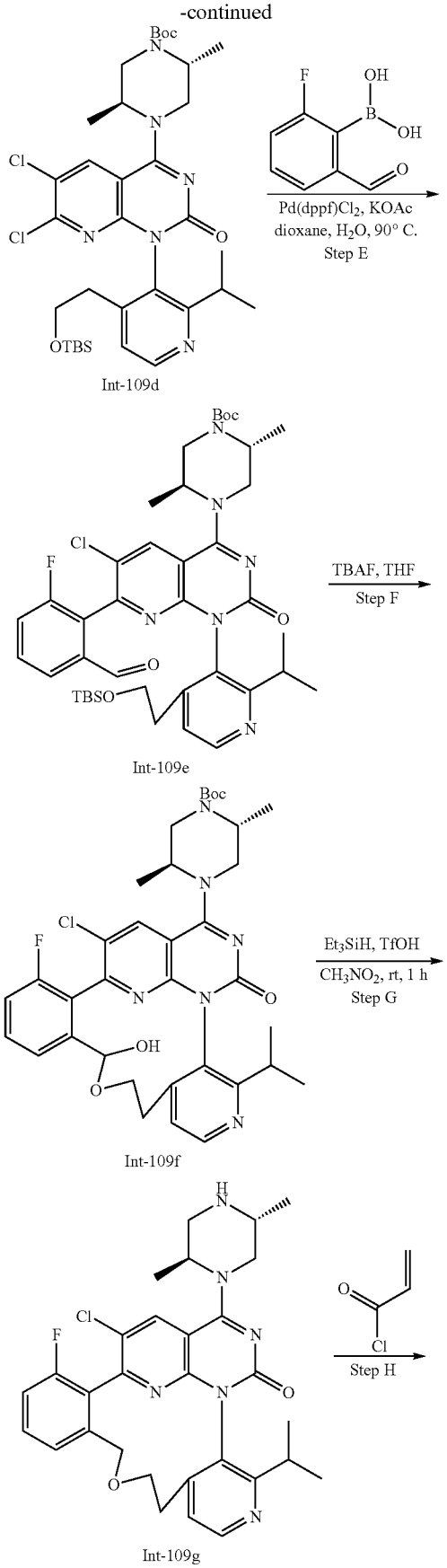

Step A: N-((4-(2-((tert-butyldimethylsilyl)oxy)ethyl)-2-isopropylpyridin-3-yl)carbamoyl)-2,5,6-trichloronicotinamide (Int-109a)

To a stirred mixture of 2,5,6-trichloronicotinamide (1.0 g, 4.4 mmol) in tetrahydrofuran (18 mL) was added oxalyl dichloride (0.43 mL, 4.9 mmol). The mixture was then heated to 65° C. for 30 min under a nitrogen atmosphere. After 30 minutes, the mixture was allowed to cool to room temperature and then concentrated under reduced pressure. To the resulting residue was added dichloromethane (10 mL). The resulting mixture was added to a mixture of 4-(2-((tert-butyldimethylsilyl)oxy)ethyl)-2-isopropylpyridin-3-amine (Int-7c, 1.3 g, 4.4 mmol) in DCM (10 mL) in one portion. The reaction mixture allowed to stir at room temperature for 5 minutes. The reaction mixture was then quenched with brine (50 mL) and extracted with dichloromethane (2×100 mL). The combined organic layers were washed with brine (60 mL), dried over sodium sulfate, filtered and the filtrate was concentrated under reduced pressure. The resulting residue was purified by silica gel column chromatography (0-30% ethyl acetate in petroleum ether) to afford N-((4-(2-((tert-butyldimethylsilyl)oxy)ethyl)-2-isopropylpyridin-3-yl)carbamoyl)-2,5,6-trichloronicotinamide (Int-109a). MS (ESI): m/z 547 [M+H]$^+$. $^1$H NMR (400 MHz, Methanol-d$_4$): δ 8.40 (d, J=4.9 Hz, 1H), 8.36 (s, 1H), 7.29 (d, J=4.9 Hz, 1H), 3.93 (t, J=6.4 Hz, 2H), 3.42-3.35 (m, 1H), 2.92 (t, J=6.2 Hz, 2H), 1.29 (d, J=6.8 Hz, 6H), 0.84 (s, 9H), 0.00 (s, 6H).

Step B: 1-(4-(2-((tert-butyldimethylsilyl)oxy)ethyl)-2-isopropylpyridin-3-yl)-6,7-dichloropyrido[2,3-d]pyrimidine-2,4(1H,3H)-dione (Int-109b)

A mixture of N-((4-(2-((tert-butyldimethylsilyl)oxy)ethyl)-2-isopropylpyridin-3-yl)carbamoyl)-2,5,6-trichloronicotinamide (Int-109a, 1.2 g, 2.2 mmol) in THF (8.0 mL) was cooled to 0° C. Potassium bis(trimethylsilyl)amide (1.0 M in THF, 4.4 mL, 4.4 mmol) was added, the mixture was allowed to warm to room temperature and was then stirred at room temperature for 30 minutes. The mixture was then quenched with saturated aqueous ammonium chloride (15 mL) and extracted with ethyl acetate (2×50 mL). The combined organic layers were washed with brine (15 mL), dried over Na$_2$SO$_4$, filtered and the filtrate was concentrated under reduced pressure to afford 1-(4-(2-((tert-butyldimethylsilyl)oxy)ethyl)-2-isopropylpyridin-3-yl)-6,7-dichloropyrido[2,3-d]pyrimidine-2,4(1H,3H)-dione (Int-109b). MS (ESI): m/z 509 [M+H]$^+$.

Step C & D: (2R,5S)-tert-butyl 4-(1-(4-(2-((tert-butyldimethylsilyl)oxy)ethyl)-2-isopropylpyridin-3-yl)-6,7-dichloro-2-oxo-1,2-dihydropyrido[2,3-d]pyrimidin-4-yl)-2,5-dimethylpiperazine-1-carboxylate (Int-109d)

To a mixture of 1-(4-(2-((tert-butyldimethylsilyl)oxy)ethyl)-2-isopropylpyridin-3-yl)-6,7-dichloropyrido[2,3-d]pyrimidine-2,4(1H,3H)-dione (Int-109b, 1.0 g, 2.0 mmol) in acetonitrile (10 mL) were added N,N-diisopropylethylamine (3.4 mL, 20 mmol) and then phosphorous oxychloride (0.37 mL, 3.9 mmol) at room temperature. The mixture was then heated to 80° C. for 30 min under N$_2$ atmosphere. After 30 minutes, the mixture was allowed to cool to room temperature. (2R,5S)-tert-butyl 2,5-dimethylpiperazine-1-carboxylate (0.98 g, 3.9 mmol) was added and the resulting mixture was stirred at room temperature for 5 min. The mixture was then quenched with water (20 mL) and extracted with ethyl acetate (3×20 mL). The combined organic layers were washed with brine (2×10 mL), dried over Na$_2$SO$_4$, filtered and the filtrate was concentrated under reduced pressure. The resulting residue was purified by silica gel column chromatography (0-50% ethyl acetate in petroleum ether) to afford (2R,5S)-tert-butyl 4-(1-(4-(2-((tert-butyldimethylsilyl)oxy)ethyl)-2-isopropylpyridin-3-yl)-6,7-dichloro-2-oxo-1,2-dihydropyrido[2,3-d]pyrimidin-4-yl)-2,5-dimethylpiperazine-1-carboxylate (Int-109d). MS (ESI): m/z 706 [M+H]$^+$.

Step E: (2R,5S)-tert-butyl 4-(1-(4-(2-((tert-butyldimethylsilyl)oxy)ethyl-2-isopropylpyridin-3-yl)-6-chloro-7-(2-fluoro-6-formylphenyl)-2-oxo-1,2-dihydropyrido[2,3-d]pyrimidin-4-yl)-2,5-dimethylpiperazine-1-carboxylate (Int-109e)

To a mixture of (2R,5S)-tert-butyl 4-(1-(4-(2-((tert-butyldimethylsilyl)oxy)ethyl)-2-isopropylpyridin-3-yl)-6,7-dichloro-2-oxo-1,2-dihydropyrido[2,3-d]pyrimidin-4-yl)-2,5-dimethylpiperazine-1-carboxylate (Int-109d, 300 mg, 0.425 mmol), potassium acetate (209 mg, 2.13 mmol) and 1,1'-bis(diphenylphosphino)ferrocene-palladium(II)dichloride dichloromethane complex (35 mg, 0.043 mmol) in 1,4-dioxane (3.0 mL) and water (0.30 mL) was added (2-fluoro-6-formylphenyl)boronic acid (93 mg, 0.55 mmol), and the mixture was heated to 90° C. for 30 min under a nitrogen atmosphere. After 30 minutes, the mixture was allowed to cool to room temperature. The mixture was then quenched with water (5.0 mL) and then extracted with ethyl acetate (3×15 mL). The combined organic layers were washed with brine (10 mL), dried over sodium sulfate and the filtrate was concentrated under reduced pressure. The resulting residue was purified by silica gel column chromatography (0-60% ethyl acetate in petroleum ether) to afford (2R,5S)-tert-butyl 4-(1-(4-(2-((tert-butyldimethylsilyl)oxy)ethyl)-2-isopropylpyridin-3-yl)-6-chloro-7-(2-fluoro-6-formylphenyl)-2-oxo-1,2-dihydropyrido[2,3-d]pyrimidin-4-yl)-2,5-dimethylpiperazine-1-carboxylate (Int-109e). MS (ESI): m/z 793 [M+H]$^+$. $^1$H NMR (500 MHz, Methanol-d$_4$) δ 9.87-9.74 (m, 1H), 8.52-8.42 (m, 1H), 8.37 (dd, J=1.4, 5.0 Hz, 1H), 7.88-7.79 (m, 1H), 7.78-7.68 (m, 1H), 7.58-7.44 (m, 1H), 7.34-7.24 (m, 1H), 4.98 (br d, J=19.5 Hz, 1H), 4.50-4.28 (m, 2H), 4.05-3.94 (m, 1H), 3.85 (br s, 1H), 3.72-3.57 (m, 3H), 2.83-2.64 (m, 1H), 2.58-2.45 (m, 2H), 1.52 (s, 12H), 1.31-1.25 (m, 3H), 1.18-1.15 (m, 3H), 0.99-0.91 (m, 3H), 0.85-0.82 (m, 9H), −0.02-−0.09 (m, 6H).

Step F: Int-109f

A mixture of (2R,5S)-tert-butyl 4-(1-(4-(2-((tert-butyldimethylsilyl)oxy)ethyl)-2-isopropylpyridin-3-yl)-6-chloro-7-(2-fluoro-6-formylphenyl)-2-oxo-1,2-dihydropyrido[2,3-d]pyrimidin-4-yl)-2,5-dimethylpiperazine-1-carboxylate (Int-109e, 220 mg, 0.277 mmol) in THF (3.0 mL) was cooled to 0° C. TBAF (1.0 M in THF, 0.56 mL, 0.56 mmol) was added. The mixture was allowed to warm to room temperature and was then stirred for 1 hour at room temperature. The mixture was then quenched with water (5.0 mL), and extracted with ethyl acetate (20 mL). The organic layer was washed with brine (2×5 mL), dried over Na$_2$SO$_4$, filtered and the filtrate was concentrated under reduced pressure. The resulting residue was purified by purified by reverse MPLC (C18, 0-60% acetonitrile gradient in water with a 0.5% TFA modifier) to afford Int-109f. MS (ESI): m/z 679 [M+H]$^+$. $^1$H NMR (400 MHz, Methanol-d$_4$) δ 9.80 (d, J=18.4 Hz, 1H), 8.65-8.46 (m, 2H), 7.86-7.40 (m, 4H), 4.99 (br s, 1H), 4.46 (br s, 2H), 4.01 (br s, 1H), 3.90-3.73 (m, 2H), 3.73-3.53 (m, 2H), 3.27-3.20 (m, 1H), 3.16-2.88 (m, 1H), 2.86-2.55 (m, 2H), 1.51 (s, 12H), 1.31-1.24 (m, 6H), 1.13-1.05 (m, 3H).

Step G: Int-1092

To a mixture of Int-109f (0.10 g, 0.15 mmol) in CH$_3$NO$_2$ (12 mL) was added triflic acid (0.13 mL, 1.5 mmol) and triethylsilane (0.24 mL, 1.5 mmol) at room temperature under a nitrogen atmosphere. The mixture was allowed to stir at room temperature for 30 minutes. The mixture was then concentrated under reduced pressure to afford Int-109g which was used in the next step without further purification. MS (ESI): m/z 563 [M+H]$^+$.

Step H: 20-chloro-2-[(2S,5R)-2,5-dimethyl-4-(prop-2-enoyl)piperazin-1-yl]-17-fluoro-6-(propan-2-yl)-10,11-dihydro-1,18-ethenopyrido[3,4-e]pyrimido[6,1-c][9,2,4]benzoxadiazacyclododecin-4(13H)-one (Ex. 109)

To a mixture of Int-109g (60 mg, 0.11 mmol) in DCM (2.0 mL) was added DIEA (0.056 mL, 0.32 mmol) and acryloyl chloride (17 µL, 0.21 mmol) at room temperature. The mixture was stirred at room temperature for 5 minutes. The mixture was then concentrated under reduced pressure and then purified by preparative TLC plate (7% MeOH in DCM on silica. The mixture was then resolved by preparative SFC Column F, Condition: 0.1% NH$_3$·H$_2$O EtOH to afford Peak 1,20-chloro-2-[(2S,5R)-2,5-dimethyl-4-(prop-2-enoyl)piperazin-1-yl]-17-fluoro-6-(propan-2-yl)-10,11-dihydro-1,18-ethenopyrido[3,4-e]pyrimido[6,1-c][9,2,4]benzoxadiazacyclododecin-4(13H)-one (Ex. 109) as a single atropisomer. MS (ESI): m/z 617 [M+H]$^+$. $^1$H NMR (500 MHz, methanol-d$_4$) δ 8.47 (d, J=5.2 Hz, 1H), 8.36 (d, J=15.7 Hz, 1H), 7.52-7.43 (m, 2H), 7.24 (d, J=7.6 Hz, 1H), 7.16 (t, J=9.0 Hz, 1H), 6.95-6.73 (m, 1H), 6.35-6.24 (m, 1H), 5.83 (dt, J=1.8, 10.7 Hz, 1H), 5.11-4.92 (m, 1H), 4.82-4.59 (m, 1H), 4.43-3.90 (m, 4H), 3.81-3.57 (m, 3H), 3.39-3.31 (m, 1H), 3.11-

3.02 (m, 1H), 2.51-2.44 (m, 2H), 1.62 (br t, J=7.2 Hz, 3H), 1.52-1.43 (m, 3H), 1.24 (d, J=6.7 Hz, 3H), 1.03 (br t, J=3.4 Hz, 3H).

Example 110: 2-[(2S,5R)-2,5-dimethyl-4-(prop-2-enoyl)piperazin-1-yl]-14,17-difluoro-20-methyl-6-(propan-2-yl)-11,12-dihydro-4H-1,18-ethenopyrido[4,3-e]pyrimido[1,6-g][1,4,7,9]benzodioxadiazacyclododecin-4-one

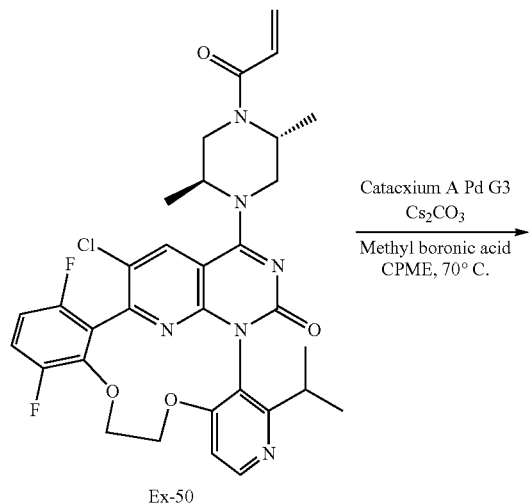

A flask containing 20-chloro-2-[(2S,5R)-2,5-dimethyl-4-(prop-2-enoyl)piperazin-1-yl]-14,17-difluoro-6-(propan-2-yl)-11,12-dihydro-4H-1,18-(ethanediylidene)pyrido[4,3-e]pyrimido[1,6-g][1,4,7,9]benzodioxadiazacyclododecin-4-one (Ex. 50) (50 mg, 0.78 mmol), methyl boronic acid (14 mg, 0.24 mmol) and Catacxium A Pd G3 (6.0 mg, 0.078 mmol) was evacuated and backfilled with nitrogen three times. Cyclopentyl methyl ether (0.40 mL) and aqueous cesium carbonate (1.5 M in H$_2$O, 0.16 mL, 0.24 mmol) were added. The mixture was then heated to 70° C. for 3 h. After 3 hours, the mixture was allowed to cool to room temperature. The mixture was then diluted with ethyl acetate (50 mL) and washed with saturated aqueous sodium chloride (3×10 mL). The organic layer was dried over sodium sulfate, filtered and the filtrate was concentrated under reduced pressure. The resulting residue was purified by silica gel column chromatography (0-100% (3:1 ethyl acetate:ethanol) gradient in hexanes) to afford 2-[(2S,5R)-2,5-dimethyl-4-(prop-2-enoyl)piperazin-1-yl]-14,17-difluoro-20-methyl-6-(propan-2-yl)-11,12-dihydro-4H-1,18-ethenopyrido[4,3-e]pyrimido[1,6-g][1,4,7,9]benzodioxadiazacyclododecin-4-one (Ex. 110). MS (ESI) m/z: 617 [M+H]$^+$. $^1$H NMR (500 MHz, Acetonitrile-d$_3$) δ 8.42 (d, J=5.6 Hz, 1H), 8.09 (d, J=13.7 Hz, 1H), 7.28 (ddd, J=11.1, 9.3, 5.3 Hz, 1H), 6.97 (td, J=8.9, 3.6 Hz, 1H), 6.89 (d, J=5.7 Hz, 1H), 6.82 (dd, J=16.8, 10.6 Hz, 0.5H), 6.71 (dd, J=16.7, 10.6 Hz, 0.5H), 6.24 (ddd, J=16.7, 4.1, 2.2 Hz, 1H), 5.75 (td, J=10.2, 2.3 Hz, 1H), 4.99 (d, J=8.1 Hz, 0.5H), 4.85-4.72 (m, 1H), 4.67-4.59 (m, 2.5H), 4.58-4.42 (m, 1H), 4.34 (d, J=13.8 Hz, 0.5H), 4.27-4.19 (m, 1H), 4.13-4.04 (m, 1H), 3.84-3.67 (m, 1H), 3.59 (ddd, J=18.2, 14.1, 3.9 Hz, 1H), 3.27 (dd, J=13.7, 4.1 Hz, 0.5H), 3.16 (pd, J=6.7, 3.7 Hz, 1H), 2.22 (s, 3H), 1.56-1.41 (m, 6H), 1.24 (d, J=6.7 Hz, 3H), 1.00 (dd, J=6.8, 2.8 Hz, 3H).

Example 111: 6-cyclopropyl-2-[(2S,5R)-2,5-dimethyl-4-(prop-2-enoyl)piperazin-1-yl]-14,17,20-trifluoro-11,12-dihydro-4H-1,18-ethenopyrido[4,3-e]pyrimido[1,6-g][1,4,7,9]benzodioxadiazacyclododecin-4-one

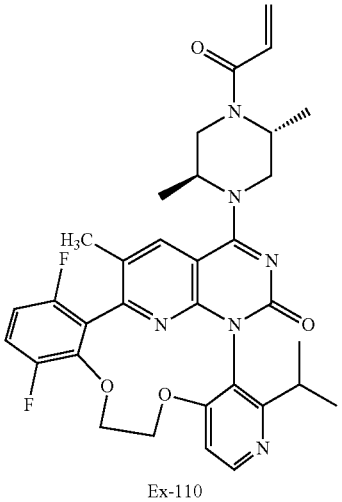

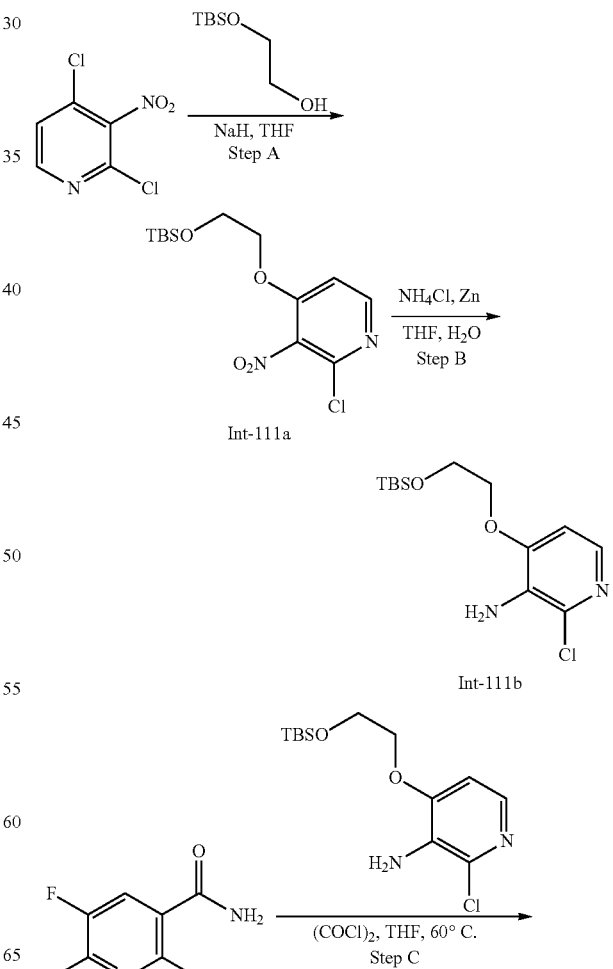

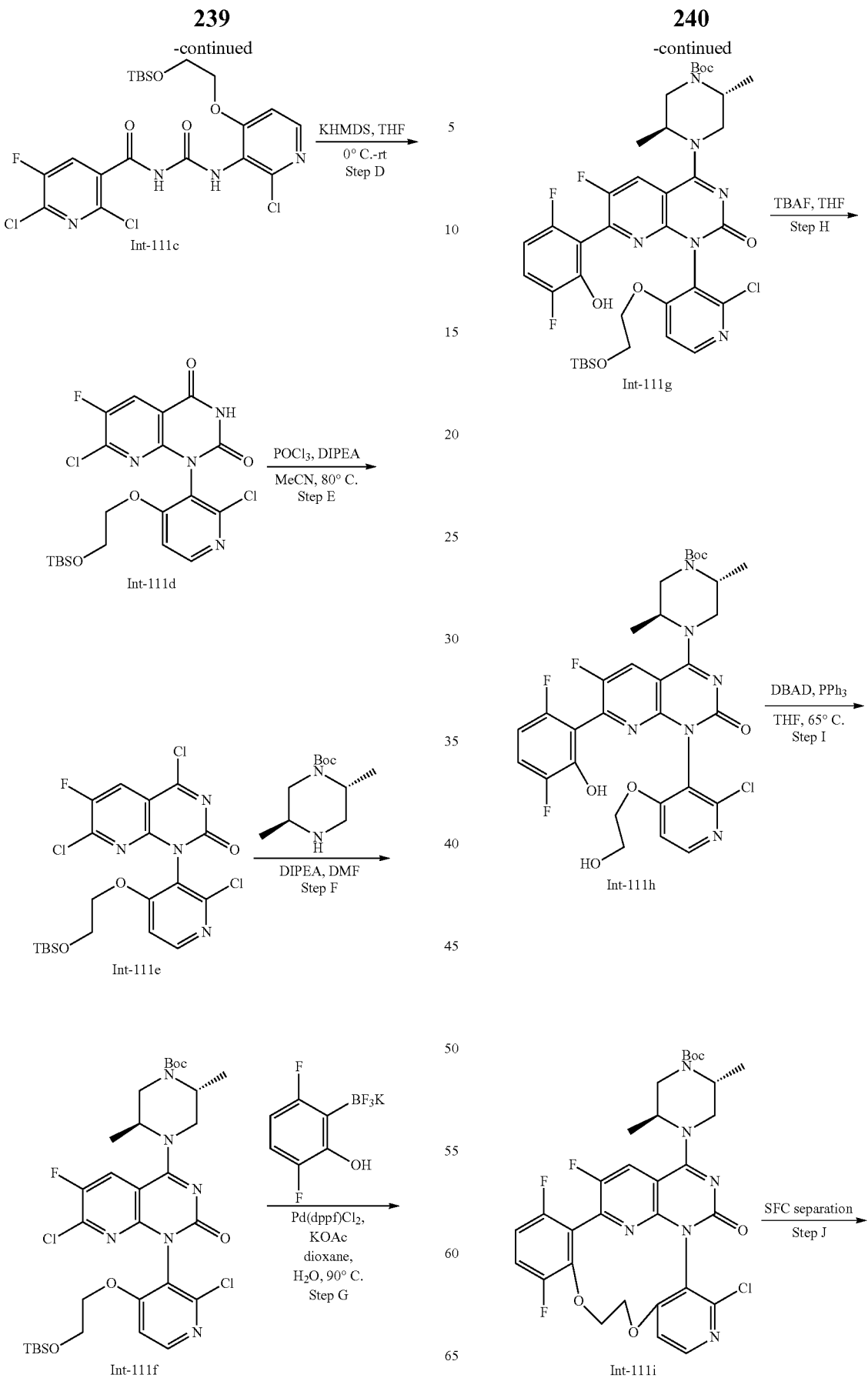

-continued

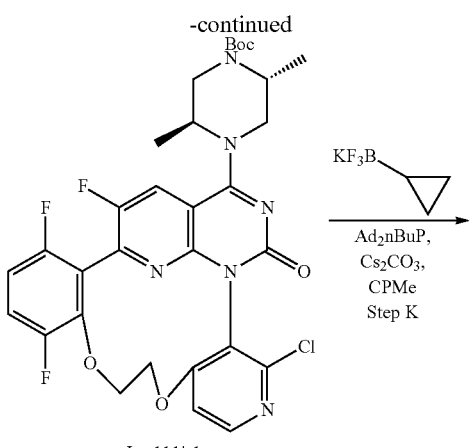

Int-111j-1

KF₃B—▷  
Ad₂nBuP,  
Cs₂CO₃,  
CPMe  
Step K

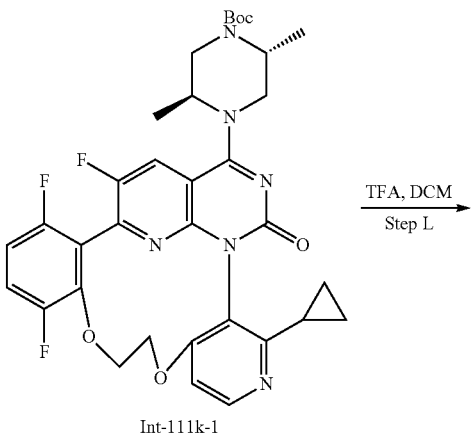

Int-111k-1

TFA, DCM  
Step L

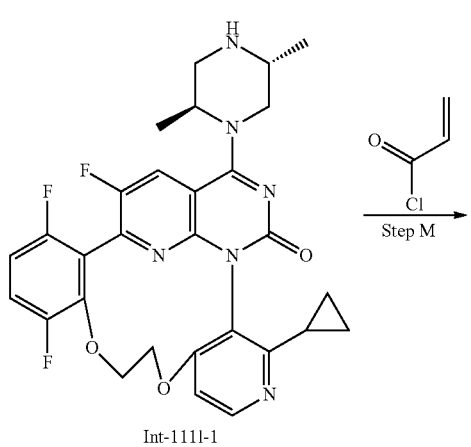

Int-111l-1

Step M

-continued

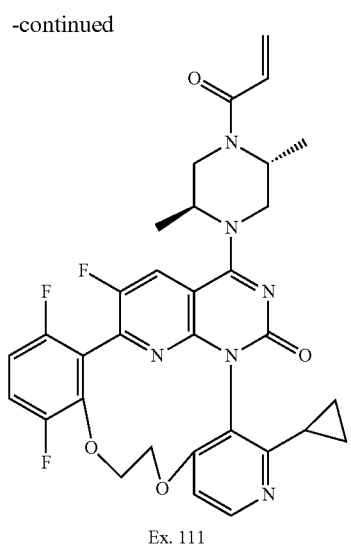

Ex. 111

Step A: 4-(2-((tert-butyldimethylsilyloxy)ethoxy)-2-chloro-3-nitropyridine(Int-111a)

To a mixture of 2-((tert-butyldimethylsilyl)oxy)ethanol (50.3 g, 285 mmol) in THF (150 mL) 0° C. was added NaH (60% dispersion in mineral oil, 15.5 g, 389 mmol). After 30 minutes, the mixture was added dropwise to a mixture of 2,4-dichloro-3-nitropyridine (50 g, 0.26 mol) in THF (150 mL) and the mixture was maintained at 0° C. for 30 minutes. After 30 minutes, the mixture was allowed to warm to room temperature and was then stirred for 3 hours. The reaction mixture was then quenched with saturated aqueous ammonium chloride (50 mL) and then extracted with ethyl acetate (3×200 mL). The combined organic layers were dried over anhydrous sodium sulfate, filtered and then concentrated under reduced pressure. The resulting residue was purified by silica gel column chromatography (0-25% ethyl acetate gradient in petroleum ether) to afford 4-(2-((tert-butyldimethylsilyl)oxy)ethoxy)-2-chloro-3-nitropyridine (Int-111a). MS (ESI): m/z 333 [M+H]⁺. ¹H NMR (500 MHz, CDCl₃) δ 8.28 (d, J=5.87 Hz, 1H), 7.00 (d, J=5.87 Hz, 1H), 4.22 (t, J=4.65 Hz, 2H), 3.91 (t, J=4.65 Hz, 2H), 0.82 (s, 9H), 0.00 (s, 6H).

Step B: 4-(2-((tert-butyldimethylsilyloxy)ethoxy)-2-chloropyridin-3-amine (Int-111b)

To a mixture of 4-(2-((tert-butyldimethylsilyl)oxy) ethoxy)-2-chloro-3-nitropyridine (10 g, 30 mmol) in THF (90 mL) at 0° C. were added a mixture of zinc powder (15.7 g, 240 mmol) and ammonium chloride (25.7 g, 481 mmol) in water (20 mL). The mixture was allowed to warm to room temperature for 15 hours. After 15 hours, the mixture was filtered and the filtered cake was washed with EtOAc (100 mL). The filtrate was then extracted with ethyl acetate (3×100 mL). The combined organic layers were washed with brine (50 mL), and saturated aqueous sodium bicarbonate (50 mL). The organic layer was then dried over anhydrous sodium sulfate and concentrated under reduced pressure. The resulting residue was purified by silica gel column chromatography (0-25% ethyl acetate gradient in petroleum ether) to afford 4-(2-((tert-butyldimethylsilyl) oxy)ethoxy)-2-chloropyridin-3-amine (Int-111b). MS (ESI): m/z 303 [M+H]⁺. ¹H NMR (500 MHz, CDCl₃) δ 7.64 (d, J=5.38 Hz, 1H), 6.61 (d, J=5.38 Hz, 1H), 4.03-4.07 (m, 2H), 3.99 (br s, 2H), 3.89-3.92 (m, 2H), 0.81 (s, 9H), 0.00 (s, 6H).

Step C: N-((4-(2-((tert-butyldimethylsilyl)oxy)ethoxy)-2-chloropyridin-3-yl)carbamoyl)-2,6-dichloro-5-fluoronicotinamide(Int-111c)

To a mixture of 2,6-dichloro-5-fluoronicotinamide (5.0 g, 24 mmol) in THF (60 mL) was added oxalyl dichloride (2.3 mL, 26 mmol, 2 M in dichloromethane) at room temperature under a nitrogen atmosphere. The mixture was then heated to 60° C. for 30 min. After 30 minutes, the mixture was allowed to cool to room temperature and was then concentrated under reduced pressure. To the resulting mixture were added THF (60 mL), and then 4-(2-((tert-butyldimethylsilyl)oxy)ethoxy)-2-chloropyridin-3-amine (Int-111b, 7.25 g, 23.9 mmol) at room temperature. After 10 minutes, the mixture was quenched with water (100 mL), adjusted to a pH ~8 with sodium bicarbonate and then extracted with EtOAc (3×100 mL). The combined organic layers were washed with brine (50 mL), dried over sodium sulfate, filtered and then concentrated under reduced pressure. The resulting mixture was purified by silica gel column chromatography (0-50% ethyl acetate gradient in petroleum ether) to afford N-((4-(2-((tert-butyldimethylsilyl)oxy)ethoxy)-2-chloropyridin-3-yl)carbamoyl)-2,6-dichloro-5-fluoronicotinamide (Int-111c). MS (ESI): m/z 537 [M+H]$^+$. $^1$H NMR (500 MHz, CDCl$_3$) δ: 9.68 (br s, 1H), 8.19 (d, J=5.87 Hz, 1H), 8.02-8.08 (m, 1H), 7.93 (d, J=7.09 Hz, 1H), 6.88 (d, J=5.87 Hz, 1H), 4.13-4.16 (m, 2H), 3.93 (t, J=4.77 Hz, 2H), 0.81 (s, 9H), 0.00 (s, 6H).

Step D: 1-(4-(2-((tert-butyldimethylsilyloxy)ethoxy)-2-chloropyridin-3-yl)-7-chloro-6-fluoropyrido[2,3-d]pyrimidine-2,4(1H,3H)-dione (Int-111d)

To a mixture of N-((4-(2-((tert-butyldimethylsilyl)oxy)ethoxy)-2-chloropyridin-3-yl)carbamoyl)-2,6-dichloro-5-fluoronicotinamide (2.0 g, 3.7 mmol) in THF (50 mL) at 0° C. under a nitrogen atmosphere was added potassium bis(trimethylsilyl)amide (1.0 m in THF, 7.4 mL, 7.4 mmol). The mixture was then allowed to warm to room temperature for 30 minutes. The mixture was then quenched with water (20 mL), adjusted to a pH~8 with sodium bicarbonate and then extracted with EtOAc (3×70 mL). The combined organic layers were washed with brine (20 mL), dried over Na$_2$SO$_4$, filtered and the mixture was concentrated under reduced pressure. The resulting residue was purified by silica gel column chromatography (0-50% ethyl acetate gradient in petroleum ether) to afford 1-(4-(2-((tert-butyldimethylsilyl)oxy)ethoxy)-2-chloropyridin-3-yl)-7-chloro-6-fluoropyrido[2,3-d]pyrimidine-2,4(1H,3H)-dione (Int-111d). MS (ESI): m/z 501 [M+H]$^+$. $^1$H NMR (400 MHz, CDCl$_3$) δ: 8.41 (d, J=5.87 Hz, 2H), 8.21 (d, J=6.4 Hz, 1H), 7.04 (d, J=5.87 Hz, 1H), 4.12-4.17 (m, 2H), 3.77-3.85 (m, 2H), 0.76 (s, 9H), −0.07 (s, 3H), −0.11 (s, 3H).

Step E: 1-(4-(2-((tert-butyldimethylsilyloxy)ethoxy)-2-chloropyridin-3-yl)-4,7-dichloro-6-fluoropyrido[2,3-d]pyrimidin-2(1H)-one(Int-11e)

To a mixture of 1-(4-(2-((tert-butyldimethylsilyl)oxy)ethoxy)-2-chloropyridin-3-yl)-7-chloro-6-fluoropyrido[2,3-d]pyrimidine-2,4(1H,3H)-dione (1.4 g, 2.8 mmol) in MCCN (10 mL) was added N,N-diisopropylethylamine (2.5 mL, 14 mmol) and phosphorous oxychloride (0.52 mL, 5.6 mmol). The mixture was then heated to 80° C. for 30 min. The mixture was then allowed to cool to room temperature and then concentrated under reduced pressure afford crude 1-(4-(2-((tert-butyldimethylsilyl)oxy)ethoxy)-2-chloropyridin-3-yl)-4,7-dichloro-6-fluoropyrido[2,3-d]pyrimidin-2(1H)-one (Int-11e) which was used without further purification or characterization. MS (ESI): m/z 519 [M+H]$^+$.

Step F: (2R,5S)-tert-butyl 4-(1-(4-(2-((tert-butyldimethylsilyl)oxy)ethoxy)-2-chloropyridin-3-yl)-7-chloro-6-fluoro-2-oxo-1,2-dihydropyrido[2,3-d]pyrimidin-4-yl)-2,5-dimethylpiperazine-1-carboxylate (Int-111f)

To a mixture of 1-(4-(2-((tert-butyldimethylsilyl)oxy)ethoxy)-2-chloropyridin-3-yl)-4,7-dichloro-6-fluoropyrido[2,3-d]pyrimidin-2(1H)-one (18.7 g, 35.9 mmol) in MCCN (180 mL) under a nitrogen atmosphere were added N,N-diisopropylethylamine (6.3 mL, 36 mmol) and (2R,5S)-tert-butyl 2,5-dimethylpiperazine-1-carboxylate (11.5 g, 53.8 mmol) at room temperature. The mixture was allowed to stir at room temperature for 16 hours. After 16 hours, the mixture was quenched with water (20 mL), adjusted to a pH~8 with sodium bicarbonate and then extracted with EtOAc (3×50 mL). The combined organic layers were washed with brine (20 mL), dried over sodium sulfate, filtered and the filtrate was concentrated under reduced pressure. The resulting mixture was purified by silica gel column chromatography (0-50% ethyl acetate gradient in petroleum ether) to afford (2R,5S)-tert-butyl 4-(1-(4-(2-((tert-butyldimethylsilyl)oxy)ethoxy)-2-chloropyridin-3-yl)-7-chloro-6-fluoro-2-oxo-1,2-dihydropyrido[2,3-d]pyrimidin-4-yl)-2,5-dimethylpiperazine-1-carboxylate (Int-111f). MS (ESI): m/z 697 [M+H]$^+$. $^1$H NMR (500 MHz, CDCl$_3$) δ 8.53 (d, J=5.9 Hz, 1H), 7.96-7.89 (m, 1H), 7.18 (d, J=5.9 Hz, 1H), 5.16-4.89 (m, 1H), 4.81-4.48 (m, 1H), 4.36-4.29 (m, 2H), 4.29-4.09 (m, 2H), 4.08-3.97 (m, 2H), 3.96-3.91 (m, 2H), 1.68 (s, 9H), 1.48-1.36 (m, 6H), 0.92 (d, J=8.1 Hz, 9H), 0.10--0.01 (m, 6H).

Step G: (2R,5S-tert-butyl 4-(1-(4-(2-((tert-butyldimethylsilyl)oxy)ethoxy)-2-chloropyridin-3-yl)-7-(3,6-difluoro-2-hydroxyphenyl)-6-fluoro-2-oxo-1,2-dihydropyrido[2,3-d]pyrimidin-4-yl-2,5-dimethylpiperazine-1-carboxylate(Int-111g)

To a mixture of (2R,5S)-tert-butyl 4-(1-(4-(2-((tert-butyldimethylsilyl)oxy)ethoxy)-2-chloropyridin-3-yl)-7-chloro-6-fluoro-2-oxo-1,2-dihydropyrido[2,3-d]pyrimidin-4-yl)-2,5-dimethylpiperazine-1-carboxylate (5.0 g, 7.2 mmol), potassium (3,6-difluoro-2-hydroxyphenyl)trifluoroborate (Int-23c, 2.0 g, 8.6 mmol) and [1,1'-bis(diphenylphosphino)ferrocene]dichloropalladium(II) (0.52 g, 0.72 mmol) in 1,4-dioxane (50 mL) and water (15 mL) under a nitrogen atmosphere was added potassium acetate (3.5 g, 36 mmol). The mixture was then heated to 90° C. for 2 hours. After 2 hours, the mixture was allowed to cool room temperature and then quenched with brine (20 mL). The mixture was then extracted with EtOAc (2×50 mL). The combined organic layers were washed with brine (20 mL), dried over sodium sulfate, filtered and then concentrated under reduced pressure. The resulting residue was purified by silica gel column chromatography (0-50% ethyl acetate gradient in petroleum ether to afford (2R,5S)-tert-butyl 4-(1-(4-(2-((tert-butyldimethylsilyl)oxy)ethoxy)-2-chloropyridin-3-yl)-7-(3,6-difluoro-2-hydroxyphenyl)-6-fluoro-2-oxo-1,2-dihydropyrido[2,3-d]pyrimidin-4-yl)-2,5-dimethylpiperazine-1-carboxylate (Int-111g). MS (ESI): m/z 791 [M+H]+. 1H NMR (500 MHz, CDCl3) δ 9.36 (br s, 1H), 8.61 (d, J=5.9 Hz, 1H), 8.15-8.06 (m, 1H), 7.32-7.25 (m, 2H), 6.87-6.80 (m, 1H), 5.29-4.95 (m, 1H), 4.92-4.50 (m, 2H), 4.45-4.35 (m, 2H), 4.34-4.21 (m, 2H), 4.16 (br s, 1H), 4.03-3.97 (m, 2H), 1.72 (s, 9H), 1.59-1.40 (m, 6H), 0.90 (d, J=4.9 Hz, 9H), 0.05 (d, J=6.1 Hz, 3H), 0.01 (d, J=10.8 Hz, 3H).

Step H: (2R,5S)-tert-butyl 4-(1-(2-chloro-4-(2-hydroxyethoxy)pyridin-3-yl)-7-(3,6-difluoro-2-hydroxyphenyl)-6-fluoro-2-oxo-1,2-dihydropyrido[2,3-d]pyrimidin-4-yl)-2,5-dimethylpiperazine-1-carboxylate (Int-111h)

To a mixture of (2R,5S)-tert-butyl 4-(1-(4-(2-((tert-butyldimethylsilyl)oxy)ethoxy)-2-chloropyridin-3-yl)-7-(3,6-difluoro-2-hydroxyphenyl)-6-fluoro-2-oxo-1,2-dihydropyrido[2,3-d]pyrimidin-4-yl)-2,5-dimethylpiperazine-1-carboxylate (5.6 g, 7.1 mmol) in THF (40 mL) at 0° C. was added tetrabutylammonium fluoride (1.0 M in THF, 14.2 mL, 14.2 mmol). The resulting mixture was allowed to stir at room temperature for 15 hours. The mixture was then poured into water, adjusted to a pH~5 with aqueous HCl (1.0 N) and extracted with EtOAc (3×80 mL). The combined organic layers were then basified to a pH~8 with saturated aqueous sodium bicarbonate, washed with brine, dried over sodium sulfate, filtered and the filtrate was concentrated under reduced pressure to afford (2R,5S)-tert-butyl 4-(1-(2-chloro-4-(2-hydroxyethoxy)pyridin-3-yl)-7-(3,6-difluoro-2-hydroxyphenyl)-6-fluoro-2-oxo-1,2-dihydropyrido[2,3-d]pyrimidin-4-yl)-2,5-dimethylpiperazine-1-carboxylate (Int-111h). MS (ESI): m/z 677 [M+H]+. 1H NMR (400 MHz, methanol-d4) δ 8.24 (dd, J=5.9, 1.0 Hz, 1H), 8.17-8.14 (m, 1H), 7.17 (dd, J=5.9, 3.4 Hz, 1H), 7.10-7.00 (m, 1H), 6.44 (dt, J=3.4, 9.0 Hz, 1H), 4.96 (br s, 1H), 4.38-4.36 (m, 1H), 4.18-4.13 (m, 1H), 3.96-3.70 (m, 1H), 3.92-3.68 (m, 1H), 3.67-3.46 (m, 3H), 3.22-3.12 (m, 2H), 1.46 (s, 9H), 1.42-1.22 (m, 6H).

Step I: Int-111i

To a mixture of (2R,5S)-tert-butyl 4-(1-(2-chloro-4-(2-hydroxyethoxy)pyridin-3-yl)-7-(3,6-difluoro-2-hydroxyphenyl)-6-fluoro-2-oxo-1,2-dihydropyrido[2,3-d]pyrimidin-4-yl)-2,5-dimethylpiperazine-1-carboxylate (5.3 g, 7.8 mmol) in THF (350 mL) were added triphenylphosphine (10.3 g, 39.1 mmol) and di-tert-butyl azodicarboxylate (9.0 g, 39 mmol). The mixture was degassed and purged with nitrogen for 1 minute. The mixture was then heated to 65° C. for 30 min. After 30 minutes, the mixture was allowed to cool to room temperature and was then concentrated under reduced pressure. The resulting residue was purified by silica gel column chromatography (0-50% ethyl acetate gradient in petroleum ether). The mixture was then further purified by MPLC (10-100% acetonitrile gradient in water with 0.5% TFA modifier) to afford Int-111i. MS (ESI): m/z 659 [M+H]+.

Step j: Int-111j-1

The atropisomers of Int-111i (2.0 g, 3.0 mmol) were separated by preparative SFC Column H, Condition: Mobile phase: A 0.1% NH3H2O MeOH, to afford Peak 1 as Int-110j-1. MS (ESI): m/z 659 [M+H]+. 1H NMR (500 MHz, CDCl3) δ 8.29 (br s, 1H), 8.13 (br s, 1H), 7.42-7.22 (m, 2H), 7.00 (br s, 1H), 4.86-4.62 (m, 4H), 4.59-4.35 (m, 2H), 4.14 (br s, 1H), 3.85 (br s, 1H), 3.65 (br s, 1H), 3.43 (br s, 1H), 1.60 (br s, 3H), 1.51 (br s, 9H), 1.36 (br s, 3H).

Step K: Int-111k-1

To a mixture of Int-111j-1 (0.10 g, 0.15 mmol) in cyclopentyl methyl ether (1.5 mL) under a nitrogen atmosphere were added potassium cyclopropyltrifluoroborate (0.22 g, 1.5 mmol), chloro[(di(1-adamantyl)-n-butylphosphine)-2-(2-aminobiphenyl)]palladium(II) (10 mg, 0.015 mmol) and aqueous cesium carbonate (0.030 M, 20 mL, 0.61 mmol). The resulting mixture was heated to 60° C. for 15 hours. After 15 hours, the mixture was allowed to cool to room temperature and was then quenched with brine (2 mL). The mixture was then extracted with EtOAc (2×10 mL). The combined organic layers were washed with brine (2 mL), dried over sodium sulfate, filtered and the filtrate was concentrated under reduced pressure. The resulting residue was purified by TLC plate (silica gel, 100% ethyl acetate) to afford Int-111k. MS (ESI): m/z 665 [M+H]+. 1H NMR (500 MHz, CDCl3) δ 8.27 (d, J=5.9 Hz, 1H), 8.11 (d, J=8.6 Hz, 1H), 7.36-7.28 (m, 1H), 7.01-6.95 (m, 2H), 4.75-4.72 (m, 2H), 4.70-4.60 (m, 2H), 4.38-4.30 (m, 1H), 4.18-4.10 (m, 1H), 3.87-3.65 (m, 2H), 3.47-3.31 (m, 2H), 1.97 (br d, J=5.9 Hz, 1H), 1.51 (br d, J=2.7 Hz, 9H), 1.48-1.27 (m, 6H), 1.04-0.92 (m, 4H).

Step L: Int-111l-1

To a mixture of Int-111k-1 (28 mg, 0.042 mmol) in dichloromethane (1.0 mL) was added trifluoroacetic acid (1.0 mL, 13 mmol). The resulting mixture was allowed to stir for 30 minutes at room temperature. The mixture was then concentrated under reduced pressure to afford Int-111l-1 which was taken on to the next step without further purification or characterization. MS (ESI): m/z 565 [M+H]+.

Step M: 6-cyclopropyl-2-[(2S,5R)-2,5-dimethyl-4-(prop-2-enoyl)piperazin-1-yl]-14,17,20-trifluoro-11,12-dihydro-4H-1,18-ethenopyrido[4,3-e]pyrimido[1,6-g][1,4,7,9]benzodioxadiazacyclododecin-4-one (Ex. 111)

To a mixture of Int-111l-1 (24 mg, 0.042 mmol) in dichloromethane (2.0 mL) were added N,N-diisopropylethylamine (13 μL, 0.076 mmol) and acryloyl chloride (0.40 mL, 0.076 mmol). The resulting mixture was allowed to stir for 30 minutes at room temperature. After 30 minutes, the mixture was concentrated under reduced pressure. The resulting residue was purified by preparative HPLC (Column: Agela DuraShell C18 150 mm*25 mm*5 um; Condition: water (0.04% NH3H2O+10 mM NH4HCO3)-ACN to afford 6-cyclopropyl-2-[(2S,5R)-2,5-dimethyl-4-(prop-2-enoyl)piperazin-1-yl]-14,17,20-trifluoro-11,12-dihydro-4H-1,18-ethenopyrido[4,3-e]pyrimido[1,6-g][1,4,7,9]benzodioxadiazacyclododecin-4-one (Ex. 111). MS (ESI): m/z 619 [M+H]+. 1H NMR (500 MHz, CDCl3) δ 8.29 (d, J=5.9 Hz, 1H), 8.16-8.11 (m, 1H), 7.43-7.25 (m, 1H), 7.11-6.95 (m, 2H), 6.93-6.69 (m, 1H), 6.32-6.28 (m, 1H), 5.86-5.82 (m, 1H), 5.02 (br s, 1H), 4.86-4.73 (m, 3H), 4.71-4.59 (m, 2H), 4.41-4.34 (m, 1H), 4.21-4.12 (m, 1H), 3.96-3.76 (m, 1H), 3.70-3.67 (m, 1H), 2.07-1.93 (m, 1H), 1.60-1.57 (m, 3H), 1.46-1.43 (m, 3H), 1.08-0.78 (m, 4H).

Example 112: 17,20-difluoro-2-[(2S)-2-methyl-4-(prop-2-enoyl)piperazin-1-yl]-6-(propan-2-yl) 10,11,12,13-tetrahydro-4H-1,18-ethenopyrido[4,3-e]pyrimido[1,6-g][1,7,9]benzotriazacyclododecin-4-one
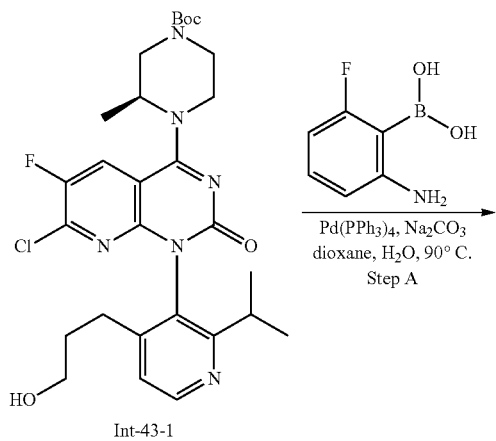
Int-43-1
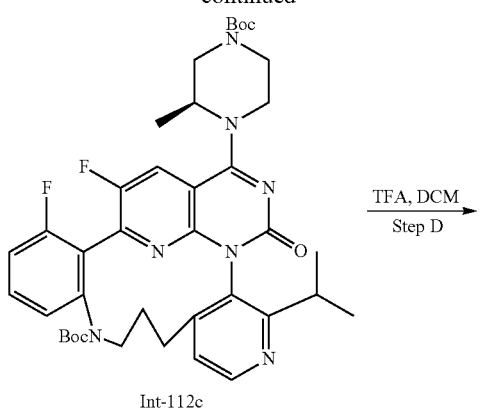
Int-112c
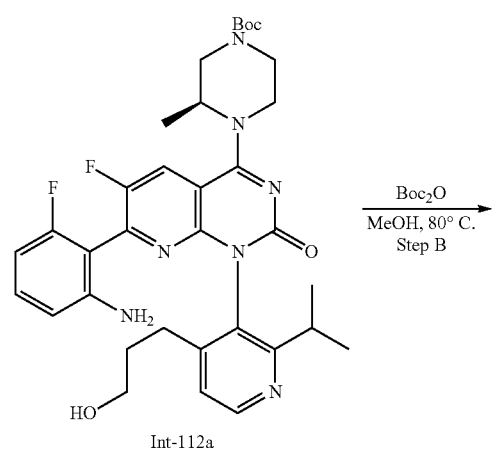
Int-112a
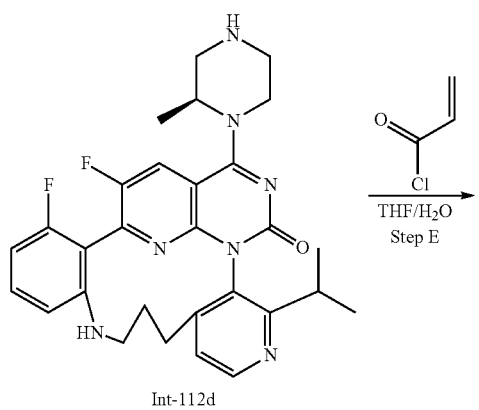
Int-112d
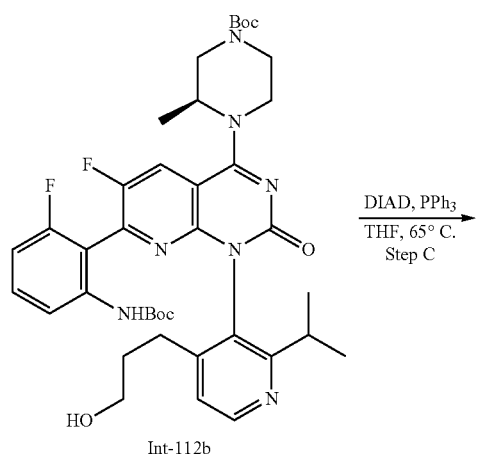
Int-112b
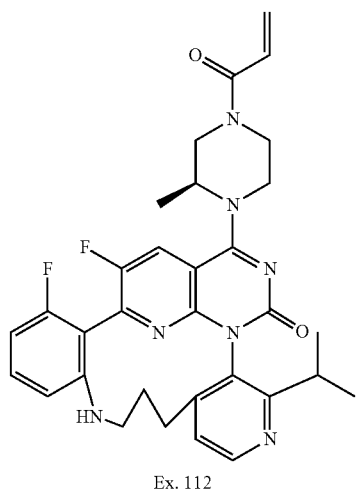
Ex. 112

Step A: (3S)-tert-butyl 4-(7-(2-amino-6-fluorophenyl)-6-fluoro-1-(4-(3-hydroxypropyl)-2-isopropylpyridin-3-yl)-2-oxo-1,2-dihydropyrido[2,3-d]pyrimidin-4-yl)-3-methylpiperazine-1l-carboxylate (Int-112a)

To a mixture of (S)-tert-butyl 4-(7-chloro-6-fluoro-1-(4-(3-hydroxypropyl)-2-isopropylpyridin-3-yl)-2-oxo-1,2-dihydropyrido[2,3-d]pyrimidin-4-yl)-3-methylpiperazine-1-carboxylate (Int-43-1, 700 mg, 1.22 mmol) in 1,4-dioxane (7.0 mL) and water (2.0 mL) were added (2-amino-6-fluorophenyl)boronic acid (377 mg, 2.43 mmol), tetrakis(triphenylphosphine)palladium(0)(141 mg, 0.122 mmol) and potassium carbonate (336 mg, 2.43 mmol) under a nitrogen atmosphere. The mixture was then heated to 90° C. for 15 hours. After 15 hours, the mixture was allowed to cool to room temperature and then quenched with brine (10 mL). The mixture was then extracted with ethyl acetate (2×30 mL). The combined organic layers were washed with brine (30 mL), dried over sodium sulfate, filtered and the filtrate was concentrated under reduced pressure. The residue was purified by silica gel column chromatography (0-100%/ethyl acetate in petroleum ether) to afford (3S)-tert-butyl 4-(7-(2-amino-6-fluorophenyl)-6-fluoro-1-(4-(3-hydroxypropyl)-2-isopropylpyridin-3-yl)-2-oxo-1,2-dihydropyrido[2,3-d]pyrimidin-4-yl)-3-methylpiperazine-1-carboxylate (Int-112a). MS (ESI): m/z 650 [M+H]$^+$.

Step B: (3S)-tert-butyl 4-(7-(2-((tert-butoxycarbonyl)amino)-6-fluorophenyl-6-fluoro-1-(4-(3-hydroxyprop yl-2-isopropylpyridin-3-yl)-2-oxo-1,2-dihydropyrido[2,3-d]pyrimidin-4-yl)-3methylpiperazine-1carboxylate (Int-112b)

To a mixture of (3S)-tert-butyl 4-(7-(2-amino-6-fluorophenyl)-6-fluoro-1-(4-(3-hydroxypropyl)-2-isopropylpyridin-3-yl)-2-oxo-1,2-dihydropyrido[2,3-d]pyrimidin-4-yl)-3-methylpiperazine-1-carboxylate (Int-112a, 620 mg, 0.95 mmol) in MeOH (6.0 mL) was added di-tert-butyl dicarbonate (3.0 mL, 13 mmol) under a nitrogen atmosphere. The mixture was then heated to 65° C. for 15 hours. After 15 hours, the mixture was allowed to cool to room temperature and then more di-tert-butyl dicarbonate (3.0 mL, 13 mmol) was added. The mixture was then heated to 65° C. for 15 hours. After 15 hours, the mixture was allowed to cool to room temperature and then more di-tert-butyl dicarbonate (3.0 mL, 13 mmol) was added. The mixture was then heated to 65° C. for 15 hours. After 15 hours, the mixture was allowed to cool to room temperature. The mixture was concentrated under reduced pressure and the resulting residue was purified by silica gel column chromatography (0-100% ethyl acetate in petroleum ether) to afford (3S)-tert-butyl 4-(7-(2-((tert-butoxycarbonyl)amino)-6-fluorophenyl)-6-fluoro-1-(4-(3-hydroxypropyl)-2-isopropylpyridin-3-yl)-2-oxo-1,2-dihydropyrido[2,3-d]pyrimidin-4-yl)-3-methylpiperazine-1-carboxylate (Int-112b). MS (ESI): m/z 750 [M+H]$^+$.

Step C: Int-112c

To a mixture of (3S)-tert-butyl 4-(7-(2-((tert-butoxycarbonyl)amino)-6-fluorophenyl)-6-fluoro-1-(4-(3-hydroxypropyl)-2-isopropylpyridin-3-yl)-2-oxo-1,2-dihydropyrido[2,3-d]pyrimidin-4-yl)-3 methylpiperazine-1-carboxylate (Int-112b, 450 mg, 0.600 mmol) in THF (35 mL) was added triphenylphosphine (1.26 g, 4.80 mmol) under a nitrogen atmosphere. The mixture was heated to 65° C. Diisopropyl azodicarboxylate (1.8 mL, 9.0 mmol) was added and the mixture was stirred for 20 minutes at 65° C. After 20 minutes, the mixture was allowed to cool to room temperature and was then concentrated under reduced pressure. The resulting residue was purified by silica gel column chromatography (0-20% methanol in dichloromethane) to afford Int-112c. MS (ESI): m/z 732 [M+H]$^+$.

Step D: Int-112d

To a mixture of Int-112c (290 mg, 0.396 mmol) in DCM (5.0 mL) was added TFA (2.0 mL), and the mixture was stirred at room temperature for 3 hours. The mixture was then concentrated under reduced pressure and the resulting residue was purified by preperative-TLC (CH$_2$Cl$_2$/MeOH=10:1) to afford Int-112d. MS (ESI): m/z 532 [M+H]$^+$.

Step E: 17,20-difluoro-2-[(2S)-2-methyl-4-(prop-2-enoyl)piperazin-1-yl]-6-(propan-2-yl)-10,11,12,13-tetrahydro-4H-1,18-ethenopyrido[4,3-e]pyrimido[1,6-g][1,7,9]benzotriazacyclododecin-4-one (Ex. 112)

A mixture of Int-112d (90 mg, 0.17 mmol) in THF (2.0 mL) and water (0.50 mL) was cooled to 0° C. under a nitrogen atmosphere. DIPEA (0.15 mL, 0.85 mmol) and acryloyl chloride (14 μL, 0.17 mmol) were added and the mixture was stirred at 0° C. for 30 minutes. The mixture was diluted with brine (10 mL) and then extracted with ethyl acetate (3×10 mL). The combined organic layers were dried over Na$_2$SO$_4$, filtered and the filtrate was concentrated under reduced pressure. The resulting residue was purified by prep-TLC (100% ethyl acetate). The racemic material was then purified by SFC Column D, Condition: 0.1% NH$_3$H$_2$O EtOH to afford 17,20-difluoro-2-[(2S)-2-methyl-4-(prop-2-enoyl)piperazin-1-yl]-6-(propan-2-yl)-10,11,12,13-tetrahydro-4H-1,18-ethenopyrido[4,3-e]pyrimido[1,6-g][1,7,9]benzotriazacyclododecin-4-one (Ex. 112). MS (ESI): m/z 586 [M+H]$^+$. $^1$H NMR (500 MHz, Methanol-d$_4$): δ 8.52 (d, J=5.2 Hz, 1H), 8.27 (br dd, J=9.1, 15.3 Hz, 1H), 7.44 (d, J=5.2 Hz, 1H), 7.34-7.25 (m, 1H), 6.94-6.79 (m, 1H), 6.74 (d, J=8.2 Hz, 1H), 6.59 (t, J=8.9 Hz, 1H), 6.34 (br d, J=16.8 Hz, 1H), 5.87 (br d, J=9.5 Hz, 1H), 4.94 (br s, 1H), 4.87-3.44 (m, 6H), 3.36 (br s, 1H), 3.00-2.82 (m, 2H), 2.72 (br d, J=16.2 Hz, 1H), 2.61-2.50 (m, 1H), 2.42 (br t, J=11.3 Hz, 1H), 2.12-1.97 (m, 1H), 1.65-1.55 (m, 3H), 1.25 (d, J=6.7 Hz, 3H), 0.98 (d, J=6.7 Hz, 3H).

Example 113: 2-[(2S,5R)-2,5-dimethyl-4-(prop-2-enoyl)piperazin-1-yl]-20-fluoro-14-hydroxy-6-(propan-2-yl)-11,12-dihydro-4H,10H-1,18-(ethanediylidene)pyrido[4,3-e]pyrimido[1,6-g][1,7,9]benzoxadiazacyclododecin-4-one
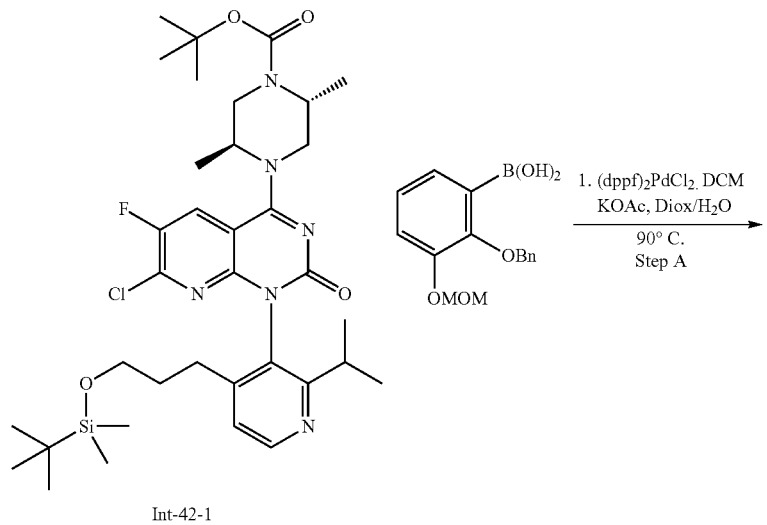
Int-42-1
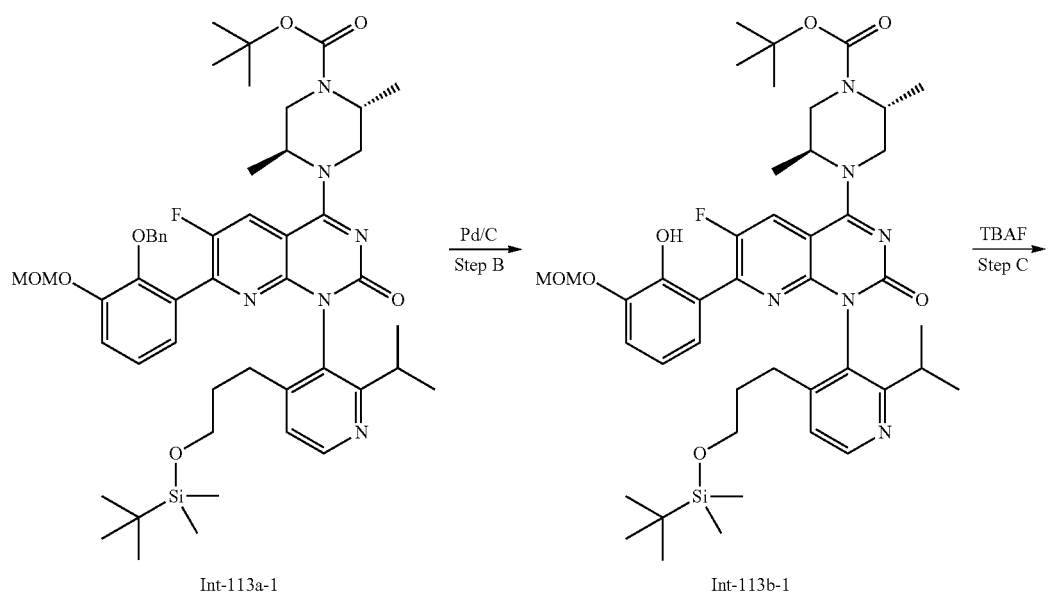
Int-113a-1  Int-113b-1

253 254

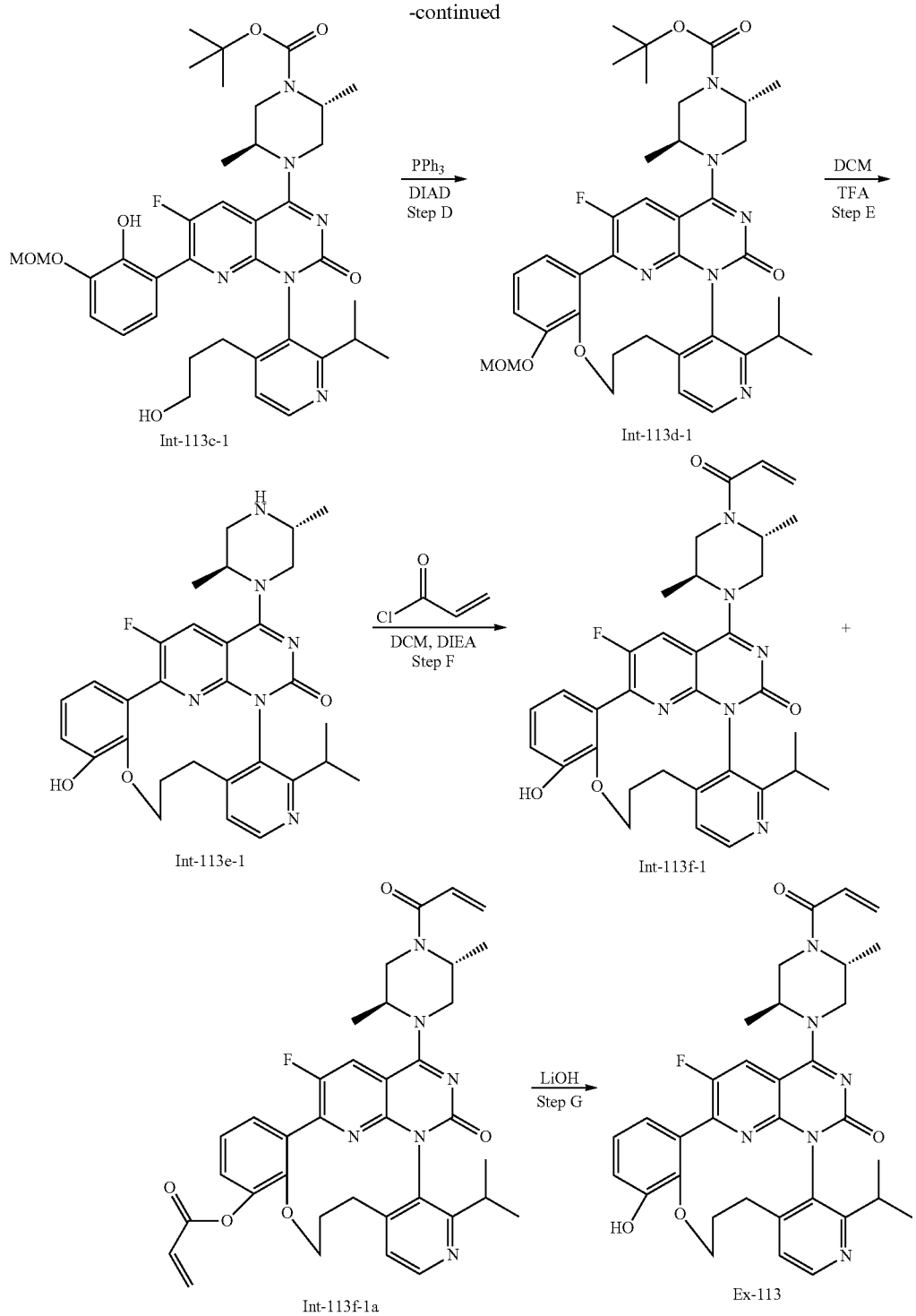

Step A: tert-butyl (2R,5S)-4-(7-(2-(benzyloxy)-3-(methoxymethoxy)phenyl)-1-(4-(3-((tert-butyldimethylsily)oxy)propyl)-2-isopropylpyridin-3-yl)-6-fluoro-2-oxo-1,2-dihydropyrido[2,3-d]pyrimidin-4-yl)-2,5-dimethylpiperazine-1l-carboxylate(Int-113a-1)

A flask containing (2-(benzyloxy)-3-(methoxymethoxy)phenyl)boronic acid (0.100 g, 0.347 mmol), potassium acetate (112 mg, 1.14 mmol), 1,1'-bis(diphenylphosphino)ferrocene-palladium(II)dichloride dichloromethane complex (23.0 mg, 0.028 mmol), tert-butyl (2R,5S)-4-(1-(4-(3-((tert-butyldimethylsilyl)oxy)propyl)-2-isopropylpyridin-3-yl)-7-chloro-6-fluoro-2-oxo-1,2-dihydropyrido[2,3-d]pyrimidin-4-yl)-2,5-dimethylpiperazine-1-carboxylate (Int-42-1, 0.200 g, 0.284 mmol) was sealed and purged with argon. Dioxane (1.2 mL) and water (0.20 mL) were added and the mixture was purged for 10 min. The reaction mixture was then heated to 100° C. for 18 hours. After 18 hours, the mixture was allowed to cool to room temperature and then diluted with saturated aqueous sodium bicarbonate (125 mL) and water (125 mL) and extracted with EtOAc (3×250 mL). The combined organic layers were dried over sodium sulfate, filtered, and concentrated under reduced pressure. The resulting residue was taken on to the next step without further purification or characterization.

Step B: tert-butyl (2R,5S)-4-(1-(4-(3-((tert-butyldimethylsilyl)oxy)propyl)-2-isopropylpyridin-3-yl)-6-fluoro-7-(2-hydroxy-3-(methoxymethoxyphenyl)-2-oxo-1,2-dihydropyrido[2,3-d]pyrimidin-4-yl)-2,5-dimethylpiperazine-1-carboxylate(Int-113b-1)

A flask containing crude tert-butyl (2R,5S)-4-(7-(2-(benzyloxy)-3-(methoxymethoxy)phenyl)-1-(4-(3-((tert-butyldimethylsilyl)oxy)propyl)-2-isopropylpyridin-3-yl)-6-fluoro-2-oxo-1,2-dihydropyrido[2,3-d]pyrimidin-4-yl)-2,5-dimethylpiperazine-1-carboxylate (Int-113a-1, 246 mg, 0.270 mmol) in EtOH (1.4 mL) was sparged with nitrogen. Palladium on carbon (10% by weight, 58 mg, 0.054 mmol) was then added. The flask was fitted with a balloon of hydrogen. Hydrogen was bubbled through the mixture via subsurface bubbling. Hydrogen was allowed to bubble through the mixture for 30 minutes. The mixture was then stirred for 18 hours. After 18 hours, the hydrogen balloon was removed and the mixture was stirred opened to atmosphere. The mixture was then filtered through CELITE and the filtrate was concentrated under reduced pressure. The resulting mixture was purified by silica gel column chromatography (0-100% (3:1 ethyl acetate:ethanol) gradient in hexanes) to afford tert-butyl (2R,5S)-4-(1-(4-(3-((tert-butyldimethylsilyl)oxy)propyl)-2-isopropylpyridin-3-yl)-6-fluoro-7-(2-hydroxy-3-(methoxymethoxy)phenyl)-2-oxo-1,2-dihydropyrido[2,3-d]pyrimidin-4-yl)-2,5-dimethylpiperazine-1-carboxylate (Int-113b-1). MS (ESI): m/z 821 [M+H]$^+$.

Step C: tert-butyl (2R,5S)-4-(6-fluoro-7-(2-hydroxy-3-(methoxymethoxyphenyl)-1-(4(3-hydroxypropyl)-2-isopropylpyridin-3-yl)-2-oxo-1,2-dihydropyrido[2,3-d]pyrimidin-4-yl)-2,5-dimethylpiperazine-1-carboxylate (Int-113c-1)

A flask containing tert-butyl (2R,5S)-4-(1-(4-(3-((tert-butyldimethylsilyl)oxy)propyl)-2-isopropylpyridin-3-yl)-6-fluoro-7-(2-hydroxy-3-(methoxymethoxy)phenyl)-2-oxo-1,2-dihydropyrido[2,3-d]pyrimidin-4-yl)-2,5-dimethylpiperazine-1-carboxylate (Int-113b-1, 186 mg, 0.227 mmol) in THF (1.0 mL) was cooled to 0° C. TBAF (1.0 M in THF, 1.0 mL, 1.0 mmol) was added and the mixture was then allowed to warm to room temperature and the mixture was stirred at room temperature for 4 hours. After 4 hours, the mixture was concentrated under reduced pressure and the mixture was purified by silica gel column chromatography (0-100% (3:1 ethyl acetate:ethanol) gradient in hexanes) to afford tert-butyl (2R,5S)-4-(6-fluoro-7-(2-hydroxy-3-(methoxymethoxy)phenyl)-1-(4-(3-hydroxypropyl)-2-isopropylpyridin-3-yl)-2-oxo-1,2-dihydropyrido[2,3-d]pyrimidin-4-yl)-2,5-dimethylpiperazine-1-carboxylate (Int-113c-1). MS (ESI): m/z 707 [M+H]$^+$.

Step D: Int-113d-1

To a mixture of tert-butyl (2R,5S)-4-(6-fluoro-7-(2-hydroxy-3-(methoxymethoxy)phenyl)-1-(4-(3-hydroxypropyl)-2-isopropylpyridin-3-yl)-2-oxo-1,2-dihydropyrido[2,3-d]pyrimidin-4-yl)-2,5-dimethylpiperazine-1-carboxylate (Int-113c-1, 0.13 g, 0.19 mmol) in THF (6.2 mL) was added triphenylphosphine (0.12 g, 0.46 mmol) followed by diisopropyl azodicarboxylate (72 μL, 0.37 mmol). The mixture was stirred for 2 hours at room temperature. After 2 hours, the mixture was concentrated under reduced pressure and then purified by silica gel column chromatography (0-100% (3:1 ethyl acetate:ethanol) gradient in hexanes) to afford Int-113d-1. MS (ESI): m/z 689 [M+H]$^+$.

Step E: Int-113e-1

To a flask containing Int-113d-1 (0.090 g, 0.13 mmol) in DCM (5.0 mL) was added TFA (1.0 ml, 13 mmol). The reaction mixture was stirred at room temperature for 18 hours. After 18 hours, the mixture concentrated under reduced pressure. The resulting residue was used without further purification or characterization.

Step F: Int-113f-1 and Int-113f-1a

To a mixture of crude Int-113e-1 (71 mg, 0.13 mmol) in dichloromethane (2.0 mL) was added DIPEA (0.23 mL, 1.3 mmol) followed by acryloyl chloride (12 μL, 0.14 mmol) 0.012 ml, 0.143 mmol). The mixture was allowed to stir for 1 hour at room temperature. After 1 hour, the mixture was concentrated under reduced pressure and then purified by silica gel column chromatography (0-100% (3:1 ethyl acetate:ethanol) gradient in hexanes) to afford a 1:1 mixture of Int-113f-1 and Int-113f-1a. This mixture was taken on to the next step without further purification.

Step G: 2-[(2S,5R)-2,5-dimethyl-4-(prop-2-enoyl) piperazin-1-yl]-20-fluoro-14-hydroxy-6-(propan-2-yl)-11,12-dihydro-4H,10H-1,18-(ethanediylidene) pyrido[4,3-e]pyrimido[1,6-g][1,7,9] benzoxadiazacyclododecin-4-one (Ex. 113)

To a 1:1 mixture of crude Int-113f-1 and Int-113f-1a (50 mg total) in THF (1.0 mL) was added lithium hydroxide (10 mg, 0.42 mmol). The reaction mixture was allowed to stir for 18 hours at room temperature. After 18 hours, the resulting mixture was purified by RP-HPLC ((C-18), Acetonitrile/Water+0.1% TFA). The fractions that contained product were pooled and then concentrated under reduced pressure to afford the desired product. The mixture was then purified further via RP-HPLC ((C-18), Acetonitrile/Water+0.1% TFA). The fractions that contained product were pooled and concentrated under reduced pressure to afford 2-[(2S,5R)-2,5-dimethyl-4-(prop-2-enoyl)piperazin-1-yl]-20-fluoro-14-hydroxy-6-(propan-2-yl)-11,12-dihydro-4H,10H-1,18-(ethanediylidene)pyrido[4,3-e]pyrimido[1,6-3][1,7,9] benzoxadiazacyclododecin-4-one (Ex. 113). MS (ESI): m/z 599 [M+H]$^+$. $^1$H NMR (500 MHz, Methanol-d$_4$): δ 8.65 (d, J=6.0 Hz, 1H), 8.19 (dd, J=19.3, 9.5 Hz, 1H), 7.95 (d, J=6.1 Hz, 1H), 7.04-7.00 (m, 1H), 6.99-6.88 (m, 2H), 6.80 (dd, J=16.8, 10.7 Hz, 1H), 6.32 (dd, J=16.7, 4.3 Hz, 1H), 5.90-5.82 (m, 1H), 5.07-5.00 (m, 1H), 5.00-4.91 (m, 1H), 4.77-4.69 (m, 1H), 4.69-4.59 (m, 1H), 4.43-4.35 (m, 1H), 4.01-3.92 (m, 1H), 3.85-3.70 (m, 2H), 3.53-3.45 (m, 1H), 2.84-2.75 (m, 1H), 2.66-2.50 (m, 2H), 2.20-2.09 (m, 1H), 1.62 (dd, J=15.3, 6.6 Hz, 3H), 1.46 (dd, J=18.8, 6.8 Hz, 3H), 1.38 (d, J=5.6 Hz, 3H), 1.18 (t, J=7.3 Hz, 3H).
Example 114: 2-[(2S,5R)-2,5-dimethyl-4-(prop-2-enoyl)piperazin-1-yl]-14,20-difluoro-6-(propan-2-yl)-11,12-dihydro-4H-1,18-(ethanediylidene)pyrido[4,3-e]pyrimido[1,6-g][1,4,7,9]benzodioxadiazacyclododecin-4-one
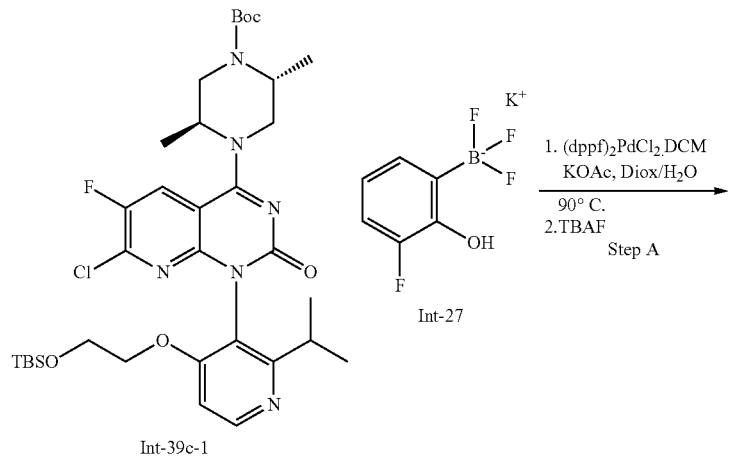
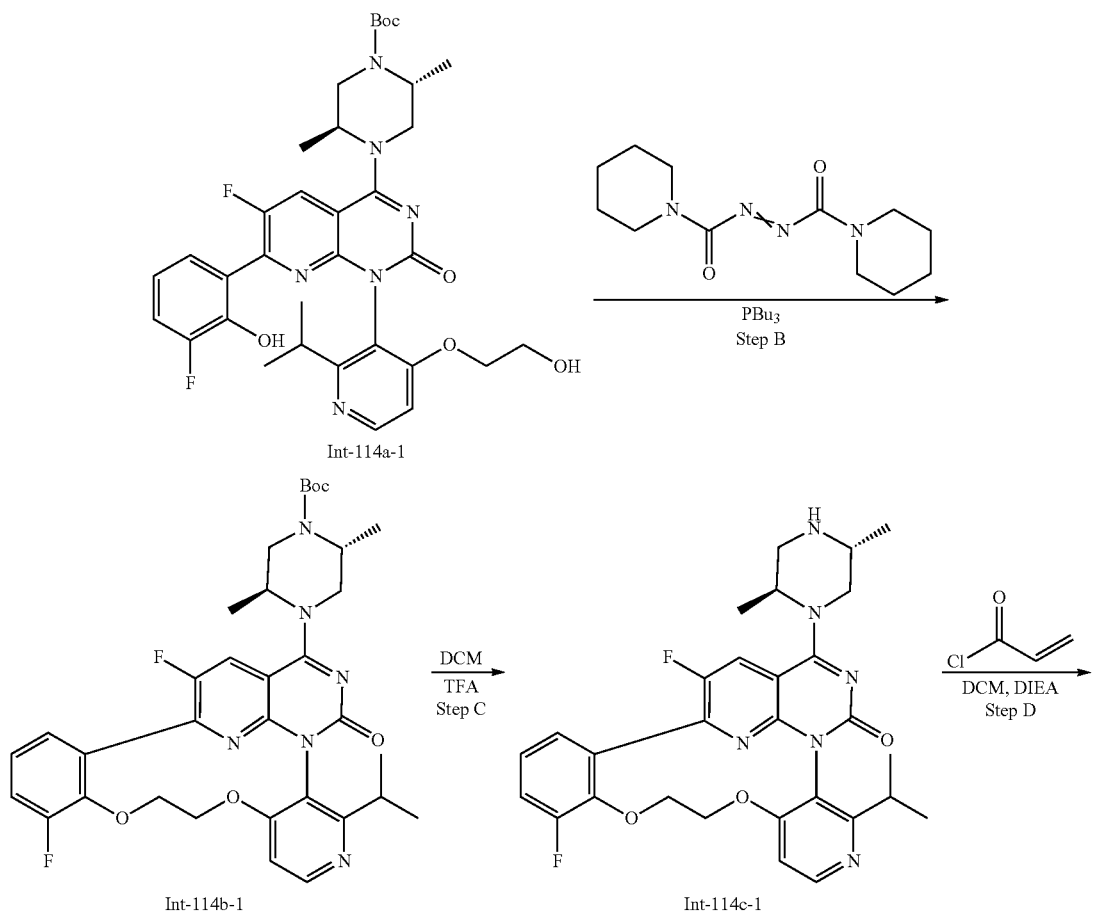

-continued

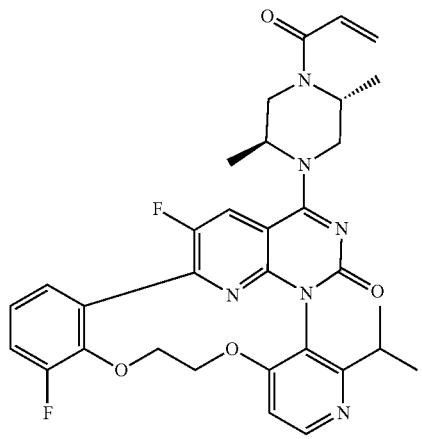

Ex-114

Step A: tert-butyl (2R,5S)-4-(6-fluoro-7-(3-fluoro-2-hydroxyphenyl)-1-(4-(2-hydroxyethoxy)-2-isopropylpyridin-3-yl)-2-oxo-1,2-dihydropyrido[2,3-d]pyrimidin-4-yl)-2,5-dimethylpiperazine-1-carboxylate (Int-114a-1)

A flask containing tert-butyl (2R,5S)-4-(1-(4-(2-((tert-butyldimethylsilyl)oxy)ethoxy)-2-isopropylpyridin-3-yl)-7-chloro-6-fluoro-2-oxo-1,2-dihydropyrido[2,3-d]pyrimidin-4-yl)-2,5-dimethylpiperazine-1-carboxylate (Int-39c-1, 0.10 g, 0.14 mmol), potassium trifluoro(3-fluoro-2-hydroxyphenyl)borate (Int-27, 40.0 mg, 0.180 mmol), potassium acetate (56 mg, 0.57 mmol), 1,1'-bis(diphenylphosphino)ferrocenepalladium(II)dichloride dichloromethane complex (12.0 mg, 0.014 mmol) was degassed with nitrogen, and then dioxane (0.60 mL) and water (0.10 mL) were added. Degassing of the mixture was continued and then the mixture was heated to 90° C. for 1 hour. After 1 hour, the mixture was allowed to cool to room temperature and was quenched with a 1:1 mixture of water and saturated aqueous sodium bicarbonate (10 mL). The mixture was extracted with ethyl acetate (2×25 mL) and the combined organic layers were then washed with brine and concentrated under reduced pressure. To the resulting residue was added THF (10 mL) and then TBAF (1.0 M in THF, 0.35 mL, 0.35 mmol). The mixture was stirred for 1.5 hours. The reaction was then quenched with saturated aqueous ammonium chloride and the mixture was washed with ethyl acetate. The organic layer was separated and then washed with brine, dried over sodium sulfate, filtered and then concentrated under reduced pressure. The resulting residue was then purified by silica gel column chromatography (0-100% (3:1 ethyl acetate:ethanol) gradient in hexanes) to afford tert-butyl (2R,5S)-4-(6-fluoro-7-(3-fluoro-2-hydroxyphenyl)-1-(4-(2-hydroxyethoxy)-2-isopropylpyridin-3-yl)-2-oxo-1,2-dihydropyrido[2,3-d]pyrimidin-4-yl)-2,5-dimethylpiperazine-1-carboxylate (Int-114a-1). $^1$H NMR (500 MHz, Acetonitrile-$d_3$): δ 11.76 (s, 1H), 8.62 (d, J=5.6 Hz, 1H), 8.13 (d, J=12.5 Hz, 1H), 7.92 (d, J=8.4 Hz, 1H), 7.25 (dd, J=10.0, 8.2 Hz, 1H), 7.05 (d, J=5.7 Hz, 1H), 6.93 (td, J=8.2, 5.2 Hz, 1H), 4.86-4.73 (m, 1H), 4.54-4.45 (m, 1H), 4.44-4.34 (m, 1H), 4.26 (d, J=13.7 Hz, 1H), 4.21-4.14 (m, 1H), 4.02-3.94 (m, 1H), 3.86-3.74 (m, 2H), 3.60-3.53 (m, 1H), 3.53-3.45 (m, 1H), 3.04-2.93 (m, 1H), 2.80 (t, J=6.1 Hz, 1H), 1.50 (s, 9H), 1.48 (s, 3H), 1.27 (d, J=6.8 Hz, 3H), 1.18 (d, J=6.7 Hz, 3H), 1.07 (d, J=6.7 Hz, 3H).

Step B: Int-114b-1

A flask containing tert-butyl (2R,5S)-4-(6-fluoro-7-(3-fluoro-2-hydroxyphenyl)-1-(4-(2-hydroxyethoxy)-2-isopropylpyridin-3-yl)-2-oxo-1,2-dihydropyrido[2,3-d]pyrimidin-4-yl)-2,5-dimethylpiperazine-1-carboxylate (Int-114a-1, 50.0 mg, 0.075 mmol) was evacuated and backfilled with a balloon of nitrogen three times. Dichloromethane (4.0 mL) and tributylphosphine (46 µL, 0.19 mmol) were added into the reaction vessel. Diazene-1,2-diylbis(piperidin-1-yl-methanone) (38 mg, 0.15 mmol) was added into the reaction vessel and the mixture was stirred for 3 hours. After 3 hours, the mixture was concentrated under reduced pressure. The resulting residue was purified by silica gel column chromatography (0-100/0 (3:1 ethyl acetate:ethanol) gradient in hexanes). The fractions containing product were pooled, concentrated under reduced pressure and then purified further via RP-HPLC (15-100% acetonitrile gradient in water with a 0.1% TFA modifier). The fractions containing product were pooled and concentrated under reduced pressure to afford Int-114b-1. MS (ESI): m/z 649 [M+H]$^+$.

Step C: Int-114c-1

To a flask containing Int-114b-1 were added dichloromethane (0.40 mL) and TFA (0.30 mL, 3.9 mmol). The mixture was stirred at room temperature for 1 hour. The mixture was then concentrated under reduced pressure. The resulting residue was used in the subsequent reaction without further purification. MS (ESI): m/z 549 [M+H]$^+$.

Step D: 2-[(2S,5R)-2,5-dimethyl-4-(prop-2-enoyl)piperazin-1-yl]-14,20-difluoro-6-(propan-2-yl)-11,12-dihydro-4H-1,18-(ethanediylidene)pyrido[4,3-e]pyrimido[1,6-g][1,4,7,9]benzodioxadiazacyclododecin-4-one (Ex.114)

A flask containing crude Int-114c-1 and dichloromethane (0.25 mL) was cooled to 0° C. N-Ethyl-N-isopropylpropan-2-amine (40 µL, 0.23 mmol) and acryloyl chloride (5.50 µL, 0.067 mmol) were added into the reaction vessel. The reaction mixture was stirred at 0° C. for one hour. The product mixture was then quenched with saturated aqueous ammonium bicarbonate (2.0 mL). The resulting mixture was extracted ethyl acetate (3×20 mL). The combined organic layers were dried over sodium sulfate, filtered and the filtrate was concentrated under reduced pressure. The resulting residue was purified by silica gel column chromatography (0-100% (3:1 ethyl acetate:ethanol) gradient in hexanes) to afford 2-[(2S,5R)-2,5-dimethyl-4-(prop-2-enoyl)piperazin-1-yl]-14,20-difluoro-6-(propan-2-yl)-11,12-dihydro-4H-1,18-(ethanediylidene)pyrido[4,3-e]pyrimido[1,6-g][1,4,7,9]benzodioxadiazacyclododecin-4-one (Ex.114). MS (ESI): m/z 603 [M+H]+. 1H NMR (500 MHz, DMSO-d6): δ 8.41 (d, J=5.7 Hz, 1H), 8.08 (dd, J=17.5, 9.2 Hz, 1H), 7.51-7.39 (m, 1H), 7.30-7.20 (m, 2H), 7.15 (d, J=5.8 Hz, 1H), 6.94-6.76 (m, 1H), 6.23-6.16 (m, 1H), 5.80-5.73 (m, 1H), 4.81-4.75 (m, 1H), 4.60-4.48 (m, 2H), 4.37-4.30 (m, 1H), 4.21 (d, J=13.5 Hz, 1H), 4.05-3.97 (m, 1H), 3.89-3.82 (m, 1H), 3.69-3.62 (m, 1H), 3.62-3.53 (m, 1H), 3.27-3.18 (m, 1H), 3.01-2.91 (m, 1H), 1.49-1.42 (m, 3H), 1.38-1.30 (m, 3H), 1.20-1.14 (m, 3H), 0.96-0.90 (m, 3H).

Example 115: 2-[(2S,5R)-2,5-dimethyl-4-(prop-2-enoyl)piperazin-1-yl]-17,20-difluoro-6-(propan-2-yl)-10,11-dihydro-1,18-ethenopyrido[3,4-e]pyrimido[6,1-c][9,2,4]benzoxadiazacyclododecin-4(13H)-one

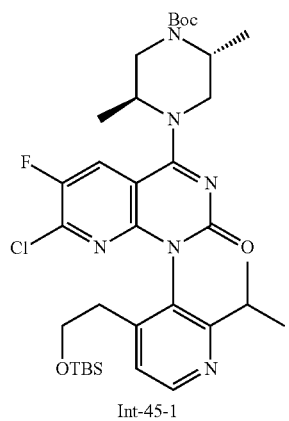

Int-45-1

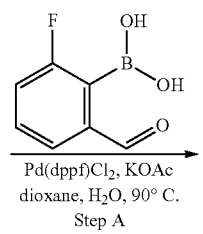

Pd(dppf)Cl2, KOAc
dioxane, H2O, 90° C.
Step A

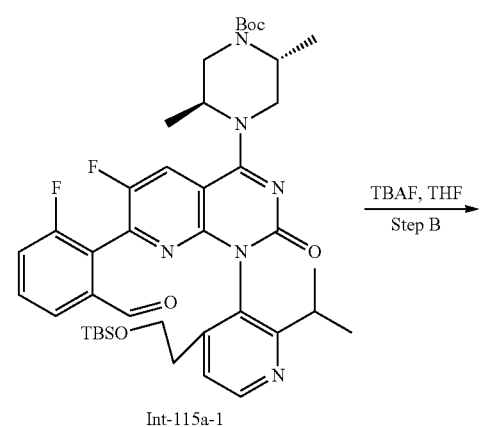

Int-115a-1

TBAF, THF
Step B

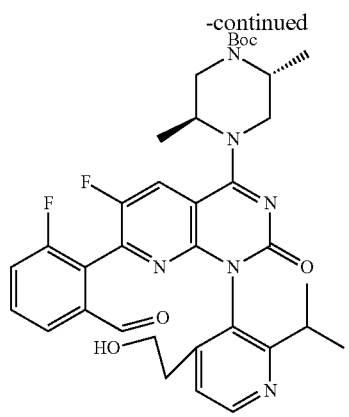

Int-115b-1

Et3SiH, TfOH
CH3NO2, rt. 1 h
Step C

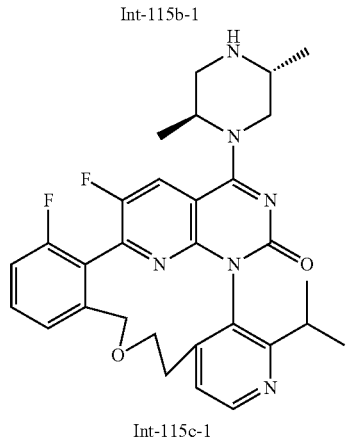

Int-115c-1

Step D

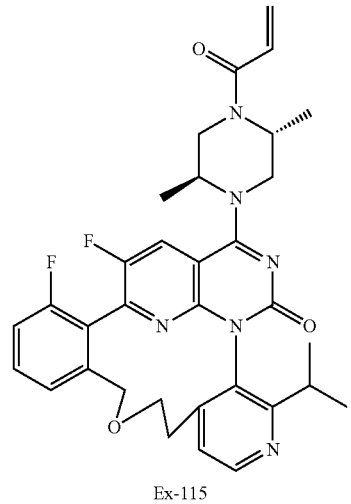

Ex-115

Step A: (2R,5S)-tert-butyl 4-(1-(4-(2-((tert-butyldimethylsilyl)oxy)ethyl)-2-isopropylpyridin-3-yl)-6-fluoro-7-(2-fluoro-6-formylphenyl)-2-oxo-1,2-dihydropyrido[2,3-d]pyrimidin-4-yl)-2,5-dimethylpiperazine-1-carboxylate (Int-115a-1)

To a mixture of (2R,5S)-tert-butyl 4-(1-(4-(2-((tert-butyldimethylsilyl)oxy)ethyl)-2-isopropylpyridin-3-yl)-7-chloro-6-fluoro-2-oxo-1,2-dihydropyrido[2,3-d]pyrimidin-4-yl)-2,5-dimethylpiperazine-1-carboxylate (Int-45-1, 0.77 g, 1.1 mmol), potassium acetate (0.55 mg, 5.6 mmol) and 1,1'-bis(diphenylphosphino)ferrocene-palladium(II)dichloride dichloromethane complex (91 mg, 0.11 mmol) in 1,4- dioxane (18 mL), water (2.0 mL) was added (2-fluoro-6-formylphenyl)boronic acid (0.38 g, 2.2 mmol). The mixture was heated to 90° C. for 30 min under a nitrogen atmosphere, cooled to room temperature and then diluted with ethyl acetate (35 mL). The mixture was washed with brine (2×15 mL), dried over Na$_2$SO$_4$, filtered and the filtrate was concentrated under reduced pressure. The resulting residue was purified by silica gel column chromatography (0-10% methanol/dichloromethane) to afford (2R,5S)-tert-butyl 4-(1-(4-(2-((tert-butyldimethylsilyl)oxy)ethyl)-2-isopropylpyridin-3-yl)-6-fluoro-7-(2-fluoro-6-formylphenyl)-2-oxo-1,2-dihydropyrido[2,3-d]pyrimidin-4-yl)-2,5-dimethylpiperazine-1-carboxylate (Int-115a-1). MS (ESI): m/z 777 [M+H]$^+$.

Step B: tert-butyl (2R,5S)-4-(6-fluoro-7-(2-fluoro-6-formylphenyl)-1-(4-(2-hydroxyethyl)-2-isopropylpyridin-3-yl)-2-oxo-1,2-dihydropyrido[2,3-d]pyrimidin-4-yl)-2,5-dimethylpiperazine-1-carboxylate (Int-115b-1)

To a mixture of (2R,5S)-tert-butyl 4-(1-(4-(2-((tert-butyldimethylsilyl)oxy)ethyl)-2-isopropylpyridin-3-yl)-6-fluoro-7-(2-fluoro-6-formylphenyl)-2-oxo-1,2-dihydropyrido[2,3-d]pyrimidin-4-yl)-2,5-dimethylpiperazine-1-carboxylate (Int-115a-1, 0.40 g, 0.52 mmol) in THF (6.0 mL) at 0° C. was added tetrabutylammonium fluoride (1.0 M in THF, 1.0 mL, 1.0 mmol). The mixture was allowed to warm to room temperature and was then stirred for 1 hour at room temperature. After 1 hour, the mixture was quenched with brine (10 mL) and extracted with ethyl acetate (40 mL). The organic layer was washed with brine (2×8 mL), dried over Na$_2$SO$_4$, filtered and the filtrate was concentrated under reduced pressure. The resulting mixture was purified by reverse phase MPLC (C18, 20-35 μm, gradient elution 0-34% MCCN in water with 0.5% trifluoroacetic acid modifier) to afford tert-butyl (2R,5S)-4-(6-fluoro-7-(2-fluoro-6-formylphenyl)-1-(4-(2-hydroxyethyl)-2-isopropylpyridin-3-yl)-2-oxo-1,2-dihydropyrido[2,3-d]pyrimidin-4-yl)-2,5-dimethylpiperazine-1-carboxylate Int-115b-1. MS (ESI): m/z 663 [M+H]$^+$. $^1$H NMR (400 MHz, Chloroform-d) δ 9.82 (s, 1H), 8.89 (br d, J=5.9 Hz, 1H), 7.92 (br d, J=8.2 Hz, 1H), 7.79-7.63 (m, 3H), 7.51-7.37 (m, 1H), 5.00 (br s, 1H), 4.73-4.39 (m, 1H), 4.39-4.15 (m, 1H), 3.95 (br s, 2H), 3.86-3.78 (m, 3H), 3.49 (br d, J=12.5 Hz, 1H), 2.89 (br s, 1H), 2.73 (br d, J=18.4 Hz, 2H), 1.52 (s, 12H), 1.44-1.38 (m, 3H), 1.32 (br d, J=5.9 Hz, 3H), 1.22-1.13 (m, 3H).

Step C: Int-115c-1

To a mixture of Int-115b-1 (0.10 g, 0.15 mmol) in CH$_3$NO$_2$ (12 mL) was added triflic acid (0.20 mL, 2.3 mmol) and triethylsilane (0.24 mL, 1.5 mmol) under a nitrogen atmosphere. The mixture was allowed to stir at room temperature for 30 min. The mixture was concentrated under reduced pressure to afford Int-115c-1 which was used without further purification. MS (ESI): m/z 547 [M+H]$^+$.

Step D: 2-[(2S,5R)-2,5-dimethyl-4-(prop-2-enoyl)piperazin-1-yl]-17,20-difluoro-6-(propan-2-yl)-10,11-dihydro-1,18-ethenopyrido[3,4-e]pyrimido[6,1-c][9,2,4]benzoxadiazacyclododecin-4(13H)-one (Ex.115)

To a mixture of Int-115c-1 (80 mg, 0.15 mmol) in dichloromethane (2.0 mL) were added N,N-diisopropylethylamine (77 μL, 0.44 mmol) and acryloyl chloride (24 μL, 0.29 mmol) at room temperature. The mixture was stirred for 5 minutes and then concentrated under reduced pressure. The resulting residue was purified by preparative TLC (7% methanol in DCM). The top spot from the preparative TLC was then purified by SFC (Column O, Condition: 45% (0.1% ammonium hydroxide/ethanol) to afford 2-[(2S,5R)-2,5-dimethyl-4-(prop-2-enoyl)piperazin-1-yl]-17,20-difluoro-6-(propan-2-yl)-10,11-dihydro-1,18-ethenopyrido[3,4-e]pyrimido[6,1-c][9,2,4]benzoxadiazacyclododecin-4(13H)-one (Ex.115): MS (ESI): m/z 601 [M+H]$^+$; $^1$H NMR (500 MHz, Methanol-d$_4$) δ 8.40 (d, J=5.2 Hz, 1H), 8.23 (dd, J=6.6, 8.9 Hz, 1H), 7.46 (d, J=5.3 Hz, 1H), 7.38 (dt, J=5.8, 7.9 Hz, 1H), 7.18-7.07 (m, 2H), 6.81-6.66 (m, 1H), 6.20 (ddd, J=1.8, 10.4, 16.7 Hz, 1H), 5.77-5.68 (m, 1H), 5.10 (br s, 1H), 4.41-4.34 (m, 1H), 4.21-4.03 (m, 3H), 3.94-3.80 (m, 2H), 3.73-3.68 (m, 1H), 3.65-3.58 (m, 1H), 3.12 (q, J=7.2 Hz, 1H), 2.86 (td, J=6.8, 13.5 Hz, 1H), 2.48-2.37 (m, 2H), 1.36-1.29 (m, 3H), 1.27 (d, J=6.6 Hz, 3H), 1.16-1.11 (m, 3H), 0.89 (d, J=6.9 Hz, 3H).

Example 116: 2-[(2S,5R)-2,5-dimethyl-4-(prop-2-enoyl)piperazin-1-yl]-20-fluoro-6-(propan-2-yl)-14-(trifluoromethyl-11,12-dihydro-4H-1,18-ethenopyrido[4,3-e]pyrimido[1,6-g][1,4,7,9]benzodioxadiazacyclododecin-4-one

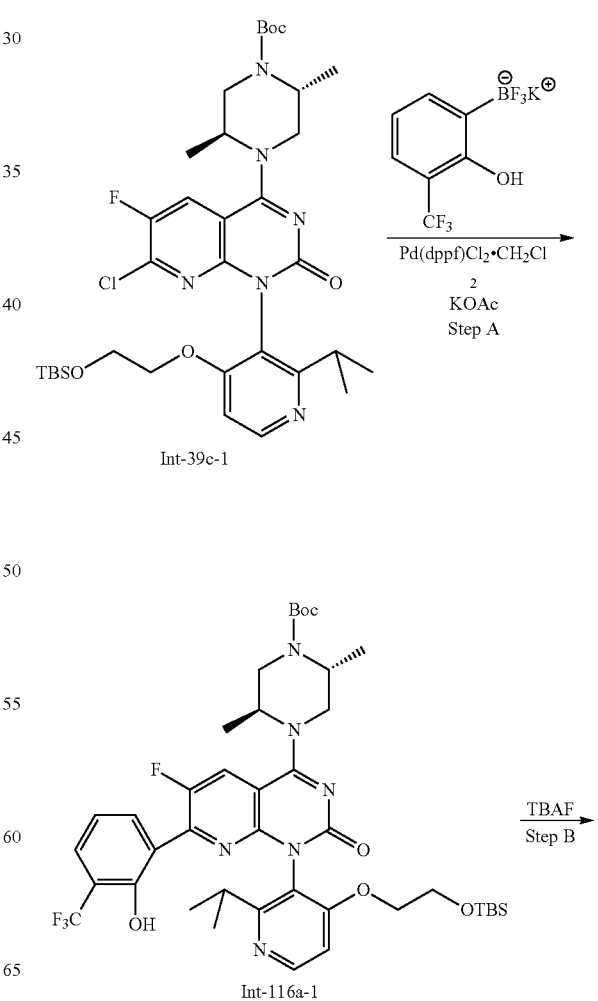

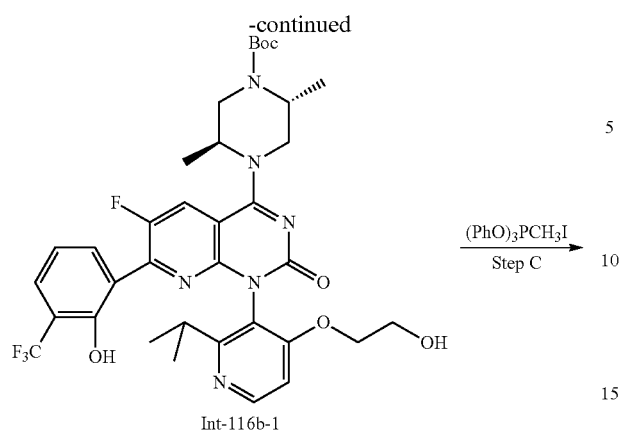

Int-116b-1

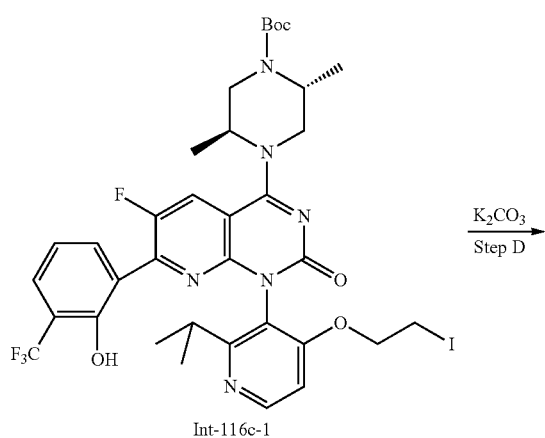

Int-116c-1

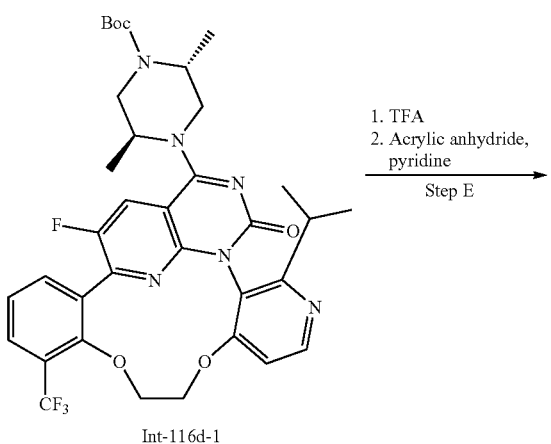

Int-116d-1

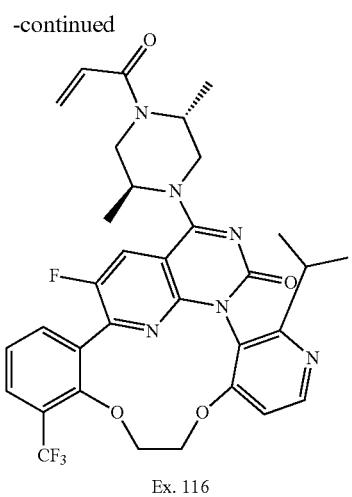

Ex. 116

Step A: tert-butyl (2R,5S)-4-(1-(4-(2-((tert-butyldimethylsilyl)oxy)ethoxy)-2-isopropylpyridin-3-yl)-6-fluoro-7-(2-hydroxy-3-(trifluoromethyl)phenyl)-2-oxo-1,2-dihydropyrido[2,3-d]pyrimidin-4-yl)-2,5-dimethylpiperazine-1-carboxylate (Int-116a)

A flask containing 1,1'-bis(diphenylphosphino)ferrocene-palladium(II)dichloride dichloromethane complex (23 mg, 0.028 mmol), potassium trifluoro(2-hydroxy-3-(trifluoromethyl)phenyl)borate (Int-30, 76 mg, 0.28 mmol), potassium acetate (83 mg, 0.85 mmol) and tert-butyl (2R,5S)-4-(1-(4-(2-((tert-butyldimethylsilyl)oxy)ethoxy)-2-isopropylpyridin-3-yl)-7-chloro-6-fluoro-2-oxo-1,2-dihydropyrido[2,3-d]pyrimidin-4-yl)-2,5-dimethylpiperazine-1-carboxylate (Int-39c, 0.20 g, 0.28 mmol) was sealed in a tube and purged with nitrogen. Dioxane (1.8 mL) and water (0.36 mL) were added and the mixture was subsurface sparged with nitrogen for 10 minutes. The mixture was heated to 100° C. for 18 hours. The mixture was concentrated under reduced pressure and the resulting residue was purified by silica gel column chromatography (0-100% (3:1 ethyl acetate:ethanol)/hexanes) to afford tert-butyl (2R,5S)-4-(1-(4-(2-((tert-butyldimethylsilyl)oxy)ethoxy)-2-isopropylpyridin-3-yl)-6-fluoro-7-(2-hydroxy-3-(trifluoromethyl)phenyl)-2-oxo-1,2-dihydropyrido[2,3-d]pyrimidin-4-yl)-2,5-dimethylpiperazine-1-carboxylate (Int-116a-1). MS (ESI) m/z: 831 [M+H]$^+$. $^1$H NMR (500 MHz, Methanol-d$_4$) δ 8.62 (d, J=5.9 Hz, 1H), 8.41-8.32 (m, 2H), 7.70 (d, J=7.1 Hz, 1H), 7.22 (d, J=5.9 Hz, 1H), 7.10 (t, J=7.9 Hz, 1H), 4.99-4.93 (m, 1H), 4.57-4.40 (m, 2H), 4.18-4.13 (m, 2H), 3.95-3.86 (m, 2H), 3.77-3.73 (m, 2H), 3.05-2.93 (m, 1H), 1.36 (d, J=6.6 Hz, 3H), 1.27 (d, J=6.8 Hz, 3H), 1.23-1.20 (m, 9H), 1.12 (d, J=6.8 Hz, 3H), 0.69 (s, 9H), −0.15 (s, 3H), −0.16 (s, 3H).

Step B: tert-butyl (2R,5S)-4-(6-fluoro-7-(2-hydroxy-3-(trifluoromethyl)phenyl)-1-(4-(2-hydroxyethoxy-2-isopropylpyridin-3-yl-2-oxo-1,2-dihydropyrido[2,3-d]pyrimidin-4-yl)-2,5-dimethylpiperazine-1-carboxylate (Int-116b-1)

To a flask containing tert-butyl (2R,5S)-4-(1-(4-(2-((tert-butyldimethylsilyl)oxy)ethoxy)-2-isopropylpyridin-3-yl)-6-fluoro-7-(2-hydroxy-3-(trifluoromethyl)phenyl)-2-oxo-1,2-dihydropyrido[2,3-d]pyrimidin-4-yl)-2,5-dimethylpiperazine-1-carboxylate (Int-116a-1, 151 mg, 0.182 mmol) in THF (2.0 ml) was added tetrabutylammonium fluoride (1.0 M in THF, 0.55 mL, 0.55 mmol). The reaction mixture was stirred at room temperature for 30 min. The reaction mixture was then concentrated under reduced pressure. The resulting residue was purified by silica gel column chromatography (0-100% (3:1 ethyl acetate:ethanol) gradient in hexanes) to afford tert-butyl (2R,5S)-4-(6-fluoro-7-(2-hydroxy-3-(trifluoromethyl)phenyl)-1-(4-(2-hydroxyethoxy)-2-isopropylpyridin-3-yl)-2-oxo-1,2-dihydropyrido[2,3-d]pyrimidin-4-yl)-2,5-dimethylpiperazine-1-carboxylate (Int-116b-1). MS (ESI) m/z: 717 [M+H]$^+$.

Step C: tert-butyl (2R,5S)-4-(6-fluoro-7-(2-hydroxy-3-(trifluoromethyl)phenyl-1-(4(2-iodoethoxy-2-isopropylpyridin-3-yl-2-oxo-1,2-dihydropyrido[2,3-d]pyrimidin-4-yl-2,5-dimethylpiperazine-1-carboxylate (Int-116c-1)

To a flask containing tert-butyl (2R,5S)-4-(6-fluoro-7-(2-hydroxy-3-(trifluoromethyl)phenyl)-1-(4-(2-hydroxyethoxy)-2-isopropylpyridin-3-yl)-2-oxo-1,2-dihydropyrido[2,3-d]pyrimidin-4-yl)-2,5-dimethylpiperazine-1-carboxylate (Int-116b-1, 50 mg, 0.070) in dichloromethane (0.70 mL) was added methyltriphenoxyphosphonium iodide (35 mg, 0.077 mmol) and the mixture was allowed to stir at room temperature for 2 h. The reaction mixture was then concentrated under reduced pressure. The resulting residue was purified by silica gel column chromatography (0-100% (3:1 ethyl acetate:ethanol)/hexanes) to tert-butyl (2R,5S)-4-(6-fluoro-7-(2-hydroxy-3-(trifluoromethyl)phenyl)-1-(4-(2-iodoethoxy)-2-isopropylpyridin-3-yl)-2-oxo-1,2-dihydropyrido[2,3-d]pyrimidin-4-yl)-2,5-dimethylpiperazine-1-carboxylate (Int-116c-1). MS (ESI) m/z: 827 [M+H]$^+$.

Step D: (Int-116d-1)

To a flask containing tert-butyl (2R,5S)-4-(6-fluoro-7-(2-hydroxy-3-(trifluoromethyl)phenyl)-1-(4-(2-iodoethoxy)-2-isopropylpyridin-3-yl)-2-oxo-1,2-dihydropyrido[2,3-d]pyrimidin-4-yl)-2,5-dimethylpiperazine-1-carboxylate (Int-116c-1, 25 mg, 0.030 mmol) in DMF (1.5 mL) was added potassium carbonate (21 mg, 0.15 mmol). The mixture was heated to 70° C. for 18 hours. After 18 hours, the mixture was allowed to cool to room temperature. The reaction mixture was filtered and the filtrate was purified by RP-HPLC (C-18 column, acetonitrile/water+0.1% TFA). The fractions containing product were concentrated under reduced pressure to afford Int-116d-1. MS (ESI) m/z: 699 [M+H]$^+$.

Step E: 2-[(2S,5R)-2,5-dimethyl-4-(prop-2-enoyl)piperazin-1-yl]-20-fluoro-6-(propan-2-yl)-14-(trifluoromethyl)-11,12-dihydro-4H-1,18-ethenopyrido[4,3-e]pyrimido[1,6-g][1,4,7,9]benzodioxadiazacyclododecin-4-one (Ex.116)

To a flask containing Int-116d-1 (5.3 mg, 7.6 µmol) in chloroform (2.0 mL) was added TFA (5.0 µL, 65 µmol) and the mixture was stirred at room temperature for 18 hours. The mixture was concentrated under reduced pressure. To the resulting residue was added DMSO (2.0 mL) followed by pyridine (20 µL, 0.25 mmol) and acrylic anhydride (50 µL, 0.43 mmol). The mixture was allowed to stir for 2 hours. The mixture was then filtered and the filtrate was purified by RP-HPLC (C-18, acetonitrile/water+0.1% TFA) to afford 2-[(2S,5R)-2,5-dimethyl-4-(prop-2-enoyl)piperazin-1-yl]-20-fluoro-6-(propan-2-yl)-14-(trifluoromethyl)-11,12-dihydro-4H-1,18-ethenopyrido[4,3-e]pyrimido[1,6-g][1,4,7,9]benzodioxadiazacyclododecin-4-one (Ex.116). MS (ESI) m/z: 653 [M+H]$^+$. $^1$H NMR (600 MHz, methanol-d$_4$) δ 8.70 (d, J=5.5 Hz, 1H), 8.25 (dd, J=23.8, 8.7 Hz, 1H), 7.97 (d, J=6.4 Hz, 1H), 7.95-7.92 (m, 1H), 7.82 (d, J=7.2 Hz, 1H), 7.45 (t, J=6.8 Hz, 1H), 6.98-6.72 (m, 1H), 6.39-6.25 (m, 1H), 5.86 (t, J=11.3 Hz, 1H), 5.39 (t, J=11.6 Hz, 1H), 4.44 (d, J=13.7 Hz, 1H), 4.35 (d, J=13.3 Hz, 1H), 4.05 (d, J=10.7 Hz, 1H), 3.97 (d, J=14.1 Hz, 1H), 3.80 (d, J=13.1 Hz, 1H), 3.59-3.52 (m, 1H), 3.48 (bs, 1H), 3.38-3.34 (m, 1H), 1.69-1.58 (m, 3H), 1.54-1.41 (m, 6H), 1.25 (s, 3H).

Example 117: 22-fluoro-9-[(2S)-2-methyl-4-(prop-2-enoyl)piperazin-1-yl]-13-(propan-2-yl)-18,19-dihydro-11H,17H-6,8-ethenopyrido[4',3':11,12]pyrimido[1',6':1,2][1,3,7]triazacyclododecino[5,6,7-hi]indazol-11-one

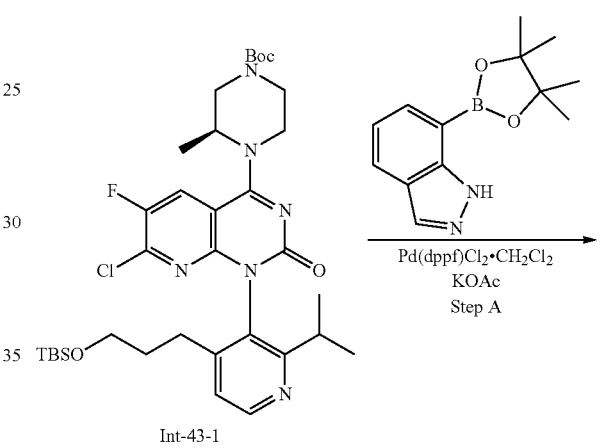

Int-43-1

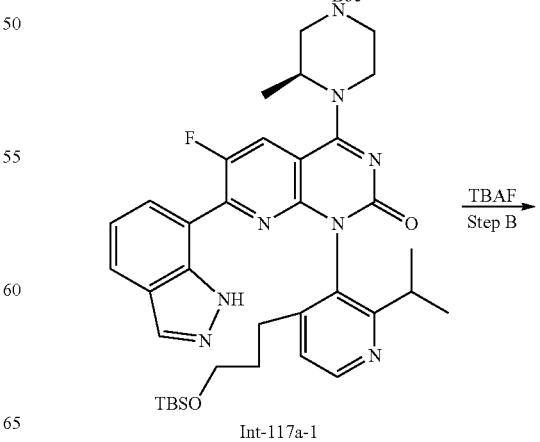

Int-117a-1

269

-continued

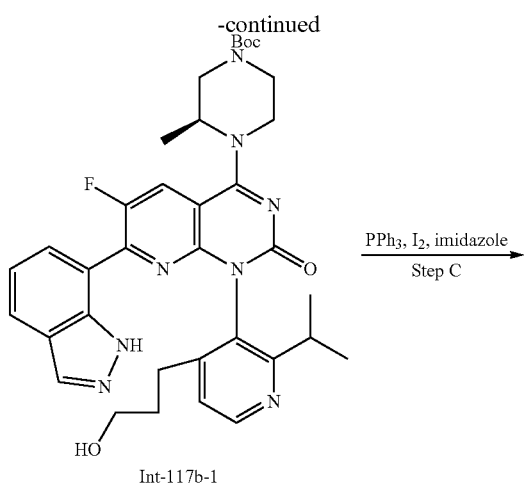
Int-117b-1

PPh₃, I₂, imidazole
Step C
→

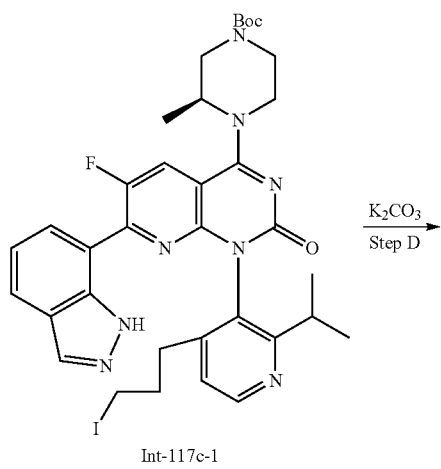
Int-117c-1

K₂CO₃
Step D
→

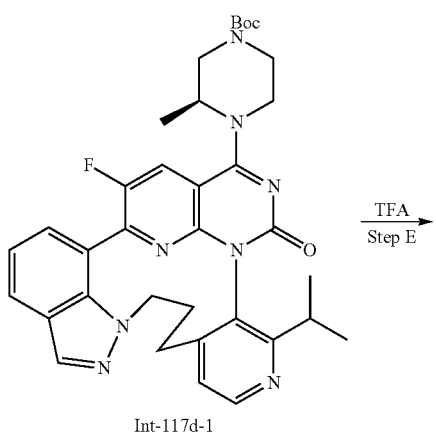
Int-117d-1

TFA
Step E
→

270

-continued

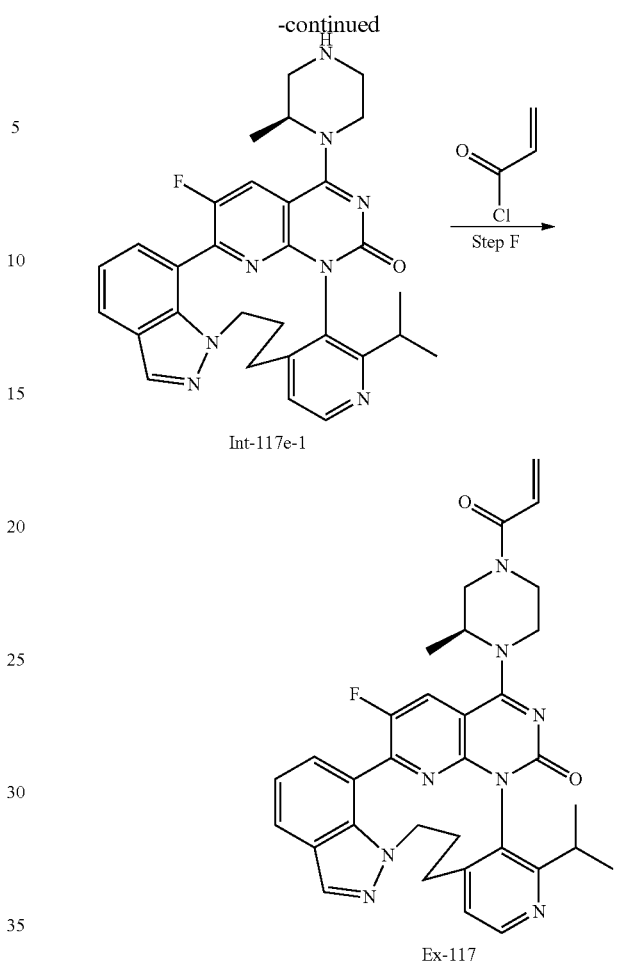

Step A: (S)-tert-butyl 4-(1-(4-(3-((tert-butyldimethylsilyl)oxy)propyl)-2-isopropylpyridin-3-yl) 6-fluoro-7-(1H-indazol-7-yl)-2-oxo-1,2-dihydropyrido[2,3-d]pyrimidin-4-yl)-3-methylpiperazine-1-carboxylate(Int-117a-1)

To a mixture of (S)-tert-butyl-4-(1-(4-(3-((tert-butyldimethylsilyl)oxy)propyl)-2-isopropylpyridin-3-yl)-7-chloro-6-fluoro-2-oxo-1,2-dihydropyrido[2,3-d]pyrimidin-4-yl)-3-methylpiperazine-1-carboxylate (0.30 g, 0.44 mmol) in 1,4-dioxane (6.0 mL) and water (1.0 mL) were added 7-(4,4,5,5-tetramethyl-1,3,2-dioxaborolan-2-yl)-1H-indazole (159 mg, 0.653 mmol), potassium acetate (Int-43-1, 171 mg, 1.74 mmol) and [1,1V-bis(diphenylphosphino)ferrocene]dichloropalladium(II), complex with dichloromethane (36 mg, 0.044 mmol) at 25° C. under a nitrogen atmosphere. The mixture was heated to 90° C. for 30 min. The mixture was allowed to cool to rt and quenched with water (10 mL). The mixture was extracted with ethyl acetate (2×50 mL). The combined organic layers were washed with brine (10 mL), dried over Na₂SO₄, filtered and the mixture was concentrated under reduced pressure. The residue was purified by silica gel column chromatography (0-100% ethyl acetate gradient in petroleum ether) to afford (S)-tert-butyl-4-(1-(4-(3-((tert-butyldimethylsilyl)oxy)propyl)-2-isopropylpyridin-3-yl)-6-fluoro-7-(1H-indazol-7-yl)-2-oxo-1,2-dihydropyrido[2,3-d]pyrimidin-4-yl)-3-methylpiperazine-1-carboxylate (Int-117a-1). MS (ESI): m/z 772 [M+H]⁺. ¹H NMR (400 MHz, Methanol-d$_4$) δ 8.80 (d, J=5.1 Hz, 1H), 8.44 (d, J=7.4 Hz, 1H), 8.36 (dd, J=16.0, 12.5 Hz, 1H), 8.04 (s, 1H), 7.98 (d, J=7.8 Hz, 1H), 7.56 (dd, J=5.1, 2.0 Hz, 1H), 7.31 (t, J=7.8 Hz, 1H), 5.14-4.94 (m, 1H), 4.53-4.33 (m, 1H), 4.20-4.09 (m, 1H), 4.01 (br d, J=13.3 Hz, 1H), 3.92-3.71 (m, 1H), 3.55-3.40 (m, 3H), 3.30-3.15 (m, 1H), 2.95-2.80 (m, 1H), 2.62-2.47 (m, 2H), 1.75 (br dd, J=13.5, 7.2 Hz, 1H), 1.69-1.59 (m, 1H), 1.55-1.49 (m, 12H), 1.25-1.19 (m, 3H), 0.89 (dd, J=6.7, 5.1 Hz, 3H), 0.65 (s, 9H), −0.17 (s, 3H), −0.22 (d, J=0.8 Hz, 3H).

Step B: (S)-tert-butyl 4-(6-fluoro-1-(2-(3-hydroxypropyl-6-isopropylphenyl-7-(1H-indazol-7-yl-2-oxo-1,2-dihydropyrido[2,3-d]pyrimidin-4-yl)-3-methylpiperazine-1-carboxylate (Int-117b-1)

To a mixture of (S)-tert-butyl 4-(1-(2-(3-((tert-butyldimethylsilyl)oxy)propyl)-6-isopropylphenyl)-6-fluoro-7-(1H-indazol-7-yl)-2-oxo-1,2-dihydropyrido[2,3-d]pyrimidin-4-yl)-3-methylpiperazine-1-carboxylate (Int117a-1, 280 mg, 0.364 mmol) in THF (5.0 mL) was added TBAF (1.0 M in THF, 0.73 mL, 0.73 mmol), and the mixture was stirred at room temperature for 1 h under a nitrogen atmosphere. After 1 h, the mixture was concentrated under reduced pressure and the resulting residue was purified by silica gel column chromatography (0-100/0 ethyl acetate gradient in petroleum ether) to afford (S)-tert-butyl-4-(6-fluoro-1-(2-(3-hydroxypropyl)-6-isopropylphenyl)-7-(1H-indazol-7-yl)-2-oxo-1,2-dihydropyrido[2,3-d]pyrimidin-4-yl)-3-methylpiperazine-1-carboxylate (Int-117b-1). MS (ESI): m/z 657 [M+H]$^+$. $^1$H NMR (Methanol-d$_4$) δ: 8.78 (d, J=5.1 Hz, 1H), 8.42 (d, J=7.6 Hz, 1H), 8.33 (dd, J=12.5, 8.3 Hz, 1H), 8.02 (s, 1H), 7.95 (d, J=8.1 Hz, 1H), 7.56 (d, J=4.2 Hz, 1H), 7.29 (t, J=7.7 Hz, 1H), 5.02 (br d, J=16.9 Hz, 1H), 4.50-4.32 (m, 1H), 4.12 (br d, J=15.2 Hz, 1H), 3.99 (br d, J=13.4 Hz, 1H), 3.80 (br d, J=12.2 Hz, 1H), 3.48-3.31 (m, 4H), 2.87-2.70 (m, 1H), 2.62-2.42 (m, 2H), 1.83-1.71 (m, 1H), 1.67-1.57 (m, 1H), 1.55-1.46 (m, 12H), 1.24-1.19 (m, 3H), 0.90-0.80 (m, 3H).

Step C: (S)-tert-butyl 4-(6-fluoro-7-(1H-indazol-7-yl-1b-1-(43-iodopropyl-2-isopropylpyridin-3-yl)-2-oxo-1,2-dihydropyrido[2,3-d]pyrimidin-4-yl-3-methylpiperazine-1-carboxylate (Int-117c-1)

To a mixture of (S)-tert-butyl-4-(6-fluoro-1-(4-(3-hydroxypropyl)-2-isopropylpyridin-3-yl)-7-(1H-indazol-7-yl)-2-oxo-1,2-dihydropyrido[2,3-d]pyrimidin-4-yl)-3-methylpiperazine-1-carboxylate (0.11 g, 0.17 mmol) in dichloromethane (2.0 mL) were added triphenylphosphine (132 mg, 0.502 mmol), I$_2$ (170 mg, 0.670 mmol) and 1H-imidazole (46 mg, 0.67 mmol) at room temperature under a nitrogen atmosphere. After 5 h, the mixture was concentrated under reduced pressure and the resulting residue was purified by silica gel column chromatography (0-10% methanol gradient in dichloromethane) to afford (S)-tert-butyl-4-(6-fluoro-7-(1H-indazol-7-yl)-1-(4-(3-iodopropyl)-2-isopropylpyridin-3-yl)-2-oxo-1,2-dihydropyrido[2,3-d]pyrimidin-4-yl)-3-methylpiperazine-1-carboxylate (Int-117c-1). MS (ESI): m/z 768 [M+H]$^+$. $^1$H NMR (400 MHz, Methanol-d$_4$) δ: 8.81 (d, J=5.1 Hz, 1H), 8.44 (d, J=7.8 Hz, 1H), 8.36 (dd, J=12.5, 9.8 Hz, 1H), 8.04 (s, 1H), 7.97 (d, J=7.8 Hz, 1H), 7.58 (d, J=5.1 Hz, 1H), 7.31 (t, J=7.8 Hz, 1H), 5.14-4.96 (m, 1H), 4.54-4.37 (m, 1H), 4.20-4.11 (m, 1H), 4.50-3.95 (m, 1H), 3.93-3.70 (m, 1H), 3.34 (s, 2H), 3.19-3.09 (m, 1H), 3.08-2.95 (m, 1H), 2.86 (br dd, J=16.8, 6.7 Hz, 1H), 2.67-2.54 (m, 2H), 2.01-1.93 (m, 1H), 1.92-1.78 (m, 1H), 1.57-1.50 (m, 12H), 1.24-1.22 (m, 3H), 0.89 (dd, J=6.7, 4.7 Hz, 3H).

Step D: Int-117d-1

To a mixture of (S)-tert-butyl-4-(6-fluoro-7-(1H-indazol-7-yl)-1-(4-(3-iodopropyl)-2-isopropylpyridin-3-yl)-2-oxo-1,2-dihydropyrido[2,3-d]pyrimidin-4-yl)-2-oxo-1,2-dihydropyrido[2,3-d]pyrimidin-4-yl)-3-methylpiperazine-1-carboxylate (Int-117c-1, 0.25 mg, 0.26 mmol) in DMF (4.0 mL) was added potassium carbonate (0.11 g, 0.78 mmol) at room temperature under a nitrogen atmosphere. The mixture was then heated to 80° C. for 5 hours. After 5 hours, the mixture was allowed to cool to room temperature and the resulting residue was purified by preparative TLC (100% ethyl acetate) to afford Int-117d. MS (ESI): m/z 639 [M+H]$^+$.

Step E: Int-117e-1

A mixture of Int-117d-1 (0.15 g, 0.19 mmol) in dichloromethane (2.0 mL) and TFA (0.40 mL) was stirred at 25° C. for 10 min under a nitrogen atmosphere. The mixture was then concentrated under reduced pressure and the residue was purified by preparative HPLC (Phenomenex Luna C18, 75 mm×30 mm, 3 μm; 15-45% acetonitrile/water with a 0.1% TFA) to afford Int-117e-1. MS (ESI): m/z 539 [M+H]$^+$.

Step F: 22-fluoro-9-[(2S)-2-methyl-4-(prop-2-enoyl)piperazin-1-yl]-13-(propan-2-yl)-18,19-dihydro-11H,17H-6,8-ethenopyrido[4',3':11,12]pyrimido[1',6':1,2][1,3,7]triazacyclododecino[5,6,7-hi]indazol-11-one (Ex. 117)

To a mixture of Int-117e-1 (80 mg, 0.12 mmol) in dichloromethane (1.0 mL) at 0° C. were added N,N-diisopropylethylamine (62 μL, 0.36 mmol) and acryloyl chloride (29 μL, 0.36 mmol). The mixture was allowed to warm to room temperature and then stirred at room temperature for 10 minutes. The mixture was concentrated under reduced pressure and the residue was purified by preparative HPLC (Agela DuraShell C18, 150 mm×25 mm, 5 μm; 29 to 59% water (0.05% NH$_3$H$_2$O+10 mM NH$_4$HCO$_3$)/acetonitrile 25 mL/min) to afford the racemic material that was purified further by preparative SFC Column D, Condition: 50% water (0.1% NH$_3$H$_2$O)/isopropanol) to afford 22-fluoro-9-[(2S)-2-methyl-4-(prop-2-enoyl)piperazin-1-yl]-13-(propan-2-yl)-18,19-dihydro-11H,17H-6,8-ethenopyrido[4',3':11,12]pyrimido[1',6':1,2][1,3,7]triazacyclododecino[5,6,7-hi]indazol-11-one (Ex. 117). MS (ESI): m/z 593 [M+H]$^+$. $^1$H NMR (400 MHz, Methanol-d$_4$) δ 8.40-8.27 (m, 2H), 8.11 (s, 1H), 7.86 (d, J=7.4 Hz, 1H), 7.44 (d, J=7.4 Hz, 1H), 7.29-7.18 (m, 2H), 6.97-6.74 (m, 1H), 6.32 (br d, J=16.0 Hz, 1H), 5.85 (br d, J=10.6 Hz, 1H), 4.97 (br s, 1H), 4.74-4.38 (m, 2H), 4.28-4.02 (m, 2H), 3.84-3.68 (m, 2H), 3.50-3.34 (m, 2H), 2.92 (quin, J=6.7 Hz, 1H), 2.84-2.72 (m, 1H), 2.46-2.20 (m, 2H), 2.14 (br d, J=14.5 Hz, 1H), 1.58 (br dd, J=6.7, 13.3 Hz, 3H), 1.22 (d, J=7.0 Hz, 3H), 0.90 (d, J=6.7 Hz, 3H).

Example 118: 17,20-difluoro-12-hydroxy-2-[(2S)-2-methyl-4-(prop-2-enoyl)piperazin-1-yl]-6-(propan-2-yl)-10,11,12,13-tetrahydro-4H-1,18-ethenopyrido[3,4-e]pyrimido[6,1-c][2,4]benzodiazacyclododecin-4-one (Ex.118-2) and 17,20-difluoro-11-hydroxy-2-[(2S)-2-methyl-4-(prop-2-enoyl)piperazin-1-yl]-6-(propan-2-yl)-10,11,12,13-tetrahydro-4H-1,18-ethenopyrido[3,4-e]pyrimido[6,1-c][2,4]benzodiazacyclododecin-4-one (Ex.118-1)
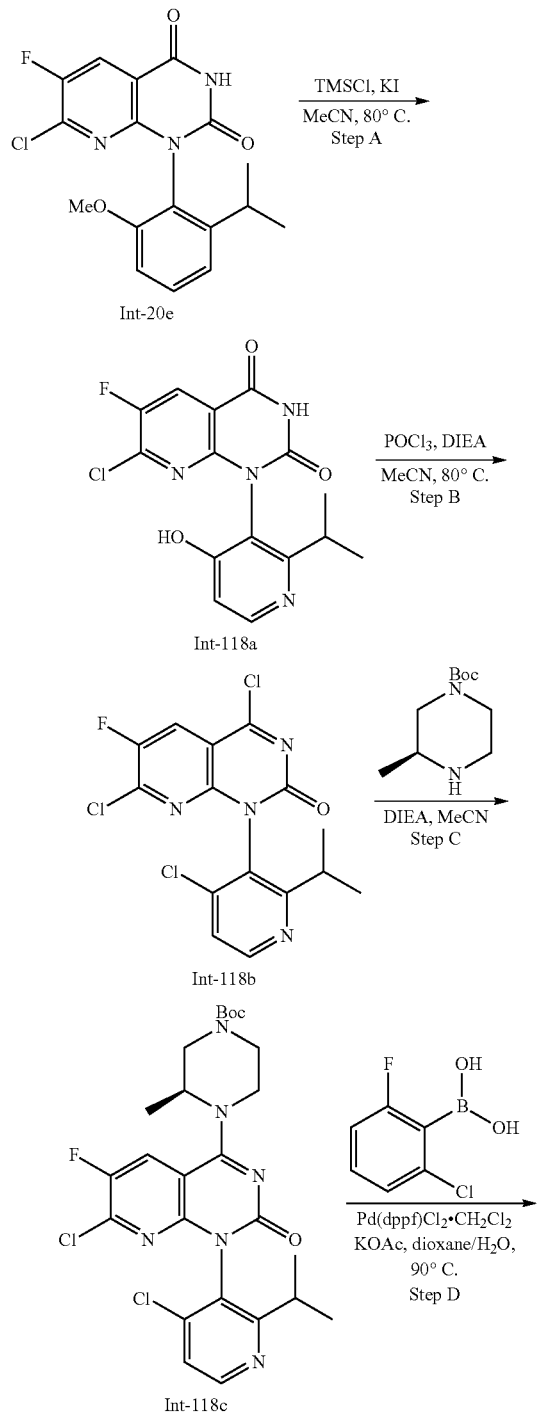
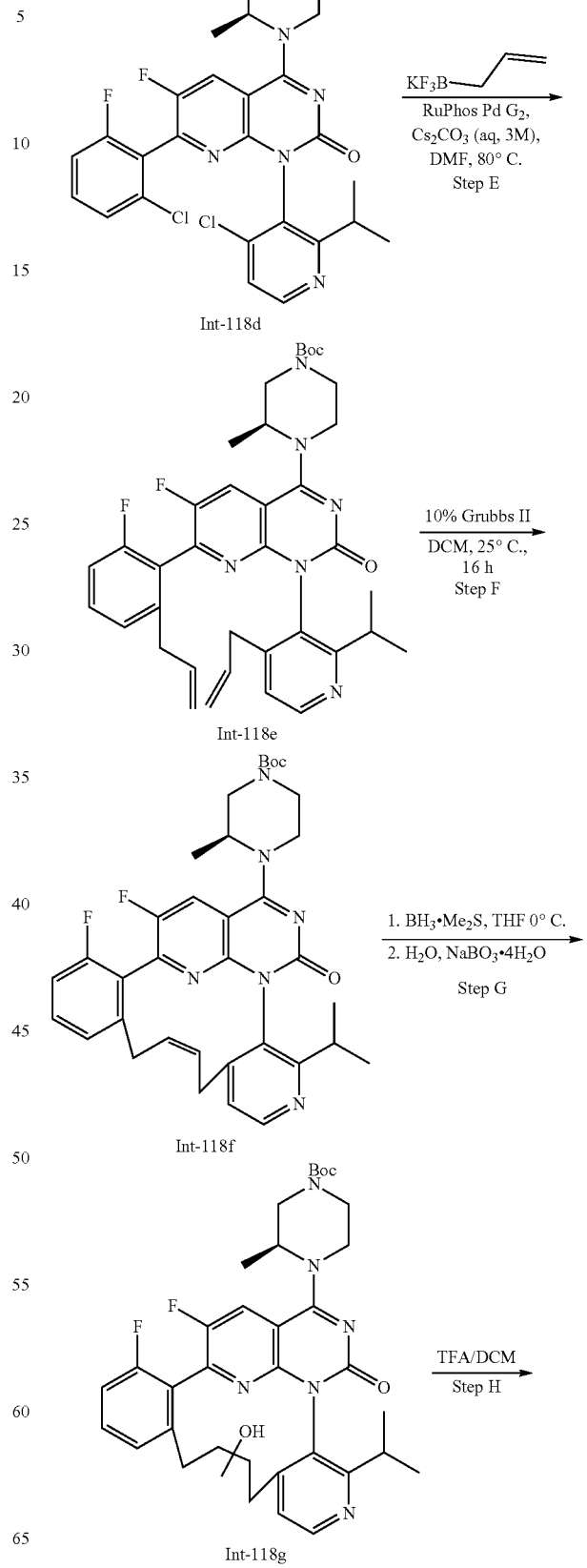

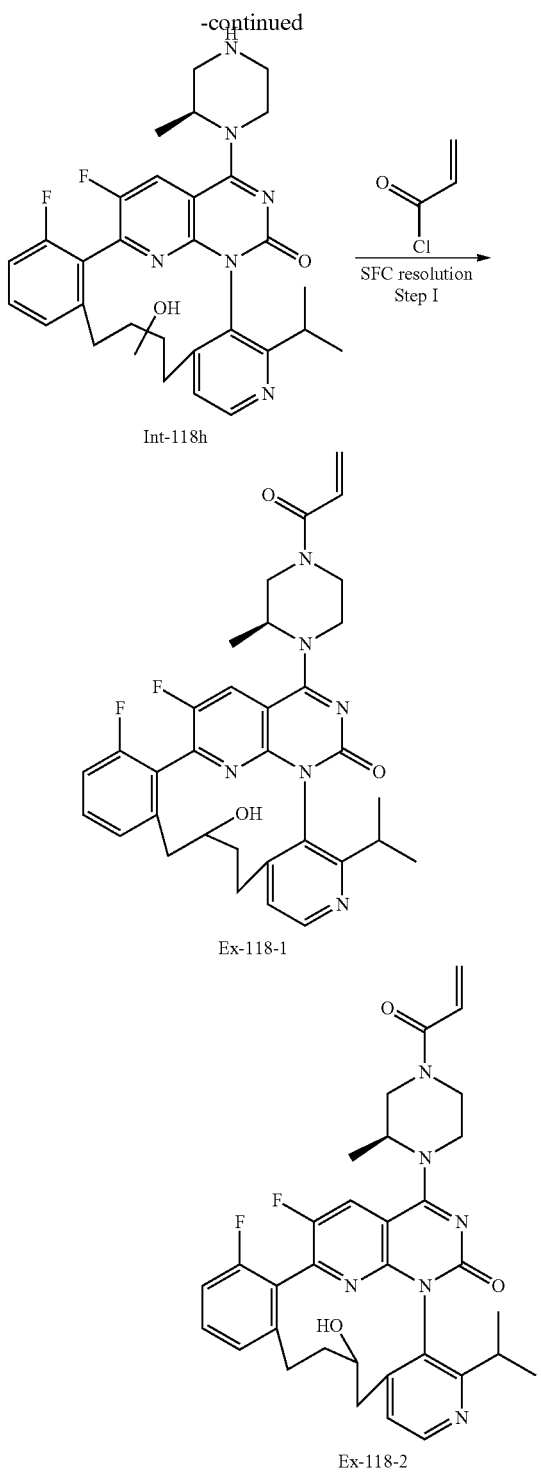

Int-118h

Ex-118-1

Ex-118-2

Step A: 7-chloro-6-fluoro-1-(4-hydroxy-2-isopropylpyridin-3-yl)pyrido[2,3-d]pyrimidine-2,4(1H,3H)-dione (Int-118a)

To a mixture of 7-chloro-6-fluoro-1-(2-isopropyl-4-methoxypyridin-3-yl)pyrido[2,3-d]pyrimidine-2,4(1H,3H)-dione (Int-20e, 4.95 g, 13.6 mmol) in acetonitrile (60 mL) was added potassium iodide (4.51 g, 27.1 mmol) and chlorotrimethylsilane (2.95 g, 27.1 mmol). The resulting mixture was heated to 80° C. for 10 hours. After 10 hours, the mixture was allowed to cool to room temperature and was then concentrated under reduced pressure. Water (10 mL) was added and the solids that formed were filtered and collected to afford 7-chloro-6-fluoro-1-(4-hydroxy-2-isopropylpyridin-3-yl)pyrido[2,3-d]pyrimidine-2,4(1H,3H)-dione (Int-118a). MS (ESI): m/z 351 [M+H]$^+$. $^1$H NMR (400 MHz, Methanol-d$_4$): δ 8.35 (d, J=7.4 Hz, 1H), 8.20 (d, J=7.0 Hz, 1H), 6.92 (d, J=7.0 Hz, 1H), 3.25-3.12 (m, 1H), 1.33-1.19 (m, 6H).

Step B: 4,7-dichloro-1-(4-chloro-2-isopropylpyridin-3-yl)-6-fluoropyrido[2,3-d]pyrimidin-2(1H-one (Int-118b)

To a mixture of 7-chloro-6-fluoro-1-(4-hydroxy-2-isopropylpyridin-3-yl)pyrido[2,3-d]pyrimidine-2,4(1H,3H)-dione (6.0 g, 17 mmol) in MCCN (80 mL) was added N-ethyl-N-isopropylpropan-2-amine (8.9 mL, 51 mmol) and POCl$_3$ (9.6 mL, 0.10 mol) at room temperature under a nitrogen atmosphere. The mixture was then heated to 80° C. for 1 hour. After 1 hour, the mixture was allowed to cool to room temperature and then concentrated under reduced pressure to afford crude 4,7-dichloro-1-(4-chloro-2-isopropylpyridin-3-yl)-6-fluoropyrido[2,3-d]pyrimidin-2(1H)-one (Int-118b) which was used without further purification. MS (ESI): m/z 387 [M+H]$^+$.

Step C: tert-butyl (S)-4-(7-chloro-1-(4-chloro-2-isopropylpyridin-3-yl)-6-fluoro-2-oxo-1,2-dihydropyrido[2,3-d]pyrimidin-4-yl)-3-methylpiperazine-1-carboxylate (Int-118c)

To a mixture of 4,7-dichloro-1-(4-chloro-2-isopropylpyridin-3-yl)-6-fluoropyrido[2,3-d]pyrimidin-2(1H)-one (6.63 g, 17.1 mmol) in acetonitrile (80 mL) were added N,N-Diisopropylethylamine (8.9 mL, 51 mmol) and (S)-tert-butyl 3-methylpiperazine-1-carboxylate (6.85 g, 34.2 mmol). The mixture was heated to 80° C. for 10 min. After 10 minutes, the mixture was allowed to cool to room temperature and was then concentrated under reduced pressure. The resulting residue was purified by silica gel column chromatography (0-33% ethyl acetate gradient in petroleum ether) to afford tert-butyl (S)-4-(7-chloro-1-(4-chloro-2-isopropylpyridin-3-yl)-6-fluoro-2-oxo-1,2-dihydropyrido[2,3-d]pyrimidin-4-yl)-3-methylpiperazine-1-carboxylate (Int-118c). MS (ESI): m/z 551 [M+H]$^+$. $^1$H NMR (400 MHz, CDCl$_3$): δ 8.60 (d, J=5.1 Hz, 1H), 7.78 (dd, J=7.4, 2.0 Hz, 1H), 7.35 (dd, J=5.3, 1.0 Hz, 1H), 4.84 (br s, 1H), 4.27 (br s, 1H), 4.11-3.88 (m, 2H), 3.64 (br s, 1H), 3.16 (br s, 2H), 2.77 (br dd, J=14.7, 7.2 Hz, 1H), 1.51 (s, 9H), 1.46 (s, 3H), 1.25 (dd, J=6.7, 3.9 Hz, 3H), 1.15 (t, J=6.5 Hz, 3H).

Step D: tert-butyl (3S)-4-(1-(4-chloro-2-isopropylpyridin-3-yl)-7-(2-chloro-6-fluorophenyl-6-fluoro-2-oxo-1,2-dihydropyrido[2,3-d]pyrimidin-4-yl)-3-methylpiperazine-1-carboxylate (Int-118d To a mixture of tert-butyl (S)-4-(7-chloro-1-(4-chloro-2-isopropylpyridin-3-yl)-6-fluoro-2-oxo-1,2-dihydropyrido[2,3-d]pyrimidin-4-yl)-3-methylpiperazine-1-carboxylate (2.0 g, 3.6 mmol) in 1,4-dioxane (20 mL) and water (2.0 mL) were added potassium acetate (1.78 g, 18.1 mmol), (2-chloro-6-fluorophenyl)boronic acid (1.9 g, 11 mmol) and 1,1'-bis(diphenylphosphino)ferrocene-palladium(II) dichloride dichloromethane complex (0.30 g, 0.36 mmol) at room temperature under a nitrogen atmosphere. The mixture was heated to 90° C. for 12 hours. After 12 hours, the mixture was allowed to cool to room temperature and then quenched with brine (10 mL). The mixture was extracted with ethyl acetate (2×50 mL). The combined organic layers were washed with brine (10 mL), dried over Na$_2$SO$_4$, filtered and the filtrate was concentrated under reduced pressure. The resulting residue was purified by silica gel column chromatography (0-50% ethyl acetate gradient in petroleum ether) to afford tert-butyl (3S)-4-(1-(4-chloro-2-isopropylpyridin-3-yl)-7-(2-chloro-6-fluorophenyl)-6-fluoro-2-oxo-1,2-dihydropyrido[2,3-d]pyrimidin-4-yl)-3-methylpiperazine-1-carboxylate (Int-118d). MS (ESI): m/z 645 [M+H]$^+$. $^1$H NMR (400 MHz, CDCl$_3$): δ 8.50 (d, J=5.5 Hz, 1H), 7.87 (d, J=8.6 Hz, 1H), 7.40-7.31 (m, 1H), 7.28 (br d, J=5.5 Hz, 1H), 7.23 (d, J=8.2 Hz, 1H), 7.05 (t, J=8.8 Hz, 1H), 4.87 (br s, 1H), 4.52-3.94 (m, 3H), 3.66 (br s, 1H), 3.29 (br s, 2H), 2.91 (br s, 1H), 1.56-1.44 (m, 12H), 1.30-1.24 (m, 3H), 1.16-0.97 (m, 3H).

Step E: tert-butyl (3S)-4-(1-(4-allyl-2-isopropylpyridin-3-yl)-7-(2-allyl-6-fluorophenyl)-6-fluoro-2-oxo-1,2-dihydropyrido[2,3-d]pyrimidin-4-yl)-3-methylpiperazine-1-carboxylate (Int-118e)

In a glovebox, a mixture of tert-butyl (3S)-4-(1-(4-chloro-2-isopropylpyridin-3-yl)-7-(2-chloro-6-fluorophenyl)-6-fluoro-2-oxo-1,2-dihydropyrido[2,3-d]pyrimidin-4-yl)-3-methylpiperazine-1-carboxylate (0.30 g, 0.46 mmol) in DMF (5.0 mL) were added potassium allyltrifluoroborate (0.20 g, 1.4 mmol), aqueous Cs$_2$CO$_3$ (3.0 M, 0.46 mL, 1.4 mmol) and (2'-amino-[1,1'-biphenyl]-2-yl)dicyclohexyl(2',6'-diisopropoxy-[1,1'-biphenyl]-2-yl)phosphoranyl)palladium(III) chloride (35 mg, 0.046 mmol) at room temperature under a nitrogen atmosphere. The mixture was then heated to 80° C. for 12 hours. After 12 hours, the mixture was allowed to cool to room temperature and was then quenched with water (30 mL). The mixture was then extracted with ethyl acetate (3×100 mL). The combined organic layers were dried over anhydrous Na$_2$SO$_4$, filtered and concentrated under reduced pressure. The resulting mixture was purified by silica gel column chromatography (0-50% ethyl acetate gradient in petroleum ether) to afford (3S)-tert-butyl 4-(1-(4-allyl-2-isopropylpyridin-3-yl)-7-(2-allyl-6-fluorophenyl)-6-fluoro-2-oxo-1,2-dihydropyrido[2,3-d]pyrimidin-4-yl)-3-methylpiperazine-1-carboxylate (Int-118e). MS (ESI): m/z 657 [M+H]$^+$. $^1$H NMR (400 MHz, CDCl$_3$): δ 8.54 (br d, J=4.3 Hz, 1H), 7.82 (br d, J=8.6 Hz, 1H), 7.38-7.29 (m, 1H), 7.50-7.06 (m, 1H), 7.04-6.94 (m, 2H), 5.72 (br s, 1H), 5.45 (br s, 1H), 5.02-4.80 (m, 4H), 4.46-4.20 (m, 2H), 4.05-3.90 (m, 1H), 3.68 (br s, 1H), 3.21 (br d, J=14.9 Hz, 1H), 3.16-2.89 (m, 4H), 2.86-2.55 (m, 1H), 1.51 (s, 12H), 1.22-1.15 (m, 3H), 1.14-1.04 (m, 2H), 0.97-0.79 (m, 3H).

Step F: Int-118f

The following reaction was divided into 10 batches of 50 mg each. To a mixture of (3S)-tert-butyl 4-(1-(4-allyl-2-isopropylpyridin-3-yl)-7-(2-allyl-6-fluorophenyl)-6-fluoro-2-oxo-1,2-dihydropyrido[2,3-d]pyrimidin-4-yl)-3-methylpiperazine-1-carboxylate (0.50 g, 0.61 mmol) in DCM (24 mL) was added Grubbs II catalyst (103 mg, 0.122 mmol) at 25° C. under a N$_2$ atmosphere. The mixture was stirred at 25° C. for 12 hours. The mixture was then concentrated under reduced pressure and the mixture was purified by silica gel column chromatography (0-50% ethyl acetate gradient in petroleum ether) to afford Int-118f. MS (ESI): m/z 629 [M+H]$^+$. $^1$H NMR (400 MHz, Methanol-d$_4$): δ 8.72-8.57 (m, 1H), 8.37-8.23 (m, 1H), 8.00-7.82 (m, 1H), 7.49-7.35 (m, 1H), 7.25-7.01 (m, 2H), 5.32-4.90 (m, 2H), 4.63-4.21 (m, 1H), 4.14 (br d, J=10.6 Hz, 1H), 4.01-3.65 (m, 2H), 3.50-3.31 (m, 6H), 3.19-2.92 (m, 2H), 1.59-1.44 (m, 12H), 1.40-1.30 (m, 3H), 1.22-1.09 (m, 3H).

Step G: Int-118i

To a mixture of Int-118f (0.50 g, 0.80 mmol) in THF (8.0 mL) was added BH$_3$·DMS (10 M in THF, 0.15 mL, 1.5 mmol) at 0° C. The mixture was allowed to warm to room temperature and was then stirred for 1 hour. Water (0.5 mL) and then sodium perborate tetrahydrate (367 mg, 2.39 mmol) was added and the mixture was allowed to stir at room temperature for 1 hour. The mixture was then quenched with saturated aqueous Na$_2$SO$_3$ (1.0 mL) and water (5.0 mL). The mixture was extracted with EtOAc (2×50 mL). The combined organic layers were dried over anhydrous Na$_2$SO$_4$, filtered and the filtrate was concentrated under reduced pressure. The resulting residue was purified by silica gel column chromatography (0-10% methanol gradient in dichloromethane) to afford Int-118g. MS (ESI): m/z 647 [M+H]$^+$.

Step H: Int-118h

To a mixture of Int-118g (0.500 g, 0.387 mmol) in DCM (6.0 mL) was added TFA (2.0 mL, 26 mmol) at 25° C. under a nitrogen atmosphere. The mixture was stirred at room temperature for 10 min. The mixture was then concentrated under reduced pressure to afford Int-118h which was used without further purification or characterization. MS (ESI): m/z 547 [M+H]$^+$.

Step I: 17,20-difluoro-11-hydroxy-2-[(2S)-2-methyl-4-(prop-2-enoyl)piperazin-1-yl]-6-(propan-2-yl)-10,11,12,13-tetrahydro-4H-1,18-ethenopyrido[3,4-e]pyrimido[6,1-c][2,4]benzodiazacyclododecin-4-one (Ex.118-1) and 17,20-difluoro-12-hydroxy-2-[(2S)-2-methyl-4-(prop-2-enoyl)piperazin-1-yl]-6-(propan-2-yl)-10,11,12,13-tetrahydro-4H-1,18-ethenopyrido[3,4-e]pyrimido[6,1-c][2,4]benzodiazacyclododecin-4-one (Ex.118-2)

To a mixture of Int-118h (0.30 g, 0.27 mmol) in DCM (1.5 mL) were added DIEA (0.14 mL, 0.82 mmol) and acryloyl chloride (67 μL, 0.82 mmol) at 0° C. The mixture was allowed to warm to room temperature and was then stirred for 10 minutes. The mixture was then concentrated under reduced pressure and the resulting residue was purified by preparative TLC plate (8% methanol in DCM, twice). The isolated mixture was then purified by SFC Column L, Condition: 0.1% NH$_3$H$_2$O IPA to afford 3 peaks. The second eluting peak corresponded to 17,20-difluoro-12-hydroxy-2-[(2S)-2-methyl-4-(prop-2-enoyl)piperazin-1-yl]-6-(propan-2-yl)-10,11,12,13-tetrahydro-4H-1,18-ethenopyrido[3,4-e]pyrimido[6,1-c][2,4]benzodiazacyclododecin-4-one (Ex.118-1). The first eluting peak (a mixture of 6 isomers) was further purified by preparative SFC Column J, Condition: 0.1% NH$_3$H$_2$O ETOH, to afford 4 peaks. The third eluting peak (a mixture of 3 isomers) was further purified by SFC Column N, Condition: 0.1% NH$_3$H$_2$O MEOH. The second eluting isomer corresponded to 17,20-difluoro-11-hydroxy-2-[(2S)-2-methyl-4-(prop-2-enoyl)piperazin-1-yl]-

6-(propan-2-yl)-10,11,12,13-tetrahydro-4H-1,18-etheno-pyrido[3,4-e]pyrimido[6,1-c][2,4]benzodiazacyclododecin-4-one (Ex.118-2).

Characterization data for 17,20-difluoro-12-hydroxy-2-[(2S)-2-methyl-4-(prop-2-enoyl)piperazin-1-yl]-6-(propan-2-yl)-10,11,12,13-tetrahydro-4H-1,18-ethenopyrido[3,4-e]pyrimido[6,1-c][2,4]benzodiazacyclododecin-4-one (Ex.118-1): $^1$H NMR (400 MHz, Methanol-d$_4$): δ 8.48 (d, J=5.1 Hz, 1H), 8.34 (br d, J=9.4 Hz, 1H), 7.51 (d, J=5.5 Hz, 1H), 7.46-7.35 (m, 1H), 7.35-7.28 (m, 1H), 7.06 (t, J=8.6 Hz, 1H), 6.82 (br d, J=11.3 Hz, 1H), 6.32 (br d, J=15.3 Hz, 1H), 5.84 (dd, J=2.0, 10.6 Hz, 1H), 5.43-5.20 (m, 1H), 4.58 (s, 1H), 4.46-4.34 (m, 1H), 4.29-4.06 (m, 1H), 4.01 (br s, 1H), 3.53-3.34 (m, 2H), 2.85 (br s, 1H), 2.65 (br s, 1H), 2.35 (br d, J=19.2 Hz, 4H), 1.86 (br s, 2H), 1.39 (br d, J=6.3 Hz, 3H), 1.23 (d, J=6.7 Hz, 3H), 0.93 (br d, J=6.7 Hz, 3H). MS (ESI): m/z 601 [M+H]$^+$. Characterization data for 17,20-difluoro-11-hydroxy-2-[(2S)-2-methyl-4-(prop-2-enoyl)piperazin-1-yl]-6-(propan-2-yl)-10,11,12,13-tetrahydro-4H-1,18-ethenopyrido[3,4-e]pyrimido[6,1-c][2,4]benzodiazacyclododecin-4-one (Ex.118-2): $^1$H NMR (400 MHz, Methanol-d$_4$): δ 8.40 (d, J=5.5 Hz, 1H), 8.35 (br d, J=9.0 Hz, 1H), 7.98 (d, J=5.1 Hz, 1H), 7.44-7.35 (m, 1H), 7.12 (br d, J=7.8 Hz, 1H), 7.02 (t, J=9.0 Hz, 1H), 6.93-6.76 (m, 1H), 6.32 (br d, J=16.4 Hz, 1H), 5.84 (dd, J=2.0, 10.6 Hz, 1H), 5.27 (br s, 1H), 4.58 (br s, 1H), 4.39 (br d, J=13.7 Hz, 1H), 4.29-4.07 (m, 1H), 3.99 (br s, 1H), 3.84-3.67 (m, 2H), 3.52-3.39 (m, 1H), 2.91-2.68 (m, 3H), 2.58 (br s, 1H), 1.69 (br d, J=10.2 Hz, 3H), 1.40 (d, J=6.7 Hz, 3H), 1.21 (d, J=7.0 Hz, 3H), 0.93 (br d, J=5.9 Hz, 3H). MS (ESI): m/z 601 [M+H]$^+$.

Example 119: 19-chloro-2-[(2S,5R)-2,5-dimethyl-4-(prop-2-enoyl)piperazin-1-yl]-16-fluoro-6-(propan-2-yl)-10,11-dihydro-4H-1,17-ethenopyrido[4,3-d]pyrimido[1,6-f][1,6,8]benzoxadiazacycloundecin-4-one

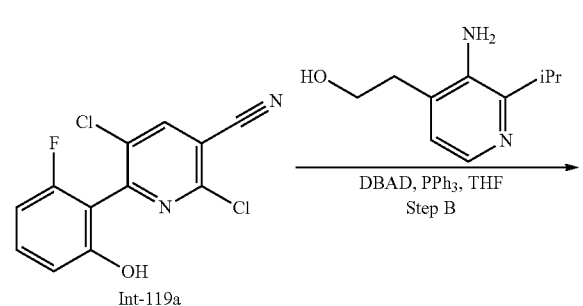

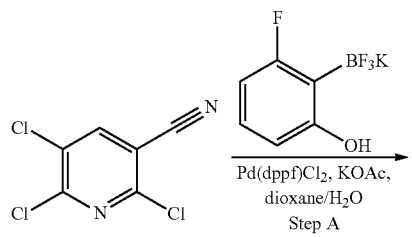

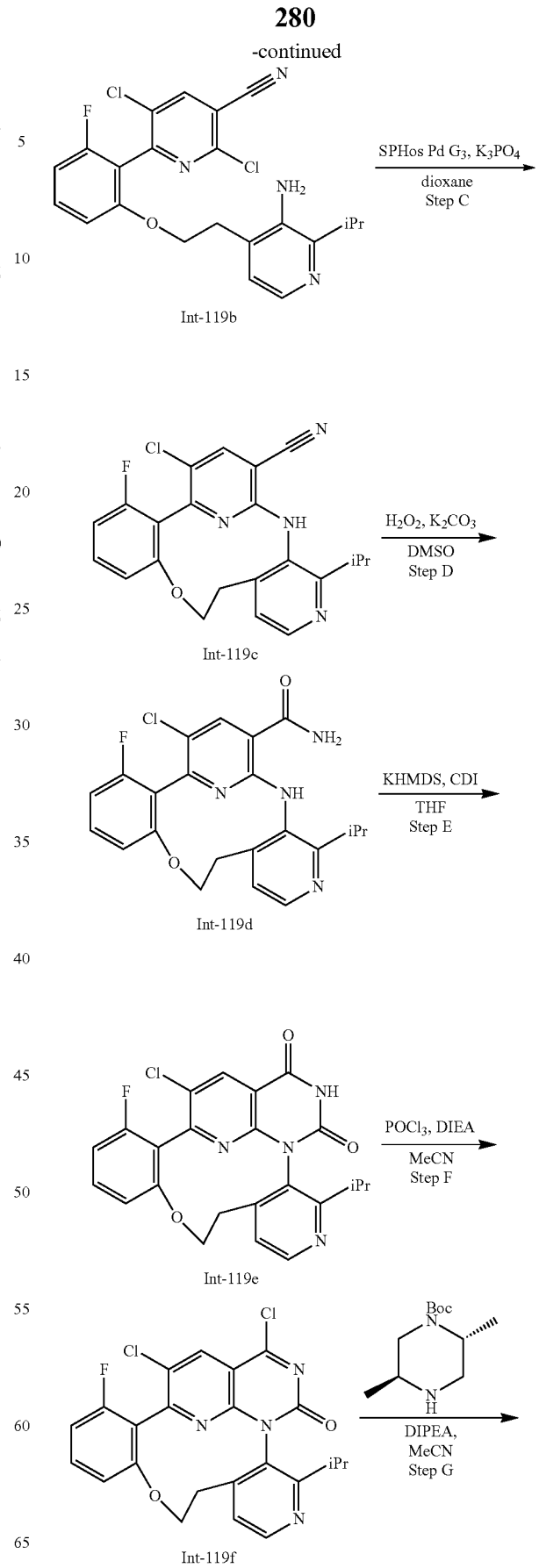

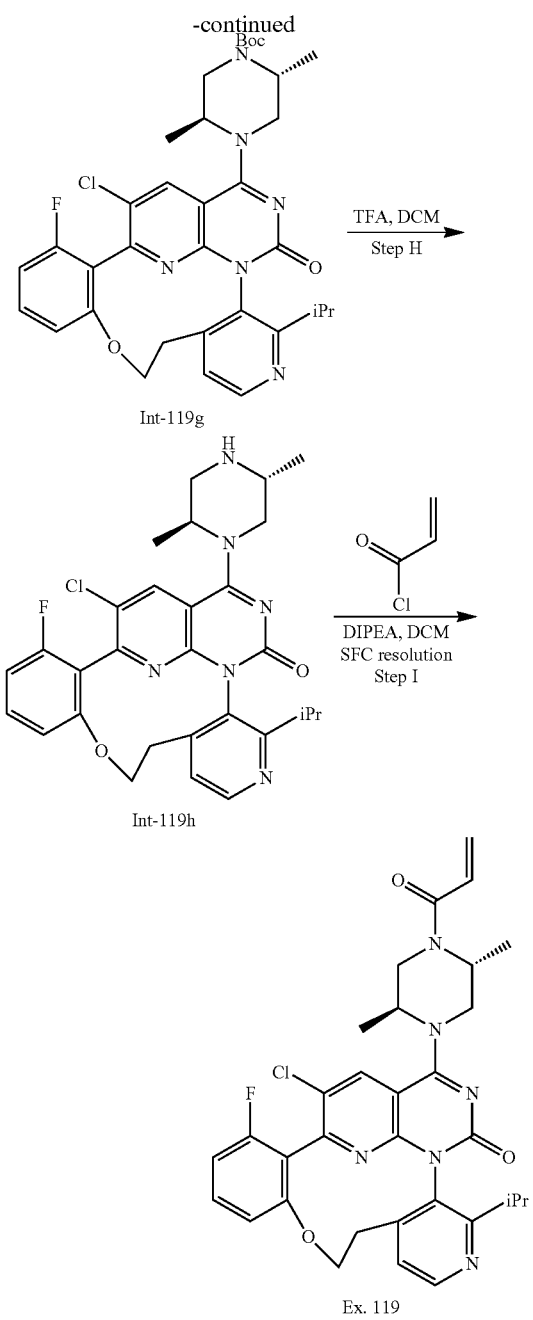

Step A: 2,5-dichloro-6-(2-fluoro-6-hydroxyphenyl) nicotinonitrile (Int-119a)

To a mixture of 2,5,6-trichloronicotinonitrile (4.00 g, 19.3 mmol) in 1,4-dioxane (40 mL) and water (8.0 mL) was added potassium acetate (3.78 g, 38.6 mmol) and [1,1'-bis(diphenylphosphino)ferrocene]palladium(II) dichloride (1.41 g, 1.93 mmol) at room temperature under a $N_2$ atmosphere. The mixture was heated to 90° C. for 5 min under a $N_2$ atmosphere. Then potassium trifluoro (2-fluoro-6-hydroxyphenyl) borate (4.62 g, 21.2 mmol) in 1,4-dioxane (24 mL) and water (8.0 mL) was added to the mixture, and the mixture was stirred at 90° C. for 2 h under a $N_2$ atmosphere. Upon cooling to room temperature, the mixture was concentrated under reduced pressure. The residue was purified by flash silica gel chromatography (Pet. ether/EtOAc=5/1) to afford 2,5-dichloro-6-(2-fluoro-6-hydroxyphenyl)nicotinonitrile (Int-119a). $^1$H NMR (400 MHz, Methanol-$d_4$) δ 8.51 (s, 1H), 7.32 (dt, J=6.8, 8.3 Hz, 1H), 6.77-6.66 (in, 2H).

Step B: 6-(2-(2-(3-amino-2-isopropylpyridin-4-yl)ethoxy-6-fluorophenyl-2,5-dichloronicotinonitrile (Int-119b)

To a mixture of 2,5-dichloro-6-(2-fluoro-6-hydroxyphenyl)nicotinonitrile (2.40 g, 8.48 mmol), 2-(3-amino-2-isopropylpyridin-4-yl)ethanol (1.99 g, 11.0 mmol) and triphenylphosphine (4.45 g, 17.0 mmol) in THF (25 mL) was added a solution of DBAD (3.90 g, 17.0 mmol) in THF (15 mL) at 0° C. The mixture was allowed to warm to 25° C. and then stirred at 25° C. for 1 h under a $N_2$ atmosphere. The reaction was then concentrated under reduced pressure. The resulting residue was purified by flash silica gel chromatography (Pet. ether/EtOAc=1/1) to afford 6-(2-(2-(3-amino-2-isopropylpyridin-4-yl)ethoxy)-6-fluorophenyl)-2,5-dichloronicotinonitrile (Int-119b). MS (ESI): m/z 445 [M+H]$^+$.

Step C: Int-119c

To a stirred mixture of 6-(2-(2-(3-amino-2-isopropylpyridin-4-yl)ethoxy)-6-fluorophenyl)-2,5-dichloronicotinonitrile (500 mg, 1.12 mmol) in 1,4-dioxane (40 mL) were added $K_3PO_4$ (357 mg, 1.68 mmol) and (2-dicyclohexylphosphino-2',6'-dimethoxybiphenyl) [2-(2'-amino-1,1'-biphenyl)]palladium(II) methanesulfonate (SPhos Pd G3, 88 mg, 0.11 mmol) in a glove box. The mixture was heated to 90° C. for 2 h under a $N_2$ atmosphere. After 2 h, the mixture was allowed to cool to room temperature, filtered and the filtrate was concentrated under reduced pressure. The resulting residue was purified by column chromatography on silica gel (Pet. ether/EtOAc=2/1) to afford Int-119c. MS (ESI): m/z 409 [M+H]$^+$.

Step D: Int-119d

To a stirred mixture of Int-119c (520 mg, 1.27 mmol) in DMSO (10 mL) was added $K_2CO_3$ (88 mg, 0.64 mmol). The mixture was stirred at 20° C. for 10 min. $H_2O_2$ (30% in water, 0.111 mL, 1.27 mmol) was added to the mixture dropwise at 20° C. After 1 h, the reaction mixture was quenched with saturated aqueous $Na_2SO_3$ (2.0 mL). The reaction mixture was diluted with EtOAc (50 mL) and the mixture was washed with brine (3×5 mL) and water (3×5 mL). The combined organic phases were dried over anhydrous $Na_2SO_4$, filtered and concentrated under reduced pressure. The residue was purified by flash silica gel chromatography (Pet. ether/EtOAc=1/1) to give Int-119d. MS (ESI): m/z 427 [M+H]$^+$.

Step E: Int-119e

To a stirred mixture of Int-119d (150 mg, 0.351 mmol) in THF (3.0 mL) was added KHMDS (1.0 M in THF, 1.05 mL, 1.05 mmol) at 20° C. After stirring at 20° C. for 10 min, CDI (63 mg, 0.39 mmol) was added. The resulting mixture was heated to 70° C. for 1 h under a nitrogen atmosphere. After 1 h, the mixture was allowed to cool to room temperature and then concentrated under reduced pressure. The resulting residue was purified by preparative TLC plate (SiO$_2$, Pet. ether/EtOAc=1/1) to afford Int-119e. MS (ESI): m/z 453 [M+H]$^+$.

Step F: Int-119f

To a stirred mixture of Int-119e (60 mg, 0.13 mmol) in acetonitrile (2.0 mL) were added DIEA (93 µL, 0.53 mmol) and POCl$_3$ (25 µL, 0.27 mmol), and the mixture was heated to 80° C. for 0.5 h. After 0.5 h, the mixture was allowed to cool to room temperature. The reaction mixture was concentrated under reduced pressure to afford Int-119f which was used in the next step without further purification. MS (ESI): m/z 471 [M+H]$^+$.

Step G: Int-1192

To a stirred mixture of Int-119f (63 mg, 0.13 mmol) in acetonitrile (2.0 mL) was added DIEA (69 µL, 0.40 mmol) and (2R,5S)-tert-butyl 2,5-dimethylpiperazine-1-carboxylate (37 mg, 0.17 mmol) at 20° C. under a nitrogen atmosphere. After 5 min, the mixture was concentrated under reduced pressure and the resulting residue was purified by column chromatography on silica gel (DCM/MeOH=20/1) to afford Int-119g. MS (ESI): m/z 649 [M+H]$^+$.

Step H: Int-119h

A stirred mixture of Int-119g (55 mg, 0.085 mmol) in DCM (2.0 mL) and TFA (0.75 mL) was stirred at 25° C. for 0.5 h. The reaction mixture was then concentrated under reduced pressure to afford Int-119h, which was used in the next step without further purification. MS (ESI): m/z 549 [M+H]$^+$.

Step I: 19-chloro-2-[(2S,5R)-2,5-dimethyl-4-(prop-2-enoyl)piperazin-1-yl]-16-fluoro-6-(propan-2-yl)-10,11-dihydro-4H-1,17-ethenopyrido[4,3-d]pyrimido[1,6-f][1,6,8]benzoxadiazacycloundecin-4-one (Ex. 119)

To a stirred mixture of Int-119h (46 mg, 0.085 mmol) in DCM (2.0 mL) were added DIEA (44 µL, 0.25 mmol) and acryloyl chloride (21 µL, 0.25 mmol) at 0° C. The mixture was allowed to warm to 25° C. and then stirred at 25° C. for 10 min. The reaction mixture was then concentrated under reduced pressure and the resulting residue was purified by preparative HPLC (Column: Agela DuraShell C18 150 mm×25 mm, 5 um; Condition: water (0.04% NH$_3$H$_2$O+10 mM NH$_4$HCO$_3$)-ACN). The fractions containing the product were combined and concentrated under reduced pressure. The atropisomers were separated by preparative SFC (Column D; Condition: 0.1% NH$_3$H$_2$O-IPA; 40% modifier; flow rate (mL/min): 80). The first eluting isomer corresponded to 19-chloro-2-[(2S,5R)-2,5-dimethyl-4-(prop-2-enoyl)piperazin-1-yl]-16-fluoro-6-(propan-2-yl)-10,11-dihydro-4H-1,17-ethenopyrido[4,3-d]pyrimido[1,6-f][1,6,8]benzoxadiazacycloundecin-4-one (Ex. 119). MS (ESI): m/z 603 [M+H]$^+$. $^1$H NMR (500 MHz, Methanol-d$_4$) δ 8.33 (d, J=5.2 Hz, 1H), 8.22 (d, J=17.2 Hz, 1H), 7.38-7.26 (m, 1H), 7.13 (d, J=5.2 Hz, 1H), 6.87 (d, J=8.2 Hz, 1H), 6.83-6.62 (m, 2H), 6.30-6.16 (m, 1H), 5.85-5.64 (m, 1H), 4.98-4.78 (m, 3H), 4.56-4.28 (m, 1H), 3.99 (br dd, J=9.2, 7.2 Hz, 1H), 3.86-3.50 (m, 2H), 3.27-3.21 (m, 1H), 2.94 (dtd, J=13.4, 6.7, 2.9 Hz, 1H), 2.85 (br dd, J=14.4, 7.4 Hz, 1H), 2.26 (dd, J=15.3, 6.4 Hz, 1H), 1.51 (br t, J=7.7 Hz, 3H), 1.37 (br dd, J=18.3, 6.7 Hz, 3H), 1.17 (d, J=6.7 Hz, 3H), 0.91 (dd, J=6.7, 3.5 Hz, 3H).

Example 120: 2-[(2S,5R)-2,5-dimethyl-4-(prop-2-enoyl)piperazin-1-yl]-14,17-difluoro-20-methyl-6-(propan-2-yl)-11,12-dihydro-4H,10H-1,18-ethenopyrido[4,3-e]pyrimido[1,6-g][1,7,9]benzoxadiazacyclododecin-4-one

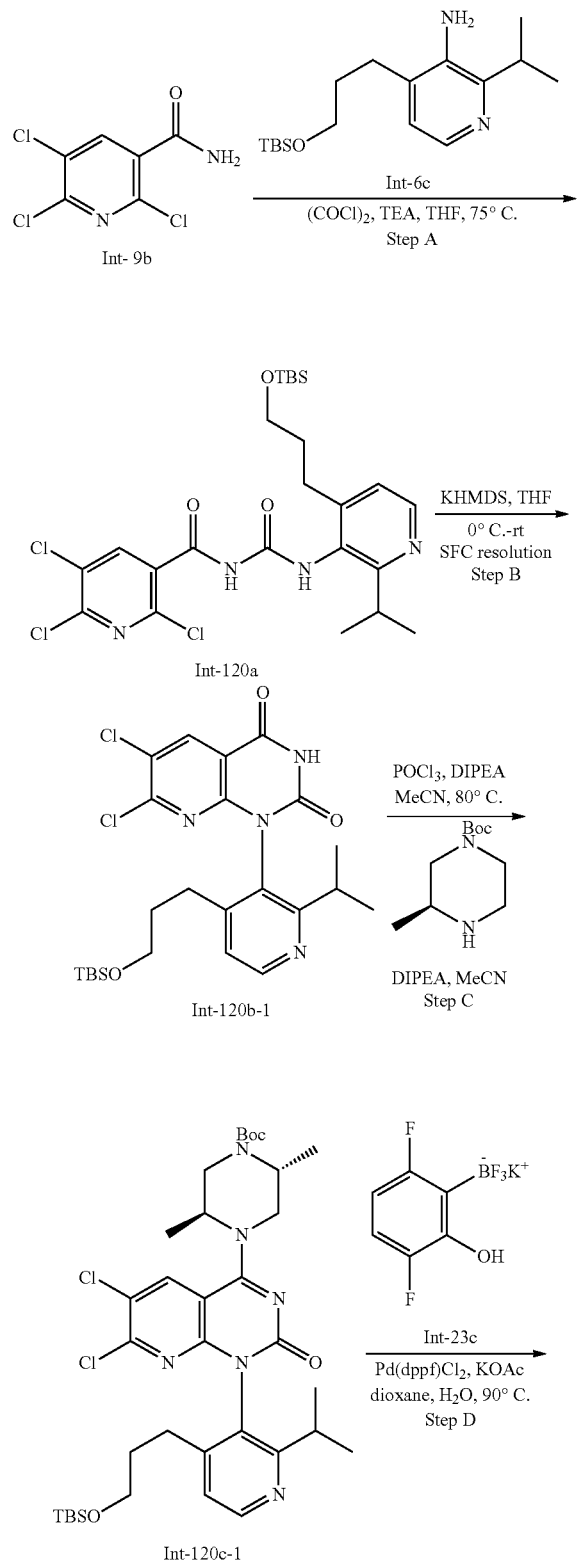

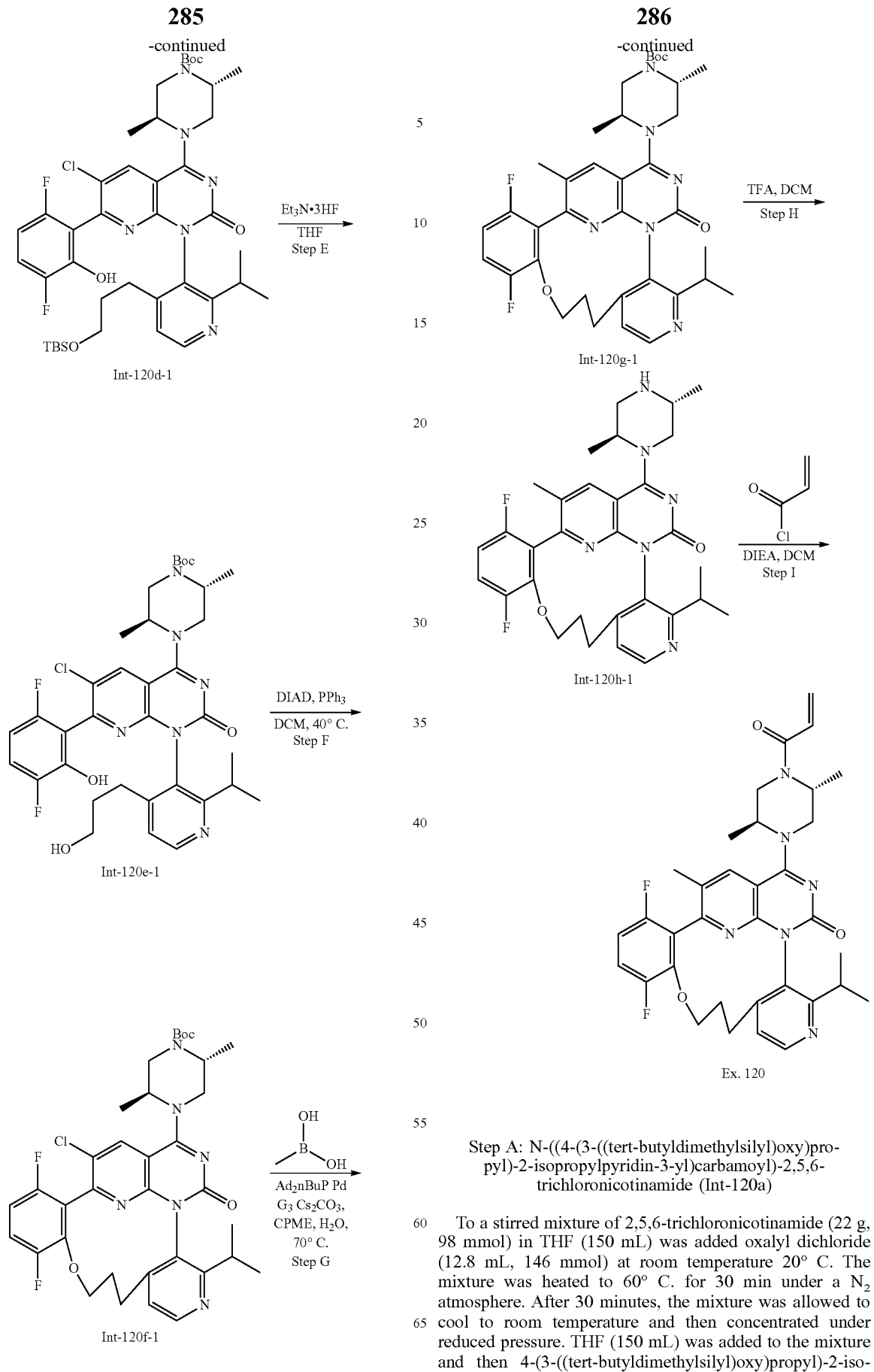

Step A: N-((4-(3-(((tert-butyldimethylsilyl)oxy)propyl)-2-isopropylpyridin-3-yl)carbamoyl)-2,5,6-trichloronicotinamide (Int-120a)

To a stirred mixture of 2,5,6-trichloronicotinamide (22 g, 98 mmol) in THF (150 mL) was added oxalyl dichloride (12.8 mL, 146 mmol) at room temperature 20° C. The mixture was heated to 60° C. for 30 min under a N₂ atmosphere. After 30 minutes, the mixture was allowed to cool to room temperature and then concentrated under reduced pressure. THF (150 mL) was added to the mixture and then 4-(3-((tert-butyldimethylsilyl)oxy)propyl)-2-isopropylpyridin-3-amine (30.1 g, 98.0 mmol) was added. The mixture was stirred at 25° C. for 10 min. The reaction mixture was then quenched with water (200 mL) and adjusted to a pH~8 with solid sodium bicarbonate. The mixture was extracted with ethyl acetate (2×300 mL). The combined organic layers were washed with brine (100 mL), dried over $Na_2SO_4$, filtered and the filtrate was concentrated under reduced pressure. The crude product was purified by flash silica gel chromatography (0~35% EtOAc/Pet. ether gradient) to afford N-((4-(3-((tert-butyldimethylsilyl)oxy)propyl)-2-isopropylpyridin-3-yl)carbamoyl)-2,5,6-trichloronicotinamide (Int-120a). MS (ESI): m/z 559 [M+H]$^+$.

Step B: 1-(4-(3-((tert-butyldimethylsilyl)oxy)propyl-2-isopropylpyridin-3-yl-6,7-dichloropyrido[2,3-d]pyrimidine-2,4(1H,3H)-dione (Int-120b-1)

To a mixture of N-((4-(3-((tert-butyldimethylsilyl)oxy)propyl)-2-isopropylpyridin-3-yl)carbamoyl)-2,5,6-trichloronicotinamide (57.0 g, 102 mmol) in THF (400 mL) was added potassium bis(trimethylsilyl)amide (1.0 M in THF, 204 mL, 204 mmol) at 0° C. under a nitrogen atmosphere. The mixture was allowed to warm to 20° C. and then stirred at 20° C. for 30 min. The reaction mixture was then quenched with saturated aqueous ammonium chloride (150 mL) and extracted with ethyl acetate (2×600 mL). The combined organic layers were washed with brine (300 mL), dried over $Na_2SO_4$, filtered and the filtrate was concentrated under reduced pressure. The crude product was purified by flash silica gel chromatography (0~30% EtOAc/Hexanes). The fractions containing product were collected and concentrated under reduced pressure. The atropisomers were separated by preparative SFC (Column V, Condition 0.1% $NH_3 \cdot H_2O$ in EtOH, 20% modifier; flow rate(mL/min): 200). The first peak that eluted corresponded to 1-(4-(3-((tert-butyldimethylsilyl)oxy)propyl)-2-isopropylpyridin-3-yl)-6,7-dichloropyrido[2,3-d]pyrimidine-2,4(1H,3H)-dione (Int-120b-1). MS (ESI): m/z 523 [M+H]$^+$.

Step C: tert-butyl (2R,5S)-4-(1-(4-(3-((tert-butyldimethylsilyl)oxy)propyl-2-isopropylpyridin-3-yl)-6,7-dichloro-2-oxo-1,2-dihydropyrido[2,3-d]pyrimidin-4-yl-2,5-dimethylpiperazine-1-carboxylate (Int-120c-1)

To a mixture of 1-(4-(3-((tert-butyldimethylsilyl)oxy)propyl)-2-isopropylpyridin-3-yl)-6,7-dichloropyrido[2,3-d]pyrimidine-2,4(1H,3H)-dione (2.29 g, 4.37 mmol) in MeCN (10 mL) were added DIEA (1.5 mL, 8.7 mmol) and $POCl_3$ (490 µL, 5.25 mmol). The mixture was heated to 80° C. for one hour. After one hour, the mixture was allowed to cool to room temperature and then concentrated under reduced pressure. The resulting mixture was placed under vacuum for 15 min. Acetonitrile (10 mL) was then added and the mixture was cooled to 0° C. DIEA (3.0 mL, 18 mmol) and a mixture of tert-butyl (2R,5S)-2,5-dimethylpiperazine-1-carboxylate (1.12 g, 5.25 mmol) in acetonitrile (0.50 mL) were added slowly. The reaction mixture was stirred for 30 mins. The mixture was then quenched with cold water and extracted with ethyl acetate. The organic layer was washed with brine, dried over $MgSO_4$, filtered and concentrated under reduced pressure. The resulting residue was purified by silica gel column chromatography (hexanes with a 3:1 mixture of ethyl acetate:ethanol) to afford tert-butyl (2R,5S)-4-(1-(4-(3-((tert-butyldimethylsilyl)oxy)propyl)-2-isopropylpyridin-3-yl)-6,7-dichloro-2-oxo-1,2-dihydropyrido[2,3-d]pyrimidin-4-yl)-2,5-dimethylpiperazine-1-carboxylate (Int-120c-1). MS (ESI): m/z 719 [M+H]$^+$.

Step D: (2R,5S)-tert-butyl 4-(1-(4-(3-((tert-butyldimethylsilyl)oxy)propyl-2-isopropylpyridin-3-yl)-6-chloro-7-(3,6-difluoro-2-hydroxyphenyl)-2-oxo-1,2-dihydropyrido[2,3-d]pyrimidin-4-yl-2,5-dimethylpiperazine-1-carboxylate (Int-120d-1)

To a stirred mixture of tert-butyl (2R,5S)-4-(1-(4-(3-((tert-butyldimethylsilyl)oxy)propyl)-2-isopropylpyridin-3-yl)-6,7-dichloro-2-oxo-1,2-dihydropyrido[2,3-d]pyrimidin-4-yl)-2,5-dimethylpiperazine-1-carboxylate (300 mg, 0.417 mmol) in 1,4-dioxane (3.0 mL) and water (0.30 mL) were added potassium (3,6-difluoro-2-hydroxyphenyl)trifluoroborate (150 mg, 0.636 mmol), potassium acetate (82 mg, 0.83 mmol) and [1,1'-bis(diphenylphosphino)ferrocene]dichloropalladium(II), complex with dichloromethane (34 mg, 0.042 mmol) at room temperature. The mixture was heated to 90° C. for 15 h under a $N_2$ atmosphere. After 15 h, the mixture was allowed to cool to room temperature. The reaction mixture was quenched with brine (10 mL), and extracted with EtOAc (2×30 mL). The combined organic layers were washed with brine (10 mL), dried over $Na_2SO_4$, filtered and the solvent was evaporated under reduced pressure. The residue was purified by flash silica gel chromatography (0~50% EtOAc/Pet. ether) to afford (2R,5S)-tert-butyl 4-(1-(4-(3-((tert-butyldimethylsilyl)oxy)propyl)-2-isopropylpyridin-3-yl)-6-chloro-7-(3,6-difluoro-2-hydroxyphenyl)-2-oxo-1,2-dihydropyrido[2,3-d]pyrimidin-4-yl)-2,5-dimethylpiperazine-1-carboxylate (Int-120d-1). MS (ESI): m/z 813 [M+H]$^+$.

Step E: (2R,5S)-tert-butyl 4-(6-chloro-7-(3,6-difluoro-2-hydroxyphenyl)-1-(43-hydroxypropyl-2-isopropylpyridin-3-yl-2-oxo-1,2-dihydropyrido[2,3-d]pyrimidin-4-yl-2,5-dimethylpiperazine-1-carboxylate (Int-120e-1)

To a stirred mixture of (2R,5S)-tert-butyl 4-(1-(4-(3-((tert-butyldimethylsilyl)oxy)propyl)-2-isopropylpyridin-3-yl)-6-chloro-7-(3,6-difluoro-2-hydroxyphenyl)-2-oxo-1,2-dihydropyrido[2,3-d]pyrimidin-4-yl)-2,5-dimethylpiperazine-1-carboxylate (210 mg, 0.258 mmol) in THF (2.0 mL) was added triethylamine trihydrofluoride (0.126 mL, 0.774 mmol) at 0° C. under a nitrogen atmosphere. The mixture was then allowed to warm to 20° C. and the mixture was stirred at 20° C. for 15 h. After 15 h, the reaction mixture was diluted with DCM (5.0 mL), quenched with saturated aqueous sodium bicarbonate (4.0 mL), and extracted with EtOAc (3×20 mL). The combined organic layers were washed with brine (20 mL), dried over $Na_2SO_4$, filtered and the filtrate was concentrated under reduced pressure to afford (2R,5S)-tert-butyl 4-(6-chloro-7-(3,6-difluoro-2-hydroxyphenyl)-1-(4-(3-hydroxypropyl)-2-isopropylpyridin-3-yl)-2-oxo-1,2-dihydropyrido[2,3-d]pyrimidin-4-yl)-2,5-dimethylpiperazine-1-carboxylate (Int-120e-1) which was used in the next step without further purification. MS (ESI): m/z 699 [M+H]$^+$.

Step F: Int-120f-1

To a stirred mixture of tert-butyl (2R,5S)-4-(1-(4-(3-((tert-butyldimethylsilyl)oxy)propyl)-2-isopropylpyridin-3-yl)-6-chloro-7-(3,6-difluoro-2-hydroxyphenyl)-2-oxo-1,2-dihydropyrido[2,3-d]pyrimidin-4-yl)-2,5-dimethylpiperazine-1-carboxylate (0.14 g, 0.20 mmol) in DCM (7.0 mL) were added triphenylphosphine (263 mg, 1.00 mmol) and DIAD (0.195 mL, 1.00 mmol). The mixture was heated to 40° C. for 1 h under a $N_2$ atmosphere. After 1 hour, the mixture was allowed to cool to room temperature and then concentrated under reduced pressure. The resulting residue was purified by flash reverse phase silica gel chromatography (0-47% $H_2O$/MeCN) to afford Int-120f-1. MS (ESI): m/z 681 [M+H]$^+$.

Step G: Int-1202-1

To a stirred mixture of Int-120f-1 (50 mg, 0.073 mmol) in cyclopentyl methyl ether (2.5 mL) and water (0.20 mL) were added methylboronic acid (13 mg, 0.22 mmol), $Cs_2CO_3$ (48 mg, 0.15 mmol) and chloro[(di(1-adamantyl)-n-butylphosphine)-2-(2-aminobiphenyl)]palladium(II) (4.9 mg, 7.3 µmol) at room temperature (20° C.) under a nitrogen atmosphere. The mixture was heated to 90° C. for 15 h. After 15 h, the mixture was allowed to cool to room temperature. The mixture was quenched with brine (10 mL) and extracted with EtOAc (3×30 mL). The combined organic layers were washed with brine (5 mL), dried over $Na_2SO_4$, filtered and the filtrate was concentrated under reduced pressure to afford Int-120g-1 which was used in the next step without further purification. MS (ESI): m/z 661 [M+H]$^+$.

Step H: Int-120h-1

To a mixture of Int-120g-1 (48 mg, 0.073 mmol) in DCM (1.0 mL) was added TFA (2.0 mL, 26 mmol) and the mixture was stirred at room temperature (20° C.) for 30 min. The mixture was then concentrated under reduced pressure to afford Int-120h-1 and used in the next step without further purification. MS (ESI): m/z 561 [M+H]$^+$.

Step I: 2-[(2S,5R)-2,5-dimethyl-4-(prop-2-enoyl)piperazin-1-yl]-14,17-difluoro-20-methyl-6-(propan-2-yl)-11,12-dihydro-4H,10H-1,18-ethenopyrido[4,3-e]pyrimido[1,6-g][1,7,9]benzoxadiazacyclododecin-4-one (Ex. 120)

To a mixture of Int-120h-1 (38 mg, 0.068 mmol) in DCM (2.0 mL) were added DIPEA (12 µL, 0.068 mmol) and acryloyl chloride (5.5 µL, 0.068 mmol). The mixture was stirred at room temperature (20° C.) for 30 min. The mixture was filtered and the filtrate was purified by preparative HPLC (Column: Agela DuraShell C18 150 mm×25 mm, 5 um; Condition: water (0.04% $NH_3H_2O$+10 mM $NH_4HCO_3$)-ACN) to afford 2-[(2S,5R)-2,5-dimethyl-4-(prop-2-enoyl)piperazin-1-yl]-14,17-difluoro-20-methyl-6-(propan-2-yl)-11,12-dihydro-4H,10H-1,18-ethenopyrido[4,3-e]pyrimido[1,6-g][1,7,9]benzoxadiazacyclododecin-4-one (Ex. 120). MS (ESI): m/z 615 [M+H]$^+$. $^1$H NMR (400 MHz, Methanol-$d_4$) δ 8.47 (d, J=5.1 Hz, 1H), 8.20 (d, J=12.1 Hz, 1H), 7.33 (d, J=5.5 Hz, 1H), 7.23 (ddd, J=11.3, 9.2, 5.3 Hz, 1H), 6.96-6.73 (m, 2H), 6.34-6.25 (m, 1H), 5.86-5.78 (m, 1H), 5.05 (br s, 1H), 4.87-4.35 (m, 3H), 3.95-3.71 (m, 1H), 3.66 (br d, J=14.1 Hz, 1H), 3.59-3.51 (m, 1H), 3.34 (s, 1H), 3.10-2.99 (m, 1H), 2.52-2.43 (m, 1H), 2.42-2.28 (m, 2H), 2.25 (s, 3H), 2.15-2.02 (m, 1H), 1.61 (br dd, J=9.0, 7.0 Hz, 3H), 1.47 (dd, J=12.3, 6.8 Hz, 3H), 1.25 (d, J=6.7 Hz, 3H), 1.03 (dd, J=6.7, 3.9 Hz, 3H).

Example 121: 2-{(2R,5S)-4-[20-chloro-14,17-difluoro-4-oxo-6-(propan-2-yl)-11,12-dihydro-4H,10H-1,18-ethenopyrido[4,3-e]pyrimido[1,6-g][1,7,9]benzoxadiazacyclododecin-2-yl]-2,5-dimethylpiperazine-1-carbonyl}prop-2-enenitrile

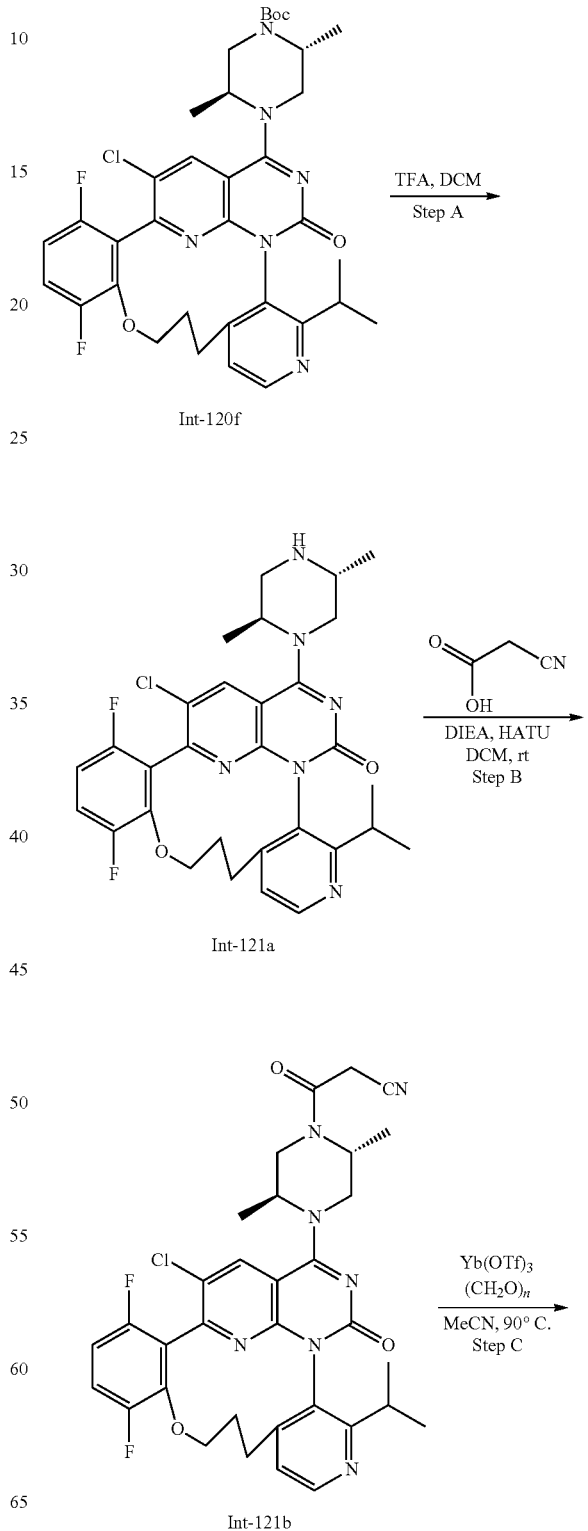

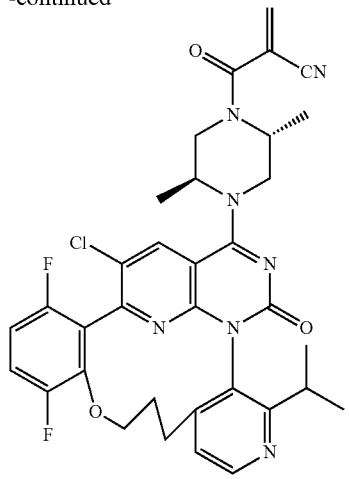

Ex. 121

Step A: Int-121a

To a solution of Int-120f (330 mg, 0.484 mmol) in CH$_2$Cl$_2$ (1.5 mL) was added TFA (0.5 mL, 6.49 mmol), and the mixture was stirred at room temperature for 30 min. The mixture was concentrated in vacuo to give Int-121a, which was used to the next step without further purification. MS (ESI): m/z 581 [M+H]$^+$.

Step B: Int-121b

To a solution of 2-cyanoacetic acid (13.2 mg, 0.155 mmol) in CH$_2$Cl$_2$ (1 mL) were added DIEA (0.108 mL, 0.620 mmol) and HATU (118 mg, 0.310 mmol) at room temperature. The mixture was stirred at room temperature for 10 min, at which point Int-121a (90 mg, 0.16 mmol) was added to the reaction solution, and the mixture was stirred at room temperature for 15 h. The mixture was quenched with water (1 mL) and extracted with DCM (2×2 mL). The combined organic layer was dried over Na$_2$SO$_4$, filtered, and the solvent was evaporated under reduced pressure to give the crude product. The crude product was purified by reverse preparative HPLC (Column: YMC-Actus Triart C18 100 mm×30 mm, 5 um; Condition: water (0.1% TFA)-MeCN) to give Int-121b. MS (ESI): m/z 648 [M+H]$^+$.

Step C: 2-{(2R,5S)-4-[20-chloro-14,17-difluoro-4-oxo-6-(propan-2-yl)-11,12-dihydro-4H,10H-1,18-ethenopyrido[4,3-e]pyrimido[1,6-g][1,7,9]benzoxadiazacyclododecin-2-yl]-2,5-dimethylpiperazine-1-carbonyl}prop-2-enenitrile (Ex. 121)

To a stirred solution of Int-121b (42 mg, 0.065 mmol) in MeCN (0.5 mL) was added paraformaldehyde (3.9 mg, 0.13 mmol), and then it was stirred at 90° C. for 30 min. Then ytterbium(III) trifluoromethanesulfonate (4.0 mg, 6.5 μmol) in MeCN (0.5 mL) was added. The resulting mixture was stirred at at 90° C. for 16 h under N$_2$ atmosphere. Without workup, the reaction mixture was purified by reverse preparative HPLC (Column: YMC-Actus Triart C18 100 mm×30 mm, 5 um; Condition: water (0.1% TFA)-MeCN) to give 2-{(2R,5S)-4-[20-chloro-14,17-difluoro-4-oxo-6-(propan-2-yl)-11,12-dihydro-4H,10H-1,18-ethenopyrido[4,3-e]pyrimido[1,6-g][1,7,9]benzoxadiazacyclododecin-2-yl]-2, 5-dimethylpiperazine-1-carbonyl}prop-2-enenitrile (Ex. 121). MS (ESI): m/z 660 [M+H]$^+$. $^1$H NMR (400 MHz, Methanol-d$_4$): δ 8.73 (d, J=5.9 Hz, 1H), 8.26 (br d, J=12.9 Hz, 1H), 7.72 (d, J=5.9 Hz, 1H), 7.31 (ddd, J=5.1, 9.3, 11.4 Hz, 1H), 6.97 (dt, J=3.5, 9.0 Hz, 1H), 6.57-6.42 (m, 2H), 4.83 (br s, 2H), 4.66 (br dd, J=2.9, 9.6 Hz, 1H), 4.43 (br s, 1H), 4.24-3.77 (m, 1H), 3.70 (br d, J=13.3 Hz, 1H), 3.56-3.49 (m, 1H), 3.39 (br s, 2H), 2.68-2.60 (m, 1H), 2.56-2.45 (m, 1H), 2.43-2.32 (m, 1H), 2.22-2.12 (m, 1H), 1.59 (br d, J=6.7 Hz, 3H), 1.51-1.41 (m, 3H), 1.34 (d, J=6.7 Hz, 3H), 1.20-1.17 (m, 3H).

Example 122: 2-1(2S,5R)-4-[4-(dimethylamino)but-2-ynoyl]-2,5-dimethylpiperazin-1-yl)-12,12,17,18,21-pentafluoro-6-(propan-2-yl)-10,11,12,13-tetrahydro-4H-1,19-(ethanediylidene)pyrido[4,3-f]pyrimido[1,6-h][1,8,10]benzoxadiazacyclotridecin-4-one

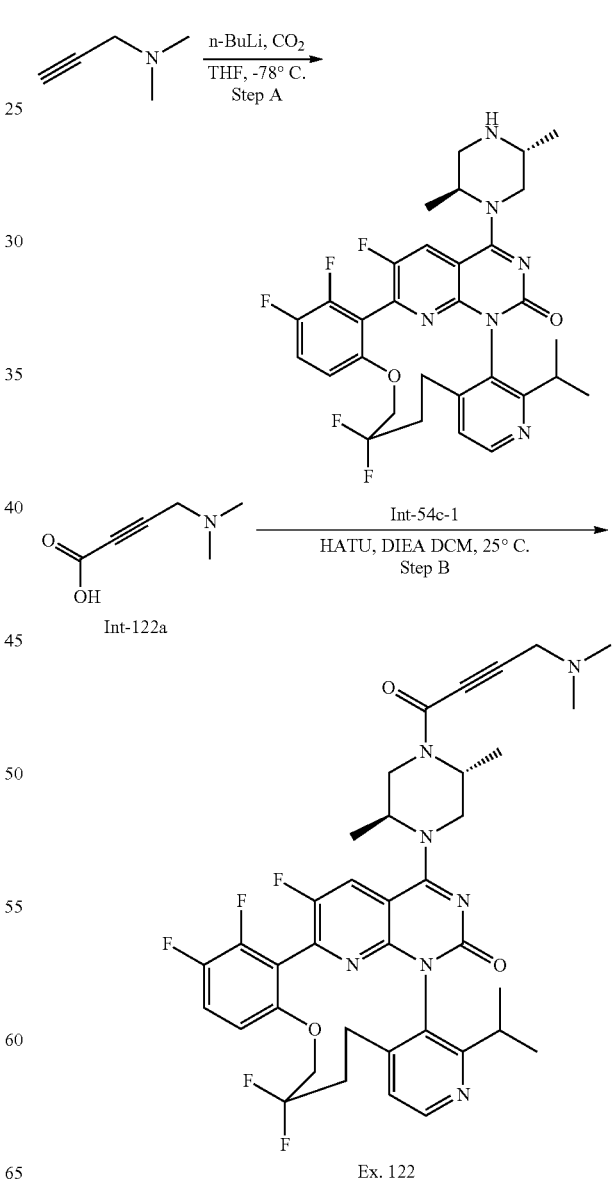

Ex. 122

Step A: 4-(dimethylamino)but-2-ynoic acid (Int-122a)

To a solution of N,N-dimethylprop-2-yn-1-amine (0.500 g, 6.01 mmol) in THF (5 mL) was added n-butyllithium (2.89 mL, 7.22 mmol) (2.5 M in hexanes) at −78° C. under an $N_2$ atmosphere. The mixture was stirred at −78° C. for 30 min, and then dry carbon dioxide was bubbled into the reaction solution for 10 min. The mixture was adjusted to pH 1 by the addition of 35% aqueous HCl (3 mL), and the reaction mixture was concentrated in vacuo to remove THF. Then the residue was dried by lyophilization. The solid was dissolved in EtOH (5 mL), and stirred at 65° C. to dissolve the solid. The clear reaction mixture was then stirred at 0° C., and a precipitate formed. The precipitate was filtered and the filtrate was concentrated in vacuo to give 4-(dimethylamino)but-2-ynoic acid (Int-122a). MS (ESI): m/z 128 $[M+H]^+$.

Step B: 2-{(2S,5R-4-[4-(dimethylamino)but-2-ynoyl]-2,5-dimethylpiperazin-1-yl}-12,12,17,18,21-pentafluoro-6-(propan-2-yl)-10,11,12,13-tetrahydro-4H-1,19-(ethanediylidene)pyrido[4,3-f]pyrimido[1,6-h][1,8,10]benzoxadiazacyclotridecin-4-one (Ex. 122)

To a solution of Int-54c-1 (20 mg, 0.033 mmol) in DCM (1 mL) were added 4-(dimethylamino)but-2-ynoic acid (6.2 mg, 0.049 mmol), DIEA (0.017 mL, 0.098 mmol) and HATU (19 mg, 0.049 mmol) at 25° C. The resulting solution was stirred at 25° C. for 1 h. The reaction mixture was concentrated in vacuo, and the residue was purified by preparative HPLC (Column: Agela DuraShell C18 150 mm×25 mm, 5 um; Condition: water (0.04% $NH_3H_2O$+10 mM $NH_4HCO_3$)-ACN) to give 2-{(2S,5R)-4-[4-(dimethylamino)but-2-ynoyl]-2,5-dimethylpiperazin-1-yl}-12,12,17,18,21-pentafluoro-6-(propan-2-yl)-10,11,12,13-tetrahydro-4H-1,19-(ethanediylidene)pyrido[4,3-f]pyrimido[1,6-h][1,8,10]benzoxadiazacyclotridecin-4-one (Ex. 122). MS (ESI): m/z 724 $[M+H]^+$. $^1$H NMR (500 MHz, $CDCl_3$): δ 8.53 (d, J=4.9 Hz, 1H), 7.90 (d, J=8.4 Hz, 1H), 7.25-7.19 (m, 1H), 7.12 (d, J=4.0 Hz, 1H), 6.88-6.79 (m, 1H), 5.14-4.80 (m, 2H), 4.46-4.36 (m, 1H), 4.18 (br t, J=13.1 Hz, 1H), 4.06-3.75 (m, 3H), 3.50 (d, J=3.4 Hz, 2H), 3.49-3.40 (m, 1H), 2.88-2.74 (m, 2H), 2.62-2.51 (m, 1H), 2.36 (d, J=3.8 Hz, 6H), 2.12-1.93 (m, 2H), 1.51 (dd, J=6.9, 11.1 Hz, 3H), 1.45-1.30 (m, 3H), 1.18 (dd, J=2.7, 6.7 Hz, 3H), 0.93 (dd, J=6.7, 10.2 Hz, 3H).

Example 123: 2-[(2S,5R)-4-(but-2-ynoyl-2,5-dimethylpiperazin-1-yl]-12,12,17,18,21-pentafluoro-6-(propan-2-yl)-10,11,12,13-tetrahydro-4H-1,19-(ethanediylidene)pyrido[4,3-f]pyrimido[1,6-h][1,8,10]benzoxadiazacyclotridecin-4-one

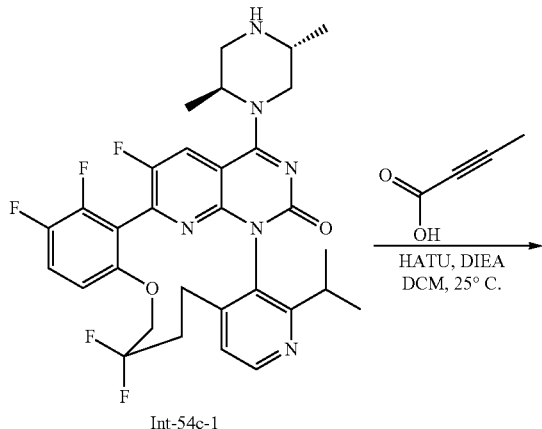

Int-54c-1

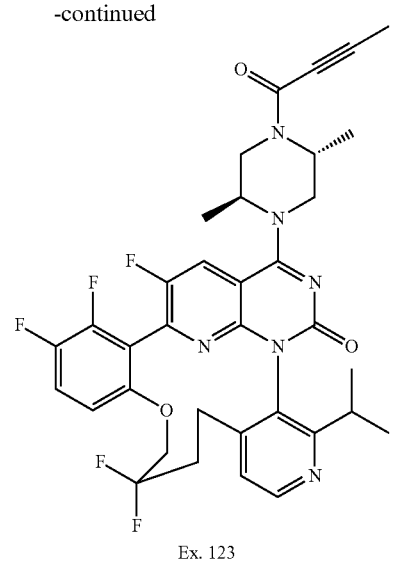

Ex. 123

To a solution of Int-54c-1 (20 mg, 0.033 mmol) in DCM (1 mL) were added but-2-ynoic acid (3.3 mg, 0.039 mmol), DIEA (0.017 mL, 0.098 mmol) and HATU (19 mg, 0.049 mmol) at 25° C., and the resulting solution was stirred at 25° C. for 1 h. The reaction mixture was concentrated in vacuo, and the residue was purified by preparative HPLC (Column: Agela DuraShell C18 150 mm×25 mm, 5 um; Condition: water (0.05% $NH_3H_2O$+10 mM $NH_4HCO_3$)-ACN) to give 2-[(2S,5R)-4-(but-2-ynoyl)-2,5-dimethylpiperazin-1-yl]-12,12,17,18,21-pentafluoro-6-(propan-2-yl)-10,11,12,13-tetrahydro-4H-1,19-(ethanediylidene)pyrido[4,3-f]pyrimido[1,6-h][1,8,10]benzoxadiazacyclotridecin-4-one (Ex. 123). MS (ESI): m/z 681 $[M+H]^+$. $^1$H NMR (500 MHz, Methanol-$d_4$): δ 8.48 (d, J=5.0 Hz, 1H), 8.33 (dd, J=8.8, 13.5 Hz, 1H), 7.40 (q, J=9.3 Hz, 1H), 7.32 (d, J=4.9 Hz, 1H), 7.08 (br d, J=9.0 Hz, 1H), 5.06 (br s, 1H), 4.82-4.49 (m, 2H), 4.33-4.19 (m, 1H), 4.13 (q, J=9.1 Hz, 1H), 3.80-3.41 (m, 3H), 2.89-2.70 (m, 3H), 2.11 (d, J=10.1 Hz, 5H), 1.61-1.50 (m, 3H), 1.46-1.28 (m, 3H), 1.18 (d, J=6.7 Hz, 3H), 0.95 (t, J=6.3 Hz, 3H).

Example 124: 2-[(2S,5R)-2,5-dimethyl-4-(2-methylprop-2-enoyl)piperazin-1-yl]-12,12,17,18,21-pentafluoro-6-(propan-2-yl)-10,11,12,13-tetrahydro-4H-1,19-(ethanediylidene)pyrido[4,3-f]pyrimido[1,6-h][1,8,10]benzoxadiazacyclotridecin-4-one

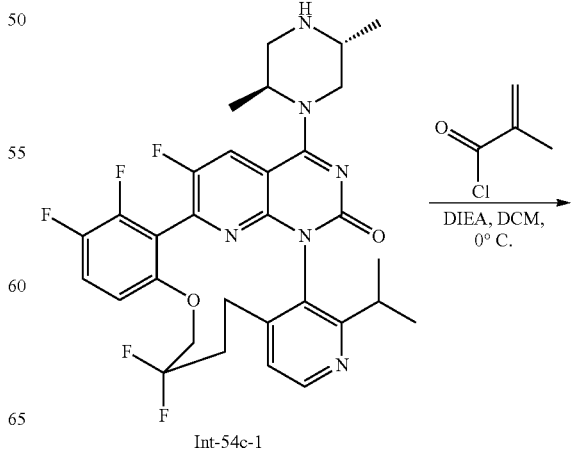

Int-54c-1

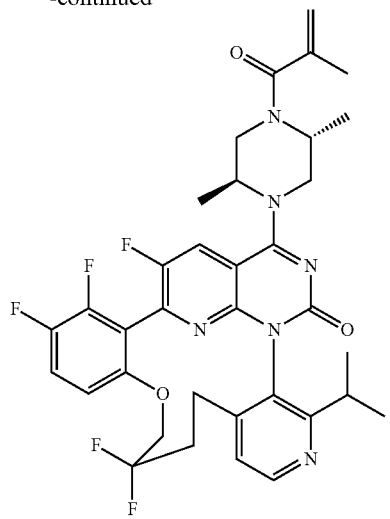

Ex. 124

To a solution of Int-54c-1 (20 mg, 0.033 mmol) in DCM (1 mL) was added DIEA (0.017 mL, 0.098 mmol) and methacryloyl chloride (6.8 mg, 0.065 mmol) at 0° C., and the resulting solution was stirred at 25° C. for 0.5 h. The solvent was removed by blowing nitrogen, and the residue was purified by preparative HPLC (Column: Agela DuraShell C18 150 mm×25 mm, 5 um; Condition: water (0.05% $NH_3H_2O$+10 mM $NH_4HCO_3$)-ACN) to give 2-[(2S,5R)-2,5-dimethyl-4-(2-methylprop-2-enoyl)piperazin-1-yl]-12,12,17,18,21-pentafluoro-6-(propan-2-yl)-10,11,12,13-tetrahydro-4H-1,19-(ethanediylidene)pyrido[4,3-f]pyrimido[1,6-h][1,8,10]benzoxadiazacyclotridecin-4-one (Ex. 124). MS (ESI): m/z 683 [M+H]$^+$. $^1$H NMR (500 MHz, Methanol-$d_4$): δ 8.48 (d, J=5.0 Hz, 1H), 8.41-8.28 (m, 1H), 7.40 (q, J=9.4 Hz, 1H), 7.32 (d, J=5.0 Hz, 1H), 7.12-7.02 (m, 1H), 5.34 (br d, J=8.1 Hz, 1H), 5.24-4.98 (m, 2H), 4.69-4.46 (m, 2H), 4.37-3.46 (m, 5H), 2.91-2.68 (m, 3H), 2.28-1.96 (m, 5H), 1.57 (d, J=6.7 Hz, 3H), 1.46-1.31 (m, 3H), 1.18 (d, J=6.7 Hz, 3H), 1.00-0.89 (m, 3H).

Example 125: 2-1(2S,5R)-4-[(2E)-4-(dimethylamino)but-2-enoyl]-2,5-dimethylpiperazin-1-yl)-12,12,17,18,21-pentafluoro-6-(propan-2-yl)-10,11,12,13-tetrahydro-4H-1,19-(ethanediylidene)pyrido[4,3-f]pyrimido[1,6-h][1,8,10]benzoxadiazacyclotridecin-4-one

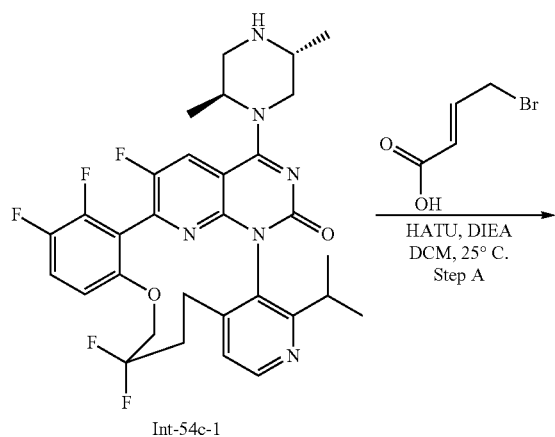

Step A: Int-125a

To a solution of Int-54c-1 (20 mg, 0.033 mmol) in DCM (1 mL) were added (E)-4-bromobut-2-enoic acid (6.4 mg, 0.039 mmol), DIEA (0.017 mL, 0.098 mmol) and HATU (19 mg, 0.049 mmol) at 25° C., and the resulting solution was stirred at 25° C. for 1 h. The reaction mixture was concentrated in vacuo to give Int-125a, which was used in the next step without further purification. MS (ESI): m/z 761 and 763 [M+H]$^+$.

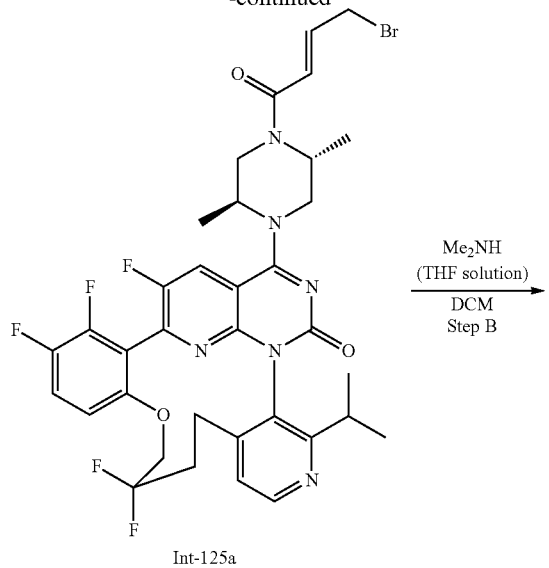

Int-125a

Step B: 2-1(2S,5R)-4-[(2E)-4-(dimethylamino)but-2-enoyl]-2,5-dimethylpiperazin-1-yl)-12,12,17,18,21-pentafluoro-6-(propan-2-yl)-10,11,12,13-tetrahydro-4H-1,19-(ethanediylidene)pyrido[4,3-f]pyrimido[1,6-h][1,8,10]benzoxadiazacyclotridecin-4-one (Ex. 125)

To a solution of Int-125a (24 mg, 0.025 mmol) in DCM (1 mL) was added dimethylamine (0.200 mL, 0.400 mmol) (2M in THF) at 25° C., and the resulting solution was stirred

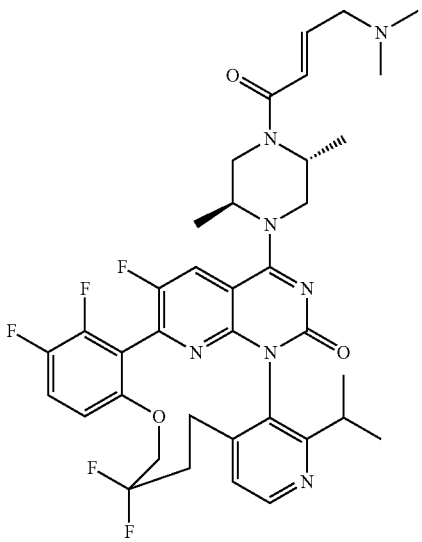

Ex. 125 at 25° C. for 1 h. The solvent was removed by blowing nitrogen, and the residue was purified by preparative HPLC (Column: Agela DuraShell C18 150 mm×25 mm, 5 um; Condition: water (0.05% NH$_3$H$_2$O+10 mM NH$_4$HCO$_3$)-ACN) to give 2-{(2S,5R)-4-[(2E)-4-(dimethylamino)but-2-enoyl]-2,5-dimethylpiperazin-1-yl}-12,12,17,18,21-pentafluoro-6-(propan-2-yl)-10,11,12,13-tetrahydro-4H-1,19-(ethanediylidene)pyrido[4,3-f]pyrimido[1,6-h][1,8,10]benzoxadiazacyclotridecin-4-one (Ex. 125). MS (ESI): m/z 726 [M+H]$^+$. $^1$H NMR (500 MHz, Methanol-d$_4$): δ 8.36 (d, J=5.0 Hz, 1H), 8.23 (dd, J=8.9, 20.0 Hz, 1H), 7.28 (q, J=9.4 Hz, 1H), 7.21 (d, J=5.0 Hz, 1H), 6.96 (br d, J=9.3 Hz, 1H), 6.88-6.75 (m, 1H), 6.74-6.64 (m, 1H), 5.01-4.78 (m, 2H), 4.62-4.24 (m, 2H), 4.01 (q, J=9.2 Hz, 1H), 3.90-3.71 (m, 2H), 3.68-3.38 (m, 3H), 2.62 (d, J=6.7 Hz, 9H), 2.16-1.88 (m, 2H), 1.45 (t, J=7.2 Hz, 3H), 1.36-1.20 (m, 3H), 1.06 (d, J=6.7 Hz, 3H), 0.82 (dd, J=6.7, 11.9 Hz, 3H).

Example 126: 2-[(2S,5R)-4-(ethenesulfonyl)-2,5-dimethylpiperazin-1-yl]-12,12,17,18,21-pentafluoro-6-(propan-2-yl)-10,11,12,13-tetrahydro-4H-1,19-(ethanediylidene)pyrido[4,3-f]pyrimido[1,6-h][1,8,10]benzoxadiazacyclotridecin-4-one

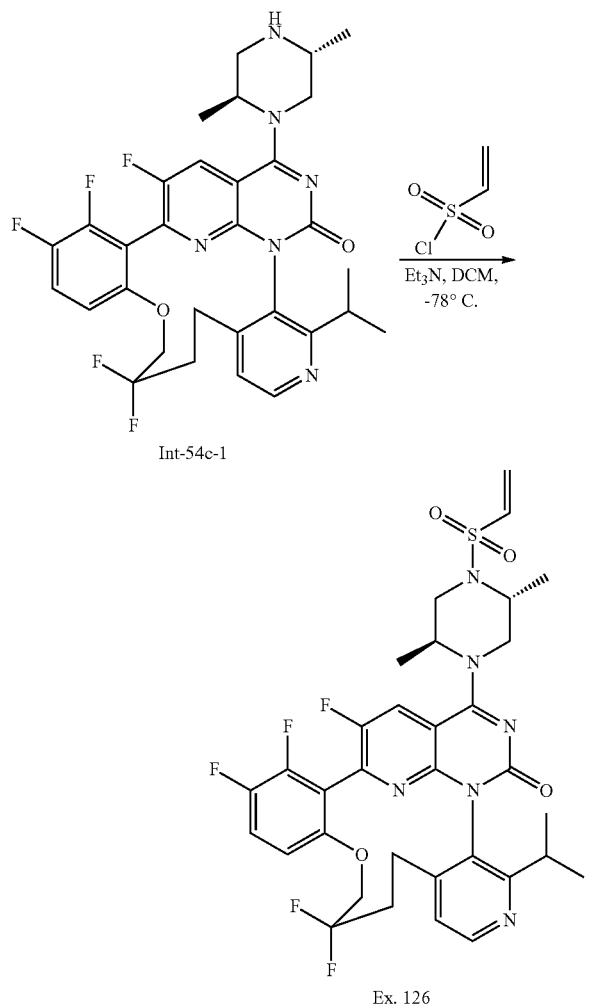

To a solution of Int-54c-1 (20 mg, 0.033 mmol) in DCM (0.5 mL) were added TEA (0.014 mL, 0.098 mmol) and ethenesulfonyl chloride (6.2 mg, 0.049 mmol) dissolved in DCM (0.5 mL) at −78° C., and the resulting solution was stirred at −78° C. for 0.5 h. The reaction mixture was quenched with MeOH (0.5 mL) at −78° C., and the solvent was removed by blowing nitrogen. The residue was purified by preparative HPLC (Column: Agela DuraShell C18 150 mm×25 mm, 5 um; Condition: water (0.05% NH$_3$H$_2$O+10 mM NH$_4$HCO$_3$)-ACN) to give 2-[(2S,5R)-4-(ethenesulfonyl)-2,5-dimethylpiperazin-1-yl]-12,12,17,18,21-pentafluoro-6-(propan-2-yl)-10,11,12,13-tetrahydro-4H-1,19-(ethanediylidene)pyrido[4,3-f]pyrimido[1,6-h][1,8,10]benzoxadiazacyclotridecin-4-one (Ex. 126). MS (ESI): m/z 705 [M+H]$^+$. $^1$H NMR (500 MHz, CDCl$_3$): δ 8.52 (d, J=4.9 Hz, 1H), 7.88 (d, J=8.4 Hz, 1H), 7.26-7.18 (m, 1H), 7.12 (d, J=4.7 Hz, 1H), 6.88-6.77 (m, 1H), 6.48 (dd, J=9.8, 16.6 Hz, 1H), 6.31 (d, J=16.5 Hz, 1H), 6.02 (d, J=9.8 Hz, 1H), 5.01 (br s, 1H), 4.32-4.22 (m, 2H), 3.99-3.89 (m, 2H), 3.64-3.57 (m, 1H), 3.51-3.45 (m, 2H), 2.87-2.74 (m, 2H), 2.61-2.49 (m, 1H), 2.12-1.95 (m, 2H), 1.60 (br s, 3H), 1.32 (d, J=6.7 Hz, 3H), 1.17 (d, J=6.7 Hz, 3H), 0.92 (d, J=6.7 Hz, 3H).

Biological Assays:

Procedure for SOS-Catalyzed Nucleotide Exchange Assay

The SOS-catalyzed nucleotide exchange assay utilizes a preformed complex of recombinant biotinylated KRAS protein containing G12C/C51S/C80L/C118S mutations (183 amino acids; biotin on K10; leader sequence which is an AviTag; referred to as SEQ ID NO: 1 or "Biotinylated KRAS G12C protein" hereafter), Bodipy-GDP, and Terbium-streptavidin. Compounds are added to this complex and then after incubation for 60 minutes, the mixture is treated with recombinant SOS protein and unlabeled GTP. Small molecule inhibitors stabilize the Bodipy-GDP complex whereas the untreated protein rapidly exchanges Bodipy-GDP for unlabeled GTP resulting in reduced TR-FRET signal.

Biotinylated KRAS G12C protein (SEQ ID NO: 1) is diluted to 2 μM in an EDTA buffer (20 mM HEPES, 150 mM sodium chloride, 10 mM EDTA, and 0.01% Tween) and incubated at room temperature for one hour. This mixture is then further diluted to 90 nM in an assay buffer (20 mM HEPES, 150 mM sodium chloride, 10 mM magnesium chloride, and 0.005% Tween) containing 15 nM of Terbium-Streptavidin (Invitrogen, catalog #PV3577) and 900 nM of Bodipy-GDP and incubated at room temperature for six hours. This solution is referred to as Biotinylated KRAS G12C mixture.

Each test compound (10 mM stock in DMSO) is diluted in DMSO to make a 10-point, 3-fold dilution series in a 384-well low dead volume microplate (Labcyte, catalog #LP-0200). Once titrations are made, 10 nL of the diluted compounds is acoustically dispensed into a 384-well plate (Corning, catalog #3820) using an Echo 550 (Labcyte).

Each well of the plate receives 3 μL Biotinylated KRAS G12C mixture that had been incubating for six hours and 3 μL of assay buffer using a BioRAPTR (Beckman Coulter) and is incubated at room temperature for 60 minutes. Each well then receives 3 μL of 240 nM recombinant human SOS protein and 9 mM GTP (Sigma, G8877) in assay buffer and is incubated at room temperature for 60 minutes.

The time-resolved fluorescence resonance energy transfer signal of the plate is measured on an Envision (PerkinElmer) plate reader: Excitation filter=340 nm; emission1=495 nm; emission2=520 nm; dichroic mirror=D400/D505; delay time=100 μs. The signal of each well is determined as the ratio of the emission at 520 nm to that at 495 nm. Percent effect of each well is determined after normalization to control wells containing DMSO (no effect) or a saturating concentration of inhibitor (max effect). The apparent effect as a function of compound concentration is fit to a four parameter logistic equation.

Procedure for Cellular Phospho-ERK Assay

NCI-H358 cells (ATCC® CRL-5807™) were cultured in T150 flask in growth medium (RPMI medium 1640-GlutaMAX™-I (ThermoFisher Scientific 61870) containing 10% fetal bovine serum (ThermoFisher Scientific 10091148)). The cells were harvested in growth medium after TrypLE (ThermoFisher scientific 12604021) digestion and were seeded in a 384-well collagen coated cell culture plate (Corning 356702) at a density of 15,000 cells/well, and incubated at 37° C., 5% $CO_2$ overnight. The compound dose-response titrations were prepared and appropriate amounts of compounds were dispensed in a 384-well intermediate plate using an Echo 550 liquid handler. RPMI medium 1640-GlutaMAX™-I were added to the intermediate plate and transferred to 384-well cell culture plate, which was incubated at 37° C., 5% $CO_2$ for 2 hours. After removal of medium from the plate, cells were lysed in lysis buffer from Alpha SureFire® Ultra™ Multiplex p-Erk and total Erk assay kit (PerkinElmer MPSU-PTERK) containing Halt™ Protease and Phosphotase inhibitor cocktail (ThermoFisher Scientific 78446) at room temperature with constant shaking at 300 rpm for 30 minutes. The cell lysates were then transferred to OptiPlate-384 plate (PerkinElmer 6005620) and the phosphorylation of Erk and total Erk levels were detected by Alpha SureFire Ultra Multiplex p-Erk kit (PerkinElmer MPSU-PTERK) following the manufacturer's protocol. Assay plates were read on an EnVision Multimode Plate Reader (PerkinElmer), and the ratio of p-Erk vs total Erk in each well was used as the final readout. Dose response curves were analyzed using a 4-parameter logistic model to calculate $IC_{50}$ values using spotfire software.

TABLE 1

In vitro apparent potency ($IC_{50}$) in the SOS-catalyzed nucleotide exchange assay with preincubation time of 60 minutes prior to addition of SOS. In vitro potency in the cellular phospho-ERK assay after 2 hour incubation.

| Example | $IC_{50}$ (nM) at 60 min (SOS) | $IC_{50}$ (nM) pERK (Cell) |
|---|---|---|
| 1a | 11 | 21 |
| 2a | 2677 | 13930 |
| 3a | 4425 | 19090 |
| 3b | 15 | 93 |
| 4a | 2.4 | 1.5 |
| 4b | 6886 | 1159 |
| 5 | 898 | 4445 |
| 6 | 9.2 | 45 |
| 7 | 6.9 | 34 |
| 8 | 3.5 | 2.2 |
| 9 | 1414 | 3832 |
| 10a | 4.3 | 6.7 |
| 10b | 2593 | 4382 |
| 11a | 19 | 395 |
| 12a | 3.9 | 6.9 |
| 13a | 7.2 | 27 |
| 13b | 8535 | 22100 |
| 14a | 8.1 | 1240 |
| 15a | 6.5 | 11 |
| 16a | 9.8 | 79 |
| 16b | 10 | 109 |
| 17a | 11 | 66 |
| 17b | 370 | 1179 |
| 18a | 10 | 35 |
| 19a | 6.8 | 117 |
| 19b | 4525 | >30,000 |
| 20a | 12 | 30 |
| 20b | 1379 | 4759 |
| 50 | 1.1 | 4.4 |
| 51-1 | 1.0 | 13 |
| 52 | 1.8 | 9.3 |
| 54 | 2.4 | 16 |
| 55 | 2.7 | 29 |
| 56 | 1.1 | 8.0 |
| 57 | 0.51 | 6.1 |
| 58 | 0.74 | 14 |
| 59 | 0.91 | 6.1 |
| 60 | 1.5 | 17 |
| 61 | 2.3 | 43 |
| 62 | 3.5 | 54 |
| 63 | 3.6 | 2.0 |
| 64 | 5.7 | 33 |
| 65 | 2.6 | 15 |
| 66 | 5.3 | 30 |
| 67 | 12 | 50 |
| 68 | 4.5 | 6.3 |
| 70 | 1.8 | 19 |
| 73 | 6.5 | 13 |
| 74 | 0.51 | 3.6 |
| 75 | 1.7 | 8.8 |
| 76 | 2.3 | 3.6 |
| 77 | 2.4 | 45 |
| 78 | 2.4 | 18 |
| 79 | 2.6 | 7.0 |
| 80 | 2.6 | 54 |
| 81 | 2.9 | 21 |
| 82 | 5.9 | 36 |
| 83 | 11 | 8.9 |
| 84 | 38 | 119 |
| 85 | 47 | 198 |
| 86 | 64 | 389 |
| 87 | 461 | 3210 |
| 88 | 1.1 | 96 |
| 89 | 71 | 4156 |
| 90 | 1.4 | 6.8 |
| 91 | 113 | 410 |
| 92 | 0.71 | 12 |
| 93 | 31 | 572 |
| 94 | 3.4 | 42 |
| 95 | 2.5 | 15 |
| 96 | 3.8 | 32 |
| 97 | 0.56 | 3.0 |
| 98 | 11 | 49 |
| 99 | 12 | 22 |
| 100 | 25 | 508 |
| 101 | 29 | 137 |
| 102 | 35 | 149 |
| 103 | 107 | 847 |
| 104 | 1468 | 8852 |
| 105 | 1910 | 3599 |
| 106 | 2553 | 5617 |
| 107 | 10 | 20 |
| 108 | 20 | 68 |
| 109 | 2.3 | 21 |
| 110 | 4.5 | 23 |
| 111 | 17 | 154 |
| 112 | 23 | 26 |
| 113 | 33 | 113 |
| 114 | 43 | 112 |
| 115 | 237 | 1021 |
| 116 | 1100 | 2726 |
| 117 | 17 | 44 |
| 118-1 | 192 | 651 |
| 118-2 | 54 | 1219 |
| 119 | 2.6 | 5.1 |
| 120 | 4.3 | 11 |
| 121 | 195 | >30000 |

Protein Sequence
Biotinylated KRAS G12C Protein

```
                                      SEQ ID NO: 1
GLNDIFEAQKIEWHETEYKLVVVGACGVGKSALTIQLIQNHFVDEYDPTIE

DSYRKQVVIDGETSLLDILDTAGQEEYSAMRDQYMRTGEGFLLVFAINNTK

SFEDIHHYREQIKRVKDSEDVPMVLVGNKSDLPSRTVDTKQAQDLARSYGI

PFIETSAKTRQGVDDAFYTLVREIRKHKEK
```

SEQUENCE LISTING

```
Sequence total quantity: 1
SEQ ID NO: 1           moltype = AA  length = 183
FEATURE                Location/Qualifiers
SITE                   10
                       note = biotin
source                 1..183
                       mol_type = protein
                       organism = synthetic construct
SEQUENCE: 1
GLNDIFEAQK IEWHETEYKL VVVGACGVGK SALTIQLIQN HFVDEYDPTI EDSYRKQVVI   60
DGETSLLDIL DTAGQEEYSA MRDQYMRTGE GFLLVFAINN TKSFEDIHHY REQIKRVKDS  120
EDVPMVLVGN KSDLPSRTVD TKQAQDLARS YGIPFIETSA KTRQGVDDAF YTLVREIRKH  180
KEK                                                                183
```

We claim:

1. A method of inhibiting KRAS G12C protein comprising contacting KRAS G12C protein with a compound or a pharmaceutically acceptable salt thereof, to inhibit the activity of the KRAS G12C protein, wherein the compound is selected from the group consisting of:

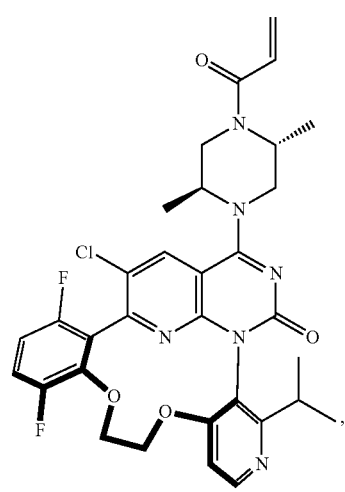

,

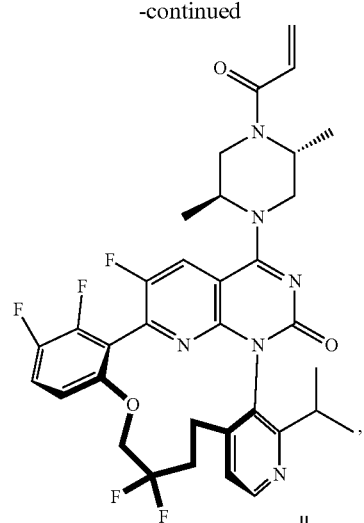

,

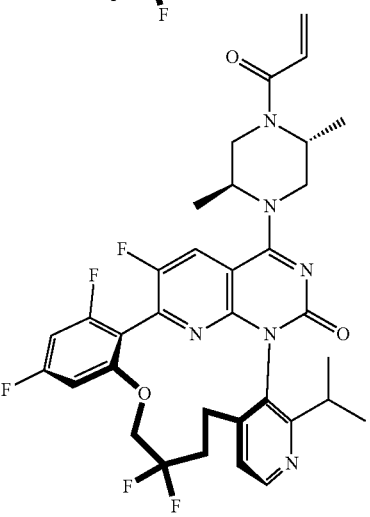

,

3. The method of inhibiting KRAS G12C protein according to claim 1, wherein the compound is:
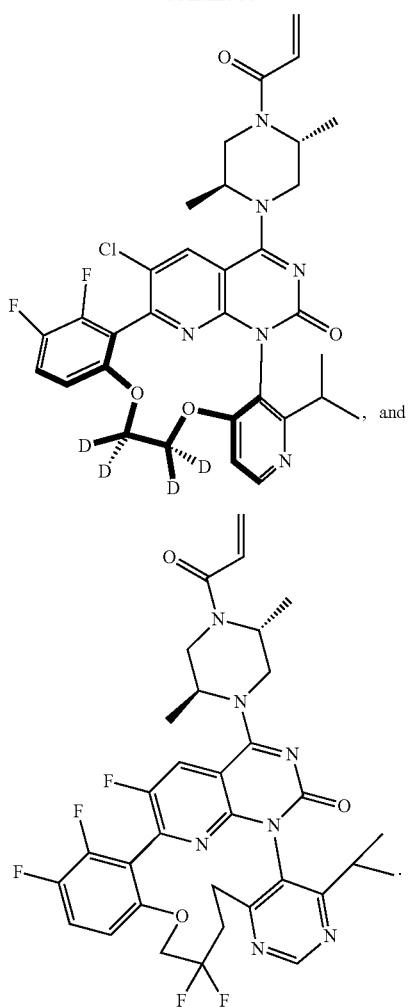
, and
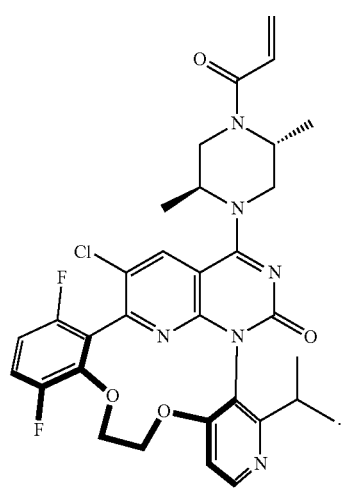
2. The method of inhibiting KRAS G12C protein according to claim 1, wherein the compound is:
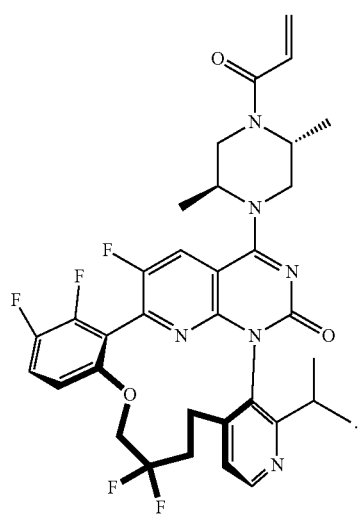
4. The method of inhibiting KRAS G12C protein according to claim 1, wherein the compound is:

5. The method of inhibiting KRAS G12C protein according to claim 1, wherein the compound is:
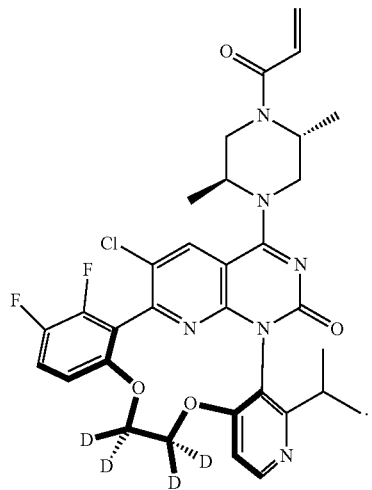
6. The method of inhibiting KRAS G12C protein according to claim 1, wherein the compound is:
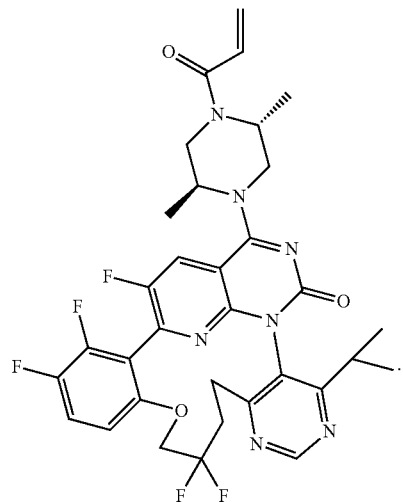 [SMILES: C=CC(=O)N1C[C@H](C)N(c2nc(=O)[nH]c3nc(-c4c(OCC(F)(F)CCc5ncnc(C(C)C)c5C)ccc(F)c4F)c(F)cc23)C[C@H]1C]
* * * * *